(12) United States Patent  
Zhang et al.

(10) Patent No.: US 11,932,658 B2
(45) Date of Patent: Mar. 19, 2024

(54) TRICYCLIC HETEROARYL-SUBSTITUTED QUINOLINE AND AZAQUINOLINE COMPOUNDS AS PAR4 INHIBITORS

(71) Applicant: BRISTOL-MYERS SQUIBB COMPANY, Princeton, NJ (US)

(72) Inventors: Xiaojun Zhang, Furlong, PA (US); Eldon Scott Priestley, Yardley, PA (US); Oz Scott Halpern, Bordentown, NJ (US); Wen Jiang, Furlong, PA (US); Samuel Kaye Reznik, Brookline, MA (US); Jeremy M. Richter, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 138 days.

(21) Appl. No.: 17/142,288

(22) Filed: Jan. 6, 2021

(65) Prior Publication Data

US 2021/0188877 A1 Jun. 24, 2021

Related U.S. Application Data

(63) Continuation of application No. 16/317,258, filed as application No. PCT/US2017/041880 on Jul. 13, 2017, now abandoned.

(Continued)

(51) Int. Cl.
C07D 491/04 (2006.01)
A61K 31/498 (2006.01)
(Continued)

(52) U.S. Cl.
CPC ............ C07D 519/00 (2013.01); A61P 7/02 (2018.01); C07D 515/14 (2013.01)

(58) Field of Classification Search
CPC .. C07D 491/04; C07D 493/04; C07D 495/04; C07D 498/04; C07D 513/04; C07D 519/00; A61K 31/498; A61P 7/02
See application file for complete search history.

(56) References Cited

U.S. PATENT DOCUMENTS 6,166,041 A 12/2000 Cavalla et al.
9,518,064 B2 12/2016 Martel et al.
(Continued)

FOREIGN PATENT DOCUMENTS

EP 0534443 A1 3/1993
EP 1348701 A1 10/2003
(Continued)

OTHER PUBLICATIONS

Beaulieu, Pierre L. et al., Discovery of the First Thumb Pocket 1 NS5B Polymerase Inhibitor (BILB 1941) with Demonstrated Antiviral Activity in Patients Chronically Infected with Genotype 1 Hepatitis C Virus (HCV), J. Med. Chem., vol. 55, pp. 7650-7666, 2012.

(Continued)

Primary Examiner — Brenda L Coleman
(74) Attorney, Agent, or Firm — Mary K. VanAtten

(57) ABSTRACT

Disclosed are compounds of Formula (I) to (VIII):

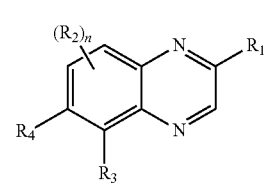

(I)

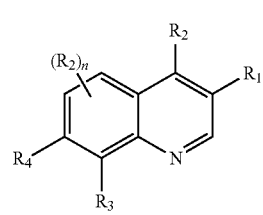

(II)

(III)

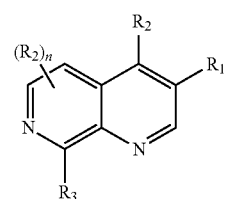

(IV)

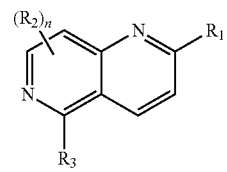

(V)

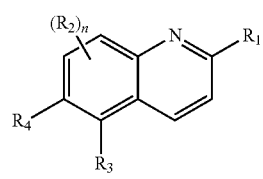

(VI)

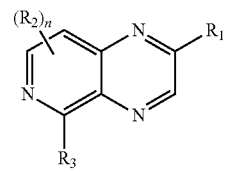

(Continued)

-continued

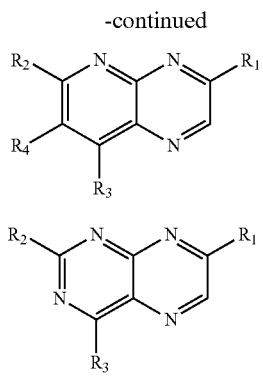

or a stereoisomer, tautomer, pharmaceutically acceptable salt, solvate or prodrug thereof, wherein $R_3$ is a tricyclic heteroaryl group substituted with $R_{3a}$ and zero to 2 $R_{3b}$; and $R_i$, $R_2$, $R_{3a}$, $R_{3b}$, $R_4$, and n are defined herein. Also disclosed are methods of using such compounds as PAR4 inhibitors, and pharmaceutical compositions comprising such compounds. These compounds are useful in inhibiting or preventing platelet aggregation, and are useful for the treatment of a thromboembolic disorder or the primary prophylaxis of a thromboembolic disorder.

19 Claims, No Drawings

Related U.S. Application Data

(60) Provisional application No. 62/362,121, filed on Jul. 14, 2016.

(51) Int. Cl.
- *A61P 7/02* (2006.01)
- *C07D 493/04* (2006.01)
- *C07D 495/04* (2006.01)
- *C07D 498/04* (2006.01)
- *C07D 513/04* (2006.01)
- *C07D 515/14* (2006.01)
- *C07D 519/00* (2006.01)

(56) References Cited

U.S. PATENT DOCUMENTS

| | | | |
|---|---|---|---|
| 9,598,419 | B1 | 3/2017 | Martel et al. |
| 9,617,279 | B1 | 4/2017 | Zhang |
| 9,688,695 | B2 | 6/2017 | Banville et al. |
| 9,862,730 | B2 | 1/2018 | Lawrence et al. |
| 10,047,103 | B2 | 8/2018 | Banville et al. |
| 10,214,544 | B2 | 2/2019 | Banville |
| 10,238,638 | B2 | 3/2019 | Ruediger et al. |
| 10,428,077 | B2 | 10/2019 | Banville et al. |
| 10,517,870 | B2 | 12/2019 | Zhang et al. |
| 2015/0119390 | A1 | 4/2015 | Martel et al. |
| 2019/0248771 | A1 | 8/2019 | Richter et al. |
| 2019/0292176 | A1 | 9/2019 | Zhang et al. |
| 2019/0300520 | A1 | 10/2019 | Fu et al. |
| 2020/0123160 | A1 | 4/2020 | Banvile et al. |

FOREIGN PATENT DOCUMENTS

| | | |
|---|---|---|
| WO | 198201706 A1 | 5/1982 |
| WO | 2005012288 A1 | 2/2005 |
| WO | 2005113522 A1 | 12/2005 |
| WO | 2006015259 A2 | 2/2006 |
| WO | 2006076529 A1 | 7/2006 |
| WO | 2007149395 A2 | 12/2007 |
| WO | 2008000643 A1 | 1/2008 |
| WO | 2008073451 A2 | 6/2008 |
| WO | 2009073497 A2 | 6/2009 |
| WO | 2009134973 A1 | 11/2009 |
| WO | 2009141386 A1 | 11/2009 |
| WO | 2010011768 A1 | 1/2010 |
| WO | 2012154888 A1 | 11/2012 |
| WO | 2013130660 A1 | 9/2013 |
| WO | 2013163241 A1 | 10/2013 |
| WO | 2013163279 A1 | 10/2013 |
| WO | 2013163244 A1 | 4/2014 |
| WO | 2015077550 A1 | 5/2015 |
| WO | 2016/138199 A1 | 9/2016 |
| WO | 2016134450 A1 | 9/2016 |
| WO | 2017019828 A1 | 2/2017 |
| WO | 2018/013772 A1 | 1/2018 |
| WO | 2018013770 A1 | 1/2018 |
| WO | 2018013774 A1 | 1/2018 |

OTHER PUBLICATIONS

Beaulieu, Pierre L. et al., "From benzimidazole to indole-5-carboxamide Thumb Pocket 1 inhibitors of HCV N55B polymerase. Part 1:Indole C-2 SAR and discovery of diamide derivatives with nanomolar potency in cell-based subgenomic replicons", Bioorganic & Medicinal Chemistry Letters, vol. 21, pp. 3658-3663 (2011).

Chen et al., "Synthesis and antiplatelet activity of ethyl 4-(1-benzyl-1H-indazol-3-yl)benzoate (YD-3) derivatives", Bioorg. Med. Chem., 16:1262-1278 (2008).

Coughlin et al., "Thrombin signaling and protease-activated receptors", Nature, 407:258-264 (2000).

Ishii, et al., "Studies on the Chemical Constituents of Rutaceous Plants. XXXVI. Synthesis of Ethyl Isodecarine", Chemical and Pharmaceutical Bulletin, Pharmaceutical Society of Japan, vol. 26(2), pp. 514-519 (1978).

Laroche, et al., "Direct heteroarylation of 5-bromothiophen-2-ylpyridine and of 8-bromoquinoline via palladium-catalysed C-H bond activation: simpler access to heteroarylated nitrogen-based derivatives", Catalysis Science & Technology, pp. 2072-2080 (2013).

Lee et al., "Synthesis of 1-Benzyl-3-(5'-hydroxymethyl-2'-furyl)indazole Analogues as Novel Antiplatelet Agents", J. Med. Chem., 44(22):3746-3749 (2001).

Prakash, et al., "N-Difluoromethylation of Imidazoles and Benzimidazoles Using the Ruppert-Prakash Reagent under Neutral Conditions", Organic Letters, vol. 16, pp. 54-57 (2014).

Tricoci et al. "Thrombin-Receptor Antagonist Vorapaxar in Acute Coronary Syndromes", N. Eng. J. Med., 366(1):20-33 (2012).

Wen, et al., "Substituted indoles as selective protease activated receptor 4(PAR-4) antagonists: Discovery and SAR of ML354", Bioorganic & Medicinal Chemistry Letters, vol. 24(19), pp. 4708-4713 (2014).

Wu et al., "Selective Inhibition of Protease-activated Receptor 4-dependent Platelet Activation by YD-3", Thromb. Haemost., 87:1026-1033 (2002).

TRICYCLIC HETEROARYL-SUBSTITUTED QUINOLINE AND AZAQUINOLINE COMPOUNDS AS PAR4 INHIBITORS

CROSS REFERENCE TO RELATED APPLICATIONS

This application is a continuation of U.S. Ser. No. 16/317,258 filed on Jan. 11, 2019, now allowed, which is a 371 International Application of PCT/US2O17/041880, filed Jul. 13, 2017, which is entitled to priority pursuant to 35 U.S.C. § 119(e) to U.S. provisional patent application No. 62/362,121, filed Jul. 14, 2016, which is incorporated herein in their entirety.

FIELD OF THE INVENTION

The present invention generally relates to tricyclic heteroaryl substituted compounds useful as inhibitors of platelet aggregation. Provided herein are tricyclic heteroaryl substituted compounds, compositions comprising such compounds, and methods of their use. The invention further pertains to pharmaceutical compositions containing at least one compound according to the invention that are useful in preventing or treating thromboembolic disorders.

BACKGROUND OF THE INVENTION

Thromboembolic diseases remain the leading cause of death in developed countries despite the availability of anticoagulants such as warfarin (COUMADIN®), heparin, low molecular weight heparins (LMWH), synthetic pentasaccharides, and antiplatelet agents such as aspirin and clopidogrel (PLAVIX®).

Current anti-platelet therapies have limitations including increased risk of bleeding as well as partial efficacy (relative cardiovascular risk reduction in the 20 to 30% range). Thus, discovering and developing safe and efficacious oral or parenteral antithrombotics for the prevention and treatment of a wide range of thromboembolic disorders remains an important goal.

Alpha-thrombin is the most potent known activator of platelet aggregation and degranulation. Activation of platelets is causally involved in atherothrombotic vascular occlusions. Thrombin activates platelets by cleaving G-protein coupled receptors termed protease activated receptors (PARs). PARs provide their own cryptic ligand present in the N-terminal extracellular domain that is unmasked by proteolytic cleavage, with subsequent intramolecular binding to the receptor to induce signaling (tethered ligand mechanism; Coughlin, S. R., Nature, 407:258-264 (2000)). Synthetic peptides that mimic the sequence of the newly formed N-terminus upon proteolytic activation can induce signaling independent of receptor cleavage. Platelets are a key player in atherothrombotic events. Human platelets express at least two thrombin receptors, commonly referred to as PAR1 and PAR4. Inhibitors of PAR1 have been investigated extensively, and several compounds, including vorapaxar and atopaxar have advanced into late stage clinical trials. Recently, in the TRACER phase III trial in ACS patients, vorapaxar did not significantly reduce cardiovascular events, but significantly increased the risk of major bleeding (Tricoci, P. et al., N. Eng. J. Med., 366(1):20-33 (2012). Thus, there remains a need to discover new antiplatelet agents with increased efficacy and reduced bleeding side effects.

There are several early reports of preclinical studies of PAR4 inhibitors. Lee, F-Y. et al., "Synthesis of 1-Benzyl-3-(5'-hydroxymethyl-2'-furyl)indazole Analogues as Novel Antiplatelet Agents", J. Med. Chem., 44(22):3746-3749 (2001) discloses in the abstract that the compound

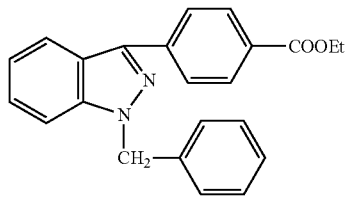

58

"was found to be a selective and potent inhibitor or protease-activated receptor type 4 (PAR4)-dependent platelet activation." Compound 58 is also referred to as YD-3 in Wu, C-C. et al., "Selective Inhibition of Protease-activated Receptor 4-dependent Platelet Activation by YD-3", Thromb. Haemost., 87:1026-1033 (2002). Also, see Chen, H. S. et al., "Synthesis and antiplatelet activity of ethyl 4-(1-benzyl-1H-indazol-3-yl)benzoate (YD-3) derivatives", Bioorg. Med. Chem., 16:1262-1278 (2008).

EP1166785 A1 and EP0667345 disclose various pyrazole derivatives which are useful as inhibitors of platelet aggregation.

The PCT publications WO2013/163279, WO2013/163244, and WO2013/163241 disclose various PAR4 antagonists which are useful as inhibitors of platelet aggregation.

There still remains a need for compounds useful as inhibitors of platelet aggregation.

Applicants have found potent compounds that have activity as PAR4 inhibitors. These compounds are provided to be useful as pharmaceuticals with desirable potency, stability, bioavailability, therapeutic index, and toxicity values that are important to their drugability.

SUMMARY OF THE INVENTION

It has been found that tricyclic heteroaryl substituted compounds in accordance with the present invention are PAR4 antagonists which inhibit platelet aggregation in gamma-thrombin induced platelet aggregation assays.

Accordingly, the present invention provides tricyclic heteroaryl substituted compounds which are PAR4 antagonists and are useful as selective inhibitors of platelet aggregation, including stereoisomers, tautomers, pharmaceutically acceptable salts, solvates, or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for the treatment or prophylaxis of thromboembolic disorders comprising administering to a patient in need of such treatment or prophylaxis a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment or prophylaxis of a thromboembolic disorder.

Other features and advantages of the invention will be apparent from the following detailed description and claims.

DETAILED DESCRIPTION

The first aspect of the present invention provides at least one compound of Formula (I), Formula (II), Formula (III), Formula (IV), Formula (V), Formula (VI), Formula (VII), or Formula (VIII):

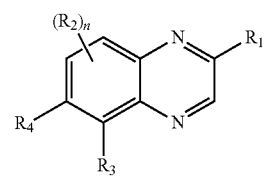
(I)

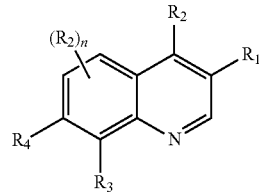
(II)

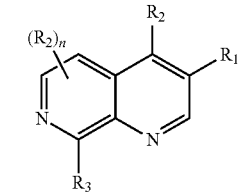
(III)

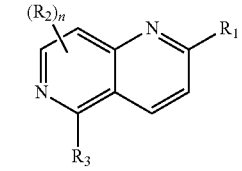
(IV)

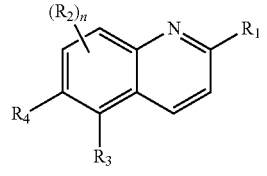
(V)

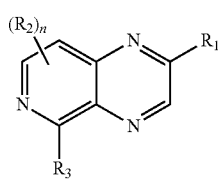
(VI)

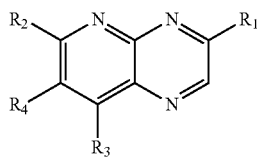
(VII)

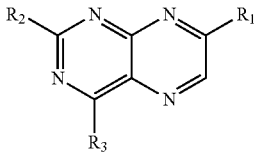
(VIII)

or a stereoisomer, tautomer, pharmaceutically acceptable salt, solvate or prodrug thereof, wherein $R_1$ is F, Cl, —OH, $C_{1-4}$ alkyl, $C_{1-4}$ fluoroalkyl, $C_{2-4}$ alkenyl, $C_{2-4}$ alkynyl, $C_{3-7}$ cycloalkyl, $C_{3-7}$ fluorocycloalkyl, $C_{1-4}$ alkoxy, $C_{1-4}$ fluoroalkoxy, $C_{2-4}$ hydroxyalkoxy, $C_{3-6}$ cycloalkoxy, ($C_{1-3}$ alkoxy)-($C_{1-3}$ alkylene), ($C_{1-3}$ alkoxy)-($C_{1-3}$ fluoroalkylene), ($C_{1-3}$ deuteroalkoxy)-($C_{1-3}$ deuteroalkylene), ($C_{1-3}$ fluoroalkoxy)-($C_{1-3}$ alkylene), ($C_{1-3}$ fluoroalkoxy)-($C_{1-3}$ fluoroalkylene), —(CH$_2$)$_{1-3}$O(phenyl), —(CH$_2$)$_{1-3}$NR$_a$R$_a$, —C(O)O($C_{1-6}$ alkyl), —C(O)NR$_a$R$_a$, —C(O)NR$_b$R$_b$, —NH$_2$, —NH($C_{1-6}$ alkyl), —N($C_{1-6}$ alkyl)$_2$, azetidinyl, pyrrolidinyl, furanyl, pyranyl, piperidinyl, morpholinyl, piperazinyl, —S(O)$_2$($C_{1-3}$ alkyl), —S(O)$_2$NR$_a$R$_a$, $C_{1-3}$ alkylthio, or $C_{1-3}$ fluoroalkylthio;

$R_2$, at each occurrence, is independently H, F, Cl, Br, —OH, —CN, $C_{1-4}$ alkyl, $C_{1-4}$ fluoroalkyl, $C_{1-4}$ hydroxyalkyl, $C_{1-3}$ aminoalkyl, $C_{2-4}$ alkenyl, $C_{2-4}$ alkynyl, $C_{3-7}$ cycloalkyl, $C_{3-7}$ fluorocycloalkyl, $C_{1-6}$ alkoxy, $C_{1-3}$ fluoroalkoxy, $C_{1-3}$ alkylthio, $C_{1-3}$ fluoroalkylthio, ($C_{1-3}$ alkoxy)-($C_{1-3}$ alkylene), ($C_{1-3}$ fluoroalkoxy)-($C_{1-3}$ alkylene), —C(O)NH$_2$, —C(O)NH($C_{1-6}$ alkyl), —C(O)N($C_{1-6}$ alkyl)$_2$, —C(O)NR$_b$R$_b$, —CH(OH)($C_{3-6}$ cycloalkyl), —CH(OH)(phenyl), CH(OH)(pyridyl), —S(O)$_2$($C_{1-3}$ alkyl), —S(O)$_2$NR$_a$R$_a$, or a cyclic group selected from phenyl, 5- to 6-membered heteroaryl, and 5- to 7-membered heterocycle, wherein said cyclic group is substituted with zero to 5 substituents independently selected from F, Cl, hydroxy, $C_{1-3}$ alkyl, $C_{1-3}$ alkoxy, cyclopropyl, and —CN; $R_3$ is:

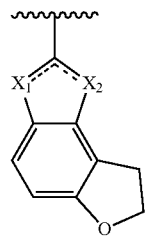 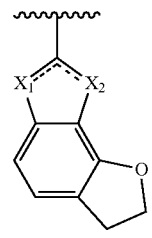 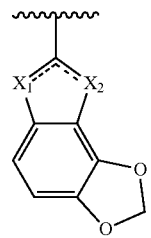

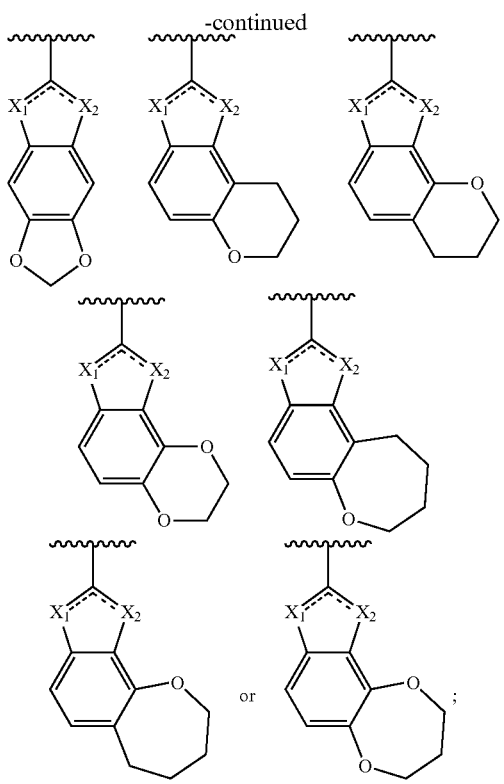

(i) $X_1$ is N and $X_2$ is S, O, or NH;
(ii) $X_1$ is O and $X_2$ is CH or N;
(iii) $X_1$ is NH and $X_2$ is CH; or
(iv) $X_1$ is CH and $X_2$ is S or NH;
and the dashed lines represent the variable position of a double bond to maintain aromaticity, each $R_3$ is substituted with $R_{3a}$ and zero to 3 $R_{3b}$;

$R_{3a}$ is
(i) H, $C_{1-6}$ hydroxyalkyl, $C_{1-6}$ hydroxyfluoroalkyl, —C(O)O($C_{1-6}$ alkyl), —$CR_aR_a$NHC(O)($C_{1-6}$ alkyl), —$CR_aR_a$NHC(O)($C_{1-6}$ fluoroalkyl), —$CR_aR_a$NHC(O)O($C_{1-6}$ alkyl), —$CR_aR_a$NHC(O)O($CH_2$)$_{1-3}$($C_{1-3}$ alkoxy), —$CR_aR_a$NHC(O)O($C_{1-4}$ fluoroalkyl), —$CR_aR_aN_aS(O)_2(C_{1-3}$ alkyl), $CR_aR_aN_aS(O)_2(C_{1-3}$ fluoroalkyl), —$CR_aR_a$OP(O)(OH)$_2$, —$CR_aR_a$NHC(O)Rx, —$CR_aR_a$NHC(O)O$R_x$, —$CR_aR_a$NHC(O)$CH_2R_x$, —$CR_aR_a$NHC(O)O$CH_2R_x$, —$CR_aR_a$OC(O)NH$R_x$, —$CR_aR_a$NHC(O)NH$R_x$, —$CR_aR_a$O$R_x$, or —$CR_aR_a$OC(O)$R_x$;
(ii) —CH(OH)$CR_hR_iR_j$ wherein $R_h$ and $R_i$ are independently H, F, $C_{1-4}$ alkyl, $C_{1-4}$ fluoroalkyl, $C_{1-3}$ alkoxy, or $C_{1-3}$ fluoroalkoxy, or taken together with the carbon atom to which they are attached, form $C_{3-8}$ cycloalkyl or 4- to 7-membered heterocyclyl ring; and $R_j$ is H, $C_{1-6}$ alkyl, $C_{1-5}$ fluoroalkyl, ($C_{1-3}$ alkoxy)-($C_{1-3}$ alkyl), $C_{3-8}$ cycloalkyl, $C_{3-8}$ heterocyclyl, aryl, or heteroaryl;

$R_x$ is $C_{3-6}$ cycloalkyl, phenyl, pyridinyl, pyridazinyl, pyrimidinyl, pyrazinyl, benzo[d]oxazolyl, benzo[d]thiazolyl, pyrrolopyridinyl, tetrahydroisoquinolinyl, tetrahydrofuranyl, tetrahydropyranyl, morpholinyl, imidazopyridinyl, or oxo-dihydrobenzo[d]oxazolyl, each substituted with zero to two substituents independently selected from F, Cl, Br, —CN, —OH, —$CH_3$, —$CF_3$, $C_{1-3}$ alkoxy, $C_{1-3}$fluoroalkyl, $C_{1-6}$ hydroxyalkyl, $C_{1-6}$ hydroxyalkoxy, $C_{1-6}$ hydroxy-fluoroalkoxy, phenoxy, —$NR_aR_a$, —C(O)$NR_aR_a$, —C(O)NH($C_{1-6}$ alkyl), —C(O)N($C_{1-6}$ alkyl)$_2$, —C(O)$NR_bR_b$, —C(O)$NR_a$($C_{1-6}$ hydroxyalkyl), —C(O)O($C_{1-6}$ alkyl), —C(O)O$C_{1-4}$alkyl, —C(O)(morpholinyl), —S(O)$_2NR_aR_a$, —CH(OH)$CH_2OH$, —CH=$CH_2$, —NHC(O)$CH_3$, —$OCH_2CH_2N(CH_3)_2$, —$OCH_2CH_2OH$, —$OCH_2CH$(Me)OH, isoxazolyl, phenoxy, phenyl, pyrrolidinyl, thiophenyl, and methyl triazolyl;

$R_{3b}$, at each occurrence, is independently H, F, Cl, Br, —CN, $C_{1-3}$ alkyl, $C_{1-3}$ fluoroalkyl, $C_{1-3}$ hydroxyalkyl, —$OCHF_2$, $C_{3-6}$ cycloalkyl, $C_{3-6}$ fluorocycloalkyl, $C_{2-4}$ alkenyl, $C_{2-4}$ alkynyl, $C_{1-3}$ alkoxy, $C_{1-3}$ alkylthio, or $C_{1-3}$ fluoroalkoxy;

$R_4$ is H, F, Cl, or —$CH_3$;

$R_a$, at each occurrence, is independently H, $C_{1-4}$alkyl, or $C_{1-4}$fluoroalkyl; two $R_b$ along with the nitrogen atom to which they are attached form a 4- to 7-membered heterocyclo ring having 1 to 2 nitrogen atoms and 0-1 oxygen or sulfur atoms; and n is zero, 1, or 2.

One embodiment provides a compound of Formula (I) to (VIII) or a salt thereof, wherein $X_1$ is N and $X_2$ is S, O, or NH; $R_3$ is substituted with $R_{3a}$ and zero to 3 $R_{3b}$; and $R_1$, $R_2$, $R_3$, $R_{3a}$, $R_{3b}$, $R_4$, and n are defined in the first aspect. Included in this embodiment are compounds in which $R_3$ is:

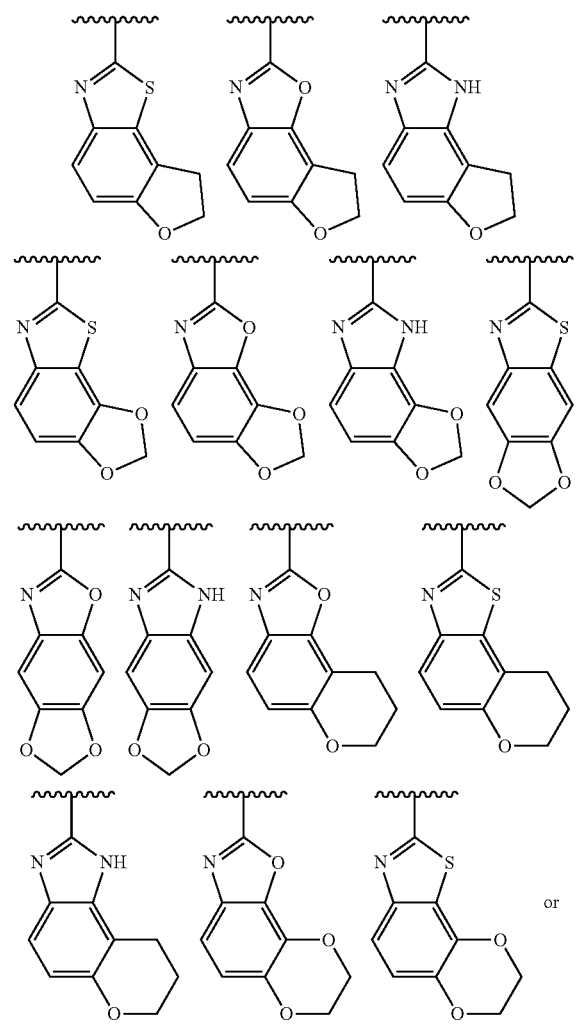

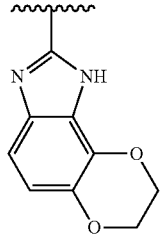

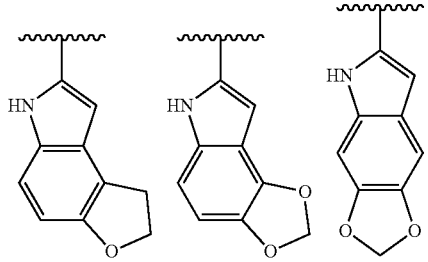

One embodiment provides a compound of Formula (I) to (VIII) or a salt thereof, wherein $X_1$ is O and $X_2$ is CH or N; $R_3$ is substituted with $R_{3a}$ and zero to 3 $R_{3b}$; and $R_1$, $R_2$, $R_3$, $R_{3a}$, $R_{3b}$, $R_4$, and n are defined in the first aspect. Included in this embodiment are compounds in which $R_3$ is:

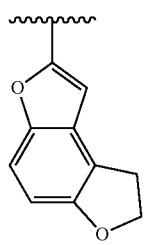 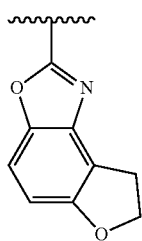 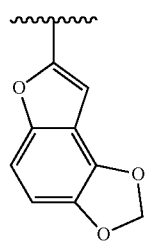

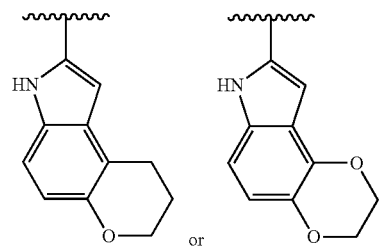

One embodiment provides a compound of Formula (I) to (VIII) or a salt thereof, wherein $X_1$ is CH and $X_2$ is S; and $R_3$ is substituted with $R_{3a}$ and zero to 3 $R_{3b}$; and $R_1$, $R_2$, $R_3$, $R_{3a}$, $R_{3b}$, $R_4$, and n are defined in the first aspect. Included in this embodiment are compounds in which $R_3$ is:

 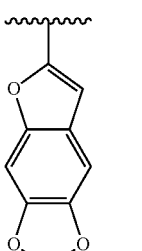

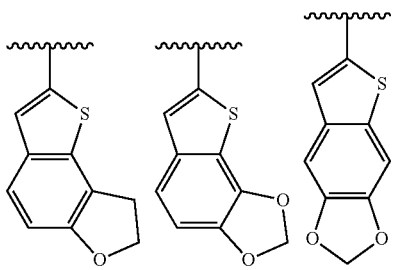

One embodiment provides a compound of Formula (I) to (VIII) or a salt thereof, wherein $X_1$ is NH and $X_2$ is CH; $R_3$ is substituted with $R_{3a}$ and zero to 3 $R_{3b}$; and $R_1$, $R_2$, $R_3$, $R_{3a}$, $R_{3b}$, $R_4$, and n are defined in the first aspect. Included in this embodiment are compounds in which $R_3$ is

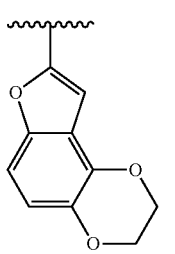 or 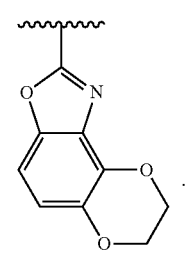.

One embodiment provides a compound of Formula (I) to (VIII) or a salt thereof, wherein $X_1$ is N and $X_2$ is S; or $X_1$ is O and $X_2$ is CH; and $R_3$ is substituted with $R_{3a}$ and zero to 3 $R_{3b}$; and $R_1$, $R_2$, $R_3$, $R_{3a}$, $R_{3b}$, $R_4$, and n are defined in the first aspect. Included in this embodiment are compounds in which $R_3$ is:

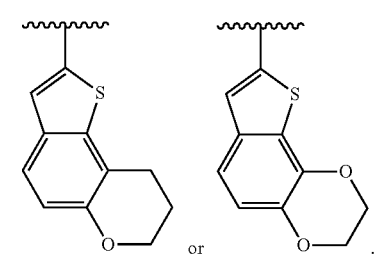

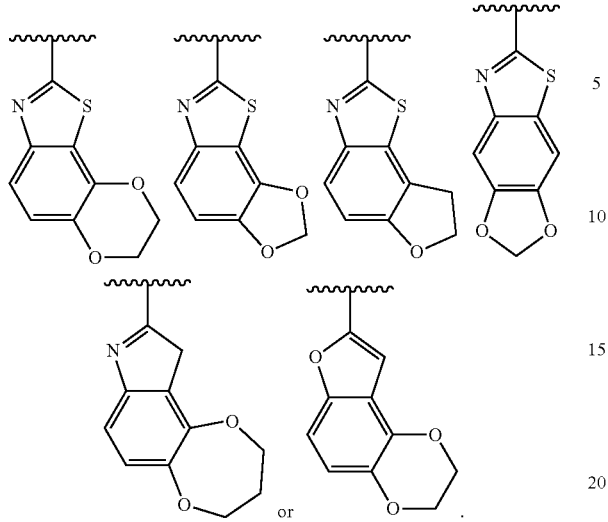

One embodiment provides a compound of Formula (I):

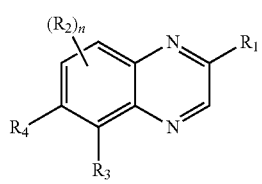

or a salt thereof, wherein
R₃ is

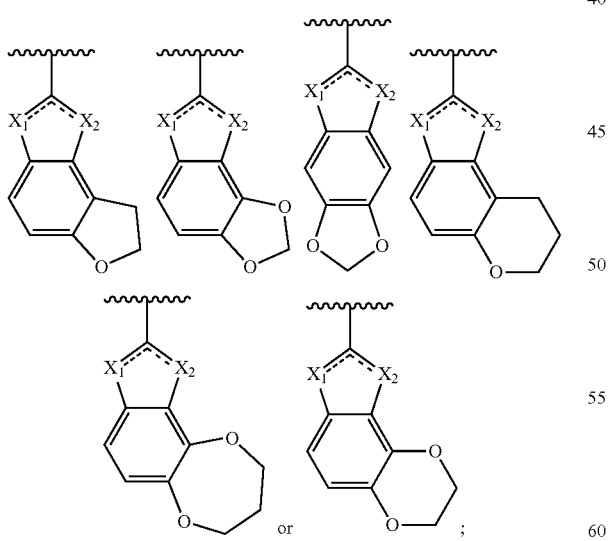

(i) $X_1$ is N and $X_2$ is S or O; or (ii) $X_1$ is O and $X_2$ is CH; and the dashed lines represent the variable position of a double bond to maintain aromaticity; each $R_3$ is substituted with $R_{3a}$ and zero to 3 $R_{3b}$; and $R_1$, $R_2$, $R_{3a}$, $R_{3b}$, $R_4$, and n are defined in the first aspect.

One embodiment provides a compound having the structure of Formula (Ia):

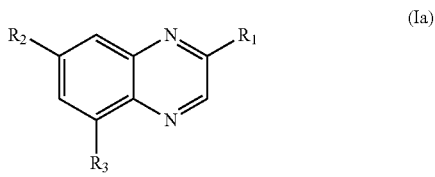

or a salt thereof, wherein: $R_1$ is —CH₃, —OCH₃, or —OCHF₂; $R_2$ is $C_1$, —CN, —CH₃, —CH₂₀H, —CH(CH₃)OH, or —CH=CH₂; $R_3$ is:

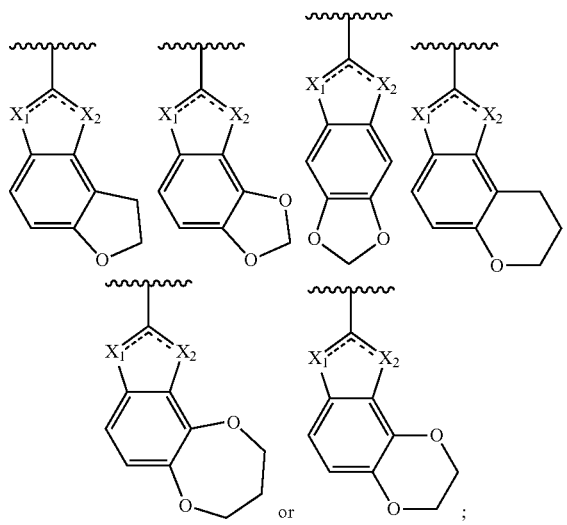

(i) $X_1$ is N and $X_2$ is S, O, or NH; (ii) $X_1$ is O and $X_2$ is CH or N; (iii) $X_1$ is NH and $X_2$ is CH; or (iv) $X_1$ is CH and $X_2$ is S; and the dashed lines represent the variable position of a double bond to maintain aromaticity; each $R_3$ is substituted with $R_{3a}$ and zero to 3 $R_{3b}$; $R_{3a}$ is H, —CH₂₀H, —CH(CH₃)OH, —CH₂CH(CH₃)OH, —CH(OH)C(CH₃)₃, —CH(OH)(trifluoromethyl cyclopropyl), —CH(OH)(trifluoromethyl cyclobutyl), —CH(OH)(methyl cyclohexyl), —CH₂NHC(O)CH₃, —CH₂NHC(O)CF₃, —CH₂NHC(O)CH₂(phenyl), —CH₂NHC(O)(morpholinyl), —CH₂NHC(O)OCH₃, —CH₂NHC(O)NH(cyclopropyl), —CH₂NHC(O)NH(phenyl), —CH₂NHC(O)OCH₃, —CH₂NHC(O)OCH₂CH₃, —CH₂NHC(O)OC(CH₃)₃, —CH₂NHC(O)OCH₂CH(CH₃)₂, —CH₂NHC(O)OCH₂C(CH₃)₃, —CH₂NHC(O)OCH₂CH₂F, —CH₂NHC(O)OCH₂CF₃, —CH₂NHC(O)OCH₂CH₂OCH₃, —CH₂NHS(O)₂CH₃, —CH₂O(methyl pyrimidinyl), —CH₂OC(O)(dimethylaminopyridinyl), —CH₂OP(O)(OH)₂, —C(O)OCH₃, —CH₂NHC(O)OR$_x$, —CH₂NHC(O)OCH₂R$_x$, or —CH₂OC(O)NHR$_x$; R$_x$ is phenyl, pyridinyl, pyridazinyl, pyrimidinyl, benzo[d]oxazolyl, benzo[d]thiazolyl, oxoisoindolinyl, pyrrolopyridinyl, tetrahydroisoquinolinyl, tetrahydrofuranyl, tetrahydropyranyl, imidazopyridinyl, or oxo-dihydrobenzo[d]oxazolyl, each substituted with zero to two substituents independently selected from F, Cl, Br, —CN, —OH, —CH₃, —CF₃, —CH₂CH₂₀H, $C_{1-2}$ alkoxy, phenoxy, —NR$_a$R$_a$, —C(O)NR$_a$R$_a$, —C(O)

OCH$_3$, —C(O)OC(CH$_3$)$_3$, —C(O)(morpholinyl), —CH(OH)CH$_2$$_0$H, —OCH$_2$CH$_2$$_0$H, —OCH$_2$CF$_2$$_0$H, —OCH$_2$CH(CH$_3$)OH, —CH═CH$_2$, —NHC(O)CH$_3$, —OCH$_2$CH$_2$N(CH$_3$)$_2$, isoxazolyl, phenoxy, phenyl, pyrrolidinyl, thiophenyl, and methyl triazolyl; and R$_a$, at each occurrence, is independently H or —CH$_3$.

One embodiment provides a compound having the structure of Formula (Ia) or a salt thereof, wherein said compound is selected from:

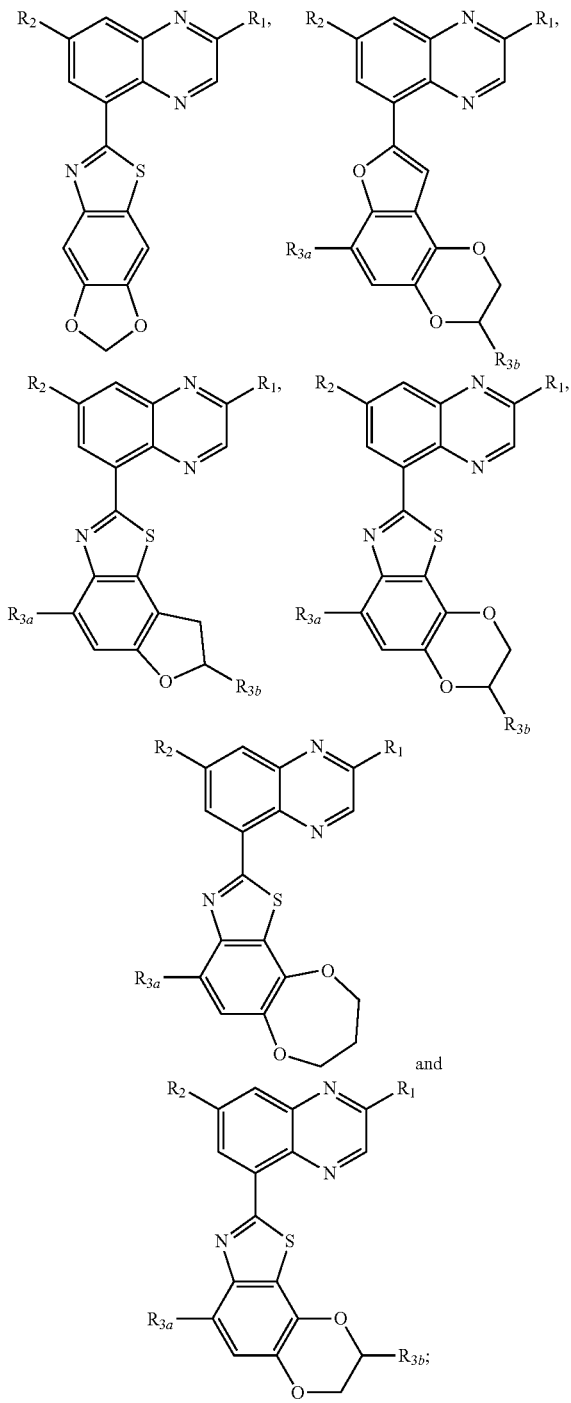

and R$_1$, R$_2$, R$_{3a}$, and R$_{3b}$ are defined in the first aspect.

One embodiment provides a compound having the structure of Formula (Ia) or a salt thereof, wherein: R$_1$ is C$_{1-3}$ alkyl or C$_{1-3}$ alkoxy; R$_2$ is C$_{1-2}$ alkyl or C$_{1-2}$ hydroxyalkyl; R$_3$ is:

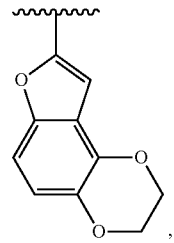

wherein R$_3$ is substituted with R$_{3a}$ and zero to 3 R$_{3b}$; R$_{3a}$ is C$_{1-3}$ hydroxyalkyl, or —CH$_2$OC(O)NHR$_x$; R$_x$ is phenyl, pyridinyl, or pyrimidinyl, each substituted with zero to 2 substituents independently selected from F, Cl, —CN, C$_{1-2}$ alkyl, or C$_{1-2}$ alkoxy; and each R$_{3b}$ is independently C$_1$, —CN, —CH$_3$, —OCH$_3$, or —OCHF$_2$. Included in this embodiment are compounds in which R$_1$ is —OCH$_3$; R$_2$ is —CH$_3$; R$_{3a}$ is —CH$_2$$_0$H or —CH$_2$OC(O)NHR$_x$; R$_x$ is pyridinyl substituted with zero to 1 substituent selected from —CH$_3$ or —OCH$_3$; and R$_{3b}$ is C$_1$ or —CH$_3$.

One embodiment provides a compound having the structure of Formula (Ia) or a salt thereof, wherein: R$_1$ is C$_{1-3}$ alkyl or C$_{1-3}$ alkoxy; R$_2$ is C$_{1-2}$ alkyl or C$_{1-2}$ hydroxyalkyl; R$_3$ is:

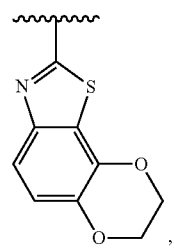

wherein R$_3$ is substituted with R$_{3a}$ and zero to 2 R$_{3b}$; R$_1$ is C$_{1-3}$ alkyl, C$_{1-2}$ fluoroalkyl, or C$_{1-3}$ alkoxy; R$_2$ is H, F, Cl, —CN, C$_{1-3}$ alkyl, C$_{1-4}$ hydroxyalkyl, or —CH═CH$_2$; R$_{3a}$ is H, C$_{1-6}$ hydroxyalkyl, —CH(OH)CHR$_i$(C$_{3-6}$ cycloalkyl), —CH$_2$NHC(O)O(C$_{1-4}$ alkyl), —CH$_2$OR$_x$, —CH$_2$OC(O)R$_x$, or —CH$_2$OC(O)NHR$_x$; R$_1$ is —CH$_3$ or —CF$_3$; R$_x$ is benzo[d]oxazolyl, imidazopyridinyl, oxodihydrobenzo[d]oxazolyl, phenyl, pyridazinyl, pyridinyl, pyrimidinyl, pyrrolopyridinyl, or tetrahydroisoquinolinyl, each substituted with zero to 2 substituents independently selected from F, Cl, Br, —CN, —OH, —CH$_3$, —CF$_3$, —CH(OH)CH$_2$$_0$H, —CH═CH$_2$, —O(C$_{1-3}$ alkyl), —OCH$_2$CH$_2$NR$_a$R$_a$, —C(O)O(C$_{1-4}$ alkyl), —C(O)NR$_a$R$_a$, —C(O)(morpholinyl), —NR$_a$R$_a$, —NHC(O)(C$_{1-3}$ alkyl), methyltriazolyl, thiophenyl, pyrrolidinyl, phenyl, and phenoxy; each R$_{3b}$ is independently F, Cl, —CH$_3$, or —CHF$_2$; and each R$_a$ is independently H or —CH$_3$. Included in this embodiment are compounds in which R$_1$ is —CH$_3$, —OCH$_3$, or —OCHF$_2$; R$_2$ is C$_1$, —CN, —CH$_3$, —CH$_2$$_0$H, —CH(CH$_3$)OH, or —CH═CH$_2$; R$_{3a}$ is H, —CH$_2$$_0$H, —CH(OH)C(CH$_3$)$_3$, —CH(OH)CH(cyclopropyl)(CF$_3$), —CH(OH)CH(cyclobutyl)(CF$_3$), —CH(OH)CH(cyclohexyl)(CH$_3$), —CH$_2$NHC(O)OC(CH$_3$)$_3$, —CH$_2$O(methyl pyrimidinyl), —CH$_2$OC(O)(dimethylamino pyridinyl), or —CH$_2$OC(O)NHR$_x$; R$_x$ is benzo[d]oxazolyl, imidazopyridinyl, oxodihydrobenzo[d]oxazolyl, phenyl, pyridazinyl, pyridinyl, pyrimidinyl, pyrrolopyridinyl, or tetrahydroisoquinolinyl, each substituted with zero to 2 substituents independently selected from F, Cl, Br, —CN, —OH, —CH$_3$, —CF$_3$, —CH(OH)CH$_{20}$H, —CH═CH$_2$, —OCH$_3$, —OCH$_2$CH$_3$, OCH$_2$CH$_2$N(CH$_3$)$_2$, —C(O)OCH$_3$, —C(O)OC(CH$_3$)$_3$, —C(O)NH$_2$, —C(O)(morpholinyl), —NH$_2$, —N(CH$_3$)$_2$, —NHC(O)CH$_3$, methyltriazolyl, thiophenyl, pyrrolidinyl, phenyl, and phenoxy; and each R$_{3b}$ is independently F, Cl, —CH$_3$, or —CHF$_2$.

One embodiment provides a compound having the structure of Formula (Ia) or a salt thereof, wherein: R$_1$ is C$_{1-3}$ alkyl or C$_{1-3}$ alkoxy; R$_2$ is C$_1$, —CN, C$_{1-2}$ alkyl or C$_{1-2}$ hydroxyalkyl; R$_3$ is:

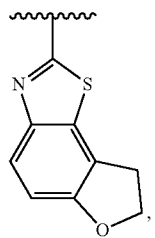

wherein R$_3$ is substituted with R$_{3a}$ and zero to 3 R$_{3b}$; R$_{3a}$ is H, C$_{1-3}$ hydroxyalkyl, —C(O)O(C$_{1-3}$ alkyl), —CH$_2$NHC(O) (C$_{1-3}$ alkyl), —CH$_2$NHC(O)(C$_{1-2}$ fluoroalkyl), —CH$_2$NHC (O)O(C$_{1-5}$ alkyl), —CH$_2$NHC(O)O(C$_{1-3}$ fluoroalkyl), —CH$_2$NHC(O)OCH$_2$CH$_2$OCH$_3$, —CH$_2$NHC(O)R$_x$, —CH$_2$NHC(O)CH$_2$R$_x$, —CH$_2$NHC(O)NHR$_x$, —CH$_2$NHC (O)OR$_x$, —CH$_2$NHC(O)OCH$_2$R$_x$, —CH$_2$OP(O)(OH)$_2$, —CH$_2$NHS(O)$_2$(C$_{1-3}$ alkyl), or —CH$_2$OC(O)NHR$_x$; R$_x$ is C$_{3-6}$ cycloalkyl, morpholinyl, oxoisoindolinyl, phenyl, pyrdinyl, pyrimidinyl, pyridazinyl, tetrahydrofuranyl, tetrahydropyranyl, each substituted with zero to 2 substituents independently selected from F, Cl, —CN, C$_{1-3}$ alkyl, C$_{1-3}$ hydroxyalkyl, C$_{1-3}$ alkoxy, —OCH$_2$CH$_{20}$H, —OCH$_2$CF$_{20}$H, —C(O)NR$_a$R$_a$, —C(O)(morpholinyl), or isoxazolyl; each R$_{3b}$ is independently F or —CH$_3$; and each R$_a$ is independently H or —CH$_3$. Included in this embodiment are compounds in which R$_1$ is —OCH$_3$ or —OCH$_2$CH$_3$; R$_2$ is C$_1$, —CN, —CH$_3$, or —CH$_{20}$H; R$_{3a}$ is H, —CH$_{20}$H, —CH(CH$_3$)OH, —CH$_2$CH(CH$_3$)OH, —C(O) OCH$_3$, —CH$_2$NHC(O)CH$_3$, —CH$_2$NHC(O)CF$_3$, —CH$_2$NHC(O)(morpholinyl), —CH$_2$NHC(O)CH$_2$(phenyl), —CH$_2$NHC(O)NH(cyclopropyl), —CH$_2$NHC(O)NH (phenyl), —CH$_2$NHC(O)O(C$_{1-5}$ alkyl), —CH$_2$NHC(O) OCH$_2$CH$_2$F, —CH$_2$NHC(O)OCH$_2$CF$_3$, —CH$_2$NHC(O) OCH$_2$CH$_2$OCH$_3$, —CH$_2$NHC(O)OR$_x$, —CH$_2$NHC(O) OCH$_2$R$_x$, —CH$_2$OP(O)(OH)$_2$, —CH$_2$NHS(O)$_2$CH$_3$, or —CH$_2$OC(O)NHR$_x$; R$_x$ is oxoisoindolinyl, phenyl, pyrdinyl, pyrimidinyl, pyridazinyl, tetrahydrofuranyl, tetrahydropyranyl, each substituted with zero to 2 substituents independently selected from F, Cl, —CN, —CH$_3$, —CH$_2$CH$_{20}$H, —OCH$_3$, —OCH$_2$CH$_{20}$H, —OCH$_2$CF$_{20}$H, —C(O)NR$_a$R$_a$, —C(O)(morpholinyl), or isoxazolyl; each R$_{3b}$ is independently F or —CH$_3$; and each R$_a$ is independently H or —CH$_3$.

One embodiment provides a compound having the structure of Formula (IIa)

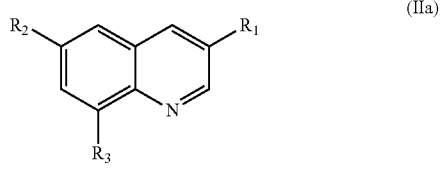

or a salt thereof, wherein: R$_1$ is —CH$_3$, —OCH$_3$, —OCH$_2$CH$_3$, or —OCHF$_2$; R$_2$ is F, Cl, —CH$_3$, —CH$_2$F, or —CHF$_2$; R$_3$ is:

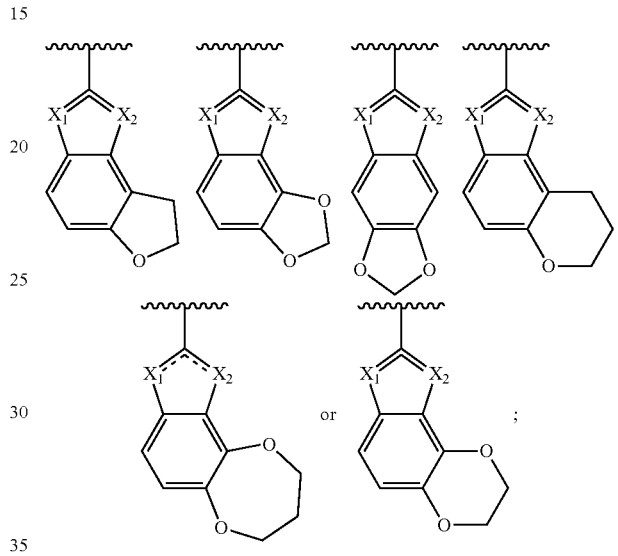

(i) X$_1$ is N and X$_2$ is S, O, or NH; (ii) X$_1$ is O and X$_2$ is CH or N; (iii) X$_1$ is NH and X$_2$ is CH; or (iv) X$_1$ is CH and X$_2$ is S; and the dashed lines represent the variable position of a double bond to maintain aromaticity; each R$_3$ is substituted with R$_{3a}$ and zero to 2 R$_{3b}$; R$_{3a}$ is H, —CH$_{20}$H, —CH(CH$_3$)OH, —CH$_2$CH(CH$_3$)OH, —CH (OH)C(CH$_3$)$_3$, —CH(OH)(trifluoromethyl cyclopropyl), —CH(OH)(trifluoromethyl cyclobutyl), —CH (OH)(methyl cyclohexyl), —CH$_2$NHC(O)CH$_3$, —CH$_2$NHC(O)CF$_3$, —CH$_2$NHC(O)CH$_2$(phenyl), —CH$_2$NHC(O)(morpholinyl), —CH$_2$NHC(O)OCH$_3$, —CH$_2$NHC(O)NH(cyclopropyl), —CH$_2$NHC(O)NH (phenyl), —CH$_2$NHC(O)OCH$_3$, —CH$_2$NHC(O) OCH$_2$CH$_3$, —CH$_2$NHC(O)OC(CH$_3$)$_3$, —CH$_2$NHC(O) OCH$_2$CH(CH$_3$)$_2$, —CH$_2$NHC(O)OCH$_2$C(CH$_3$)$_3$, —CH$_2$NHC(O)OCH$_2$CH$_2$F, —CH$_2$NHC(O) OCH$_2$CF$_3$, —CH$_2$NHC(O)OCH$_2$CH$_2$OCH$_3$, —CH$_2$NHS(O)$_2$CH$_3$, —CH$_2$O(methyl pyrimidinyl), —CH$_2$OC(O)(dimethylaminopyridinyl), —CH$_2$OP(O) (OH)$_2$, —C(O)OCH$_3$, —CH$_2$NHC(O)OR$_x$, —CH$_2$NHC(O)OCH$_2$R$_x$, or —CH$_2$OC(O)NHR$_x$; R$_x$ is phenyl, pyridinyl, pyridazinyl, pyrimidinyl, benzo[d] oxazolyl, benzo[d]thiazolyl, oxoisoindolinyl, pyrrolopyridinyl, tetrahydroisoquinolinyl, tetrahydrofuranyl, tetrahydropyranyl, imidazopyridinyl, or oxo-dihydrobenzo[d]oxazolyl, each substituted with zero to two substituents independently selected from F, Cl, Br, —CN, —OH, —CH$_3$, —CF$_3$, —CH$_2$CH$_{20}$H, C$_{1-2}$ alkoxy, phenoxy, —NR$_a$R$_a$, —C(O)NR$_a$R$_a$, —C(O) OCH$_3$, —C(O)OC(CH$_3$)$_3$, —C(O)(morpholinyl), —CH(OH)CH$_{20}$H, —OCH$_2$CH$_{20}$H, —OCH$_2$CF$_{20}$H, —OCH$_2$CH(CH$_3$)OH, —CH═CH$_2$, —NHC(O)CH$_3$, —OCH₂CH₂N(CH₃)₂, isoxazolyl, phenoxy, phenyl, pyrrolidinyl, thiophenyl, and methyl triazolyl; R₃ᵦ is F, —CH₃, or —CH(OH)C(CH₃)₃; and Rₐ, at each occurrence, is independently H or —CH₃.

One embodiment provides a compound having the structure of Formula (IIa), wherein said compound is selected from:

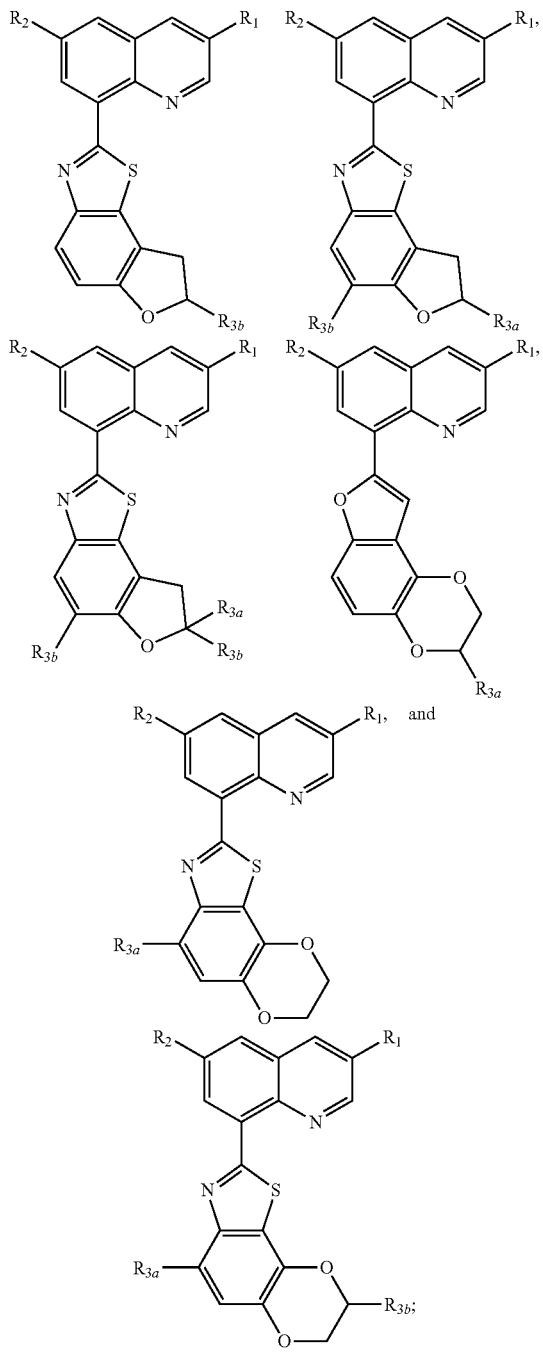

and R₁, R₂, R₃ₐ, and R₃ᵦ are defined in the first aspect.

One embodiment provides a compound having the structure of Formula (IIa) or a salt thereof, wherein: R₁ is C₁₋₃ alkoxy or C₁₋₃ fluoroalkoxy; R₂ is F, Cl, —CN, C₁₋₃ alkyl, or C₁₋₃ fluoroalkyl; R₃ is:

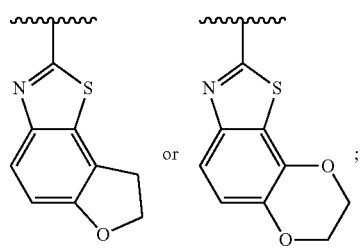 [SMILES: *c1nc2ccc3c(c2s1)CCO3 ; *c1nc2ccc3c(c2s1)OCCO3]

each R₃ is substituted with R₃ₐ and zero to 2 R₃ᵦ; R₃ₐ is C₁₋₆ hydroxyalkyl or —CH₂OC(O)NHRₓ; Rₓ is phenyl, pyridinyl, or pyrimidinyl, each substituted with zero or 1 substituent selected from C₁₋₃ alkyl, —C(O)NRₐRₐ, and C₁₋₄ alkoxy; each R₃ᵦ is independently H, F, Cl, —CH₃, or —CF₃; and each Rₐ is independently H or —CH₃. Included in this embodiment are compounds in which R₁ is —OCH₃, OCH₂CH₃, or —OCHF₂; R₂ is F, C₁, —CH₃, —CH₂F, or —CHF₂; each R₃ is substituted with R₃ₐ and zero to 2 R₃ᵦ; R₃ₐ is —CH₂₀H, —CH(OH)C(CH₃)₃, or —CH₂OC(O)NHRₓ; Rₓ is phenyl, pyridinyl, or pyrimidinyl, each substituted with zero or 1 substituent selected from —CH₃, —C(O)NH₂, —OCH₂CH₂₀H, and —OCH₂CH(CH₃)OH; and each R₃ᵦ is independently F or —CH₃.

One embodiment provides a compound having the structure of Formula (Ia), wherein: R₁ is —CH₃, —OCH₃, or —OCHF₂; R₂ is C₁, —CN, —CH₃, —CH₂₀H, —CH(CH₃)OH, or —CH=CH₂; R₃ is:

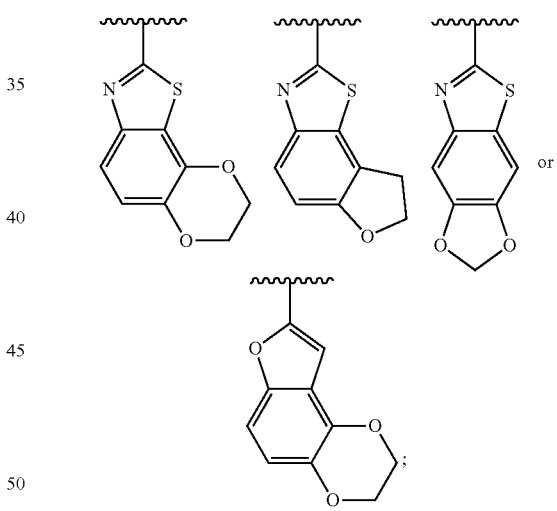

each R₃ is substituted with R₃ₐ and zero to 2 R₃ᵦ; R₃ₐ is H, C₁₋₆ hydroxyalkyl, —C(O)O(C₁₋₆ alkyl), —CRₐRₐNHC(O)(C₁₋₆ alkyl), —CRₐRₐNHC(O)(C₁₋₆ fluoroalkyl), —CRₐRₐNHC(O)O(C₁₋₆ alkyl), —CRₐRₐNHC(O)O(CH₂)i 3(C₁₋₃ alkoxy), —CRₐRₐNHC(O)O(C₁₋₄ fluoroalkyl), —CRₐRₐNₐS(O)₂(C₁₋₃ alkyl), —CRₐRₐOP(O)(OH)₂, —CRₐRₐNHC(O)Rₓ, —CRₐRₐNHC(O)ORₓ, —CRₐRₐNHC(O)CH₂Rₓ, —CRₐRₐNHC(O)OCH₂Rₓ, —CRₐRₐOC(O)NHRₓ, —CRₐRₐNHC(O)NHRₓ, —CRₐRₐORₓ, or —CRₐRₐOC(O)Rₓ; Rₓ is C₃₋₆ cycloalkyl, phenyl, pyridinyl, pyridazinyl, pyrimidinyl, pyrazinyl, benzo[d]oxazolyl, benzo[d]thiazolyl, pyrrolopyridinyl, tetrahydroisoquinolinyl, tetrahydrofuranyl, tetrahydropyranyl, morpholinyl, imidazopyridinyl, or oxodihydrobenzo[d]oxazolyl, each substituted with zero to two substituents independently selected from F, Cl, Br, —CN, —OH, —CH₃, —CF₃, C₁₋₃ alkoxy, C₁₋₃fluoroalkyl, C₁₋₆ hydroxyalkyl, C₁₋₆ hydroxyalkoxy, C₁₋₆ hydroxy-fluoro-alkoxy, phenoxy, —NR$_a$R$_a$, —C(O)NR$_a$R$_a$, —C(O)NH (C₁₋₆ alkyl), —C(O)N(C₁₋₆ alkyl)₂, —C(O)NR$_b$R$_b$, —C(O) NR$_a$(C₁₋₆hydroxyalkyl), —C(O)O(C₁₋₆ alkyl), —C(O) OC₁₋₄ alkyl, —C(O)(morpholinyl), —CH(OH)CH$_{20}$H, —CH═CH₂, —NHC(O)CH₃, —OCH₂CH₂N(CH₃)₂, —OCH₂CH$_{20}$H, —OCH₂CH(Me)OH, isoxazolyl, phenoxy, phenyl, pyrrolidinyl, thiophenyl, and methyl triazolyl; and R$_1$ and R$_2$ are defined in the first aspect.

One embodiment provides a compound of Formula (Ia) or a salt thereof, wherein R$_{3a}$ is —CR$_a$R$_a$OC(O)NHR$_x$ and R$_x$ is phenyl, pyridinyl, pyridazinyl, pyrimidinyl, benzo[d]oxazolyl, benzo[d]thiazolyl, pyrrolopyridinyl, tetrahydroisoquinolinyl, imidazopyridinyl, or oxo-dihydrobenzo[d]oxazolyl, each substituted with zero to two substituents independently selected from F, Cl, Br, —CN, —OH, —CH₃, —CF₃, C₁₋₂ alkoxy, phenoxy, —NR$_a$R$_a$, —C(O)NH₂, —C(O)NH(C₁₋₆ alkyl), —C(O)N(C₁₋₆ alkyl)₂, —C(O)NR$_b$R$_b$, —C(O)OC (CH₃)₃, —C(O)OCH₃, —C(O)(morpholinyl), —CH(OH) CH$_{20}$H, —CH═CH₂, —NHC(O)CH₃, —OCH₂CH₂N (CH₃)₂, —OCH₂CH$_{20}$H, —OCH₂CH(Me)OH, phenyl, pyrrolidinyl, thiophenyl, and methyl triazolyl. Included in this embodiment are compounds in which R$_x$ is phenyl, pyridinyl, pyridazinyl, pyrimidinyl, benzo[d]oxazolyl, benzo[d]thiazolyl, pyrrolopyridinyl, tetrahydroisoquinolinyl, imidazopyridinyl, or oxo-dihydrobenzo[d]oxazolyl, each substituted with zero to two substituents independently selected from F, Cl, Br, —CN, —OH, —CH₃, —CF₃, C₁₋₂ alkoxy, phenoxy, —NR$_a$R$_a$, —C(O)NH₂, —C(O)OC (CH₃)₃, —C(O)OCH₃, —C(O)(morpholinyl), —CH(OH) CH$_{20}$H, —CH═CH₂, —NHC(O)CH₃, —OCH₂CH₂N (CH₃)₂, phenyl, pyrrolidinyl, thiophenyl, and methyl triazolyl. Also included in this embodiment are compounds in which R$_x$ is: (i) pyridazinyl, benzo[d]oxazolyl, benzo[d] thiazolyl, pyrrolopyridinyl, tetrahydroisoquinolinyl, methyl imidazopyridinyl, or oxo-dihydrobenzo[d]oxazolyl; (ii) phenyl substituted with zero to 1 substituent selected from —CN and —C(O)(morpholinyl); (iii) pyridinyl substituted with zero to two substituents independently selected from F, Cl, Br, —CN, —OH, —CH₃, —CF₃, C₁₋₂ alkoxy, phenoxy, —NH₂, —N(CH₃)₂, —C(O)NH₂, —C(O)OC(CH₃)₃, —C(O)OCH₃, —CH(OH)CH$_{20}$H, —CH═CH₂, —NHC(O) CH₃, —OCH₂CH₂N(CH₃)₂, phenyl, pyrrolidinyl, thiophenyl, and methyl triazolyl; or (iv) pyrimidinyl substituted with C₁ or —CH₃; and R₁, R₂, R₃, R$_a$, and R$_b$ are defined in the first aspect.

One embodiment provides a compound of Formula (I) to (VIII) or a salt thereof, wherein R₁ is —OCHF₂ or —OCH₃; and R₂, R₃, R$_{3a}$, R$_{3b}$, R₄, and n are defined in the first aspect. Included in this embodiment are compounds of which R₁ is —OCH₃. Also included are compounds in which R₁ is —OCH₃ and R₂ is —CH₃.

One embodiment provides a compound of Formula (Ia) or a salt thereof, wherein R₁ is —OCHF₂ or —OCH₃; and R₂, R₃, R$_{3a}$, and R$_{3b}$ are defined in the first aspect. Included in this embodiment are compounds of which R₁ is —OCH₃. Also included are compounds in which R₁ is —OCH₃ and R₂ is —CH₃.

One embodiment provides a compound having the structure of Formula (Ia), wherein: R₁ is —CH₃, —OCH₃, or —OCHF₂; R₂ is C₁, —CN, —CH₃, —CH$_{20}$H, —CH(CH₃) OH, or —CH═CH₂; R₃ is:

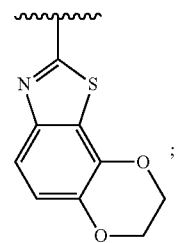 [SMILES: *c1nc2ccc3c(c2s1)OCCO3]

each R₃ is substituted with R$_{3a}$ and zero to 2 R$_{3b}$; R$_{3a}$ is H, —CH$_{20}$H, —CH₂NHC(O)OC(CH₃)₃, —CH₂OC(O)(dimethylaminopyridinyl), or —CH₂OC(O)NHR$_x$; R$_x$ is: (i) pyridazinyl, benzo[d]oxazolyl, benzo[d]thiazolyl, pyrrolopyridinyl, tetrahydroisoquinolinyl, methyl imidazopyridinyl, or oxo-dihydrobenzo[d]oxazolyl; (ii) phenyl substituted with zero to 1 substituent selected from —CN and —C(O) (morpholinyl); (iii) pyridinyl substituted with zero to two substituents independently selected from F, Cl, Br, —CN, —OH, —CH₃, —CF₃, C₁₋₂ alkoxy, phenoxy, —NH₂, —N(CH₃)₂, —C(O)NH₂, —C(O)OC(CH₃)₃, —C(O)OCH₃, —CH(OH)CH$_{20}$H, —CH═CH₂, —NHC(O)CH₃, —OCH₂CH₂N(CH₃)₂, phenyl, pyrrolidinyl, thiophenyl, and methyl triazolyl; or (iv) pyrimidinyl substituted with C₁ or —CH₃; and R$_{3b}$, at each occurrence, is independently H, F, Cl, Br, —CN, C₁₋₃ alkyl, C₁₋₃ fluoroalkyl, —OCHF₂, C₃₋₆ cycloalkyl, C₃₋₆ fluorocycloalkyl, C₂₋₄ alkenyl, C₂₋₄ alkynyl, C₁₋₃ alkoxy, or C₁₋₃ fluoroalkoxy.

One embodiment provides a compound having the structure of Formula (Ia), wherein said compound is selected from:

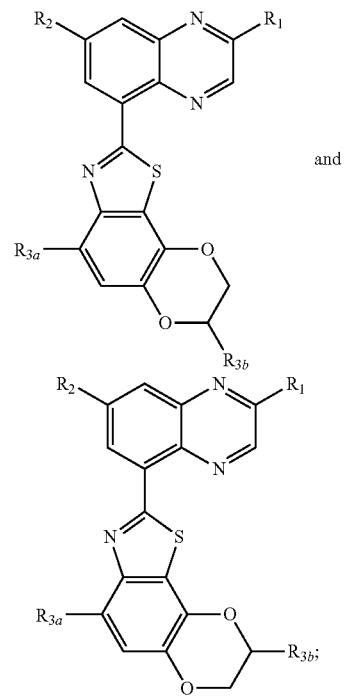

and and R₁, R₂, R$_{3a}$, and R$_{3b}$ are defined in the first aspect. Included in this embodiment are compounds in which R₁ is —CH₃, —OCH₃, or —OCHF₂; R₂ is C₁, —CN, —CH₃, —CH$_{20}$H, —CH(CH₃)OH, or —CH═CH₂; R$_{3a}$ is H, —CH$_{20}$H, —CH₂NHC(O)OC(CH₃)₃, —CH₂OC(O)(dimethylaminopyridinyl), or —CH$_2$OC(O)NHR$_x$; R$_x$ is: (i) pyridazinyl, benzo[d]oxazolyl, benzo[d]thiazolyl, pyrrolopyridinyl, tetrahydroisoquinolinyl, methyl imidazopyridinyl, or oxo-dihydrobenzo[d]oxazolyl; (ii) phenyl substituted with zero to 1 substituent selected from —CN and —C(O) (morpholinyl); (iii) pyridinyl substituted with zero to two substituents independently selected from F, Cl, Br, —CN, —OH, —CH$_3$, —CF$_3$, C$_{1-2}$ alkoxy, phenoxy, —NH$_2$, —N(CH$_3$)$_2$, —C(O)NH$_2$, —C(O)OC(CH$_3$)$_3$, —C(O)OCH$_3$, —CH(OH)CH$_{20}$H, —CH=CH$_2$, —NHC(O)CH$_3$, —OCH$_2$CH$_2$N(CH$_3$)$_2$, phenyl, pyrrolidinyl, thiophenyl, and methyl triazolyl; or (iv) pyrimidinyl substituted with C$_1$ or —CH$_3$; and R$_{3b}$, at each occurrence, is independently H, F, Cl, Br, —CN, C$_{1-3}$ alkyl, C$_{1-3}$ fluoroalkyl, —OCHF$_2$, C$_{3-6}$ cycloalkyl, C$_{3-6}$ fluorocycloalkyl, C$_{2-4}$ alkenyl, C$_{2-4}$ alkynyl, C$_{1-3}$ alkoxy, or C$_{1-3}$ fluoroalkoxy.

One embodiment provides a compound or a salt thereof, selected from (4-chloro-2-(2-methoxy-7-methylquinoxalin-5-yl)-7,8-dihydrobenzofuro[5,4-d]thiazol-7-yl)methyl (6-methoxypyridin-3-yl)carbamate (17);

(4-chloro-2-(2-methoxy-7-methylquinoxalin-5-yl)-7,8-dihydrobenzofuro[5,4-d]thiazol-7-yl)methylpyridin-3-ylcarbamate (18);

(4-chloro-2-(2-methoxy-7-methylquinoxalin-5-yl)-7,8-dihydrobenzofuro[5,4-d]thiazol-7-yl) methyl(6-methylpyridin-3-yl)carbamate (19);

(R)-(4-chloro-2-(2-methoxy-7-methylquinoxalin-5-yl)-7,8-dihydrobenzofuro[5,4-d]thiazo 1-7-yl)methyl(6-methylpyridin-3-yl)carbamate (20);

(R)-(2-(2-methoxy-7-methylquinoxalin-5-yl)-7,8-dihydrobenzofuro[5,4-d]thiazol-7-yl)me thyl (2-methylpyrimidin-5-yl)carbamate (144);

(R)-(5-fluoro-2-(2-methoxy-7-methylquinoxalin-5-yl)-7,8-dihydrobenzofuro[5,4-d]thiazo 1-7-yl)methyl (2-methylpyrimidin-5-yl)carbamate (145);

(S)-(5-fluoro-2-(2-methoxy-7-methylquinoxalin-5-yl)-7,8-dihydrobenzofuro[5,4-d]thiazol-7-yl)methanol (146);

(S)-(4-chloro-2-(2-methoxy-7-methylquinoxalin-5-yl)-7,8-dihydrobenzofuro[5,4-d]thiazo 1-7-yl)methyl(6-methylpyridin-3-yl)carbamate (147);

(4-chloro-2-(7-(hydroxymethyl)-2-methoxyquinoxalin-5-yl)-7,8-dihydrobenzofuro[5,4-d]thiazol-7-yl)methyl(6-methylpyridin-3-yl)carbamate (148);

(S)-(2-(2-methoxy-7-methylquinoxalin-5-yl)-7,8-dihydrobenzofuro[5,4-d]thiazol-7-yl)me thanol (149);

(S)-(2-(2-methoxy-7-methylquinoxalin-5-yl)-7,8-dihydrobenzofuro[5,4-d]thiazol-7-yl)me thyl(2-methylpyrimidin-5-yl)carbamate (150);

(S)-(5-fluoro-2-(2-methoxy-7-methylquinoxalin-5-yl)-7,8-dihydrobenzofuro[5,4-d]thiazol-7-yl)methyl (2-methylpyrimidin-5-yl) carbamate (151);

(S)-(2-(2-ethoxy-7-methylquinoxalin-5-yl)-5-fluoro-7,8-dihydrobenzofuro[5,4-d]thiazol-7-yl)methanol (152);

(R)-(2-(2-ethoxy-7-methylquinoxalin-5-yl)-5-fluoro-7,8-dihydrobenzofuro[5,4-d]thiazol-7-yl)methyl(2-methylpyrimidin-5-yl)carbamate (153);

(R)-(5-fluoro-2-(2-methoxy-7-methylquinoxalin-5-yl)-7,8-dihydrobenzofuro[5,4-d]thiazo 1-7-yl)methyl (5-cyanopyridin-3-yl)carbamate (154);

(R)-(5-fluoro-2-(2-methoxy-7-methylquinoxalin-5-yl)-7,8-dihydrobenzofuro[5,4-d]thiazo 1-7-yl)methyl (2-(2-hydroxyethyl)pyrimidin-5-yl)carbamate (155); (S)-methyl 2-(2-methoxy-7-methylquinoxalin-5-yl)-7,8-dihydrobenzofuro[5,4-d]thiazole-7-carboxyla te (156);

(R)-(5-fluoro-2-(2-methoxy-7-methylquinoxalin-5-yl)-7,8-dihydrobenzofuro[5,4-d]thiazo 1-7-yl)methyl pyridin-3-ylcarbamate (157);

(R)-(5-fluoro-2-(2-methoxy-7-methylquinoxalin-5-yl)-7,8-dihydrobenzofuro[5,4-d]thiazo 1-7-yl)methyl pyridazin-4-ylcarbamate (158);

(R)-(5-fluoro-2-(2-methoxy-7-methylquinoxalin-5-yl)-7,8-dihydrobenzofuro[5,4-d]thiazol-7-yl)methyl (6-methylpyridin-3-yl)carbamate (159);

(R)-(5-fluoro-2-(2-methoxy-7-methylquinoxalin-5-yl)-7,8-dihydrobenzofuro[5,4-d]thiazol-7-yl)methyl (2-methylpyridin-4-yl)carbamate (160);

(R)-(5-fluoro-2-(2-methoxy-7-methylquinoxalin-5-yl)-7,8-dihydrobenzofuro[5,4-d]thiazo 1-7-yl)methyl (5-fluoropyridin-3-yl)carbamate (161);

(R)-(5-fluoro-2-(2-methoxy-7-methylquinoxalin-5-yl)-7,8-dihydrobenzofuro[5,4-d]thiazol-7-yl)methyl (3-cyanophenyl)carbamate (162);

(R)-(5-fluoro-2-(2-methoxy-7-methylquinoxalin-5-yl)-7,8-dihydrobenzofuro[5,4-d]thiazol-7-yl)methyl (2-methoxypyridin-4-yl)carbamate (163);

(R)-(5-fluoro-2-(2-methoxy-7-methylquinoxalin-5-yl)-7,8-dihydrobenzofuro[5,4-d]thiazo 1-7-yl)methyl (6-methoxypyridin-3-yl)carbamate (164);

(R)-(5-fluoro-2-(2-methoxy-7-methylquinoxalin-5-yl)-7,8-dihydrobenzofuro[5,4-d]thiazo 1-7-yl)methyl (6-(2-hydroxyethoxy)pyridin-3-yl)carbamate (165);

(R)-(5-fluoro-2-(2-methoxy-7-methylquinoxalin-5-yl)-7,8-dihydrobenzofuro[5,4-d]thiazo 1-7-yl)methyl (6-(2,2-difluoro-3-hydroxypropoxy)pyridin-3-yl)carbamate (166);

(5-fluoro-2-(2-methoxy-7-methylquinoxalin-5-yl)-7-methyl-7,8-dihydrobenzofuro[5,4-d]thiazol-7-yl)methanol (167);

(R)-(5-fluoro-2-(2-methoxy-7-methylquinoxalin-5-yl)-7,8-dihydrobenzofuro[5,4-d]thiazo 1-7-yl)methyl(5-methoxypyridin-3-yl)carbamate (168);

(R)-(5-fluoro-2-(2-methoxy-7-methylquinoxalin-5-yl)-7,8-dihydrobenzofuro[5,4-d]thiazol-7-yl)methyl (4-(morpholine-4-carbonyl) phenyl)carbamate (169);

(R)-(5-fluoro-2-(2-methoxy-7-methylquinoxalin-5-yl)-7,8-dihydrobenzofuro[5,4-d]thiazo 1-7-yl)methyl (6-fluoropyridin-3-yl)carbamate (170);

(2-(2-methoxy-7-methylquinoxalin-5-yl)-7-methyl-7,8-dihydrobenzofuro[5,4-d]thiazol-7-yl)methanol (171);

(S)-(5-fluoro-2-(2-methoxy-7-methylquinoxalin-5-yl)-7-methyl-7,8-dihydrobenzofuro[5,4-d]thiazol-7-yl)methanol (172);

(R)-(5-fluoro-2-(2-methoxy-7-methylquinoxalin-5-yl)-7,8-dihydrobenzofuro[5,4-d]thiazo 1-7-yl)methyl (2-(2-hydroxyethoxy)pyrimidin-5-yl)carbamate (173);

(S)-(5-fluoro-2-(2-methoxy-7-methylquinoxalin-5-yl)-7-methyl-7,8-dihydrobenzofuro[5,4-d]thiazol-7-yl)methyl (2-methylpyrimidin-5-yl)carbamate (174);

(S)-(5-fluoro-2-(2-methoxy-7-methylquinoxalin-5-yl)-7-methyl-7,8-dihydrobenzofuro[5,4-d]thiazol-7-yl)methyl pyridin-3-ylcarbamate (175);

(S)-(5-fluoro-2-(2-methoxy-7-methylquinoxalin-5-yl)-7-methyl-7,8-dihydrobenzofuro[5,4-d]thiazol-7-yl)methyl (3-cyanophenyl)carbamate (176);

(R)-(5-fluoro-2-(2-methoxy-7-methylquinoxalin-5-yl)-7,8-dihydrobenzofuro[5,4-d]thiazol-7-yl)methyl (2-methoxypyrimidin-5-yl)carbamate (177);

(R)-(5-fluoro-2-(2-methoxy-7-methylquinoxalin-5-yl)-7,8-dihydrobenzofuro[5,4-d]thiazo 1-7-yl)methyl(3-oxoisoindolin-5-yl)carbamate (178);

(R)-(5-fluoro-2-(2-methoxy-7-methylquinoxalin-5-yl)-7,8-dihydrobenzofuro[5,4-d]thiazo 1-7-yl)methyl (3-cyano-5-fluorophenyl)carbamate (179);
(R)-(5-fluoro-2-(2-methoxy-7-methylquinoxalin-5-yl)-7,8-dihydrobenzofuro[5,4-d]thiazol-7-yl)methyl (3-carbamoylphenyl)carbamate (180);
(R)-(5-fluoro-2-(2-methoxy-7-methylquinoxalin-5-yl)-7-methyl-7,8-dihydrobenzofuro[5,4-d]thiazol-7-yl)methanol (181);
(R)-(5-fluoro-2-(2-methoxy-7-methylquinoxalin-5-yl)-7-methyl-7,8-dihydrobenzofuro[5,4-d]thiazol-7-yl)methyl (2-methylpyrimidin-5-yl)carbamate (182);
(R)-(5-fluoro-2-(2-methoxy-7-methylquinoxalin-5-yl)-7-methyl-7,8-dihydrobenzofuro [5,4-d]thiazol-7-yl)methyl pyridin-3-ylcarbamate (183);
(R)-(5-fluoro-2-(2-methoxy-7-methylquinoxalin-5-yl)-7-methyl-7,8-dihydrobenzofuro[5,4-d]thiazol-7-yl)methyl (3-cyanophenyl)carbamate (184);
(R)-(5-fluoro-2-(2-methoxy-7-methylquinoxalin-5-yl)-7,8-dihydrobenzofuro[5,4-d]thiazol-7-yl)methyl pyrimidin-5-ylcarbamate (185); 2-(2-methoxy-7-methylquinoxalin-5-yl)-7,7-dimethyl-7,8-dihydrobenzofuro[5,4-d]thiazol e (186);
(S)-(2-(2-methoxy-7-methylquinoxalin-5-yl)-7-methyl-7,8-dihydrobenzofuro[5,4-d]thiazo 1-7-yl)methanol (187);
(R)-(2-(2-methoxy-7-methylquinoxalin-5-yl)-7-methyl-7,8-dihydrobenzofuro[5,4-d]thiaz ol-7-yl)methanol (188);
(2-(2-methoxy-7-methylquinoxalin-5-yl)-8-methyl-7,8-dihydrobenzofuro[5,4-d]thiazol-7-yl)methanol (189);
(S)-2-(2-methoxy-7-methylquinoxalin-5-yl)-7,8-dihydrobenzofuro[5,4-d]thiazol-7-yl)etha nol (190); Methyl ((2-(2-methoxy-7-methylquinoxalin-5-yl)-7,8-dihydrobenzofuro [5,4-d]thiazol-7-yl)methyl)carbamate (191); Phenyl ((2-(2-methoxy-7-methylquinoxalin-5-yl)-7,8-dihydrobenzofuro[5,4-d]thiazol-7-yl)methy l)carbamate (192); benzyl ((2-(2-methoxy-7-methylquinoxalin-5-yl)-7,8-dihydrobenzofuro[5,4-d]thiazol-7-yl)methy 1) carbamate (193);
(R)-(2-(2-methoxy-7-methylquinoxalin-5-yl)-7-methyl-7,8-dihydrobenzofuro[5,4-d]thiazol-7-yl)methyl (2-methylpyrimidin-5-yl)carbamate (194);
(R)-(2-(2-methoxy-7-methylquinoxalin-5-yl)-7-methyl-7,8-dihydrobenzofuro[5,4-d]thiazol-7-yl)methyl pyridin-3-ylcarbamate (195);
(R)-(2-(2-methoxy-7-methylquinoxalin-5-yl)-7-methyl-7,8-dihydrobenzofuro[5,4-d]thiazol-7-yl)methyl(3-cyanophenyl) carbamate (196); ethyl((2-(2-methoxy-7-methylquinoxalin-5-yl)-7,8-dihydrobenzofuro [5,4-d]thiazol-7-yl) methyl)carbamate (197); Isobutyl ((2-(2-methoxy-7-methylquinoxalin-5-yl)-7,8-dihydrobenzofuro[5,4-d]thiazol-7-yl)methy 1)carbamate (198);
cis-5-fluoro-2-(2-methoxy-7-methylquinoxalin-5-yl)-8-methyl-7,8-dihydrobenzofuro[5,4-d]thiazol-7-yl)methanol (199);
5-fluoro-2-(2-methoxy-7-methylquinoxalin-5-yl)-7,7-dimethyl-7,8-dihydrobenzofuro[5,4-d]thiazole (200);
trans-5-fluoro-2-(2-methoxy-7-methylquinoxalin-5-yl)-8-methyl-7,8-dihydrobenzofuro[5,4-d]thiazol-7-yl)methanol (201); (S)-tert-butyl ((5-fluoro-2-(2-methoxy-7-methylquinoxalin-5-yl)-7,8-dihydrobenzofuro[5,4-d]thiazol-7-yl)methyl)carbamate (202);
(R)-(5-fluoro-2-(2-methoxy-7-methylquinoxalin-5-yl)-7,8-dihydrobenzofuro[5,4-d]thiazo 1-7-yl)methyl (3-(dimethylcarbamoyl)phenyl)carbamate (203);
(R)-(5-fluoro-2-(2-methoxy-7-methylquinoxalin-5-yl)-7,8-dihydrobenzofuro[5,4-d]thiazo 1-7-yl)methyl (4-(dimethylcarbamoyl)phenyl)carbamate (204);
(R)-(5-fluoro-2-(2-methoxy-7-methylquinoxalin-5-yl)-7,8-dihydrobenzofuro[5,4-d]thiazo 1-7-yl)methyl (5-carbamoylpyridin-3-yl)carbamate (205);
(R)-(5-fluoro-2-(2-methoxy-7-methylquinoxalin-5-yl)-8,8-dimethyl-7,8-dihydrobenzofur o[5,4-d]thiazol-7-yl)methanol (206);
(R)-(5-fluoro-2-(2-methoxy-7-methylquinoxalin-5-yl)-7,8-dihydrobenzofuro[5,4-d]thiazo 1-7-yl)methyl (4-(oxazol-2-yl)phenyl)carbamate (207);
(R)-(5-fluoro-2-(2-methoxy-7-methylquinoxalin-5-yl)-7,8-dihydrobenzofuro[5,4-d]thiazo 1-7-yl)methyl (4-(methylcarbamoyl)phenyl)carbamate (208);
(S)-N-((5-fluoro-2-(2-methoxy-7-methylquinoxalin-5-yl)-7,8-dihydrobenzofuro[5,4-d]thiazol-7-yl)methyl)acetamide (209); (S)-methyl ((5-fluoro-2-(2-methoxy-7-methylquinoxalin-5-yl)-7,8-dihydrobenzofuro[5,4-d]thiazol-7-yl)methyl)carbamate (210); (S)-benzyl ((5-fluoro-2-(2-methoxy-7-methylquinoxalin-5-yl)-7,8-dihydrobenzofuro[5,4-d]thiazol-7-yl)methyl) carbamate (211); (S)-phenyl ((5-fluoro-2-(2-methoxy-7-methylquinoxalin-5-yl)-7,8-dihydrobenzofuro[5,4-d]thiazol-7-yl)methyl)carbamate (212); (S)-p-tolyl ((5-fluoro-2-(2-methoxy-7-methylquinoxalin-5-yl)-7,8-dihydrobenzofuro[5,4-d]thiazol-7-yl)methyl) carbamate (213); (S)-4-chlorophenyl ((5-fluoro-2-(2-methoxy-7-methylquinoxalin-5-yl)-7,8-dihydrobenzofuro[5,4-d]thiazol-7-yl)methyl)carbamate (214);
(S)-2,2,2-trifluoro-N-((5-fluoro-2-(2-methoxy-7-methylquinoxalin-5-yl)-7,8-dihydrobenz ofuro[5,4-d]thiazol-7-yl)methyl)acetamide (215); (S)-4-methoxyphenyl ((5-fluoro-2-(2-methoxy-7-methylquinoxalin-5-yl)-7,8-dihydrobenzofuro[5,4-d]thiazol-7-yl)methyl)carbamate (216);
(R)-N-((5-fluoro-2-(2-methoxy-7-methylquinoxalin-5-yl)-7,8-dihydrobenzofuro [5,4-d]thiazol-7-yl)methyl)-2-phenylacetamide (217); (R)-methyl ((5-fluoro-2-(2-methoxy-7-methylquinoxalin-5-yl)-7,8-dihydrobenzofuro[5,4-d]thiazol-7-yl)methyl) carbamate (218);
(R)-N-((5-fluoro-2-(2-methoxy-7-methylquinoxalin-5-yl)-7,8-dihydrobenzofuro[5,4-d]thiazol-7-yl)methyl)acetamide (219); (R)-phenyl ((5-fluoro-2-(2-methoxy-7-methylquinoxalin-5-yl)-7,8-dihydrobenzofuro[5,4-d]thiazol-7-yl)methyl) carbamate (220); (R)-benzyl ((5-fluoro-2-(2-methoxy-7-methylquinoxalin-5-yl)-7,8-dihydrobenzofuro[5,4-d]thiazol-7-yl)methyl)carbamate (221);
(R)-2,2,2-trifluoro-N-((5-fluoro-2-(2-methoxy-7-methylquinoxalin-5-yl)-7,8-dihydrobenz ofuro[5,4-d]thiazol-7-yl)methyl)acetamide (222); (R)-tert-butyl ((5-fluoro-2-(2-methoxy-7-methylquinoxalin-5-yl)-7,8-dihydrobenzofuro[5,4-d]thiazol-7-yl)methyl)carbamate (223); (S)-isobutyl ((2-(2-methoxy-7-methylquinoxalin-5-yl)-7,8-dihydrobenzofuro[5,4-d]thiazol-7-yl)methy 1) carbamate (224); (S)-benzyl ((2-(2-methoxy-7-methylquinoxalin-5-yl)-7,8-dihydrobenzofuro[5,4-d]thiazol-7-yl)methy 1)carbamate (225); (S)-methyl ((2-(2-methoxy-7-methylquinoxalin-5-yl)-7,8-dihydrobenzofuro[5,4-d]thiazol-7-yl)methy 1) carbamate (226); (S)-tetrahydro-2H-pyran-4-yl ((2-(2-methoxy-7-methylquinoxalin-5-yl)-7,8-dihydrobenzofuro[5,4-d]thiazol-7-yl)methy 1)carbamate (227); (S)-N-((2-(2-methoxy-7-methylquinoxalin-5-yl)-7,8-dihydrobenzofuro[5,4-d]thiazol-7-yl) methyl) methanesulfonamide (228); (Tetrahydrofuran-3-yl)methyl (((S)-2-(2-methoxy-7-methylquinoxalin-5-yl)-7,8-dihydrobenzofuro[5,4-d]thiazol-7-yl)m ethyl)carbamate (229); (R)-tetrahydrofuran-3-yl (((S)-2-(2-methoxy-7-methylquinoxalin-5-yl)-7,8-dihydrobenzofuro[5,4-d]thiazol-7-yl)m ethyl)carbamate (230); (S)-3-cyanobenzyl ((2-(2-methoxy-7-methylquinoxalin-5-yl)-7,8-dihydrobenzofuro[5,4-d]thiazol-7-yl)methy 1) carbamate (231); (S)-pyridin-3-ylmethyl ((2-(2-methoxy-7-methylquinoxalin-5-yl)-7,8-dihydrobenzofuro[5,4-d]thiazol-7-yl)methy 1)carbamate (232); (S)-pyridin-4-ylmethyl ((2-(2-methoxy-7-methylquinoxalin-5-yl)-7,8-dihydrobenzofuro[5,4-d]thiazol-7-yl)methy 1) carbamate (233); Tetrahydro-2H-pyran-3-yl (((S)-2-(2-methoxy-7-methylquinoxalin-5-yl)-7,8-dihydrobenzofuro[5,4-d]thiazol-7-yl)m ethyl)carbamate (234); (Tetrahydro-2H-pyran-2-yl)methyl (((S)-2-(2-methoxy-7-methylquinoxalin-5-yl)-7,8-dihydrobenzofuro [5,4-d]thiazol-7-yl)methyl)carbamate (235); (S)-tetrahydrofuran-3-yl (((S)-2-(2-methoxy-7-methylquinoxalin-5-yl)-7,8-dihydrobenzofuro[5,4-d]thiazol-7-yl)m ethyl)carbamate (236); (S)-(5-fluoro-2-(2-methoxy-7-methylquinoxalin-5-yl)-7-methyl-7,8-dihydrobenzofuro[5,4-d]thiazol-7-yl)methyl dihydrogen phosphate (237);((7S,8S)-5-fluoro-2-(2-methoxy-7-methylquinoxalin-5-yl)-8-methyl-7,8-dihydrobe nzofuro[5,4-d]thiazol-7-yl) methanol (238); ((7R,8R)-5-fluoro-2-(2-methoxy-7-methylquinoxalin-5-yl)-8-methyl-7,8-dihydrobenzofur o[5,4-d]thiazol-7-yl) methanol (239); (S)-methyl ((5-fluoro-2-(2-methoxy-7-methylquinoxalin-5-yl)-7-methyl-7,8-dihydrobenzofuro[5,4-d]thiazol-7-yl)methyl) carbamate (240); (S)-isobutyl ((5-fluoro-2-(2-methoxy-7-methylquinoxalin-5-yl)-7-methyl-7,8-dihydrobenzofuro[5,4-d]thiazol-7-yl)methyl) carbamate (241); (S)-tert-butyl ((5-fluoro-2-(2-methoxy-7-methylquinoxalin-5-yl)-7-methyl-7,8-dihydrobenzofuro[5,4-d]thiazol-7-yl)methyl) carbamate (242); (R)-1-((S)-2-(2-methoxy-7-methylquinoxalin-5-yl)-7,8-dihydrobenzofuro[5,4-d]thiazol-7-yl)ethanol(243); (S)-tert-butyl ((2-(2-methoxy-7-methylquinoxalin-5-yl)-7,8-dihydrobenzofuro[5,4-d]thiazol-7-yl)methy 1)carbamate (244); (S)-tetrahydro-2H-pyran-4-yl ((5-fluoro-2-(2-methoxy-7-methylquinoxalin-5-yl)-7,8-dihydrobenzofuro[5,4-d]thiazol-7-yl)methyl)carbamate (245); (S)-isobutyl ((5-fluoro-2-(2-methoxy-7-methylquinoxalin-5-yl)-7,8-dihydrobenzofuro[5,4-d]thiazol-7-yl)methyl)carbamate (246); (S)-2-fluoroethyl ((5-fluoro-2-(2-methoxy-7-methylquinoxalin-5-yl)-7,8-dihydrobenzofuro[5,4-d]thiazol-7-yl)methyl)carbamate (247); (S)-1-((5-fluoro-2-(2-methoxy-7-methylquinoxalin-5-yl)-7,8-dihydrobenzofuro[5,4-d]thia zol-7-yl)methyl)-3-phenylurea (248); (S)-2,2,2-trifluoroethyl ((5-fluoro-2-(2-methoxy-7-methylquinoxalin-5-yl)-7,8-dihydrobenzofuro[5,4-d]thiazol-7-yl)methyl)carbamate (249); (S)-2-methoxyethyl ((5-fluoro-2-(2-methoxy-7-methylquinoxalin-5-yl)-7,8-dihydrobenzofuro [5,4-d]thiazol-7-yl)methyl)carbamate (250); (R)-(5-fluoro-2-(2-methoxy-7-methylquinoxalin-5-yl)-7-methyl-7,8-dihydrobenzofuro[5,4-d]thiazol-7-yl)methyl (2-(2-hydroxyethoxy)pyrimidin-5-yl)carbamate (251); ((7R,8R)-5-fluoro-2-(2-methoxy-7-methylquinoxalin-5-yl)-8-methyl-7,8-dihydrobenzofur o[5,4-d]thiazol-7-yl)methyl (2-(2-hydroxyethoxy)pyrimidin-5-yl)carbamate (252); ((7S,8S)-2-(7-chloro-2-methoxyquinoxalin-5-yl)-5-fluoro-8-methyl-7,8-dihydrobenzofuro [5,4-d]thiazol-7-yl)methanol (253); 8-((7S,8S)-5-fluoro-7-(hydroxymethyl)-8-methyl-7,8-dihydrobenzofuro [5,4-d]thiazol-2-yl)-3-methoxyquinoxaline-6-carbonitrile (254); Methyl (((7S,8S)-5-fluoro-2-(2-methoxy-7-methylquinoxalin-5-yl)-8-methyl-7,8-dihydrobenzofu ro[5,4-d]thiazol-7-yl)methyl)carbamate (255); Isobutyl (((7S,8S)-5-fluoro-2-(2-methoxy-7-methylquinoxalin-5-yl)-8-methyl-7,8-dihydrobenzofu ro[5,4-d]thiazol-7-yl)methyl) carbamate (256); (S)-1-cyclopropyl-3-((5-fluoro-2-(2-methoxy-7-methylquinoxalin-5-yl)-7,8-dihydrobenzo furo[5,4-d]thiazol-7-yl)methyl)urea (257); (S)-N-((5-fluoro-2-(2-methoxy-7-methylquinoxalin-5-yl)-7,8-dihydrobenzofuro[5,4-d]thi azol-7-yl)methyl) morpholine-4-carboxamide (258); ((7S,8S)-2-(2-ethoxy-7-methylquinoxalin-5-yl)-5-fluoro-8-methyl-7,8-dihydrobenzofuro[5,4-d]thiazol-7-yl)methanol (259); (S)-ethyl ((5-fluoro-2-(2-methoxy-7-methylquinoxalin-5-yl)-7,8-dihydrobenzofuro[5,4-d]thiazol-7-yl) methyl)carbamate (260); (S)-neopentyl ((5-fluoro-2-(2-methoxy-7-methylquinoxalin-5-yl)-7,8-dihydrobenzofuro[5,4-d]thiazol-7-yl)methyl)carbamate (261); (R)-(2-(6-chloro-3-methoxyquinolin-8-yl)-5-fluoro-7,8-dihydrobenzofuro[5,4-d]thiazol-7-yl) methyl (2-methylpyrimidin-5-yl)carbamate (267); (R)-(5-fluoro-2-(3-methoxy-6-methylquinolin-8-yl)-7,8-dihydrobenzofuro[5,4-d]thiazol-7-yl)methyl (2-methylpyrimidin-5-yl)carbamate (269); (R)-(2-(6-chloro-3-ethoxyquinolin-8-yl)-5-fluoro-7,8-dihydrobenzofuro[5,4-d]thiazol-7-yl)methyl (2-methylpyrimidin-5-yl)carbamate (270); (R)-(2-(6-chloro-3-(difluoromethoxy)quinolin-8-yl)-5-fluoro-7,8-dihydrobenzofuro[5,4-d]thiazol-7-yl)methyl (2-methylpyrimidin-5-yl)carbamate (273); (R)-(5-fluoro-2-(6-fluoro-3-methoxyquinolin-8-yl)-7,8-dihydrobenzofuro[5,4-d]thiazol-7-yl)methyl (2-methylpyrimidin-5-yl)carbamate (280); (R)-(2-(6-chloro-3-methoxyquinolin-8-yl)-5-fluoro-7,8-dihydrobenzofuro[5,4-d]thiazol-7-yl)methanol (282); (R)-(2-(6-chloro-3-methoxyquinolin-8-yl)-5-fluoro-7,8-dihydrobenzofuro[5,4-d]thiazol-7-yl)methyl pyridin-3-ylcarbamate (283); (R)-(2-(6-chloro-3-methoxyquinolin-8-yl)-5-fluoro-7,8-dihydrobenzofuro[5,4-d]thiazol-7-yl)methyl (3-carbamoylphenyl)carbamate (284); (S)-(2-(6-chloro-3-methoxyquinolin-8-yl)-5-fluoro-7-methyl-7,8-dihydrobenzofuro[5,4-d]thiazol-7-yl)methanol (285);

(R)-(2-(6-chloro-3-methoxyquinolin-8-yl)-5-fluoro-7-methyl-7,8-dihydrobenzofuro[5,4-d]thiazol-7-yl)methyl (2-(2-hydroxyethoxy)pyrimidin-5-yl)carbamate (286); and ((7S,8S)-2-(6-chloro-3-methoxyquinolin-8-yl)-5-fluoro-8-methyl-7,8-dihydrobenzofuro[5,4-d]thiazol-7-yl)methanol (290).

One embodiment provides
1-(2-(2-methoxy-7-methylquinoxalin-5-yl)-8,9-dihydro-7H-[1,4]dioxepino[2',3':3,4]benzo[1,2-d]thiazol-4-yl)-2,2-dimethylpropan-1-ol (264).

One embodiment provides a compound or a salt thereof, selected from (R)-(4-chloro-2-(2-methoxy-7-methylquinoxalin-5-yl)-7,8-dihydro-[1,4]dioxino[2',3':3,4]benzo[1,2-d]thiazol-7-yl)methyl(6-methoxypyridin-3-yl)carbamate (1);

(S)-(4-chloro-2-(2-methoxy-7-methylquinoxalin-5-yl)-7,8-dihydro-[1,4]dioxino[2',3':3,4]benzo[1,2-d]thiazol-7-yl)methyl (6-methoxypyridin-3-yl)carbamate (2);

(2-(2-methoxy-7-methylquinoxalin-5-yl)-4-methyl-7,8-dihydro-[1,4]dioxino[2',3':3,4]benzo[1,2-d]thiazol-7-yl)methyl(2-hydroxypyridin-4-yl)carbamate (3);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl(6-methoxypyridin-3-yl)carbamate (4);

(R)-(2-(2-methoxy-7-methylquinoxalin-5-yl)-4-methyl-7,8-dihydro-[1,4]dioxino[2',3':3,4]benzo[1,2-d]thiazol-7-yl)methylpyridin-3-ylcarbamate (5);

(2-(2-methoxy-7-methylquinoxalin-5-yl)-4-methyl-7,8-dihydro-[1,4]dioxino[2',3':3,4]benzo[1,2-d]thiazol-7-yl)methylpyridin-3-yl carbonate (6); tert-butyl((2-(2-(difluoromethoxy)-7-methylquinoxalin-5-yl)-4-fluoro-7,8-dihydro-[1,4]dioxino[2',3':3,4]benzo[1,2-d]thiazol-7-yl)methyl)carbamate (21);

(2-(2-(difluoromethoxy)-7-methylquinoxalin-5-yl)-4-fluoro-7,8-dihydro-[1,4]dioxino[2',3':3,4]benzo[1,2-d]thiazol-8-yl)methanol (22);

tert-butyl((2-(2-(difluoromethoxy)-7-methylquinoxalin-5-yl)-4-fluoro-7,8-dihydro-[1,4]dioxino[2',3':3,4]benzo[1,2-d]thiazol-8-yl)methyl)carbamate (23);

(4-fluoro-2-(2-methoxy-7-methylquinoxalin-5-yl)-7,8-dihydro-[1,4]dioxino[2',3':3,4]benzo[1,2-d]thiazol-8-yl)methylphenylcarbamate (24);

(R)-(4-chloro-2-(2-methoxy-7-methylquinoxalin-5-yl)-7,8-dihydro-[1,4]dioxino[2',3':3,4]benzo[1,2-d]thiazol-7-yl)methyl(5-chloropyridin-3-yl)carbamate (25);

(R)-(4-chloro-2-(2-methoxy-7-methylquinoxalin-5-yl)-7,8-dihydro-[1,4]dioxino[2',3':3,4]benzo[1,2-d]thiazol-7-yl)methylphenyl carbamate (26);

(R)-(4-chloro-2-(2-methoxy-7-methylquinoxalin-5-yl)-7,8-dihydro-[1,4]dioxino[2',3':3,4]benzo[1,2-d]thiazol-7-yl)methyl(3-cyanophenyl)carbamate (27);

(R)-(4-chloro-2-(2-methoxy-7-methylquinoxalin-5-yl)-7,8-dihydro-[1,4]dioxino[2',3':3,4]benzo[1,2-d]thiazol-7-yl)methyl(5-fluoropyridin-3-yl)carbamate (28);

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (6-fluoropyridin-3-yl)carbamate (29);

(R)-(4-chloro-2-(2-methoxy-7-methylquinoxalin-5-yl)-7,8-dihydro-[1,4]dioxino[2',3':3,4]benzo[1,2-d]thiazol-7-yl)methylpyridin-4-ylcarbamate (30);

(R)-(4-chloro-2-(2-methoxy-7-methylquinoxalin-5-yl)-7,8-dihydro-[1,4]dioxino[2',3':3,4]benzo[1,2-d]thiazol-7-yl)methylpyridin-3-ylcarbamate (31);

(R)-(4-chloro-2-(2-methoxy-7-methylquinoxalin-5-yl)-7,8-dihydro-[1,4]dioxino[2',3':3,4]benzo[1,2-d]thiazol-7-yl)methyl(6-chloropyridin-3-yl)carbamate (32);

(R)-(4-chloro-2-(2-methoxy-7-methylquinoxalin-5-yl)-7,8-dihydro-[1,4]dioxino[2',3':3,4]benzo[1,2-d]thiazol-7-yl)methyl(2-methylpyridin-4-yl)carbamate (33);

(R)-(4-chloro-2-(2-methoxy-7-methylquinoxalin-5-yl)-7,8-dihydro-[1,4]dioxino[2',3':3,4]benzo[1,2-d]thiazol-7-yl)methylpyridazin-4-ylcarbamate (34);

(R)-(4-chloro-2-(2-methoxy-7-methylquinoxalin-5-yl)-7,8-dihydro-[1,4]dioxino[2',3':3,4]benzo[1,2-d]thiazol-7-yl)methyl(6-cyanopyridin-3-yl)carbamate (35);

(R)-(4-chloro-2-(2-methoxy-7-methylquinoxalin-5-yl)-7,8-dihydro-[1,4]dioxino[2',3':3,4]benzo[1,2-d]thiazol-7-yl)methyl(2-methoxypyridin-4-yl) carbamate (36);

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (5-cyanopyridin-3-yl)carbamate (37);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (6-cyanopyridin-3-yl)carbamate (38);

(R)-(4-chloro-2-(2-methoxy-7-methylquinoxalin-5-yl)-7,8-dihydro-[1,4]dioxino[2',3':3,4]benzo[1,2-d]thiazol-7-yl)methyl benzo[d]thiazol-5-ylcarbamate (39);

(R)-(4-chloro-2-(2-methoxy-7-methylquinoxalin-5-yl)-7,8-dihydro-[1,4]dioxino[2',3':3,4]benzo[1,2-d]thiazol-7-yl)methyl benzo[d]thiazol-6-ylcarbamate (40);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (6-fluoropyridin-3-yl)carbamate (41);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (5-fluoropyridin-3-yl)carbamate (42);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (5-methoxypyridin-3-yl)carbamate (43);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (2-methylpyridin-4-yl)carbamate (44);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (2-methoxypyridin-4-yl)carbamate (45);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (3-cyanophenyl)carbamate (46);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (6-chloropyridin-3-yl) carbamate (47);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl pyridin-4-ylcarbamate (48);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl benzo[d]thiazol-5-ylcarbamate (49);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl benzo[d]thiazol-6-ylcarbamate (50);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (5-cyanopyridin-3-yl)carbamate (51);

(R)-(2-(2,7-dimethylquinoxalin-5-yl)-4-methyl-7,8-dihydro-[1,4]dioxino[2',3':3,4]benzo[1,2-d]thiazol-7-yl)methyl (6-(dimethylamino) pyridin-3-yl) carbamate (52);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (6-(thiophen-2-yl) pyridin-3-yl)carbamate (53);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (3-methyl-3H-imidazo[4,5-b]pyridin-6-yl)carbamate (54);

(R)-(2-(2-methoxy-7-methylquinoxalin-5-yl)-4-methyl-7,8-dihydro-[1,4]dioxino[2',3':3,4]benzo [1,2-d]thiazol-7-yl) methyl (6-(3-methyl-1H-1,2,4-triazol-1-yl)pyridin-3-yl)carbamate (55);

(R)-(2-(2-methoxy-7-methylquinoxalin-5-yl)-4-methyl-7,8-dihydro-[1,4]dioxino [2',3':3,4]benzo[1,2-d]thiazol-7-yl) methyl (6-methylpyridin-3-yl)carbamate (56);

(R)-(2-(2-methoxy-7-methylquinoxalin-5-yl)-4-methyl-7,8-dihydro-[1,4]dioxino[2',3':3,4]benzo [1,2-d]thiazol-7-yl) methyl (5-methylpyridin-3-yl)carbamate (57);

(R)-(4-chloro-2-(2-methoxy-7-methylquinoxalin-5-yl)-7,8-dihydro-[1,4]dioxino[2',3':3,4]benzo[1,2-d] thiazol-7-yl) methyl (2-chloropyrimidin-5-yl)carbamate (58);

(R)-(2-(2-methoxy-7-methylquinoxalin-5-yl)-4-methyl-7,8-dihydro-[1,4]dioxino[2',3':3,4]benzo[1,2-d]thiazol-7-yl) methyl (2-chloropyrimidin-5-yl)carbamate (59);

(R)-(4-chloro-2-(2-methoxy-7-methylquinoxalin-5-yl)-7,8-dihydro-[1,4]dioxino[2',3':3,4]benzo[1,2-d]thiazol-7-yl) methyl (5,6-dimethylpyridin-3-yl) carbamate (60);

(R)-(2-(2-methoxy-7-methylquinoxalin-5-yl)-4-methyl-7,8-dihydro-[1,4]dioxino [2',3':3,4]benzo[1,2-d]thiazol-7-yl) methyl (6-fluoro-5-methylpyridin-3-yl)carbamate (61);

(R)-(4-chloro-2-(2,7-dimethylquinoxalin-5-yl)-7,8-dihydro-[1,4]dioxino[2',3':3,4]benzo[1,2-d]thiazol-7-yl) methyl (6-methylpyridin-3-yl)carbamate (62);

(R)-(4-chloro-2-(2,7-dimethylquinoxalin-5-yl)-7,8-dihydro-[1,4]dioxino[2',3':3,4]benzo[1,2-d]thiazol-7-yl) methyl (5-methylpyridin-3-yl)carbamate (63);

(R)-(4-chloro-2-(2-methoxy-7-methylquinoxalin-5-yl)-7,8-dihydro-[1,4]dioxino[2',3':3,4]benzo[1,2-d]thiazol-7-yl) methyl (6-fluoro-5-methylpyridin-3-yl)carbamate (64);

(R)-(4-chloro-2-(2-methoxy-7-methylquinoxalin-5-yl)-7,8-dihydro-[1,4]dioxino[2',3':3,4]benzo [1,2-d]thiazol-7-yl) methyl (6-(dimethylamino)pyridin-3-yl)carbamate (65);

(R)-(4-chloro-2-(2-methoxy-7-methylquinoxalin-5-yl)-7,8-dihydro-[1,4]dioxino[2',3':3,4]benzo [1,2-d]thiazol-7-yl) methyl(2-oxo-2,3-dihydrobenzo[d]oxazol-6-yl)carbamate (66);

(R)-(4-chloro-2-(2-methoxy-7-methylquinoxalin-5-yl)-7,8-dihydro-[1,4]dioxino[2',3':3,4]benzo[1,2-d] thiazol-7-yl) methyl (3-methyl-3H-imidazo[4,5-b]pyridin-6-yl)carbamate (67); (R)-(4-fluoro-2-(2-methoxy-7-methylquinoxalin-5-yl)-7,8-dihydro-[1,4]dioxino [2',3':3,4]benzo [1,2-d]thiazol-7-yl)methyl (6-methoxypyridin-3-yl)carbamate (68);

(R)-(4-chloro-2-(2-methoxy-7-methylquinoxalin-5-yl)-7,8-dihydro-[1,4]dioxino[2',3':3,4]benzo[1,2-d] thiazol-7-yl) methyl (6-(3-methyl-1H-1,2,4-triazol-1-yl)pyridin-3-yl) carbamate (69);

(R)-(4-fluoro-2-(2-methoxy-7-methylquinoxalin-5-yl)-7,8-dihydro-[1,4]dioxino[2',3':3,4]benzo[1,2-d]thiazol-7-yl) methyl pyridin-3-ylcarbamate (70);

(R)-(4-fluoro-2-(2-methoxy-7-methylquinoxalin-5-yl)-7,8-dihydro-[1,4]dioxino[2',3':3,4]benzo[1,2-d]thiazol-7-yl) methyl(6-fluoropyridin-3-yl)carbamate (71);

(R)-(4-fluoro-2-(2-methoxy-7-methylquinoxalin-5-yl)-7,8-dihydro-[1,4]dioxino[2',3':3,4]benzo[1,2-d]thiazol-7-yl) methyl(3-cyanophenyl)carbamate (72);

(R)-(4-fluoro-2-(2-methoxy-7-methylquinoxalin-5-yl)-7,8-dihydro-[1,4]dioxino[2',3':3,4]benzo[1,2-d]thiazol-7-yl) methyl pyridin-4-ylcarbamate (73);

(4-(difluoromethyl)-2-(2-methoxy-7-methylquinoxalin-5-yl)-7,8-dihydro-[1,4]dioxino[2',3':3,4]benzo[1,2-d]thiazol-7-yl) methyl (2-methylpyridin-4-yl) carbamate (74);

(R)-(4-fluoro-2-(2-methoxy-7-methylquinoxalin-5-yl)-7,8-dihydro-[1,4]dioxino[2',3':3,4]benzo[1,2-d]thiazol-7-yl) methyl (2-methylpyridin-4-yl)carbamate (75);

(R)-(4-fluoro-2-(2-methoxy-7-methylquinoxalin-5-yl)-7,8-dihydro-[1,4]dioxino[2',3':3,4]benzo[1,2-d]thiazol-7-yl) methyl (6-methylpyridin-3-yl)carbamate (76);

(2-(2-methoxy-7-methylquinoxalin-5-yl)-4-methyl-7,8-dihydro-[1,4]dioxino [2',3':3,4]benzo[1,2-d]thiazol-7-yl) methyl (5-carbamoylpyridin-3-yl)carbamate (77);

(2-(2-methoxy-7-methylquinoxalin-5-yl)-4-methyl-7,8-dihydro-[1,4]dioxino[2',3':3,4]benzo[1,2-d]thiazol-7-yl) methyl (1-oxo-1,2,3,4-tetrahydroisoquinolin-7-yl)carbamate (78);

(2-(2-methoxy-7-methylquinoxalin-5-yl)-4-methyl-7,8-dihydro-[1,4]dioxino[2',3':3,4]benzo[1,2-d]thiazol-7-yl) methyl (2-methylpyrimidin-5-yl)carbamate (79);

(R)-(4-(difluoromethyl)-2-(2-methoxy-7-methylquinoxalin-5-yl)-7,8-dihydro-[1,4]dioxin o[2',3':3,4]benzo[1,2-d] thiazol-7-yl) methyl (6-methylpyridin-3-yl)carbamate (80);

(R)-(4-(difluoromethyl)-2-(2-methoxy-7-methylquinoxalin-5-yl)-7,8-dihydro-[1,4]dioxin o[2',3':3,4]benzo[1,2-d] thiazol-7-yl) methyl (6-methoxypyridin-3-yl)carbamate (81);

(2-(2-methoxy-7-methylquinoxalin-5-yl)-4-methyl-7,8-dihydro-[1,4]dioxino[2',3':3,4]ben zo[1,2-d]thiazol-7-yl) methyl benzo[d]oxazol-5-ylcarbamate (82);

(R)-(4-fluoro-2-(7-(hydroxymethyl)-2-methoxyquinoxalin-5-yl)-7,8-dihydro-[1,4]dioxino [2',3':3,4]benzo[1,2-d]thiazol-7-yl) methyl pyridin-3-ylcarbamate (83);

(R)-(2-(7-(difluoromethyl)-2-methoxyquinoxalin-5-yl)-4-methyl-7,8-dihydro-[1,4]dioxin o[2',3':3,4]benzo[1,2-d] thiazol-7-yl)methyl (2-methylpyridin-4-yl)carbamate (84);

(R)-(4-fluoro-2-(7-(hydroxymethyl)-2-methoxyquinoxalin-5-yl)-7,8-dihydro-[1,4]dioxino [2',3':3,4]benzo[1,2-d]thiazol-7-yl) methyl(2-methylpyridin-4-yl)carbamate (85);

(2-(2-methoxy-7-vinylquinoxalin-5-yl)-4-methyl-7,8-dihydro-[1,4]dioxino[2',3':3,4]benzo [1,2-d]thiazol-7-yl) methyl (6-methoxypyridin-3-yl)carbamate (86);

(2-(7-(hydroxymethyl)-2-methoxyquinoxalin-5-yl)-4-methyl-7,8-dihydro-[1,4]dioxino[2',3':3,4]benzo[1,2-d] thiazol-7-yl)methyl (6-methoxypyridin-3-yl)carbamate (87);

(2-(7-(1-hydroxyethyl)-2-methoxyquinoxalin-5-yl)-4-methyl-7,8-dihydro-[1,4]dioxino[2',3':3,4]benzo[1,2-d] thiazol-7-yl)methyl (6-methoxypyridin-3-yl)carbamate (88);

(2-(2-methoxy-7-vinylquinoxalin-5-yl)-4-methyl-7,8-dihydro-[1,4]dioxino[2',3':3,4]benzo [1,2-d]thiazol-7-yl) methyl pyridin-3-ylcarbamate (89);

(2-(7-(hydroxymethyl)-2-methoxyquinoxalin-5-yl)-4-methyl-7,8-dihydro-[1,4]dioxino[2',3':3,4]benzo[1,2-d] thiazol-7-yl)methyl pyridin-3-ylcarbamate (90);

(R)-(2-(7-cyano-2-methoxyquinoxalin-5-yl)-4-methyl-7,8-dihydro-[1,4]dioxino[2',3':3,4]benzo [1,2-d]thiazol-7-yl) methyl (6-methylpyridin-3-yl)carbamate (91);

(R)-(2-(7-cyano-2-methoxyquinoxalin-5-yl)-4-methyl-7,8-dihydro-[1,4]dioxino[2',3':3,4]benzo[1,2-d] thiazol-7-yl) methyl (2-methylpyridin-4-yl)carbamate (92);

(R)-(2-(7-cyano-2-methoxyquinoxalin-5-yl)-4-methyl-7,8-dihydro-[1,4]dioxino[2',3':3,4]benzo[1,2-d] thiazol-7-yl) methyl pyridin-3-ylcarbamate (93);

(R)-(2-(7-cyano-2-methoxyquinoxalin-5-yl)-4-methyl-7,8-dihydro-[1,4]dioxino[2',3':3,4]benzo[1,2-d]thiazol-7-yl) methyl (6-methoxypyridin-3-yl)carbamate (94);

(2-(7-chloro-2-methoxyquinoxalin-5-yl)-4-methyl-7,8-dihydro-[1,4]dioxino[2',3':3,4]benz o[1,2-d]thiazol-7-yl) methyl pyridin-3-ylcarbamate (95);

(2-(7-chloro-2-methoxyquinoxalin-5-yl)-4-methyl-7,8-dihydro-[1,4]dioxino [2',3':3,4]benzo[1,2-d]thiazol-7-yl)methyl (6-fluoropyridin-3-yl)carbamate (96);

(2-(7-chloro-2-methoxyquinoxalin-5-yl)-4-methyl-7,8-dihydro-[1,4]dioxino[2',3':3,4]benz o [1,2-d]thiazol-7-yl) methyl (6-methylpyridin-3-yl)carbamate (97);

(R)-(2-(7-(hydroxymethyl)-2-methoxyquinoxalin-5-yl)-4-methyl-7,8-dihydro-[1,4]dioxin o [2',3':3,4]benzo[1,2-d]thiazol-7-yl)methyl (6-methoxypyridin-3-yl)carbamate (98);

(R)-(2-(7-(hydroxymethyl)-2-methoxyquinoxalin-5-yl)-4-methyl-7,8-dihydro-[1,4]dioxin o [2',3':3,4]benzo[1,2-d]thiazol-7-yl)methyl (2-methylpyridin-4-yl)carbamate (99);

(R)-(2-(7-(hydroxymethyl)-2-methoxyquinoxalin-5-yl)-4-methyl-7,8-dihydro-[1,4]dioxin o [2',3':3,4]benzo[1,2-d]thiazol-7-yl)methyl (6-methylpyridin-3-yl)carbamate (100);

(R)-(2-(7-(hydroxymethyl)-2-methoxyquinoxalin-5-yl)-4-methyl-7,8-dihydro-[1,4]dioxin o [2',3':3,4]benzo[1,2-d]thiazol-7-yl)methyl pyridin-3-ylcarbamate (101);

(R)-(2-(2-methoxy-7-methylquinoxalin-5-yl)-7,8-dihydro-[1,4]dioxino[2',3':3,4]benzo[1,2-d] thiazol-7-yl)methyl (6-methylpyridin-3-yl)carbamate (102);

(R)-(2-(2-methoxy-7-methylquinoxalin-5-yl)-7,8-dihydro-[1,4]dioxino [2',3':3,4]benzo[1,2-d]thiazol-7-yl) methyl (2-methylpyrimidin-5-yl)carbamate (103);

(R)-(2-(2-methoxy-7-methylquinoxalin-5-yl)-7,8-dihydro-[1,4]dioxino[2',3':3,4]benzo[1,2-d]thiazol-7-yl) methyl (6-methoxypyridin-3-yl)carbamate (104);

(R)-(2-(2-methoxy-7-methylquinoxalin-5-yl)-7,8-dihydro-[1,4]dioxino[2',3':3,4]benzo[1,2-d]thiazol-7-yl)methyl (6-cyanopyridin-3-yl)carbamate (105);

(R)-(2-(2-methoxy-7-methylquinoxalin-5-yl)-7,8-dihydro-[1,4]dioxino[2',3':3,4]benzo [1,2-d]thiazol-7-yl)methyl (2-oxo-2,3-dihydrobenzo [d]oxazol-6-yl)carbamate (106);

(R)-(2-(2-methoxy-7-methylquinoxalin-5-yl)-7,8-dihydro-[1,4]dioxino[2',3':3,4]benzo [1,2-d]thiazol-7-yl)methyl 1H-pyrrolo[2,3-b] pyridin-5-ylcarbamate (107);

(R)-(2-(2-methoxy-7-methylquinoxalin-5-yl)-7,8-dihydro-[1,4]dioxino[2',3':3,4]benzo[1,2-d]thiazol-7-yl)methyl pyridin-3-ylcarbamate (108);

(R)-(2-(2-methoxy-7-methylquinoxalin-5-yl)-7,8-dihydro-[1,4]dioxino[2',3':3,4]benzo[1,2-d] thiazol-7-yl)methyl (6-bromopyridin-3-yl)carbamate (109);

(R)-(2-(2-methoxy-7-methylquinoxalin-5-yl)-7,8-dihydro-[1,4]dioxino[2',3':3,4]benzo[1,2-d]thiazol-7-yl) methyl (6-vinylpyridin-3-yl)carbamate 110);

((R)-2-(2-methoxy-7-methylquinoxalin-5-yl)-7,8-dihydro-[1,4]dioxino[2',3':3,4]benzo [1,2-d]thiazol-7-yl)methyl (6-((S)-1,2-dihydroxyethyl)pyridin-3-yl)carbamate (111);

(R)-(2-(2-methoxy-7-methylquinoxalin-5-yl)-7,8-dihydro-[1,4]dioxino[2',3':3,4]benzo[1,2-d]thiazol-7-yl)methyl (6-fluoropyridin-3-yl)carbamate (112);

(R)-(2-(2-methoxy-7-methylquinoxalin-5-yl)-7,8-dihydro-[1,4]dioxino[2',3':3,4]benzo[1,2-d]thiazol-7-yl)methyl (5-cyanopyridin-3-yl)carbamate (113);

(R)-(2-(2-methoxy-7-methylquinoxalin-5-yl)-7,8-dihydro-[1,4]dioxino[2',3':3,4]benzo [1,2-d]thiazol-7-yl)methyl (4-(morpholine-4-carbonyl)phenyl)carbamate (114);

(2-(2-methoxy-7-methylquinoxalin-5-yl)-4-methyl-7,8-dihydro-[1,4]dioxino[2',3':3,4]ben zo [1,2-d]thiazol-7-yl)methyl (6-chloropyridin-3-yl)carbamate (115);

(2-(2-methoxy-7-methylquinoxalin-5-yl)-4-methyl-7,8-dihydro-[1,4]dioxino[2',3':3,4]ben zo[1,2-d]thiazol-7-yl) methyl (6-(dimethylamino)pyridin-3-yl)carbamate (116);

(2-(2-methoxy-7-methylquinoxalin-5-yl)-4-methyl-7,8-dihydro-[1,4]dioxino[2',3':3,4]ben zo[1,2-d]thiazol-7-yl) methyl (2-phenylpyridin-4-yl)carbamate (117);

(2-(2-methoxy-7-methylquinoxalin-5-yl)-4-methyl-7,8-dihydro-[1,4]dioxino[2',3':3,4]ben zo[1,2-d]thiazol-7-yl) methyl (2-fluoropyridin-4-yl)carbamate (118);

(2-(2-methoxy-7-methylquinoxalin-5-yl)-4-methyl-7,8-dihydro-[1,4]dioxino[2',3':3,4]ben zo[1,2-d]thiazol-7-yl) methyl (5,6-dimethylpyridin-3-yl)carbamate (119);

(2-(2-methoxy-7-methylquinoxalin-5-yl)-4-methyl-7,8-dihydro-[1,4]dioxino[2',3':3,4]ben zo[1,2-d]thiazol-7-yl) methyl (6-methylpyridin-3-yl)carbamate (120);

(2-(2-methoxy-7-methylquinoxalin-5-yl)-4-methyl-7,8-dihydro-[1,4]dioxino [2',3':3,4]benzo[1,2-d]thiazol-7-yl) methyl (6-phenoxypyridin-3-yl)carbamate (121);

(2-(2-methoxy-7-methylquinoxalin-5-yl)-4-methyl-7,8-dihydro-[1,4]dioxino[2',3':3,4]ben zo [1,2-d]thiazol-7-yl) methyl (6-fluoro-5-methylpyridin-3-yl)carbamate (122);

(2-(2-methoxy-7-methylquinoxalin-5-yl)-4-methyl-7,8-dihydro-[1,4]dioxino[2',3':3,4]ben zo [1,2-d]thiazol-7-yl) methyl (6-hydroxypyridin-3-yl)carbamate (123);

(2-(2-methoxy-7-methylquinoxalin-5-yl)-4-methyl-7,8-dihydro-[1,4]dioxino[2',3':3,4]ben zo[1,2-d]thiazol-7-yl) methyl (5-methylpyridin-3-yl)carbamate (124);

(2-(2-methoxy-7-methylquinoxalin-5-yl)-4-methyl-7,8-dihydro-[1,4]dioxino[2',3':3,4]ben zo[1,2-d]thiazol-7-yl) methyl (6-phenylpyridin-3-yl)carbamate (125);

(2-(2-methoxy-7-methylquinoxalin-5-yl)-4-methyl-7,8-dihydro-[1,4]dioxino[2',3':3,4]ben zo[1,2-d]thiazol-7-yl) methyl (5-phenylpyridin-3-yl)carbamate (126);

(2-(2-methoxy-7-methylquinoxalin-5-yl)-4-methyl-7,8-dihydro-[1,4]dioxino[2',3':3,4]benzo[1,2-d]thiazol-7-yl) methyl (6-(thiophen-2-yl)pyridin-3-yl) carbamate (127);

(2-(2-methoxy-7-methylquinoxalin-5-yl)-4-methyl-7,8-dihydro-[1,4]dioxino[2',3':3,4]benzo[1,2-d]thiazol-7-yl) methyl (6-(2-(dimethylamino)ethoxy) pyridin-3-yl)carbamate (128);

(2-(2-methoxy-7-methylquinoxalin-5-yl)-4-methyl-7,8-dihydro-[1,4]dioxino[2',3':3,4]ben zo[1,2-d]thiazol-7-yl) methyl (3-methyl-3H-imidazo [4,5-b] pyridin-6-yl)carbamate (129);

(2-(2-methoxy-7-methylquinoxalin-5-yl)-4-methyl-7,8-dihydro-[1,4]dioxino[2',3':3,4]ben zo[1,2-d]thiazol-7-yl) methyl (6-(3-methyl-1H-1,2,4-triazol-1-yl)pyridin-3-yl) carbamate (130);

(2-(2-methoxy-7-methylquinoxalin-5-yl)-4-methyl-7,8-dihydro-[1,4]dioxino[2',3':3,4]ben zo[1,2-d]thiazol-7-yl) methyl (6-(trifluoromethyl)pyridin-3-yl)carbamate (131);

(2-(2-methoxy-7-methylquinoxalin-5-yl)-4-methyl-7,8-dihydro-[1,4]dioxino[2',3':3,4]ben zo[1,2-d]thiazol-7-yl) methyl (5-chloropyridin-3-yl)carbamate (132);

(2-(2-methoxy-7-methylquinoxalin-5-yl)-4-methyl-7,8-dihydro-[1,4]dioxino[2',3':3,4]ben zo[1,2-d]thiazol-7-yl) methyl (6-ethoxypyridin-3-yl)carbamate (133); methyl 4-(((((2-(2-methoxy-7-methylquinoxalin-5-yl)-4-methyl-7, 8-dihydro-[1,4]dioxino[2',3':3,4]benzo[1,2-d]thiazol-7-yl)methoxy)carbonyl)amino) picolinate (134);

(2-(2-methoxy-7-methylquinoxalin-5-yl)-4-methyl-7,8-dihydro-[1,4]dioxino[2',3':3,4]benzo[1,2-d]thiazol-7-yl) methyl (5-methylpyridin-3-yl)carbamate (135);

tert-butyl 4-(5-(((((2-(2-methoxy-7-methylquinoxalin-5-yl)-4-methyl-7,8-dihydro-[1,4]dioxino[2',3':3,4]benzo[1,2-d]thiazol-7-yl)methoxy)carbonyl)amino)pyridin-2-yl) piperazine-1-carboxylate (136);

(2-(2-methoxy-7-methylquinoxalin-5-yl)-4-methyl-7,8-dihydro-[1,4]dioxino[2',3':3,4]ben zo[1,2-d]thiazol-7-yl)methyl (6-(pyrrolidin-1-yl) pyridin-3-yl)carbamate (137); methyl
5-((((2-(2-methoxy-7-methylquinoxalin-5-yl)-4-methyl-7,8-dihydro-[1,4]dioxino[2',3':3,4]benzo[1,2-d]thiazol-7-yl)methoxy)carbonyl) amino)nicotinate (138); tert-butyl
3-((((2-(2-methoxy-7-methylquinoxalin-5-yl)-4-methyl-7,8-dihydro-[1,4]dioxino[2',3':3,4]benzo[1,2-d]thiazol-7-yl)methoxy)carbonyl) amino)-7,8-dihydro-1,6-naphthyridine-6(5H)-carboxylate (139);
(2-(2-methoxy-7-methylquinoxalin-5-yl)-4-methyl-7,8-dihydro-[1,4]dioxino[2',3':3,4]ben zo[1,2-d]thiazol-7-yl)methyl (6-acetamidopyridin-3-yl)carbamate (140);
(2-(2-methoxy-7-methylquinoxalin-5-yl)-4-methyl-7,8-dihydro-[1,4]dioxino[2',3':3,4]ben zo[1,2-d]thiazol-7-yl)methyl (6-aminopyridin-3-yl)carbamate (141); and
(2-(2-methoxy-7-methylquinoxalin-5-yl)-4-methyl-7,8-dihydro-[1,4]dioxino[2',3':3,4]ben zo[1,2-d]thiazol-7-yl)methyl 1H-pyrrolo[2,3-b]pyridin-5-ylcarbamate (142).

One embodiment provides a compound or a salt thereof selected from
(R)-(6-chloro-8-(2-methoxy-7-methylquinoxalin-5-yl)-2,3-dihydro-[1,4]dioxino[2,3-e]benzofuran-3-yl)methyl (6-methylpyridin-3-yl)carbamate (7);
(R)-(6-chloro-8-(2-methoxy-7-methylquinoxalin-5-yl)-2,3-dihydro-[1,4]dioxino[2,3-e]be nzofuran-3-yl) methyl (2-methylpyridin-4-yl)carbamate (8);
(R)-(6-chloro-8-(2-methoxy-7-methylquinoxalin-5-yl)-2,3-dihydro-[1,4]dioxino[2,3-e]be nzofuran-3-yl)methyl (6-methoxypyridin-3-yl) carbamate (9);
(R)-(6-chloro-8-(2-methoxy-7-methylquinoxalin-5-yl)-2,3-dihydro-[1,4]dioxino[2,3-e]benzofuran-3-yl)methyl pyridin-3-ylcarbamate (10);
(R)-(8-(2-methoxy-7-methylquinoxalin-5-yl)-2,3-dihydro-[1,4]dioxino[2,3-e]benzofuran-3-yl)methyl (6-methylpyridin-3-yl)carbamate (11);
(R)-(8-(2-methoxy-7-methylquinoxalin-5-yl)-2,3-dihydro-[1,4]dioxino[2,3-e]benzofuran-3-yl)methyl (2-methylpyridin-4-yl)carbamate (12);
(R)-(8-(2-methoxy-7-methylquinoxalin-5-yl)-2,3-dihydro-[1,4]dioxino[2,3-e]benzofuran-3-yl)methyl (6-methoxypyridin-3-yl)carbamate (13);
(R)-(8-(2-methoxy-7-methylquinoxalin-5-yl)-6-methyl-2,3-dihydro-[1,4]dioxino [2,3-e]benzofuran-3-yl)methyl (6-methylpyridin-3-yl)carbamate (14);
(R)-(8-(2-methoxy-7-methylquinoxalin-5-yl)-6-methyl-2,3-dihydro-[1,4]dioxino[2,3-e]be nzofuran-3-yl) methyl (2-methylpyridin-4-yl) carbamate (15); and
(R)-(8-(2-methoxy-7-methylquinoxalin-5-yl)-6-methyl-2,3-dihydro-[1,4]dioxino[2,3-e]benzofuran-3-yl) methyl (6-methoxypyridin-3-yl)carbamate (16).

One embodiment provides 6-(2-(methoxymethyl)-7-methylquinoxalin-5-yl)-[1,3]dioxolo[4',5':4,5]benzo[1,2-d]thiaz ole (143).

One embodiment provides
1-(7-(2-methoxy-7-methylquinoxalin-5-yl)-[1,3]dioxolo[4',5':3,4]benzo[1,2-d]thiazol-5-yl)-2,2-dimethylpropan-1-ol (263).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group —NH$_2$.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "aminoalkyl" as used herein is intended to include both branched and straight-chain saturated aliphatic hydrocarbon groups substituted with one or more amino groups. For example, "$C_{1-4}$ aminoalkyl" is intended to include $C_1$, $C_2$, $C_3$, and $C_4$ alkyl groups substituted with one or more amino groups. Representative examples of aminoalkyl groups include, but are not limited to, —$CH_2NH_2$, —$CH_2CH_2NH_2$, and —$CH_2CH(NH_2)CH_3$.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and $C_{1-4}$ hydroxyalkyl.

The term "hydroxy-deuteroalkyl" includes both branched and straight-chain saturated alkyl groups substituted with one or more hydroxyl groups and one or more deuterium atoms. Representative examples of hydroxy-deuteroalkyl groups include, but are not limited to, —$CD_2OH$ and —$CH(CD_3)_2OH$.

The term "hydroxy-fluoroalkyl" includes both branched and straight-chain saturated alkyl groups substituted with one or more hydroxyl groups and one or more fluorine atoms. Representative examples of hydroxy-fluoroalkyl groups include, but are not limited to, —$CF_2OH$ and —$CF_2CH_2OH$.

As used herein, "alkylene" refers to a bivalent alkyl radical having the general formula —$(CH_2)n$-, where n is 1 to 10. Non-limiting examples include methylene, dimethylene, trimethylene, tetramethylene, pentamethylene, and hexamethylene. For example, "$C_{1-6}$ alkylene" denotes straight and branched chain alkylene groups with one to six carbon atoms. Further, for example, "$C_{0-4}$ alkylene" denotes a bond and straight and branched chain alkylene groups with one to four carbon atoms.

As used herein, "deuteroalkylene" refers to an alkylene group in which one or more hydrogen atoms have been replaced with deuterium atoms. For example, "$C_{1-6}$ deuteroalkylene" denotes straight and branched chain deuteroalkylene groups with one to six carbon atoms.

As used herein, "fluoroalkylene" refers to an alkylene group substituted with one or more fluorine atoms. For example, "$C_{1-6}$ fluoroalkylene" denotes straight and branched chain fluoroalkylene groups with one to six carbon atoms.

The term "alkenyl" refers to a straight or branched chain hydrocarbon radical containing from 2 to 12 carbon atoms and at least one carbon-carbon double bond. Exemplary such groups include ethenyl or allyl. For example, "$C_{2-6}$ alkenyl" denotes straight and branched chain alkenyl groups with two to six carbon atoms.

The term "alkynyl" refers to a straight or branched chain hydrocarbon radical containing from 2 to 12 carbon atoms and at least one carbon to carbon triple bond. Exemplary such groups include ethynyl. For example, "$C_{2-6}$ alkynyl" denotes straight and branched chain alkynyl groups with two to six carbon atoms.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "fluorocycloalkyl" refers to a cycloalkyl group in which one or more hydrogen atoms are replaced by fluoro group(s).

The term "cycloalkylalkylene" refers to a cycloalkyl group attached through an alkylene group to the patent molecular moiety. For example, "($C_{3-6}$ cycloalkyl)-($C_{0-2}$ alkylene)" denotes a $C_{3-6}$ cycloalkyl group attached through a bond or a $C_{1-2}$ alkylene to the parent molecular moiety.

The term "alkoxy," as used herein, refers to an alkyl group attached to the parent molecular moiety through an oxygen atom, for example, methoxy group (—$OCH_3$). For example, "$C_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "hydroxyalkoxy" represent a hydroxyalkyl group as defined above attached through an oxygen linkage (—O—). For example, "$C_{1-4}$ hydroxyalkoxy" is intended to include $C_1$, $C_2$, $C_3$, and $C_4$ hydroxyalkoxy groups.

The term "cycloalkoxy," as used herein, refers to a cycloalkyl group attached to the parent molecular moiety through an oxygen atom, for example, cyclopropoxy group (—O(cyclopropyl)).

The term "alkoxyalkoxy" as used herein, refers to an alkoxy group attached through an alkoxy group to the patent molecular moiety. For example, "($C_{1-3}$ alkoxy)-($C_{1-6}$ alkoxy)" denotes a $C_{1-3}$ alkoxy group attached through a $C_{1-6}$ alkoxy group to the parent molecular moiety.

The term "alkoxyalkylene" as used herein, refers to an alkoxy group attached through an alkylene group to the patent molecular moiety. For example, "($C_{1-3}$ alkoxy)-($C_{1-3}$ alkylene)" denotes a $C_{1-3}$ alkoxy group attached through a $C_{1-3}$ alkylene to the parent molecular moiety.

The term "fluoroalkoxyalkylene" as used herein, refers to a fluoroalkoxy group attached through an alkylene group. For example, "($C_{1-2}$ fluoroalkoxy)-($C_{1-2}$ alkylene)" denotes a $C_{1-2}$ fluoroalkoxy group attached through a $C_{1-2}$ alkylene to the parent molecular moiety.

The term "alkoxy-fluoroalkylene" as used herein, refers to an alkoxy group attached through a fluoroalkylene group to the patent molecular moiety. For example, "($C_{1-3}$ alkoxy)-($C_{1-3}$ fluoroalkylene)" denotes a $C_{1-3}$ alkoxy group attached through a $C_{1-3}$ fluoroalkylene to the parent molecular moiety.

The term "deuteroalkoxy-deuteroalkylene" as used herein, refers to a deuteroalkoxy group attached through a deuteroalkylene group to the patent molecular moiety. For example, "($C_{1-3}$ deuteroalkoxy)-($C_{1-3}$ deuteroalkylene)" denotes a $C_{1-3}$ deuteroalkoxy group attached through a $C_{1-3}$ deuteroalkylene to the parent molecular moiety.

The term "alkylthio," as used herein, refers to an alkyl group attached to the parent molecular moiety through a sulfur atom, for example, methylthio group (—SCH$_3$). For example, "C$_{1-3}$ alkylthio" denotes alkylthio groups with one to three carbon atoms.

The term "aryl," as used herein, refers to a group of atoms derived from a molecule containing aromatic ring(s) by removing one hydrogen that is bonded to the aromatic ring(s). Representative examples of aryl groups include, but are not limited to, phenyl, naphthyl, indanyl, indenyl, and 1,2,3,4-tetrahydronaphth-5-yl. The aryl ring may be unsubstituted or may contain one or more substituents as valence allows.

The term "benzyl," as used herein, refers to a methyl group in which one of the hydrogen atoms is replaced by a phenyl group. The phenyl ring may be unsubstituted or may contain one or more substituents as valence allows.

The term "aryloxy," as used herein, refers to an aryl group attached through an oxygen group.

The term "phenoxy," as used herein, refers to a phenyl group attached through an oxygen group (—O-phenyl). The phenyl ring may be unsubstituted or may contain one or more substituents as valence allows.

The term "heteroatom" refers to oxygen (O), sulfur (S), and nitrogen (N).

The term "heterocyclo" or "heterocyclyl" may be used interchangeably and refer to non-aromatic 3- to 7-membered monocyclic groups and 6- to 11-membered bicyclic groups, in which at least one of the rings has at least one heteroatom (O, S or N), said heteroatom containing ring preferably having 1 to 3 heteroatoms independently selected from O, S, and/or N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic group may contain only carbon atoms and may be saturated, partially saturated, or unsaturated. The heterocyclo group may be attached at any available nitrogen or carbon atom. The heterocyclo ring may be unsubstituted or may contain one or more substituents as valence allows.

Exemplary monocyclic heterocyclyl groups include oxetanyl, azetidinyl, pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl. Exemplary bicyclic heterocyclo groups include quinuclidinyl.

The term "heteroaryl" refers to substituted and unsubstituted aromatic 5- or 6-membered monocyclic groups and 9- or 10-membered bicyclic groups which have at least one heteroatom (O, S or N) in at least one of the rings, said heteroatom-containing ring preferably having 1, 2, or 3 heteroatoms independently selected from O, S, and/or N.

Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridinyl, furopyridinyl, dihydroisoindolyl, and tetrahydroquinolinyl.

The term "heteroaryloxy," as used herein, refers to a heteroaryl group attached through an oxygen group to the patent molecular moiety.

The term "arylalkylene" refers to an aryl group attached through an alkylene group to the patent molecular moiety. For example, "aryl(C$_{1-2}$ alkylene)" refers to an aryl group attached through a C$_{1-2}$ alkylene to the parent molecular moiety.

The term "heteroarylalkylene" refers to a heteroaryl group attached through an alkylene group to the patent molecular moiety. For example, "heteroaryl(C$_{1-2}$ alkylene)" refers to a heteroaryl group attached through a C$_{1-2}$ alkylene to the parent molecular moiety.

The term "aryloxyalkylene" refers to an aryloxy group attached through an alkylene group to the patent molecular moiety. For example, "aryloxy-(C$_{1-2}$ alkylene)" refers to an aryloxy group attached through a C$_{1-2}$ alkylene to the parent molecular moiety.

The term "heteroaryloxyalkylene" refers to a heteroaryloxy group attached through an alkylene group to the patent molecular moiety. For example, "heteroaryloxy-(C$_{1-2}$ alkylene)" refers to a heteroaryloxy group attached through a C$_{1-2}$ alkylene to the parent molecular moiety.

The compounds of the present invention can be provided as amorphous solids or crystalline solids. Lyophilization can be employed to provide the compounds as amorphous solids.

It should further be understood that solvates (e.g., hydrates) of the Compounds of Formulas (I) to (VIII) are also within the scope of the present invention. The term "solvate" means a physical association of a compound of Formulas (I) to (VIII) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates.

Exemplary solvates include hydrates, ethanolates, methanolates, isopropanolates, acetonitrile solvates, and ethyl acetate solvates. Methods of solvation are known in the art.

In addition, compounds of Formulas (I) to (VIII), subsequent to their preparation, can be isolated and purified to obtain a composition containing an amount by weight equal to or greater than 99% of a compound of Formulas (I) to (VIII) ("substantially pure"), which is then used or formulated as described herein. Such "substantially pure" compounds of Formulas (I) to (VIII) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as —$CD_3$.

Biology

The term "PAR4 antagonist" denotes an inhibitor of platelet aggregation which binds PAR4 and inhibits PAR4 cleavage and/or signaling. Typically, PAR4 activity is reduced in a dose dependent manner by at least 10%, 20%, 30%, 40%, 50%, 60%, 70%, 80%, 90%, or 100% compared to such activity in a control cell. The control cell is a cell that has not been treated with the compound. PAR4 activity is determined by any standard method in the art, including those described herein (for example calcium mobilization in PAR4 expressing cells, platelet aggregation, platelet activation assays measuring e.g., calcium mobilization, P-selectin or $CD_{40}L$ release, or thrombosis and hemostasis models). In certain embodiments, platelet activation is measured by changes in the platelet cytoplasm, by changes of the platelet membrane, by changes in the levels of analytes released by platelets, by the changes in the morphology of the platelet, by the ability of platelets to form thrombi or platelet aggregates in flowing or stirred whole blood, by the ability of platelets to adhere to a static surface which is derivatized with relevant ligands (e.g., von Willebrand Factor, collagen, fibrinogen, other extracellular matrix proteins, synthetic fragments of any of the proteins, or any combination thereof), by changes in the shape of the platelets, or any combinations thereof. In one embodiment, platelet activation is measured by changes in the levels of one or more analytes released by platelets. For example, the one or more analytes released by platelets can be P-selectin (CD62p), CD63, ATP, or any combination thereof. In a particular embodiment, platelet activation is measured by the level of binding of fibrinogen or GPIIbIIIa antibodies to platelets. In other embodiments, platelet activation is measured by the degree of phosphorylation of vasodilator-stimulated phosphoprotein (VASP) upon platelet activation. In yet other embodiments, platelet activation is measured by the level of platelet-leukocyte aggregates. In certain embodiments, platelet activation is measured by proteomics profiling. The term "PAR4 antagonist" also includes a compound that inhibits both PAR1 and PAR4.

Preferably, compounds of the invention have $IC_{50}$ values in the PAR4 FLIPR Assay (described hereinafter) of about 10 μM, preferably 1 μM or less, more preferably 100 nM or less, and even more preferably 10 nM or less. PAR4 FLIPR assay data for compounds of the present invention is presented in the Table.

In some embodiments, the present invention provides a pharmaceutical composition, which includes a pharmaceutically acceptable carrier and a therapeutically effective amount of a compound of Formulas (I), (II), (III), (IV), (V), (VI), (VII), or (VIII), preferably, a compound selected from one of the examples, more preferably, Examples 1 to 292, or stereoisomers, tautomers, pharmaceutically acceptable salts, or solvates thereof, alone or in combination with another therapeutic agent.

In some embodiments, the present invention provides a pharmaceutical composition which further includes another therapeutic agent(s). In a preferred embodiment, the present invention provides a pharmaceutical composition, wherein the additional therapeutic agent(s) are an anti-platelet agent or a combination thereof. Preferably, the anti-platelet agent(s) are P2Y12 antagonists and/or aspirin. Preferably, the P2Y12 antagonists are clopidogrel, ticagrelor, or prasugrel. In another preferred embodiment, the present invention provides a pharmaceutical composition, wherein the additional therapeutic agent(s) are an anticoagulant or a combination thereof. Preferably, the anticoagulant agent(s) are a FXa inhibitor, a thrombin inhibitor, or a FXIa inhibitor. Preferably, the FXa inhibitors are apixaban, rivaroxaban, edoxaban, or betrixaban. Preferably, the thrombin inhibitor is dabigatran.

It is desirable to find compounds with advantageous and improved characteristics compared with known anti-platelet agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; (h) improved therapeutic index with less propensity for bleeding; and (h) factors that improve manufacturing costs or feasibility.

As used herein, the term "patient" encompasses all mammalian species.

As used herein, the term "subject" refers to any human or nonhuman organism that could potentially benefit from treatment with a PAR4 antagonist. Exemplary subjects include human beings of any age with risk factors for cardiovascular disease, or patients that have already experienced one episode of cardiovascular disease. Common risk factors include, but are not limited to, age, male sex, hypertension, smoking or smoking history, elevation of triglycerides, elevation of total cholesterol or LDL cholesterol.

In some embodiments, the subject is a species having a dual PAR1/PAR4 μlatelet receptor repertoire. As used herein, the term "dual PAR1/PAR4 μlatelet receptor repertoire" means that a subject expresses PAR1 and PAR4 in platelets or their precursors. Exemplary subjects having a dual PAR1/PAR4 μlatelet receptor repertoire include human beings, non-human primates, and guinea pigs.

In other embodiments, the subject is a species having a dual PAR3/PAR4 μlatelet receptor repertoire. As used herein, the term "dual PAR3/PAR4 μlatelet receptor repertoire" means that a subject expresses PAR3 and PAR4 in platelets or their precursors. Exemplary subjects having a dual PAR3/PAR4 μlatelet receptor repertoire include rodents and rabbits.

As used herein, "treating" or "treatment" cover the treatment of a disease-state in a mammal, particularly in a human, and include: (a) inhibiting the disease-state, i.e., arresting its development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit and/or antagonize PAR4 and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi) within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, atrial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, atrial fibrillation is frequently associated with thromboembolic disorders. Risk factors for atrial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population. (Levitan, N. et al., *Medicine* (Baltimore), 78(5):285-291 (1999); Levine M. et al., *N. Engl. J. Med.*, 334(11):677-681 (1996); Blom, J. W. et al., *JAMA*, 293(6):715-722 (2005)). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and anti-angiogenic drugs. Thus, it is common clinical practice to dose patients having advanced tumors with heparin or low molecular heparin to prevent thromboembolic disorders. A number of low molecular weight heparin preparations have been approved by the FDA for these indications.

The term "pharmaceutical composition," as used herein, means any composition, which contains at least one therapeutically or biologically active agent and is suitable for administration to the patient. Any of these formulations can be prepared by well-known and accepted methods of the art. See, for example, Gennaro, A. R., ed., *Remington: The Science and Practice of Pharmacy*, 20th Edition, Mack Publishing Co., Easton, Pa. (2000).

The invention includes administering to a subject a pharmaceutical composition that includes a compound that binds to PAR4 and inhibits PAR4 cleavage and/or signaling (referred to herein as a "PAR4 antagonist" or "therapeutic compound").

The pharmaceutical composition is administered using methods known in the art. Preferably, the compound is administered orally, rectally, nasally, by inhalation, topically or parenterally, e.g., subcutaneously, intraperitoneally, intramuscularly, and intravenously. The compound is optionally formulated as a component of a cocktail of therapeutic drugs to treat a thromboembolic disorder. In one embodiment, the pharmaceutical composition is administered orally.

The therapeutic compounds described herein are formulated into pharmaceutical compositions utilizing conventional methods. For example, a PAR4 antagonist is formulated in a capsule or a tablet for oral administration. Capsules may contain any standard pharmaceutically acceptable materials such as gelatin or cellulose. Tablets may be formulated in accordance with conventional procedures by compressing mixtures of a therapeutic compound with a solid carrier and a lubricant. Examples of solid carriers include starch and sugar bentonite. The compound is administered in the form of a hard shell tablet or a capsule containing a binder, e.g., lactose or mannitol, a conventional filler, and a tableting agent. Other formulations include an ointment, suppository, paste, spray, patch, cream, gel, resorbable sponge, or foam. Such formulations are produced using methods well known in the art. The compositions of the invention are also useful for parenteral administration, such as intravenous, subcutaneous, intramuscular, and intraperitoneal. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The preferred dose of the PAR4 antagonist is a biologically active dose. A biologically active dose is a dose that will inhibit cleavage and/or signaling of PAR4 and have an anti-thrombotic effect. Desirably, the PAR4 antagonist has the ability to reduce the activity of PAR4 by at least 5%, 10%, 20%, 30%, 40%, 50%, 60%, 70%, 80%, 90%, 100%, or more than 100% below untreated control levels. The levels of PAR4 in platelets is measured by any method known in the art, including, for example, receptor binding assay, platelet aggregation, platelet activation assays (e.g., p-selectin expression by FACS), Western blot or ELISA analysis using PAR4 cleavage sensitive antibodies. Alternatively, the biological activity of PAR4 is measured by assessing cellular signaling elicited by PAR4 (e.g., calcium mobilization or other second messenger assays).

In some embodiments, a therapeutically effective amount of a PAR4 compound is preferably from about less than 100 mg/kg, 50 mg/kg, 10 mg/kg, 5 mg/kg, 1 mg/kg, or less than 1 mg/kg. In a more preferred embodiment, the therapeutically effective amount of the PAR4 compound is less than 5 mg/kg. In a most preferred embodiment, the therapeutically effective amount of the PAR4 compound is less than 1 mg/kg. Effective doses vary, as recognized by those skilled in the art, depending on route of administration and excipient usage.

The activity of the PAR4 antagonists of the present invention can be measured in a variety of in vitro assays. Exemplary assays are shown below.

The FLIPR assay is an exemplary in vitro assay for measuring the activity of the PAR4 antagonists of the present invention. In this assay, intracellular calcium mobilization is induced in PAR4 expressing cells by a PAR4 agonist and calcium mobilization is monitored.

AYPGKF is a known PAR4 agonist. An alternative PAR4 agonist is H-Ala-Phe(4-F)-Pro-Gly-Trp-Leu-Val-Lys-Asn-Gy-NH$_2$. As shown in Example B of WO2013/163279, H-Ala-Phe(4-F)-Pro-Gly-Trp-Leu-Val-Lys-Asn-Gly-NH$_2$ was validated as a PAR4 agonist in the FLIPR assay. A side-by-side comparison of the IC$_{50}$ values of ~180 compounds were performed using AYPGKF versus H-Ala-Phe(4-F)-Pro-Gly-Trp-Leu-Val-Lys-Asn-Gy-NH$_2$. The results demonstrated a strong correlation between the two assays. Additionally, H-Ala-Phe(4-F)-Pro-Gly-Trp-Leu-Val-Lys-Asn-Gy-NH$_2$ has improved agonist activity as compared to AYPGKF with an EC$_{50}$ value that is 10 fold lower than the EC$_{50}$ value for AYPGKF in the FLIPR assay. H-Ala-Phe(4-F)-Pro-Gly-Trp-Leu-Val-Lys-Asn-Gy-NH$_2$ can be synthesized using methods well known to those of skill in the art.

The FLIPR assay can also be used as a counterscreen to test agonist activity or PAR1 antagonist activity in a cell line that expresses both PAR1 and PAR4. The PAR1 antagonist activity can be tested by the ability of the compound to inhibit calcium mobilization induced by the PAR1 agonist peptide SFLLRN or other PAR1 agonist peptides.

The compounds of the current invention can be tested in vitro for their ability to inhibit platelet aggregation induced by gamma-thrombin as shown below. Gamma-thrombin, a proteolytic product of alpha-thrombin which no longer interacts with PAR1, selectively cleaves and activates PAR4 (Soslau, G. et al., "Unique pathway of thrombin-induced platelet aggregation mediated by glycoprotein Ib", *J. Biol. Chem.*, 276:21173-21183 (2001)). Platelet aggregation can be monitored in a 96-well microplate aggregation assay format or using standard platelet aggregometer. The aggregation assay can also be employed to test the selectivity of the compound for inhibiting platelet aggregation induced by PAR4 agonist peptides, PAR1 agonist peptide, ADP, or thromboxane analogue U46619.

The compounds of the current invention can be tested in vitro for their ability to inhibit platelet aggregation induced by alpha-thrombin as shown below. Alpha-thrombin activates both PAR1 and PAR4. The ability of a selective PAR4 antagonist of the present invention to inhibit platelet aggregation can be measured using a standard optical aggregometer.

The compounds of the current invention can be tested in vitro for their ability to inhibit platelet aggregation induced by tissue factor as shown below. The conditions in this assay mimic the physiological events during thrombus formation. In this assay, platelet aggregation in human PRP is initiated by the addition of tissue factor and CaCl$_2$. Tissue factor, the initiator of the extrinsic coagulation cascade, is highly elevated in human atherosclerotic plaque. Exposure of blood to tissue factor at the atherosclerotic site triggers a robust generation of thrombin and induces the formation of obstructive thrombi.

The activity of the PAR4 antagonists of the present invention can also be measured in a variety of in vivo assays. Exemplary mammals that can provide models of thrombosis and hemostasis to test the effectiveness of the PAR4 antagonists of the present invention as antithrombotic agents include, but are not limited to, guinea pigs and primates. Relevant efficacy models include, but are not limited to, electrically-induced carotid arterial thrombosis, FeCl$_3$-induced carotid artery thrombosis and arteriovenous-shunt thrombosis. Models of kidney bleeding time, renal bleeding time and other bleeding time measurements can be used to assess the bleeding risk of the antithrombotic agents described in the current invention.

Assays

Materials
1) PAR1 and PAR4 Agonist Peptides

SFFLRR is a known high affinity PAR1 selective agonist peptide. (Reference Seiler, S. M., "Thrombin receptor antagonists", *Seminars in Thrombosis and Hemostasis*, 22(3):223-232 (1996).) The PAR4 agonist peptides AYPGKF and H-Ala-Phe(4-F)-Pro-Gly-Trp-Leu-Val-Lys-Asn-Gly-NH$_2$ were synthesized. H-Ala-Phe(4-F)-Pro-Gly-Trp-Leu-Val-Lys-Asn-Gly-NH$_2$ showed improved PAR4 agonist activity over AYPGKF in the FLIPR assay (EC$_{50}$ value of 8 μM for H-Ala-Phe(4-F)-Pro-Gly-Trp-Leu-Val-Lys-Asn-Gly-NH$_2$ and 60 μM for AYPGKF) and in washed platelet aggregation assay (EC$_{50}$ value of 0.9 μM for H-Ala-Phe(4-F)-Pro-Gly-Trp-Leu-Val-Lys-Asn-Gy-NH$_2$ and 12 μM for AYPGKF).

2) PAR4 Expressing Cells

HEK293 cells stably expressing PAR4 were generated by a standard method of transfection of human PAR4 (F2R$_{23}$) cDNA expression vector and selected based on PAR4 protein expression or mRNA expression. Those cells demonstrated functional responses to PAR4 agonist peptide-induced intracellular calcium elevation using FLIPR® (Fluorometric Imaging Plate Reader; Molecular Devices Corp.). These cells also express endogenous PAR1 and can elicit calcium signal upon stimulation with PAR1 agonist peptide. Therefore, the same cells were also used to determine selectivity against PAR1 and agonist activity for both receptors. Cells from HEK293 PAR4 Clone 1.2A (BMS Arctic ID 383940) were propagated and used for calcium mobilization studies.

3) Preparation of Platelet Rich Plasma (PRP)

Human blood was collected in 3.8% sodium citrate at a ratio of 1 ml per 9 ml blood and centrifuged in a Sorvall® RT6000B centrifuge at 900 revolution per minute (rpm) at room temperature (RT) for 15 minutes. PRP was collected and used for aggregation assay. Refludan (Berlex Labs, Wayne, NJ), a recombinant hirudin, at a final concentration of 1 unit/mL was added to the sample to selectively prevent PAR1 activation induced by residual alpha-thrombin contamination. The remaining blood sample was centrifuged at 2500 rpm at room temperature for 5 minutes to collect platelet-poor plasma (PPP).

4) Preparation of Washed Platelets (WP)

Human blood was collected in ACD (85 mM tri-sodium citrate, 78 mM citric acid, 110 mM D-glucose, pH 4.4) at a ratio of 1.4 ml per 10 ml blood. PRP was isolated by centrifugation at 170 g for 14 minutes and platelets were further pelleted by centrifugation at 1300 g for 6 minutes. Platelets were washed once with 10 ml ACD containing 1 mg/ml bovine serum albumin. Platelets were resuspended at ~2.5×10$^8$/ml in Tyrode's Buffer (137 mM NaCl, 2 mM KCl, 1.0 mM MgCl$_2$, 1 mM CaCl$_2$), 5 mM glucose, 20 mM HEPES pH 7.4).

FLIPR Assay in PAR4-Expressing HEK293 Cells

FLIPR-based calcium mobilization assay in HEK293 cells was used to measure PAR4 antagonism, agonism, and selectivity against PAR1. The activity of the PAR4 antagonists of the present invention were tested in PAR4 expressing cells by monitoring H-Ala-Phe(4-F)-Pro-Gly-Trp-Leu-Val-Lys-Asn-Gy-NH$_2$-induced intracellular calcium mobilization. Counter screens for agonist activity and PAR1 antagonist activity were also performed. Briefly, PAR1/PAR4-expressing HEK293 cells were grown in DMEM (Life Technology, Grand Island, NY) containing 10% heat-inactivated FBS, 1% Penicillin-Streptomycin, 10 μg/mL blasticidin, and 100 μg/mL Zeocin at 37° C. with 5% CO$_2$. Cells were plated overnight prior to the experiment in a black 384-well Purecoat Amine clear bottom plate (Becton Dickinson Biosciences, San Jose, CA) at 10,000 cells/well in 30 μL growth medium and incubated in a humidified chamber at 37° C. with 5% CO$_2$ overnight. Prior to compound addition, the cell medium was replaced with 40 μL of 1× calcium and magnesium-containing Hank's Balanced Saline Solution (HBSS) (with 20 mM HEPES) and 1:1000 diluted fluorescent calcium indicator (Codex Biosolutions, Gaithersburg, MD). After a 30 minute incubation period at 37° C. and a further 30 minute incubation and equilibration period at room temperature, 20 μL test compound (diluted in 1×HBSS buffer) was added at various concentrations at 0.17% dimethyl sulfoxide (DMSO) final concentration. Changes in fluorescence intensity were measured using a Functional Drug Screening System (FDSS, Hamamatsu, Japan) to determine agonist activities. The cells were then incubated for 30 minutes at room temperature followed by addition of 20 μL of agonist peptide for antagonist activity measurement. The PAR4 agonist peptide (H-Ala-Phe(4-F)-Pro-Gly-Trp-Leu-Val-Lys-Asn-Gy-NH$_2$) and the PAR1 agonist peptide (SFFLRR) were routinely tested to ensure a proper response at the EC$_{50}$ value in the assay (~5 μM for PAR4 agonist peptide and ~2 μM for PAR1 agonist peptide). Compound potency was derived from 11-point concentration-response curves.

Gamma Thrombin Induced Platelet Aggregation Assays

The ability of the compounds of the current invention to inhibit platelet aggregation induced by gamma-thrombin was tested in a 96-well microplate aggregation assay format. Briefly, 90 μL of PRP or washed platelets were pre-incubated for 5 minutes at 37° C. with 3-fold serially diluted test compound, which was prepared as a 100-fold stock solution in dimethyl sulfoxide (DMSO). Aggregation was initiated by addition of 10 μL of gamma-thrombin (Haematologic Technologies, Inc. Essex Junction, VT) at 50-100 nM final concentration, which was titrated daily to achieve 80% platelet aggregation. The plate was then placed into a SpectraMax® Plus Plate Reader (Molecular Devices) at 37° C. Platelet aggregation was monitored at a wavelength of 405 nm using a kinetic analysis mode. Prior to the first data collection time point, the plate was shaken for 10 seconds to allow thorough mixing. Data was subsequently collected every 10 seconds for up to 7 minutes total. Data was collected using SoftMax® 5.4.1 software and exported to Microsoft Excel for analysis. The optical density (OD) values at the time point that achieved 75% platelet activation by agonist alone were used for analysis. The OD value from a PRP sample without any treatment served as ODmaximum, and the OD value from a PPP sample containing no platelets served as the ODminimum. Inhibition of platelet aggregation (IPA) was calculated based on the formula: % IPA=(100-100*[ODcompound−ODminimum] /[ODmaximum−ODminimum]). The IC$_{50}$ value of the test compound was calculated by fitting the % IPA values to the one-site concentration response equation: Y=A+(B-A)/{+(C/X)^D]}, using XLfit for 32 bit Excel® Version 2 Build 30 (ID Business Solutions Limited).

The aggregation assays were also employed to test the selectivity of the compound against other platelet receptors by using SFFLRR for PAR1, collagen (Chrono-Log, Havertown, PA) for collagen receptors, ADP for P2Y1 and P2Y12 and U46619 (Cayman Chemical, Ann Arbor, MI) for thromboxane receptors.

Alpha-thrombin Induced Platelet Aggregation Assays

The ability of PAR4 antagonists to inhibit platelet aggregation induced by alpha-thrombin can be tested using human washed platelets. The antagonists are pre-incubated with washed platelets for 20 min. Aggregation is initiated by addition of 1.5 nM alpha-thrombin (Haematologic Technologies, Essex Junction, VT) to 300 l of washed platelets at stirring speed of 1000 rpm. Platelet aggregation is monitored using an Optical Aggregometer (Chrono-Log, Havertown, PA) and the area under the curve (AUC) at 6 min was measured. IC$_{50}$ values are calculated using vehicle control as 0% inhibition.

Tissue Factor-Induced Platelet Aggregation Assay

The ability of PAR1 or PAR4 antagonists to inhibit platelet aggregation induced by endogenous thrombin can be tested in a tissue factor driven aggregation assay. Aggregation is initiated by addition of CaCl$_2$) and recombinant human tissue factor, which results in the generation of thrombin through activation of the coagulation pathway in the plasma. Anticoagulant agents such as corn trypsin inhibitor (Haematologic Technologies, Essex Junction, VT) at 50 μg/ml and PEFABLOC® FG (Centerchem, Norwalk, CT) are also added to the sample to prevent fibrin clot formation during the time of the study. Platelet aggregation is monitored using standard instrumentation including optical aggregometer or impedance aggregometer.

TABLE

| Ex. No. | PAR4 FLIPR assay (IC$_{50}$, nM) | Ex. No. | PAR4 FLIPR assay (IC$_{50}$, nM) |
|---|---|---|---|
| 1 | 1.6 | 147 | 14 |
| 2 | 130 | 148 | 0.7 |
| 3 | 12 | 149 | 1.5 |
| 4 | 0.8 | 150 | 5.4 |
| 5 | 1.8 | 151 | 3.9 |
| 6 | 10 | 152 | 11 |
| 7 | 1.0 | 153 | 2.4 |
| 8 | 1.4 | 154 | 6.3 |
| 9 | 1.8 | 155 | 13 |
| 10 | 8.5 | 156 | 28 |
| 11 | 1.3 | 157 | 0.8 |
| 12 | 3.8 | 158 | ND |
| 13 | 1.2 | 159 | 0.6 |
| 14 | 2.9 | 160 | 0.6 |
| 15 | 3.2 | 161 | 1.1 |
| 16 | 3.0 | 162 | 0.7 |
| 17 | 3.1 | 163 | 160 |
| 18 | 5.7 | 164 | 1.6 |
| 19 | 2.6 | 165 | 1.0 |
| 20 | 3.2 | 166 | 1.1 |
| 21 | 10 | 167 | 3.1 |
| 22 | 8.8 | 168 | 5.0 |
| 23 | 9.4 | 169 | 6.6 |
| 24 | 9.0 | 170 | 5.7 |
| 25 | 25 | 171 | 45 |
| 26 | 10 | 172 | 1.1 |
| 27 | 2.2 | 173 | 1.3 |
| 28 | 480 | 174 | 30 |
| 29 | 2.9 | 175 | 19 |
| 30 | 3.6 | 176 | 6.1 |
| 31 | 0.9 | 177 | 2.8 |
| 32 | 1.8 | 178 | 2.3 |
| 33 | 2.8 | 179 | 2.4 |
| 34 | 3.3 | 180 | 1.6 |
| 35 | 1.4 | 181 | 52 |
| 36 | 1.7 | 182 | 2.6 |
| 37 | 1.5 | 183 | 2.3 |
| 38 | 1.3 | 184 | 1.8 |
| 39 | 18 | 185 | 6.9 |
| 40 | 97 | 186 | 8.8 |
| 41 | 1.6 | 187 | 1.7 |
| 42 | 50 | 188 | 130 |
| 43 | 7.9 | 189 | 11 |
| 44 | 0.8 | 190 | 24 |
| 45 | 1.1 | 191 | 7.1 |
| 46 | 1.0 | 192 | 8.3 |
| 47 | 1.2 | 193 | 5.3 |

| Ex. No. | PAR4 FLIPR assay (IC$_{50}$, nM) | Ex. No. | PAR4 FLIPR assay (IC$_{50}$, nM) |
|---|---|---|---|
| 48 | 25 | 194 | 2.5 |
| 49 | 49 | 195 | 3.5 |
| 50 | 140 | 196 | 1.6 |
| 51 | 16 | 197 | 22 |
| 52 | 2.7 | 198 | 3.1 |
| 53 | 54 | 199 | 71 |
| 54 | 1.6 | 200 | 7.9 |
| 55 | 21 | 201 | 7.8 |
| 56 | 1.0 | 202 | 6.5 |
| 57 | 9.7 | 203 | 2.3 |
| 58 | 8.8 | 204 | 2.3 |
| 59 | 8.3 | 205 | 1.3 |
| 60 | 6.9 | 206 | 370 |
| 61 | 23 | 207 | 2.2 |
| 62 | 1.0 | 208 | 1.1 |
| 63 | 4.3 | 209 | 26 |
| 64 | 2.5 | 210 | 2.9 |
| 65 | 16 | 211 | 1.3 |
| 66 | 1.5 | 212 | 2.1 |
| 67 | 0.6 | 213 | 3.6 |
| 68 | 1.0 | 214 | 26 |
| 69 | 1.7 | 215 | 2.3 |
| 70 | 25 | 216 | 2.1 |
| 71 | 2.9 | 217 | 120 |
| 72 | 7.7 | 218 | 15 |
| 73 | 12 | 219 | 180 |
| 74 | 8.6 | 220 | 38 |
| 75 | 4.9 | 221 | 5.9 |
| 76 | 2.7 | 222 | >500 |
| 77 | 15 | 223 | 5.8 |
| 78 | 8.6 | 224 | 4.0 |
| 79 | 29 | 225 | 0.6 |
| 80 | 33 | 226 | 1.4 |
| 81 | 39 | 227 | 1.3 |
| 82 | 55 | 228 | 190 |
| 83 | 29 | 229 | 20 |
| 84 | 33 | 230 | 6.4 |
| 85 | 15 | 231 | 5.8 |
| 86 | 6.3 | 232 | 3.3 |
| 87 | 2.0 | 233 | 6.6 |
| 88 | 4.4 | 234 | 4.3 |
| 89 | 20 | 235 | 4.1 |
| 90 | 2.7 | 236 | 2.7 |
| 91 | 1.1 | 237 | 40 |
| 92 | 1.4 | 238 | 1.3 |
| 93 | 20 | 239 | 49.0 |
| 94 | 29 | 240 | 32 |
| 95 | 140 | 241 | 8.6 |
| 96 | 12 | 242 | 9.3 |
| 97 | 64 | 243 | 9.7 |
| 98 | 1.4 | 244 | 100 |
| 99 | 2.0 | 245 | 24 |
| 100 | 1.8 | 246 | 5.0 |
| 101 | 2.8 | 247 | 0.7 |
| 102 | 2.3 | 248 | 7.0 |
| 103 | 2.8 | 249 | 1.0 |
| 104 | 1.9 | 250 | 2.3 |
| 105 | 1.6 | 251 | 0.9 |
| 106 | 2.0 | 252 | 88 |
| 107 | 1.7 | 253 | 2.7 |
| 108 | 1.8 | 254 | 0.6 |
| 109 | 2.6 | 255 | 1.4 |
| 110 | 1.6 | 256 | 0.7 |
| 111 | 2.3 | 257 | 50 |
| 112 | 7.1 | 258 | 8.1 |
| 113 | 1.9 | 259 | 1.1 |
| 114 | 1.0 | 260 | 1.0 |
| 115 | 1.4 | 261 | 1.1 |
| 116 | 3.4 | 262 | 2.3 |
| 117 | 1.1 | 263 | 5.7 |
| 118 | 16 | 264 | 15 |
| 119 | 2.1 | 265 | 1.9 |
| 120 | 0.9 | 266 | 2.1 |
| 121 | 8.2 | 267 | 1.8 |
| 122 | 2.5 | 268 | 4.4 |
| 123 | 18 | 269 | 2.7 |
| 124 | 3.2 | 270 | 2.2 |
| 125 | 35 | 271 | 4.9 |
| 126 | 67.0 | 272 | 3.3 |
| 127 | 130 | 273 | 6.4 |
| 128 | 4.0 | 274 | 5.0 |
| 129 | 1.6 | 275 | 12 |
| 130 | 1.5 | 276 | 140 |
| 131 | 2.0 | 277 | 2.3 |
| 132 | 3.9 | 278 | 19 |
| 133 | 150 | 279 | 9.1 |
| 134 | 3.3 | 280 | 2.4 |
| 135 | 1.4 | 281 | 9.0 |
| 136 | 210 | 282 | 36 |
| 137 | 6.1 | 283 | 2.2 |
| 138 | 3.4 | 284 | 2.8 |
| 139 | 2.1 | 285 | 1.5 |
| 140 | 230 | 286 | 1.0 |
| 141 | 170 | 287 | 1.6 |
| 142 | 2.9 | 288 | 2.2 |
| 143 | 5.5 | 289 | 1.8 |
| 144 | 1.2 | 290 | 0.8 |
| 145 | 1.8 | 291 | 59 |
| 146 | 1.1 | 292 | 1.1 |

The following table sets out the results obtained employing various compounds of the invention tested in the FLIPR assay. ND indicates "not determined". Values are reported to at most two significant figures.

Methods of Preparation

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Wuts et al. (Greene's Protective Groups In Organic Synthesis, 4th Edition, Wiley-Interscience (2006).

Compounds of Formula I of this invention can be obtained by palladium catalyzed cross coupling of aryl halides of Formula Ia with organometallic species R$_3$-M as shown in Scheme 1.

Scheme 1

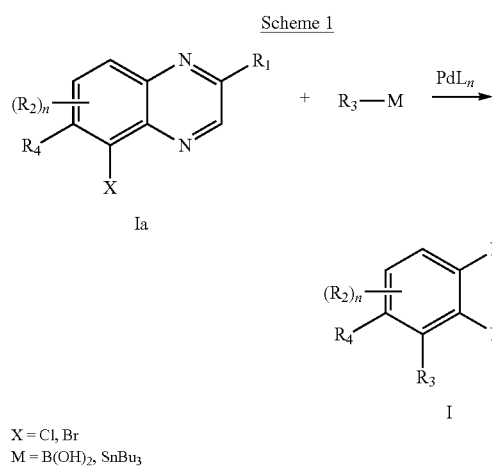

X = Cl, Br
M = B(OH)$_2$, SnBu$_3$

Alternatively, compounds of Formula I can also be prepared from palladium catalyzed cross coupling of arylboronic acids of Formula Ib with halides R$_3$-X shown in Scheme 2.

Scheme 2

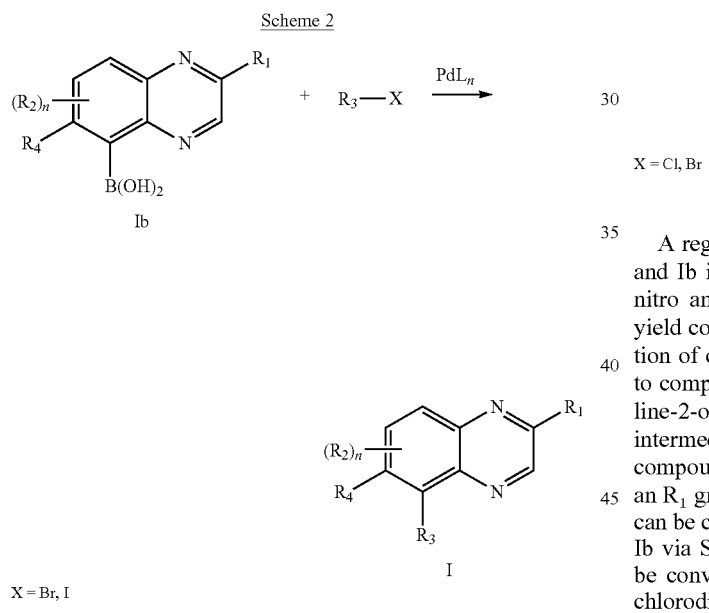

X = Br, I

One way to prepare the quinoxalines of Formula Ia and Ib is through the condensation reaction of the diamine Ic with ketoaldehyde Id, as shown in Scheme 3. In general, the condensation will give two regioisomers that may be separated by chromatography. Structures of Formula Ia can be converted to boronic acid Ib via Suzuki-Miyaura reaction.

Scheme 3

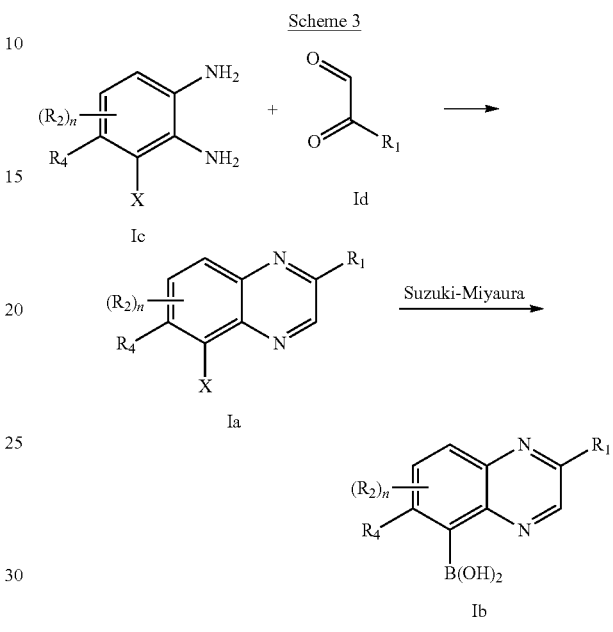

X = Cl, Br

A regio specific synthesis of quinoxalines of Formula Ia and Ib is shown in Scheme 4. A properly protected ortho-nitro aniline Ie is alkylated with methyl bromoacetate to yield compound If Deprotection of compound If and reduction of compound Ig should initiate cyclization to give rise to compound Ih. Compound Ih can be oxidized to quinoxaline-2-one of Formula II, which can be converted to the intermediate Ij with oxophosphorus halides. The halides in compound Ij can be displaced with a nucleophile containing an R$_1$ group to compound Ia, and compounds of Formula Ia can be converted to corresponding boronic acids of Formula Ib via Suzuki-Miyaura reaction. Intermediate Ii could also be converted to Ik by condensation reaction with sodium chlorodifluoroacetate in the presence of a base such as K$_2$CO$_3$. The difluoroalkoxy may be displaced with a nucleophile containing an R$_1$ group to compound Ia.

Scheme 4

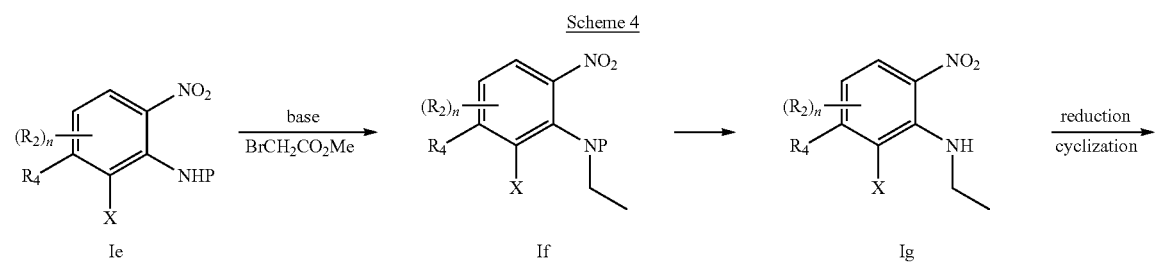

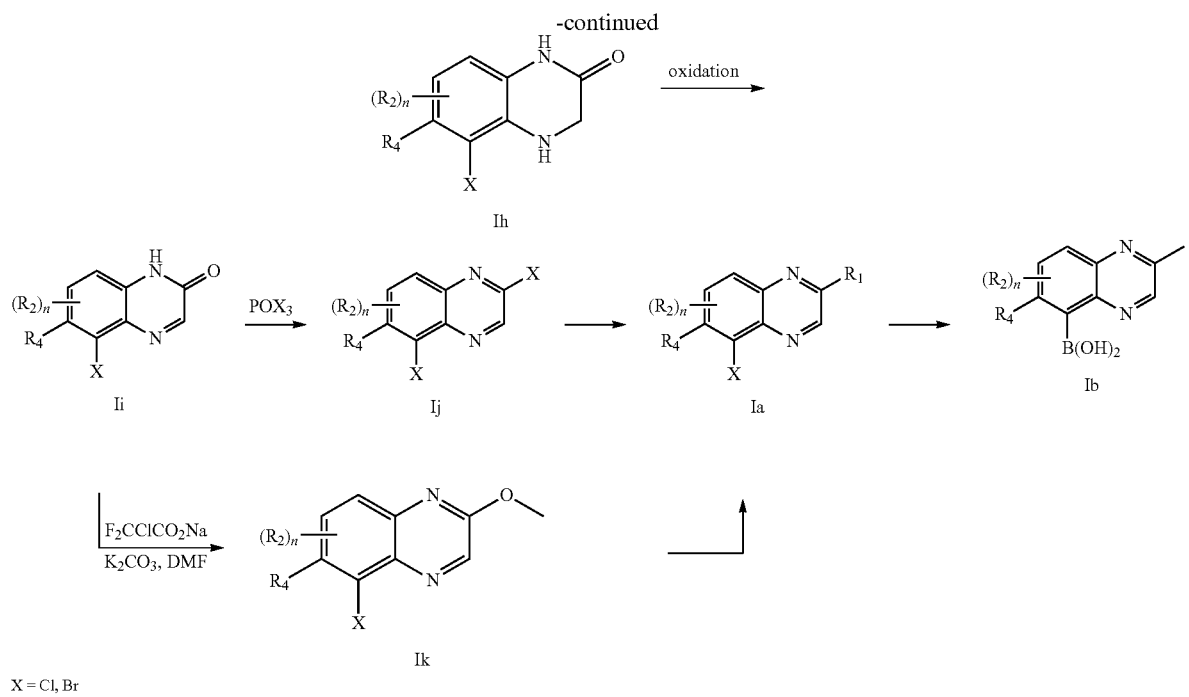

X = Cl, Br

Compounds of Formula II of this invention can be obtained as shown in Scheme 5. Compound IIa can be condensed with dicarbonyl IIb to give compound IIc. Acid catalyzed cyclization provides the key bromide IId. Palladium catalyzed cross coupling reaction with an appropriate boronic acid furnishes compound II.

Scheme 5

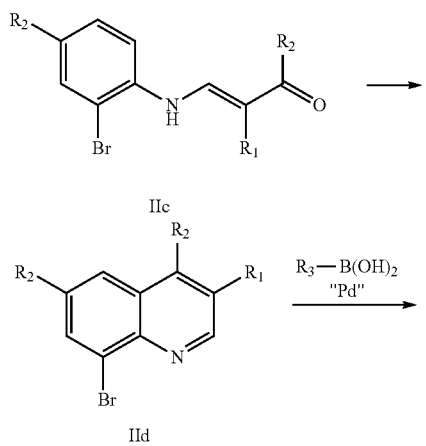

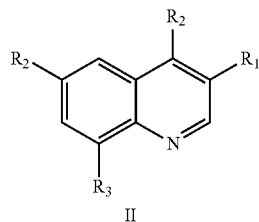

Compounds of Formula III of this invention can be obtained as shown in Scheme 6. Compound IIIa can be condensed with dimethylacetal IIIb to give compound IIIc. Acid catalyzed cyclization and triflate formation provides the key coupling partner IIId. Palladium catalyzed cross coupling reaction with an appropriate boronic acid furnishes the compound of Formula III Scheme 6

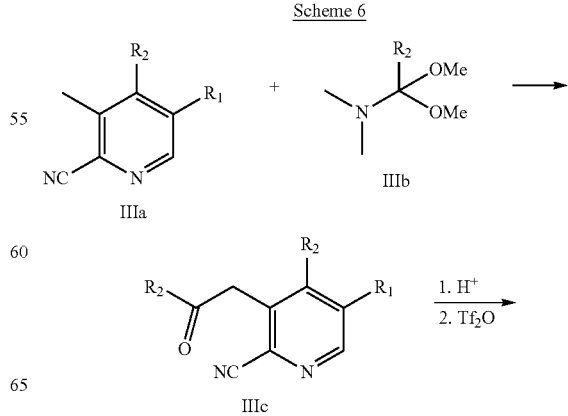

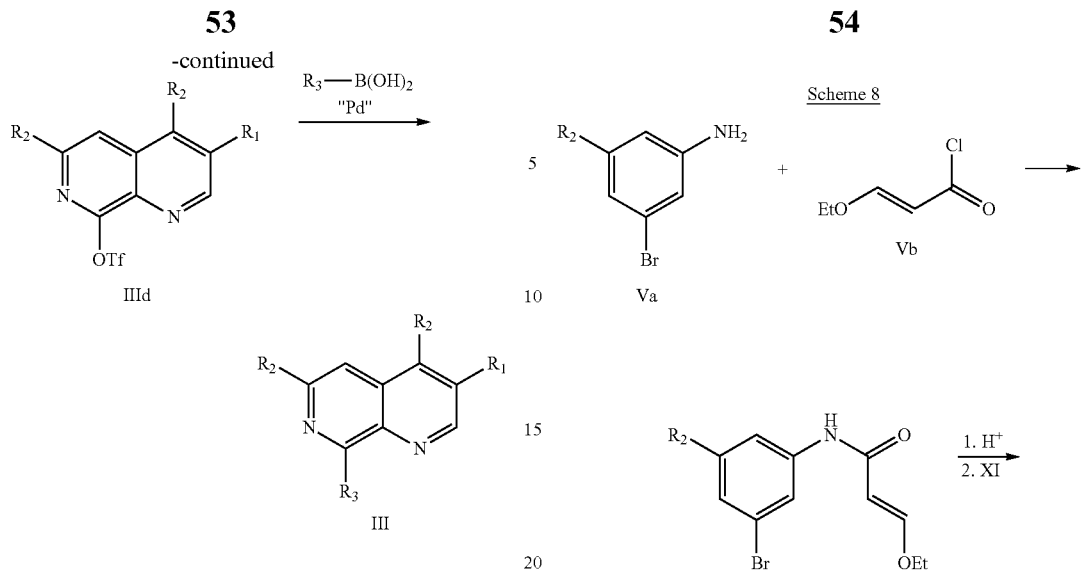

Compounds of Formula IV of this invention can be obtained as shown in Scheme 7. Compound IVa can be condensed with dimethylacetal IVb to give compound IVc. Acid catalyzed cyclization and triflate formation provides the key coupling partner IVd. Palladium catalyzed cross coupling reaction with an appropriate boronic acid furnishes the compound of Formula IV.

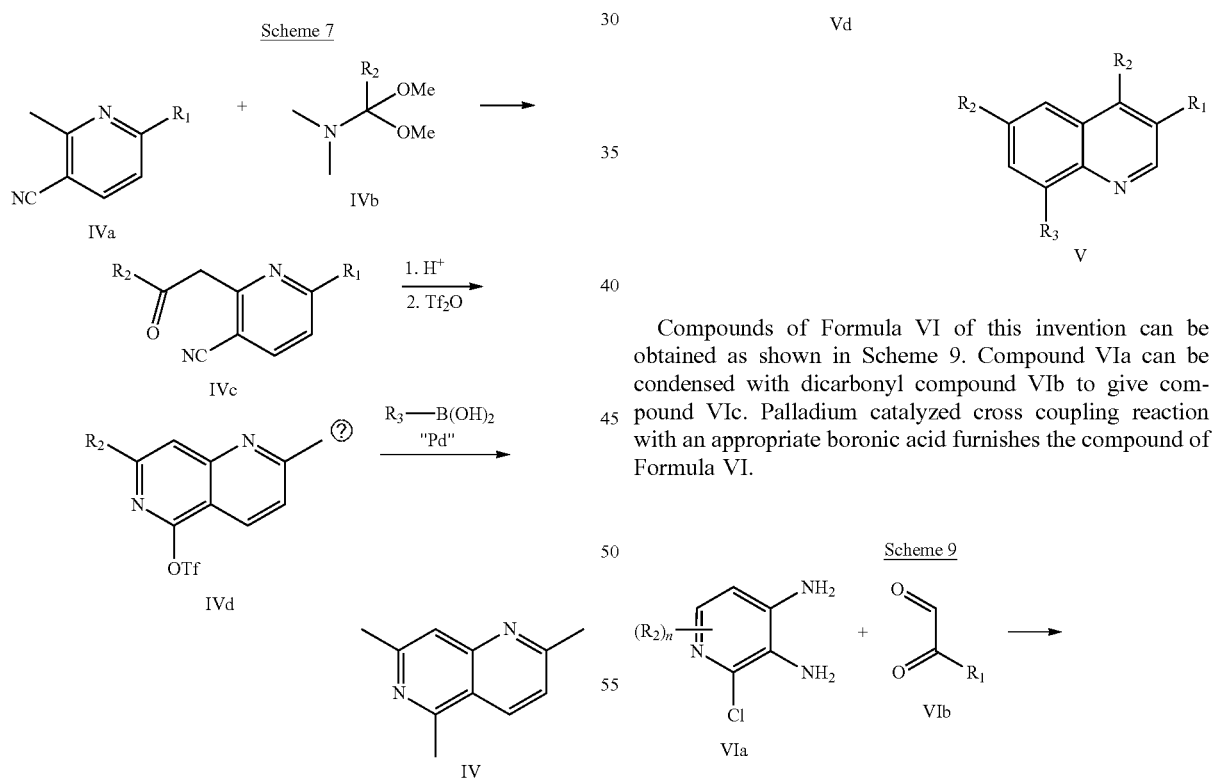

Compounds of Formula V of this invention can be obtained as shown in Scheme 8. Compound Va can be condensed with acid chloride Vb to give compound Vc. Acid catalyzed cyclization and carbonyl alkylation provides the key bromide Vd. Palladium catalyzed cross coupling reaction with an appropriate boronic acid furnishes the compound of Formula V.

Compounds of Formula VI of this invention can be obtained as shown in Scheme 9. Compound VIa can be condensed with dicarbonyl compound VIb to give compound VIc. Palladium catalyzed cross coupling reaction with an appropriate boronic acid furnishes the compound of Formula VI.

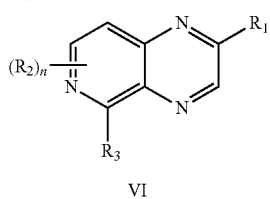

VI

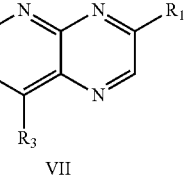

VII

In this invention, compounds of Formula VII can be obtained through the synthetic route shown in Scheme 10. Beginning with aryl chloride VIIa, palladium catalyzed cross coupling of various boronic acids or stannanes yields substituted anilines of structure VIIb. Nitration of compound VIIb and reduction of compound VIIc allows access to compounds of Formula VIId. Base mediated condensation of dianiline VIId with substituted bromo-ketones provides heterocycles of Formula VIIe. A final palladium-catalyzed cross coupling with aryl boronic acids or stannanes then furnishes the compounds of Formula VII.

Compounds of Formula VIII of this invention can be obtained by palladium catalyzed cross coupling of aryl boronic acids or stannanes with aryl chloride VIIIc as shown in Scheme 11. Compound VIIIa can be condensed with amidines to give compound VIIIb. Phosphorul Vlride conversion of compound VIIIb to aryl chloride VIIIc followed by palladium-catalyzed cross coupling with aryl boronic acids or stannanes furnishes the compound of Formula VIII.

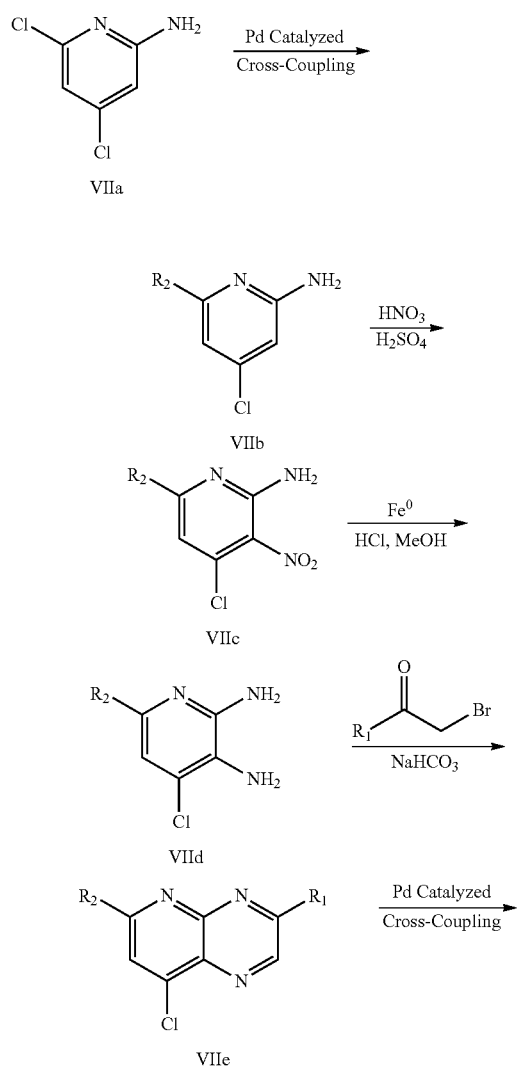

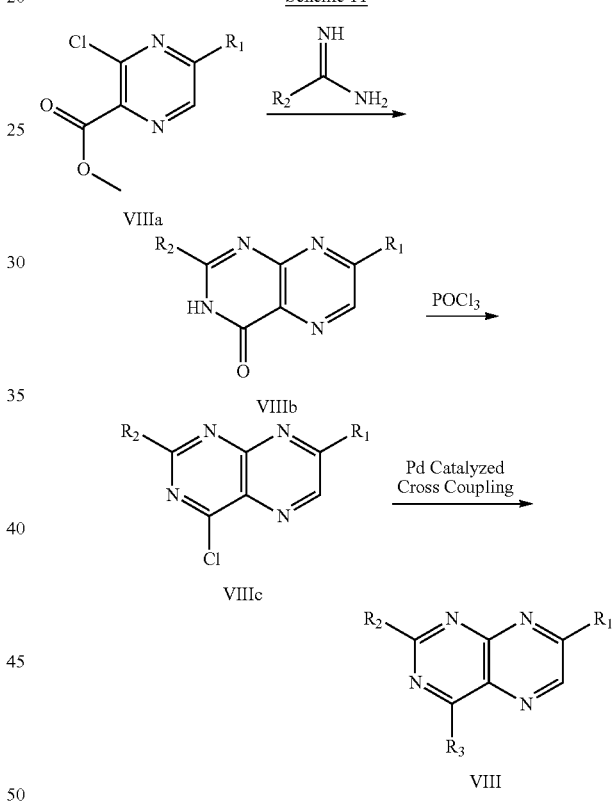

$R_3$-X, in which $R_3$ is a 7,8-dihydro-[1,4]dioxino[2',3':3,4]benzo[1,2-d]thiazole, can be prepared using the synthetic route described in Scheme 12. Phenol aldehyde of Formula IX is alkylated with an epoxide of Formula X to give epoxy aldehyde of Formula XI. Bayer-Villiger oxidation of compound XI generates formate XII, which can be converted to (2,3-dihydrobenzo[b][1,4]dioxin-2-yl)methanol of Formula XIII. Protection of alcohol in compound XIII and nitration yields nitrobenzene of Formula XIV, which can be reduced to the aniline XV. An oxidative cyclization of compound XV using a bromine source, such as trimethylbenzylammonium tribromide, should give rise to a benzothiazole of Formula XVI. A Sandmeyer reaction converts the amine in compound XVI to the halide of Formula $R_3$-X. Using a chirally pure epoxide of Formula X would constitute a chiral synthesis of $R_3$-X.

Scheme 12

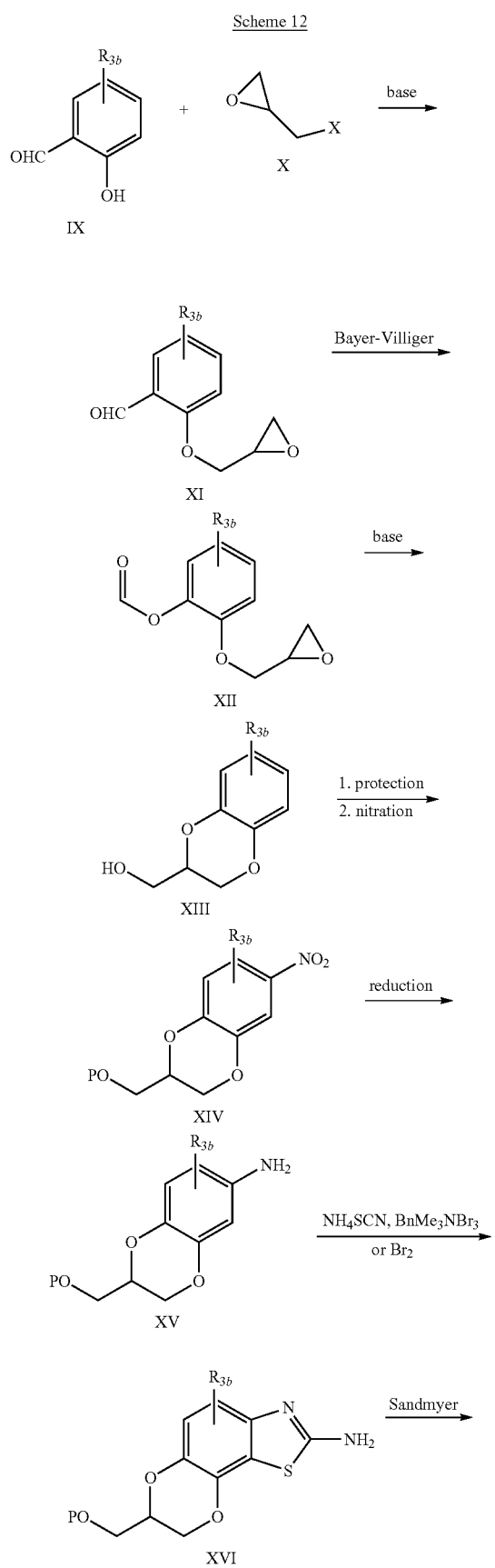

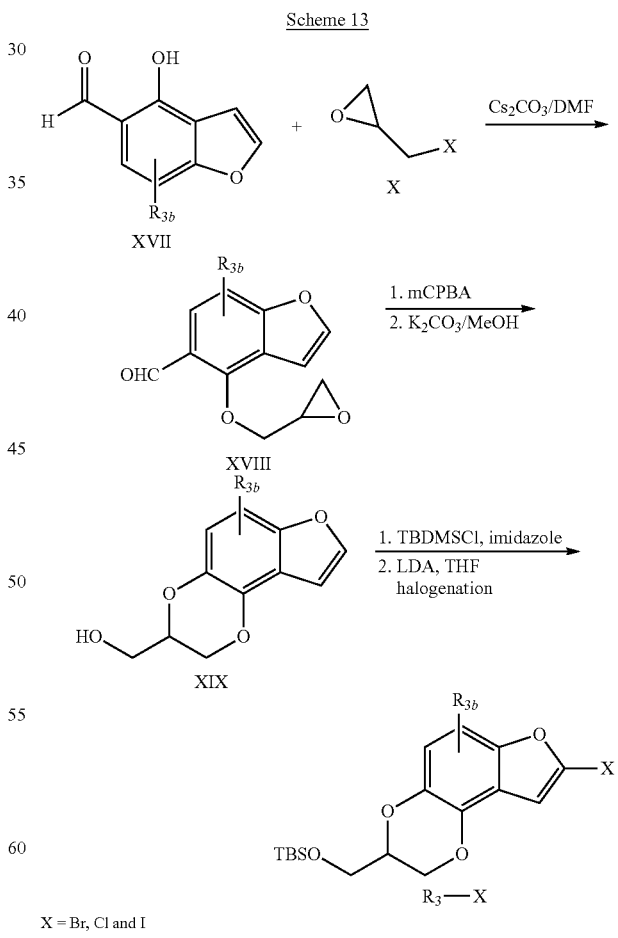

X = Br, Cl $R_3$-X, in which $R_3$ is a 2,3-dihydro-[1,4]dioxino[2,3-e] benzofuran, can be prepared using the synthetic route in Scheme 13. Alkylation of compound XVII with epoxide of Formula X gives rise to epoxy aldehyde of Formula XVIII. Bayer-Villiger oxidation of compound XVIII with mCPBA, followed by hydrolysis of the formate and intramolecular cyclization in the presence of a base such as $K_2CO_3$, yields (2,3-dihydro-[1,4]dioxino[2,3-e]benzofuran-3-yl)methanol of Formula XIX. Protection of the alcohol in compound XIX and halogenation after C-2 deprotonation gives rise to $R_3$-X, in which $R_3$ is a cyclic benzofuran. Using a chirally pure epoxide of Formula X would constitute a chiral synthesis of $R_3$-X.

Scheme 13

X = Br, Cl and I $R_3$-X, in which $R_3$ is a 7,8-dihydrobenzofuro[5,4-d]thiazole, can be prepared using the synthetic route in Scheme 14.

Compound XX can be alkylated with allyl bromide in the presence of a base such as K₂CO₃ to give compound XXI. Claisen rearrangement of XXI in a solvent such as N,N-diethylaniline at heating yields ortho-allyl phenol XXII. Epoxidation of compound XXII with mCPBA, followed by intramolecular cyclization of the phenol to the epoxide gives rise to compound of Formula R₃-X, in which R₃ is a 7,8-dihydrobenzofuro[5,4-d]thiazole.

Scheme 14

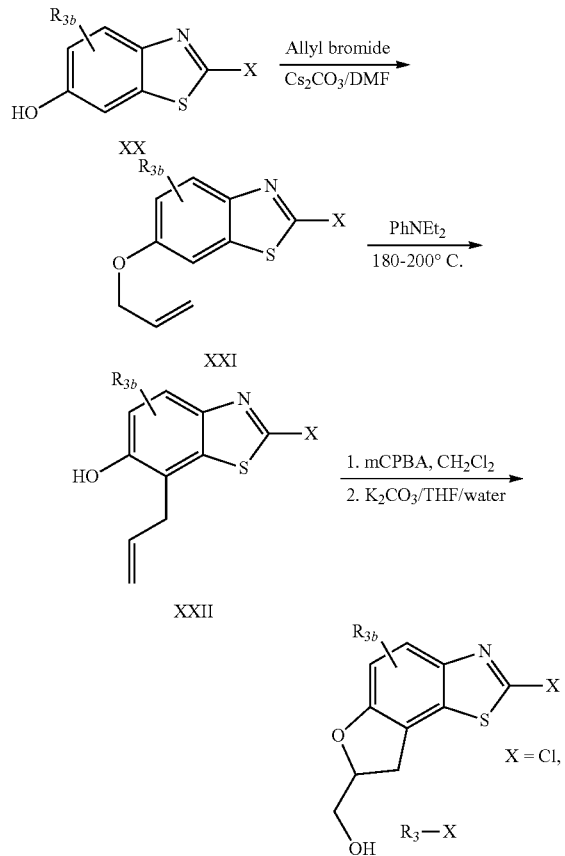

General Methods

The following methods were used in the exemplified Examples, except where noted otherwise.

Products were analyzed by reverse phase analytical HPLC carried out on a Shimadzu Analytical HPLC system running Discovery VP software using one of the following methods Method A: PHENOMENEX® Luna C18 column (4.6×50 mm or 4.6×75 mm) eluted at 4 mL/min with 2, 4 or 8 min gradient from 100% A to 100% B (A: 10% methanol, 89.9% water, 0.1% TFA; B: 10% water, 89.9% methanol, 0.1% TFA, UV 220 nm).

Method B: PHENOMENEX® Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm).

Method C: PHENOMENEX® Luna C18 column (4.6×50 mm or 4.6×75 mm) eluted at 4 mL/min with a 2, 4 or 6 min gradient from 100% A to 100% B (A: 10% methanol, 89.9% water, 0.1% H₃PO₄; B: 10% water, 89.9% methanol, 0.1% H₃PO₄, UV 220 nm).

Method D: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% NH₄OAc; B: 10% water, 89.9% methanol, 0.1% NH₄OAc, UV 220 nm).

Method E: BEH C18 2.11×50 mm; A: water+0.05% TFA; B: acetonitrile+0.05% TFA; wavelength 220 nm; flow rate 0.8 mL/min; 0% B to 100% B in 1 minute, gradient time 1.5 min.

Method F: BEH C18 2.1×50 mm; A: water+0.05% TFA; B: acetonitrile+0.05% TFA; wavelength 220 nm; flow rate 0.8 mL/min; 0% B to 50% B in 1 minute, gradient time 1.5 min.

Method G: BEH C18 2.1×50 mm; A: water+0.05% TFA; B: acetonitrile+0.05% TFA; wavelength 220 nm; flow rate 0.8 mL/min; 50% B to 100% B in 1 minute, gradient time 1.5 min.

Reverse phase preparative HPLC was carried out using a Shimadzu Preparative HPLC system running Discovery VP software using one of the following methods.

Method A: PHENOMENEX® Axia Luna 5 μM C18 30×75 mm column with a min gradient at 40 mL/min from 100% A to 100% B (A: 10% acetonitrile, 89.9% water, 0.1% TFA; B: 10% water, 89.9% acetonitrile, 0.1% TFA, UV 220 nm).

Method B: YMC Sunfire 5 μM C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm).

Method C: XBridge C18, 19×200 mm column, 5-μm particles; Mobile Phase A: 5:95 acetonitrile: water with 0.1% trifluoroacetic acid; Mobile Phase B: 95:5 acetonitrile: water with 0.1% trifluoroacetic acid; Flow: 20 mL/min.

Method D: Waters XBridge C18, 19×100 mm column, 5-μm particles; Mobile Phase A: 5:95 acetonitrile: water with 10-mM ammonium acetate; Mobile Phase B: 95:5 acetonitrile: water with 10-mM ammonium acetate; Flow: 20 mL/min.

Method E: PHENOMENEX® Luna 5 μM C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm).

Method F: PHENOMENEX® Luna 5 μM C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm).

Method G: Waters XBridge C18, 19×200 mm, 5-μm particles; Mobile Phase A: 5:95 acetonitrile:water with 0.1% formic acid; Mobile Phase B: 95:5 acetonitrile:water with 0.1% formic acid; Flow: 20 mL/min.

LCMS chromatograms were obtained on a Shimadzu HPLC system running Discovery VP software, coupled with a Waters ZQ mass spectrometer running MassLynx version 3.5 software using Method A: A linear gradient using solvent A (10% acetonitrile, 90% water, 0.1% of TFA) and solvent B (90% acetonitrile, 10% water, 0.1% of TFA); 0-100% of solvent B over 2 min and then 100% of solvent B over 1 min. Column: PHENOMENEX® Luna 3u C18(2) (2.0×30 mm). Flow rate was 5 ml/min. And UV detection was set to 220 nm. The LC column was maintained at room temperature.

Method B: A linear gradient using solvent A (10% methanol, 90% water, 0.1% of TFA) and solvent B (90% methanol, 10% water, 0.1% of TFA); 0-100% of solvent B over 4 min and then 100% of solvent B over 1 min. Column: PHE- NOMENEX® Luna 5u C18 (4.5×30 mm). Flow rate was 4 ml/min. And UV detection was set to 220 nm. The LC column was maintained at room temperature.

Method C: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 3u C18(2) (2.0×30 mm). Flow rate was 1 ml/min. And UV detection was set to 220 nm. The LC column was maintained at room temperature.

Method D: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 3u C18(2) (4.5×30 mm). Flow rate was 5 ml/min. And UV detection was set to 220 nm. The LC column was maintained at room temperature.

Method E: 30-95% acetonitrile in water with 0.1% TFA in 8 min run, Waters Xbridge 4.6×50 mm 5 um C18, flow rate 1.2 mL/min and UV detection was set to 220 nm. The LC column was maintained at room temperature.

Method F: 10-95% methanol in water, 0.1% TFA in a 10 min run, PHENOMENEX® Onyx Monolithic 4.6×100 mm 5 um C18, flow rate 2.0 mL/mL and UV detection was set to 220 nm. The LC column was maintained at room temperature.

Method G: 5-95% acetonitrile in water, 10 mM of modifier in 6 min run, Waters Xbridge 2.1×50 mm 5 um C18, flow rate 1.0 mL/min and UV detection was set to 220 nm. The LC column was maintained at room temperature.

Method H: BEH C18 2.1×50 mm; A: water+0.05% TFA; B: acetonitrile+0.05% TFA; wavelength 220 nm; flow rate 0.8 mL/min; gradient time 1.5 min; 2 to 98% B.

Method I: BEH C18 2.1×50 mm; A: water+0.05% TFA; B: acetonitrile+0.05% TFA; wavelength 220 nm; flow rate 0.8 mL/min; gradient time 1.5 min; 2 to 52% B.

Method J: BEH C18 2.1×50 mm; A: water+0.05% TFA; B: acetonitrile+0.05% TFA; wavelength 220 nm; flow rate 0.8 mL/min; gradient time 1.5 min; 48 to 98% B.

Method K: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm.

Method L: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm.

In addition, the following orthogonal HPLC conditions were used to check the purity of the compounds Method A: Two analytical LC/MS injections were used to determine the final purity. Injection1 condition: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Sunfire C18 3.5 um (4.6×150 mm). Flow rate was 2 ml/min. And UV detection was set to 220 nm. The LC column was maintained at room temperature. Injection 2 conditions: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Xbridge Phenyl 3.5 um (4.6×150 mm). Flow rate was 2 ml/min. And UV detection was set to 220 nm. The LC column was maintained at room temperature.

Method B: Two analytical LC/MS injections were used to determine the final purity. Injection 1 conditions: Column: Waters Acquity UPLC BEH C18, 2.1×50 mm, 1.7-am particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm.

EXAMPLES

The invention is further defined in the following Examples. It should be understood that the Examples are given by the way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather is defined by the claims appended hereto.

ABBREVIATIONS

AcO acetyl (—OC(O)CH$_3$)
AcOH acetic acid
Boc tert-butoxycarbonyl
Boc$_2$O di(tert-butoxycarbonyl) ether
DAST (diethylamino)sulfur trifluoride
DCM dichloromethane
DIAD diisopropyl azodicarboxylate
DIEA diisopropylethylamine
DMAP dimethylaminopyridine
DMF dimethylformamide
DMSO dimethylsulfoxide
EtOAc ethyl acetate
EtOH ethanol
IPA isopropanol
mCPBA 3-chloroperbenzoic acid
MeCN acetonitrile
MeOH methanol
n-BuLi n-butyl lithium
NH$_4$OAc ammonium acetate
NBS N-bromosuccinimide
NCS N-chlorosuccinimide
NMP N-methylpyrrolidinone
Pd/C palladium on carbon
PdCl$_2$(dppf)—CH$_2$Cl$_2$ [1,1'-bis(diphenylphosphino)ferrocene]dichloropalladium(II), dichloromethane adduct
Pd(Ph$_3$P)$_4$ tetrakis(triphenylphosphine)palladium
Pd(OAc)$_2$ palladium acetate
TBAF tetrabutylammonium fluoride
TBDMS-Cl tert-butyldimethylsilyl chloride
TCL thin layer chromatography
TEA triethylamine
TFA trifluoroacetate
THE tetrahydrofuran HPLC high pressure liquid chromatography
LCMS liquid chromatography-mass spectroscopy
MS mass spectrometry
g gram(s)
h or hr hour(s)
min. minute(s)
mL milliliter(s)
mmol millimole(s)
RT retention time Intermediate I-1

2-(difluoromethoxy)-7-methyl-5-(4,4,5,5-tetramethyl-1,3,2-dioxaborolan-2-yl)

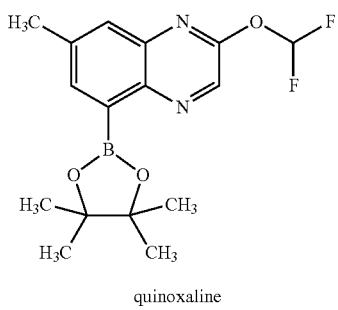

(I-1)

quinoxaline

Intermediate I-1A: tert-butyl N-(2-bromo-4-methyl-6-nitrophenyl)-N-[(tert-butoxy) carbonyl]carbamate

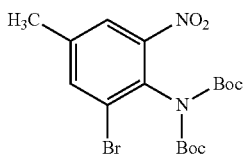

(I-1A)

To a solution of 2-bromo-4-methyl-6-nitroaniline (9.6 g, 41.6 mmol) in THF (60 mL) was added DMAP (0.508 g, 4.16 mmol), followed by BOC$_2$O (22.67 g, 104 mmol) as a solid. The mixture was stirred at room temperature overnight. Solvent was removed under vacuum. The crude product was dissolved in a small amount of chloroform and charged to a 120 g silica gel cartridge (2 separate columns) which was eluted with 5% EtOAc in hexanes for 4 min., then a 12 min gradient from 5% to 30% EtOAc in hexanes.

The desired fractions were combined and concentrated to give Intermediate I-1A (17.12 g, 39.7 mmol, 96% yield) as a white solid. $^1$H NMR (500 MHz, chloroform-d) δ 7.80-7.79 (m, 1H), 7.73 (dd, J=1.9, 0.8 Hz, 1H), 2.48 (s, 3H), 1.42 (s, 18H); LC-MS: method A, RT=1.90 min, MS (ESI) m/z: 230.0 and 232.0 (M-2 Boc)$^+$.

Intermediate I-1B: tert-butyl (2-bromo-4-methyl-6-nitrophenyl)carbamate

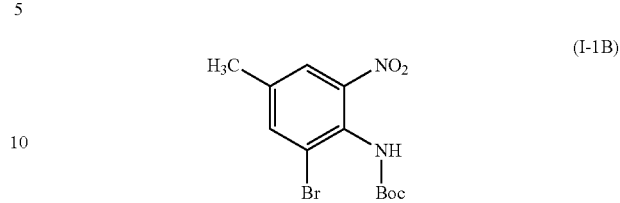

(I-1B)

To a solution of Intermediate I-1A (17.1 g, 39.6 mmol) in dichloromethane (60 mL) was added TFA (6.11 mL, 79 mmol) and the mixture was stirred at room temperature for 1.0 h. The reaction was quenched by addition of saturated sodium bicarbonate, extracted with dichloromethane (3×), dried over sodium sulfate. After evaporation of solvent, Intermediate I-1B was obtained as a yellow solid (12.88 g, 88% yield): $^1$H NMR (500 MHz, chloroform-d) δ 7.71 (d, J=1.1 Hz, 1H), 7.68 (dd, J=1.9, 0.8 Hz, 1H), 2.42 (s, 3H), 1.51 (s, 9H); LC-MS: method A, RT=1.53 min, MS (ESI) m/z: 231.0 and 233.0 (M-Boc)$^+$.

Intermediate I-1C: methyl 2-((2-bromo-4-methyl-6-nitrophenyl)(tert-butoxycarbonyl) amino)acetate

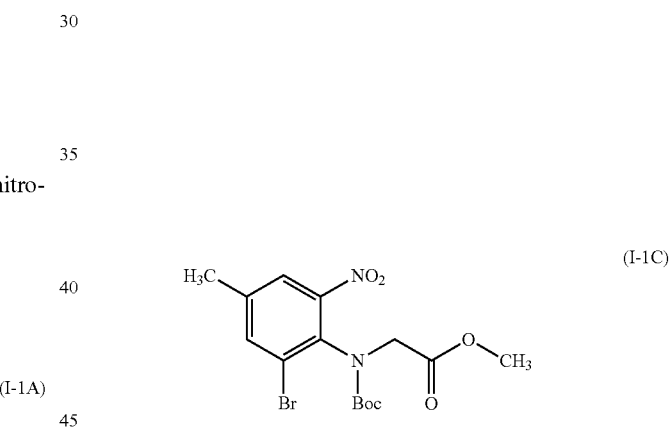

(I-1C)

Intermediate I-1B (12 g, 26.3 mmol) was dissolved in DMF (80 mL), cooled with a water bath. Cs$_2$CO$_3$ (25.8 g, 79 mmol) was added. The dark brown solution was stirred at room temperature for 10 min, then methyl 2-bromoacetate (4.37 mL, 47.6 mmol) was added dropwise. After addition of methyl bromoacetate, the brown color faded to yellow. The mixture was stirred at room temperature for 1.0 h, diluted with EtOAc, quenched with water. The organic layer was collected, washed with brine, dried over sodium sulfate. After evaporation of solvent, the crude product was dissolved in a small amount of chloroform and charged to a 330 g silica gel cartridge which was eluted with 5% EtOAc in hexanes for 5 min., then a 12 min gradient from 5% to 50% EtOAc in hexanes. The desired fractions were combined and concentrated to give Intermediate I-1C (15.2 g, 37.7 mmol, 95% yield) as an yellow oil. $^1$H NMR (500 MHz, chloroform-d) indicated a mixture of rotamers: δ 7.75-7.67 (m, 2H), 4.61-3.97 (m, 2H), 3.76 and 3.69 (s, 3H), 2.48 and 2.43 (s, 3H), 1.55 and 1.37 (s, 9H); LC-MS: method A, RT=1.70 min, MS (ESI) m/z: 303.0 and 305.0 (M-Boc)$^+$.

Intermediate I-1D: methyl 2-((2-bromo-4-methyl-6-nitrophenyl)amino)acetate

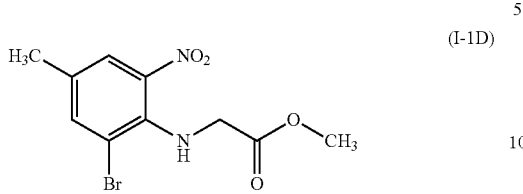
(I-1D)

To Intermediate I-1C (15.2 g, 37.7 mmol) was added 4.0 N HCl in dioxane (47.1 ml, 188 mmol) and the mixture was stirred at room temperature overnight. Solvent was removed under vacuum, chased with EtOAc (2×) to give Intermediate I-1D (13.6 g, 40.1 mmol, 106% yield) as a yellow solid. $^1$H NMR (500 MHz, methanol-d4) δ 7.88 (dd, J=1.9, 0.6 Hz, 1H), 7.80 (dd, J=1.9, 0.6 Hz, 1H), 4.47 (d, J=17.3 Hz, 1H), 4.08 (d, J=17.1 Hz, 1H), 3.69 (s, 3H), 2.46 (s, 3H); LC-MS: Method A, RT=1.94 min, MS (ESI) m/z: 303.1 and 305.1 (M+H)$^+$.

Intermediate I-IE: 5-bromo-7-methyl-3,4-dihydroquinoxalin-2(1H)-one

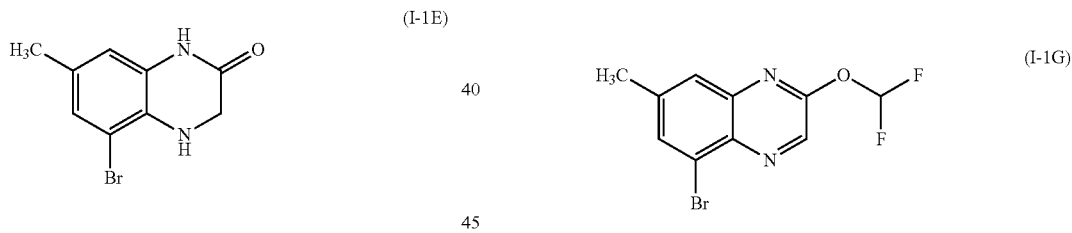
(I-1E)

To a solution of Intermediate I-1D (13.6 g, 40.1 mmol) in MeOH (100 mL) in a 1 L flask cooled with water bath was added concentrated HCl (13.35 mL, 160 mmol), followed by tin(II) chloride dihydrate (36.1 g, 160 mmol). The mixture was stirred at 68° C. for 2.5 h. MeOH was removed under vacuum. The crude was partitioned in water (100 mL)/EtOAc (200 mL), and the pH was adjusted to neutral with 4.0 N NaOH (ca 90 mL). The white precipitate formed was very fine particle that was very hard to remove by filtration. The mixture was transferred to a separatory funnel. The organic layer was collected. The aqueous was further extracted (2×200 mL) with EtOAc. The combined organic layer was washed with water (2×) and brine (2×), dried over sodium sulfate. After evaporation of solvent, Intermediate I-1E (8.36 g, 34.7 mmol, 87% yield) was obtained as a pale yellow solid. $^1$H NMR (500 MHz, DMSO-d$_6$) δ 10.37 (s, 1H), 6.87 (dd, J=1.8, 0.7 Hz, 1H), 6.56 (dd, J=1.1, 0.6 Hz, 1H), 5.46 (s, 1H), 3.76 (d, J=2.2 Hz, 2H), 2.14 (s, 3H); LC-MS: method A, RT=1.66 min, MS (ESI) m/z: 241.0 and 243.0 (M+H)$^+$.

Intermediate I-1F: 5-bromo-7-methylquinoxalin-2-ol

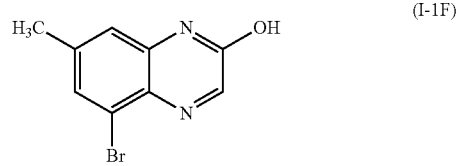
(I-1F)

To a suspension of Intermediate I-1E (6.7 g, 27.8 mmol) in MeOH (50 mL) in a 1 L flask was added 30% hydrogen peroxide (28.4 mL, 278 mmol), followed by 4.0 N NaOH (20.84 mL, 83 mmol). The mixture was stirred at room temperature for 5 min, then gently heated at 60° C. After 15 min heating, the reaction turned strongly exothermic, suggesting an initiation of the reaction. The heating bath was removed and stirring continued for 30 min until the mixture turned completely clear. After cooled to room temperature with a water bath, MeOH was removed under vacuum. The mixture was then neutralized with 2.0 N HCl (to pH 2-3) under ice cooling. The precipitate formed was collected by filtration, washed with water, dried under vacuum in the air for 1.0 h and then at vacuum at 60° C. for 2.0 h, and under high vacuum to give Intermediate I-1F (6.55 g, 27.4 mmol, 99% yield) as a off-white solid. $^1$H NMR (500 MHz, DMSO-d$_6$) δ 12.52 (br. s., 1H), 8.17 (s, 1H), 7.49 (d, J=1.1 Hz, 1H), 7.08 (s, 1H), 2.40 (s, 3H; LC-MS: method A, RT=1.62 min, MS (ESI) m/z: 239.0 and 241.0 (M+H)$^+$.

Intermediate I-G: 5-bromo-2-(difluoromethoxy)-7-methylquinoxaline (I-1G)

A mixture of Intermediate I-1F (7.4 g, 26.9 mmol) and potassium carbonate (18.56 g, 134 mmol) in DMF (120 mL) was heated at 100° C. for 5 min. Sodium 2-chloro-2,2-difluoroacetate (16.40 g, 107.6 mmol) was added in one portion, and the mixture was stirred at 100° C. for 10 min. The mixture turned from yellow slurry to brown. The mixture was cooled to room temperature, diluted with EtOAc and water, extracted with EtOAc (3×). The combined organic layer was washed with brine, dried over sodium sulfate. After evaporation of solvent, the crude product was dissolved in a small amount of chloroform/toluene and purified with a 330 g ISCO column eluted with 5% dichloromethane in hexanes for 3 min, then 5-70% DCM/hexanes for 40 min (12 min gradient time). The desired fractions were combined, concentrated to give Intermediate I-1G (6.0 g, 20.76 mmol, 77% yield) as a slightly yellow solid. $^1$H NMR (500 MHz, chloroform-d) δ 8.64 (s, 1H), 7.89 (d, J=1.7 Hz, 1H), 7.68 (dd, J=1.8, 1.0 Hz, 1H), 7.63 (t, $J_{HF}$=71.80 Hz, 1H), 2.59 (s, 3H); $^{19}$F NMR (471 MHz, chloroform-d) δ −89.82 (s, 2F); LC-MS: method A, RT=2.09 min, MS (ESI) m/z: 289.0 and 291.0 (M+H)$^+$.

Intermediate I-1

A mixture of Intermediate I-1G (1.04 g, 3.60 mmol), bis(pinacolato)diboron (1.370 g, 5.40 mmol), potassium acetate (0.883 g, 8.99 mmol) and $PdCl_2(dppf)$—$CH_2Cl_2$ adduct (0.147 g, 0.180 mmol) in dioxane (14 mL) was degassed by bubbling argon for 10 min. The reaction vial was sealed and heated in microwave reactor at 135° C. for 30 min. The mixture was diluted with EtOAc/water, insoluble material was removed by filtration. The filtrate was extracted with EtOAc, washed with brine and dried over sodium sulfate. After evaporation of solvent, the crude product was dissolved in a small amount of toluene and charged to a 40 g silica gel cartridge which was eluted with 5% EtOAc in hexanes for 2 min., then a 18 min gradient from 5% to 75% EtOAc in hexanes. The desired fractions were concentrated and lyophilized to give Intermediate I-1 (0.93 g, 72% yield) as a pale solid. $^1$HNMR was complicated by the presence of two sets of signals. $^{19}$F NMR indicated a single compound. $^{19}$F NMR (471 MHz, chloroform-d) δ −89.64 (s., 2F). LC-MS: method A, RT=2.01 min, MS (ESI) m/z: 225.0 (boronic acid)$^+$.

Intermediate I-2

2-(methoxymethyl)-7-methyl-5-(4,4,5,5-tetramethyl-1,3,2-dioxaborolan-2-yl)quinoxaline

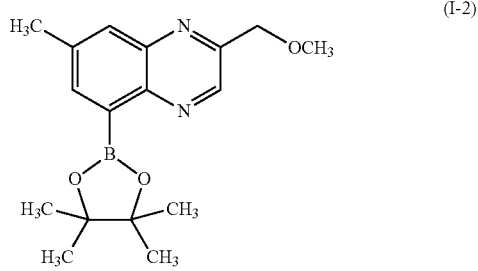 [SMILES: COCc1cnc2c(B3OC(C)(C)C(C)(C)O3)cc(C)cc2n1]

(I-2)

Intermediate I-2A: 1-diazo-3-methoxypropan-2-one

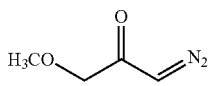

(I-2A)

To 2-methoxyacetyl chloride (2.4 g, 22.12 mmol) in MeCN (40 mL) cooled with ice-bath was added (diazomethyl)trimethylsilane 2.0 M in diethyl ether (19.35 mL, 38.7 mmol). The mixture was allowed to stir at room temperature overnight. Solvent was removed under reduced pressure. The crude product was purified by flash chromatography (loading in chloroform, 0% to 50% EtOAc in hexane over 18 min using a 40 g silica gel cartridge). The desired fractions were combined and concentrated (bath temp below 35° C.) to yield Intermediate I-2A (1.82 g, 15.95 mmol, 72.1% yield) as a yellow liquid. $^1$H NMR (500 MHz, chloroform-d) δ 5.73 (br. s., 1H), 3.97 (br. s., 2H), 3.43 (s, 3H); LC-MS: method A, RT=0.43 min, MS (ESI) m/z: 137.0 (M+Na)$^+$.

Intermediate I-2B3: 1-bromo-3-methoxypropan-2-one

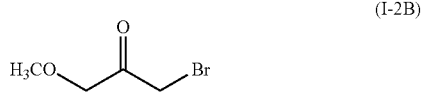

(I-2B)

To Intermediate I-2A (1.6 g, 14.02 mmol) in diethyl ether (20 mL) at 0° C. was added aqueous HBr 48% (2.4 mL, 21.03 mmol) dropwise. After stirring at 0° C. for 5 min and at room temperature for 10 min, the reaction mixture was diluted with EtOAc, washed with water, saturated sodium bicarbonate (2×) and brine. The organic layer was dried over sodium sulfate, concentrated (keep bath temp below 30° C.) to give Intermediate I-2B (1.5 g, 8.98 mmol, 64.1% yield) as a slightly yellow liquid. $^1$H NMR indicated >92% purity. The compound was used immediately for the next step without further purification. $^1$H NMR (500 MHz, chloroform-d) δ 4.24 (s, 2H), 4.03 (s, 2H), 3.45 (s, 3H), consistent with literature report (*J. Org. Chem.* 1981, 217).

Intermediate I-2C: tert-butyl (2-bromo-4-methyl-6-nitrophenyl)(3-methoxy-2-oxopropyl)carbamate

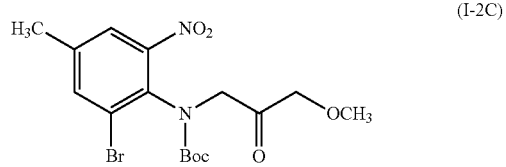 [SMILES: COCC(=O)CN(C(=O)OC(C)(C)C)c1c(Br)cc(C)cc1[N+](=O)[O-]]

(I-2C)

To Intermediate I-1B (1.98 g, 5.98 mmol) in DMF (20 mL) at 0° C. was added $Cs_2CO_3$ (3.41 g, 10.46 mmol). The brown solution was stirred at 0° C. for 10 min, followed by addition of Intermediate I-2B (1.498 g, 8.97 mmol) in acetonitrile (5.0 mL). The brown solution turned yellow. The mixture was stirred at 0° C. for 15 min., diluted with EtOAc, washed with water, brine, dried over sodium sulfate and concentrated. The crude product was purified by flash chromatography (loading in chloroform, 0% to 60% EtOAc in hexane over 18 min using a 80 g silica gel cartridge). The desired fractions were combined and concentrated to yield Intermediate I-2C (2.4 g, 5.75 mmol, 96% yield) as yellow oil. $^1$NMR indicated presence of two rotamers. $^1$H NMR (500 MHz, chloroform-d) δ 7.70-7.65 (m, 2H), 4.55 (d, J=17.9 Hz, 1H), 4.18 (d, J=17.9 Hz, 1H), 4.32 and 4.14 (d, J=1.4 Hz, 2H), 3.44 and 3.40 (s, 3H), 2.45 and 2.40 (s, 3H), 1.49 and 1.35 (s, 9H); LC-MS: method A, RT=1.89 min, MS (ESI) m/z: 317 and 319 (M-Boc)$^+$.

Intermediate I-2D 6-bromo-3-hydroxy-3-(methoxymethyl)-8-methyl-1-oxo-1,3,4,5-tetrahydrobenzo[c][1,2,5]oxadiazepin-1-ium

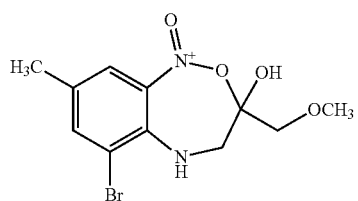

(I-2D)

To Intermediate I-2C (1.67 g, 4.00 mmol) in ethyl acetate (10 mL) was added 4.0 N HCl in dioxane (10.01 mL, 40.0 mmol) and the mixture was stirred at room temperature for 20 min. Solvent was removed under vacuum, chased with EtOAc once to give Intermediate I-2D (1.25 g, 99%) as a yellow oil. $^1$H NMR (400 MHz, chloroform-d) δ 7.75-7.66 (m, 2H), 4.13-3.98 (m, 1H), 3.78-3.56 (m, 3H), 3.50 and 3.44 (m, 3H), 2.39 (s, 3H); LC-MS: method A, RT=1.47 min, MS (ESI) m/z: 317.0 and 319.0 (M+H)$^+$.

Intermediate I-2E:
5-bromo-2-(methoxymethyl)-7-methylquinoxaline

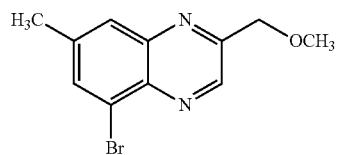

(I-2E)

Intermediate I-2D (1.25 g, 3.9 mmol) was dissolved in THF (30 mL). Concentrated HCl (0.986 mL, 12.01 mmol) was added, followed by tin(II) chloride dihydrate (3.61 g, 16.01 mmol). The mixture was placed and stirred in an oil bath pre-heated at 40° C. for 4.0 h. The reaction mixture was diluted with EtOAc/water, The organic phase was neutralized with saturated sodium bicarbonate and stirred at room temperature for 15 min, the precipitate was removed by filtration with a pad of wet celite. The filtrate was collected. The organic layer was washed with brine, dried over sodium sulfate and concentrated. The crude product was purified by flash chromatography (loading in chloroform, 0% to 60% EtOAc in hexane over 20 min using a 120 g silica gel cartridge). The desired fractions were combined and concentrated to yield Intermediate I-2E (0.57 g, 1.920 mmol, 48.0% yield) as a brown solid: $^1$H NMR (400 MHz, chloroform-d) δ 9.03 (s, 1H), 7.95 (d, J=1.5 Hz, 1H), 7.84 (dd, J=1.8, 1.1 Hz, 1H), 4.84 (s, 2H), 3.56 (s, 3H), 2.60 (s, 3H); Intermediate I-2E was contaminated with ca 10% of a side product 5-bromo-2,7-dimethylquinoxaline.

Intermediate I-2

A mixture of Intermediate I-2E (900 mg, 3.37 mmol), bis(pinacolato)diboron (1369 mg, 5.39 mmol), potassium acetate (661 mg, 6.74 mmol) and PdCl$_2$(dppf)—CH$_2$Cl$_2$ adduct (110 mg, 0.135 mmol) in dioxane (15 mL) was degassed by bubbling argon for 10 min. The reaction vial was sealed and heated in microwave reactor at 130° C. for 30 min. The mixture was diluted with EtOAc/water, insoluble material was removed by filtration. The filtrate was extracted with EtOAc, washed with brine and dried over sodium sulfate, concentrated. The crude product was purified by flash chromatography (loading in chloroform, 0% to 20% dichloromethane in MeOH over 15 min using a 40 g silica gel cartridge). The desired fractions were combined and concentrated and further purified by prep IPLC (method A, 10-80% B in 8 mins; with a flow rate of 40 mL/min).

The desired fractions were placed in a SpeedVac overnight to remove solvent. The material was dissolved in EtOAc, washed with diluted saturated sodium bicarbonate (to remove TFA), brine, dried over sodium sulfate, concentrated and lyophilized to give Intermediate I-2 (360 mg, 1.550 mmol, 46% yield) as a slightly colored solid. LC-MS: method A, RT=1.73 min, MS (ESI) m/z: 233.1 boronic acid (M+H)$^+$.

Intermediate I-6

(2-bromo-4-chloro-7,8-dihydro-[1,4]dioxino[2',3':3,4]benzo[1,2-d]thiazol-7-yl)methanol

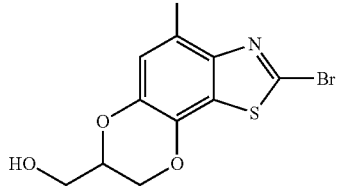

(I-6)

Intermediate I-6A:
5-chloro-2-(oxiran-2-ylmethoxy)benzaldehyde

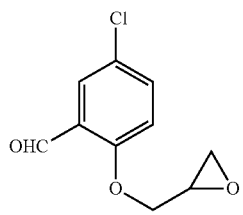

(I-6A)

To a solution of 5-chloro-2-hydroxybenzaldehyde (1.1 g, 7.03 mmol) in DMF (15 mL) was added Cs$_2$CO$_3$ (5.04 g, 15.46 mmol), followed by 2-(bromomethyl)oxirane (1.083 mL, 12.65 mmol). The mixture was stirred at room temperature for 10 min, and then at 50° C. for 1.5 h. HPLC and TLC indicated a clean reaction. After cooling to room temperature, the reaction mixture was diluted with EtOAc/water. The organic layer was collected, washed with brine and dried over sodium sulfate. After evaporation of solvent, the crude product was dissolved in a small amount of chloroform and charged to a 40 g silica gel cartridge which was eluted with hexanes for 2 min., then a 15 min gradient from 0% to 50% EtOAc in hexanes. The desired fractions were combined and concentrated to give Intermediate I-6A (1.30 g, 6.11 mmol, 87% yield) as a colorless oil. ¹H NMR (400 MHz, chloroform-d) δ 10.46 (s, 1H), 7.80 (d, J=2.6 Hz, 1H), 7.49 (dd, J=8.8, 2.6 Hz, 1H), 6.97 (d, J=8.8 Hz, 1H), 4.41 (dd, J=11.2, 2.6 Hz, 1H), 4.04 (dd, J=11.2, 5.7 Hz, 1H), 3.41 (ddt, J=5.8, 4.2, 2.7 Hz, 1H), 2.96 (t, J=4.4 Hz, 1H), 2.79 (dd, J=4.7, 2.5 Hz, 1H); LC-MS: method A, RT=1.64 min, MS (ESI) m/z: No (M+H)⁺.

Intermediate I-6B:
5-chloro-2-(oxiran-2-ylmethoxy)phenyl formate

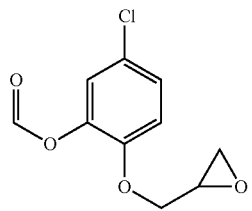

(I-6B)

To a stirred solution of Intermediate I-6A (1.3 g, 6.11 mmol) in dichloromethane (20 mL) cooled with a water bath was added mCPBA (2.075 g, 9.02 mmol). Trifluoroacetic acid (0.471 mL, 6.11 mmol) in dichloromethane (6 mL) was added dropwise. The mixture was stirred at room temperature for 2.0 h. TLC indicated a completion of reaction. The reaction was quenched by addition of saturated sodium bicarbonate, followed by 10% sodium thiosulfite (20.0 mL), extracted with dichloromethane. The organic layers were collected, washed with saturated sodium bicarbonate, brine and dried over sodium sulfate. After evaporation of solvent, the crude product was dissolved in a small amount of chloroform and charged to a 40 g silica gel cartridge which was eluted with hexanes for 2 min., then a 18 min gradient from 0% to 40% EtOAc in hexanes. The desired fractions were combined and concentrated to give Intermediate I-6B (1.02 g, 4.46 mmol, 73.0% yield) as a colorless oil (purity ca 90%). ¹H NMR (400 MHz, chloroform-d) δ 8.27 (s, 1H), 7.22 (dd, J=8.8, 2.6 Hz, 1H), 7.15 (d, J=2.4 Hz, 1H), 6.99 (d, J=8.8 Hz, 1H), 4.29 (dd, J=11.2, 2.9 Hz, 1H), 4.00 (dd, J=11.2, 5.7 Hz, 1H), 3.33 (ddt, J=5.7, 4.2, 2.8 Hz, 1H), 2.93-2.89 (m, 1H), 2.74 (dd, J=4.8, 2.6 Hz, 1H); LC-MS: method A, RT=1.58 min, MS (ESI) m/z:251.0 and 253.0 (M+Na)⁺.

Intermediate I-6C: (7-chloro-2,3-dihydrobenzo[b][1,4]dioxin-2-yl)methanol

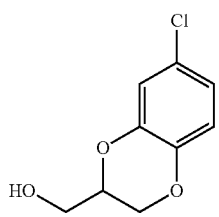

(I-6C)

To Intermediate I-6B (1.02 g, 4.46 mmol) in MeOH (20 mL) was added potassium carbonate (1.850 g, 13.38 mmol). The mixture was stirred at room temperature overnight. HPLC and TLC indicated a completion of reaction. The mixture was treated with 1.0 N HCl (14 mL). Methanol was removed under vacuum. The residue was partitioned between EtOAc/water. The organic layer was washed with brine, dried over sodium sulfate. After evaporation of solvent, Intermediate I-6C (0.90 g, 4.49 mmol, 101% yield) was obtained as a colorless oil. It was used for the next step without further purification. ¹H NMR (400 MHz, chloroform-d) δ 6.93 (dd, J=1.8, 1.1 Hz, 1H), 6.84-6.82 (m, 2H), 4.34-4.29 (m, 1H), 4.29-4.25 (m, 1H), 4.15-4.11 (m, 1H), 3.95-3.84 (m, 2H); LC-MS: method A, RT=1.69 min, MS (ESI) m/z: No (M+H)⁺.

Intermediate I-6D: (7-chloro-2,3-dihydrobenzo[b][1,4]dioxin-2-yl)methyl acetate

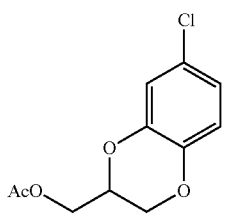

(I-6D)

To a solution of Intermediate I-6C (0.95 g, 4.74 mmol) in THF (15 mL) at 0° C. was added TEA (1.650 mL, 11.84 mmol), followed by acetyl chloride (0.421 mL, 5.92 mmol) in THF (3.0 mL) dropwise. The mixture was stirred at 0° C. for 10 min, and at room temperature for 1.0 h. HPLC indicated a clean reaction. The mixture was diluted with EtOAc, washed with water. The organic layer was washed with 0.5 N HCl, saturated sodium bicarbonate, brine and dried over sodium sulfate. After evaporation of solvent, Intermediate I-6D (1.15 g, 4.27 mmol, 90% yield) was obtained as an oil. It was used for the next step without further purification. ¹H NMR (400 MHz, chloroform-d) δ 6.92 (dd, J=1.9, 0.8 Hz, 1H), 6.83-6.80 (m, 2H), 4.42-4.37 (m, 1H), 4.33-4.26 (m, 3H), 4.04 (dd, J=11.6, 6.9 Hz, 1H), 2.12 (s, 3H); LC-MS: method A, RT=1.94 min, MS (ESI) m/z: 265.0 and 267.0 (M+Na)⁺.

Intermediate I-6E: (7-chloro-6-nitro-2,3-dihydrobenzo[b][1,4]dioxin-2-yl)methyl acetate

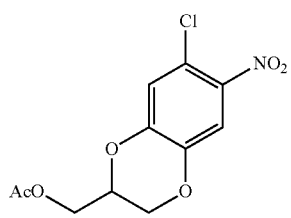

(I-6E)

To a solution of Intermediate I-6D (1.1 g, 4.53 mmol) in acetic acid (3.0 mL) cooled at 0° C. with an ice-bath was added fuming nitric acid (1.058 mL, 22.67 mmol) dropwise. The mixture was stirred at 0° C. for 2.0 h, and then at room temperature for 1.0 h. LCMS and TLC indicated a clean reaction. It was quenched with ice water. The aqueous layer was removed and the organic layer was washed with saturated sodium bicarbonate (3×), brine and dried over sodium sulfate. After evaporation of solvent, Intermediate I-6E (1.2 g, 3.84 mmol, 85% yield) was obtained as a slightly yellow solid that was used for the next step without further purification. ¹H NMR (400 MHz, chloroform-d) δ 7.64 (s, 1H), 7.09 (s, 1H), 4.53-4.48 (m, 1H), 4.41-4.34 (m, 3H), 4.12 (dd, J=11.8, 7.2 Hz, 1H), 2.15 (s, 3H); LC-MS: method A, RT=1.87 min, MS (ESI) m/z: 246.0 and 248.0 (M-Ac)$^+$.

Intermediate I-6F: (6-amino-7-chloro-2,3-dihydrobenzo[b][1,4]dioxin-2-yl)methyl acetate

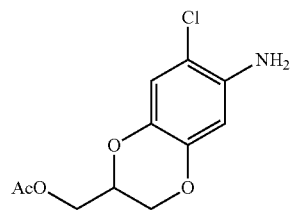
(I-6F)

To a solution of Intermediate I-6E (1.2 g, 4.17 mmol) in MeOH (15 mL) and THF (15 mL) cooled with an water bath was added ammonium chloride (3.57 g, 66.7 mmol) and zinc dust (2.182 g, 33.4 mmol). The mixture was stirred at room temperature for 1.0 h. HPLC and LCMS indicated a clean reaction. MeOH was removed under vacuum. The residue was diluted with EtOAc/saturated sodium bicarbonate and stirred at room temperature for 3 min. The mixture was filtered through a pad of wet celite to remove insoluble material. The filtrate was collected, organic layer was washed with brine, dried over sodium sulfate, concentrated to give Intermediate I-6F (1.0 g, 3.88 mmol, 93% yield) as a yellow solid. ¹H NMR (400 MHz, chloroform-d) δ 6.87 (s, 1H), 6.36 (s, 1H), 4.34-4.24 (m, 4H), 4.04 (dd, J=11.6, 6.5 Hz, 1H), 2.14 (s, 3H); LC-MS: method A, RT=1.21 min, MS (ESI) m/z: 258.0 (M+H)$^+$.

Intermediate I-6G: (2-amino-4-chloro-7,8-dihydro-[1,4]dioxino[2',3':3,4]benzo[1,2-d]thiazol-7-yl)methyl acetate

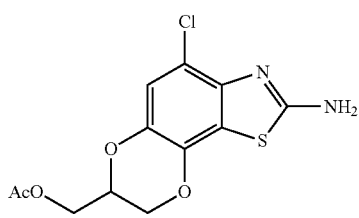
(I-6G)

To Intermediate I-6F (1.25 g, 4.85 mmol) dissolved in acetonitrile (20 mL) was added ammonium thiocyanate (0.554 g, 7.28 mmol). The mixture was stirred at room temperature for 10 min. Benzyltrimethylammonium tribromide (1.986 g, 5.09 mmol) in acetonitrile (8 mL) was added dropwise (5 min). The mixture was stirred at room temperature overnight. IPLC and LCMS indicated a clean reaction. The mixture was diluted with EtOAc/THF/saturated sodium bicarbonate. The insoluble material was removed by filtration. The organic layer of the filtrate was collected, washed with brine, dried over sodium sulfate. After evaporation of solvent, Intermediate I-6G (1.5 g, 4.05 mmol, 84% yield) was obtained as a yellow solid. ¹HNMR and IPLC indicated ca 90% purity. It was used for the next step without further purification. ¹H NMR (400 MHz, chloroform-d) δ 6.98 (s, 1H), 5.71 (br. s., 2H), 4.41-4.34 (m, 4H), 4.21-4.16 (m, 1H), 2.14 (s, 3H); LC-MS: method A, RT=1.50 min, MS (ESI) m/z: 315.0 and 317.0 (M+H)$^+$.

Intermediate I-6H: (2-bromo-4-chloro-7,8-dihydro-[1,4]dioxino[2',3':3,4]benzo[1,2-d]thiazol-7-yl) methyl acetate

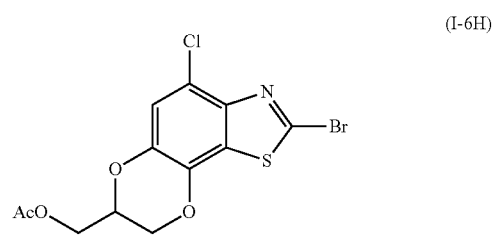 [SMILES: CC(=O)OCC1COc2c(cc(Cl)c3nc(Br)sc23)O1]
(I-6H)

Tert-butyl nitrite (1.102 mL, 8.34 mmol) was added to copper(II) bromide (1.810 g, 8.10 mmol) in dry acetonitrile (16 mL) under argon. The mixture was stirred at room temperature for 10 min. A suspension of Intermediate I-6G (1.5 g, 4.77 mmol) in dry acetonitrile (20 mL) was added dropwise. The reaction mixture was stirred at room temperature for 2.5 h. IPLC and LCMS indicated a clean reaction. Acetonitrile was removed under vacuum, the reaction mixture was diluted with EtOAc, quenched with 1.0 N HCl. The organic layer was collected, washed with 0.5 N HCl (2×), saturated sodium bicarbonate, brine and dried over sodium sulfate. After evaporation of solvent, the crude product was purified by flash chromatography (loading in chloroform, 0% to 40% EtOAc in hexane over 12 min using a 40 g silica gel cartridge). The desired fractions were combined and concentrated to yield Intermediate I-6H (1.45 g, 3.83 mmol, 80% yield) as an orange solid. ¹H NMR (400 MHz, chloroform-d) δ 7.16 (s, 1H), 4.53-4.44 (m, 3H), 4.40-4.36 (m, 1H), 4.21 (dd, J=11.4, 7.0 Hz, 1H), 2.15 (s, 3H); LC-MS: method A, RT=2.11 min, MS (ESI) m/z: 378.0, 380.0 and 382.0 (M+H)$^+$.

Intermediate I-6I: (2-bromo-4-chloro-7,8-dihydro-[1,4]dioxino[2',3':3,4]benzo[1,2-d]thiazol-7-yl) methanol

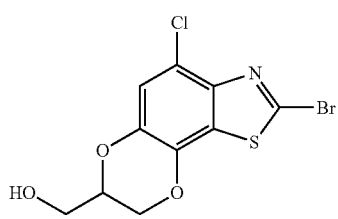
(I-6I)

To Intermediate I-6H (1.45 g, 3.83 mmol) dissolved in THF (15 mL) and cooled with an ice-bath was added 1.0 N NaOH (4.60 mL, 4.60 mmol). After 2 min stirring, MeOH (3.0 mL) was added. After another 20 min stirring at 0° C., HPLC indicated a clean reaction. 1.0 N HCl (5.0 mL) was added. The mixture was diluted with EtOAc/THF/water. The organic layer was collected, washed with saturated sodium bicarbonate, brine and dried over sodium sulfate. After evaporation of solvent, Intermediate I-6I (1.30 g, 3.86 mmol, 101% yield) was obtained as a slightly yellow solid. $^1$H NMR (400 MHz, chloroform-d) δ 7.03 (s, 1H), 4.39-4.33 (m, 1H), 4.21-4.06 (m, 2H), 3.77-3.67 (m, 2H); LC-MS: method A, RT=1.90 min, MS (ESI) m/z: 338.0 and 340.0 (M+H)$^+$.

Intermediate I-6J (4-chloro-2-(2-(difluoromethoxy)-7-methylquinoxalin-5-yl)-7,8-dihydro-[1,4]dioxino[2',3':3,4]benzo[1,2-d]thiazol-7-yl)methanol

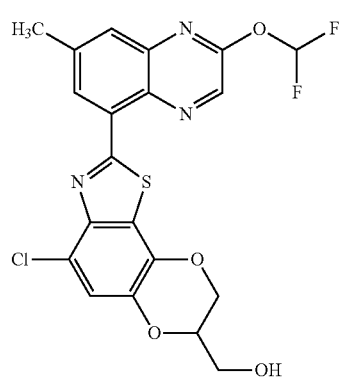

(I-6J)

To Intermediate I-1 (297 mg, 1.168 mmol), Intermediate I-6I (393 mg, 1.168 mmol) and PdCl$_2$(dppf)—CH$_2$Cl$_2$ adduct (38.1 mg, 0.047 mmol) was added toluene (7.50 mL) and EtOH (2.5 mL). The mixture was sonicated for 1 min, and flushed with argon. To this was added sodium carbonate, 2M (1.022 mL, 2.043 mmol). The reaction mixture was heated in a microwave reactor at 130° C. for 30 min. HPLC and LCMS indicated a clean reaction. The crude reaction mixture was directly loaded on a ISCO column for purification. The crude product was purified by flash chromatography (5% to 60% EtOAc in hexane over 12 min using a 40 g silica gel cartridge). The desired fractions were combined and concentrated to yield Intermediate I-6J (494 mg, 1.060 mmol, 91% yield) as a yellow solid. LC-MS: method A, RT=2.45 min, MS (ESI) m/z: 466.0 and 468.0 (M+H)$^+$.

Intermediate I-6

To Intermediate I-6J (494 mg, 1.060 mmol) dissolved in THF (8 mL) and MeOH (6.0 mL) at room temperature was added 4.3 M sodium methoxide in MeOH (1.973 mL, 8.48 mmol). The reaction mixture was stirred at room temperature for 2.0 h. LCMS indicated a clean reaction. Methanol was removed under vacuum. The reaction mixture was diluted with EtOAc, quenched with 0.5 N HCl (10.0 mL). The organic layer was washed with saturated sodium bicarbonate, brine, dried and concentrated to give Intermediate I-6 (430 mg, 1.000 mmol, 94% yield) as a yellow solid. $^1$H NMR (500 MHz, DMSO-d$_6$) δ 8.78 (s, 1H), 8.58 (s, 1H), 7.87 (s, 1H), 7.30 (s, 1H), 5.19 (t, J=5.4 Hz, 1H), 4.59 (d, J=11.3 Hz, 1H), 4.35 (d, J=5.5 Hz, 1H), 4.25 (dd, J=11.3, 7.7 Hz, 1H), 4.09 (s, 3H), 3.77-3.68 (m, 2H), 2.66 (s, 3H); LC-MS: method A, RT=2.42 min, MS (ESI) m/z: 430.1 (M+H)$^+$.

Intermediate I-7

(2-(2-methoxy-7-methylquinoxalin-5-yl)-4-methyl-7,8-dihydro-[1,4]dioxino[2',3':3,4]benzo[1,2-d]thiazol-7-yl)methanol

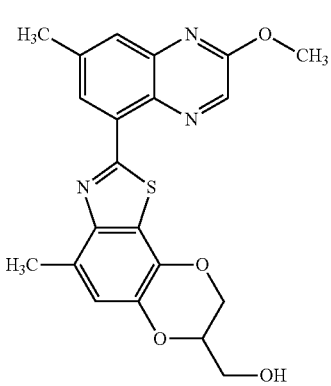

(I-7)

Intermediate I-7A:
5-methyl-2-(oxiran-2-ylmethoxy)benzaldehyde

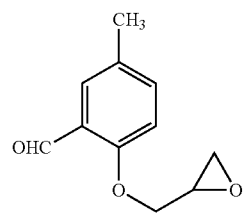

(I-7A)

To a solution of 2-hydroxy-5-methylbenzaldehyde (1.96 g, 14.40 mmol) in DMF (30 mL) was added Cs$_2$CO$_3$ (10.32 g, 31.7 mmol), followed by 2-(bromomethyl)oxirane (2.218 mL, 25.9 mmol). The mixture was stirred at room temperature for 10 min, and then at 50° C. for 1.5 h. HPLC and TLC indicated a clean reaction. After cooling to room temperature, the reaction mixture was diluted with EtOAc/water. The organic layer was collected, washed with brine and dried over sodium sulfate. After evaporation of solvent, the crude product was dissolved in a small amount of chloroform and charged to a 40 g silica gel cartridge which was eluted with hexanes for 2 min., then a 15 min gradient from 0% to 50% EtOAc in hexanes. The desired fractions were combined and concentrated to give Intermediate I-7A (2.69 g, 14.00 mmol, 97% yield) as a white solid. $^1$H NMR (400 MHz, chloroform-d) δ 10.52 (s, 1H), 7.67 (d, J=2.2 Hz, 1H), 7.39-7.34 (m, 1H), 6.91 (d, J=8.4 Hz, 1H), 4.37 (dd, J=11.1, 3.0 Hz, 1H), 4.07 (dd, J=11.2, 5.7 Hz, 1H), 3.42 (ddt, J=5.7, 4.1, 2.7 Hz, 1H), 2.98-2.94 (m, 1H), 2.81 (dd, J=4.8, 2.6 Hz, 1H), 2.34 (s, 3H); LC-MS: method A, RT=1.53 min, MS (ESI) m/z: 215.0 (M+Na)$^+$.

Intermediate I-7B: 5-methyl-2-(oxiran-2-ylmethoxy)phenyl formate

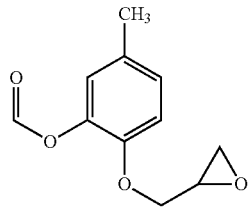

To a stirred solution of Intermediate I-7A (2.66 g, 13.84 mmol) in dichloromethane (40 mL) cooled with a water bath was added mCPBA (4.70 g, 20.41 mmol). Trifluoroacetic acid (1.066 mL, 13.84 mmol) in dichloromethane (10 mL) was added dropwise. The mixture was stirred at room temperature for 2.0 h. TLC indicated a completion of reaction. The reaction was quenched by addition of saturated sodium bicarbonate, followed by 10% sodium thiosulfite (20.0 mL), extracted with dichloromethane. The organic layers were collected, washed with saturated sodium bicarbonate, brine and dried over sodium sulfate. After evaporation of solvent, the crude product was dissolved in a small amount of chloroform and charged to a 80 g silica gel cartridge which was eluted with hexanes for 2 min., then a 18 min gradient from 0% to 35% EtOAc in hexanes. The desired fractions were combined and concentrated to give Intermediate I-7B (2.6 g, 12.49 mmol, 90% yield) as a colorless oil (purity ca 90%). $^1$H NMR (400 MHz, chloroform-d) δ 8.31 (s, 1H), 7.06-7.01 (m, 1H), 6.96-6.92 (m, 2H), 4.24 (dd, J=11.2, 3.1 Hz, 1H), 4.01 (dd, J=11.2, 5.5 Hz, 1H), 3.35-3.30 (m, 1H), 2.90 (dd, J=4.8, 4.2 Hz, 1H), 2.74 (dd, J=5.1, 2.6 Hz, 1H), 2.32 (s, 3H); LC-MS: method A, RT=1.48 min, MS (ESI) m/z: 231.0 (M+Na)$^+$.

Intermediate I-7C: (7-methyl-2,3-dihydrobenzo[b][1,4]dioxin-2-yl)methanol

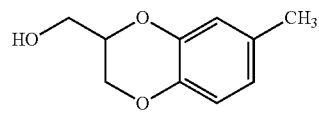

To Intermediate I-7B (2.6 g, 12.49 mmol) in MeOH (60 mL) was added potassium carbonate (5.18 g, 37.5 mmol). The mixture was stirred at room temperature overnight. HPLC and TLC indicated a completion of reaction. The mixture was treated with 1.0 N HCl (35 mL). Methanol was removed under vacuum. The residue was partitioned between EtOAc/water. The organic layer was washed with brine, dried over sodium sulfate. After evaporation of solvent, Intermediate I-7C (2.3 g, 12.76 mmol, 102% yield) was obtained as a colorless oil. It was used for the next step without further purification. $^1$H NMR (400 MHz, chloroform-d) δ 6.78 (d, J=8.1 Hz, 1H), 6.72 (d, J=1.5 Hz, 1H), 6.68-6.64 (m, 1H), 4.30-4.23 (m, 2H), 4.12-4.08 (m, 1H), 3.93-3.80 (m, 2H), 2.26 (s, 3H); LC-MS: method A, RT=1.56 min, MS (ESI) m/z: 203.0 (M+Na)$^+$.

Intermediate I-7D: (7-methyl-2,3-dihydrobenzo[b][1,4]dioxin-2-yl)methyl acetate

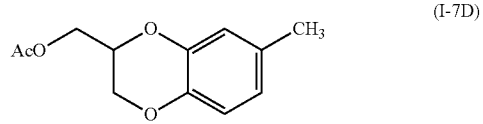 [SMILES: CC(=O)OCC1COc2ccc(C)cc2O1]

To a solution of Intermediate I-7C (2.4 g, 13.32 mmol) in THF (40 mL) at 0° C. was added TEA (4.64 mL, 33.3 mmol), followed by acetyl chloride (1.184 mL, 16.65 mmol) in THF (3.0 mL) dropwise. The mixture was stirred at 0° C. for 10 min, and at room temperature for 1.0 h. HPLC indicated a clean reaction. The mixture was diluted with EtOAc, washed with water. The organic layer was washed with 0.5 N HCl, saturated sodium bicarbonate, brine and dried over sodium sulfate. After evaporation of solvent, Intermediate I-7D (2.8 g, 12.60 mmol, 95% yield) was obtained as an oil. It was used for the next step without further purification. $^1$H NMR (400 MHz, chloroform-d) δ 6.77 (d, J=8.1 Hz, 1H), 6.73 (d, J=1.3 Hz, 1H), 6.68-6.64 (m, 1H), 4.42-4.35 (m, 1H), 4.31 (dd, J=5.3, 4.4 Hz, 2H), 4.29-4.24 (m, 1H), 4.04 (dd, J=11.4, 6.8 Hz, 1H), 2.26 (s, 3H), 2.12 (s, 3H); LC-MS: method A, RT=1.85 min, MS (ESI) m/z: 245.0 (M+Na)$^+$.

Intermediate I-7E: (7-methyl-6-nitro-2,3-dihydrobenzo[b][1,4]dioxin-2-yl)methyl acetate

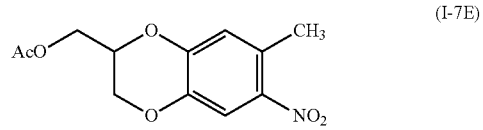

To a solution of Intermediate I-7D (2.8 g, 12.60 mmol) in acetic acid (6.0 mL) cooled at 0° C. with an ice-bath was added fuming nitric acid (2.058 mL, 44.1 mmol) dropwise. The mixture was stirred at 0° C. for 1.0 h. LCMS and TLC indicated a clean reaction. It was quenched with ice water. The aqueous was removed and the organic layer was washed with saturated sodium bicarbonate (3×), brine and dried over sodium sulfate. After evaporation of solvent, Intermediate I-7E (3.1 g, 11.60 mmol, 92% yield) was obtained as a yellow solid that was used for the next step without further purification. $^1$H NMR (400 MHz, chloroform-d) δ 7.70 (s, 1H), 6.83 (s, 1H), 4.48 (dd, J=7.0, 2.4 Hz, 1H), 4.39-4.30 (m, 3H), 4.09 (dd, J=11.7, 7.0 Hz, 1H), 2.55 (s, 3H), 2.13 (s, 3H); LC-MS: method A, RT=1.86 min, MS (ESI) m/z: 268.0 (M+H)$^+$.

Intermediate I-7F: (6-amino-7-methyl-2,3-dihydrobenzo[b][1,4]dioxin-2-yl)methyl acetate

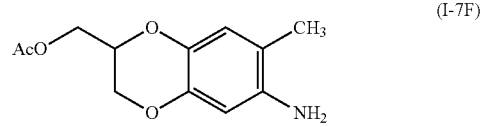 [SMILES: CC(=O)OCC1COc2cc(N)c(C)cc2O1]

To a solution of Intermediate I-7E (0.36 g, 1.347 mmol) in MeOH (4.0 mL) and THF (4.0 mL) was added ammonium chloride (1.153 g, 21.55 mmol) and zinc dust (0.705 g, 10.78 mmol). The mixture was stirred at room temperature for 1.0 h. HPLC, TLC and LCMS indicated a clean reaction. MeOH was removed under vacuum. The residue was diluted with EtOAc/saturated sodium bicarbonate and stirred at room temperature for 10 min. The mixture was filtered to remove insoluble material. The filtrate was collected, organic layer was washed with brine, dried over sodium sulfate, concentrated to give Intermediate I-7F (0.32 g, 1.349 mmol, 100% yield) as a yellow solid. $^1$H NMR (400 MHz, chloroform-d) δ 6.63 (s, 1H), 6.25 (s, 1H), 4.33-4.27 (m, 3H), 4.23 (dd, J=11.3, 1.9 Hz, 1H), 4.04-3.98 (m, 1H), 2.11 (s, 3H), 2.08 (s, 3H); LC-MS: method A, RT=1.02 min, MS (ESI) m/z: 238.0 (M+H)$^+$.

Intermediate I-7G: (2-amino-4-methyl-7,8-dihydro-[1,4]dioxino[2',3':3,4]benzo[1,2-d]thiazol-7-yl)methyl acetate

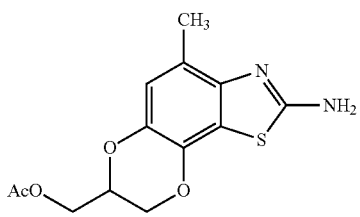

To Intermediate I-7F (2.47 g, 10.41 mmol) dissolved in acetonitrile (40 mL) was added ammonium thiocyanate (1.189 g, 15.62 mmol). The mixture was stirred at room temperature for 10 min. Benzyltrimethylammonium tribromide (4.26 g, 10.93 mmol) in acetonitrile (15 mL) was added dropwise (5 min). The mixture was stirred at room temperature overnight. HPLC and LCMS indicated a clean reaction. The mixture was diluted with EtOAc/THF/saturated sodium bicarbonate. The insoluble material was removed by filtration. The organic layer of the filtrate was collected, washed with brine, dried over sodium sulfate. After evaporation of solvent, Intermediate I-7G (2.76 g, 9.38 mmol, 90% yield) was obtained as a yellow solid. $^1$HNMR and IPLC indicated ca 90% purity. It was used for the next step without further purification. $^1$H NMR (400 MHz, methanol-d4) δ 6.65 (s, 1H), 4.38-4.32 (m, 2H), 4.31-4.27 (m, 2H), 4.13-4.06 (m, 1H), 2.36 (s, 3H), 2.07 (s, 3H); LC-MS: method A, RT=1.37 min, MS (ESI) m/z: 295.0 (M+H)$^+$.

Intermediate I-7H (2-bromo-4-methyl-7,8-dihydro-[1,4]dioxino[2',3':3,4]benzo[1,2-d]thiazol-7-yl)methyl acetate

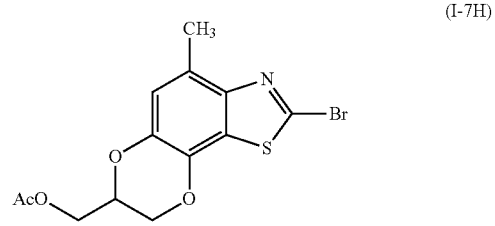 [SMILES: CC(=O)OCC1COc2c(cc(C)c3nc(Br)sc23)O1]

Tert-butyl nitrite (0.424 mL, 3.21 mmol) was added to copper(II) bromide (0.697 g, 3.12 mmol) in dry acetonitrile (8 mL) under argon. The mixture was stirred at room temperature for 10 min. A suspension of Intermediate I-7G (0.54 g, 1.835 mmol) in dry acetonitrile (8 mL) was added dropwise. The reaction mixture was stirred at room temperature for 1.5 h. IPLC and LCMS indicated a clean reaction. Acetonitrile was removed under vacuum, the reaction mixture was diluted with EtOAc, quenched with 1.0 N HCl. The organic layer was collected, washed with 0.5 N HCl (2×), saturated sodium bicarbonate, brine and dried over sodium sulfate. After evaporation of solvent, Intermediate I-7H (0.64 g, 1.787 mmol, 97% yield) was obtained as a brown solid. It was used for next step without further purification. $^1$H NMR (400 MHz, chloroform-d) δ 6.90 (d, J=0.9 Hz, 1H), 4.50-4.32 (m, 4H), 4.19 (dd, J=11.3, 6.9 Hz, 1H), 2.61 (d, J=0.9 Hz, 3H), 2.16-2.13 (s, 3H); LC-MS: method A, RT=2.15 min, MS (ESI) m/z: 358.0 and 360.0 (M+H)$^+$.

Intermediate I-7I: (2-bromo-4-methyl-7,8-dihydro-[1,4]dioxino[2',3':3,4]benzo[1,2-d]thiazol-7-yl)methanol

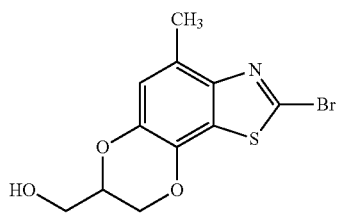

To Intermediate I-7H (0.64 g, 1.787 mmol) dissolved in THF (10 mL) and cooled with an ice-bath was added 1.0 N NaOH (2.144 mL, 2.144 mmol). After 10 min stirring, MeOH (1.2 mL) was added. After another 20 min stirring at 0° C., HPLC indicated a clean reaction. 1.0 N HCl (2.5 mL) was added. The mixture was diluted with EtOAc/THF/water. The organic layer was collected, washed with saturated sodium bicarbonate, brine and dried over sodium sulfate. After evaporation of solvent, Intermediate I-7I (0.55 g, 1.740 mmol, 97% yield) was obtained as a brown solid. $^1$H NMR (400 MHz, chloroform-d) δ 6.89 (s, 1H), 4.44 (d, J=11.2 Hz, 1H), 4.33 (br. s., 1H), 4.29-4.21 (m, 1H), 4.03-3.87 (m, 2H), 2.61 (s, 3H), 1.95 (br. s., 1H); LC-MS: method A, RT=1.95 min, MS (ESI) m/z: 316.0 and 318.0 (M+H)⁺.

Intermediate I-7J (2-(2-(difluoromethoxy)-7-methylquinoxalin-5-yl)-4-methyl-7,8-dihydro-[1,4]dioxino[2',3':3,4]benzo[1,2-d]thiazol-7-yl)methanol

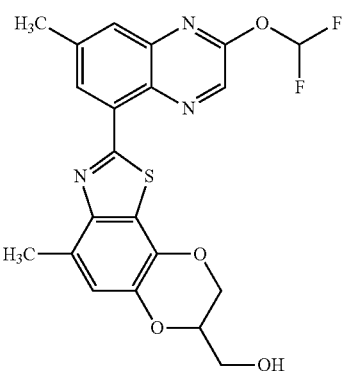

(I-7J)

To Intermediate I-1 (348 mg, 1.370 mmol), Intermediate I-7I (433 mg, 1.370 mmol) and PdCl₂(dppf)—CH₂Cl₂ adduct (44.7 mg, 0.055 mmol) was added toluene (6 mL) and EtOH (2.000 mL). The mixture was sonicated for 1 min, and flushed with argon. To this was added sodium carbonate, 2M (1.370 mL, 2.74 mmol). The reaction mixture was heated in a microwave reactor at 130° C. for 30 min. HPLC and LCMS indicated a clean reaction. The reaction mixture was directly loaded on an ISCO column for purification. The crude product was purified by flash chromatography (10% to 75% EtOAc in hexane over 15 min using a 80 g silica gel cartridge). The desired fractions were combined and concentrated to yield Intermediate I-7J (520 mg, 1.167 mmol, 85% yield) as a yellow solid. LC-MS: method A, RT=2.40 min, MS (ESI) m/z: 446.0 (M+H)⁺.

Intermediate I-7

To Intermediate I-7J (520 mg, 1.167 mmol) dissolved in THF (8.0 mL) and MeOH (10 mL) at room temperature was added sodium methoxide (378 mg, 7.00 mmol). The cloudy reaction mixture was stirred at room temperature for 2.0 h. LCMS indicated ca 40% starting material present. Then DMF (6.0 mL) was added, and the reaction turned to a clear solution. The reaction mixture was heated at 55° C. for 4.0 h. Methanol was removed under vacuum. The reaction mixture was diluted with EtOAc, quenched with 0.5 N HCl (10 mL). The organic layer was washed with saturated sodium bicarbonate, brine, dried and concentrated to give Intermediate I-7 (470 mg, 1.148 mmol, 98% yield) as a yellow solid. ¹H NMR (500 MHz, DMSO-d₆) δ 8.73 (s, 1H), 8.57 (s, 1H), 7.80 (br. s., 1H), 6.95 (s, 1H), 5.13 (br. s., 1H), 4.53 (d, J=11.3 Hz, 1H), 4.29 (br. s., 1H), 4.23-4.16 (m, 1H), 4.08 (s, 3H), 3.77-3.65 (m, 2H), 2.64 (s, 3H); LC-MS: method A, RT=2.45 min, MS (ESI) m/z: 410.1 (M+H)⁺.

Intermediate I-9

(2-methoxy-7-methylquinoxalin-5-yl)boronic acid

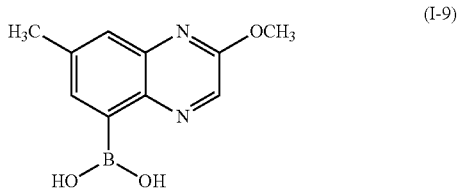 [SMILES: COc1cnc2c(B(O)O)cc(C)cc2n1]

(I-9)

Intermediate I-9A:
5-bromo-2-methoxy-7-methylquinoxaline

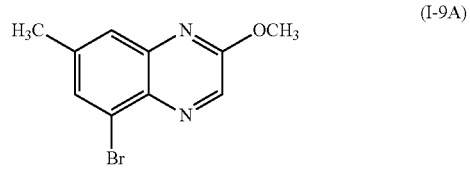

(I-9A)

To Intermediate I-1G (3.13 g, 10.83 mmol) dissolved in THF (20 mL) and MeOH (15 mL) at room temperature was added 4.3 M sodium methoxide in MeOH (7.55 mL, 32.5 mmol). The reaction mixture was stirred at room temperature over night. Methanol was removed under vacuum. The reaction mixture was diluted with EtOAc, quenched with 0.5 N HCl (30.0 mL). The organic layer was washed with saturated sodium bicarbonate, brine, dried and concentrated to give Intermediate I-9A (2.7 g, 10.67 mmol, 99% yield) as a slightly yellow solid. ¹H NMR (500 MHz, chloroform-d) δ 8.48 (s, 1H), 7.72 (d, J=1.7 Hz, 1H), 7.60 (dd, J=1.8, 1.0 Hz, 1H), 4.10 (s, 3H), 2.53 (s, 3H); LC-MS: Method A, 30 to 100% B. RT=1.71 min, MS (ESI) m/z: 253.0 and 255.0 (M+H)⁺.

Intermediate I-9

A mixture of Intermediate I-9A (700 mg, 2.77 mmol), bis(pinacolato)diboron (1053 mg, 4.15 mmol), potassium acetate (679 mg, 6.91 mmol) and PdCl₂(dppf)—CH₂Cl₂ adduct (113 mg, 0.138 mmol) in dioxane (14 mL) was degassed by bubbling argon for 5 min. It was then heated at 130° C. for 40 min. The reaction mixture was mixed with EtOAc/water and stirred at room temperature for 15 min. The insoluble material was removed by filtration through a pad of wet celite. The organic layer was washed with brine, dried over sodium sulfate and concentrated. The crude product was purified by flash chromatography (loading in chloroform, 5% to 100% EtOAc in hexane over 15 min using a 80 g silica gel cartridge). The desired fractions were combined, concentrated and lyophilized to yield to yield Intermediate I-9 (362 mg, 1.659 mmol, 60% yield) as a solid. ¹H NMR (500 MHz, methanol-d4) δ 8.41 (s, 1H), 7.69 (br. s., 1H), 7.49 (br. s., 1H), 4.10 (s, 3H), 2.56 (s, 3H). LC-MS: method H, RT=0.83 min, MS (ESI) m/z: 219.1 (M+H)⁺.

Intermediate I-14

5-iodo-7-methylquinoxalin-2(1H)-one

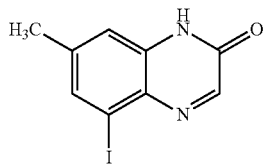
(I-14)

Intermediate I-14A: 2-iodo-4-methyl-6-nitroaniline

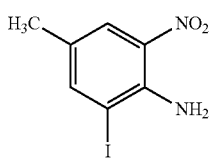
(I-14A)

Iodine (4.59 g, 18.07 mmol) was dissolved in EtOH (65.7 mL). 4-methyl-2-nitroaniline (2.5 g, 16.43 mmol) then silver sulfate (5.64 g, 18.07 mmol) were added and the reaction mixture was allowed to stir for 18 hours. The reaction mixture was diluted with EtOAc, filtered through a sintered glass funnel, and concentrated in vacuo. The crude material was redissolved in EtOAc and washed with saturated $Na_2S_2O_3$, saturated $NaHCO_3$, then brine, dried ($Na_2SO_4$), filtered, and concentrated in vacuo to give Intermediate I-14A (4.65 g, 16.72 mmol, 100%) as an orange solid: $^1$H NMR (400 MHz, CHLOROFORM-d) δ 7.97 (d, J=1.0 Hz, 1H), 7.78 (d, J=2.0 Hz, 1H), 6.49 (br. s., 2H), 2.26 (s, 3H); LC-MS: Method H, RT=0.98 min, MS (ESI) m/z: 279.0 (M+H)$^+$.

Intermediate I-14B: bis-tert-butyl (2-iodo-4-methyl-6-nitroaniline)bis carbamate

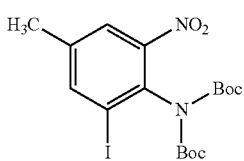
(I-14B)

Intermediate I-14A (4.65 g, 16.72 mmol), DMAP (0.204 g, 1.672 mmol), and Boc$_2$O (9.71 mL, 41.8 mmol) were dissolved in THF (27.9 mL) and stirred for 18 hours. The reaction mixture was diluted with water and extracted with EtOAc. The organic layer was washed with brine, dried (Na$_2$SO$_4$), filtered, and concentrated in vacuo. The crude material was purified by column chromatography (ISCO, 220 g silica gel column, 50 minute gradient from 0 to 100% EtOAc in hexanes), to give Intermediate I-14B (5.4 g, 11.29 mmol, 67.5%) as a light yellow solid: $^1$H NMR (400 MHz, CHLOROFORM-d) δ 7.94 (s, 1H), 7.78 (s, 1H), 2.43 (s, 3H), 1.40 (s, 18H); LC-MS: Method H, RT=1.10 min, MS (ESI) m/z: (bis-deboc mass observed) 278.9 (M+H)$^+$.

Intermediate I-14C: methyl 2-((tert-butoxycarbonyl)(2-iodo-4-methyl-6-nitrophenyl) amino)acetate

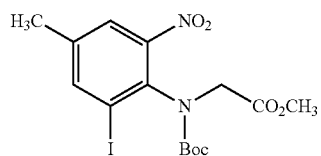
(I-14C)

Intermediate I-14B (5.4 g, 11.29 mmol) was dissolved in DCM (18.82 mL) and TFA (1.740 mL, 22.58 mmol) and stirred for 30 minutes. The reaction mixture was diluted with DCM, quenched with saturated NaHCO$_3$, washed with brine, dried (Na$_2$SO4), filtered, and concentrated in vacuo. The crude material was dissolved in DMF (18.82 mL). Cs$_2$CO$_3$ (9.20 g, 28.2 mmol) was added and stirred for 15 minutes. The reaction turned deep red. Methyl bromoacetate (1.249 mL, 13.55 mmol) was added and the reaction mixture was allowed to stir 24 hours. The reaction turned from deep red to yellow. The reaction mixture was diluted with EtOAc, washed with water, then brine, dried (Na$_2$SO$_4$), filtered, and concentrated in vacuo. The crude material was purified by column chromatography (ISCO, 220 g silica gel column, 50 minute gradient from 0 to 100% EtOAc in hexanes) to give Intermediate I-14C (3.51 g, 7.80 mmol, 69.1%) as an orange solid: LC-MS: Method H, RT=1.00 min, MS (ESI) m/z: (deboc mass observed) 350.9 (M+H)$^+$.

Intermediate I-14D: methyl 2-((2-iodo-4-methyl-6-nitrophenyl)amino)acetate

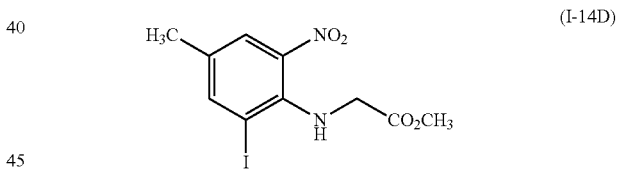
(I-14D)

Intermediate I-14C (3.51 g, 7.80 mmol) was dissolved in HCl in dioxane (4 M, 9.75 mL, 39.0 mmol) and stirred for 1 hour. The reaction mixture was concentrated in vacuo to give Intermediate I-14D, which was used directly in the subsequent step without purification: LC-MS: Method H, RT=0.79 min, MS (ESI) m/z: 350.9 (M+H)$^+$.

Intermediate I-14E: 5-iodo-7-methyl-3,4-dihydroquinoxalin-2(1H)-one

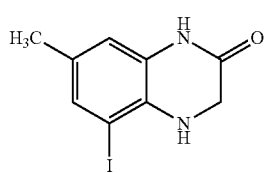
(I-14E)

Intermediate I-14D (2.73 g, 7.80 mmol) was dissolved in MeOH (28.4 mL). HCl (2.60 mL, 31.2 mmol) then tin(II) chloride dihydrate (7.04 g, 31.2 mmol) were added and the reaction mixture was heated to 65° C. for 3.5 hours. The reaction mixture was cooled to ambient temperature, neutralized with 10 N NaOH and diluted with brine then EtOAc. Vigorous stirring was allowed for 15 minutes. The mixture was filtered through celite and concentrated in vacuo to give Intermediate I-14E (1.77 g, 6.14 mmol, 79.0%) as an orange solid: $^1$H NMR (400 MHz, CHLOROFORM-d) δ 7.57 (br. s., 1H), 7.17 (s, 1H), 6.48 (s, 1H), 4.17 (br. s., 1H), 4.02 (d, J=1.8 Hz, 2H), 2.21 (s, 3H); LC-MS: Method H, RT=0.82 min, MS (ESI) m/z: 289.0 (M+H)$^+$.

Intermediate I-14

Intermediate I-14E (1.7696 g, 6.14 mmol) was suspended in MeOH (17.86 mL). NaOH (18.43 mL, 18.43 mmol) then $H_2O_2$ (3.23 mL, 36.9 mmol) were added and the reaction mixture was stirred for 24 hours. More $H_2O_2$ (3.23 mL, 36.9 mmol) was added and the reaction mixture was stirred for 24 hours. More $H_2O_2$ (3.23 mL, 36.9 mmol) was added and the reaction mixture was stirred for 24 hours. The reaction mixture was diluted with ca 50 mL of water then about 50 mL of brine. The mixture was evaporated under a nitrogen stream to remove MeOH. The aqueous material was extracted thrice with EtOAc. During the extractions, an off-white solid precipitated. This precipitate was collected by suction filtration as to give Intermediate I-14 (1.35 g, 4.72 mmol, 77.0%): $^1$H NMR (400 MHz, DMSO-d$_6$) δ 12.44 (br. s., 1H), 8.11 (s, 1H), 7.72 (d, J=1.5 Hz, 1H), 7.09 (s, 1H), 2.37 (s, 3H); LC-MS: Method H, RT=0.80 min, MS (ESI) m/z: 287.0 (M+H)$^+$.

Intermediate I-15

(2-(ethoxycarbonyl)-7-methylquinoxalin-5-yl)boronic acid

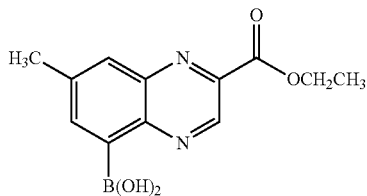

(I-15)

Intermediate I-15A:
3-bromo-5-methylbenzene-1,2-diamine

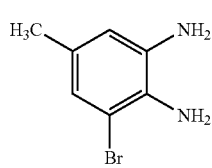

(I-15A)

2-bromo-4-methyl-6-nitroaniline (5.00 g, 21.64 mmol) was dissolved in MeOH (148 mL) and THF (18.50 mL). Ammonium chloride (23.15 g, 433 mmol) then zinc (14.15 g, 216 mmol) were added and the reaction mixture was heated to 40° C. for 1 h. The reaction mixture was cooled to ambient temperature, concentrated in vacuo, re-dissolved in EtOAc and saturated $Na_2CO_3$, and stirred vigorously for 10 minutes. The mixture was filtered through a sintered glass funnel and washed with more EtOAc. The organic layer was further washed twice with water, washed with brine, dried with sodium sulfate, filtered, and concentrated in vacuo to yield Intermediate I-15A (4.35 g, 21.63 mmol, 100% yield). $^1$H NMR (400 MHz, CHLOROFORM-d) δ 6.81 (s, 1H), 6.48 (s, 1H), 3.66 (br. s., 2H), 3.46 (br. s., 2H), 2.19 (s, 3H). LC-MS: method H, RT=0.93 min, MS (ESI) m/z: 201.0 (M+H)$^+$.

Intermediate I-15B: ethyl
5-bromo-7-methylquinoxaline-2-carboxylate

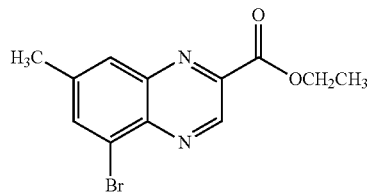

(I-15B)

Intermediate I-15A (4.35 g, 21.63 mmol) and ethyl 3-bromo-2-oxopropanoate (3.63 mL, 26.0 mmol) were dissolved in NMP (72.1 mL) and allowed to stir at room temperature for 18 h open to air. The reaction mixture was diluted with water and EtOAc. The layers were separated and the aqueous layer was back extracted with EtOAc (x3). The combined organic layer was washed with brine, dried with sodium sulfate, and concentrated under reduced pressure. The reaction mixture was purified by ISCO column using 0-40% EtOAc in hexanes on a 220 g column to yield a mixture of regioisomers. The reaction mixture was purified by SFC on a Chiralcel OD-H, 30×250 mm, 5 micron column using 20% IPA/80% $CO_2$ with 85 mL/min, 100 Bar, 40° C. to yield Intermediate I-15B (0.936 g, 3.17 mmol, 14.66% yield) as a yellow solid. $^1$H NMR (400 MHz, CHLOROFORM-d) δ 9.48 (s, 1H), 8.01 (s, 1H), 7.99 (s, 1H), 4.53 (q, J=7.0 Hz, 2H), 2.55 (s, 3H), 1.44 (t, J=7.2 Hz, 3H). LC-MS: method H, RT=1.15 min, MS (ESI) m/z: 295.1 (M+H)$^+$.

Intermediate I-15

A mixture of Intermediate I-15B (0.100 g, 0.339 mmol), bis(pinacolato)diboron (0.129 g, 0.508 mmol), potassium acetate (0.083 g, 0.847 mmol) in dioxane (3.39 mL) were degassed by bubbling argon for 5 min. $PdCl_2(dppf)$—$CH_2Cl_2$ adduct (0.014 g, 0.017 mmol) was added and the mixture was sealed and heated in microwave at 130° C. for 30 min. The reaction mixture was diluted with water and EtOAc. The layers were separated and the organic layer was washed with brine, dried with sodium sulfate, and concentrated under reduced pressure to yield a brown oil. The reaction mixture was purified on Prep HPLC using Method A to yield Intermediate I-15 (0.027 g, 0.104 mmol, 30.6% yield) as an off white solid. LC-MS: method H, RT=1.15 min, MS (ESI) m/z: 261.2 (M+H)$^+$.

Intermediate I-16

(5-bromo-7-methylquinoxalin-2-yl)methyl methanesulfonate

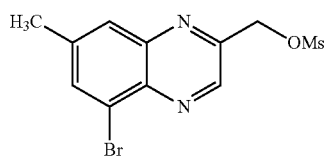

(I-16)

Intermediate I-16A:
(5-bromo-7-methylquinoxalin-2-yl)methanol

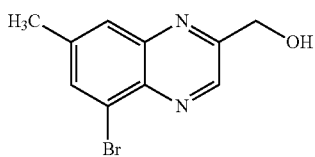

(I-16A)

NaBH$_4$ (25.6 mg, 0.678 mmol) and CaCl$_2$ (37.6 mg, 0.339 mmol) were dissolved in THF (2 ml) and the mixture was stirred at room temperature for 30 min. A solution of I-15B (100 mg, 0.34 mmol) in THF (1 mL) was added. The mixture was stirred at room temperature overnight. The reaction was diluted with EtOAc, washed with water, then brine, dried (Na$_2$SO$_4$), filtered, and concentrated in vacuo. The crude material was purified by column chromatography (ISCO, 12 g silica gel column, 19 minute gradient from 0 to 100% EtOAc in hexanes) to yield Intermediate I-16A (63 mg, 0.249 mmol, 73.5% yield) as a yellow solid. $^1$H NMR (500 MHz, CHLOROFORM-d) δ 8.85 (s, 1H), 7.92 (d, J=1.7 Hz, 1H), 7.79 (dd, J=1.7, 1.1 Hz, 1H), 5.04 (s, 2H), 3.73 (br. s., 1H), 2.58 (s, 3H).

Intermediate I-16

I-16A (0.050 g, 0.198 mmol) was dissolved in DCM (3 ml) and treated with TEA (0.083 ml, 0.593 mmol). To this solution was added methanesulfonic anhydride (0.041 g, 0.237 mmol) and the reaction was allowed to stir at room temperature for 1 h. Reaction was diluted with EtOAc and sat'd sodium bicarbonate. The layers were separated and the organic layer was washed with brine, dried with sodium sulfate and concentrated under reduced pressure. Used without further purification in the next step. MS (ESI) m/z: 331.0 (M+H)+.

Intermediate I-25

2-(methoxymethyl)-7-methyl-5-(4,4,5,5-tetramethyl-1,3,2-dioxaborolan-2-yl) quinoxaline, D$_5$

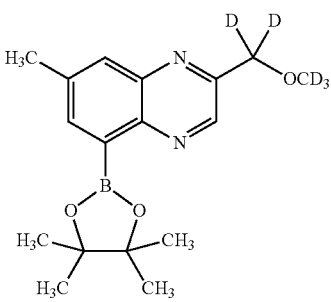

(I-25)

Intermediate I-25A:
5-bromo-2-(methoxymethyl)-7-methylquinoxaline, d$_5$

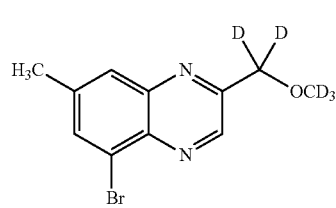

(I-25A)

CD$_3$ONa was prepared by dissolving sodium metal (60 mg, 2.500 mmol) in CD$_3$OD (0.405 mL, 10 mmol) for 30 minutes. Intermediate I-16 (207 mg, 0.625 mmol) was dissolved in THF (12 mL). CD$_3$ONa (71.3 mg, 1.250 mmol) was added, and the reaction mixture was allowed to stir at room temperature for 18 h. The reaction mixture was partially concentrated in vacuo to remove THF, diluted with EtOAc and washed with water, washed with brine, dried with sodium sulfate, filtered, and concentrated in vacuo to yield Intermediate I-25A (0.118 g, 0.432 mmol, 69% yield). $^1$H NMR (400 MHz, CHLOROFORM-d) δ 9.01 (s, 1H), 7.93 (d, J=1.5 Hz, 1H), 7.82 (dd, J=1.8, 0.9 Hz, 1H), 2.58 (s, 3H). LC-MS: method H, RT=0.90 min, MS (ESI) m/z: 272.1 (M+H)+.

Intermediate I-25

Intermediate I-25A (117.6 mg, 0.432 mmol), bis(pinacolato)diboron (165 mg, 0.648 mmol), and potassium acetate (106 mg, 1.080 mmol) were dissolved in dioxane (4321 µl) and degassed for 5 minutes by bubbling with argon. PdCl$_2$ (dppf)—CH$_2$Cl$_2$ adduct (28.2 mg, 0.035 mmol) was added and the reaction mixture was degassed for an additional 10 minutes. The reaction mixture was heated to 130° C. in the microwave for 45 minutes. The reaction mixture was diluted with EtOAc and water and filtered. The reaction mixture was further extracted twice with EtOAc. The combined organic layers were washed with brine, dried with sodium sulfate, filtered, and concentrated in vacuo to yield Intermediate I-25 (0.097 g, 0.302 mmol, 70% yield). LC-MS: method H, RT=0.75 min, MS (ESI) m/z: 238.2 (M+H)⁺. Observed the mass of the boronic acid in LC/MS.

Intermediate I-26

(R)-(2-chloro-4-methyl-7,8-dihydro-[1,4]dioxino[2', 3':3,4]benzo[1,2-d]thiazol-7-yl)methy 1 acetate

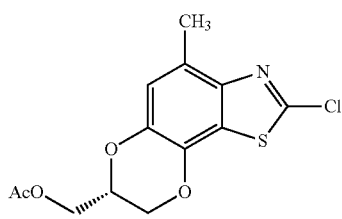
(I-26)

Intermediate I-26A: (R)-5-methyl-2-(oxiran-2-yl-methoxy)benzaldehyde

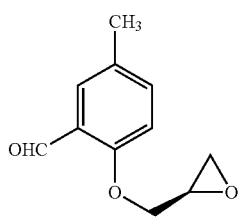
(I-26A)

To a solution of 2-hydroxy-5-methylbenzaldehyde (5 g, 36.7 mmol) in DMF (80 mL) was added (R)-oxiran-2-ylmethyl 3-nitrobenzenesulfonate (10.47 g, 40.4 mmol) and $Cs_2CO_3$ (35.9 g, 110 mmol). The mixture was stirred at room temperature overnight. LCMS indicated a completion of the reaction. The mixture was diluted with EtOAc and water, extracted with EtOAc. The combined organic layer was washed with brine, dried over $MgSO_4$ and concentrated. The crude sample was purified with a 120 g ISCO column eluted with 0-100% EtOAc/hexanes for 40 min. The desired fraction was collected and concentrated to give Intermediate I-26A (7 g, 36.4 mmol, 99% yield) as colorless oil. ¹H NMR (400 MHz, chloroform-d) δ 10.50 (s, 1H), 7.65 (d, J=2.2 Hz, 1H), 7.35 (ddd, J=8.6, 2.4, 0.7 Hz, 1H), 6.90 (d, J=8.6 Hz, 1H), 4.36 (dd, J=11.1, 3.0 Hz, 1H), 4.05 (dd, J=11.1, 5.6 Hz, 1H), 3.40 (ddt, J=5.6, 4.1, 2.8 Hz, 1H), 2.94 (dd, J=4.7, 4.1 Hz, 1H), 2.80 (dd, J=4.8, 2.6 Hz, 1H), 2.32 (s, 3H); LC-MS: method C, RT=1.59 min, MS (ESI) m/z: 193.0 (M+H)⁺.

Intermediate I-26B: (S)-(7-methyl-2,3-dihydrobenzo[b][1,4]dioxin-2-yl)methanol SCH₃

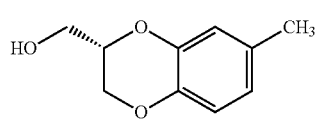
(I-26B)

To a stirred solution of Intermediate I-26A (7 g, 36.4 mmol) in dichloromethane (100 mL) cooled with an ice bath was added mCPBA (12.36 g, 53.7 mmol). Trifluoroacetic acid (2.81 mL, 36.4 mmol) in dichloromethane (10 mL) was added dropwise. Ice bath was removed and the mixture was stirred at room temperature for 1.0 h. TLC and LCMS indicated no starting material remaining. The reaction mixture was quenched by addition of saturated sodium bicarbonate, followed by 10% sodium thiosulfite (20.0 mL), extracted with dichloromethane. The organic layers were collected, washed with saturated sodium bicarbonate, brine and dried over sodium sulfate. After evaporation of solvent, the crude product was dissolved in MeOH (100 mL), and $K_2CO_3$ (15.10 g, 109 mmol) was added. The mixture was stirred overnight at room temperature.

The reaction mixture was diluted with EtOAc and water, extracted with EtOAc, the combined organic layer was washed with brine, dried over $MgSO_4$ and concentrated. The crude sample was purified with a 120 g ISCO column eluted with 0-100% EtOAc/hexanes for 40 min. The desired fractions were combined and concentrated to give Intermediate I-26B (4.65 g, 25.8 mmol, 70.9% yield). ¹H NMR (400 MHz, chloroform-d) δ 6.78 (d, J=8.1 Hz, 1H), 6.73 (d, J=1.3 Hz, 1H), 6.69-6.63 (m, 1H), 4.33-4.21 (m, 2H), 4.15-4.05 (m, 1H), 3.96-3.76 (m, 2H), 2.26 (s, 3H). LC-MS: method C, RT=1.55 min, MS (ESI) m/z: 209.0 (M+H)⁺.

Intermediate I-26C: (R)-(7-methyl-2,3-dihydrobenzo[b][1,4]dioxin-2-yl)methyl acetate

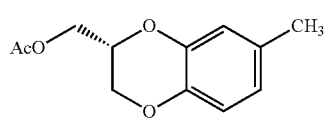
(I-26C)

To a solution of Intermediate I-26B (4.6 g, 25.5 mmol) in THF (100 mL) at 0° C. was added TEA (8.89 mL, 63.8 mmol), followed by acetyl chloride in DCM (31.9 mL, 31.9 mmol) dropwise. The mixture was stirred at 0° C. for 10 min, and at room temperature for 1.0 h. The mixture was diluted with EtOAc, washed with water. The organic layer was washed with 0.5 N HCl, saturated sodium bicarbonate, brine and dried over sodium sulfate. After evaporation of solvent, Intermediate I-26C (5.3 g, 23.85 mmol, 93% yield) was obtained as a yellow oil. It was used for the next step without further purification. ¹H NMR (400 MHz, chloroform-d) δ 6.76 (d, J=8.1 Hz, 1H), 6.72 (d, J=1.3 Hz, 1H), 6.68-6.61 (m, 1H), 4.40-4.33 (m, 1H), 4.30 (dd, J=5.1, 4.4 Hz, 2H), 4.25 (dd, J=11.3, 2.3 Hz, 1H), 4.03 (dd, J=11.4, 6.8 Hz, 1H), 2.25 (s, 3H), 2.11 (s, 3H). LC-MS: method C, RT=1.92 min, MS (ESI) m/z: 245.0 (M+H)⁺.

Intermediate I-26D: (R)-(7-methyl-6-nitro-2,3-dihydrobenzo[b][1,4]dioxin-2-yl)methyl acetate

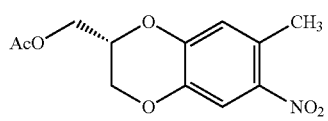
(I-26D)

To a solution of Intermediate I-26C (4.15 g, 18.67 mmol) in acetic acid (40 mL) cooled at 0° C. with an ice-bath was added fuming nitric acid (4.36 mL, 93 mmol) dropwise. The mixture was stirred at 0° C. for 1 h, then at room temperature for 30 min. TLC (PMA stain) indicated a completion of the reaction. It was quenched with ice water. The aqueous was removed and the organic layer was washed with saturated sodium bicarbonate (3×), brine and dried over sodium sulfate. After evaporation of solvent, Intermediate I-26D (4.6 g, 17.21 mmol, 92% yield) was obtained as an off-white solid which was used for the next step without further purification. $^1$H NMR (400 MHz, chloroform-d) δ 7.71 (s, 1H), 6.83 (s, 1H), 4.54-4.45 (m, 1H), 4.39-4.28 (m, 3H), 4.09 (dd, J=11.9, 7.0 Hz, 1H), 2.55 (d, J=0.4 Hz, 3H), 2.13 (s, 3H). LC-MS: method C, RT=1.90 min, MS (ESI) m/z: 290.0 (M+H)$^+$.

Intermediate I-26E: (R)-(6-amino-7-methyl-2,3-dihydrobenzo[b][1,4]dioxin-2-yl)methyl acetate

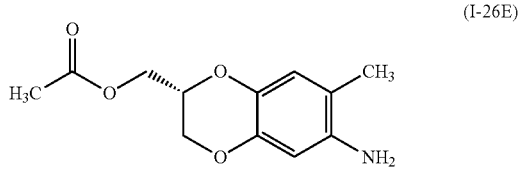 [SMILES: CC(=O)OC[C@H]1COc2cc(N)c(C)cc2O1]

(I-26E)

To a solution of Intermediate I-26D (5.3 g, 19.83 mmol) in MeOH (80 mL) and THF (80 mL) cooled with an ice bath was added ammonium chloride (16.97 g, 317 mmol) and zinc dust (10.37 g, 159 mmol). The mixture was stirred at 0° C. for 30 min, and at room temperature for 1.0 h. MeOH and THF were removed under vacuum. The residue was diluted with EtOAc/saturated sodium bicarbonate and stirred at room temperature for 3 min. The mixture was filtered through a pad of wet celite to remove insoluble material. The filtrate was collected, organic layer was washed with brine, dried over sodium sulfate, concentrated to give Intermediate I-26E (4.7 g, 19.81 mmol, 100% yield) as off-white solid. $^1$H NMR (400 MHz, chloroform-d) δ 6.63 (s, 1H), 6.25 (s, 1H), 4.38-4.20 (m, 4H), 4.06-3.95 (m, 1H), 3.35 (br. s., 2H), 2.11 (s, 3H), 2.09 (s, 3H). LC-MS: method C, RT=1.14 min, MS (ESI) m/z: 238.0 (M+H)$^+$.

Intermediate I-26F: (R)-(2-amino-4-methyl-7,8-dihydro-[1,4]dioxino[2',3':3,4]benzo[1,2-d]thiazol-7-yl)methyl acetate

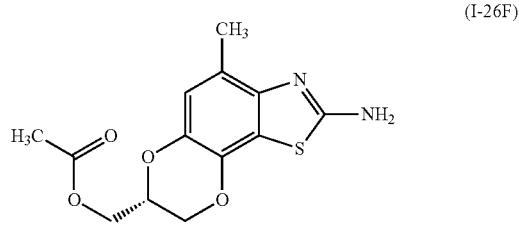 [SMILES: CC(=O)OC[C@H]1COc2c(cc(C)c3nc(N)sc23)O1]

(I-26F)

To Intermediate I-26E (4.7 g, 19.81 mmol) dissolved in acetonitrile (120 mL) was added ammonium thiocyanate (2.262 g, 29.7 mmol). The mixture was stirred at room temperature for 10 min. Benzyltrimethylammonium tribromide (8.11 g, 20.80 mmol) in acetonitrile (20 mL) was added dropwise (5 min). The reaction mixture was stirred at room temperature overnight, diluted with EtOAc/THF/saturated sodium bicarbonate. The insoluble material was removed by filtration. The organic layer of the filtrate was collected, washed with brine, dried over sodium sulfate. After evaporation of solvent, Intermediate I-26F (5.8 g, 19.71 mmol, 99% yield) was obtained as a yellow solid. $^1$H NMR (400 MHz, chloroform-d) δ 6.73 (d, J=0.7 Hz, 1H), 5.10 (s, 2H), 4.47-4.28 (m, 4H), 4.14 (dd, J=11.3, 6.9 Hz, 1H), 2.45 (d, J=0.7 Hz, 3H), 2.12 (s, 3H). LC-MS: method C, RT=1.46 min, MS (ESI) m/z: 295.0 (M+H)$^+$.

Intermediate I-26

To a suspension of Intermediate I-26F (5.8 g, 19.71 mmol) in dry acetonitrile (80 mL) was added copper (II) chloride (4.5 g, 33.5 mmol), followed by tert-butyl nitrite (4.56 mL, 34.5 mmol) dropwise. The reaction mixture was stirred at room temperature for 2 hrs. LCMS indicated a completion of the reaction. Acetonitrile was removed under vacuum, the reaction mixture was diluted with EtOAc, quenched with 1.0 N HCl. The organic layer was collected, washed with 0.5 N HCl (2×), saturated sodium bicarbonate, brine and dried over sodium sulfate. After evaporation of solvent, the crude product was purified with a 220 g ISCO column eluted with 0% to 70% EtOAc in hexanes over 60 min. The desired fraction was collected and concentrated to yield Intermediate I-26 (3.9 g, 12.43 mmol, 63.1% yield) as an off-white solid. $^1$H NMR (400 MHz, chloroform-d) δ 6.89 (d, J=0.7 Hz, 1H), 4.55-4.28 (m, 4H), 4.18 (dd, J=11.4, 7.0 Hz, 1H), 2.59 (s, 3H), 2.13 (s, 3H). LC-MS: method C, RT=2.18 min, MS (ESI) m/z: 314.0 (M+H)$^+$.

Intermediate I-27

7-((tert-butyldimethylsilyloxy)methyl)-2-methoxy-5-(4,4,5,5-tetramethyl-1,3,2-dioxaborolan-2-yl)quinoxaline

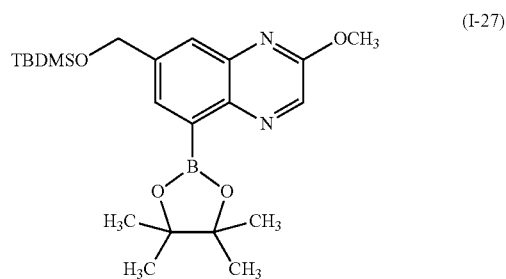 [SMILES: COc1cnc2c(B3OC(C)(C)C(C)(C)O3)cc(CO[Si](C)(C)C(C)(C)C)cc2n1]

(I-27)

Intermediate I-27A:
8-bromo-3-methoxyquinoxaline-6-carbaldehyde

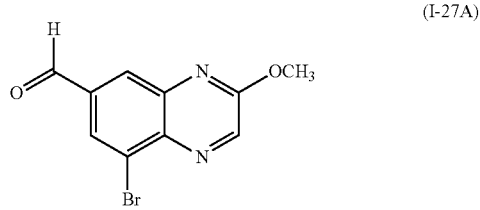 [SMILES: COc1cnc2c(Br)cc(C=O)cc2n1]

(I-27A)

To a solution of Intermediate I-9A (1 g, 3.95 mmol) in CCl₄ (20 mL) was added NBS (1.547 g, 8.69 mmol) and benzoic peroxide (0.115 g, 0.474 mmol). The mixture was heated at reflux (95° C. oil bath) for 3 h. TLC and LCMS indicated completion of the reaction. The mixture was cooled to room temperature and filtered. The filtrate was concentrated to a yellow solid. The crude sample was dissolved in THF (10 ml) and silver nitrate (6.71 g, 39.5 mmol) in water (10 ml) was added. The mixture was stirred at 95° C. for 1 h. LCMS indicated completion of the reaction. The mixture was cooled to room temperature and poured to 60 ml of water. The mixture was filtered and the filter cake was washed with CHCl₃ for three times. The combined filtrate was extracted with CHCl₃ and the organic layer was combined, washed with NaHCO₃ and brine dried over MgSO₄ and concentrated to Intermediate I-27A (1 g, 3.74 mmol, 95% yield). The crude sample was used for next step without purification. LC-MS: method C, RT=1.84 min, MS (ESI) m/z: 267 and 269 (M+H)⁺.

Intermediate I-27B: (8-bromo-3-methoxyquinoxalin-6-yl)methanol N OCH₃

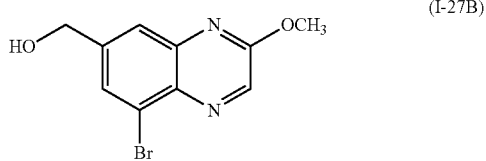 [SMILES: COc1cnc2c(Br)cc(CO)cc2n1]
(I-27B)

Intermediate I-27A (1.055 g, 3.95 mmol) suspended in THF (10 mL) and MeOH (10 mL) was treated with NaBH₄ (0.149 g, 3.95 mmol) at room temperature for 15 min. The reaction mixture turned to a clear solution. LCMS indicated a completion of the reaction. Saturated NH₄Cl was added to quench the reaction. After stirring at room temperature for 10 min, it was diluted with EtOAc and water. The organic layer was washed with brine, dried over MgSO₄ and concentrated. The crude product was purified with a 120 g ISCO column eluted with 0-100% EtOAc in hexanes. The desired fraction was collected and concentrated to give Intermediate I-27B (380 mg, 1.412 mmol, 35.7% yield). ¹H NMR (400 MHz, chloroform-d) δ 8.54 (s, 1H), 8.01-7.77 (m, 2H), 4.90 (s, 2H), 4.13 (s, 3H). LC-MS: method C, RT=1.64 min, MS (ESI) (m z) 269 and 271 (M+H)⁺.

Intermediate I-27C 5-bromo-7-((tert-butyldimethylsilyloxy)methyl)-2-methoxyquinoxaline

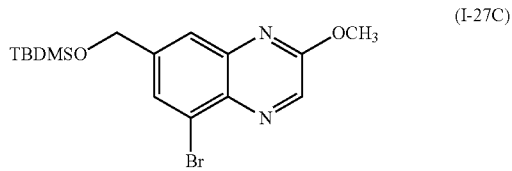 [SMILES: COc1cnc2c(Br)cc(CO[Si](C)(C)C(C)(C)C)cc2n1]
(I-27C)

To a stirred solution of Intermediate I-27B (380 mg, 1.412 mmol) in DMF (5 mL) was added TBDMS-Cl (319 mg, 2.118 mmol) and imidazole (173 mg, 2.54 mmol). The reaction mixture was stirred at room temperature for 1.0 h. TLC and LCMS indicated a clean reaction. The mixture was partitioned between EtOAc/water. The organic layer was washed with water, brine, dried over sodium sulfate. After evaporation of solvent, the crude product was dissolved in a small amount of chloroform and charged to a 40 g silica gel cartridge which was eluted with hexanes for 3 min., then a 20 min gradient from 0% to 15% EtOAc in hexanes. The desired fractions were combined and concentrated to give Intermediate I-27C (480 mg, 1.252 mmol, 89% yield) as a white solid. LC-MS: method C, RT=2.74 min, MS (ESI) (m z) 383 and 385 (M+H)⁺.

Intermediate I-27

A mixture of Intermediate I-27C (100 mg, 0.261 mmol), bis(pinacolato)diboron (99 mg, 0.391 mmol), potassium acetate (64.0 mg, 0.652 mmol) in dioxane (2 mL) was degassed with argon for 5 min, then PdCl₂(dppf)—CH₂Cl₂ adduct (10.65 mg, 0.013 mmol) was added. The mixture was sealed and heated in microwave reactor at 130° C. for 30 min. LCMS indicated a clean reaction. The mixture was diluted with EtOAc/water, insoluble material was removed by filtration. The filtrate was extracted with EtOAc, washed with brine, dried over sodium sulfate. After evaporation of solvent, the crude product was dissolved in a small amount of toluene and charged to a 40 g silica gel cartridge which was eluted with 5% EtOAc in hexanes for 2 min., then a 18 min gradient from 5% to 75% EtOAc in hexanes. The desired fractions were combined, concentrated and lyophilized to give Intermediate I-27 (105 mg, 0.244 mmol, 94% yield) as a pale solid. ¹H NMR (400 MHz, chloroform-d) δ 8.39 (s, 1H), 8.12 (d, J=2.0 Hz, 1H), 7.96 (dt, J=2.0, 1.0 Hz, 1H), 4.96 (s, 2H), 4.13 (s, 3H), 1.45 (s, 12H), 1.00 (s, 9H), 0.16 (s, 6H). LC-MS: method C, RT=2.73 min, MS (ESI) (m z) 349 (M+H)⁺ (boronic acid).

Intermediate I-28

7-chloro-2-methoxy-5-(4,4,5,5-tetramethyl-1,3,2-dioxaborolan-2-yl)quinoxaline

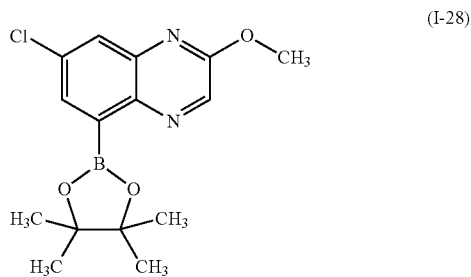 [SMILES: COc1cnc2c(B3OC(C)(C)C(C)(C)O3)cc(Cl)cc2n1]
(I-28)

Intermediate I-28A: 2-bromo-4-chloro-6-nitroaniline

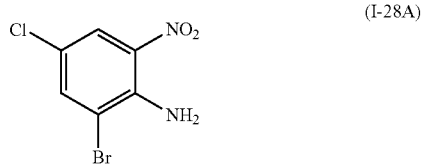 [SMILES: Nc1c(Br)cc(Cl)cc1[N+](=O)[O-]]
(I-28A)

To 4-chloro-2-nitroaniline (10 g, 57.9 mmol) in acetic acid (50 mL) was cooled to 0° C. with an ice bath. Bromine (3.28 mL, 63.7 mmol) was added dropwise and the mixture was stirred at room temperature for 1 hr, and then poured into ice water. The precipitated solid was filtered and was washed with water several times. The filter cake was re-dissolved in EtOAc, dried over sodium sulfate, filtered and concentrated in vacuo to give the title compound as a yellow solid (14.66 g, 100%). $^1$H NMR (400 MHz, DMSO-$d_6$) δ 8.08 (d, J=2.4 Hz, 1H), 8.02 (d, J=2.6 Hz, 1H), 7.27 (br s, 2H); LC-MS: method H, RT=1.15 min, MS (ESI) m/z: 250.9 and 252.9 (M+H)$^+$.

Intermediate I-28B: tert-butyl N-(2-bromo-4-chloro-6-nitrophenyl)-N-[(tert-butoxy)carbonyl]carbamate

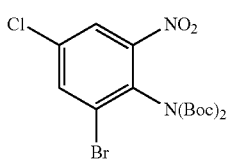

(I-28B)

In a round bottom flask charged with a stirring bar, Intermediate I-28A (5 g, 19.88 mmol) was dissolved in THF (30 mL). DMAP (0.243 g, 1.988 mmol) was added, followed by di-tert-butyl dicarbonate (11.54 mL, 49.7 mmol). The reaction mixture was stirred at room temperature for 1 hour, and then solvent was removed on a rotary evaporator. The residue was purified by flash chromatography (120 g silica gel column, eluted with 0-100% EtOAc/hexane) to give the title compound as a white solid (8.2 g, 18.1 mmol, 91%). $^1$H NMR (400 MHz, chloroform-d) δ 7.97 (d, J=2.4 Hz, 1H), 7.90 (d, J=2.4 Hz, 1H), 1.42 (s, 18H); LC-MS: method H, RT=1.04 min, MS (ESI) m/z: 250.9 and 252.9 (M+H−2Boc)$^+$.

Intermediate I-28C: tert-butyl (2-bromo-4-chloro-6-nitrophenyl)carbamate

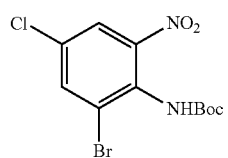

(I-28C)

To a solution of Intermediate I-28B (8.2 g, 18.15 mmol) in DCM (50 mL) was added TFA (2.80 mL, 36.3 mmol) and the mixture was stirred at room temperature for 1 hour. Saturated NaHCO$_3$(aq. 30 mL) was added to the mixture. After stirring at room temperature for 10 minutes, the layers were separated and the aqueous layer was extracted by DCM (30 mL×2). The combined organic solution was washed with brine, dried over Na$_2$SO$_4$ and concentrated to give the title compound as a yellow solid (6.32 g, 18.0 mmol, 99%). $^1$H NMR (400 MHz, DMSO-$d_6$) δ 9.45 (br s, 1H), 8.24 (d, J=2.4 Hz, 1H), 8.12 (d, J=2.4 Hz, 1H), 1.43 (br s, 9H); LC-MS: method H, RT=0.82 min, MS (ESI) m/z: 250.9 and 252.9 (M+H-Boc)$^+$.

Intermediate I-28D: methyl 2-((2-bromo-4-methyl-6-nitrophenyl)amino)acetate

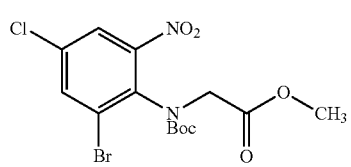

(I-28D)

To a solution of Intermediate I-28C (6.32 g, 18.0 mmol) in DMF (30 mL) was added Cs$_2$CO$_3$ (14.64 g, 44.9 mmol. Methyl 2-bromoacetate (5.50 g, 36.0 mmol) was added dropwise and the mixture was stirred at room temperature for 30 minutes. The reaction mixture was diluted with 100 mL of EtOAc and 50 mL of water. After separation, the aqueous layer was extracted by EtOAc (50 mL), and the combined organic layers were washed with brine and concentrated. The residue was purified by flash chromatography (120 g silica gel column, eluted with 0-50% EtOAc/hexane) to give the title compound (7.55 g, 17.8 mmol, 99%) as a yellow oil. $^1$H NMR (400 MHz, chloroform-d) δ 7.92-7.81 (m, 2H), 4.58 (d, J=17.6 Hz, 1H), 3.99 (d, J=17.4 Hz, 1H), 3.69 (s, 3H), 1.38 (s, 9H); LC-MS: method H, RT=1.23 min, MS (ESI) m/z: 366.9 and 368.9 (M+H−56)$^+$.

Intermediate I-28E: methyl 2-((2-bromo-4-chloro-6-nitrophenyl)amino)acetate, TFA salt

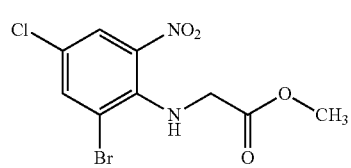

(I-28E)

Intermediate I-28D (5.6 g, 13.22 mmol) was dissolved in DCM (30 mL) and was treated with TFA (10.18 mL, 132 mmol) at room temperature overnight. On the next day, the solvent was removed and the crude product was used in the next step without purification. LC-MS: method H, RT=1.22 min, MS (ESI) m/z: 323.0 and 324.9 (M+H)$^+$.

Intermediate I-28F: 5-bromo-7-chloro-3,4-dihydroquinoxalin-2(1H)-one

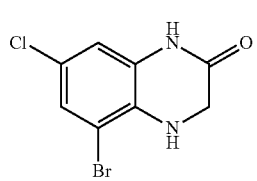

(I-28F)

In a round bottom flask charged with a stirring bar, Intermediate I-28E (6.0 g, 18.55 mmol) was dissolved in MeOH (60 mL), and concentrated HCl (4.64 mL, 55.6 mmol) was added, followed by SnCl$_2$ (14.07 g, 74.2 mmol). The reaction mixture was stirred at 60° C. overnight. On the next day, after cooling to room temperature, another 2 eq. of SnCl$_2$ was added to the reaction mixture. After 2 h at 60° C., the reaction mixture was cooled to room temperature; the precipitate was filtered, washed with small amount of MeOH, and dried to give a white solid as desired product. The filtrate was concentrated on a rotary evaporator and then partitioned between 150 mL of EtOAc and 30 mL of water. 4M NaOH (aq.) was added to adjust the pH to 12. The solid was filtered on a Celite pad and the filter cake was washed with EtOAc. The layers were separated and the aqueous phase was extracted twice with EtOAc. The combined organic phases were washed with saturated NaHCO$_3$(aq.), brine, dried over Na$_2$SO$_4$, filtered, and concentrated in vacuo to give additional product. Combining material gave Intermediate I-28F (3.55 g, 13.58 mmol, 73.2% yield) as a white solid. $^1$H NMR (400 MHz, DMSO-d$_6$) δ 10.53 (s, 1H), 7.12 (d, J=2.2 Hz, 1H), 6.85-6.66 (m, 1H), 5.83 (s, 1H), 3.82 (d, J=2.0 Hz, 2H); LC-MS: method H, RT=1.02 min, MS (ESI) m/z: 261.0 and 263.0 (M+H)$^+$.

Intermediate I-28G:
5-bromo-7-chloroquinoxalin-2-ol

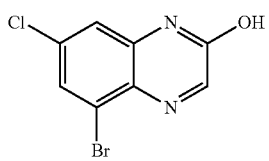

(I-28G)

In 1 L round bottom flask charged with a stirring bar, Intermediate I-28F (3.84 g, 14.7 mmol) was suspended in MeOH (50 mL), and H$_2$O$_2$ (15.00 mL, 147 mmol, 30% in water) was added, followed by 4N NaOH (11.01 mL, 44.1 mmol). The mixture was stirred at room temperature for 5 minutes, and then heated at 60° C. for 15 minutes. Heating was removed and the reaction mixture was stirred at room temperature over the weekend. Another 5 mL of H$_2$O$_2$ was added and the mixture was stirred at room temperature for 2 h. The reaction mixture was concentrated on a rotary evaporator. The residual mixture was cooled in an ice bath, and 6 N HCl was added to adjust the pH value to 2-3, followed by 200 mL of EtOAc. After shaking and separation, the aqueous layer was extracted with EtOAc (50 mL×2). The combined organic phases were combined and dried over Na$_2$SO$_4$. Solvent was removed in vacuo gave the title compound as a brown solid. (2.51 g, 9.70 mmol, 66%). $^1$H NMR (400 MHz, DMSO-d$_6$) δ 12.63 (br s, 1H), 8.23 (s, 1H), 7.73 (d, J=2.0 Hz, 1H), 7.31 (d, J=2.0 Hz, 1H); LC-MS: method H, RT=1.01 min, MS (ESI) m/z: 258.9 and 260.9 (M+H)$^+$.

Intermediate I-28H:
5-bromo-7-chloro-2-methoxyquinoxaline

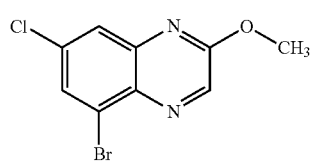

(I-28H)

In a round bottom flask charged with a stirring bar, Intermediate I-28G (1.60 g, 6.17 mmol) was suspended in POCl$_3$ (10 mL, 107 mmol), and the mixture was refluxed for 2 h. Excess POCl$_3$ was removed on a rotary evaporator and the residue was dried in vacuo for 30 minutes to give a brown solid. This brown solid was suspended in MeOH (30 mL), and anhydrous K$_2$CO$_3$ (1.704 g, 12.33 mmol) was added. The mixture was stirred at room temperature for 10 minutes, and then refluxed for 2 h. After cooling to room temperature, the solvent was removed on a rotary evaporator. The residue was dissolved in 100 ml of EtOAc, washed with water, brine, dried over Na$_2$SO$_4$, filtered, and concentrated to give the crude product. The crude product was purified by flash chromatography (80 g silica gel column, 0-50% EtOAc/Hexane) to give Intermediate I-28H (1.02 g, 3.73 mmol, 60.5% yield) as a yellow solid. $^1$H NMR (400 MHz, chloroform-d) δ 8.53 (s, 1H), 7.87-7.83 (m, 2H), 4.12 (s, 3H); LC-MS: method J, RT=0.96 min, MS (ESI) m/z: 273.0 and 275.0 (M+H)$^+$.

Intermediate I-28

In a microwave vial charged with a stirring bar, Intermediate I-28H (330 mg, 1.207 mmol), bis(pinacolato)diboron (460 mg, 1.810 mmol), potassium acetate (296 mg, 3.02 mmol) were mixed with 1,4-dioxane (10 mL). After degassing with bubbling N$_2$ for 10 minutes, PdCl$_2$(dppf)—CH$_2$Cl$_2$ adduct (49.3 mg, 0.060 mmol) was added. The vial was sealed and was heated in a microwave reactor at 120° C. for 60 minutes. After cooling to room temperature, the reaction mixture was diluted by adding 40 mL of EtOAc and 30 mL of water. After separation, the aqueous layer was extracted with EtOAc (20 mL×2). The combined organic layers were dried over Na$_2$SO$_4$ and concentrated on a rotary evaporator. The residue was purified by flash chromatography (40 g silica gel column, 0-100% EtOAc/Hexane gradient in 10 minutes, 100% EtOAc for 10 minutes) to give Intermediate I-28 as a yellow solid. (293 mg, 76%). $^1$H NMR (400 MHz, chloroform-d) δ 8.53 (s, 1H), 7.92-7.85 (m, 2H), 4.08 (s, 3H), 1.45 (s, 12H); LC-MS: method H, RT=1.09 min, MS (ESI) m/z: 239.1 (M+H−82)$^+$.

Intermediate I-29

7-chloro-2-(methoxymethyl)-5-(4,4,5,5-tetramethyl-1,3,2-dioxaborolan-2-yl)quinoxaline

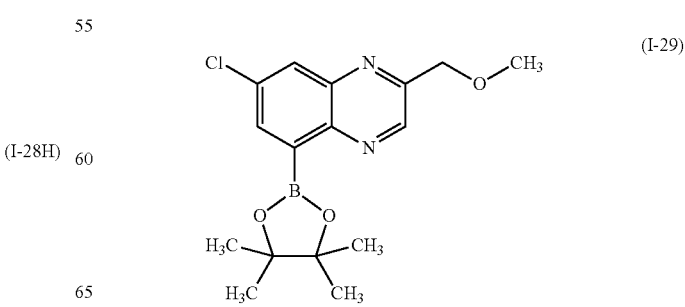

(I-29)

Intermediate I-29A: tert-butyl (2-bromo-4-chloro-6-nitrophenyl)(3-methoxy-2-oxopropyl)carbamate

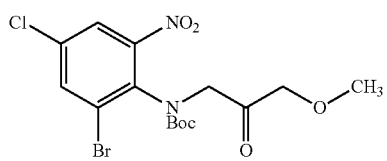

(I-29A)

To Intermediate I-28C (2.0 g, 5.69 mmol)) in DMF (20 mL) at 0° C. was added cesium carbonate (3.24 g, 9.96 mmol). The brown solution was stirred at 0° C. for 10 min, followed by addition of Intermediate I-2B (1.140 g, 6.83 mmol) in DMF (5.0 mL). The brown solution turned yellow. The mixture was stirred at 0° C. for 15 min. The mixture was diluted with EtOAc, washed with water, brine, dried over sodium sulfate and concentrated. The crude product was purified by flash chromatography (80 g silica gel column, 0% to 60% EtOAc/Hexane over 18 min) to yield Intermediate I-29A (2.01 g, 81%) as a yellow oil. $^1$H NMR (400 MHz, chloroform-d) δ 7.95-7.80 (m, 2H), 4.65 (d, J=18.3 Hz, 1H), 4.22 (d, J=18.0 Hz, 1H), 4.09 (s, 2H), 3.42 (s, 3H), 1.37 (s, 9H); LC-MS: method H, RT=1.20 min, MS (ESI) m/z: 383.0 (M+H−54)$^+$.

Intermediate I-29B: 5-bromo-7-chloro-2-(methoxymethyl)quinoxaline

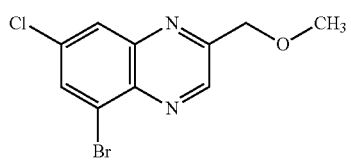

(I-29B)

To Intermediate I-29A (2.0 g, 4.57 mmol) in ethyl acetate (10 mL) was added HCl in 1,4-dioxane (11.42 mL, 45.7 mmol) and the mixture was stirred at room temperature for 20 min. LCMS indicated a clean reaction. Solvent was removed under vacuum, and chased with EtOAc once to give the deprotected intermediate as yellow oil. The deprotected intermediate was dissolved in THF (40 mL). Concentrated HCl (aq.) (1.142 mL, 13.71 mmol) was added, followed by SnCl$_2$ (3.47 g, 18.28 mmol). The mixture was stirred in an oil bath at 40° C. for 4.0 h. After cooling to room temperature, the reaction mixture was diluted with EtOAc (100 mL)/water (50 mL). The organic phase was neutralized with saturated sodium bicarbonate, stirred at room temperature for 15 min, and the precipitate was removed by filtration with a pad of wet Celite. The organic solution was washed with brine, dried over sodium sulfate and concentrated. The crude product was purified by flash chromatography (loading in chloroform, 0% to 40% EtOAc in hexane over 20 min using an 80 g silica gel cartridge) to yield Intermediate I-29B as a brown solid (0.48 g, 36.5%). $^1$H NMR (400 MHz, chloroform-d) δ 9.07 (s, 1H), 8.06 (s, 2H), 4.83 (s, 2H), 3.56 (s, 3H); LC-MS: method J, RT=1.20 min, MS (ESI) m/z: 287.1, 289.0 (M+H)$^+$.

Intermediate I-29

In a microwave vial charged with a stirring bar, Intermediate I-29B (475 mg, 1.652 mmol), bis(pinacolato)diboron (629 mg, 2.478 mmol) and potassium acetate (405 mg, 4.13 mmol) were mixed in 1,4-dioxane (10 mL). After degassing with bubbling N$_2$ for 10 minutes, Pd(dppf)$_2$Cl$_2$·CH$_2$Cl$_2$ (67.5 mg, 0.083 mmol) was added. The vial was sealed and was irradiated in the microwave at 120° C. for 60 minutes. Solvent was removed and the residue was purified by flash chromatography (24 g silica gel column, 0-100% EtOAc/Hexane) to give Intermediate I-29 (432 mg, 76%) as an off-white solid. $^1$H NMR (400 MHz, chloroform-d) δ 9.07 (s, 1H), 8.12 (d, J=2.4 Hz, 1H), 8.08 (d, J=2.2 Hz, 1H), 4.78 (s, 2H), 3.51 (s, 3H), 1.24 (s, 12H); LC-MS: method J, RT=1.20 min, MS (ESI) m/z: 253.0 (M+H−82)$^+$.

Intermediate I-30 to Intermediate I-34 were synthesized by following the general procedures described in Intermediate I-29.

| Intermediate | Structure | LCMS [M + H]$^+$ m/z | LCMS RT(Min)/ Method |
|---|---|---|---|
| I-30 | 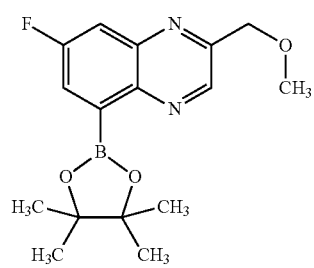 [SMILES: COCc1cnc2c(B3OC(C)(C)C(C)(C)O3)cc(F)cc2n1] | 237.1* | 1.00/H |

-continued

| Intermediate | Structure | LCMS [M + H]+ m/z | LCMS RT(Min)/ Method |
|---|---|---|---|
| I-31 | 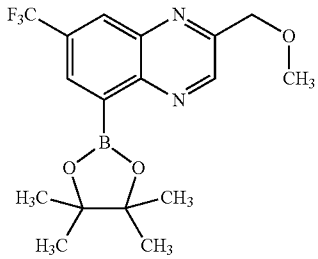 [SMILES: COCc1cnc2c(B3OC(C)(C)C(C)(C)O3)cc(C(F)(F)F)cc2n1] | 287.2* | 0.61/J |
| I-32 | 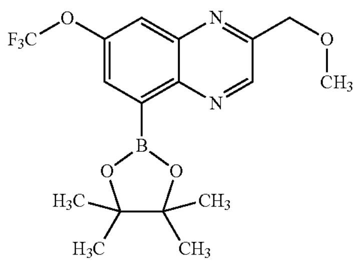 [SMILES: COCc1cnc2c(B3OC(C)(C)C(C)(C)O3)cc(OC(F)(F)F)cc2n1] | 303.2* | 0.73/J |
| I-33 | 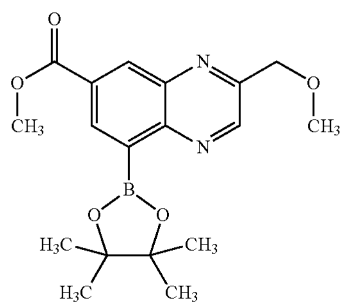 [SMILES: COCc1cnc2c(B3OC(C)(C)C(C)(C)O3)cc(C(=O)OC)cc2n1] | 277.1* | 0.92/J |
| I-34 | 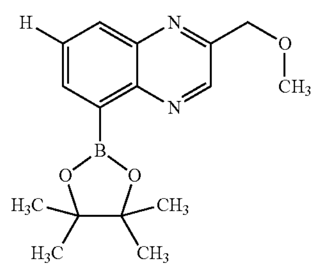 [SMILES: COCc1cnc2c(B3OC(C)(C)C(C)(C)O3)cccc2n1] | 219.1* | 0.86/H |

*(M + H)+ of boronic acid

Intermediate I-35

(7-(hydroxymethyl)-2-methoxyquinoxalin-5-yl)boronic acid

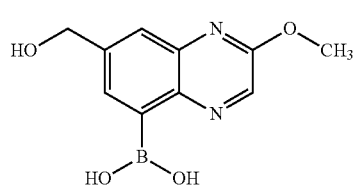

(I-35)

Intermediate I-35A: 4-bromo-2-chloro-6-nitroaniline

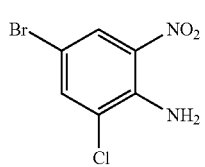

(I-35A)

A mixture of 4-bromo-2-nitroaniline (10.82 g, 49.9 mmol) and NCS (8.32 g, 62.3 mmol) in DMF (100 mL) was heated to 100° C. for 1h. After cooling to room temperature, the solution was poured into ice water. The yellow precipitate was collected by filtration and was washed with water. The solid was dissolved in dichloromethane (100 mL) and the organic phase was washed with water and brine, dried (Na$_2$SO$_4$), filtered, and concentrated to yield the title compound (11.54 g, 45.9 mmol, 92% yield) as a yellow solid. $^1$H NMR (400 MHz, chloroform-d) δ 8.26 (d, J=2.2 Hz, 1H), 7.67 (d, J=2.2 Hz, 1H), 6.57 (br s, 2H).

Intermediate I-35B: tert-butyl N-(4-bromo-2-chloro-6-nitrophenyl)-N-[(tert-butoxy) carbonyl]carbamate

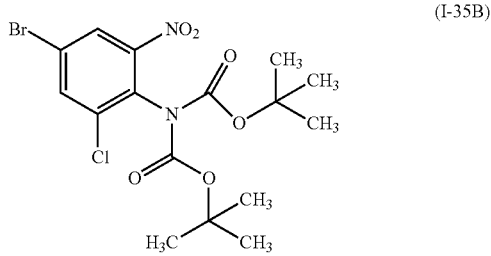 [SMILES: CC(C)(C)OC(=O)N(C(=O)OC(C)(C)C)c1c(Cl)cc(Br)cc1[N+](=O)[O-]]

Intermediate I-35B (11.75 g, 87%) was made as a yellow solid from Intermediate I-35A (7.52 g, 29.9 mmol) via the same procedure as Intermediate I-28B. $^1$H NMR (400 MHz, chloroform-d) δ 8.08 (d, J=2.2 Hz, 1H), 7.89 (d, J=2.2 Hz, 1H), 1.42 (s, 18H).

Intermediate I-35C: tert-butyl (4-bromo-2-chloro-6-nitrophenyl)carbamate

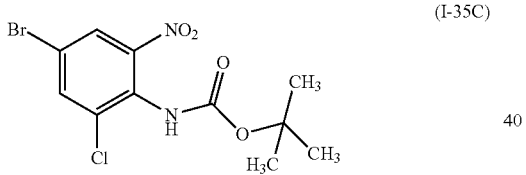

Intermediate I-35C (5.2 g, 14.8 mmol, 98%) was made as a brown waxy solid from Intermediate I-35B (6.8 g, 15.0 mmol) via the same procedure as Intermediate I-28C. $^1$H NMR (400 MHz, chloroform-d) δ 8.00 (d, J=2.2 Hz, 1H), 7.81 (d, J=2.2 Hz, 1H), 6.92 (br s, 1H), 1.50 (s, 9H).

Intermediate I-35D: methyl 2-((4-bromo-2-chloro-6-nitrophenyl)(tert-butoxycarbonyl) amino)acetate

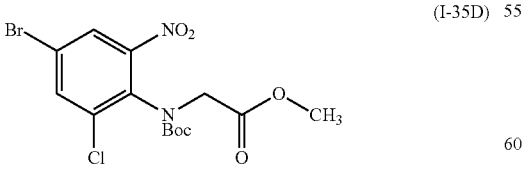

Intermediate I-35D (5.4 g, 12.8 mmol, 87%) was made as a yellow oil from Intermediate I-35C (5.2 g, 14.8 mmol) via the same procedure as Intermediate I-28D. $^1$H NMR (400 MHz, chloroform-d) δ 7.99 (d, J=2.2 Hz, 1H), 7.88-7.85 (m, 1H), 4.49 (d, J=17.4 Hz, 1H), 4.07 (d, J=17.4 Hz, 1H), 3.71-3.67 (m, 3H), 1.37 (s, 9H); LC-MS: method H, RT=1.04 min, MS (ESI) m/z: 323.0 and 325.0 (M+H−100)$^+$.

Intermediate I-35E: methyl 2-((4-bromo-2-chloro-6-nitrophenyl)amino)acetate

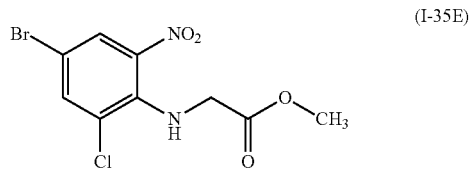 [SMILES: COC(=O)CNc1c(Cl)cc(Br)cc1[N+](=O)[O-]]

Intermediate I-35E (4.15 g, 12.8 mmol, 100%) was made as a brown oil from Intermediate I-35D (5.44 g, 12.8 mmol) via the same procedure as Intermediate I-28E. LC-MS: method H, RT=1.0 min, MS (ESI) m/z: 323.1 and 325.0 (M+H)$^+$.

Intermediate I-35F: 7-bromo-5-chloro-3,4-dihydroquinoxalin-2(1H)-one

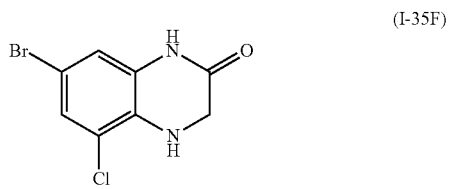

Intermediate I-35F (3.02 g, 11.55 mmol, 73%) was made as a white solid from Intermediate I-35E (5.1 g, 15.8 mmol) via the same procedure as Intermediate I-28F. $^1$H NMR (400 MHz, DMSO-d$_6$) δ 10.54 (s, 1H), 7.10 (d, J=2.0 Hz, 1H), 6.83 (d, J=2.2 Hz, 1H), 6.02 (s, 1H), 3.82 (d, J=1.8 Hz, 2H); LC-MS: method H, RT=0.84 min, MS (ESI) m/z: 261.0 and 263.0 (M+H)$^+$.

Intermediate I-35G: 7-bromo-5-chloroquinoxalin-2(1H)-one

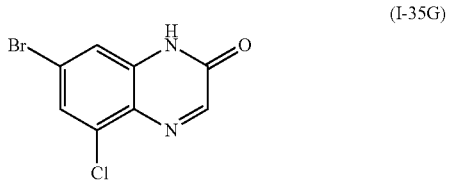 [SMILES: O=c1cnc2c(Cl)cc(Br)cc2[nH]1]

Intermediate I-35G (3.40 g, 13.10 mmol, 70%) was made as an off-white solid from Intermediate I-35F (4.85 g, 18.5 mmol) via the same procedure as Intermediate I-28G. $^1$H NMR (400 MHz, DMSO-d$_6$) δ 7.76 (s, 1H), 7.21 (d, J=2.2 Hz, 1H), 7.11 (d, J=2.2 Hz, 1H); LC-MS: method H, RT=1.08 min, MS (ESI) m/z: 259.1 and 261.1 (M+H)$^+$.

Intermediate I-35H: 7-bromo-5-chloro-2-methoxyquinoxaline

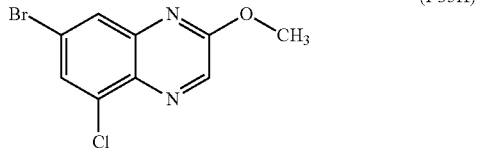

(I-35H)

Intermediate I-35H (2.13 g, 7.79 mmol, 86%) was made as a yellow solid from Intermediate I-35G (2.34 g, 9.02 mmol) via the same procedure as Intermediate I-28H. $^1$H NMR (400 MHz, chloroform-d) δ 8.55 (s, 1H), 7.98 (d, J=2.2 Hz, 1H), 7.80 (d, J=2.0 Hz, 1H), 4.12 (s, 3H); LC-MS: method H, RT=1.07 min, MS (ESI) m/z: 273.1 and 275.1 (M+H)$^+$.

Intermediate I-35I: 5-chloro-2-methoxy-7-vinylquinoxaline

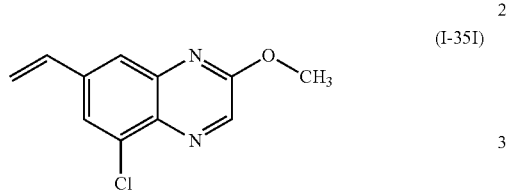

(I-35I)

To a vial charged with a stirring bar was added Intermediate I-35H (0.7 g, 2.56 mmol), potassium vinyltrifluoroborate (0.377 g, 2.82 mmol), cesium carbonate (1.668 g, 5.12 mmol), (s)-2,2'-bis(diphenylphosphino)-1,1'-binaphthalene (0.159 g, 0.256 mmol) and diacetoxypalladium (0.029 g, 0.128 mmol). After applying vacuum and refilling with N$_2$ three times, DMF (10 mL) was added and N$_2$ was bubbled through the solution for 10 minutes. The vial was sealed, stirred at room temperature for 10 minutes, and then heated at 80° C. for 3 h. After cooling to room temperature, the reaction mixture was diluted with 60 mL of EtOAc, washed with water and brine, dried over Na$_2$SO$_4$, filtered and concentrated. The crude product was purified by flash chromatography (0-50% EtOAc/Hexane in 12 minutes, 50-100% EtOAc/Hexane in 6 minutes, 40 g silica gel column) to give the title compound (470 mg, 2.130 mmol, 83% yield) as an off-white solid. $^1$H NMR (400 MHz, chloroform-d) δ 8.51 (s, 1H), 7.79 (d, J=2.0 Hz, 1H), 7.73 (d, J=1.8 Hz, 1H), 6.83 (dd, J=17.5, 10.9 Hz, 1H), 5.96 (d, J=17.4 Hz, 1H), 5.48 (d, J=11.0 Hz, 1H), 4.12 (s, 3H); LC-MS: method H, RT=1.02 min, MS (ESI) m/z: 221.1.

Intermediate I-35J: 8-chloro-3-methoxyquinoxaline-6-carbaldehyde

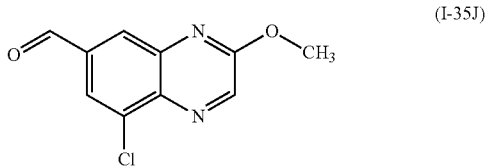

(I-35J)

In a round bottom flask charged with a stirring bar, Intermediate I-35I (470 mg, 2.130 mmol) was dissolved in THF (20 mL)/water (6 mL), and treated with sodium periodate (1367 mg, 6.39 mmol) and osmium tetroxide (0.271 mL, 0.043 mmol). The mixture was stirred at room temperature for 4 h, and then reaction mixture was diluted by adding 40 mL of EtOAc and 20 mL of water. The organic phase was washed with saturated aqueous Na$_2$S$_2$O$_3$ (3×) and brine, dried over Na$_2$SO$_4$, and filtered. The filtrate was concentrated on a rotary evaporator to give the title compound (457 mg, 2.053 mmol, 96% yield) as a yellow solid. $^1$H NMR (400 MHz, chloroform-d) δ 10.17 (s, 1H), 8.67 (s, 1H), 8.27 (d, J=1.8 Hz, 1H), 8.16 (d, J=1.8 Hz, 1H), 4.17 (s, 3H); LC-MS: method H, RT=0.88 min, MS (ESI) m/z: 223.2.

Intermediate I-35K: (8-chloro-3-methoxyquinoxalin-6-yl)methanol

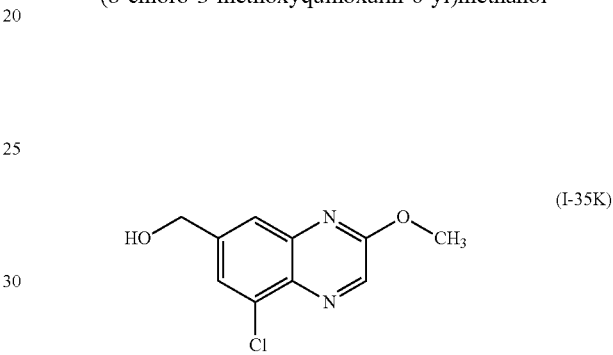

(I-35K)

In a round bottom flask charged with a stirring bar, Intermediate I-35J (421 mg, 1.89 mmol) was dissolved in toluene (10 mL) and mixed with sodium triacetoxyborohydride (882 mg, 4.16 mmol). The mixture was stirred at 60° C. for 4 h. After cooling to room temperature, the solvent was removed on a rotary evaporator. The residue was dissolved in 30 mL of EtOAc and 20 mL of water. The organic phase was washed with brine, dried over Na$_2$SO$_4$, filtered and concentrated on a rotary evaporator to give the title compound (0.415 g, 1.847 mmol, 98% yield) as an off-white solid. $^1$H NMR (400 MHz, chloroform-d) δ 8.55 (s, 1H), 7.79-7.75 (m, 1H), 7.70 (d, J=1.8 Hz, 1H), 4.89 (s, 2H), 4.12 (s, 3H), 1.94 (br s, 1H); LC-MS: method H, RT=0.75 min, MS (ESI) m/z: 225.2.

Intermediate I-35

A microwave tube was charged with Pd$_2$(dba)$_3$ (48.9 mg, 0.053 mmol), X-Phos (102 mg, 0.214 mmol), bis(pinacolato)diboron (814 mg, 3.21 mmol), and potassium acetate (315 mg, 3.21 mmol). The tube was capped and then evacuated and backfilled with argon three times. Intermediate I-35K (240 mg, 1.068 mmol) in 1,4-dioxane (10 mL) was added via syringe, followed by flushing the reaction mixture with N$_2$ for 10 minutes. The reaction mixture was heated at 110° C. in a microwave reactor for 30 minutes. After cooling to room temperature, the reaction mixture was concentrated in vacuo and the residue was purified by flash chromatography (40 g silica gel, 0-100% EtOAc, then 0-10% MeOH/DCM) to give Intermediate I-35 (121 mg, 0.517 mmol, 48.4% yield) as a grey solid. LC-MS: method H, RT=0.75 min, MS (ESI) m/z: 235.2.

Intermediate I-36

2-methoxy-6,7-dimethyl-5-(4,4,5,5-tetramethyl-1,3,2-dioxaborolan-2-yl)quinoxaline

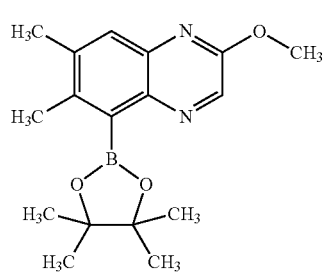
(I-36)

Intermediate I-36A:
2-bromo-3,4-dimethyl-6-nitroaniline

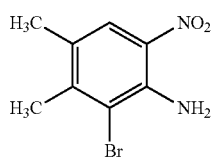
(I-36A)

From commercially available 4,5-dimethyl-2-nitroaniline (5.76 g, 34.7 mmol), Intermediate I-36A was prepared as a yellow solid (7.78 g, 31.7 g, 114%) via the same procedure as Intermediate I-28A. $^1$H NMR (400 MHz, DMSO-$d_6$) δ 7.90 (s, 1H), 7.11 (br s, 2H), 2.38 (s, 3H), 2.26 (s, 3H); LC-MS: method H, RT=1.22 min, MS (ESI) m/z: 245.1 and 247.0 (M+H)$^+$.

Intermediate I-36B: t-butyl

N-(2-bromo-3,4-dimethyl-6-nitrophenyl)-N-[(tert-butoxy)carbonyl]carbamate

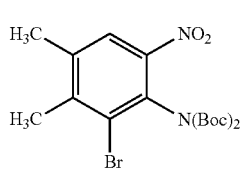
(I-36B)

Intermediate I-36B (9.2 g, 19.2 mmol, 65.1%) was made as a yellow solid from Intermediate I-36A (7.78 g, 20.66 mmol) via the same procedure as Intermediate I-28B. $^1$H NMR (400 MHz, chloroform-d) δ 7.83 (s, 1H), 2.51 (s, 3H), 2.46 (s, 3H), 1.41 (s, 18H); LC-MS: method J, RT=1.03 min, MS (ESI) m/z: 445.1 and 447.0 (M+H)$^+$.

Intermediate I-36C: tert-butyl
(2-bromo-3,4-dimethyl-6-nitrophenyl)carbamate

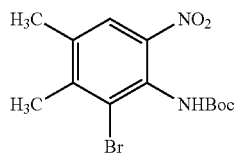
(I-36C)

Intermediate I-36C (6.6 g, 19.1 mmol, 93%) was made as a yellow solid from Intermediate I-36B (9.2 g, 1.30 mmol) via the same procedure as Intermediate I-28C. $^1$H NMR (400 MHz, DMSO-$d_6$) δ 9.18 (br s, 1H), 7.80 (s, 1H), 2.42 (s, 3H), 2.39 (s, 3H), 1.50-1.22 (m, 9H); LC-MS: method J, RT=0.88 min, MS (ESI) m/z: 245.0 and 247.0 (M+H–100)$^+$.

Intermediate I-36D: methyl 2-((2-bromo-3,4-dimethyl-6-nitrophenyl)(tert-butoxycarbonyl)amino)acetate

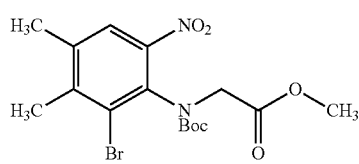
(I-36D)

Intermediate I-36D (3.21 g, 7.69 mmol, 87%) was made as an orange oil from Intermediate I-36C (3.05 g, 8.84 mmol) via the same procedure as Intermediate I-28D. LC-MS: method H, RT=1.27 min, MS (ESI) m/z: 317.0 and 319.1 (M+H–100)$^+$.

Intermediate I-36E: methyl 2-((2-bromo-3,4-dimethyl-6-nitrophenyl)amino)acetate

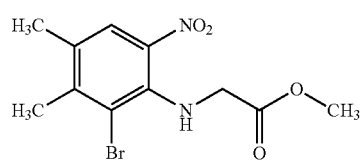
(I-36E)

Intermediate I-36E (2.43 g, 7.67 mmol, 100%) was made as a brown solid from Intermediate I-36D (3.2 g, 7.67 mmol) via the same procedure as Intermediate I-28E. LC-MS: method H, RT=1.22 min, MS (ESI) m/z: 317.0 and 319.0 (M+H)$^+$.

Intermediate I-36F: 5-bromo-6,7-dimethyl-3,4-dihydroquinoxalin-2(1H)-one

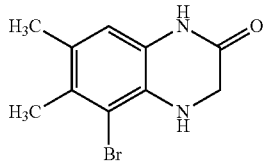
(I-36F)

Intermediate I-36F (1.69 g, 6.62 mmol, 86%) was made as a white solid from Intermediate I-36E (2.43 g, 7.67 mmol) via the same procedure as Intermediate I-28F. LC-MS: method H, RT=1.04 min, MS (ESI) m/z: 255.1 and 257.0 (M+H)+.

Intermediate I-36G:
5-bromo-6,7-dimethylquinoxalin-2(1H)-one

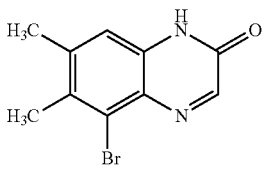
(I-36G)

Intermediate I-36G (1.12 g, 4.43 mmol, 86%) was made as a white solid from Intermediate I-36F (1.26 g, 4.94 mmol) via the same procedure as Intermediate I-28G. LC-MS: method H, RT=1.03 min, MS (ESI) m/z: 253.0 and 255.1 (M+H)+.

Intermediate I-36H:
5-bromo-2-methoxy-6,7-dimethylquinoxaline

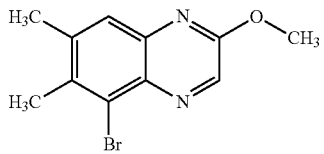
(I-36H)

Intermediate I-36H (0.79 g, 2.97 mmol, 67.2%) was made as a white solid from Intermediate I-36G (1.12 g, 4.43 mmol) via the same procedure as Intermediate I-28H. $^1$H NMR (400 MHz, chloroform-d) δ 8.48 (s, 1H), 7.61 (s, 1H), 4.10 (s, 3H), 2.61 (s, 3H), 2.53 (s, 3H); LC-MS: method H, RT=1.19 min, MS (ESI) m/z: 267.0 and 268.8 (M+H)+.

Intermediate I-36

Intermediate I-36 (0.50 g, 2.14 mmol, 72.5%) was made as a brown solid from Intermediate I-36H (0.79 g, 2.96 mmol) via the same procedure as Intermediate I-28I. LC-MS: method H, RT=0.96 min, MS (ESI) m/z: 232.9 (M+H−82)+.

Intermediate I-37

2 (5-fluoro-3-methoxy-8-(4,4,5,5-tetramethyl-1,3,2-dioxaborolan-2-yl)quinoxalin-6-yl) methanol

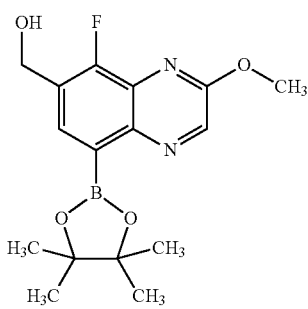
(I-37)

Intermediate I-37A:
4-bromo-6-chloro-3-fluoro-2-nitroaniline

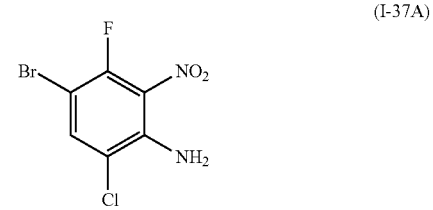 [SMILES: Nc1c(Cl)cc(Br)c(F)c1[N+](=O)[O-]]
(I-37A)

A mixture of 4-bromo-3-fluoro-2-nitroaniline (1.0 g, 4.26 mmol), NCS (0.710 g, 5.32 mmol) in DMF (10 mL) was heated to 100° C. for 1 h. After cooling to room temperature, the reaction mixture was diluted by adding 40 mL of DCM and 30 mL of water. After shaking and separation, aqueous layer was extracted with DCM (20 mL×2). Then organic phases were combined and washed with brine, dried over Na$_2$SO$_4$, filtered concentrated on a rotary evaporator, dried on high vacuum pump to give 4-bromo-6-chloro-3-fluoro-2-nitroaniline (1.22 g, 4.53 mmol, 106% yield) as brown oil. $^1$H NMR (400 MHz, chloroform-d) δ 7.64 (d, J=6.4 Hz, 1H), 6.02 (br s, 2H); $^{19}$F NMR (376 MHz, chloroform-d) δ −109.56 (s, 1F).

Intermediate I-37B: t-butyl

N-(4-bromo-6-chloro-3-fluoro-2-nitrophenyl)-N-[(tert-butoxy)carbonyl]carbamate

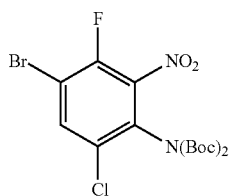
(I-37B)

Intermediate I-37A (1.22 g, 4.53 mmol) was dissolved in THF (10 mL) and mixed with di-tert-butyl dicarbonate (1.976 g, 9.06 mmol) at room temperature, DMAP (0.055 g, 0.453 mmol) was added. The mixture was stirred at room temperature over night. On next day, solvent was removed on a rotary evaporator and residue was purified by flash chromatography for purification (40 g silica gel column, 0-50% EtOAc/Hexane gradient) to give the title compound (1.141 g, 2.429 mmol, 53.7% yield) as a white solid. $^1$H NMR (400 MHz, chloroform-d) δ 7.86 (d, J=6.4 Hz, 1H), 1.43 (s, 18H); $^{19}$F NMR (376 MHz, chloroform-d) δ −114.28 (s, 1F).

Intermediate I-37C: tert-butyl (4-bromo-6-chloro-3-fluoro-2-nitrophenyl)carbamate

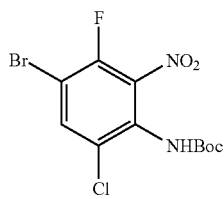

(I-37C)

Intermediate I-37C (0.85 g, 2.3 mmol, 95%) was made as a yellow solid from Intermediate I-37B (9.2 g, 1.30 mmol) via the same procedure as Intermediate I-28C. $^1$H NMR (400 MHz, chloroform-d) δ 7.82 (d, J=6.4 Hz, 1H), 6.61 (br s, 1H), 1.50 (s, 9H); $^{19}$F NMR (376 MHz, chloroform-d) δ −112.58 (br s, 1F).

Intermediate I-37D: methyl 2-((4-bromo-6-chloro-3-fluoro-2-nitrophenyl)(tert-butoxycarbonyl)amino)acetate

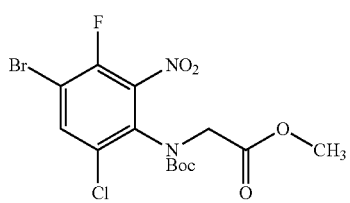

(I-37D)

Intermediate I-37D (0.68 g, 1.55 mmol, 68%) was made as a colorless oil from Intermediate I-37C (0.85 g, 2.30 mmol) via the same procedure as Intermediate I-28D. $^1$H NMR (400 MHz, chloroform-d) δ 7.85 (d, J=6.4 Hz, 1H), 4.44 (d, J=17.4 Hz, 1H), 3.96-3.89 (m, 1H), 3.74 (s, 3H), 1.40 (s, 9H); $^{19}$F NMR (376 MHz, chloroform-d) 6-114.08 (s, 1F); LC-MS: method H, RT=1.05 min, MS (ESI) m/z: 341.1 and 343.0 (M+H−100)$^+$.

Intermediate I-37E: methyl 2-((4-bromo-6-chloro-3-fluoro-2-nitrophenyl)amino)acetate

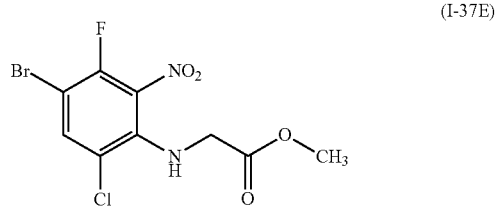 [SMILES: COC(=O)CNc1c(Cl)cc(Br)c(F)c1[N+](=O)[O-]]

(I-37E)

Intermediate I-37E (0.53 g, 1.55 mmol, 100%) was made as brown oil from Intermediate I-37D (0.68 g, 1.55 mmol) via the same procedure as Intermediate I-28E. LC-MS: method H, RT=1.01 min, MS (ESI) m/z: 341.1 and 343.0 (M+H)$^+$.

Intermediate I-37F: 7-bromo-5-chloro-8-fluoro-3,4-dihydroquinoxalin-2(1H)-one

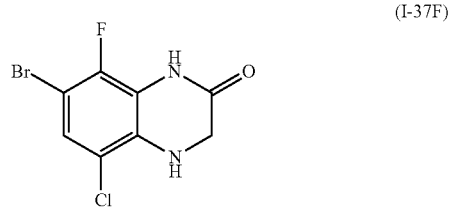

(I-37F)

Intermediate I-37F (0.34 g, 1.22 mmol, 79%) was made as a yellow oil from Intermediate I-37E (0.53 g, 1.55 mmol) via the same procedure as Intermediate I-28F. $^1$H NMR (400 MHz, acetone) δ 9.51 (br s, 1H), 7.17 (d, J=6.4 Hz, 1H), 5.72 (br s, 1H), 4.05-3.97 (m, 2H); $^{19}$F NMR (376 MHz, acetone) δ 47.90 (br s, 1F); LC-MS: method I, RT=1.17 min, MS (ESI) m/z: 279.0 and 281.1 (M+H)$^+$.

Intermediate I-37G: 7-bromo-5-chloro-8-fluoroquinoxalin-2(1H)-one

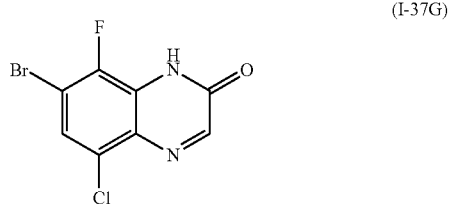 [SMILES: O=c1cnc2c(Cl)cc(Br)c(F)c2[nH]1]

(I-37G)

Intermediate I-37G (0.31 g, 1.10 mmol, 90%) was made as a yellow solid from Intermediate I-37F (0.34 g, 1.22 mmol) via the same procedure as Intermediate I-28G. LC-MS: method H, RT=0.77 min, MS (ESI) m/z: 277.0 and 279.0 (M+H)$^+$.

Intermediate I-37H: 7-bromo-5-chloro-8-fluoro-2-methoxyquinoxaline

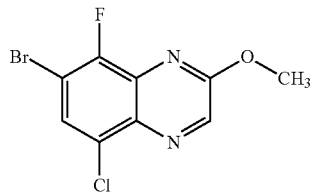

(I-37H)

Intermediate I-37G (306 mg, 1.103 mmol) was treated with POCl₃ (3 mL, 32.2 mmol) and heated to refluxing for 1 hour. After cooling to room temperature, extra POCl₃ was removed on a rotary evaporator and residue was dried on HVAC for 1 hour. Then it was dissolved in anhydrous MeOH (10 mL) and K₂CO₃ (517 mg, 3.74 mmol) was added. After stirring at room temperature for 10 minutes, let mixture reflux for 2 h. Then reaction mixture was cooled to room temperature. Most of MeOH was removed on a rotary evaporator and residue was dissolved in 30 mL of EtOAc and 15 mL of H₂O. After separation, organic phase was washed with brine, dried over Na₂SO₄, filtered and concentrated on a rotary evaporator. The residue was purified by flash chromatography column (40 g silica gel, 0-100% EtOAc/Hexane gradient). Solvent was remove to afford Intermediate I-37H (85 mg, 0.292 mmol, 26.4% yield) as a yellow solid. H NMR (400 MHz, chloroform-d) δ 8.60 (s, 1H), 7.82 (d, J=6.2 Hz, 1H), 4.18 (s, 3H); ¹⁹F NMR (376 MHz, chloroform-d) δ −119.01 (s, 1F); LC-MS: method H, RT=1.05 min, MS (ESI) m/z: 291.0 and 293.1 (M+H)⁺.

Intermediate I-37I: 5-chloro-8-fluoro-2-methoxy-7-vinylquinoxaline

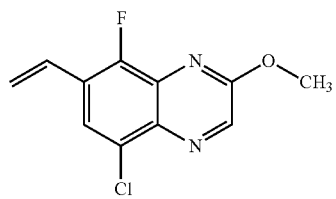

(I-37I)

A vial charged with a stirring bar was added Intermediate I-37H (83 mg, 0.285 mmol), potassium trifluoro(vinyl)borate (36.2 mg, 0.270 mmol), cesium carbonate (186 mg, 0.569 mmol), (s)-2,2'-bis(diphenylphosphino)-1,1'-binaphthalene (35.5 mg, 0.057 mmol) and Pd(OAc)₂ (6.39 mg, 0.028 mmol). After applying vacuum and refilling with N₂ three times, DMF (1.0 mL) was added and mixture was degasses with bubbling N₂ for 10 minutes. Vial was sealed and was stir at room temperature for 10 minutes, then heated at 120° C. for 2 h. After cooling to room temperature, the reaction mixture was diluted by adding 20 mL of EtOAc and washed with water and brine, dried over Na₂SO₄ and filtered. Solvent was removed to afford the crude product, which was purified by flash chromatography (24 g silica gel column, 0-100% EtOAc/Hexane gradient in 10 minutes). Solvent was removed to afford Intermediate I-37I (43 mg, 0.180 mmol, 63.3% yield) as a yellow solid.); LC-MS: method H, RT=1.05 min, MS (ESI) m/z: 239.0 (M+H)⁺.

Intermediate I-37J: 8-chloro-5-fluoro-3-methoxyquinoxaline-6-carbaldehyde

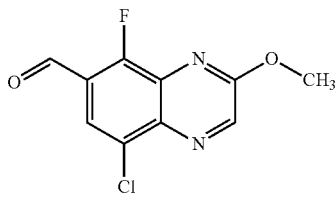

(I-37J)

Intermediate I-37I (43 mg, 0.180 mmol) was dissolved in THF (3 mL))/water (1 mL). Sodium periodate (116 mg, 0.541 mmol) was added, followed by osmium tetroxide (0.023 mL, 3.60 μmol). The mixture was stirred at room temperature for 6 h. Then reaction mixture was diluted by adding 30 mL of EtOAc and 20 mL of water. After separation, organic phase was washed with saturated aqueous Na₂S₂O₃ three times, brine, dried over Na₂SO₄ and filtered. Concentration on a rotary evaporator gave Intermediate I-37J (32 mg, 0.133 mmol, 73.8% yield) as light yellow solid. ¹H NMR (400 MHz, chloroform-d) δ 10.58 (s, 1H), 8.70 (s, 1H), 8.07 (d, J=5.9 Hz, 1H), 4.22 (s, 3H); LC-MS: method H, RT=0.90 min, MS (ESI) m/z: 241.0 (M+H)⁺.

Intermediate I-37K: (8-chloro-5-fluoro-3-methoxyquinoxalin-6-yl)methanol

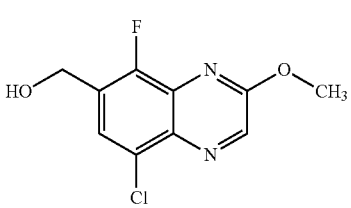

(I-37K)

Intermediate I-37J (32 mg, 0.133 mmol) was dissolved in toluene (1 mL) and mixed with sodium triacetoxyborohydride (62.0 mg, 0.293 mmol). The mixture was stirred at 60° C. for 4 hour. Then reaction mixture was cooled to room temperature, solvent was removed on a rotary evaporator. The residue was dissolved in 20 mL of EtOAc and 10 mL of water. After separation, organic phase was washed with brine, passed over Na₂SO₄, concentrated on a rotary evaporator to give Intermediate I-37K (26 mg, 0.107 mmol, 81% yield) as a solid. ¹H NMR (400 MHz, chloroform-d) δ 8.58 (s, 1H), 7.80 (d, J=6.2 Hz, 1H), 4.97 (d, J=4.4 Hz, 2H), 4.17 (s, 3H), 2.10-2.03 (m, 1H); LC-MS: method H, RT=0.75 min, MS (ESI) m/z: 243.0 (M+H)⁺.

Intermediate I-37

In a microwave tube was charged with Pd₂(dba)₃ (4.91 mg, 5.36 μmol), XPhos (10.22 mg, 0.021 mmol), bis(pinacolato)diboron (82 mg, 0.321 mmol) and potassium acetate (31.5 mg, 0.321 mmol). The microwave tube was capped, evacuated and backfilled with argon (this sequence was carried out two times). Intermediate I-37J (26 mg, 0.107 mmol) in 1,4-dioxane (1 ml) was added via syringe, followed by flushing the reaction mixture with $N_2$ for 10 minutes. The microwave tube was sealed and the reaction mixture was heated at 130° C. in a microwave reactor for 30 minutes. After cooling to room temperature, the reaction mixture was removed. Intermediate I-37 was used without purification in the next step. LC-MS: method H, RT=0.65 min, MS (ESI) m/z: 253.1 (M+H)+.

Intermediate I-38

3-methoxy-8-(4,4,5,5-tetramethyl-1,3,2-dioxaborolan-2-yl)quinoxaline-6-carbonitrile

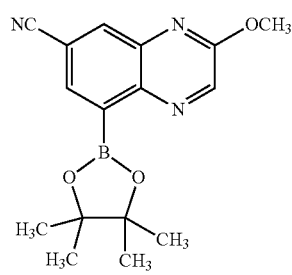

(I-38)

Intermediate I-38A: 8-bromo-3-oxo-1,2,3,4-tetrahydroquinoxaline-6-carbonitrile

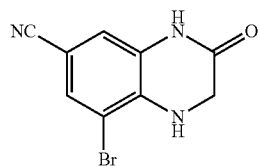

(I-38A)

Intermediate I-38A was synthesized from 4-amino-3-nitrobenzonitrile via the route described in Intermediate I-28. LC-MS: method I, RT=0.94 min, MS (ESI) m/z: 252.0 and 253.9 (M+H)+.

Intermediate I-38B: 8-bromo-3-oxo-3,4-dihydroquinoxaline-6-carbonitrile

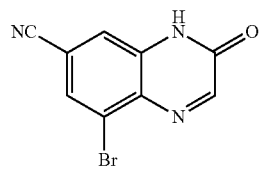

(I-38B)

In a round bottom flask charged with a stirring bar, Intermediate I-38A (394 mg, 1.563 mmol) was suspended in DMF (10 mL), and manganese dioxide (1359 mg, 15.63 mmol) was added. The mixture was stirred at room temperature for 60 minutes. LCMS showed starting material remained. Another 10 eq. of manganese dioxide (1359 mg, 15.63 mmol) was added, and the mixture was stirred at room temperature overnight. On the next day, the solid was filtered and solvent was removed on a rotary evaporator and dried on HVAC to give the title compound (100 mg, 0.400 mmol, 25.6% yield) as a yellow solid. $^1$H NMR (400 MHz, DMSO-$d_6$) δ 8.32 (s, 1H), 7.95 (d, J=2.6 Hz, 1H), 7.65 (s, 1H); LC-MS: method A, RT=2.42 min, MS (ESI) m/z: 248.0 and 250.0 (M+H)+.

Intermediate I-38

Intermediate I-38 was synthesized in two steps from Intermediate I-38B via the route described in Intermediate I-28. LC-MS: method A, RT=0.97 min, MS (ESI) m/z: 230.1 (M+H)+ of boronic acid.

Intermediate I-39

4-bromo-7,8-dihydro-[1,4]dioxino[2',3':3,4]benzo[1,2-d]thiazol-2-amine

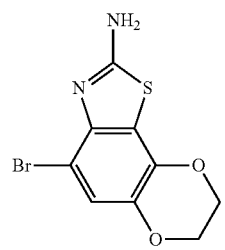

(I-39)

Intermediate I-39A: 7-bromo-2,3-dihydrobenzo[b][1,4]dioxin-6-amine

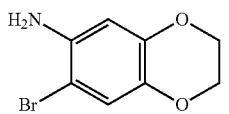

(I-39A)

6-Bromo-7-nitro-2,3-dihydrobenzo[b][1,4]dioxine (0.9 g, 3.46 mmol) was dissolved in MeOH (23.6 mL) and THF (2.96 mL). Ammonium chloride (3.70 g, 69.2 mmol) and zinc dust (2.26 g, 34.6 mmol) were added and the reaction mixture was heated to 40° C. After 2 hours, the reaction mixture was concentrated in vacuo. The crude material was redissolved in EtOAc/saturated $Na_2CO_3$ and allowed to stir vigorously for 15 minutes. The mixture was filtered through a scintered glass funnel to remove the precipitates. The organic layer was washed with water then brine, dried ($Na_2SO_4$), filtered, and concentrated in vacuo. The crude material was purified by column chromatography (ISCO, 40 g silica gel column, 19 minute gradient from 0 to 100% EtOAc in hexanes) to give Intermediate I-39A (594 mg, 2.58 mmol, 75% as an orange solid: $^1$H NMR (400 MHz, CHLOROFORM-d) δ 6.95 (s, 1H), 6.33 (s, 1H), 4.23-4.19 (m, 2H), 4.18-4.14 (m, 2H); LC-MS: Method H, RT=0.66 min, MS (ESI) m/z: 230/232 (M+H)+

Intermediate I-39

Intermediate I-39A (0.594 g, 2.58 mmol) was dissolved in MeCN (12.9 mL). Ammonium thiocyanate (0.295 g, 3.87 mmol) was added, followed by benzyltrimethylammonium tribromide (1.01 g, 2.58 mmol). After stirring overnight, the reaction mixture was diluted with saturated NaHCO$_3$ and the solid collected by suction filtration and washed with water. The crude material was purified by column chromatography (ISCO, 40 g silica gel column, 19 minute gradient from 0 to 100% EtOAc in DCM) to give Intermediate I-39 (195 mg, 0.679 mmol, 26%) as an off-white solid: $^1$H NMR (400 MHz, CHLOROFORM-d) δ 7.08 (s, 1H), 5.30 (s, 2H), 4.38-4.33 (m, 2H), 4.30-4.25 (m, 2H); LC-MS: Method H, RT=0.75 min, MS (ESI) m/z: 287/289 (M+H)$^+$

Intermediate I-40

1-(2-bromo-6,7-dihydroxybenzo[d]thiazol-4-yl)-2,2-dimethylpropan-1-one

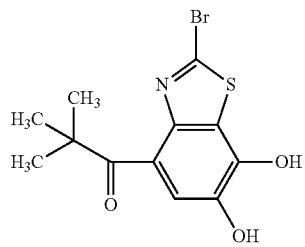

(I-40)

Intermediate I-40A: methyl 2-amino-6,7-dimethoxybenzo[d]thiazole-4-carboxylate

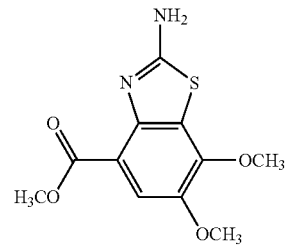

(I-40A)

Methyl 2-amino-4,5-dimethoxybenzoate (5 g, 23.7 mmol) was dissolved in MeCN (47.3 mL). Ammonium thiocyanate (2.70 g, 35.5 mmol) was added, followed by benzyltrimethylammonium tribromide (9.23 g, 23.7 mmol). After stirring 4 days, the reaction mixture was diluted with saturated NaHCO$_3$. The solid precipitate was collected by suction filtration and washed with water to give Intermediate I-40A (4.59 g, 17.1 mmol, 72%) as an orange solid: $^1$H NMR (400 MHz, METHANOL-d$_4$) δ 7.57 (s, 1H), 4.01 (s, 3H), 3.91 (s, 3H), 3.89 (s, 3H); LC-MS: Method H, RT=0.66 min, MS (ESI) m/z: 269.0 (M+H)$^+$

Intermediate I-40B: methyl 2-chloro-6,7-dimethoxybenzo[d]thiazole-4-carboxylate

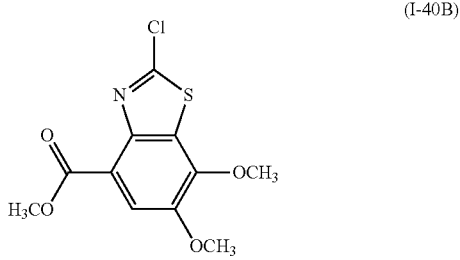 [SMILES: COC(=O)c1cc(OC)c(OC)c2sc(Cl)nc12]

(I-40B)

Copper(II) chloride (3.22 g, 24 mmol) and t-butyl nitrite (3.05 mL, 25.7 mmol) were dissolved in MeCN (68.4 mL) and allowed to stir 10 minutes. Intermediate I-40A (4.59 g, 17.1 mmol) was added and the reaction mixture was heated to 60° C. After 2 hours, the reaction mixture was concentrated in vacuo, diluted with EtOAc, washed with 1 N HCl, saturated NaHCO$_3$, then brine, dried (Na$_2$SO$_4$), filtered, and concentrated in vacuo. The crude material was purified by column chromatography (ISCO, 120 g silica gel column, 32 minute gradient from 0 to 100% EtOAc in hexanes) to give Intermediate I-40B (2.88 g, 10 mmol, 58%) as a light pink solid: 1H NMR (400 MHz, CHLOROFORM-d) δ 7.82 (s, 1H), 4.13 (s, 3H), 4.04 (s, 3H), 4.01 (s, 3H); LC-MS: Method H, RT=0.99 min, MS (ESI) m/z: 288.1 (M+H)$^+$

Intermediate I-40C: (2-chloro-6,7-dimethoxybenzo[d]thiazol-4-yl)methanol

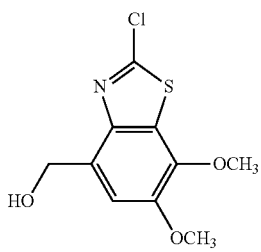

(I-40C)

Intermediate I-40B (2.88 g, 10.01 mmol) was dissolved in toluene (66.7 mL) and THF (33.4 mL) and cooled to −78° C. DIBAL-H (1 M in toluene, 22 mL, 22 mmol) was added and the reaction mixture was allowed to slowly warm to ambient temperature. After stirring overnight, the reaction was quenched with saturated Rochelle's salt. After stirring overnight, the reaction mixture was extracted with EtOAc, washed with water, then brine, dried (Na$_2$SO$_4$), filtered, and concentrated in vacuo to give Intermediate I-40C (2.5 g, 9.63 mmol, 96%) as a white solid: 1H NMR (400 MHz, CHLOROFORM-d) δ 7.16 (s, 1H), 5.06 (d, J=6.4 Hz, 2H), 4.02 (s, 3H), 3.98 (s, 3H); LC-MS: Method H, RT=0.90 min, MS (ESI) m/z: 260.0 (M+H)$^+$

Intermediate I-40D: 2-chloro-6,7-dimethoxybenzo[d]thiazole-4-carbaldehyde

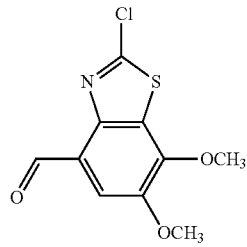

(I-40D)

Intermediate I-40C (2.5 g, 9.63 mmol) was dissolved in CHCl3 (64.2 mL). Manganese dioxide (5.02 g, 57.8 mmol) was added and the reaction mixture was heated to 40° C. After 2 days, the reaction mixture was filtered through celite and concentrated in vacuo to give Intermediate I-40D (2.28 g, 8.84 mmol, 92%) as an orange solid: $^1$H NMR (400 MHz, CHLOROFORM-d) δ 10.78 (s, 1H), 7.72 (s, 1H), 7.29 (s, 1H), 4.17 (s, 3H), 4.02 (s, 3H); LC-MS: Method H, RT=0.99 min, MS (ESI) m/z: 257.9 (M+H)$^+$

Intermediate I-40E 1-(2-chloro-6,7-dimethoxybenzo[d]thiazol-4-yl)-2,2-dimethylpropan-1-ol

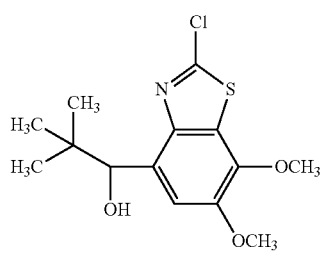

(I-40E)

Intermediate I-40D (0.5 g, 1.940 mmol) was dissolved in THF (9.70 mL) and cooled to −78° C. tert-Butylmagnesium chloride (1 M in THF, 5.82 mL, 5.82 mmol) was added and the reaction mixture was warmed to 0° C. After 2 hours, the reaction mixture was quenched with saturated NH$_4$Cl and extracted with EtOAc. The organic layer was washed with water, then brine, dried (Na$_2$SO$_4$), filtered, and concentrated in vacuo. The crude material was purified by column chromatography (ISCO, 40 g silica gel column, 19 minute gradient from 0 to 100% EtOAc in hexanes). The isolate was repurified by column chromatography (ISCO, 40 g silica gel column, 19 minute gradient from 0 to 40% EtOAc in DCM) to give Intermediate I-40E (263 mg, 0.836 mmol, 43%) as a yellow solid: $^1$H NMR (400 MHz, CHLOROFORM-d) δ 7.07 (s, 1H), 4.92 (d, J=7.5 Hz, 1H), 4.02 (s, 3H), 3.96 (s, 3H), 3.66 (d, J=7.5 Hz, 1H), 0.99 (s, 9H); LC-MS: Method H, RT=1.13 min, MS (ESI) m/z: 316.0 (M+H)$^+$

Intermediate I-40F 1-(2-chloro-6,7-dimethoxybenzo[d]thiazol-4-yl)-2,2-dimethylpropan-1-one

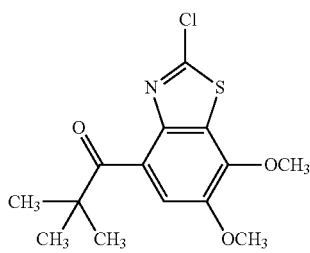

(I-40F)

Intermediate I-40E (240 mg, 0.76 mmol) was dissolved in toluene (7.6 mL). Manganese dioxide (396 mg, 4.56 mmol) was added and the reaction mixture was heated to 100° C. After heating overnight, the reaction mixture was filtered through celite and concentrated in vacuo to give Intermediate I-40F (216 mg, 0.687 mmol, 90%) as a clear oil: $^1$H NMR (400 MHz, CHLOROFORM-d) δ 6.97 (s, 1H), 4.04 (s, 3H), 3.96 (s, 3H), 1.34 (s, 9H); LC-MS: Method H, RT=1.21 min, MS (ESI) m/z: 314.0 (M+H)$^+$

Intermediate I-40

Intermediate I-40F (215 mg, 0.685 mmol) and boron tribromide (1 M in THF, 2.06 mL, 2.06 mmol) were dissolved in DCM (6.85 mL). After 2 hours, the reaction mixture was diluted with 1 N HCl and extracted thrice with DCM. The combined organic layers were washed with brine, dried (Na$_2$SO$_4$), filtered, and concentrated in vacuo to give Intermediate I-40 (225 mg, 0.683 mmol, 100%) as a white solid: $^1$H NMR (400 MHz, METHANOL-d$_4$) δ 6.92 (s, 1H), 1.27 (s, 9H); LC-MS: Method H, RT=0.94 min, MS (ESI) m/z: 330/332 (M+H)$^+$.

Intermediate I-41

6-chloro-3-methoxy-8-(4,4,5,5-tetramethyl-1,3,2-dioxaborolan-2-yl)quinoline

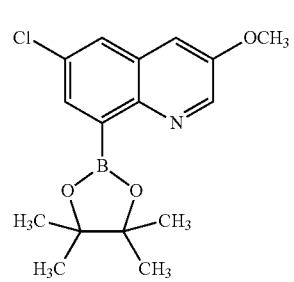

(I-41)

Intermediate I-41A:
8-bromo-6-chloro-3-methoxyquinoline

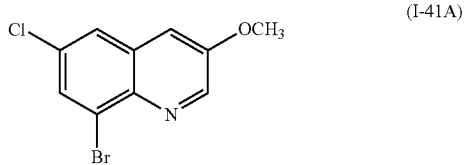 [SMILES: COc1cnc2c(Br)cc(Cl)cc2c1]

Intermediate I-43 (2 g, 6.78 mmol), potassium carbonate (2.81 g, 20.3 mmol), and methyl iodide (0.848 mL, 13.6 mmol) were dissolved in acetone (67.8 mL) and heated to 50° C. in a sealed tube. After heating overnight, the reaction mixture was diluted with EtOAc, washed with water, then brine, dried (Na$_2$SO$_4$), filtered, and concentrated in vacuo to give Intermediate I-41A (2.04 g, 7.48 mmol) as a yellow solid: $^1$H NMR (400 MHz, CHLOROFORM-d) δ 8.76 (d, J=2.6 Hz, 1H), 7.86 (d, J=2.2 Hz, 1H), 7.70 (d, J=2.2 Hz, 1H), 7.29 (d, J=2.9 Hz, 1H), 3.97 (s, 3H); LC-MS: Method H, RT=1.07 min, MS (ESI) m/z: 272/274 (M+H)$^+$

Intermediate I-41

Intermediate I-41A (1 g, 3.67 mmol), bispinacolatodiboron (1.86 g, 7.34 mmol), potassium acetate (0.900 g, 9.17 mmol), and PdCl$_2$(dppf)—CH$_2$Cl$_2$ adduct (0.240 g, 0.294 mmol) were stored on HIVAC for 15 minutes then were dissolved in dry 1,4-dioxane (18.4 mL) and degassed for 15 minutes by bubbling with argon. The reaction mixture was heated to 130° C. in the microwave for 40 minutes. The reaction mixture was diluted with EtOAc and washed with water then brine, dried (Na$_2$SO$_4$), filtered, and concentrated in vacuo. The crude material was purified by column chromatography (ISCO, 80 g silica gel column, 29 minute gradient from 0 to 100% EtOAc in DCM, followed by 0 to 20% MeOH in DCM) to give Intermediate I-41 (368 mg, 1.15 mmol, 31.4%) as a brown solid: LC-MS: Method H, RT=0.81 min, MS (ESI) m/z: 237.9 (boronic acid mass observed, M+H)$^+$.

Intermediate I-42

(R)-(2-chloro-7,8-dihydro-[1,4]dioxino[2',3':3,4]benzo[1,2-d]thiazol-7-yl)methyl (2-methylpyrimidin-5-yl)carbamate

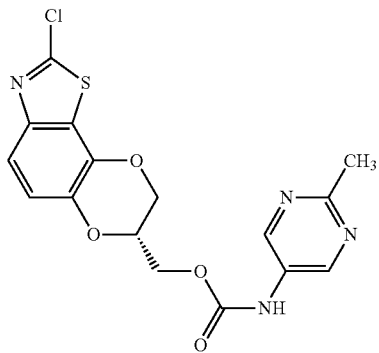

Intermediate 287D (0.292 g, 1.133 mmol) was dissolved in THF (22.7 mL). Phosgene solution (15% in toluene, 8.64 mL, 11.33 mmol) was then added. After 2 days, the reaction mixture was concentrated in vacuo and stored on HIVAC for 3 hours. The reaction mixture was dissolved in THF (22.7 mL). 2-Methylpyrimidin-5-amine (0.148 g, 1.36 mmol) and pyridine (0.916 mL, 11.3 mmol) were added. After stirring overnight, the reaction mixture was concentrated in vacuo. The crude material was purified by column chromatography (ISCO, 40 g silica gel column, 19 minute gradient from 0 to 100% EtOAc in hexanes) to give Intermediate I-42 (260 mg, 0.66 mmol, 58%) as a white solid: $^1$H NMR (400 MHz, CHLOROFORM-d) δ 8.75 (br. s., 2H), 7.49 (d, J=8.8 Hz, 1H), 7.08 (d, J=8.8 Hz, 1H), 6.71 (br. s., 1H), 4.58-4.45 (m, 4H), 4.24 (dd, J=11.3, 6.7 Hz, 1H), 2.72 (s, 3H); LC-MS: Method H, RT=0.97 min, MS (ESI) m/z: 393.1 (M+H)$^+$.

Intermediate I-43

8-bromo-6-chloroquinolin-3-ol, HCl

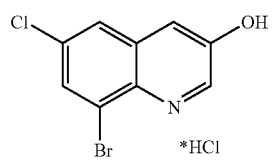

Intermediate I-43A:
3-(benzyloxy)-8-bromo-6-chloroquinoline

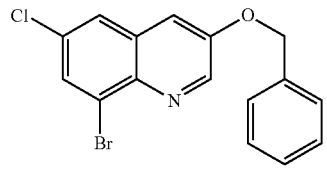

Intermediate I-44 (5 g, 21.32 mmol), 2-(benzyloxy)acetaldehyde (3.20 g, 21.3 mmol), and sodium methoxide solution (0.5 M in MeOH, 46.9 mL, 23.5 mmol) were dissolved in MeOH (42.6 mL) and heated to reflux. After heating overnight, the reaction mixture was diluted with saturated NH$_4$Cl, partially concentrated in vacuo and diluted with EtOAc. The layers were separated and the organic layer was washed with brine, dried (Na$_2$SO$_4$), filtered, and concentrated in vacuo. The crude material was purified by column chromatography (ISCO, 330 g silica gel column, 30 minute gradient from 0 to 17% EtOAc in hexanes) to give Intermediate I-43A (4.97 g, 14.3 mmol, 67%) as a yellow solid: $^1$H NMR (500 MHz, CHLOROFORM-d) δ 8.85 (d, J=2.8 Hz, 1H), 7.89 (d, J=1.9 Hz, 1H), 7.69 (d, J=2.2 Hz, 1H), 7.52-7.48 (m, 2H), 7.48-7.43 (m, 2H), 7.43-7.38 (m, 1H), 7.37 (d, J=2.8 Hz, 1H), 5.24 (s, 2H); LC-MS: Method H, RT=1.46 min, MS (ESI) m/z: 348/350 (M+H)$^+$.

Intermediate I-43

Intermediate I-43A (4.87 g, 14 mmol) and pentamethylbenzene (14.5 g, 98 mmol) were dissolved in DCM (279 mL) and cooled to −78° C. Boron trichloride (1 M in heptane, 36.3 mL, 36.3 mmol) was then added and the reaction mixture was allowed to slowly warm to ambient temperature. After stirring overnight, the reaction mixture was diluted with hexanes and 1 N HCl and allowed to stir for 1 hour. The resulting solid was collected by suction filtration, rinsing with water and hexanes to give Intermediate I-43 (3.39 g, 11.5 mmol, 82%) as an off-white solid: $^1$H NMR (400 MHz, METHANOL-$d_4$) δ 8.59 (d, J=2.6 Hz, 1H), 7.84 (d, J=2.2 Hz, 1H), 7.80 (d, J=2.0 Hz, 1H), 7.47 (d, J=2.6 Hz, 1H); LC-MS: Method H, RT=0.92 min, MS (ESI) m/z: 258/260 (M+H)$^+$.

Intermediate I-44

2-amino-3-bromo-5-chlorobenzaldehyde

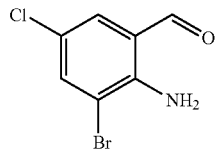

(I-44)

Intermediate I-44A: methyl
2-amino-3-bromo-5-chlorobenzoate

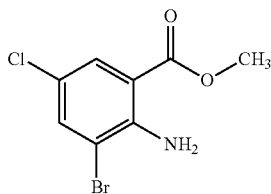

(I-44A)

Methyl 2-amino-5-chlorobenzoate (18.1 g, 97 mmol) and NBS (17.3 g, 97 mmol) were dissolved in AcOH (195 mL) and heated to 120° C. After 1.5 hours, the reaction mixture was cooled to ambient temperature and diluted with EtOAc. The reaction was then quenched with vigorous stirring with saturated NaHCO$_3$. The layers were separated and the organic layer further washed with brine, dried (Na$_2$SO$_4$), filtered, and concentrated in vacuo to give Intermediate I-44A (25.7 g, 97 mmol, 100%) as a yellow solid: $^1$H NMR (400 MHz, CHLOROFORM-d) δ 7.87 (d, J=2.4 Hz, 1H), 7.59 (d, J=2.4 Hz, 1H), 6.36 (br. s., 2H), 3.92 (s, 3H); LC-MS: Method H, RT=1.20 min, MS (ESI) m/z: 264/266 (M+H)$^+$.

Intermediate I-44B:
(2-amino-3-bromo-5-chlorophenyl)methanol

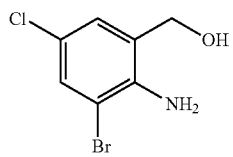

(I-44B)

Intermediate I-44A (25.7 g, 97 mmol) was dissolved in THF (324 mL). Lithium borohydride (4.23 g, 194 mmol) was added and the reaction mixture was heated to 50° C. After 2 hours, the reaction mixture was diluted with water and stirred for 30 minutes. All of the lithium borohydride had not dissolved, so concentrated HCl was added carefully to speed up the quenching process. The reaction mixture was then extracted thrice with EtOAc. The combined organic layers were washed with brine, dried (Na$_2$SO$_4$), filtered, and concentrated in vacuo to give Intermediate I-44B (23.9 g, 101 mmol, 100%) as a white solid: $^1$H NMR (400 MHz, CHLOROFORM-d) δ 7.43 (d, J=2.4 Hz, 1H), 7.05 (d, J=2.4 Hz, 1H), 4.72 (br. s., 2H), 4.68 (d, J=5.9 Hz, 2H), 1.63 (t, J=5.8 Hz, 1H); LC-MS: Method H, RT=1.11 min, MS (ESI) m/z: 236/238 (M+H)$^+$.

Intermediate I-44

Intermediate I-44B (23.9 g, 101 mmol) was dissolved in CHCl$_3$ (674 mL). Manganese dioxide (17.6 g, 202 mmol) was added and the reaction mixture was heated to 40° C. After heating for 2 days, more manganese dioxide (17.6 g, 202 mmol) was added and heating was continued. After heating overnight, the reaction mixture was filtered through celite and concentrated in vacuo to give Intermediate I-44 (22 g, 94 mmol, 93%) as a yellow solid: $^1$H NMR (400 MHz, CHLOROFORM-d) δ 9.79 (s, 1H), 7.64 (d, J=2.4 Hz, 1H), 7.49 (d, J=2.4 Hz, 1H), 6.70 (br. s., 2H); LC-MS: Method H, RT=1.27 min, compound did not ionize.

Intermediate I-45

(R)-(2-chloro-5-fluoro-7,8-dihydrobenzofuro[5,4-d]thiazol-7-yl)methyl (2-methylpyrimidin-5-yl)carbamate

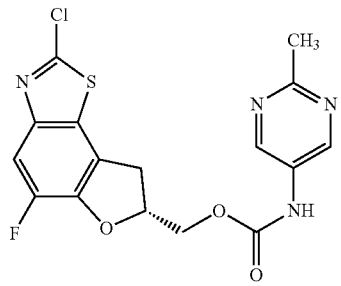

(I-45)

Intermediate 145D (0.2 g, 0.658 mmol) was dissolved in THF (13.15 mL). Phosgene solution (15% in toluene, 5.01 mL, 6.58 mmol) was then added. After stirring for 2 days, the reaction mixture was concentrated in vacuo and stored on HIVAC for 3 hours. The reaction mixture was dissolved in THF (13.2 mL). 2-Methylpyrimidin-5-amine (0.086 g, 0.789 mmol) and pyridine (0.532 mL, 6.58 mmol) were then added. After stirring overnight, the reaction mixture was concentrated in vacuo. The crude material was purified by column chromatography (ISCO, 40 g silica gel column, 19 minute gradient from 0 to 100% EtOAc in hexanes) to give Intermediate I-45 (213 mg, 0.541 mmol, 82%) as a white solid: $^1$H NMR (400 MHz, CHLOROFORM-d) δ 8.74 (br. s., 2H), 7.57 (d, J=10.3 Hz, 1H), 6.70 (br. s., 1H), 5.38-5.31 (m, 1H), 4.57 (dd, J=12.1, 3.1 Hz, 1H), 4.44 (dd, J=12.0, 6.3

Hz, 1H), 3.52 (dd, J=15.7, 9.8 Hz, 1H), 3.21 (dd, J=16.0, 7.2 Hz, 1H), 2.70 (s, 3H); LC-MS: Method H, RT=0.96 min, MS (ESI) m/z: 395.0 (M+H)+.

Intermediate I-46

3-methoxy-6-methyl-8-(4,4,5,5-tetramethyl-1,3,2-dioxaborolan-2-yl)quinoline

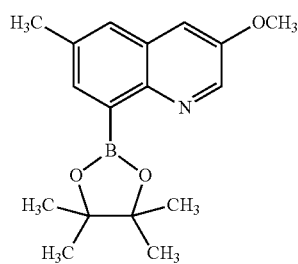

(I-46)

Intermediate I-47 (183 mg, 0.726 mmol), bispinacolatodiboron (369 mg, 1.45 mmol), potassium acetate (178 mg, 1.82 mmol), and PdCl$_2$(dppf)—CH$_2$Cl$_2$ adduct (47.4 mg, 0.058 mmol) were stored on HIVAC for 15 minutes then were dissolved in dry 1,4-dioxane (7.26 mL) and degassed for 15 minutes by bubbling with argon. The reaction mixture was heated to 130° C. in the microwave for 40 minutes. The reaction mixture was diluted with EtOAc and washed with water then brine, dried (Na$_2$SO$_4$), filtered, and concentrated in vacuo. The crude material was purified by column chromatography (ISCO, 24 g silica gel column, 19 minute gradient from 0 to 100% EtOAc in DCM then 0 to 20% MeOH in DCM) to give Intermediate I-46 (108 mg, 0.36 mmol, 50%) as a brown solid: LC-MS: Method H, RT=0.80 min, MS (ESI) m/z: 218.0 (boronic acid observed, M+H)+.

Intermediate I-47

8-bromo-3-methoxy-6-methylquinoline

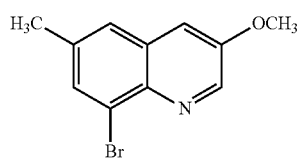

(I-47)

Intermediate I-47A: methyl 2-amino-3-bromo-5-methylbenzoate

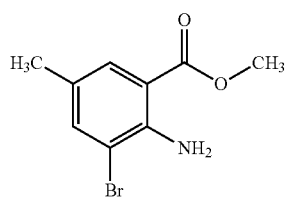

(I-47A)

2-Amino-3-bromo-5-methylbenzoic acid (3.8 g, 16.5 mmol) was dissolved in MeOH (33.0 mL). Thionyl chloride (3.62 mL, 49.6 mmol) was added carefully dropwise and the reaction mixture was heated to 65° C. After stirring for 8 days, the reaction mixture was concentrated in vacuo. The crude material was redissolved in EtOAc, washed with 1 N NaOH, water, then brine, dried (Na$_2$SO$_4$), filtered, and concentrated in vacuo to give Intermediate I-47A (3.38 g, 13.9 mmol, 84%) as an orange oil: $^1$H NMR (400 MHz, CHLOROFORM-d) δ 7.66 (d, J=1.1 Hz, 1H), 7.43 (d, J=1.8 Hz, 1H), 6.14 (br. s., 2H), 3.88 (s, 3H), 2.22 (s, 3H); LC-MS: Method H, RT=1.18 min, MS (ESI) m/z: 244/246 (M+H)+.

Intermediate I-47B:
(2-amino-3-bromo-5-methylphenyl)methanol

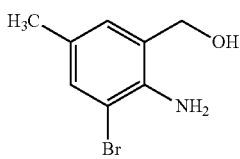

(I-47B)

Intermediate I-47A (3.38 g, 13.8 mmol) was dissolved in THF (46.2 mL). Lithium borohydride (0.603 g, 27.7 mmol) was added and the reaction mixture was heated to 50° C. After 1 hour, the reaction mixture was diluted with water and stirred for 30 minutes. All of the lithium borohydride had not dissolved, so concentrated HCl was added carefully to speed up the quenching process. The reaction mixture was then extracted thrice with EtOAc. The combined organic layers were washed with brine, dried (Na$_2$SO$_4$), filtered, and concentrated in vacuo to give Intermediate I-47B (2.85 g, 13.2 mmol, 95%) as a white solid: $^1$H NMR (400 MHz, CHLOROFORM-d) δ 7.23 (d, J=1.1 Hz, 1H), 6.84 (d, J=1.3 Hz, 1H), 4.65 (s, 2H), 4.53 (br. s., 2H), 2.22 (s, 3H); LC-MS: Method H, RT=1.00 min, MS (ESI) m/z: 216/218 (M+H)+.

Intermediate I-47C:
2-amino-3-bromo-5-methylbenzaldehyde

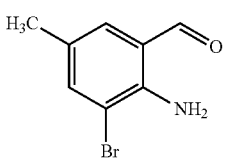

(I-47C)

Intermediate I-47B (2.85 g, 13.2 mmol) was dissolved in CHCl$_3$ (88 mL). Manganese dioxide (6.88 g, 79 mmol) was added and the reaction mixture was heated to 40° C. After heating overnight, the reaction mixture was filtered through celite and concentrated in vacuo to give Intermediate I-47C (2.72 g, 12.7 mmol, 96%) as a yellow solid: $^1$H NMR (400 MHz, CHLOROFORM-d) δ 9.78 (s, 1H), 7.47 (d, J=1.5 Hz, 1H), 7.28-7.26 (m, 1H), 6.49 (br. s., 2H), 2.28 (s, 3H); LC-MS: Method H, RT=1.26 min, MS (ESI) m/z: 214/216 (M+H)+.

Intermediate I-47D: 3-(benzyloxy)-8-bromo-6-methylquinoline

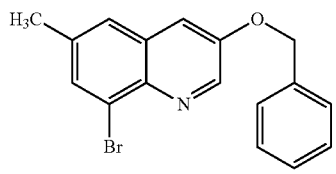
(I-47D)

Intermediate I-47C (2.72 g, 12.7 mmol), 2-(benzyloxy) acetaldehyde (1.91 g, 12.7 mmol), and sodium methoxide (0.5 M in MeOH, 28.0 mL, 13.98 mmol) were dissolved in MeOH (50.8 mL) and heated to reflux. After heating overnight, the reaction mixture was diluted with saturated NH$_4$Cl, partially concentrated in vacuo and diluted with EtOAc. The layers were separated and the organic layer was washed with brine, dried (Na$_2$SO$_4$), filtered, and concentrated in vacuo. The crude material was purified by column chromatography (ISCO, 220 g silica gel column, 41 minute gradient from 0 to 40% EtOAc in hexanes) to give Intermediate I-47D (1.86 g, 5.67 mmol, 45%) as a yellow solid: $^1$H NMR (400 MHz, CHLOROFORM-d) δ 8.79 (d, J=2.9 Hz, 1H), 7.74 (d, J=1.5 Hz, 1H), 7.51-7.46 (m, 2H), 7.45-7.40 (m, 3H), 7.39-7.33 (m, 2H), 5.20 (s, 2H), 2.49 (s, 3H); LC-MS: Method H, RT=1.22 min, MS (ESI) m/z: 328/330 (M+H)$^+$.

Intermediate I-47E: 8-bromo-6-methylquinolin-3-ol

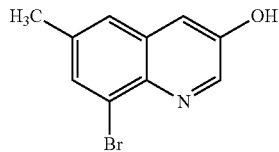
(I-47E)

Intermediate I-47D (1.86 g, 5.67 mmol) and pentamethylbenzene (5.88 g, 39.7 mmol) were dissolved in DCM (113 mL) and cooled to −78° C. Boron trichloride (1 M in heptane, 14.7 mL, 14.7 mmol) was added and the reaction mixture was allowed to warm slowly to ambient temperature. After stirring overnight, the reaction mixture was diluted with hexanes and 1 N HCl and allowed to stir for 1 hour. The aqueous layer still contained product by LCMS. The aqueous layer was neutralized with NaOH until approximately pH 7 and copious amounts of precipitates were formed. The precipitate was collected by suction filtration to give Intermediate I-47E (829 mg, 3.48 mmol, 62%) as an off-white solid: $^1$H NMR (400 MHz, METHANOL-d$_4$) δ 8.50 (d, J=2.6 Hz, 1H), 7.72 (s, 1H), 7.51 (s, 1H), 7.43 (d, J=1.8 Hz, 1H), 2.47 (s, 3H); LC-MS: Method H, RT=0.82 min, MS (ESI) m/z: 238/240 (M+H)$^+$.

Intermediate I-47

Intermediate I-47E (200 mg, 0.728 mmol), K$_2$CO$_3$ (302 mg, 2.18 mmol), and methyl iodide (91 μl, 1.46 mmol) were dissolved in acetone (7.29 mL) and heated to 50° C. in a sealed tube. After heating overnight, the reaction mixture was diluted with EtOAc, washed with water, then brine, dried (Na$_2$SO$_4$), filtered, and concentrated in vacuo to give Intermediate I-47 (207 mg, 0.82 mmol, 100%) as a yellow solid: $^1$H NMR (400 MHz, CHLOROFORM-d) δ 8.71 (d, J=2.9 Hz, 1H), 7.74 (d, J=1.8 Hz, 1H), 7.46 (s, 1H), 7.29 (d, J=2.9 Hz, 1H), 3.95 (s, 3H), 2.50 (s, 3H); LC-MS: Method H, RT=1.06 min, MS (ESI) m/z: 252/254 (M+H)$^+$.

Intermediate I-48

6-chloro-3-ethoxy-8-(4,4,5,5-tetramethyl-1,3,2-dioxaborolan-2-yl)quinoline

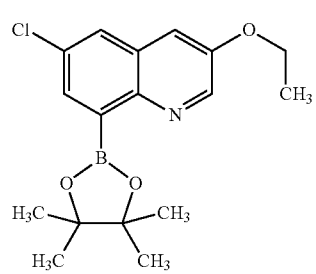
(I-48)

Intermediate I-48A: 8-bromo-6-chloro-3-ethoxyquinoline

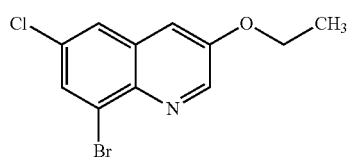
(I-48A)

Intermediate I-43 (300 mg, 1.02 mmol), K$_2$CO$_3$ (422 mg, 3.05 mmol), and iodoethane (163 μL, 2.03 mmol) were dissolved in acetone (10 mL) and heated to 50° C. in a sealed tube. After heating overnight, the reaction mixture was diluted with EtOAc, washed with water, then brine, dried (Na$_2$SO$_4$), filtered, and concentrated in vacuo to give Intermediate I-48A (319 mg, 1.11 mmol, 100%) as a light yellow solid: $^1$H NMR (400 MHz, CHLOROFORM-d) δ 8.74 (d, J=2.6 Hz, 1H), 7.85 (d, J=2.2 Hz, 1H), 7.67 (d, J=2.2 Hz, 1H), 7.28-7.24 (m, 1H), 4.17 (q, J=6.9 Hz, 2H), 1.52 (t, J=7.0 Hz, 3H); LC-MS: Method H, RT=1.22 min, MS (ESI) m/z: 286/288 (M+H)$^+$.

Intermediate I-48

Intermediate I-48A (319 mg, 1.11 mmol), bispinacolatodiboron (565 mg, 2.23 mmol), potassium acetate (273 mg, 2.78 mmol), and PdCl$_2$(dppf)—CH$_2$Cl$_2$ adduct (72.7 mg, 0.089 mmol) were stored on HIVAC for 15 minutes then were dissolved in dry 1,4-dioxane (5.67 mL) and degassed for 15 minutes by bubbling with argon. The reaction mixture was heated to 130° C. in the microwave for 40 minutes. The reaction mixture was diluted with EtOAc and washed with water then brine, dried (Na$_2$SO$_4$), filtered, and concentrated in vacuo. The crude material was purified by column chromatography (ISCO, 80 g silica gel column, 29 minute gradient from 0 to 100% EtOAc in DCM, followed by 0 to 20% MeOH in DCM) to give Intermediate I-48 (114 mg, 0.343 mmol, 31%) as a brown solid: LC-MS: Method H, RT=0.88 min, MS (ESI) m/z: 251.9 (boronic acid mass observed, M+H)+.

Intermediate I-49

6-chloro-3-(difluoromethoxy)-8-(4,4,5,5-tetramethyl-1,3,2-dioxaborolan-2-yl)quinoline

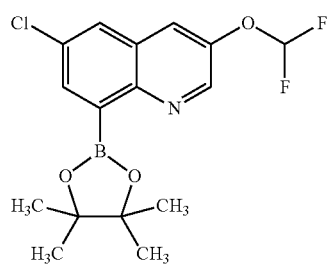

Intermediate I-49A:
8-bromo-6-chloro-3-(difluoromethoxy)quinoline

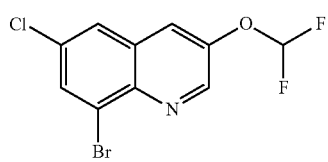

Intermediate I-43 (0.5 g, 1.7 mmol) and K$_2$CO$_3$ (1.17 g, 8.48 mmol) were suspended in DMF (17 mL) and heated to 100° C. Sodium 2-chloro-2,2-difluoroacetate (1.03 g, 6.78 mmol) was then added. After heating for 1 hour, the reaction mixture was cooled to ambient temperature, diluted with water, and extracted thrice with EtOAc. The combined organic extracts were washed with brine, dried (Na$_2$SO$_4$), filtered, and concentrated in vacuo. The crude material was purified by column chromatography (ISCO, 12 g silica gel column, 17 minute gradient from 0 to 50% EtOAc in hexanes) to give Intermediate I-49A (342 mg, 1.11 mmol, 66%) as a light yellow solid: $^1$H NMR (400 MHz, CHLOROFORM-d) δ 8.87 (d, J=2.6 Hz, 1H), 8.02 (d, J=2.0 Hz, 1H), 7.80 (d, J=2.4 Hz, 1H), 7.78 (d, J=2.0 Hz, 1H), 6.88-6.49 (m, 1H); LC-MS: Method H, RT=1.09 min, MS (ESI) m/z: 308/310 (M+H)+.

Intermediate I-49

Intermediate I-49A (340 mg, 1.1 mmol), bispinacolatodiboron (560 mg, 2.2 mmol), potassium acetate (270 mg, 2.76 mmol), and PdCl$_2$(dppf)—CH$_2$Cl$_2$ adduct (72.0 mg, 0.088 mmol) were stored on HIVAC for 15 minutes then were dissolved in dry 1,4-dioxane (5.51 mL) and degassed for 15 minutes by bubbling with argon. The reaction mixture was heated to 130° C. in the microwave for 40 minutes. The reaction mixture was diluted with EtOAc and washed with water then brine, dried (Na$_2$SO$_4$), filtered, and concentrated in vacuo. The crude material was purified by column chromatography (ISCO, 80 g silica gel column, 29 minute gradient from 0 to 100% EtOAc in DCM, followed by 0 to 20% MeOH in DCM) to give Intermediate I-49 (175 mg, 0.492 mmol, 45%) as a brown solid: LC-MS: Method H, RT=0.93 min, MS (ESI) m/z: 274.1 (boronic acid mass observed, M+H)+.

Intermediate I-50

6-(difluoromethyl)-3-methoxy-8-(4,4,5,5-tetramethyl-1,3,2-dioxaborolan-2-yl)quinoline

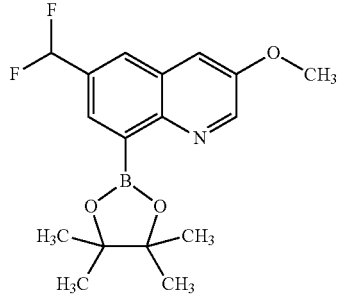

Intermediate I-50A:
8-bromo-3-methoxyquinoline-6-carbaldehyde

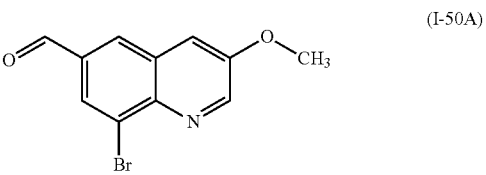

Intermediate I-47 (152 mg, 0.602 mmol) and selenium dioxide (401 mg, 3.61 mmol) were suspended in 1,4-dioxane (3.01 mL) and heated to 180° C. in the microwave for 8 hours. The reaction mixture was filtered and concentrated in vacuo. The solids were then suspended in DCM and the insoluble material removed by suction filtration to give Intermediate I-50A (170 mg, 0.639 mmol, 100%) as a white solid: $^1$H NMR (400 MHz, CHLOROFORM-d) δ 10.15 (s, 1H), 8.93 (d, J=2.9 Hz, 1H), 8.39 (d, J=1.8 Hz, 1H), 8.25 (d, J=1.5 Hz, 1H), 7.56 (d, J=2.9 Hz, 1H), 4.04 (s, 3H); LC-MS: Method H, RT=0.89 min, MS (ESI) m/z: 266/268 (M+H)+.

Intermediate I-50B:
8-bromo-6-(difluoromethyl)-3-methoxyquinoline

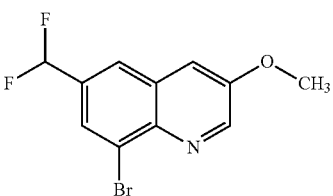

Intermediate I-50A (50 mg, 0.188 mmol) and deoxofluor (104 μl, 0.564 mmol) were dissolved in DCM (940 μL). After stirring overnight, the reaction mixture was diluted carefully with water then extracted thrice with DCM. The combined organic layers were washed with saturated NaHCO₃ then brine, dried (Na₂SO₄), filtered, and concentrated in vacuo. The crude material was purified by column chromatography (ISCO, 12 g silica gel column, 17 minute gradient from 0 to 100% EtOAc in hexanes) to give Intermediate I-50B (37 mg, 0.129 mmol, 68%) as a white solid: ¹H NMR (400 MHz, CHLOROFORM-d) δ 8.88 (d, J=2.9 Hz, 1H), 8.03 (d, J=1.5 Hz, 1H), 7.89 (d, J=1.3 Hz, 1H), 7.46 (d, J=2.9 Hz, 1H), 6.96-6.64 (t, J=56 Hz, 1H), 4.02 (s, 1H); LC-MS: Method H, RT=0.98 min, MS (ESI) m/z: 288/290 (M+H)⁺.

Intermediate I-50

Intermediate I-50B (37 mg, 0.128 mmol), bispinacolatodiboron (65.2 mg, 0.257 mmol), potassium acetate (31.5 mg, 0.321 mmol), and PdCl₂(dppf)—CH₂Cl₂ adduct (8.39 mg, 10.3 μmol) were stored on HIVAC for 15 minutes then were dissolved in dry 1,4-dioxane (642 μL) and degassed for 15 minutes by bubbling with argon. The reaction mixture was heated to 130° C. in the microwave for 40 minutes. The reaction mixture was diluted with EtOAc and washed with water then brine, dried (Na₂SO₄), filtered, and concentrated in vacuo to give Intermediate I-50. The crude material was used directly in the subsequent step: LC-MS: Method H, RT=0.80 min, MS (ESI) m/z: 254.1 (boronic acid mass observed, M+H)⁺.

Intermediate I-51

6-(fluoromethyl)-3-methoxy-8-(4,4,5,5-tetramethyl-1,3,2-dioxaborolan-2-yl)quinoline

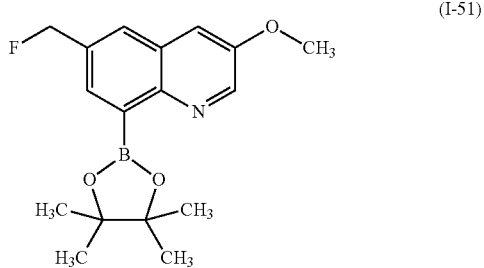 [SMILES: COc1cnc2c(B3OC(C)(C)C(C)(C)O3)cc(CF)cc2c1]

(I-51)

Intermediate I-51A:
(8-bromo-3-methoxyquinolin-6-yl)methanol

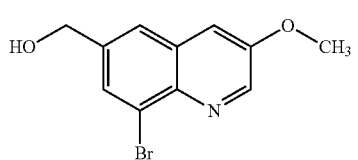

(I-51A)

Intermediate I-50A (50 mg, 0.188 mmol) was dissolved in MeOH (1.88 mL) and cooled to 0° C. Sodium borohydride (14.2 mg, 0.376 mmol) was then added. After 1 hour, the reaction mixture was diluted with EtOAc, washed with water, then brine, dried (Na₂SO₄), filtered, and concentrated in vacuo to give Intermediate I-51A (38.6 mg, 0.144 mmol, 77%) as a white solid: ¹H NMR (400 MHz, CHLOROFORM-d) δ 8.79 (d, J=2.9 Hz, 1H), 7.92 (d, J=1.8 Hz, 1H), 7.72 (s, 1H), 7.40 (d, J=2.9 Hz, 1H), 4.89 (d, J=5.1 Hz, 2H), 4.00 (s, 3H), 1.89 (t, J=5.6 Hz, 1H); LC-MS: Method H, RT=0.73 min, MS (ESI) m/z: 268/270 (M+H)⁺.

Intermediate I-51B:
8-bromo-6-(fluoromethyl)-3-methoxyquinoline

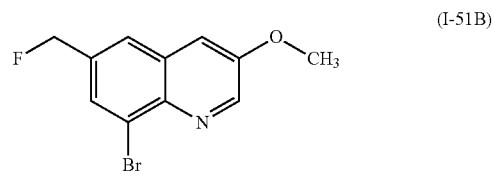

(I-51B)

Intermediate I-51A (38 mg, 0.142 mmol) and Deoxofluor (78 μL, 0.425 mmol) were dissolved in DCM (709 μL). After stirring overnight, the reaction mixture was diluted carefully with water then extracted thrice with DCM. The combined organic layers were washed with saturated NaHCO₃ then brine, dried (Na₂SO₄), filtered, and concentrated in vacuo. The crude material was purified by column chromatography (ISCO, 12 g silica gel column, 17 minute gradient from 0 to 100% EtOAc in hexanes) to give Intermediate I-51B (29 mg, 0.109 mmol, 77%) as a white solid: ¹H NMR (400 MHz, CHLOROFORM-d) δ 8.83 (d, J=2.9 Hz, 1H), 7.91 (s, 1H), 7.73 (s, 1H), 7.41 (d, J=2.6 Hz, 1H), 5.62-5.48 (t, J=48 Hz, 2H), 4.00 (s, 3H); LC-MS: Method H, RT=0.94 min, MS (ESI) m/z: 270/272 (M+H)⁺.

Intermediate I-51

Intermediate I-51B (29 mg, 0.107 mmol), bispinacolatodiboron (54.5 mg, 0.215 mmol), potassium acetate (26.3 mg, 0.268 mmol), and PdCl₂(dppf)—CH₂Cl₂ adduct (7.01 mg, 8.59 μmol) were stored on HIVAC for 15 minutes then were dissolved in dry 1,4-dioxane (537 μL) and degassed for 15 minutes by bubbling with argon. The reaction mixture was heated to 130° C. in the microwave for 40 minutes. The reaction mixture was diluted with EtOAc and washed with water then brine, dried (Na₂SO₄), filtered, and concentrated in vacuo to give Intermediate I-51, which was used directly for the subsequent step: LC-MS: Method H, RT=0.68 min, MS (ESI) m/z: 236.1 (boronic acid mass observed, M+H)⁺.

Intermediate I-52

6-fluoro-3-methoxy-8-(4,4,5,5-tetramethyl-1,3,2-dioxaborolan-2-yl)quinoline

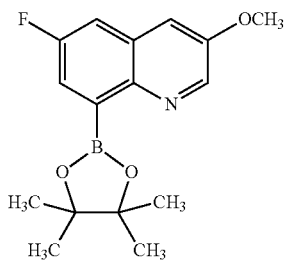

Intermediate I-52A:
(2-amino-3-bromo-5-fluorophenyl)methanol

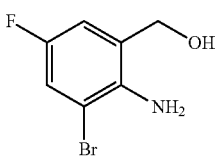

Methyl 2-amino-3-bromo-5-fluorobenzoate (0.910 g, 3.67 mmol) was dissolved in THF (12.23 ml). LiBH$_4$ (0.160 g, 7.34 mmol) was added and the reaction mixture was heated to 50° C. for 2 hours. The reaction mixture was diluted with water and stirred for 30 minutes. The reaction mixture was then extracted thrice with EtOAc. The combined organic layers were washed with brine, dried (Na$_2$SO$_4$), filtered, and concentrated in vacuo to yield Intermediate I-52A (0.799 g, 3.63 mmol, 99% yield) as a white solid. $^1$H NMR (400 MHz, CHLOROFORM-d) δ 7.20 (dd, J=7.7, 2.9 Hz, 1H), 6.86 (dd, J=8.4, 2.9 Hz, 1H), 4.68 (s, 2H), 4.52 (d, J=12.8 Hz, 2H), 1.89-1.69 (m, 1H). LC-MS: method H, RT=0.94 min, MS (ESI) m/z: 219.9 (M+H)$^+$.

Intermediate I-52B:
2-amino-3-bromo-5-fluorobenzaldehyde

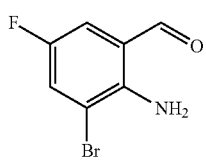

Intermediate I-52A (0.799 g, 3.63 mmol) was dissolved in CHCl$_3$ (24.21 ml). Manganese dioxide (1.263 g, 14.52 mmol) was added and the reaction mixture was heated to 40° C. overnight. The reaction mixture was filtered through celite and concentrated in vacuo to yield Intermediate I-52B (0.750 g, 3.44 mmol, 95%). $^1$H NMR (400 MHz, CHLOROFORM-d) δ 9.80 (s, 1H), 7.48 (dd, J=7.5, 2.9 Hz, 1H), 7.25 (dd, J=7.9, 2.9 Hz, 1H), 6.55 (br. s., 2H).

Intermediate I-52C:
3-(benzyloxy)-8-bromo-6-fluoroquinoline

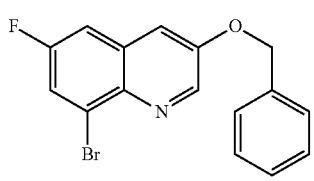

Intermediate I-52B (0.800 g, 3.67 mmol), 2-(benzyloxy)acetaldehyde (0.551 g, 3.67 mmol), and sodium methoxide (8.07 ml, 4.04 mmol) were dissolved in MeOH (7.34 ml) and heated to reflux overnight. The reaction mixture was diluted with saturated NH$_4$Cl, partially concentrated in vacuo and diluted with EtOAc. The layers were separated and the organic layer was washed with brine, dried (Na$_2$SO$_4$), filtered, and concentrated in vacuo. Purified on ISCO using 80 g column eluting with 0-60% gradient of EtOAc in hexanes to yield Intermediate I-52C (0.363 g, 1.093 mmol, 30%). $^1$H NMR (500 MHz, CHLOROFORM-d) δ 8.83 (d, J=2.5 Hz, 1H), 7.72 (dd, J=8.1, 2.6 Hz, 1H), 7.52-7.49 (m, 2H), 7.45 (t, J=7.3 Hz, 2H), 7.41 (d, J=2.8 Hz, 2H), 7.34 (dd, J=8.7, 2.6 Hz, 1H), 5.24 (s, 2H). LC-MS: method H, RT=1.38 min, MS (ESI) m/z: 331.9 (M+H)$^+$.

Intermediate I-52D: 8-bromo-6-fluoroquinolin-3-ol

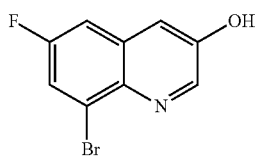

Intermediate I-52C (0.363 g, 1.093 mmol) and pentamethylbenzene (1.134 g, 7.65 mmol) were dissolved in DCM (21.86 ml) and cooled to −78° C. Boron trichloride (1 M in heptane) (2.84 ml, 2.84 mmol) was added and the reaction mixture was allowed to warm to room temperature overnight. The reaction mixture was diluted with hexanes and 1 N HCl and allowed to stir for 1 hour. The resulting solid was collected by suction filtration, washing with water and hexanes to yield Intermediate I-52D (0.176 g, 0.727 mmol, 66.5% yield): $^1$H NMR (400 MHz, METHANOL-d$_4$) δ 8.53 (d, J=2.9 Hz, 1H), 7.68 (dd, J=8.4, 2.6 Hz, 1H), 7.49-7.37 (m, 2H). LC-MS: method H, RT=1.12 min, MS (ESI) m/z: 241.9 (M+H)$^+$.

Intermediate I-52E:
8-bromo-6-fluoro-3-methoxyquinoline

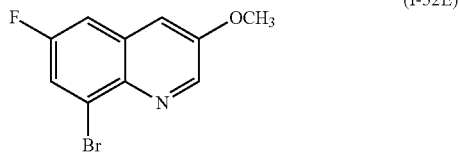

Intermediate I-52D (0.095 g, 0.341 mmol), $K_2CO_3$ (0.141 g, 1.023 mmol), and methyl iodide (0.043 ml, 0.682 mmol) were dissolved in acetone (3.41 ml) and heated to 50° C. in a sealed tube overnight. The reaction mixture was diluted with EtOAc, washed with water, then brine, dried ($Na_2SO_4$), filtered, and concentrated in vacuo to yield Intermediate I-52E (0.060 g, 0.234 mmol, 68.7% yield). $^1$H NMR (400 MHz, CHLOROFORM-d) δ 8.76 (dd, J=2.8, 0.6 Hz, 1H), 7.72 (dd, J=8.0, 2.8 Hz, 1H), 7.37 (dd, J=8.8, 2.6 Hz, 1H), 7.35 (d, J=2.6 Hz, 1H), 4.00 (s, 3H). LC-MS: method H, RT=1.31 min, MS (ESI) m/z: 255.8 (M+H)$^+$.

Intermediate I-52

Intermediate I-52E (0.087 g, 0.340 mmol), Bispin (0.173 g, 0.679 mmol), potassium acetate (0.083 g, 0.849 mmol), and $PdCl_2$(dppf)—$CH_2Cl_2$ adduct (0.022 g, 0.027 mmol) were stored on HIVAC for 15 minutes then were dissolved in 1,4-dioxane (3 ml) and degassed for 15 minutes by bubbling with argon. The reaction mixture was heated to 130° C. in the microwave for 40 minutes. The reaction mixture was diluted with EtOAc and washed with water then brine, dried ($Na_2SO_4$), filtered, and concentrated in vacuo to yield Intermediate I-52 (0.103 g, 0.170 mmol, 50%). This material was dissolved in DMF to make a stock solution of 10 mg per mL and used without further purification. LC-MS: method H, RT=1.10 min, MS (ESI) m/z: 221.9 (M+H)$^+$. See the mass of the boronic acid in the LC/MS.

Intermediate I-53

(2-(difluoromethoxy)-7-methylquinoxalin-5-yl)boronic acid

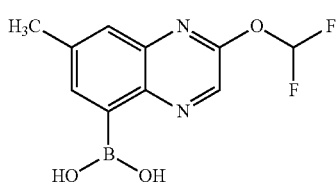

A mixture of Intermediate I-1G (3.85 g, 13.32 mmol), bis(pinacolato)diboron (5.07 g, 19.98 mmol), potassium acetate (3.27 g, 33.3 mmol) and $PdCl_2$(dppf)—$CH_2Cl_2$ adduct (0.435 g, 0.533 mmol) in dioxane (60 mL) was degassed by bubbling argon for 10 min. The reaction vial was sealed and heated at 90° C. overnight, at which time HPLC and LCMS indicated a clean reaction. After standing at room temperature for a week, the reaction mixture was poured into water, diluted with EtOAc, stirred at room temperature for 10 min. The mixture was filtered through a pad of wet celite. The organic layer was washed with brine, dried over sodium sulfate and concentrated. The crude product was purified by flash chromatography (loading in toulene, 5% to 100% EtOAc (containing 1% MeOH) in hexane over 20 min using a 120 g silica gel cartridge). The desired fractions were combined and concentrated to yield 2.5 g of crude product. The crude product was triturated with acetonitrile. The precipitate was collected by filtration to give 1.0 g of Intermediate I-53. The filtrate was concentrated and further purified by preparative HPLC (method A, 30-100% B in 8 min. Then 100% B in 4 min.). The desired fractions were placed in a SpeedVac overnight to remove solvent, then lyophilized to give additional 1.0 g of Intermediate I-53. $^1$H NMR (500 MHz, DMSO-$d_6$) δ 8.88 (s, 2H), 8.81 (s, 1H), 8.04 (d, J=1.9 Hz, 1H), 7.86 (t, $J_{HF}$=71.6 Hz, 1H), 7.83-7.79 (m, 1H), 2.57 (s, 3H); LC-MS: method H, 2 to 98% B. RT=0.798 min, MS (ESI) m/z: 255.00 (M+H)$^+$.

Intermediate I-54

2-(2-((tert-butyldiphenylsilyl)oxy)ethyl)pyrimidin-5-amine

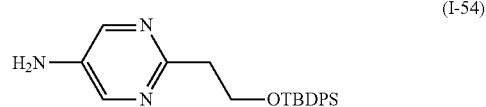

Intermediate I-54A: 3-hydroxypropanimidamide, HCl

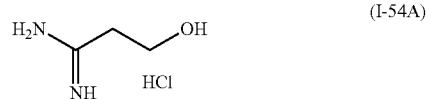

To a mixture of MeOH (5 mL, 124 mmol)/toluene (30.1 mL) at 0° C. was added acetyl chloride (3.00 mL, 42.2 mmol) slowly over 10 minutes. The reaction mixture was allowed to stir at 0° C. for 10 minutes then at room temperature for 10 minutes. The reaction mixture was cooled to 0° C. and 3-hydroxypropanenitrile (1.5 g, 21.10 mmol) dissolved in 5 mL of toluene added and the reaction mixture was allowed to stir at room temperature for 18 h. The reaction mixture was cooled to 0° C. and 7N ammonia in MeOH (15.07 mL, 106 mmol) was added carefully over 5 minutes. The reaction mixture was then allowed to warm to room temperature and stirred for 18 h at room temperature.

The mixture was then filtered through celite and the filter cake washed with 2:1 toluene/MeOH. The filtrate was concentrated to yield Intermediate I-54A in quantitative yield. The product was brought forward without further purification. $^1$H NMR (400 MHz, DMSO-$d_6$) δ 3.70 (t, J=5.9 Hz, 2H), 2.77 (t, J=5.9 Hz, 2H).

Intermediate I-54B: methyl 2-(2-hydroxyethyl)pyrimidine-5-carboxylate

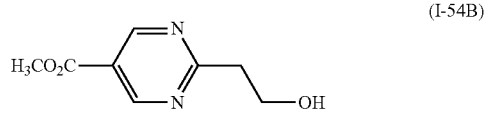 [SMILES: COC(=O)c1cnc(CCO)nc1]
(I-54B)

Intermediate I-54A (8.9 g, 71.4 mmol) was dissolved in DMF (200 ml). While the solution stirred at room temperature, sodium (Z)-2-(dimethoxymethyl)-3-methoxy-3-oxo-prop-1-en-1-olate (16.5 g, 83 mmol) was added in portionwise and the reaction mixture was stirred at room temperature for 18 h.

The reaction mixture was then concentrated under reduced pressure and heat. The resulting residue was then suspended in 10:1 DCM:MeOH and run through a pad of silica gel/celite which was washed with 500 mL of a 10:1 DCM/MeOH mixture. The filtrate was concentrated to yield Intermediate I-54B (10.5 g, 57.6 mmol, 81% yield), as a red oil. The product was brought forward without further purification. LC-MS: Method H, MS (ESI) m/z: 183.0 (M+H)$^+$. $^1$H NMR (400 MHz, DMSO-d$_6$) δ 9.16 (s, 2H), 4.69 (t, J=5.4 Hz, 1H), 4.03-3.79 (m, 5H), 3.12 (t, J=6.6 Hz, 2H).

Intermediate I-54C: methyl 2-(2-((tert-butyldiphenylsilyl)oxy)ethyl)pyrimidine-5-carboxylate

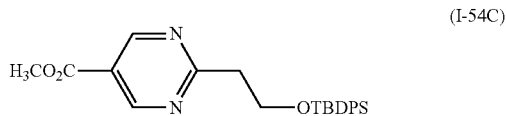
(I-54C)

To the solution of Intermediate I-54B (4 g, 21.96 mmol) in THE (80 mL) was added DMAP (0.134 g, 1.098 mmol), TEA (7.65 mL, 54.9 mmol) and TBDPS-Cl (8.46 mL, 32.9 mmol). The reaction mixture was stirred for 18 h at room temperature. Next, 5 mL of methanol was added and the reaction mixture stirred for 10 minutes at room temperature followed by evaporation under reduced pressure. The crude product was purified by silica gel chromatography on a 120 g silica column using petroleum ether, chloroform and EtOAc as eluent. First an eluent of 0-100% chloroform in petroleum ether was used followed by an eluent of 0-100% EtOAc in chloroform. Fractions containing desired product were collected and concentrated to yield Intermediate I-54C (7.5 g, 17.9 mmol, 82% yield), as a colorless oil. LC-MS: Method H, MS (ESI) m/z: 421.2 (M+H)$^+$. $^1$H NMR (400 MHz, CHLOROFORM-d) δ 9.16 (s, 2H), 7.73-7.28 (m, 10H), 4.22 (t, J=6.4 Hz, 2H), 3.97 (s, 4H), 3.30 (t, J=6.4 Hz, 2H), 0.98-0.94 (m, 9H).

Intermediate I-54D: 2-(2-((tert-butyldiphenylsilyl)oxy)ethyl)pyrimidine-5-carboxylic acid

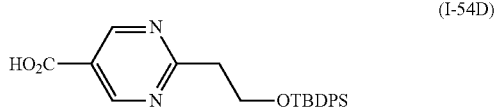
(I-54D)

Intermediate I-54C (2.14 g, 5.09 mmol) was dissolved in THF (60 mL). 1M aq.

LiOH (15.26 mL, 15.26 mmol) was added and the reaction mixture was allowed to stir at room temperature for 1 hour. The majority of the THE was concentrated under reduced pressure and the reaction mixture was acidified with 10% citric acid to pH 4-5 then extracted 3× with EtOAc. The combined organic layer was washed with brine, dried with sodium sulfate, filtered and concentrated to yield Intermediate I-54D (2.07 g, 5.09 mmol, 100% yield), as a clear glass. LC-MS: Method H, MS (ESI) m/z: 407.2 (M+H)$^+$. $^1$H NMR (400 MHz, DMSO-d$_6$) δ 9.13 (s, 2H), 7.76-7.23 (m, 10H), 4.19 (t, J=6.3 Hz, 2H), 3.25 (t, J=6.3 Hz, 2H), 0.90 (s, 9H).

Intermediate I-54

Intermediate I-54D (5.5 g, 13.53 mmol) was dissolved in THE (350 mL). TEA (9.43 mL, 67.6 mmol) was added to the mixture followed by diphenyl phosphorazidate (9.31 g, 33.8 mmol) at room temperature. The reaction mixture was heated to 65° C. under a reflux condenser for 22 hours. The reaction mixture was then allowed to cool to room temperature and water (175 mL) was added. The mixture was stirred at room temperature for 2 hours and 15 minutes. The majority of THE was evaporated off under reduced pressure and the mixture was then diluted with water and a small amount of brine and extracted 3× with a total of ~500 mL of EtOAc. The organic layer was washed with brine, dried with sodium sulfate, filtered and concentrated. The resulting residue was dissolved in methylene chloride before being charged to a 330 g column which was eluted with a gradient from 0-20% MeOH/DCM. Fractions containing desired product were collected and concentrated to yield Intermediate I-54, (1.135 g, 3.01 mmol, 22% yield), as an orange oil. LC-MS: Method H, MS (ESI) m/z: 378.2. (M+H)$^+$. $^1$H NMR (500 MHz, DMSO-d$_6$) δ 8.04 (s, 2H), 7.59-7.53 (m, 4H), 7.47-7.31 (m, 6H), 5.76 (s, 2H), 4.02 (t, J=6.7 Hz, 2H), 2.97 (t, J=6.7 Hz, 2H), 0.92 (s, 9H).

Intermediate I-55

6-(2-((tert-butyldimethylsilyl)oxy)ethoxy)pyridin-3-amine

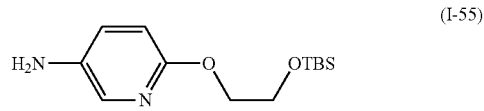 [SMILES: CC(C)(C)[Si](C)(C)OCCOc1ccc(N)cn1]
(I-55)

Intermediate I-55A: 2-((5-nitropyridin-2-yl)oxy)ethanol

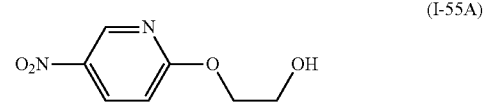 [SMILES: O=[N+]([O-])c1ccc(OCCO)nc1]
(I-55A)

Ethylene glycol (0.883 mL, 15.84 mmol) was dissolved in DMF (10 mL) at 0° C. Sodium hydride (253 mg, 6.33 mmol, 60% in mineral oil) was added to the reaction mixture portion wise and the reaction mixture was stirred for 10 minutes at 0° C. Next, 2-fluoro-5-nitropyridine (450 mg, 3.17 mmol) dissolved in 1 mL of DMF was added to the reaction mixture which was allowed to stir for 15 minutes at room temperature. The mixture was then quenched with saturated ammonium chloride and extracted with EtOAc (1×). The organic layer was then washed with 10% aq. LiCl (3×), brine (1×), dried with sodium sulfate, filtered and concentrated to yield Intermediate I-55A, (530 mg, 2.88 mmol, 91% yield), as a clear oil which was was brought forward without further purification. LC-MS: Method H, MS (ESI) m/z: 185.1 (M+H)$^+$. $^1$H NMR (400 MHz, CHLOROFORM-d) δ 9.09 (d, J=2.9 Hz, 1H), 8.41 (dd, J=9.0, 2.9 Hz, 1H), 6.92 (dd, J=9.2, 0.4 Hz, 1H), 4.65-4.54 (m, 2H), 4.09-3.96 (m, 2H), 2.32 (t, J=5.9 Hz, 1H).

Intermediate I-55B: 2-(2-((tert-butyldimethylsilyl)oxy)ethoxy)-5-nitropyridine-N

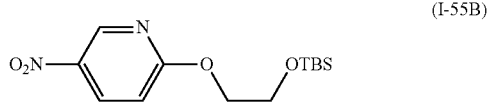 [SMILES: CC(C)(C)[Si](C)(C)OCCOc1ccc([N+](=O)[O-])cn1]

(I-55B)

Intermediate I-55A (530 mg, 2.88 mmol) was dissolved in dichloromethane (20 mL) along with TEA (0.521 mL, 3.74 mmol) and DMAP (70.3 mg, 0.576 mmol). TBS-Cl (521 mg, 3.45 mmol) was added to the reaction mixture which was allowed to stir at room temperature for 18 h. The reaction mixture was then quenched with saturated aq. sodium bicarbonate and extracted with DCM (2×). The organic layer was washed with brine (1×), dried with sodium sulfate, filtered and concentrated. The resulting residue was dissolved in methylene chloride before being charged to a 40 g silica gel cartridge which was eluted with a 15 min gradient from 0-100% EtOAc in hexane. The desired fractions were collected and concentrated to yield Intermediate I-55B, (700 mg, 2.346 mmol, 82% yield), as a clear oil. LC-MS: Method H, RT=1.25 min, MS (ESI) m/z: 299.2 (M+H)$^+$. $^1$H NMR (400 MHz, CHLOROFORM-d) δ 8.98 (d, J=2.4 Hz, 1H), 8.27 (dd, J=9.0, 2.9 Hz, 1H), 6.80-6.72 (m, 1H), 4.47-4.35 (m, 2H), 3.90 (dd, J=5.6, 4.5 Hz, 2H), 0.84-0.73 (m, 9H), 0.03-0.01 (m, 6H).

Intermediate I-55

Intermediate I-55B (700 mg, 2.346 mmol) was dissolved in ethyl acetate (10 mL).

Pd-C(125 mg, 0.117 mmol) was added to the reaction mixture which was evacuated and backfilled with 1 atm of hydrogen 3× and stirred under 1 atm of hydrogen at room temperature for 3 h. The reaction mixture was then filtered through a pad of celite and the filtrate was concentrated to yield Intermediate I-55, (561 mg, 2.090 mmol, 89% yield), as a yellow oil. The product was brought forward without further purification. LC-MS: Method H, MS (ESI) m/z: 289.2 (M+H)$^+$. $^1$H NMR (400 MHz, CHLOROFORM-d) δ 7.59-7.53 (m, 1H), 7.01-6.86 (m, 1H), 6.58-6.47 (m, 1H), 4.27-4.14 (m, 2H), 3.96-3.80 (m, 2H), 3.37-3.11 (m, 2H), 0.86-0.77 (m, 10H), 0.00 (s, 6H).

Intermediate I-56

6-(3-((tert-butyldimethylsilyl)oxy)-2,2-difluoropropoxy)pyridin-3-amine

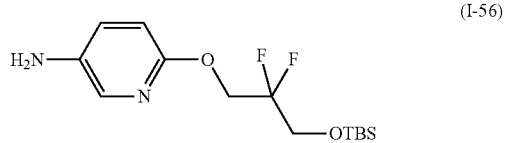

(I-56)

Intermediate I-56A: 2,2-difluoro-3-((5-nitropyridin-2-yl)oxy)propan-1-ol

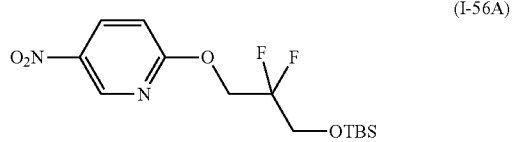 [SMILES: CC(C)(C)[Si](C)(C)OCC(F)(F)COc1ccc([N+](=O)[O-])cn1]

(I-56A)

2,2-difluoropropane-1,3-diol (394 mg, 3.52 mmol) was dissolved in DMF (10 mL). Sodium hydride (77 mg, 1.934 mmol) was added to the mixture at 0° C. and the reaction mixture was stirred at 0° C. for 10 minutes. 2-fluoro-5-nitropyridine (250 mg, 1.758 mmol) dissolved in 1 mL of DMF was then added to the reaction mixture which was allowed to stir at room temperature for 1 hour. The mixture was then quenched with saturated ammonium chloride and diluted with EtOAc. The organic layer was washed with 10% aq. LiCl (3×), and brine (1×), dried with sodium sulfate, filtered and concentrated to yield 2,2-difluoro-3-((5-nitropyridin-2-yl)oxy)propan as a yellow oil. To the crude intermediate dissolved in DCM (9 mL) was added TEA (1137 μl, 8.16 mmol) and DMAP (39.9 mg, 0.326 mmol) followed by TBS-Cl (738 mg, 4.89 mmol). The reaction mixture stirred for 18 h at room temperature. 5 mL of MeOH was then added to the reaction mixture which was allowed to stir for 10 minutes at room temperature. The reaction mixture was then quenched with saturated sodium bicarbonate and extracted DCM (3×). The organic layer was washed with brine (1×), dried with sodium sulfate, filtered and concentrated. The resulting residue was dissolved in a small amount of methylene chloride and charged to a 40 g silica gel cartridge which was eluted with a 15 min gradient from 0-100% EtOAc in hexane. Fractions containing desired product were concentrated to yield Intermediate I-56A (204 mg, 0.586 mmol, 36% yield) as a clear oil. LC-MS: Method H, MS (ESI) m/z: 349.2 (M+H)$^+$. $^1$H NMR (400 MHz, CHLOROFORM-d) δ 9.01 (dd, J=2.9, 0.4 Hz, 1H), 8.34 (dd, J=9.1, 2.8 Hz, 1H), 6.86 (dd, J=9.0, 0.4 Hz, 1H), 4.66 (t, J=12.4 Hz, 2H), 3.85 (t, J=12.2 Hz, 2H), 0.81-0.78 (m, 9H), 0.00 (s, 6H).

Intermediate I-56

Intermediate I-56A (204 mg, 0.586 mmol) was dissolved in EtOAc (10 mL). Pd-C(18.69 mg, 0.176 mmol) was added to the solution and the flask was evacuated and backfilled with 1 atm of hydrogen 3×. The reaction mixture was stirred under 1 atm of hydrogen for 18 h and then filtered through celite and the celite pad washed with excess EtOAc. The filtrate was concentrated to yield Intermediate I-56 in quantitative yield as a green oil. The product was brought forward without further purification. LC-MS: Method H, MS (ESI) m/z: 319. (M+H)+. 1H NMR (400 MHz, CHLOROFORM-d) δ 7.60-7.54 (m, 1H), 7.02-6.95 (m, 1H), 6.63-6.50 (m, 1H), 4.45 (t, J=12.5 Hz, 2H), 3.86 (t, J=12.4 Hz, 2H), 0.81 (s, 9H), 0.00 (s, 6H).

Intermediate I-57

2-(2-((tert-butyldimethylsilyl)oxy)ethoxy)pyrimidin-5-amine

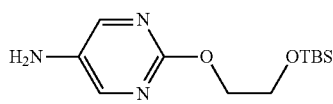

(I-57)

Intermediate I-57A:
2-((5-nitropyrimidin-2-yl)oxy)ethanol

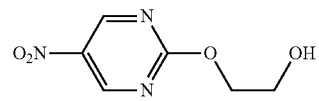

(I-57A)

2-chloro-5-nitropyrimidine (1 g, 6.27 mmol) was mixed with ethylene glycol (8 5 ml, 143 mmol) and DIEA (3.28 ml, 18.81 mmol) was added. The mixture was stirred at 80° C. for 20 minutes and was then poured into 30 mL of ice water. 40 mL of EtOAc was added to the mixture followed by 20 mL of 1N aq. HCl. EtOAc (30 mL×3) was used to extracted aq. Layer. The combined organic layer was washed with brine, dried with sodium sulfate, filtered and concentrated to give Intermediate I-57A in quantitative yield as a yellow oil. The product was brought forward without further purification. 1H NMR (400 MHz, CHLOROFORM-d) δ 9.33 (s, 2H), 4.73-4.51 (m, 2H), 4.08-3.96 (m, 2H), 2.41 (br. s., 1H).

Intermediate I-57B: 2-(2-((tert-butyldimethylsilyl)oxy)ethoxy)-5-nitropyrimidine

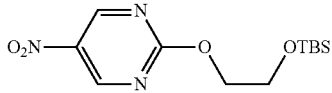

(I-57B)

Intermediate I-57A (1.23 g, 6.64 mmol) was mixed with tert-butylchlorodimethylsilane (2.003 g, 13.29 mmol) in DCM (20 ml). Imidazole (0.905 g, 13.29 mmol) was added to the reaction mixture and the reaction mixture stirred at room temperature for 30 minutes. The solid was filtered off and the filter cake was washed with a small amount of DCM. The filtrate was mixed with 30 g of silica gel, evaporated to dryness and loaded on CombiFlash (80 g column, 0-50% EtOAc/Hexane) for purification. The fractions containing desired product were collected and concentrated to give Intermediate I-57B, (1.73 g, 5.78 mmol, 87% yield), as a light yellow solid. LC-MS: Method H, MS (ESI) m/z: 300.0 (M+H)+. 1H NMR (400 MHz, CHLOROFORM-d) δ ppm 9.30 (2H, s), 4.61 (2H, dd, J=5.50, 4.62 Hz), 4.02 (2H, dd, J=5.61, 4.73 Hz), 0.88 (9H, s), 0.09 (6H, s).

Intermediate I-57

Intermediate I-57B (1.73 g, 5.78 mmol) was dissolved in THF (40 ml). Wet Pd-C (0.307 g, 0.289 mmol) was then added to the solution. The mixture was then evacuated and backfilled with hydrogen 3×, and the mixture was stirred under 1 atm H2 for 7 hours at room temperature. The catalyst was filtered off over a pad of celite which was washed with a small amount of EtOAc. The filtrate was concentrated to yield Intermediate I-57, (1.53 g, 5.68 mmol, 98% yield), as a gray solid. LC-MS: Method H, MS (ESI) m/z: 270.1 (M+H)+. 1H NMR (400 MHz, CHLOROFORM-d) δ ppm 8.05 (2H, s), 4.35 (2H, t, J=5.50 Hz), 3.97 (2H, t, J=5.61 Hz), 1.69 (2H, d, J=5.06 Hz), 0.89 (9H, s), 0.08 (6H, s).

Intermediate I-58

(S)-2-(2-((tert-butyldimethylsilyl)oxy)propoxy)pyrimidin-5-amine

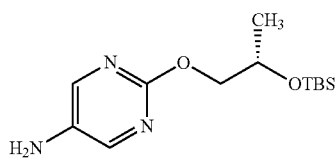

(I-58)

Intermediate I-58A: (S)-ethyl 2-((tert-butyldimethylsilyl)oxy)propanoate

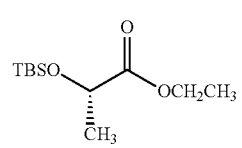

(I-58A)

(S)-ethyl 2-hydroxypropanoate (1.50 g, 12.70 mmol), imidazole (1.73 g, 2.2 equiv.) and TBS-Cl (3.83 g, 2.0 equiv.) were dissolved in DCM (0.1 M). The reaction mixture was allowed to stir at room temperature for 18 h. The reaction mixture was then diluted with 1.5 M dipotassium phosphate solution and extracted with EtOAc (3×). The combined organic layer was washed with brine (1×), dried with sodium sulfate, filtered and concentrated. The resulting residue was dissolved in a small amount of methylene chloride and purified by silica gel chromatography to yield Intermediate I-58A (2.3 g, 9.90 mmol, 78% yield) as a clear oil. 1H NMR (400 MHz, CHLOROFORM-d) δ 4.35-4.28 (m, 1H), 4.18 (t, J=7.5 Hz, 2H), 1.40 (d, J=6.8 Hz, 3H), 1.28 (t, J=7.2 Hz, 3H), 0.91 (s, 9H), 0.10 (s, 3H), 0.07 (s, 3H).

Intermediate I-58B: (S)-2-((tert-butyldimethylsilyl)oxy)propan-1-ol

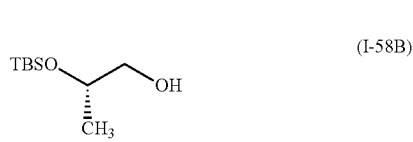
(I-58B)

Intermediate I-58A (2.2 g, 9.47 mmol) was dissolved in THF (100 ml) and the solution was cooled to −78° C. To the reaction mixture was added DIBAL-H (23.67 ml, 23.67 mmol) and the reaction mixture was allowed to warm to room temperature and stirred for 3 h at room temperature before being quenched with saturated Rochelle's salt. The quenched reaction mixture was stirred for 18 h at room temperature and then extracted with EtOAc (3×). The combined organic layer was washed with brine, dried with sodium sulfate, filtered and concentrated under reduced pressure to yield Intermediate I-58B in quantitative yield. $^1$H NMR (400 MHz, CHLOROFORM-d) δ 3.87-3.77 (m, J=2.6 Hz, 1H), 3.46-3.37 (m, 1H), 3.32-3.21 (m, 1H), 1.03 (d, J=6.4 Hz, 3H), 0.82 (s, 9H), 0.00 (s, 6H).

Intermediate I-58C: (S)-5-bromo-2-(2-((tert-butyldimethylsilyl)oxy)propoxy)pyrimidine

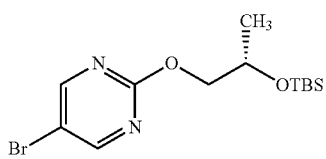
(I-58C)

Triphenylphosphine (2.88 g, 10.98 mmol) was dissolved in THF (143 ml) and the solution was cooled to 0° C. DIAD (1.941 ml, 9.98 mmol) was added and reaction mixture was allowed to stir for 5 minutes at 0° C. (S)-2-((tert-butyldimethylsilyl)oxy) propan-1-ol (1.9 g, 9.98 mmol) was added to the reaction mixture and the reaction mixture was allowed to stir for 10 minutes at 0° C. 5-bromopyrimidin-2-ol (1.5 g, 8.57 mmol) was then added to the reaction mixture which was allowed to warm to room temperature slowly and stirred for 72 hours at room temperature. The reaction mixture was then diluted with water and extracted with EtOAc (3×). The combined organic layer was washed with brine (1×), dried with sodium sulfate, filtered and concentrated. The resulting residue was dissolved in a small amount of methylene chloride before being charged to an 80 g silica gel cartridge which was eluted with a 30 min gradient from 0-100% EtOAc in hexane. Fractions containing desired product were collected and concentrated to yield Intermediate I-58C (1.9 g, 5.47 mmol, 55% yield). $^1$H NMR (400 MHz, CHLOROFORM-d) δ 8.52 (s, 2H), 4.34-4.26 (m, 1H), 4.18 (s, 1H), 4.15-4.05 (m, 1H), 1.24 (d, J=6.2 Hz, 3H), 0.87 (s, 9H), 0.07 (d, J=8.1 Hz, 5H). LC-MS: Method H, MS (ESI) m/z: 349.1 (M+H)$^+$.

Intermediate I-58D (S)-2-(2-((tert-butyldimethylsilyl)oxy)propoxy)-N-(diphenylmethylene)pyrimidin-5-amine

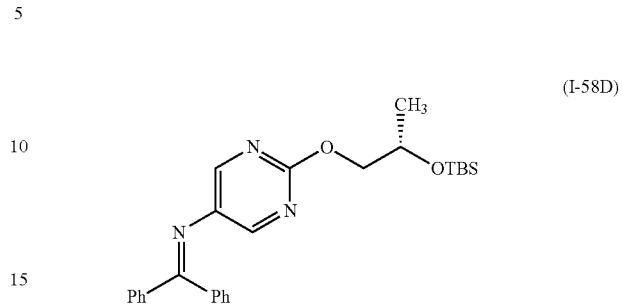
(I-58D)

To a vial containing Intermediate I-58C (1.9 g, 5.47 mmol), Pd(OAc)$_2$ (0.123 g, 0.547 mmol), BINAP (0.681 g, 1.094 mmol) and Cs$_2$CO$_3$ (2.139 g, 6.56 mmol) was added toluene (10.94 ml) followed by diphenylmethanimine (1.010 ml, 6.02 mmol). The vial was sealed, evacuated and back-filled with Ar (3×), then reaction mixture was heated to 105° C. and stirred overnight. The reaction mixture was diluted with EtOAc and washed with 1M aq. NaOH (1×) and brine (1×). The organic layer was dried with sodium sulfate, filtered and concentrated. The resulting residue was dissolved in methylene chloride before being purified by silica gel chromatography to provide Intermediate I-58D (1.9 g, 78% yield). LC-MS: Method H, MS (ESI) m/z: 448.2 (M+H)$^+$. $^1$H NMR (400 MHz, CHLOROFORM-d) δ 7.95 (s, 2H), 7.78-7.71 (m, 2H), 7.53-7.30 (m, 6H), 7.16-7.06 (m, 2H), 4.31-4.11 (m, 2H), 4.08-4.01 (m, 1H), 1.22 (d, J=5.9 Hz, 3H), 0.87 (s, 9H), 0.05 (d, J=9.9 Hz, 6H).

Intermediate I-58

Intermediate I-58D (1.9 g, 4.24 mmol) was dissolved in 90:10:0.1 MeOH/water/TFA (14 ml) and the solution stirred for 15 minutes at room temperature then basified with 1.5 M dipotassium phosphate solution and extracted with EtOAc (3×). The combined organic layer was washed with brine (1×), dried with sodium sulfate, filtered and concentrated. The resulting residue was dissolved in methylene chloride and charged to an 80 g silica gel cartridge which was eluted with a 30 min gradient from 0-15% MeOH in methylene chloride. Fractions containing the desired product were concentrated to yield Intermediate I-58 (210 mg, 0.741 mmol, 17% yield). LC-MS: RT=1.01 min, Method H, MS (ESI) m/z: 284.2 (M+H)$^+$. $^1$H NMR (400 MHz, DMSO-d$_6$) δ 7.92 (s, 2H), 4.93 (s, 2H), 4.16-3.83 (m, J=7.4, 5.6 Hz, 3H), 1.12 (d, J=6.2 Hz, 3H).

Intermediate I-59

(R)-2-(2-((tert-butyldimethylsilyl)oxy)propoxy)pyrimidin-5-amine

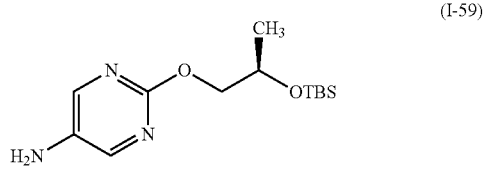 [SMILES: C[C@H](COc1ncc(N)cn1)O[Si](C)(C)C(C)(C)C]
(I-59)

This intermediate was prepared from (R)-ethyl 2-hydroxypropanoate in the same manner as described for Intermediate I-58. LC-MS: Method H, MS (ESI) m/z: 284.2 (M+H)$^+$. $^1$H NMR (400 MHz, CHLOROFORM-d) δ 7.97 (s, 2H), 4.20-4.06 (m, 2H), 4.01-3.93 (m, 1H), 3.29 (br. s., 2H), 1.17 (d, J=6.2 Hz, 3H), 0.81 (s, 9H), 0.01 (d, J=6.2 Hz, 6H). MS (ESI) m/z: 284.2 (M+H)$^+$.

Example 1

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (6-methoxypyridin-3-yl)carbamate

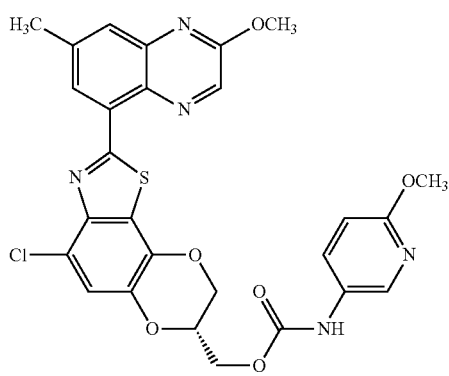

(1)

Intermediate 1A: [7-chloro-4-(2-methoxy-7-methylquinoxalin-5-yl)-10,13-dioxa-3-thia-5-azatricyclo[7.4.0.0^{2,6}]trideca-1(9), 2(6), 4,7-tetraen-11-yl]methyl chloroformate

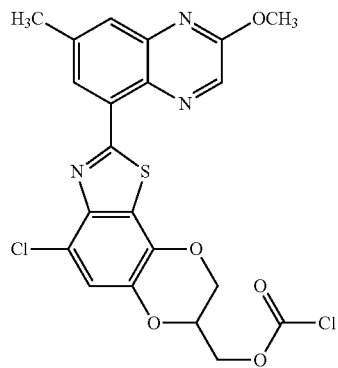

(1A)

To a solution of Intermediate I-6 (77 mg, 0.179 mmol) in THF (2.0 mL) at room temperature was added 15% phosgene in toluene (0.632 mL, 0.896 mmol) and the mixture was stirred at room temperature overnight. IPLC indicated the reaction was complete. Solvent was removed under vacuum to give Intermediate 1A (87 mg). It was used for the next step without any purification.

Intermediate 1B (4-chloro-2-(2-methoxy-7-methylquinoxalin-5-yl)-7,8-dihydro-[1,4]dioxino[2',3':3,4]benz o[1,2-d]thiazol-7-yl)methyl (6-methoxypyridin-3-yl)carbamate

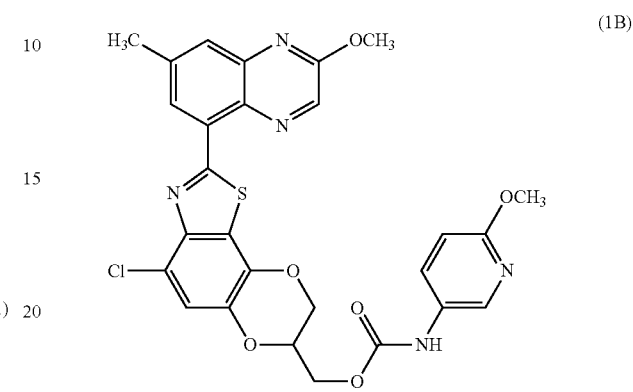

(1B)

To a solution of 6-methoxypyridin-3-amine (78 mg, 0.626 mmol) in DCM (1.5 mL) was added DIEA (0.250 mL, 1.430 mmol), followed by addition of Intermediate 1A (88 mg, 0.179 mmol) in THF (2.0 mL). The mixture was stirred at room temperature for 1.0 h. IPLC and LCMS indicated a completion of reaction. The reaction mixture was diluted with EtOAc, washed with 0.5 N HCl, saturated sodium bicarbonate, brine and dried over sodium sulfate. After evaporation of solvent, the crude product was dissolved in 8.0 mL mixture of DMSO/MeOH (2:1). The crude residue was purified using a preparative IPLC (method A, 80-100% B in 10 mins; then 100% B in 2 mins; RT=6.5 min). The desired fractions were placed in a SpeedVac overnight to remove solvent, then transferred to a flask (with EtOAc as solvent), concentrated to give Intermediate 1B (70 mg, 0.115 mmol, 64.1% yield) as a yellow solid. $^1$H NMR (500 MHz, DMSO-d$_6$) δ 9.87 (br. s., 1H), 8.74 (br. s., 1H), 8.55 (br. s., 1H), 8.25 (br. s., 1H), 7.85-7.76 (m, 2H), 7.32 (br. s., 1H), 6.81 (d, J=8.5 Hz, 1H), 4.73-4.63 (m, 2H), 4.51-4.41 (m, 2H), 4.32 (t, J=8.4 Hz, 1H), 4.08 (br. s., 3H), 3.81 (br. s., 3H), 2.65 (br. s., 3H); LC-MS: method A, RT=2.65 min, MS (ESI) m/z: 580.1 and 582.1 (M+H)$^+$. Analytical IPLC purity (method A): 95%.

Example 1

Intermediate 1B (70 mg, 0.121 mmol) was subject to a chiral SFC separation using the following condition: Instrument: Berger Multigram II Prep SFC Column: Chiralpak AS-H, 30×250 mm, 5 micron; Mobile Phase: 30% MeOH/70% CO$_2$; Flow Conditions: 85 mL/min, 150 Bar, 40° C.; Detector Wavelength: 234 nm. Two peaks were obtained corresponding to the two enantiomers. The fast eluting fraction (RT=18.5 min) was combined, concentrated, lyophilized to give Example 1 (26 mg, 0.043 mmol, 35.3% yield) as a slightly yellow solid. $^1$H NMR (400 MHz, THF) δ 8.80 (br. s., 1H), 8.67 (d, J=1.5 Hz, 1H), 8.47 (s, 1H), 8.06 (br. s., 1H), 7.73 (d, J=7.3 Hz, 1H), 7.68 (d, J=0.9 Hz, 1H), 7.05 (s, 1H), 6.55 (d, J=8.8 Hz, 1H), 4.51-4.44 (m, 2H), 4.35 (d, J=4.6 Hz, 2H), 4.18 (dd, J=11.9, 7.7 Hz, 1H), 4.00 (s, 3H), 3.72 (s, 3H), 2.55 (s, 3H); LC-MS: BEH C18 2.1×50 mm; A: water+0.05% TFA; B: acetonitrile+0.05% TFA; wavelength 220 nm; flow rate 0.8 mL/min; gradient time 1.5 min; 2 to 98% B. RT=1.27 min, MS (ESI) m/z: 580.1 (M+H)⁺. Analytical HPLC purity (method A): 95%.

Example 2

(S)-(4-chloro-2-(2-methoxy-7-methylquinoxalin-5-yl)-7,8-dihydro-[1,4]dioxino[2',3':3,4]benzo[1,2-d]thiazol-7-yl)methyl (6-methoxypyridin-3-yl)carbamate

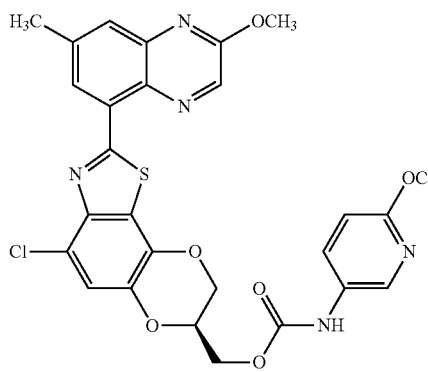

(2)

Example 2 was obtained from the second (slow eluting fraction, RT=22.7 min) peak in the separation of Intermediate 1B (27.6 mg, 0.045 mmol, 37.5% yield): $^1$H NMR (400 MHz, THF) δ 8.91 (br. s., 1H), 8.78 (d, J=2.0 Hz, 1H), 8.58 (s, 1H), 8.16 (br. s., 1H), 7.84 (d, J=8.4 Hz, 1H), 7.80-7.76 (m, 1H), 7.15 (s, 1H), 6.66 (d, J=8.8 Hz, 1H), 4.62-4.54 (m, 2H), 4.45 (d, J=4.8 Hz, 2H), 4.29 (dd, J=11.8, 7.8 Hz, 1H), 4.11 (s, 3H), 3.83 (s, 3H), 2.66 (s, 3H); LC-MS: BEH C18 2.1×50 mm; A: water+0.05% TFA; B: acetonitrile+0.05% TFA; wavelength 220 nm; flow rate 0.8 mL/min; gradient time 1.5 min; 2 to 98% B. RT=1.27 min, MS (ESI) m/z: 580.1 (M+H)⁺. Analytical HPLC (method A): RT=12.36 min, 95% purity.

Example 3

(2-(2-methoxy-7-methylquinoxalin-5-yl)-4-methyl-7,8-dihydro-[1,4]dioxino[2',3':3,4]benzo[1,2-d]thiazol-7-yl)methyl (2-hydroxypyridin-4-yl)carbamate

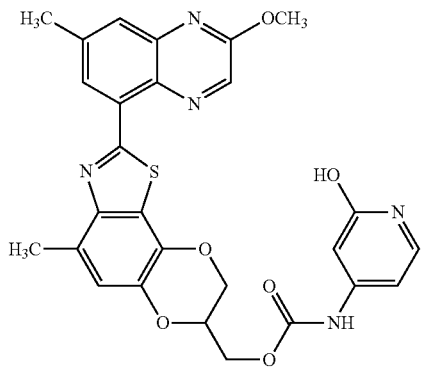

(3)

Intermediate 3A: [4-(2-methoxy-7-methylquinoxalin-5-yl)-7-methyl-10,13-dioxa-3-thia-5-azatricyclo[7.4.0.0^{2,6}]trideca-1(9), 2(6), 4,7-tetraen-11-yl]methyl chloroformate

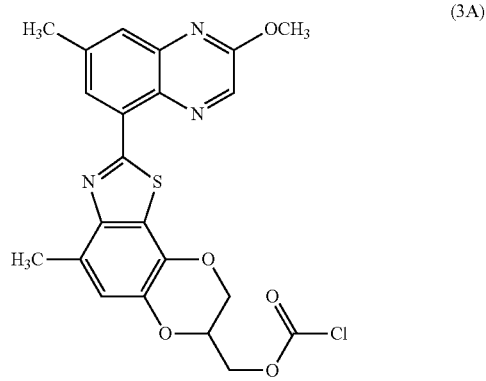 [SMILES: COc1cnc2c(-c3nc4c(C)cc5c(c4s3)OCC(COC(=O)Cl)O5)cc(C)cc2n1]

(3A)

To a suspension of Intermediate I-7 (87 mg, 0.212 mmol) in THF (3.0 mL) at room temperature was added 15% phosgene in toluene (0.749 mL, 1.062 mmol). The cloudy mixture gradually turned to a clear solution after stirring at room temperature for 2.0 h. The reaction mixture was left stirring at room temperature overnight. Solvent was completely removed under high vacuum to give Intermediate 3A (90 mg). It was used for the next step without purification.

Example 3

To a solution of 4-aminopyridin-2-ol (18.67 mg, 0.170 mmol) in DCM (0.8 mL) was added DIEA (0.074 mL, 0.424 mmol), followed by addition of Intermediate 3A (20 mg, 0.042 mmol) in THF (0.8 mL). The reaction mixture was stirred at room temperature for 1.0 h. HPLC and LCMS indicated a completion of reaction. The reaction was quenched by addition of a small amount of MeOH/water/0.1% TFA. Solvent was removed under vacuum. The crude was dissolved in DMSO and purified via preparative LC/MS (method D, 70-100% B over 10 minutes, then a 5-minute hold at 100% B). Fractions containing the desired product were combined and dried via centrifugal evaporation to yield Example 3 (12.0 mg). $^1$H NMR (500 MHz, DMSO-d$_6$) δ 10.63 (br. s., 1H), 8.75 (s, 1H), 8.59 (s, 1H), 8.24 (d, J=5.5 Hz, 1H), 7.83 (s, 1H), 7.58 (s, 1H), 7.43 (d, J=5.8 Hz, 1H), 6.99 (s, 1H), 4.67 (br. s., 1H), 4.61 (d, J=11.6 Hz, 1H), 4.56-4.43 (m, 2H), 4.33-4.26 (m, 1H), 4.09 (s, 3H), 2.69 (s, 3H), 2.65 (s, 3H); LC-MS: method H, RT=2.75 min, MS (ESI) m/z: 564.3 (M+H$_2$O)⁺. Analytical HPLC purity (method B): 97%.

Example 4

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (6-methoxypyridin-3-yl)carbamate

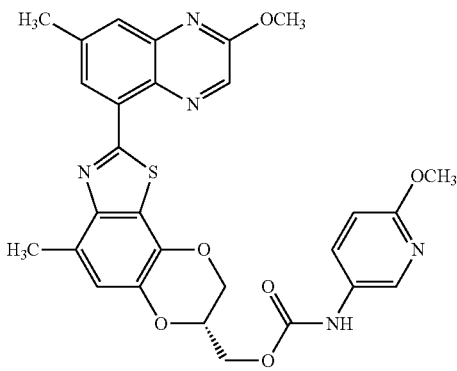

(4)

Intermediate 4A: (2-(2-methoxy-7-methylquinoxalin-5-yl)-4-methyl-7,8-dihydro-[1,4]dioxino[2',3':3,4]benzo[1,2-d]thiazol-7-yl)methyl (6-methoxypyridin-3-yl)carbamate

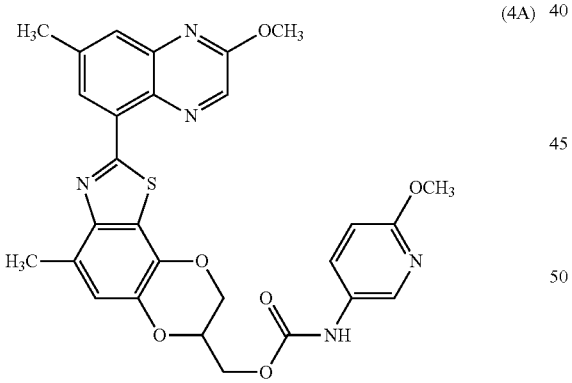

(4A)

To a solution of 6-methoxypyridin-3-amine (101 mg, 0.816 mmol) in DCM (2.0 mL) was added DIEA (0.326 mL, 1.865 mmol), followed by addition of Intermediate 3A (110 mg, 0.233 mmol) in THF (2.0 mL). The reaction mixture was stirred at room temperature for 1.0 h. HPLC and LCMS indicated a completion of reaction. The reaction mixture was diluted with EtOAc, quenched with 0.5 N HCl. The organic layer was collected, washed with saturated sodium bicarbonate, brine, dried over sodium sulfate and concentrated. The crude product was dissolved in a mixture of DMSO/MeOH (2:1, 10 mL) and purified by prep HPLC (method A, 80-100% B in 10 min; then 100% B in 2 min; RT=6.5 min). The desired fractions were placed in a SpeedVac overnight to remove solvent, then transferred with EtOAc to a flask. Solvent was removed to give Intermediate 4A (96 mg, 0.163 mmol, 69.9% yield) as yellow solid. $^1$H NMR (400 MHz, THF) δ 8.91 (br. s., 1H), 8.74 (d, J=1.8 Hz, 1H), 8.57 (s, 1H), 8.17 (br. s., 1H), 7.85 (d, J=7.5 Hz, 1H), 7.75 (dd, J=1.8, 0.9 Hz, 1H), 6.88 (d, J=0.9 Hz, 1H), 6.66 (d, J=9.0 Hz, 1H), 4.58-4.49 (m, 2H), 4.43 (d, J=4.8 Hz, 2H), 4.25 (dd, J=11.6, 7.6 Hz, 1H), 4.10 (s, 3H), 3.83 (s, 3H), 2.71 (d, J=0.4 Hz, 3H), 2.64 (s, 3H); LC-MS: method A, RT=2.24 min, MS (ESI) m/z: 560.2 (M+H)$^+$.

Example 4

Intermediate 4A (90 mg, 0.161 mmol) was subject to a chiral SFC separation using the following condition: Instrument: Berger Multigram II Prep; Column: Chiralpak AS-H, 30×250 mm, 5 micron; Mobile Phase: 40% MeOH/60% CO$_2$; Flow Conditions: 85 mL/min, 100 Bar, 35° C.; Detector Wavelength: 220 nm. The first peak (fast eluting fraction, RT=10.7 min) was combined, concentrated and lyophilized to give Example 4 (35 mg, 0.059 mmol, 36.9% yield). $^1$H NMR (400 MHz, THF) δ 8.91 (br. s., 1H), 8.74 (d, J=1.8 Hz, 1H), 8.57 (s, 1H), 8.17 (br. s., 1H), 7.85 (d, J=7.5 Hz, 1H), 7.75 (dd, J=1.8, 0.9 Hz, 1H), 6.88 (d, J=0.9 Hz, 1H), 6.66 (d, J=9.0 Hz, 1H), 4.58-4.49 (m, 2H), 4.43 (d, J=4.8 Hz, 2H), 4.25 (dd, J=11.6, 7.6 Hz, 1H), 4.10 (s, 3H), 3.83 (s, 3H), 2.71 (d, J=0.4 Hz, 3H), 2.64 (s, 3H); LC-MS: method A, RT=2.24 min, MS (ESI) m/z: 560.2 (M+H)$^+$. Analytical HPLC purity (method A): 95%.

Example 5

(R)-(2-(2-methoxy-7-methylquinoxalin-5-yl)-4-methyl-7,8-dihydro-[1,4]dioxino[2',3':3,4]benzo[1,2-d]thiazol-7-yl)methyl pyridin-3-ylcarbamate

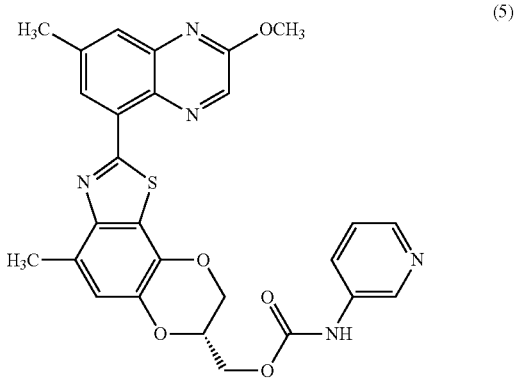 [SMILES: COc1cnc2c(-c3nc4c(C)cc5c(c4s3)OC[C@H](COC(=O)Nc3cccnc3)O5)cc(C)cc2n1]

(5)

151

Intermediate 5A: (2-(2-methoxy-7-methylquinoxalin-5-yl)-4-methyl-7,8-dihydro-[1,4]dioxino[2',3':3,4]benzo[1,2-d]thiazol-7-yl)methyl pyridin-3-ylcarbamate

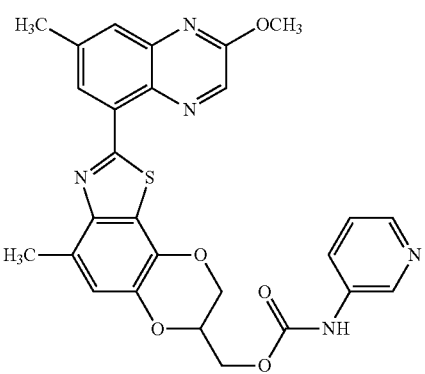

(5A)

To a solution of pyridin-3-amine (77 mg, 0.816 mmol) in DCM (0.5 mL) was added DIEA (0.326 mL, 1.865 mmol), followed by addition of Intermediate 3A (110 mg, 0.233 mmol) in THE (0.5 mL). The reaction mixture was stirred at room temperature for 1.0 h. IPLC and LCMS indicated a completion of reaction. The reaction mixture was diluted with EtOAc, quenched with water. The organic layer was collected, washed with saturated sodium bicarbonate, brine, dried over sodium sulfate and concentrated. The crude product was dissolved in a mixture of DMSO/MeOH (2:1, 14 mL) and purified by prep IPLC (method A, 50-100% B in 10 min; then 100% B in 2 min; RT=3.8 min). The desired fractions were placed in a SpeedVac overnight to remove solvent, then transferred with EtOAc to a flask. Solvent was removed to give Intermediate 5A (65 mg, 0.117 mmol, 50.0% yield) as yellow solid. $^1$H NMR (500 MHz, DMSO-$d_6$) δ 10.25 (br. s., 1H), 8.76 (s, 1H), 8.73 (br. s., 1H), 8.60 (s, 1H), 8.31 (d, J=4.1 Hz, 1H), 8.01 (d, J=8.0 Hz, 1H), 7.84 (s, 1H), 7.48 (dd, J=8.1, 4.8 Hz, 1H), 7.00 (s, 1H), 4.67 (d, J=3.3 Hz, 1H), 4.64-4.59 (m, 1H), 4.53-4.43 (m, 2H), 4.30 (dd, J=11.4, 7.3 Hz, 1H), 4.10 (s, 3H), 2.69 (s, 3H), 2.65 (s, 3H); LC-MS: method A, RT=2.10 min, MS (ESI) m/z:530.2 (M+H)$^+$. Analytical IPLC purity (method B): 100%.

Example 5

Intermediate 5A (62 mg, 0.117 mmol) was subject to a chiral SFC separation using the following condition: Instrument: Berger Multigram II Prep; Column: Chiralpak AS-H, 30×250 mm, 5 micron; Mobile Phase: 40% MeOH/60% CO$_2$; Flow Conditions: 85 mL/min, 100 Bar, 35° C.; Detector Wavelength: 220 nm. The first peak (fast eluting fraction, RT=9.2 min) was combined, concentrated and lyophilized to give Example 5 (25 mg). $^1$H NMR (500 MHz, THF) δ 9.18 (br. s., 1H), 8.74 (d, J=1.7 Hz, 1H), 8.57 (s, 1H), 8.03 (br. s., 1H), 7.75 (s, 1H), 6.88 (s, 1H), 4.59-4.51 (m, 2H), 4.46 (d, J=5.0 Hz, 2H), 4.26 (dd, J=11.3, 7.2 Hz, 1H), 4.10 (s, 3H), 2.71 (s, 3H), 2.65 (s, 3H); LC-MS: method H, 2 to 98% B. RT=0.99 min, MS (ESI) m/z: 530.0 (M+H)$^+$. Analytical HPLC purity (method A): 97%.

152

Example 6

(2-(2-methoxy-7-methylquinoxalin-5-yl)-4-methyl-7,8-dihydro-[1,4]dioxino[2',3':3,4]ben zo[1,2-d]thiazol-7-yl)methyl pyridin-3-yl carbonate

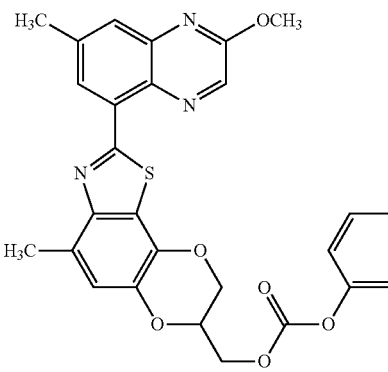

(6)

To a solution of pyridin-3-ol (13.70 mg, 0.144 mmol) in DCM (0.8 mL) was added DIEA (0.063 mL, 0.360 mmol), followed by addition of Intermediate 3A (17 mg, 0.036 mmol) in THE (0.8 mL). The reaction mixture was stirred at room temperature for 1.0 h. HPLC and LCMS indicated a completion of reaction. The reaction was quenched by addition of a small amount of MeOH/water/0.1% TFA (HPLC solvent). Solvent was removed under vacuum. The crude material was purified via preparative LC/MS (method D, 65-95% B over 15 minutes, then a 5-minute hold at 100% B). Fractions containing the desired product were combined and dried via centrifugal evaporation to yield Example 6 (10.1 mg). $^1$H NMR (500 MHz, DMSO-$d_6$) δ 8.77 (s, 1H), 8.60 (dd, J=5.4, 2.3 Hz, 2H), 8.54 (dd, J=4.7, 1.1 Hz, 1H), 7.85-7.80 (m, 2H), 7.54 (dd, J=8.3, 4.7 Hz, 1H), 7.04 (d, J=0.8 Hz, 1H), 4.77-4.71 (m, 1H), 4.67-4.55 (m, 3H), 4.32 (dd, J=11.4, 7.0 Hz, 1H), 4.10 (s, 3H), 2.70 (s, 3H), 2.66 (s, 3H); LC-MS: method H, RT=2.31 min, MS (ESI) m/z: 531.2 (M+H)$^+$. Analytical HPLC purity (method B): 93%.

Example 7

(R)-(6-chloro-8-(2-methoxy-7-methylquinoxalin-5-yl)-2,3-dihydro-[1,4]dioxino[2,3-e]be nzofuran-3-yl)methyl (6-methylpyridin-3-yl)carbamate

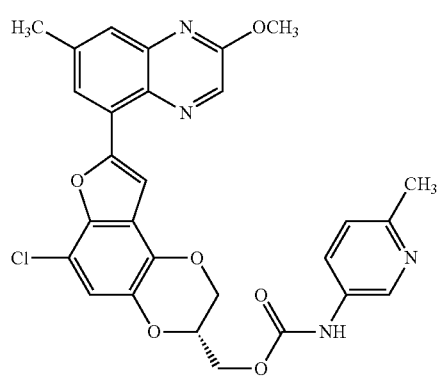

(7)

Intermediate 7A: 1-chloro-2-(2,2-diethoxyethoxy)-4-methoxybenzene

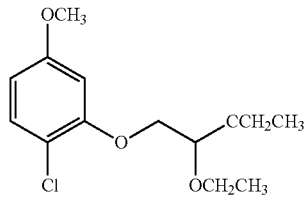

(7A)

To a suspension of sodium hydride (60%) (0.371 g, 9.27 mmol) in DMF (8.0 mL) was added 2-chloro-5-methoxyphenol (0.98 g, 6.18 mmol) in DMF (3.0 mL) at room temperature. After hydrogen evolution was ceased (20 min at 60° C. oil bath), 2-bromo-1,1-diethoxyethane (1.162 mL, 7.72 mmol) was added. The reaction mixture was heated at 160° C. for 4.0 h. HPLC indicated a completion of reaction. After it was cooled to room temperature, the reaction mixture was diluted with EtOAc/water. The organic layer was washed with saturated sodium bicarbonate, brine, dried over sodium sulfate and concentrated to give Intermediate 7A (1.8 g, 6.55 mmol, 106% yield) as light yellow oil. It was used for the next step without further purification. $^{1}$H NMR (400 MHz, chloroform-d) δ 7.23 (d, J=8.6 Hz, 1H), 6.52 (d, J=2.9 Hz, 1H), 6.44 (dd, J=8.7, 2.8 Hz, 1H), 4.87 (t, J=5.2 Hz, 1H), 4.03 (d, J=5.3 Hz, 2H), 3.85-3.78 (m, 2H), 3.77 (s, 3H), 3.73-3.66 (m, 2H), 1.25 (t, J=7.0 Hz, 9H); LC-MS: method H, 2 to 98% B. RT=1.02 min, MS (ESI) m/z: 229.0 and 231.0 (M-OEt)$^{+}$.

Intermediate 7B: 7-chloro-4-methoxybenzofuran

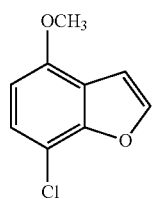

(7B)

A mixture of Amberlyst-15 (2.3 g, 6.37 mmol) in chlorobenzene (100 mL) was heated at reflux (oil bath temperature 165° C.) to remove water by azeotropic distillation. Distillate was removed until the volume remaining in the flask was about 80 mL. To this mixture was added dropwise over 1.0 h a solution of Intermediate 7A (1.75 g, 6.37 mmol) in chlorobenzene (9.0 mL). The reaction mixture was stirred at reflux with constant water removal for additional 1.0 h. HPLC and TLC indicated a complete conversion of starting material. After cooled to room temperature, the Amberlyst-15 was removed by filtration. The filtrate was concentrated under vacuum and loaded directly to ISCO column for purification. The crude product was purified by flash chromatography (loading in chloroform, 0% to 30% EtOAc in hexane over 15 min using a 40 g silica gel cartridge). The desired fractions were combined and concentrated to yield Intermediate 7B (0.84 g, 4.60 mmol, 72.2% yield) as colorless oil that solidified overnight. $^{1}$H NMR (500 MHz, chloroform-d) δ 7.59 (d, J=2.2 Hz, 1H), 7.20 (d, J=8.3 Hz, 1H), 6.90 (d, J=2.2 Hz, 1H), 6.59 (d, J=8.5 Hz, 1H), 3.92 (s, 3H); LC-MS: method A, RT=1.98 min, MS (ESI) m/z: No MS (M+H)$^{+}$.

Intermediate 7C: 7-chlorobenzofuran-4-ol

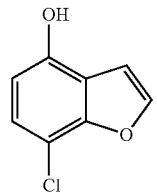

(7C)

To Intermediate 7B (675 mg, 3.70 mmol) and tetrabutylammonium iodide (1434 mg, 3.88 mmol) in dichloromethane (12 mL) at −78° C. was added 1.0 M boron trichloride in heptane (8.69 mL, 8.69 mmol) dropwise. The reaction mixture was stirred at −78° C. for 30 min. The cooling bath was removed and the reaction mixture was stirred at room temperature for 1.0 h. HPLC and TLC indicated a completion of the reaction. The mixture was poured into saturated sodium bicarbonate and ice, stirred for 20 min, extracted with EtOAc. The organic layer was collected, washed with 10% $Na_2S_2O_3$, water, brine and dried over sodium sulfate. After evaporation of solvent, the crude product was dissolved in a small amount of chloroform and charged to a 12 g silica gel cartridge which was eluted with hexanes for 1 min., then a 15 min gradient from 5% to 30% EtOAc in hexanes. The desired fractions were combined and concentrated to give Intermediate 7C (600 mg, 3.56 mmol, 96% yield) as a white solid. $^{1}$H NMR (400 MHz, chloroform-d) δ 7.61 (d, J=2.2 Hz, 1H), 7.13 (d, J=8.4 Hz, 1H), 6.88 (d, J=2.4 Hz, 1H), 6.59 (d, J=8.4 Hz, 1H), 5.31 (s, 1H); LC-MS: method A, RT=1.69 min, MS (ESI) m/z: No MS (M+H)$^{+}$.

Intermediate 7D: 7-chloro-4-hydroxybenzofuran-5-carbaldehyde

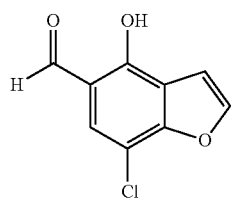

(7D)

To a solution of Intermediate 7C (307 mg, 1.821 mmol), magnesium chloride (337 mg, 3.64 mmol), triethylamine (1.269 mL, 9.11 mmol) and paraformaldehyde (273 mg, 9.11 mmol) were added. The reaction mixture was heated to reflux at 80° C. (oil bath) under argon for 3.5 h. HPLC and TLC indicated a complete conversion of starting material. The reaction mixture was cooled to room temperature, diluted with EtOAc, quenched with 1.0 N HCl (8.0 mL)/water and stirred at room temperature for 15 min until the cloudy solution turned clear. The mixture was passed through a pad of wet celite. The organic layer was collected, washed with brine, dried over sodium sulfate and concentrated. The crude product was purified by flash chromatography (loading in chloroform, 0% to 30% EtOAc in hexane over 15 min using a 12 g silica gel cartridge). The desired fractions were combined and concentrated to yield Intermediate 7D (322 mg, 1.639 mmol, 90% yield) as a white solid. ¹H NMR (400 MHz, chloroform-d) δ 11.88 (s, 1H), 9.87 (s, 1H), 7.68 (d, J=2.2 Hz, 1H), 7.46 (s, 1H), 7.06 (d, J=2.2 Hz, 1H); LC-MS: method H, 2 to 98% B. RT=0.89 min, MS (ESI) m/z: No MS (M+H)⁺.

Intermediate 7E: (R)-7-chloro-4-(oxiran-2-yl-methoxy)benzofuran-5-carbaldehyde

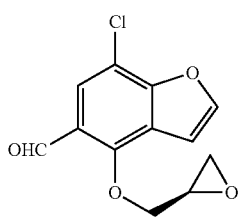

(7E)

To a solution of Intermediate 7D (545 mg, 2.77 mmol) in DMF (10 mL) was added (R)-oxiran-2-ylmethyl 3-nitrobenzenesulfonate (791 mg, 3.05 mmol) and Cs₂CO₃ (2258 mg, 6.93 mmol). The reaction mixture was heated at 50° C. overnight. TLC indicated a completion of the reaction. The mixture was diluted with EtOAc and water, extracted with EtOAc, the combined organic layer was washed with brine, dried with sodium sulfate and concentrated. The crude product was triturated with EtOAc/hexanes (1:3). The precipitate was collected to give Intermediate 7E (610 mg). The filtrate was concentrated and further purified with ISCO to give additional product (70 mg) as a white solid: ¹H NMR (400 MHz, methanol-d₄) δ 10.44 (s, 1H), 7.86 (d, J=2.2 Hz, 1H), 7.76 (s, 1H), 7.22 (d, J=2.4 Hz, 1H), 4.79 (dd, J=11.2, 2.4 Hz, 1H), 4.31 (dd, J=11.2, 6.4 Hz, 1H), 3.51-3.44 (m, 1H), 2.98-2.94 (m, 1H), 2.83 (dd, J=4.8, 2.6 Hz, 1H); LC-MS: method H, 2 to 98% B. RT=0.85 min, MS (ESI) m/z: 253.0 and 255.0 (M+H)⁺.

Intermediate 7F: (S)-(6-chloro-2,3-dihydro-[1,4]dioxino[2,3-e]benzofuran-3-yl)methanol

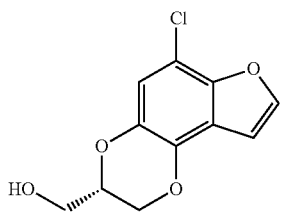

(7F)

To a stirred solution of Intermediate 7E (609 mg, 2.410 mmol) in dichloromethane (16 mL) cooled with an ice bath was added mCPBA (818 mg, 3.56 mmol). Trifluoroacetic acid (0.186 mL, 2.410 mmol) in dichloromethane (2.0 mL) was added dropwise. Ice bath was removed and the reaction mixture was stirred at room temperature for 1.0 h. TLC indicated a completion of reaction. The reaction was quenched by addition of saturated sodium bicarbonate, followed by 10% sodium thiosulfite (12.0 mL), extracted with dichloromethane. The organic layer was collected, washed with saturated sodium bicarbonate, brine and dried over sodium sulfate. After evaporation of solvent, the intermediate formate was obtained as a slightly brown solid (700 mg). The intermediate formate was dissolved in MeOH (14 mL) and THF (3.0 mL). K₂CO₃ (999 mg, 7.23 mmol) was added, and the reaction mixture was stirred at room temperature for 25 min. HPLC and TLC suggested completion of reaction. The reaction mixture was diluted with EtOAc and water, extracted with EtOAc, the combined organic layer was washed with brine, dried with sodium sulfate and concentrated. The crude product was purified by flash chromatography (loading in chloroform, 10% to 50% EtOAc in hexane over 10 min using a 12 g silica gel cartridge). The desired fractions were combined and concentrated to yield Intermediate 7F (522 mg, 2.169 mmol, 90% yield) as a clear oil. ¹H NMR (400 MHz, chloroform-d) δ 7.57 (d, J=2.0 Hz, 1H), 6.91 (s, 1H), 6.82 (d, J=2.2 Hz, 1H), 4.40 (dd, J=11.0, 2.0 Hz, 1H), 4.30-4.24 (m, 1H), 4.23-4.17 (m, 1H), 3.97-3.83 (m, 2H); LC-MS: method H, 2 to 98% B. RT=0.81 min, MS (ESI) m/z: 240.9 and 242.9 (M+H)⁺.

Intermediate 7G (R)-tert-butyl((6-chloro-2,3-dihydro-[1,4]dioxino[2,3-e]benzofuran-3-yl)methoxy)dimethylsilane

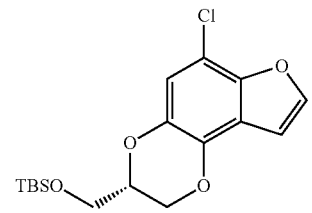

(7G)

To a stirred solution of Intermediate 7F (590 mg, 2.452 mmol) in DMF (8 mL) was added TBDMS-Cl (554 mg, 3.68 mmol) and imidazole (300 mg, 4.41 mmol). The reaction mixture was stirred at room temperature for 1.5 h. HPLC and TLC indicated a completion of the reaction. The mixture was partitioned between EtOAc/water. The organic layer was washed with water, brine and dried over sodium sulfate. After evaporation of solvent, the crude product was dissolved in a small amount of chloroform and charged to a 12 g silica gel cartridge which was eluted with hexanes for 3 min., then a 10 min gradient from 0% to 20% EtOAc in hexanes. The desired fractions were combined and concentrated to give Intermediate 7G (795 mg, 2.240 mmol, 91% yield) as clear oil. ¹H NMR (400 MHz, chloroform-d) δ 7.58 (d, J=2.2 Hz, 1H), 6.89 (s, 1H), 6.83 (d, J=2.2 Hz, 1H), 4.43 (dd, J=10.8, 1.8 Hz, 1H), 4.26-4.19 (m, 1H), 4.19-4.13 (m, 1H), 3.96-3.90 (m, 1H), 3.84-3.78 (m, 1H), 0.93-0.91 (s, 9H), 0.11 and 0.10 (s, 6H); LC-MS: method H, 2 to 98% B. RT=1.32 min, MS (ESI) m/z: 355.0 and 357.0 (M+H)⁺.

Intermediate 7H: (R)-tert-butyl((6-chloro-8-iodo-2,3-dihydro-[1,4]dioxino[2,3-e]benzofuran-3-yl)methoxy)dimethylsilane

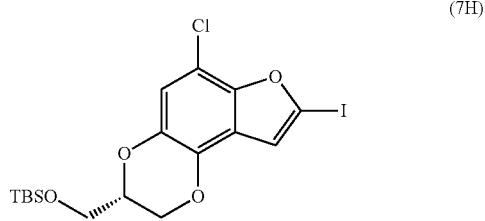 [SMILES: CC(C)(C)[Si](C)(C)OC[C@H]1COc2c(cc(Cl)c3oc(I)cc23)O1]

(7H)

To diisopropylamine (0.163 mL, 1.141 mmol) in THF (3.0 mL) at −78° C. was added 1.6 N n-BuLi in hexanes (0.713 mL, 1.141 mmol). The reaction mixture was stirred at −78° C. for 20 min. Intermediate 7G (270 mg, 0.761 mmol) in THF (1.0 mL) was added dropwise. The reaction mixture was stirred at −78° C. for 0.5 h. Iodine (290 mg, 1.141 mmol) in THF (1.0 mL) was added dropwise until the brown color persisted (ca 1.2 eq). The reaction mixture was stirred at −78° C. for 0.5 h, then at room temperature for 15 min. The reaction mixture was diluted with EtOAc, quenched with saturated ammonium chloride (3.0 mL) and 10% $Na_2S_2O_3$ (4.0 mL). After stirring at room temperature for 10 min, the organic layer was washed with brine, dried over sodium sulfate. After evaporation of solvent, Intermediate 7H (330 mg, 0.686 mmol, 90% yield) was obtained as a slightly brown oil. It was used for the next step without further purification. $^1$H NMR (400 MHz, chloroform-d) δ 7.00 (s, 1H), 6.81 (s, 1H), 4.40 (dd, J=11.0, 2.0 Hz, 1H), 4.24-4.18 (m, 1H), 4.17-4.10 (m, 1H), 3.94-3.89 (m, 1H), 3.82-3.76 (m, 1H), 0.92-0.91 (m, 9H), 0.10 and 0.09 (s, 6H); LC-MS: method H, 2 to 98% B. RT=1.38 min, MS (ESI) m/z: 480.9 (M+H)$^+$.

Intermediate 7I (R)-5-(3-(((tert-butyldimethylsilyl)oxy)methyl)-6-chloro-2,3-dihydro-[1,4]dioxino[2,3-e]benzofuran-8-yl)-2-(difluoromethoxy)-7-methylquinoxaline

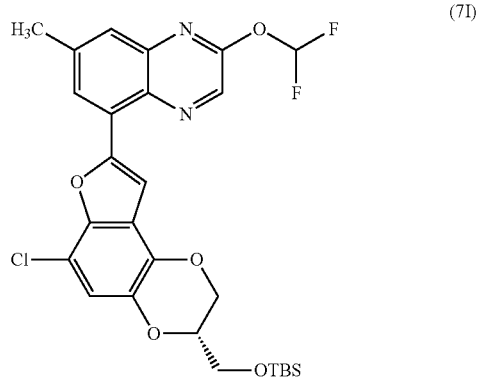 [SMILES: Cc1cc(-c2cc3c4c(cc(Cl)c3o2)O[C@@H](CO[Si](C)(C)C(C)(C)C)CO4)c2ncc(OC(F)F)nc2c1]

(7I)

To Intermediate I-1 (174 mg, 0.686 mmol), Intermediate 7H (330 mg, 0.686 mmol) and $PdCl_2$(dppf)—$CH_2Cl_2$ adduct (22.42 mg, 0.027 mmol) was added toluene (4.5 mL) and EtOH (1.5 mL). The mixture was sonicated for 1 min, and flushed with argon. To this was added sodium carbonate (2M, 0.601 mL, 1.201 mmol). The reaction mixture was heated in a microwave reactor at 120° C. for 30 min. HPLC and LCMS indicated a completion of the reaction. The crude reaction mixture was directly loaded on an ISCO column for purification. The crude product was purified by flash chromatography (loading in chloroform, 0% to 20% EtOAc in hexane over 15 min using a 24 g silica gel cartridge). The desired fractions were combined and concentrated to yield Intermediate 7I (210 mg, 0.373 mmol, 54.3% yield) as an yellow solid. $^1$H NMR (400 MHz, chloroform-d) δ 8.62 (s, 1H), 8.26 (d, J=1.8 Hz, 1H), 8.15 (s, 1H), 7.67-7.65 (m, 1H), 7.65 (t, JHF=71.65 Hz, 1H), 6.92 (s, 1H), 4.47 (dd, J=10.6, 1.5 Hz, 1H), 4.29-4.24 (m, 1H), 4.22-4.18 (m, 1H), 3.98-3.92 (m, 1H), 3.83 (dd, J=10.8, 6.4 Hz, 1H), 2.65 (s, 3H), 0.92 (s, 9H), 0.11 (s, 3H), 0.11 (s, 3H); $^{19}$F NMR (376 MHz, chloroform-d) δ −89.71 (s, 1F); LC-MS: method H, 2 to 98% B. RT=1.50 min, MS (ESI) m/z: 563.2 (M+H)$^+$.

Intermediate 7J (R)-5-(3-(((tert-butyldimethylsilyl)oxy)methyl)-6-chloro-2,3-dihydro-[1,4]dioxino[2,3-e]benzofuran-8-yl)-2-methoxy-7-methylquinoxaline

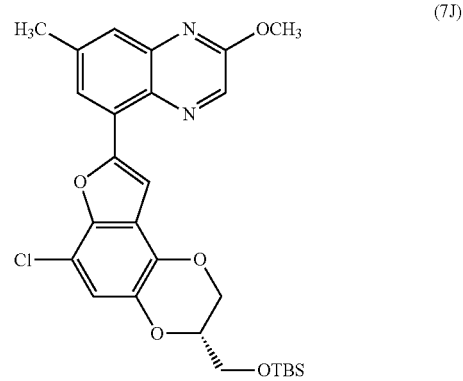 [SMILES: COc1cnc2c(-c3cc4c5c(cc(Cl)c4o3)O[C@@H](CO[Si](C)(C)C(C)(C)C)CO5)cc(C)cc2n1]

(7J)

To Intermediate 7I (210 mg, 0.373 mmol) dissolved in THF (6 mL) and MeOH (3.0 mL) at room temperature was added 4.3 M sodium methoxide in MeOH (0.390 mL, 1.678 mmol). The reaction mixture was stirred at room temperature overnight. LCMS indicated a completion of the reaction. The reaction mixture was quenched with 1.0 N HCl (1.492 mL, 1.492 mmol), diluted with EtOAc. The organic layer was washed with brine, dried and concentrated to give Intermediate 7J (200 mg, 0.379 mmol, 102% yield) as yellow film. This was used for the next step without further purification. LC-MS method H, 2 to 98% B. RT=1.61 min, MS (ESI) m/z: 527.2 (M+H)$^+$.

Intermediate 7K (S)-(6-chloro-8-(2-methoxy-7-methylquinoxalin-5-yl)-2,3-dihydro-[1,4]dioxino[2,3-e]ben

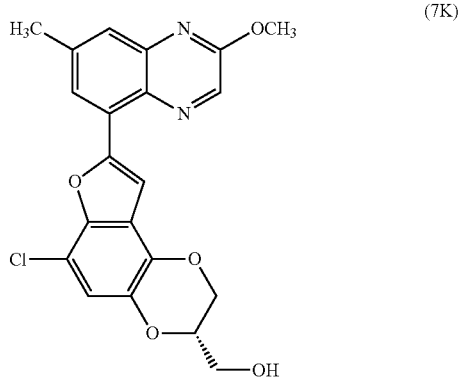 [SMILES: COc1cnc2c(-c3cc4c5c(cc(Cl)c4o3)O[C@@H](CO)CO5)cc(C)cc2n1]

(7K)

To a solution of Intermediate 7J (210 mg, 0.398 mmol) in THF (3 mL) was added triethylamine trihydrofluoride (0.662 mL, 3.98 mmol) dropwise. The reaction mixture was stirred at room temperature for 1 h. IPLC indicated ca 60% conversion. Another portion of triethylamine trihydrofluoride (0.662 mL, 3.98 mmol) was added, and the reaction mixture was stirred at room temperature for 2.0 h. IPLC and LCMS indicated a clean conversion. The reaction mixture was diluted with EtOAc, washed with 1.5 M dipotassium phosphate, brine, dried over sodium sulfate and concentrated to give Intermediate 7K (162 mg, 0.373 mmol, 94% yield) as an yellow solid. It was used for the next step without further purification. $^1$H NMR (400 MHz, DMSO-$d_6$) δ 8.65 (s, 1H), 8.05 (s, 1H), 7.99 (d, J=1.8 Hz, 1H), 7.66 (dd, J=1.8, 0.9 Hz, 1H), 7.01 (s, 1H), 4.52 (dd, J=11.2, 2.0 Hz, 1H), 4.25-4.21 (m, 1H), 4.19-4.14 (m, 1H), 3.75-3.65 (m, 2H), 2.60 (s, 3H); LC-MS: method H, 2 to 98% B. RT=1.18 min, MS (ESI) m/z: 413.1 and 415.1 (M+H)$^+$.

Intermediate 7L: [(11R)-7-chloro-4-(2-methoxy-7-methylquinoxalin-5-yl)-5,10,13-trioxatricyclo[7.4.0.0^{2,6}]trideca-1(9), 2(6), 3,7-tetraen-11-yl] methyl chloroformate

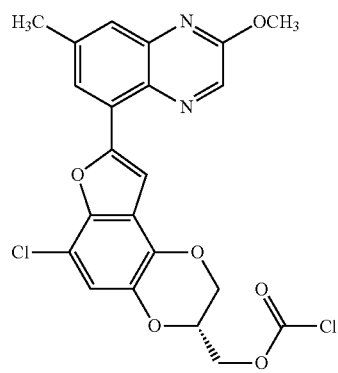

(7L)

To a solution of Intermediate 7K (100 mg, 0.242 mmol) in THF (3.0 mL) at room temperature was added 15% phosgene in toluene (0.683 mL, 0.969 mmol). The reaction mixture was left stirring at room temperature overnight. Solvent was completely removed under high vacuum to give Intermediate 7L (115 mg, 0.242 mmol, 100% yield) as a slightly yellow solid. It was used for the next step without purification. LC-MS: method H, 2 to 98% B. RT=1.31 min, MS (ESI) m/z: 475.1 (M+H)$^+$.

Example 7

To a solution of 6-methylpyridin-3-amine (18.20 mg, 0.168 mmol) in DCM (0.8 mL) was added DIEA (0.059 mL, 0.337 mmol), followed by addition of Intermediate 7L (18.20 mg, 0.168 mmol) in THF (0.8 mL). The reaction mixture was stirred at room temperature for 1.0 h, quenched by addition of a small amount of MeOH/water/0.1% TFA. Solvent was removed under vacuum. The crude was dissolved in DMSO and purified via preparative LC/MS (method C, 40-80% B over 15 minutes, then a 5-minute hold at 100% B). Fractions containing the desired product were combined and dried via centrifugal evaporation to yield Example 7 (7.5 mg). $^1$H NMR (500 MHz, DMSO-$d_6$) δ 10.41 (br. s., 1H), 8.72-8.66 (m, 2H), 8.09 (s, 1H), 8.07-8.01 (m, 2H), 7.71 (s, 1H), 7.54 (d, J=8.3 Hz, 1H), 7.12 (s, 1H), 4.66-4.59 (m, 2H), 4.54-4.43 (m, 2H), 4.32-4.25 (m, 1H), 4.07 (s, 3H), 2.62 (s, 3H), 2.53 (s, 3H); LC-MS: method H, RT=2.20 min, MS (ESI) m/z: 547.2 (M+H)$^+$. Analytical HPLC purity (method B): 98%.

Example 8

(R)-(6-chloro-8-(2-methoxy-7-methylquinoxalin-5-yl)-2,3-dihydro-[1,4]dioxino[2,3-e]be nzofuran-3-yl) methyl (2-methylpyridin-4-yl)carbamate

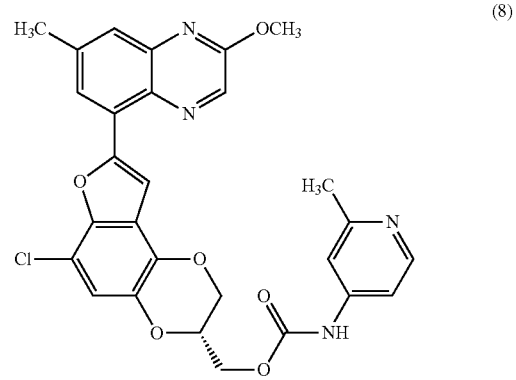 [SMILES: COc1cnc2c(-c3cc4c5c(cc(Cl)c4o3)O[C@@H](COC(=O)Nc3ccnc(C)c3)CO5)cc(C)cc2n1]

(8)

To a solution of 2-methylpyridin-4-amine (18.20 mg, 0.168 mmol) in DCM (0.8 mL) was added DIEA (0.059 mL, 0.337 mmol), followed by addition of Intermediate 7L (18.20 mg, 0.168 mmol) in THF (0.8 mL). The reaction mixture was stirred at room temperature for 1.0 h, quenched by addition of a small amount of MeOH/water/0.1% TFA. Solvent was removed under vacuum. The crude was dissolved in DMSO and purified via preparative LC/MS (method C, 45-90% B over 15 minutes, then a 5-minute hold at 100% B). Fractions containing the desired product were combined and dried via centrifugal evaporation to yield Example 8 (14.9 mg). $^1$H NMR (500 MHz, DMSO-$d_6$) δ 11.30 (br. s., 1H), 8.70 (s, 1H), 8.54 (d, J=6.6 Hz, 1H), 8.09 (s, 1H), 8.02 (s, 1H), 7.76-7.67 (m, 3H), 7.11 (s, 1H), 4.70-4.49 (m, 4H), 4.34-4.27 (m, 1H), 4.08 (s, 3H), 2.61 (br. s., 6H); LC-MS: method H, RT=2.25 min, MS (ESI) m/z: 547.1 (M+H)$^+$. Analytical HPLC purity (method B): 100%.

Example 9

(R)-(6-chloro-8-(2-methoxy-7-methylquinoxalin-5-yl)-2,3-dihydro-[1,4]dioxino[2,3-e]be nzofuran-3-yl) methyl (6-methoxypyridin-3-yl)carbamate

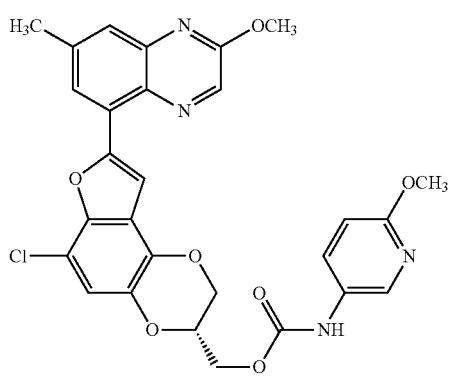

(9)

To a solution of 6-methoxypyridin-3-amine (20.90 mg, 0.168 mmol) in DCM (0.8 mL) was added DIEA (0.059 mL, 0.337 mmol), followed by addition of Intermediate 7L (20.90 mg, 0.168 mmol) in THE (0.8 mL). The reaction mixture was stirred at room temperature for 1.0 h, quenched by addition of a small amount of MeOH/water/0.1% TFA. Solvent was removed under vacuum. The crude was dissolved in DMSO and purified via preparative LC/MS (method C, 65-100% B over 15 minutes, then a 5-minute hold at 100% B). Fractions containing the desired product were combined and dried via centrifugal evaporation to yield Example 9 (10.1 mg). $^1$H NMR (500 MHz, DMSO-$d_6$) δ 9.84 (br. s., 1H), 8.70 (s, 1H), 8.25 (br. s., 1H), 8.08 (s, 1H), 8.02 (br. s., 1H), 7.79 (d, J=6.3 Hz, 1H), 7.70 (br. s., 1H), 7.11 (s, 1H), 6.81 (d, J=8.8 Hz, 1H), 4.60 (d, J=9.4 Hz, 2H), 4.49-4.37 (m, 2H), 4.27 (t, J=9.2 Hz, 1H), 4.07 (s, 3H), 3.81 (s, 3H), 2.61 (s, 3H); LC-MS: method H, RT=2.66 min, MS (ESI) m/z: 563.2 (M+H)$^+$. Analytical HPLC purity (method B): 96%.

Example 10

(R)-(6-chloro-8-(2-methoxy-7-methylquinoxalin-5-yl)-2,3-dihydro-[1,4]dioxino[2,3-e]be nzofuran-3-yl) methyl pyridin-3-ylcarbamate

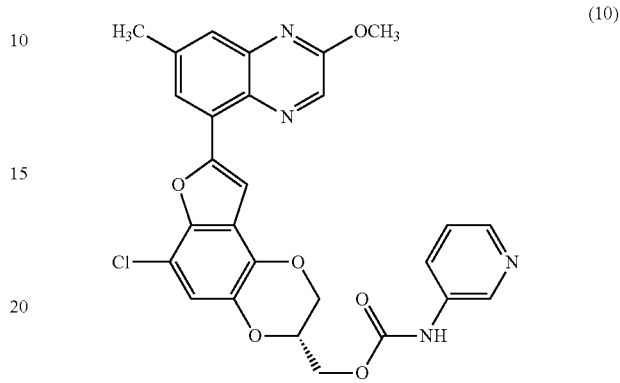

(10)

To a solution of pyridin-3-amine (3.17 mg, 0.034 mmol) in DCM (0.8 mL) was added DIEA (0.059 mL, 0.337 mmol), followed by addition of Intermediate 7L (16 mg, 0.034 mmol) in THE (0.8 mL). The reaction mixture was stirred at room temperature for 1.0 h, quenched by addition of a small amount of MeOH/water/0.1% TFA. Solvent was removed under vacuum. The crude was dissolved in DMSO and purified via preparative LC/MS (method C, 40-80% B over 15 minutes, then a 5-minute hold at 100% B). Fractions containing the desired product were combined and dried via centrifugal evaporation to yield Example 10 (9.0 mg). $^1$H NMR (500 MHz, DMSO-$d_6$) δ 10.30 (br. s., 1H), 8.74 (br. s., 1H), 8.71 (s, 1H), 8.32 (br. s., 1H), 8.11 (s, 1H), 8.07-8.00 (m, 2H), 7.72 (s, 1H), 7.50 (br. s., 1H), 7.13 (s, 1H), 4.67-4.59 (m, 2H), 4.54-4.41 (m, 2H), 4.29 (t, J=9.4 Hz, 1H), 4.08 (s, 3H), 2.62 (s, 3H); LC-MS: method H, RT=2.18 min, MS (ESI) m/z:533.2 (M+H)$^+$. Analytical HPLC purity (method B): 97%.

Example 11

(R)-(8-(2-methoxy-7-methylquinoxalin-5-yl)-2,3-dihydro-[1,4]dioxino[2,3-e]benzofuran-3-yl)methyl (6-methylpyridin-3-yl)carbamate

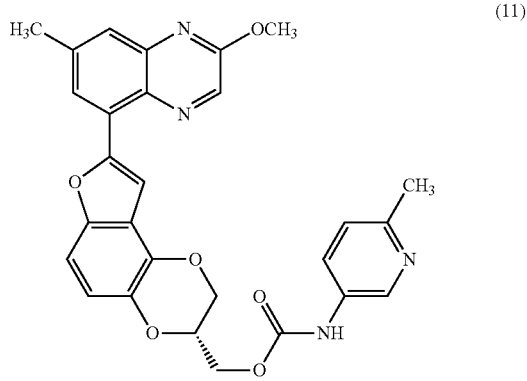

(11)

Intermediate 11A:
1-bromo-2-(2,2-diethoxyethoxy)-4-methoxybenzene

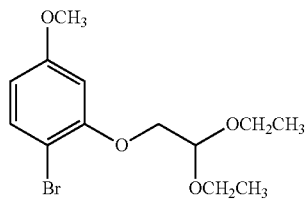

(11A)

To a suspension of sodium hydride (60%) (0.801 g, 20.02 mmol) in DMF (24 mL) was added 2-bromo-5-methoxyphenol (2.71 g, 13.35 mmol) in DMF (6.0 mL) dropwise at room temperature. After hydrogen evolution was ceased (20 min at 60° C. oil bath), 2-bromo-1,1-diethoxyethane (2.510 mL, 16.68 mmol) was added. The reaction mixture was heated at 160° C. overnight. After cooled to room temperature, the reaction mixture was diluted with EtOAc/water. The organic layer was washed with brine, dried over sodium sulfate and concentrated to give Intermediate 11 A (5.0 g, 14.10 mmol, 106% yield) as a light brown oil. It was used for the next step without further purification. $^1$H NMR (400 MHz, chloroform-d) δ 7.39 (d, J=8.6 Hz, 1H), 6.50 (d, J=2.9 Hz, 1H), 6.41 (dd, J=8.8, 2.6 Hz, 1H), 4.87 (t, J=5.2 Hz, 1H), 4.02 (d, J=5.3 Hz, 2H), 3.85-3.78 (m, 2H), 3.77 (s, 3H), 3.74-3.67 (m, 2H), 1.26 (t, J=7.0 Hz, 6H); LC-MS: method H, 2 to 98% B. RT=1.04 min, MS (ESI) m/z: 275.0 and 277.0 (M-OEt)$^+$.

Intermediate 11B: 7-bromo-4-methoxybenzofuran

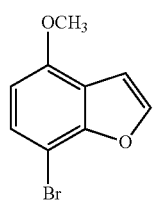

(11B)

A mixture of Amberlyst-15 (5.0 g, 15.66 mmol) in chlorobenzene (200 mL) was heated at reflux (oil bath temperature 165° C.) to remove water by azeotropic distillation. Distillate was removed until the volume remaining in the flask was about 160 mL. To this mixture was then added dropwise over 1.0 h a solution of Intermediate 11A (5.0 g, 15.66 mmol) in chlorobenzene (10 mL). The reaction mixture was stirred at reflux with constant water removal for additional 0.5 h. HPLC indicated a complete conversion of starting material. After cooled to room temperature, the Amberlyst-15 was removed by filtration. The filtrated was concentrated under high vacuum, and loaded directly to ISCO column for purification. The crude product was purified by flash chromatography (loading in chloroform, 0% to 30% EtOAc in hexane over 15 min using a 40 g silica gel cartridge). The desired fractions were combined and concentrated to yield Intermediate 11B (2.31 g, 10.17 mmol, 64.9% yield) as colorless oil. $^1$H NMR (400 MHz, chloroform-d) δ 7.59 (d, J=1.5 Hz, 1H), 7.38-7.32 (d, J=8.36 Hz, 1H), 6.92 (d, J=2.0 Hz, 1H), 6.60-6.54 (d, J=8.36 Hz, 1H), 3.93 (s, 3H); LC-MS: method H, 2 to 98% B. RT=0.98 min, MS (ESI) m/z: 226.8 and 228.8 (M+H)$^+$.

Intermediate 11C: 7-bromobenzofuran-4-ol

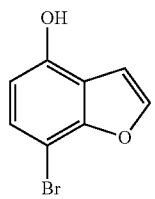

(11C)

To Intermediate 11B (2.3 g, 10.13 mmol) in dichloromethane (20 mL) was added tetrabutylammonium iodide (3.93 g, 10.64 mmol). The mixture was cooled to −78° C., and 1.0 M boron trichloride in heptane (22.29 mL, 22.29 mmol) was added dropwise. The reaction mixture was stirred at −78° C. for 30 min. Then the cooling bath was removed and the reaction mixture was stirred at room temperature for 1.0 h. HPLC and TLC indicated a completion of the reaction. The mixture was poured into saturated sodium bicarbonate and ice, stirred for 20 min, extracted with dichloromethane. The organic layer was collected, washed with 10% $Na_2S_2O_3$, water, brine and dried over sodium sulfate. After evaporation of solvent, the crude product was dissolved in a small amount of chloroform and charged to a 40 g silica gel cartridge which was eluted with 5% EtOAc in hexanes for 1 min., then a 12 min gradient from 5% to 85%. The desired fractions were combined and concentrated to give Intermediate 11C (2.0 g, 9.39 mmol, 93% yield) as a white solid. $^1$H NMR (400 MHz, chloroform-d) δ 7.61 (d, J=2.2 Hz, 1H), 7.28 (d, J=8.4 Hz, 1H), 6.91 (d, J=2.4 Hz, 1H), 6.56 (d, J=8.4 Hz, 1H), 5.22 (s, 1H); LC-MS: method H, 2 to 98% B. RT=0.81 min, MS (ESI) m/z: No MS (M+H)$^+$.

Intermediate 11D: 7-bromo-4-hydroxybenzofuran-5-carbaldehyde

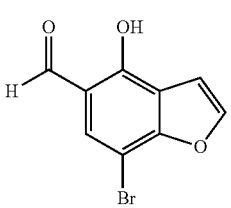

(11D)

To a solution of Intermediate 11C (1.88 g, 8.83 mmol), magnesium chloride (1.633 g, 17.65 mmol), triethylamine (6.15 mL, 44.1 mmol) and paraformaldehyde (1.325 g, 44.1 mmol) were added. The reaction mixture was heated to reflux at 80° C. (oil bath) under argon for 4.0 h and at room temperature overnight. The reaction mixture was diluted with EtOAc, quenched with 1.0 N HCl to pH 2.0, and stirred at room temperature for 15 min until the cloudy solution turned clear. The mixture was filtered through a pad of wet celite, the organic layer was collected, washed with brine, dried over sodium sulfate and concentrated. The crude product was purified by flash chromatography (loading in chloroform, 0% to 40% EtOAc in hexane over 15 min using a 80 g silica gel cartridge). The desired fractions were combined and concentrated to yield Intermediate 11D (1.8 g, 7.47 mmol, 85% yield) as a white solid. ¹H NMR (400 MHz, chloroform-d) δ 11.88 (s, 1H), 9.87 (s, 1H), 7.69 (d, J=2.2 Hz, 1H), 7.61 (s, 1H), 7.09 (d, J=2.2 Hz, 1H); LC-MS: method H, 2 to 98% B. RT=0.90 min, MS (ESI) m/z: No MS (M+H)⁺.

Intermediate 11E: (R)-7-bromo-4-(oxiran-2-ylmethoxy)benzofuran-5-carbaldehyde

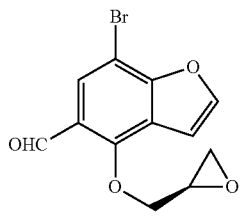

(11E)

To a solution of Intermediate 11D (1.91 g, 7.92 mmol) in DMF (50 mL) was added (R)-oxiran-2-ylmethyl 3-nitrobenzenesulfonate (2.260 g, 8.72 mmol) and Cs₂CO₃ (6.45 g, 19.81 mmol). The reaction mixture was heated at 50° C. overnight. TLC indicated a completion of the reaction. The mixture was diluted with EtOAc and water, extracted with EtOAc, the combined organic layer was washed with saturated sodium bicarbonate (2×), brine (2×) and dried with sodium sulfate and concentrated. The crude product was triturated with EtOAc/hexanes (1:3). The precipitate was collected to give Intermediate 11E (1.93 g). The filtrate was concentrated and further purified with ISCO to give additional product (60 mg). ¹H NMR (400 MHz, chloroform-d) δ 10.45 (s, 1H), 7.98 (s, 1H), 7.72 (d, J=2.2 Hz, 1H), 7.09 (d, J=2.2 Hz, 1H), 4.64 (dd, J=11.0, 2.9 Hz, 1H), 4.30 (dd, J=11.0, 5.9 Hz, 1H), 3.46-3.40 (m, 1H), 2.95 (dd, J=4.8, 4.2 Hz, 1H), 2.79 (dd, J=4.8, 2.4 Hz, 1H); LC-MS: method H, 2 to 98% B. RT=2.87 min, MS (ESI) m/z: 297.0 and 299.0 (M+H)⁺.

Intermediate 11F: (S)-(6-bromo-2,3-dihydro-[1,4]dioxino[2,3-e]benzofuran-3-yl) methanol

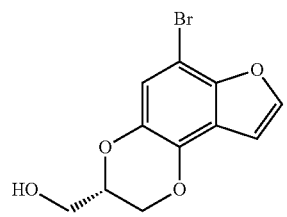

(11F)

To a stirred suspension of Intermediate 11E (2.0 g, 6.73 mmol) in dichloromethane (50 mL) cooled with an ice bath was added mCPBA (2.285 g, 9.93 mmol). Trifluoroacetic acid (0.519 mL, 6.73 mmol) in dichloromethane (8 mL) was added dropwise. Ice bath was removed and the reaction mixture was stirred at room temperature for 1.0 h. TLC indicated a completion of reaction. The reaction mixture was quenched by addition of 1.5 M dipotassium phosphate, followed by 10% sodium thiosulfite (25 mL), extracted with dichloromethane. The organic layer was collected, washed with saturated sodium bicarbonate, brine and dried over sodium sulfate. After evaporation of solvent, the intermediate formate was obtained as a white solid (2.1 g).

The intermediate formate was dissolved in MeOH (50 mL) and THF (20 mL). K₂CO₃ (2.79 g, 20.20 mmol) was added, and the reaction mixture was stirred at room temperature for 25 min. Methanol was removed under vacuum. The crude mixture was treated with water and EtOAc. The organic layer was washed with brine, dried with sodium sulfate and concentrated. The crude product was purified by flash chromatography (loading in chloroform, 15% to 100% EtOAc in hexane over 10 min using a 40 g silica gel cartridge). The desired fractions were combined and concentrated to yield Intermediate 11F (1.8 g, 5.81 mmol, 86% yield) as brown oil. ¹H NMR (400 MHz, chloroform-d) δ 7.58 (d, J=2.0 Hz, 1H), 7.07 (s, 1H), 6.85 (d, J=2.0 Hz, 1H), 4.40 (dd, J=11.0, 2.0 Hz, 1H), 4.30-4.24 (m, 1H), 4.23-4.17 (m, 1H), 3.98-3.84 (m, 2H); LC-MS: method H, 2 to 98% B. RT=0.82 min, MS (ESI) m/z: 285.0 and 287.0 (M+H)⁺.

Intermediate 11G: (R)-((6-bromo-2,3-dihydro-[1,4]dioxino[2,3-e]benzofuran-3-yl) methoxy)(tert-butyl)dimethylsilane

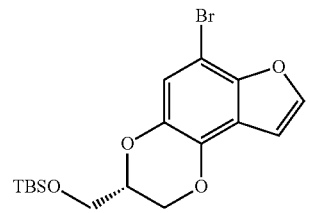

(11G)

To a stirred solution of Intermediate 11F (1.8 g, 6.31 mmol) in DMF (20 mL) was added TBDMS-Cl (1.427 g, 9.47 mmol) and imidazole (0.774 g, 11.36 mmol). The reaction mixture was stirred at room temperature for 1.5 h. IPLC and TLC indicated a completion of the reaction. The mixture was partitioned between EtOAc/water. The organic layer was washed with water, brine and dried over sodium sulfate. After evaporation of solvent, the crude product was dissolved in a small amount of chloroform and charged to a 40 g silica gel cartridge which was eluted with hexanes for 2 min., then a 10 min gradient from 0% to 25% EtOAc in hexanes. The desired fractions were combined and concentrated to give Intermediate 11G (2.42 g, 5.76 mmol, 91% yield) as clear oil. ¹H NMR (400 MHz, chloroform-d) δ 7.58 (d, J=2.0 Hz, 1H), 7.04 (s, 1H), 6.86 (d, J=2.2 Hz, 1H), 4.43 (dd, J=10.9, 1.9 Hz, 1H), 4.21 (ddd, J=6.5, 4.5, 2.0 Hz, 1H), 4.19-4.10 (m, 1H), 3.96-3.91 (m, 1H), 3.84-3.78 (m, 1H), 0.92 (s, 9H), 0.11 (s, 3H), 0.10 (s, 3H); LC-MS: method H, 2 to 98% B. RT=1.31 min, MS (ESI) m/z: 400.9 (M+H)⁺.

Intermediate 11H: (R)-tert-butyl((2,3-dihydro-[1,4]dioxino[2,3-e]benzofuran-3-yl) methoxy)dimethylsilane

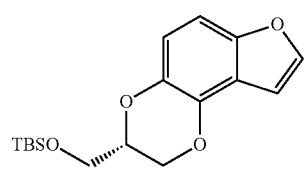
(11H)

To Intermediate 11G (563 mg, 1.410 mmol) in ethanol (10 mL) was added 10% Pd/C (190 mg, 1.410 mmol) under argon, followed by addition of 2.0 M sodium carbonate (2.115 mL, 4.23 mmol). The reaction mixture was stirred at room temperature under a hydrogen balloon for 30 min. HPLC and LCMS indicated a completion of the reaction. Pd/C was removed by filtration. The filtrate was diluted with EtOAc. The organic layer was washed with water, brine dried over sodium sulfate and concentrated to give Intermediate 11H (429 mg, 1.339 mmol, 95% yield) as clear oil. It was used for the next step without further purification. $^1$H NMR (400 MHz, chloroform-d) δ 7.52 (d, J=2.2 Hz, 1H), 7.00 (dd, J=8.8, 0.9 Hz, 1H), 6.84 (d, J=8.6 Hz, 1H), 6.80 (dd, J=2.2, 0.9 Hz, 1H), 4.45 (dd, J=10.8, 2.0 Hz, 1H), 4.23 (ddt, J=6.9, 4.6, 2.2 Hz, 1H), 4.17-4.12 (m, 1H), 3.95 (dd, J=10.7, 4.5 Hz, 1H), 3.85-3.79 (m, 1H), 0.92 (s, 9H), 0.11 (s, 3H), 0.10 (s, 3H); LC-MS: method H, 2 to 98% B. RT=1.24 min, MS (ESI) m/z: 321.2 (M+H)$^+$.

Intermediate 11I: (S)-(8-iodo-2,3-dihydro-[1,4]dioxino[2,3-e]benzofuran-3-yl)methanol

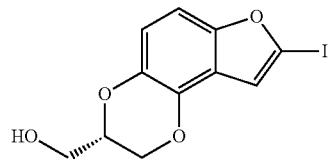
(11I)

To diisopropylamine (0.158 mL, 1.109 mmol) in THF (3.0 mL) at −78° C. was added 1.6 N n-BuLi in hexanes (0.693 mL, 1.109 mmol). The reaction mixture was stirred at −78° C. for 20 min. Intermediate 11H (237 mg, 0.740 mmol) in THF (1.0 mL) was added dropwise. The reaction mixture was stirred at −78° C. for 0.5 h. Iodine (263 mg, 1.035 mmol) in THF (1.0 mL) was added dropwise until the brown color persisted (ca 1.2 eq), and the reaction mixture was stirred at −78° C. for 0.5 h, then at room temperature for 15 min. IPLC and LCMS indicated a mixture of two compounds, corresponding to mono and di-iodination. The reaction mixture was diluted with EtOAc, quenched with saturated ammonium chloride (3.0 mL) and 10% Na$_2$S$_2$O$_3$ (4.0 mL). After stirring at room temperature for 10 min, the organic layer was washed with brine, dried over sodium sulfate. After evaporation of solvent, the crude product (320 mg, 0.717 mmol) was stirred in acetonitrile (9 mL), water (1 mL) and TFA (0.110 mL, 1.434 mmol) at room temperature overnight. Solvent was removed under vacuum. The crude residue was purified using a preparative IPLC (method A, 30-100% B in 10 min; then 100% B in 2 min). The desired fractions were combined and concentrated to give Intermediate 11I (70 mg, 0.211 mmol, 29.4% yield) as viscous oil: $^1$H NMR (400 MHz, chloroform-d) δ 6.98-6.93 (m, 2H), 6.77 (d, J=8.8 Hz, 1H), 4.37 (dd, J=11.0, 2.0 Hz, 1H), 4.28-4.21 (m, 1H), 4.20-4.14 (m, 1H), 3.95-3.82 (m, 2H); LC-MS: method A, RT=1.90 min, MS (ESI) m/z: 355.0 (M+Na)$^+$.

Intermediate 11J (S)-(8-(2-(difluoromethoxy)-7-methylquinoxalin-5-yl)-2,3-dihydro-[1,4]dioxino[2,3-e]benzofuran-3-yl)methanol

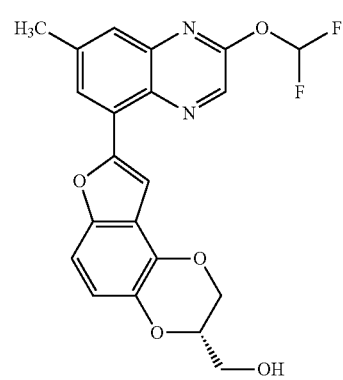
(11J)

To Intermediate I-1 (53.5 mg, 0.211 mmol), Intermediate 11I (70 mg, 0.211 mmol) and PdCl$_2$(dppf)—CH$_2$Cl$_2$ adduct (8.61 mg, 10.54 µmol) was added toluene (1.8 mL) and EtOH (0.6 mL). The mixture was sonicated for 1 min, and flushed with argon. Next, sodium carbonate (2M, 0.184 mL, 0.369 mmol) was added to the mixture. The reaction mixture was heated in a microwave reactor at 120° C. for 30 min. HPLC and LCMS indicated a completion of the reaction. The crude reaction mixture was directly loaded on an ISCO column for purification. The crude product was purified by flash chromatography (loading in chloroform, 5% to 60% EtOAc in hexane over 12 min using a 12 g silica gel cartridge). The desired fractions were combined and concentrated to yield Intermediate 11J (63 mg, 0.152 mmol, 72.1% yield) as an yellow solid. LC-MS: Method A, 40 to 100% B. RT=2.10 min, MS (ESI) m/z: 415.0 (M+H)$^+$.

Intermediate 11K: (S)-(8-(2-methoxy-7-methylquinoxalin-5-yl)-2,3-dihydro-[1,4]dioxino[2,3-e]benzofuran-3-yl)methanol

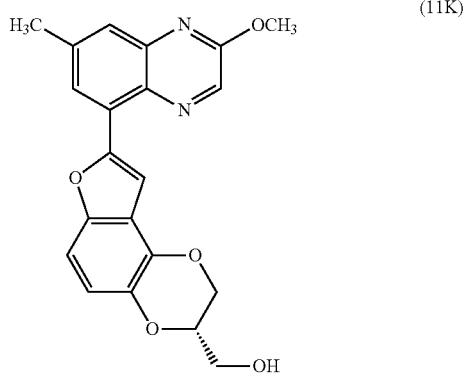 [SMILES: COc1cnc2c(-c3cc4c5c(ccc4o3)O[C@@H](CO)CO5)cc(C)cc2n1]

(11K)

To Intermediate 11J (63 mg, 0.152 mmol) dissolved in THF (2 mL) and MeOH (1.0 mL) at room temperature was added 4.3 M sodium methoxide in MeOH (0.177 mL, 0.760 mmol). The reaction mixture was stirred at room temperature overnight. LCMS indicated a completion of the reaction. The reaction mixture was quenched with 1.0 N HCl (0.608 mL, 0.608 mmol), diluted with EtOAc. The organic layer was washed with brine, dried and concentrated to give Intermediate 11K (54 mg, 0.140 mmol, 92% yield) as yellow solid. $^1$H NMR (500 MHz, chloroform-d) δ 8.53 (s, 1H), 8.14 (s, 1H), 8.11 (d, J=1.4 Hz, 1H), 7.64 (s, 1H), 7.10 (d, J=8.8 Hz, 1H), 6.93 (d, J=8.8 Hz, 1H), 4.49 (dd, J=11.0, 1.9 Hz, 1H), 4.39-4.34 (m, 1H), 4.32-4.27 (m, 1H), 4.14 (s, 3H), 4.03-3.98 (m, 1H), 3.97-3.91 (m, 1H), 2.64 (s, 3H); LC-MS: Method A, 40 to 100% B. RT=2.11 min, MS (ESI) m/z: 379.2 (M+H)$^+$.

Intermediate 11L: [(11R)-4-(2-methoxy-7-methylquinoxalin-5-yl)-5,10,13-trioxatricyclo[7.4.0.0^{2,6}]trideca-1(9), 2(6), 3,7-tetraen-11-yl]methyl chloroformate

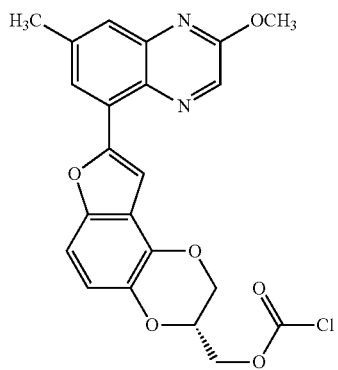

(11L)

To a solution of Intermediate 11K (54 mg, 0.143 mmol) in THF (2.0 mL) at room temperature was added 15% phosgene in toluene (0.403 mL, 0.571 mmol). The reaction mixture was left stirring at room temperature overnight. Solvent was completely removed under high vacuum to give Intermediate 11L (60 mg, 0.136 mmol, 95% yield) as a slightly yellow solid. It was used for the next step without purification. LC-MS: Method A, 50 to 100% B. RT=2.40 min, MS (ESI) m/z: 441.1 (M+H)$^+$.

Example 11

To a solution of 6-methylpyridin-3-amine (14.72 mg, 0.136 mmol) in DCM (0.8 mL) was added DIEA (0.048 mL, 0.272 mmol), followed by addition of Intermediate 11L (14.72 mg, 0.136 mmol) in THF (0.8 mL). The reaction mixture was stirred at room temperature for 1.0 h, quenched by addition of a small amount of MeOH/water/0.1% TFA. Solvent was removed under vacuum. The crude was dissolved in DMSO and purified via preparative LC/MS (method C, 40-80% B over 17 minutes, then a 7-minute hold at 100% B). Fractions containing the desired product were combined and dried via centrifugal evaporation to yield Example 11 (5.0 mg). $^1$H NMR (500 MHz, DMSO-d$_6$) δ 10.33 (br. s., 1H), 8.71 (s, 1H), 8.67 (br. s., 1H), 8.06 (d, J=3.9 Hz, 2H), 8.02 (d, J=8.3 Hz, 1H), 7.69 (s, 1H), 7.49 (d, J=8.5 Hz, 1H), 7.20 (d, J=8.8 Hz, 1H), 6.96 (d, J=8.5 Hz, 1H), 4.63-4.57 (m, 2H), 4.54-4.48 (m, 1H), 4.47-4.40 (m, 1H), 4.26 (dd, J=11.7, 7.8 Hz, 1H), 4.08 (s, 3H), 2.60 (s, 3H); 2.50 (s, 3H); LC-MS: method H, RT=2.40 min, MS (ESI) m/z: 513.3 (M+H)$^+$. Analytical HPLC purity (method B): 96%.

Example 12

(R)-(8-(2-methoxy-7-methylquinoxalin-5-yl)-2,3-dihydro-[1,4]dioxino[2,3-e]benzofuran-3-yl)methyl (2-methylpyridin-4-yl)carbamate

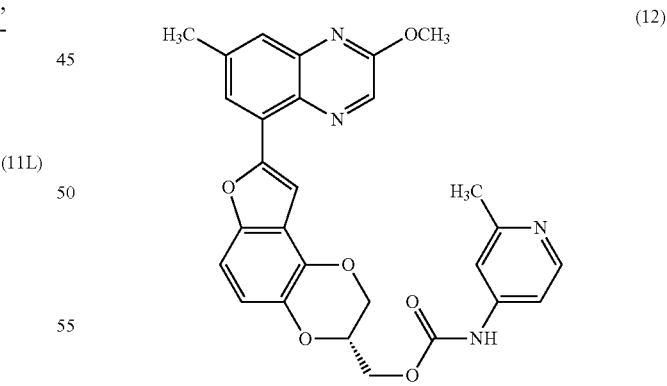

(12)

To a solution of 2-methylpyridin-4-amine (14.72 mg, 0.136 mmol) in DCM (0.8 mL) was added DIEA (0.048 mL, 0.272 mmol), followed by addition of Intermediate 11L (14.72 mg, 0.136 mmol) in THF (0.8 mL). The reaction mixture was stirred at room temperature for 1.0 h, quenched by addition of a small amount of MeOH/water/0.1% TFA. Solvent was removed under vacuum. The crude was dissolved in DMSO and purified via preparative LC/MS (method C, 40-80% B over 16 minutes, then a 7-minute hold at 100% B). Fractions containing the desired product were combined and dried via centrifugal evaporation to yield Example 12 (11.0 mg). $^1$H NMR (500 MHz, DMSO-$d_6$) δ 11.25 (br. s., 1H), 8.71 (s, 1H), 8.53 (d, J=6.6 Hz, 1H), 8.07 (s, 2H), 7.75-7.67 (m, 3H), 7.21 (d, J=8.8 Hz, 1H), 6.96 (d, J=8.8 Hz, 1H), 4.66-4.56 (m, 3H), 4.54-4.47 (m, 1H), 4.28 (dd, J=11.3, 7.2 Hz, 1H), 4.08 (s, 3H), 2.61 (s, 6H); LC-MS: method H, RT=2.04 min, MS (ESI) m/z: 513.2 (M+H)$^+$. Analytical HPLC purity (method B): 98%.

Example 13

(R)-(8-(2-methoxy-7-methylquinoxalin-5-yl)-2,3-dihydro-[1,4]dioxino[2,3-e]benzofuran-3-yl)methyl (6-methoxypyridin-3-yl)carbamate

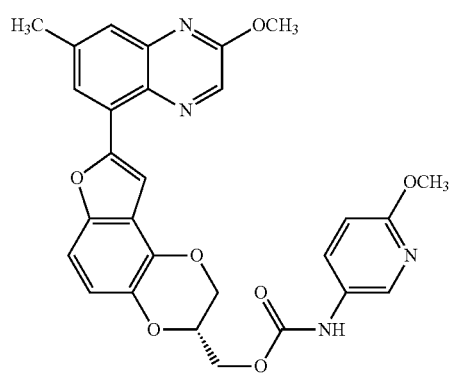

(13)

To a solution of 6-methoxypyridin-3-amine (16.90 mg, 0.136 mmol) in DCM (0.8 mL) was added DIEA (0.048 mL, 0.272 mmol), followed by addition of Intermediate 11L (16.90 mg, 0.136 mmol) in THF (0.8 mL). The reaction mixture was stirred at room temperature for 1.0 h. HPLC and LCMS indicated a completion of reaction. The reaction was quenched by addition of a small amount of MeOH/water/0.1% TFA. Solvent was removed under vacuum. The crude was dissolved in DMSO and purified via preparative LC/MS (method C, 60-100% B over 16 minutes, then a 7-minute hold at 100% B). Fractions containing the desired product were combined and dried via centrifugal evaporation to yield Example 13 (6.7 mg). $^1$H NMR (500 MHz, DMSO-$d_6$) δ 8.71 (s, 1H), 8.25 (br. s., 1H), 8.07 (br. s., 2H), 7.80 (d, J=8.3 Hz, 1H), 7.68 (s, 1H), 7.20 (d, J=8.8 Hz, 1H), 6.96 (d, J=8.8 Hz, 1H), 6.81 (d, J=9.1 Hz, 1H), 4.62-4.54 (m, 2H), 4.48-4.43 (m, 1H), 4.42-4.36 (m, 1H), 4.25 (dd, J=11.0, 7.4 Hz, 1H), 4.08 (s, 3H), 3.82 (s, 3H), 2.60 (s, 3H); LC-MS: method H, RT=2.43 min, MS (ESI) m/z: 529.2 (M+H)$^+$. Analytical HPLC purity (method B): 98%.

Example 14

(R)-(8-(2-methoxy-7-methylquinoxalin-5-yl)-6-methyl-2,3-dihydro-[1,4]dioxino[2,3-e]benzofuran-3-yl)methyl (6-methylpyridin-3-yl)carbamate

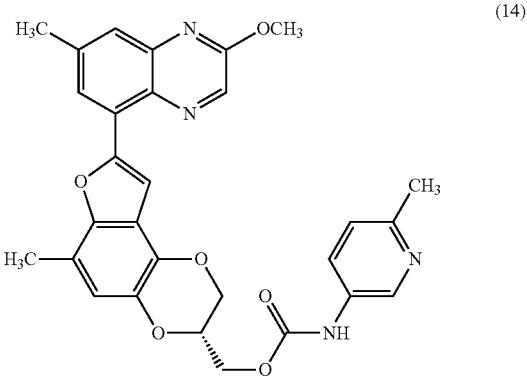

(14)

Intermediate 14A: (R)-tert-butyldimethyl((6-methyl-2,3-dihydro-[1,4]dioxino[2,3-e]benzofuran-3-yl)methoxy)silane

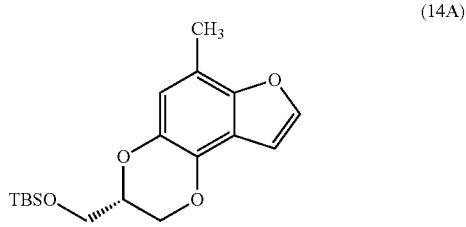 [SMILES: Cc1cc2c(c3ccoc13)OC[C@H](CO[Si](C)(C)C(C)(C)C)O2]

(14A)

To a microwave vial containing PdCl$_2$(dppf)—CH$_2$Cl$_2$ adduct (25.4 mg, 0.031 mmol) was added Intermediate 1 IG (355 mg, 0.889 mmol) in THF (5.0 mL). 2.0 M Dimethyl zinc in toluene (0.889 mL, 1.778 mmol) was added dropwise. The reaction mixture was sealed and heated at 78° C. for 2.0 h with stirring. HPLC and LCMS indicated a completion of the reaction. After it was cooled to ambient temperature, the reaction mixture was diluted with EtOAc, quenched by dropwise addition of 0.5 N HCl. The organic layer was washed with brine, dried over sodium sulfate and concentrated. The crude product was purified by flash chromatography (loading in chloroform, 0% to 25% EtOAc in hexane over 12 min using a 12 g silica gel cartridge). The desired fractions were combined and concentrated to yield Intermediate 14A (268 mg, 0.800 mmol, 90% yield) as colorless oil. $^1$H NMR (500 MHz, chloroform-d) δ 7.53 (d, J=1.9 Hz, 1H), 6.79 (d, J=2.2 Hz, 1H), 6.66 (s, 1H), 4.41 (dd, J=11.0, 2.2 Hz, 1H), 4.24-4.20 (m, 1H), 4.16-4.12 (m, 1H), 3.93 (dd, J=10.7, 4.7 Hz, 1H), 3.81 (dd, J=10.7, 6.9 Hz, 1H), 2.42 (d, J=0.8 Hz, 3H), 0.92 (s, 9H), 0.11 (s, 3H), 0.10 (s, 3H); LC-MS: method H, 2 to 98% B. RT=1.30 min, MS (ESI) m/z: 335.2 (M+H)$^+$.

Intermediate 14B (S)-(8-iodo-6-methyl-2,3-dihydro-[1,4]dioxino[2,3-e]benzofuran-3-yl)methanol

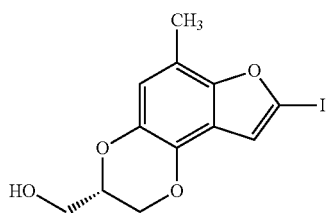
(14B)

To diisopropylamine (0.230 mL, 1.614 mmol) in THF (3.0 mL) at −78° C. was added 1.6 N n-BuLi in hexanes (1.009 mL, 1.614 mmol). The reaction mixture was stirred at −78° C. for 20 min. Intermediate 14A (360 mg, 1.076 mmol) in THF (1.0 mL) was added dropwise. The reaction mixture was stirred at −78° C. for 0.5 h. Iodine (382 mg, 1.507 mmol) in THF (1.0 mL) was added dropwise until the brown color persisted (ca 1.2 eq), and the reaction mixture was stirred at −78° C. for 0.5 h, then at room temperature overnight. The reaction mixture was diluted with EtOAc, quenched with saturated ammonium chloride (3.0 mL) and 10% $Na_2S_2O_3$ (4.0 mL). After stirring at room temperature for 10 min, the organic layer was washed with brine, dried over sodium sulfate. After evaporation of solvent, the crude product (480 mg, 1.043 mmol) was stirred in acetonitrile (9 mL), water (1 mL) and TFA (0.056 mL, 0.730 mmol) over the weekend. Solvent was removed under vacuum. The crude residue was purified using a preparative HPLC (method A, 40-100% B in 10 min; then 100% B in 2 min). The desired fractions were combined and concentrated to give Intermediate 14B (480 mg, 1.043 mmol). $^1$H NMR (400 MHz, chloroform-d) δ 6.92 (s, 1H), 6.56 (d, J=0.9 Hz, 1H), 4.33 (dd, J=11.1, 2.1 Hz, 1H), 4.26-4.19 (m, 1H), 4.17-4.10 (m, 1H), 3.92-3.80 (m, 2H), 2.36 (d, J=0.7 Hz, 3H); LC-MS: method A, RT=2.00 min, MS (ESI) m/z: 369.0 (M+Na)$^+$.

Intermediate 14C (S)-(8-(2-(difluoromethoxy)-7-methylquinoxalin-5-yl)-6-methyl-2,3-dihydro-[1,4]dioxino [2,3-e]benzofuran-3-yl)methanol

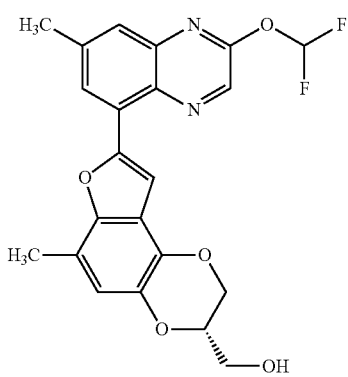
(14C)

To Intermediate I-1 (66.0 mg, 0.260 mmol), Intermediate 14B (90 mg, 0.260 mmol) and $PdCl_2$(dppf)—$CH_2Cl_2$ adduct (10.62 mg, 0.013 mmol) was added toluene (1.8 mL) and EtOH (0.6 mL). The mixture was sonicated for 1 min, and flushed with argon. To this was added sodium carbonate (2M, 0.228 mL, 0.455 mmol). The reaction mixture was heated in a microwave reactor at 120° C. for 30 min. HPLC and LCMS indicated a completion of the reaction. The crude reaction mixture was directly loaded on an ISCO column for purification. The crude product was purified by flash chromatography (loading in chloroform, 5% to 60% EtOAc in hexane over 10 min using a 12 g silica gel cartridge). The desired fractions were combined and concentrated to yield Intermediate 14C (65 mg, 0.152 mmol, 58.4% yield) as an yellow solid. LC-MS: Method A, 40 to 100% B. RT=2.22 min, MS (ESI) m/z: 429.1 (M+H)$^+$.

Intermediate 14D (S)-(8-(2-methoxy-7-methylquinoxalin-5-yl)-6-methyl-2,3-dihydro-[1,4]dioxino[2,3-e]be nzofuran-3-yl)methanol

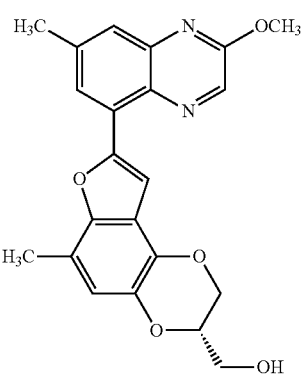
(14D)

To Intermediate 14C (65 mg, 0.152 mmol) dissolved in THF (2 mL) and MeOH (1.0 mL) at room temperature was added 4.3 M sodium methoxide in MeOH (0.176 mL, 0.759 mmol). The reaction mixture was stirred at room temperature overnight. LCMS indicated a completion of the reaction. The reaction mixture was quenched with 1.0 N HCl (0.607 mL, 0.607 mmol), diluted with EtOAc. The organic layer was washed with brine, dried and concentrated to give Intermediate 14D (54 mg, 0.132 mmol, 87% yield) as yellow film. This was used for the next step without further purification. $^1$H NMR (500 MHz, DMSO-$d_6$) δ 8.72 (s, 1H), 8.10 (d, J=1.7 Hz, 1H), 8.06 (s, 1H), 7.70 (d, J=0.8 Hz, 1H), 6.79 (d, J=0.8 Hz, 1H), 5.13 (t, J=5.8 Hz, 1H), 4.52 (dd, J=11.1, 2.1 Hz, 1H), 4.17 (dd, J=11.1, 7.6 Hz, 1H), 4.11 (s, 3H), 3.79-3.74 (m, 1H), 3.73-3.67 (m, 1H), 2.64 (s, 3H), 2.51 (s, 3H); LC-MS: Method A, 40 to 100% B. RT=2.27 min, MS (ESI) m/z 393.2 (M+H)$^+$.

Intermediate 14E (R)-(8-(2-methoxy-7-methylquinoxalin-5-yl)-6-methyl-2,3-dihydro-[1,4]dioxino[2,3-e]benzofuran-3-yl)methyl carbonochloridate

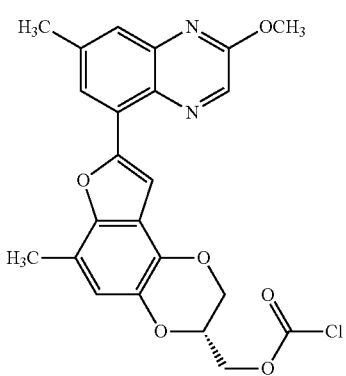

(14E)

To a solution of Intermediate 14D (54 mg, 0.138 mmol) in THF (2.0 mL) at room temperature was added 15% phosgene in toluene (0.388 mL, 0.550 mmol). The reaction mixture was left stirring at room temperature overnight. Solvent was removed under high vacuum to give Intermediate 14E (60 mg, 0.132 mmol, 96% yield) as a slightly yellow solid. It was used for the next step without purification. LC-MS: Method A, 50 to 100% B. RT=2.20 min, MS (ESI) m/z: 455.1 $(M+H)^+$.

Example 14

To a solution of 6-methylpyridin-3-amine (14.26 mg, 0.132 mmol) in DCM (0.8 mL) was added DIEA (0.046 mL, 0.264 mmol), followed by addition of Intermediate 14E (14.26 mg, 0.132 mmol) in THF (0.8 mL). The reaction mixture was stirred at room temperature for 1.0 h, quenched by addition of a small amount of MeOH/water/0.1% TFA. Solvent was removed under vacuum. The crude was dissolved in DMSO and purified via preparative LC/MS (method C, 45-90% B over 16 minutes, then a 7-minute hold at 100% B). Fractions containing the desired product were combined and dried via centrifugal evaporation to yield Example 14 (5.3 mg). $^1$H NMR (500 MHz, DMSO-$d_6$) δ 10.30 (br. s., 1H), 8.70 (s, 1H), 8.66 (br. s., 1H), 8.08 (s, 1H), 8.05 (s, 1H), 8.00 (d, J=8.3 Hz, 1H), 7.68 (s, 1H), 7.47 (d, J=8.5 Hz, 1H), 6.79 (s, 1H), 4.59-4.52 (m, 2H), 4.51-4.40 (m, 2H), 4.23 (dd, J=11.6, 7.2 Hz, 1H), 4.08 (s, 3H), 2.61 (s, 3H), 2.47 (s, 3H); LC-MS: method H, RT=2.13 min, MS (ESI) m/z: 527.2 $(M+H)^+$. Analytical IPLC purity (method B): 95%.

Example 15

(R)-(8-(2-methoxy-7-methylquinoxalin-5-yl)-6-methyl-2,3-dihydro-[1,4]dioxino[2,3-e]benzofuran-3-yl)methyl (2-methylpyridin-4-yl)carbamate

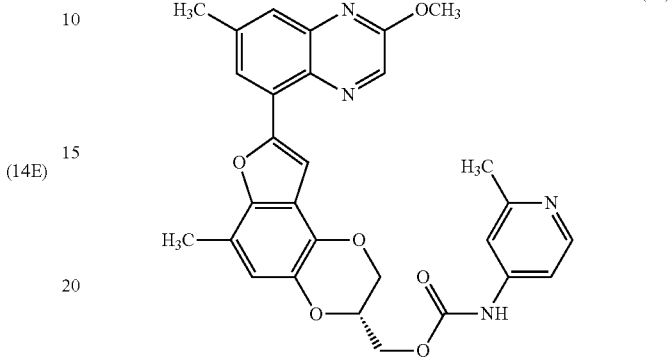

(15)

To a solution of 2-methylpyridin-4-amine (14.26 mg, 0.132 mmol) in DCM (0.8 mL) was added DIEA (0.046 mL, 0.264 mmol), followed by addition of Intermediate 14E (14.26 mg, 0.132 mmol) in THF (0.8 mL). The reaction mixture was stirred at room temperature for 1.0 h, quenched by addition of a small amount of MeOH/water/0.1% TFA. Solvent was removed under vacuum. The crude was dissolved in DMSO and purified via preparative LC/MS (method C, 65-100% B over 20 minutes, then a 5-minute hold at 100% B). Fractions containing the desired product were combined and dried via centrifugal evaporation to yield the Example 15 (12.9 mg). $^1$H NMR (500 MHz, DMSO-$d_6$) δ 8.70 (s, 1H), 8.43 (d, J=6.3 Hz, 1H), 8.09 (s, 1H), 8.05 (s, 1H), 7.69 (s, 1H), 7.57 (s, 1H), 7.53 (d, J=5.8 Hz, 1H), 6.79 (s, 1H), 4.61-4.51 (m, 3H), 4.50-4.44 (m, 1H), 4.24 (dd, J=11.3, 6.9 Hz, 1H), 4.08 (s, 3H), 2.62 (s, 3H), 2.49 (s, 3H); LC-MS: method H, RT=2.15 min, MS (ESI) m/z: 527.3 $(M+H)^+$. Analytical HPLC purity (method B): 97%.

Example 16

(R)-(8-(2-methoxy-7-methylquinoxalin-5-yl)-6-methyl-2,3-dihydro-[1,4]dioxino[2,3-e]benzofuran-3-yl)methyl (6-methoxypyridin-3-yl)carbamate

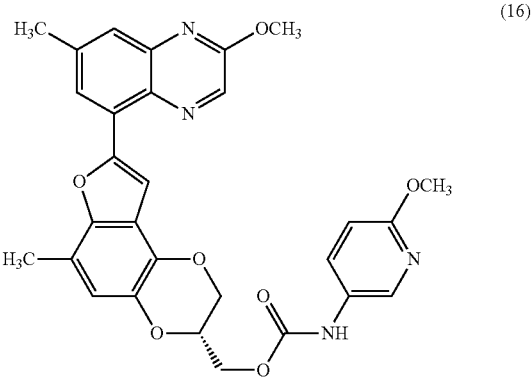 [SMILES: COc1ccc(NC(=O)OC[C@H]2COc3c(cc(C)c4oc(-c5cc(C)cc6nc(OC)cnc56)cc34)O2)cn1]

(16)

To a solution of 6-methoxypyridin-3-amine (16.38 mg, 0.132 mmol) in DCM (0.8 mL) was added DIEA (0.046 mL, 0.264 mmol), followed by addition of Intermediate 14E (16.38 mg, 0.132 mmol) in THF (0.8 mL). The reaction mixture was stirred at room temperature for 1.0 h, quenched by addition of a small amount of MeOH/water/0.1% TFA. Solvent was removed under vacuum. The crude was dissolved in DMSO and purified via preparative LC/MS (method C, 60-100% B over 16 minutes, then a 7-minute hold at 100% B). Fractions containing the desired product were combined and dried via centrifugal evaporation to yield Example 16 (8.9 mg). $^1$H NMR (500 MHz, DMSO-$d_6$) δ 8.70 (s, 1H), 8.25 (br. s., 1H), 8.09 (s, 1H), 8.05 (s, 1H), 7.80 (d, J=7.7 Hz, 1H), 7.68 (s, 1H), 6.83-6.78 (m, 2H), 4.54 (d, J=9.6 Hz, 2H), 4.46-4.41 (m, 1H), 4.41-4.35 (m, 1H), 4.21 (dd, J=11.6, 7.4 Hz, 1H), 4.08 (s, 3H), 3.82 (s, 3H), 2.61 (s, 3H), 2.49 (s, 3H); LC-MS: method H, RT=2.73 min, MS (ESI) m/z: 543.5 (M+H)$^+$. Analytical HPLC purity (method B): 95%.

Example 17

(4-chloro-2-(2-methoxy-7-methylquinoxalin-5-yl)-7,8-dihydrobenzofuro[5,4-d]thiazol-7-yl)methyl (6-methoxypyridin-3-yl)carbamate

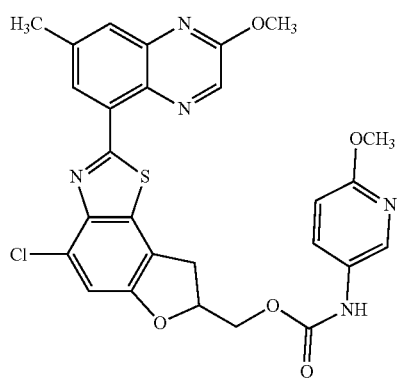

Intermediate 17A: (6-chloro-2,3-dihydrobenzofuran-2-yl)methyl acetate

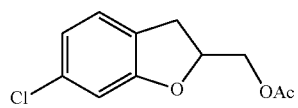

To a solution of (6-chloro-2,3-dihydrobenzofuran-2-yl)methanol (0.735 g, 3.98 mmol) in THF (9 mL) at 0° C. was added TEA (1.387 mL, 9.95 mmol), followed by acetyl chloride (0.354 mL, 4.98 mmol) in THF (3.0 mL) dropwise. The reaction mixture was stirred at 0° C. for 10 min, and at room temperature for 1.0 h. IPLC indicated a completion of the reaction. The mixture was diluted with EtOAc, washed with water. The organic layer was washed with 0.5 N HCl, saturated sodium bicarbonate, brine and dried over sodium sulfate. After evaporation of solvent, the crude product was purified by flash chromatography (loading in chloroform, 0% to 40% EtOAc in hexane over 12 min using a 24 g silica gel cartridge). The desired fractions were combined and concentrated to yield Intermediate 17A (0.9 g, 3.97 mmol, 100% yield) as oil. $^1$H NMR (500 MHz, chloroform-d) δ 7.06 (d, J=8.0 Hz, 1H), 6.83 (dd, J=8.0, 1.9 Hz, 1H), 6.80 (d, J=1.9 Hz, 1H), 5.07-4.98 (m, 1H), 4.32 (dd, J=12.1, 3.6 Hz, 1H), 4.21 (dd, J=11.8, 6.9 Hz, 1H), 3.27 (dd, J=15.8, 9.5 Hz, 1H), 2.94 (ddd, J=15.7, 7.2, 0.8 Hz, 1H), 2.09 (s, 3H); LC-MS: method H, 2 to 98% B. RT=0.94 min, MS (ESI) m/z: 227.0 (M+H)$^+$.

Intermediate 17B: (6-chloro-5-nitro-2,3-dihydrobenzofuran-2-yl)methyl acetate

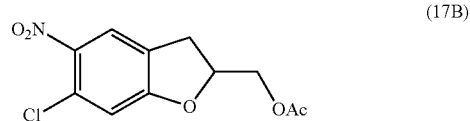 [SMILES: CC(=O)OCC1Cc2cc([N+](=O)[O-])c(Cl)cc2O1]

To a solution of Intermediate 17A (0.9 g, 3.97 mmol) in acetic acid (3 mL) cooled at 0° C. with an ice-bath was added fuming nitric acid (0.927 mL, 19.85 mmol) dropwise. The reaction mixture was stirred at 0° C. for 0.5 h, and then at room temperature overnight. It was quenched with ice water/EtOAc. The organic layer was washed with 1.5 M dipotassium phosphate (3×), brine, dried over sodium sulfate and concentrated. The crude product was purified by flash chromatography (loading in chloroform, 0% to 60% EtOAc in hexane over 15 min using a 24 g silica gel cartridge). The desired fractions were combined and concentrated to yield Intermediate 17B (0.611 g, 2.249 mmol, 56.6% yield): $^1$H NMR (500 MHz, chloroform-d) δ 7.86 (t, J=1.2 Hz, 1H), 6.92 (s, 1H), 5.18 (dddd, J=9.6, 7.1, 6.1, 3.6 Hz, 1H), 4.37 (dd, J=12.4, 3.6 Hz, 1H), 4.28-4.22 (m, 1H), 3.38 (ddd, J=16.2, 9.6, 1.1 Hz, 1H), 3.06 (ddd, J=16.2, 7.2, 1.1 Hz, 1H), 2.09 (s, 3H); LC-MS: method H, 2 to 98% B. RT=0.90 min, MS (ESI) m/z: 272.0 (M+H)$^+$.

Intermediate 17C: (5-amino-6-chloro-2,3-dihydrobenzofuran-2-yl)methyl acetate

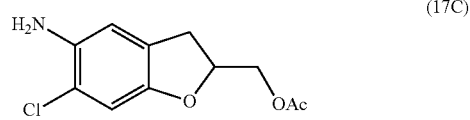

To a solution of Intermediate 17B (0.61 g, 2.246 mmol) in MeOH (6) and THF (4) cooled with an water bath was added ammonium chloride (1.922 g, 35.9 mmol) and zinc dust (1.174 g, 17.96 mmol). The reaction mixture was stirred at room temperature overnight. MeOH was removed under vacuum. The residue was diluted with EtOAc/1.5 M dipotassium phosphate and stirred at room temperature for 3 min. The mixture was filtered through a pad of wet celite to remove insoluble material. The filtrate was collected, organic layer was washed with brine, dried over sodium sulfate, concentrated. The crude product was purified by flash chromatography (loading in chloroform, 5% to 85% EtOAc in hexane over 10 min using a 12 g silica gel cartridge). The desired fractions were combined and concentrated to yield Intermediate 17C (0.49 g, 2.028 mmol, 90% yield) as slightly yellow oil which turned to solid after standing at room temperature. $^1$H NMR (500 MHz, methanol-$d_4$) δ 6.79-6.76 (m, 1H), 6.65 (s, 1H), 4.97-4.90 (m, 1H), 4.29-4.24 (m, 1H), 4.23-4.18 (m, 1H), 3.28-3.20 (m, 1H), 2.94 (ddd, J=16.0, 7.0, 1.0 Hz, 1H), 2.04 (s, 3H); LC-MS: method H, 2 to 98% B. RT=0.6 min, MS (ESI) m/z: 242.1 (M+H)$^+$.

Intermediate 17D: (2-amino-4-chloro-7,8-dihydrobenzofuro[5,4-d]thiazol-7-yl)methyl acetate

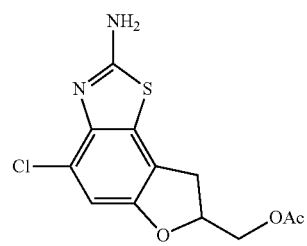

(17D)

To Intermediate 17C (0.49 g, 2.028 mmol) in acetonitrile (8 mL) was added ammonium thiocyanate (0.232 g, 3.04 mmol). The reaction mixture was stirred at room temperature for 10 min. Benzyltrimethylammonium tribromide (0.830 g, 2.129 mmol) in acetonitrile (4 mL) was added dropwise (5 min). The reaction mixture was stirred at room temperature overnight. IPLC and LCMS indicated a completion of the reaction. Most of the acetonitrile was removed under vacuum. The mixture was diluted with EtOAc/THF/ saturated sodium bicarbonate. The insoluble material was removed by filtration over a pad of wet celite. The organic layer of the filtrate was collected, washed with brine, dried over sodium sulfate. After evaporation of solvent, the crude product was triturated with EtOAc/hexanes (1:3). Intermediate 17D (0.42 g, 1.406 mmol, 69.3% yield) was collected as a pale yellow solid. $^1$H NMR (500 MHz, DMSO-$d_6$) δ 7.61 (s, 2H), 6.82 (s, 1H), 5.13-5.06 (m, 1H), 4.30-4.25 (m, 1H), 4.22-4.16 (m, 1H), 3.28 (m, 1H), 2.99 (dd, J=16.0, 7.4 Hz, 1H), 2.03 (s, 3H); LC-MS: method H, 2 to 98% B. RT=0.68 min, MS (ESI) m/z: 299.1 (M+H)$^+$.

Intermediate 17E: (2-bromo-4-chloro-7,8-dihydrobenzofuro[5,4-d]thiazol-7-yl)methyl acetate

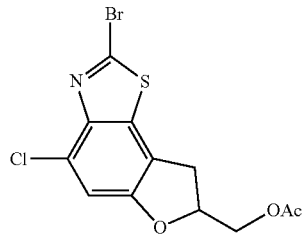

(17E)

Tert-butyl nitrite (0.325 mL, 2.460 mmol) was added to copper (II) bromide (0.534 g, 2.390 mmol) in dry acetonitrile (5 mL) under argon. The reaction mixture was stirred at room temperature for 10 min. A suspension of Intermediate 17D (0.42 g, 1.406 mmol) in dry acetonitrile (6 mL) was added dropwise. The reaction mixture was stirred at room temperature for 2.0 h. IPLC and LCMS indicated a completion of the reaction. Acetonitrile was removed under vacuum, the reaction mixture was diluted with EtOAc, quenched with 1.0 N HCl. The organic layer was collected, washed with 0.5 N HCl (2×), saturated sodium bicarbonate, brine and dried over sodium sulfate. After evaporation of solvent, the crude product was purified by flash chromatography (loading in chloroform, 5% to 50% EtOAc in hexane over 12 min using a 12 g silica gel cartridge). The desired fractions were combined and concentrated to yield Intermediate 17E (0.36 g, 0.993 mmol, 70.6% yield) as an yellow solid. $^1$H NMR (500 MHz, chloroform-d) δ 7.03 (s, 1H), 5.22-5.15 (m, 1H), 4.40-4.35 (m, 1H), 4.28 (dd, J=12.1, 6.3 Hz, 1H), 3.39 (dd, J=15.7, 9.6 Hz, 1H), 3.08 (dd, J=15.7, 7.2 Hz, 1H), 2.09 (s, 3H); LC-MS: method H, 2 to 98% B. RT=1.01 min, MS (ESI) m/z: 364.0 and 366.0 (M+H)$^+$.

Intermediate 17F: (2-bromo-4-chloro-7,8-dihydrobenzofuro[5,4-d]thiazol-7-yl)methanol

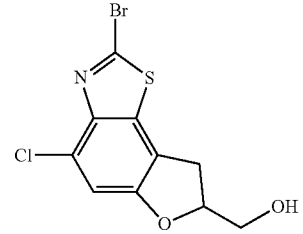

(17F)

To Intermediate 17E (0.36 g, 0.993 mmol) dissolved in THF (3.0 mL) and cooled with an ice-bath was added 1.0 N NaOH (1.261 mL, 1.261 mmol). After 2 min stirring, MeOH (0.8 mL) was added dropwise. After another 20 min stirring at 0° C., HPLC indicated a completion of the reaction. 1.0 N HCl (1.0 mL) was added. The mixture was diluted with EtOAc/THF/water. The organic layer was collected, washed with saturated sodium bicarbonate, brine and dried over sodium sulfate. After evaporation of solvent, Intermediate 17F (0.3 g, 0.936 mmol, 94% yield) was obtained as a white solid. $^1$H NMR (500 MHz, chloroform-d) δ 7.01 (s, 1H), 5.14-5.07 (m, 1H), 3.95 (d, J=12.1 Hz, 1H), 3.83-3.77 (m, 1H), 3.32 (dd, J=15.7, 9.6 Hz, 1H), 3.17 (dd, J=15.7, 7.4 Hz, 1H), 1.90-1.85 (m, 1H); LC-MS: method H, 2 to 98% B. RT=0.86 min, MS (ESI) m/z: 322.0 and 324.0 (M+H)$^+$.

Intermediate 17G (4-chloro-2-(2-(difluoromethoxy)-7-methylquinoxa-lin-5-yl)-7,8-dihydrobenzofuro[5,4-d]thiazol-7-yl) methanol

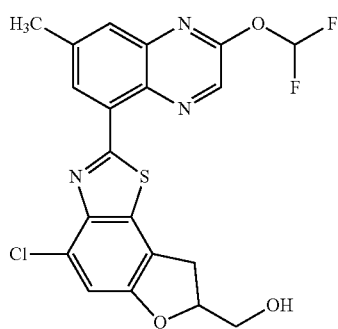

(17G)

To Intermediate I-1 (79 mg, 0.312 mmol), Intermediate 17F (100 mg, 0.312 mmol) and PdCl$_2$ PdCl$_2$(dppf)—CH$_2$Cl$_2$ adduct (10.19 mg, 0.012 mmol) was added toluene (2.25 mL) and EtOH (0.75 mL). The mixture was sonicated for 1 min, and flushed with argon. To the mixture was added sodium carbonate (2M, 0.312 mL, 0.624 mmol). The reaction mixture was heated in a microwave reactor at 130° C. for 45 min. HPLC and LCMS indicated a completion of the reaction. The crude reaction mixture was diluted with EtOAc/water. The insoluble material was removed by filtration. The organic layer was washed with brine, dried over sodium sulfate and concentrated. The crude product was purified by flash chromatography (loading in chloroform, 5% to 75% EtOAc in hexane over 10 min using a 12 g silica gel cartridge). The desired fractions were combined and concentrated to yield Intermediate 17G (88 mg, 0.196 mmol, 62.7% yield) as a yellow solid. LC-MS: method H, 2 to 98% B. RT=1.13 min, MS (ESI) m/z: 450.1 (M+H)$^+$.

Intermediate 17H (4-chloro-2-(2-methoxy-7-methylquinoxalin-5-yl)-7,8-dihydrobenzofuro[5,4-d]thiazol-7-yl)methanol

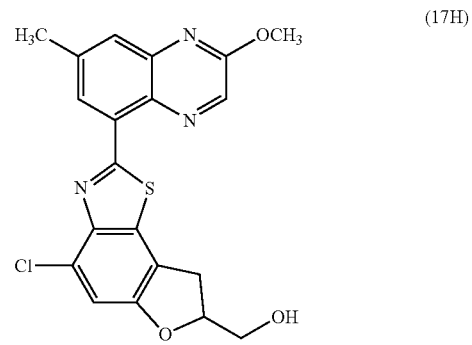 [SMILES: COc1cnc2c(-c3nc4c(Cl)cc5c(c4s3)CC(CO)O5)cc(C)cc2n1]

(17H)

To Intermediate 17G (88 mg, 0.196 mmol) dissolved in THF (2.0 mL) at room temperature was added 4.0 M sodium methoxide in MeOH (0.245 mL, 0.978 mmol). The reaction mixture was stirred at room temperature for 2 h. LCMS indicated a completion of the reaction. The reaction mixture was quenched with 0.5 N HCl (2.0 mL), diluted with EtOAc/THF/water. The organic layer was washed with saturated sodium bicarbonate, brine, dried and concentrated to give Intermediate 17H (80 mg, 0.193 mmol, 99% yield) as an yellow solid. $^1$H NMR (500 MHz, DMSO-d$_6$) δ 8.72 (s, 1H), 8.56 (d, J=1.7 Hz, 1H), 7.82 (dd, J=1.8, 1.0 Hz, 1H), 7.19 (s, 1H), 5.10-5.06 (m, 2H), 4.08 (s, 3H), 3.73-3.68 (m, 1H), 3.67-3.61 (m, 1H), 3.42 (dd, J=15.7, 9.6 Hz, 1H), 3.19 (dd, J=15.7, 7.2 Hz, 1H), 2.64 (s, 3H); LC-MS: method H, 2 to 98% B. RT=1.15 min, MS (ESI) m/z: 414.1 (M+H)$^+$.

Intermediate 17I (4-chloro-2-(2-methoxy-7-methylquinoxalin-5-yl)-7,8-dihydrobenzofuro[5,4-d]thiazol-7-yl)methyl carbonochloridate

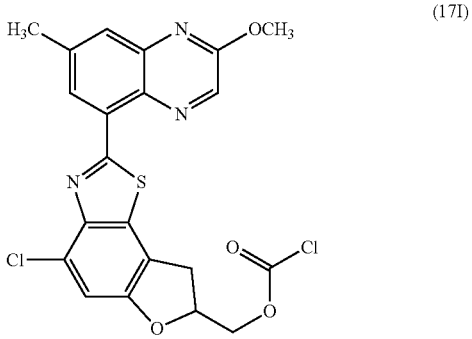 [SMILES: COc1cnc2c(-c3nc4c(Cl)cc5c(c4s3)CC(COC(=O)Cl)O5)cc(C)cc2n1]

(17I)

To a suspension of Intermediate 17H (80 mg, 0.193 mmol) in THF (4.0 mL) at room temperature was added 15% phosgene in toluene (0.545 mL, 0.773 mmol). The reaction mixture was left stirring at room temperature overnight. HPLC and LCMS indicated the reaction mixture was ca 70% complete. Solvent was completely removed under high vacuum to give Intermediate 17I (90 mg, 0.094 mmol, 48.9% yield) as a slightly yellow solid. It was used for the next step without purification. LC-MS: Method A, 40 to 100% B. RT=2.56 min, MS (ESI) m/z: 476.1 (M+H)⁺.

Example 17

To a solution of 6-methoxypyridin-3-amine (18.76 mg, 0.151 mmol) in DMF (0.8 mL) was added DIEA (0.053 mL, 0.302 mmol), followed by addition of Intermediate 171 (18 mg, 0.038 mmol) in DMF (0.8 mL). The reaction mixture was stirred at room temperature for 1.0 h, quenched by addition of a small amount of MeOH/water/0.1% TFA. The crude was dissolved in DMSO and purified via preparative LC/MS (method C, 65-100% B over 20 minutes, then a 5-minute hold at 100% B). Fractions containing the desired product were combined and dried via centrifugal evaporation to yield Example 17 (3.5 mg, 5.90 µmol, 15.60% yield): $^1$H NMR (500 MHz, DMSO-$d_6$) δ 8.76 (s, 1H), 8.59 (s, 1H), 8.22 (br. s., 1H), 7.86 (s, 1H), 7.27 (s, 1H), 6.52 (s, 1H), 5.33 (d, J=6.6 Hz, 1H), 4.47 (d, J=9.6 Hz, 1H), 4.33 (dd, J=11.8, 6.9 Hz, 1H), 4.09 (s, 3H), 3.79 (br. s., 3H), 3.57 (dd, J=16.1, 9.8 Hz, 1H), 2.66 (s, 3H); LC-MS: method H, RT=2.52 min, MS (ESI) m/z: 564.2 (M+H)⁺. Analytical HPLC purity (method B): 95%.

Example 18

(4-chloro-2-(2-methoxy-7-methylquinoxalin-5-yl)-7,8-dihydrobenzofuro[5,4-d]thiazol-7-yl)methyl pyridin-3-ylcarbamate

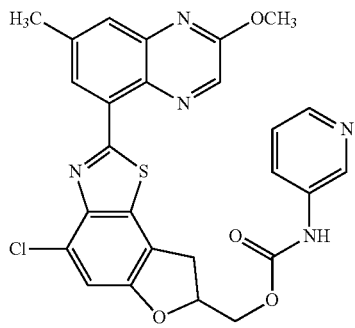

(18)

To a solution of pyridin-3-amine (14.23 mg, 0.151 mmol) in DMF (0.8 mL) was added DIEA (0.053 mL, 0.302 mmol), followed by addition of Intermediate 171 (18 mg, 0.038 mmol) in DMF (0.8 mL). The reaction mixture was stirred at room temperature for 1.0 h, quenched by addition of a small amount of MeOH/water/0.1% TFA. The crude was dissolved in DMSO and purified via preparative LC/MS (method C, 40-100% B over 20 minutes, then a 5-minute hold at 100% B). Fractions containing the desired product were combined and dried via centrifugal evaporation to yield Example 18 (4.2 mg, 7.31 µmol, 19.36% yield). $^1$H NMR (500 MHz, DMSO-$d_6$) δ 10.07 (br. s., 1H), 8.71 (s, 1H), 8.65 (br. s., 1H), 8.56 (s, 1H), 8.25 (br. s., 1H), 7.92 (br. s., 1H), 7.83 (s, 1H), 7.38 (br. s., 1H), 7.25 (s, 1H), 5.34 (br. m., 1H), 4.51 (d, J=9.8 Hz, 1H), 4.39 (dd, J=12.1, 6.9 Hz, 1H), 4.09 (s, 3H), 3.49 (br. m., 1H), 3.26 (dd, J=15.7, 7.5 Hz, 1H), 2.65 (s, 3H); LC-MS: method H, RT=2.78 min, MS (ESI) m/z: 534.1 (M+H)⁺. Analytical HPLC purity (method B): 93%.

Example 19

(4-chloro-2-(2-methoxy-7-methylquinoxalin-5-yl)-7,8-dihydrobenzofuro[5,4-d]thiazol-7-yl)methyl (6-methylpyridin-3-yl)carbamate

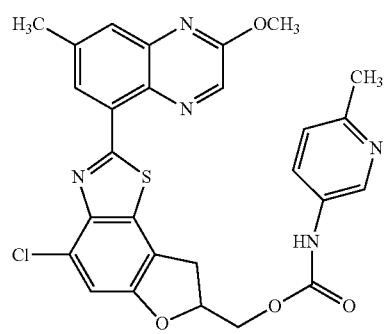

(19)

To a solution of 6-methylpyridin-3-amine (16.35 mg, 0.151 mmol) in DMF (0.8 mL) was added DIEA (0.053 mL, 0.302 mmol), followed by addition of Intermediate 171 (18 mg, 0.038 mmol) in DMF (0.8 mL). The reaction mixture was stirred at room temperature for 1.0 h, quenched by addition of a small amount of MeOH/water/0.1% TFA. The crude was dissolved in DMSO and purified via preparative LC/MS (method C, 40-100% B over 20 minutes, then a 5-minute hold at 100% B). Fractions containing the desired product were combined and dried via centrifugal evaporation to yield Example 19 (3.4 mg, 5.96 µmol, 15.76% yield). $^1$H NMR (500 MHz, DMSO-$d_6$) δ 8.71 (s, 1H), 8.56 (s, 1H), 7.97 (s, 3H), 7.82 (s, 1H), 7.25 (s, 1H), 5.35 (d, J=6.7 Hz, 1H), 4.51 (d, J=2.4 Hz, 1H), 4.41 (d, J=7.0 Hz, 1H), 4.09 (s, 3H), 3.55 (m, 1H), 3.25 (m, 1H), 2.65 (s, 3H), 2.45 (s, 3H); LC-MS: method H, RT=2.81 min, MS (ESI) m/z: 549.2 (M+H)⁺. Analytical HPLC purity (method B): 96%.

Example 20

(R)-(4-chloro-2-(2-methoxy-7-methylquinoxalin-5-yl)-7,8-dihydrobenzofuro[5,4-d]thiazo 1-7-yl)methyl (6-methylpyridin-3-yl)carbamate

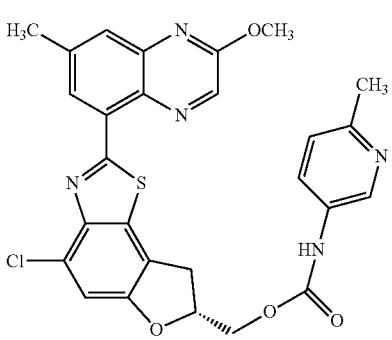

(20)

Intermediate 20A: (2-bromo-4-chloro-7,8-dihydrobenzofuro[5,4-d]thiazol-7-yl)methyl (6-methylpyridin-3-yl)carbamate

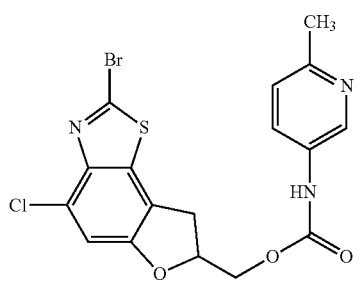

(20A)

To a solution of Intermediate 17F (195 mg, 0.608 mmol) in THF (5.0 mL) was added DIEA (0.351 mL, 2.007 mmol) followed by 15% phosgene in toluene (0.858 mL, 1.217 mmol) at 0° C. After 30 min stirring at 0° C., the reaction mixture was concentrated to white salts. The white salts were retaken in THF (5.0 mL), 6-methylpyridin-3-amine (92 mg, 0.852 mmol) was added, followed by DIEA (0.2 mL). The reaction mixture was stirred at room temperature for 30 min. The reaction mixture was diluted with EtOAc/water. The organic layer was washed with brine, dried over sodium sulfate and concentrated. The crude product was purified by flash chromatography (loading in chloroform, 10% to 100% EtOAc in hexane over 12 min using a 12 g silica gel cartridge). The desired fractions were combined and concentrated to yield Intermediate 20A (225 mg, 0.495 mmol, 81% yield) as a white solid. $^1$H NMR (500 MHz, CHLOROFORM-d) δ 8.35 (br. s., 1H), 7.81 (br. s., 1H), 7.10 (br. s., 1H), 7.02 (s, 1H), 6.88 (br. s., 1H), 5.27-5.20 (m, 1H), 4.51 (dd, J=12.0, 3.2 Hz, 1H), 4.38 (dd, J=12.0, 5.9 Hz, 1H), 3.42 (dd, J=15.7, 9.9 Hz, 1H), 3.14 (dd, J=15.7, 7.2 Hz, 1H), 2.50 (s, 3H); LC-MS: method H. RT=0.74 min, MS (ESI) m/z: 456.0 and 458.0 (M+H)$^+$.

Intermediate 20B (4-chloro-2-(2-methoxy-7-methylquinoxalin-5-yl)-7,8-dihydrobenzofuro[5,4-d]thiazol-7-yl)methyl (6-methylpyridin-3-yl)carbamate

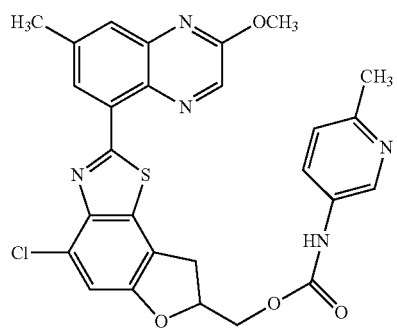

(20B)

To Intermediate I-9 (47.9 mg, 0.220 mmol), Intermediate 20A (100 mg, 0.220 mmol) and PdCl$_2$(dppf)—CH$_2$Cl$_2$ adduct (8.98 mg, 11.00 μmol) was added toluene (2.4 mL) and EtOH (0.8 mL). The mixture was sonicated for 1 min, and flushed with argon. To this was added sodium carbonate (2M, 0.220 mL, 0.440 mmol). The reaction mixture was heated in a microwave reactor at 135° C. for 45 min. HPLC indicated a completion of the reaction. The reaction mixture was directly loaded on a ISCO column for purification. The crude product was purified by flash chromatography (loading in chloroform, 0% to 85% EtOAc in CH$_2$Cl$_2$ over 10 min using a 12 g silica gel cartridge). The desired fractions were combined and concentrated to yield the crude product (100 mg) which was further purified by prep IPLC (method A, 40-100% B in 10 min; then 100% B in 2 min). The desired fractions were placed in a SpeedVac overnight to remove solvent, then lyophilized to give Intermediate 20B (73 mg, 0.133 mmol, 60.6% yield) as yellow solid. $^1$H NMR (500 MHz, DMSO-d$_6$) δ 8.71 (s, 1H), 8.56 (s, 1H), 7.97 (s, 3H), 7.82 (s, 1H), 7.25 (s, 1H), 5.35 (d, J=6.7 Hz, 1H), 4.51 (d, J=2.4 Hz, 1H), 4.41 (d, J=7.0 Hz, 1H), 4.09 (s, 3H), 3.55 (m, 1H), 3.25 (m, 1H), 2.65 (s, 3H), 2.45 (s, 3H); LC-MS: method H, RT=2.81 min, MS (ESI) m/z: 549.2 (M+H)$^+$.

Example 20

Intermediate 20B (73 mg, 0.133 mmol) was subject to chiral SFC for separation using the following conditions: Instrument: Burger Multigram II SFC; Column: Chiralpak IB, 30×250 mm, 5 micron; Mobile Phase: 40% MeOH/60% CO$_2$; Flow Conditions: 85 mL/min, 150 Bar, 40° C.; Detector Wavelength: 220 nm Injection Details: 1 mL of 12 mg/mL in MeOH/THF 1:1. The fast eluting fractions (first peak, RT=13.5 min) were concentrated and lyophilized to give Example 20 (31 mg, 0.055 mmol): $^1$H NMR (500 MHz, THF) δ 8.99 (br. s., 1H), 8.74 (d, J=1.7 Hz, 1H), 8.50 (s, 1H), 8.40 (br s, 1H), 7.91-7.81 (m, 1H), 7.76-7.72 (m, 1H), 7.07-7.02 (m, 1H), 5.30-5.23 (m, 1H), 4.49-4.44 (m, 1H), 4.42-4.36 (m, 1H), 4.09 (s, 3H), 3.50 (dd, J=15.5, 9.8 Hz, 1H), 3.26 (dd, J=15.4, 7.4 Hz, 1H), 2.64 (s, 3H), 2.38 (s, 3H); LC-MS: Method A, 40 to 100% B. RT=1.91 min, MS (ESI) m/z: 548.3 (M+H)$^+$. Analytical HPLC purity (method A): 98%.

Example 21 tert-butyl ((2-(2-(difluoromethoxy)-7-methylquinoxalin-5-yl)-4-fluoro-7,8-dihydro-[1,4]dioxino[2',3':3,4]benzo[1,2-d]thiazol-7-yl)methyl)carbamate

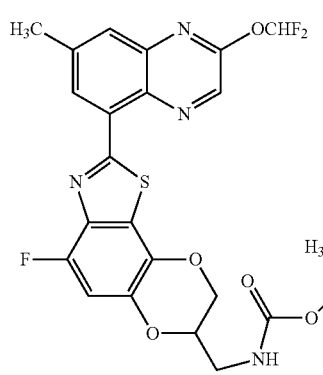

(21)

Intermediate 21A: 5-fluoro-2-(oxiran-2-ylmethoxy)benzaldehyde

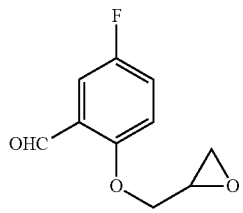

(21A)

To a solution of 5-fluoro-2-hydroxybenzaldehyde (1.1 g, 7.85 mmol) in DMF (20 mL) was added Cs$_2$CO$_3$ (5.63 g, 17.27 mmol), followed by 2-(bromomethyl)oxirane (1.210 mL, 14.13 mmol). The mixture was stirred at room temperature for 10 min, and at 50° C. for 1.5 h. After cooling to room temperature, the reaction mixture was diluted with EtOAc/water. The organic layer was collected, washed with brine and dried over sodium sulfate. After evaporation of solvent, the crude product was dissolved in a small amount of chloroform and charged to a 40 g silica gel cartridge which was eluted with hexanes for 3 min., then a 15 min gradient from 0% to 40% EtOAc in hexanes. The desired fractions were combined and concentrated to give Intermediate 21A (1.5 g, 7.65 mmol, 97% yield) as clear oil. $^1$H NMR (500 MHz, chloroform-d) δ 10.49 (d, J=3.3 Hz, 1H), 7.54 (dd, J=8.0, 3.3 Hz, 1H), 7.28-7.24 (m, 1H), 7.01 (dd, J=9.1, 3.9 Hz, 1H), 4.42 (dd, J=11.0, 2.8 Hz, 1H), 4.06 (dd, J=11.1, 5.9 Hz, 1H), 3.42 (ddt, J=5.7, 4.1, 2.8 Hz, 1H), 2.99-2.96 (m, 1H), 2.81 (dd, J=4.8, 2.6 Hz, 1H); $^{19}$F NMR (471 MHz, -d) δ -121.54 (s, 1F); LC-MS: method H, RT=1.44 min, MS (ESI) m/z: 219.0(M+Na)$^+$.

Intermediate 21B: 5-fluoro-2-(oxiran-2-ylmethoxy)phenyl formate

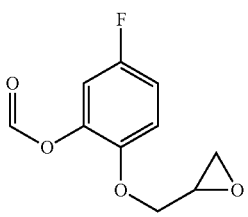

(21B)

To a stirred solution of Intermediate 21A (1.5 g, 7.65 mmol) in dichloromethane (30 mL) was added mCPBA (2.419 g, 10.51 mmol). Trifluoroacetic acid (0.589 mL, 7.65 mmol) in dichloromethane (5.0 mL) was added. The mixture was stirred at room temperature for 3.0 h. TLC indicated a completion of reaction. 10% sodium thiosulfite (10.0 mL) was added to quench the reaction. Solvent was removed under vacuum. The residue was partitioned between EtOAc/ saturated sodium bicarbonate. The organic layers were collected, washed with saturated sodium bicarbonate, brine and dried over sodium sulfate. After evaporation of solvent, the crude product was dissolved in a small amount of chloroform and charged to a 40 g silica gel cartridge which was eluted with hexanes for 3 min., then a 15 min gradient from 0% to 40% EtOAc in hexanes. The desired fractions were combined and concentrated to give Intermediate 21B (1.33 g, 5.33 mmol, 69.7% yield) as a colorless oil (purity ca 85%). $^1$H NMR (500 MHz, chloroform-d) δ 8.28 (s, 1H), 7.04-7.00 (m, 1H), 6.99-6.96 (m, 1H), 6.92 (dd, J=8.1, 2.9 Hz, 1H), 4.27 (dd, J=11.3, 2.8 Hz, 1H), 3.98 (dd, J=11.3, 5.8 Hz, 1H), 3.35-3.31 (m, 1H), 2.91 (dd, J=4.8, 4.3 Hz, 1H), 2.73 (dd, J=5.0, 2.8 Hz, 1H); $^{19}$F NMR (471 MHz, CHLOROFORM-d) 6-119.97 (s, 1F); LC-MS: method H, RT=1.35 min, MS (ESI) m/z: does not ionize. (M+H)$^+$.

Intermediate 21C: (7-fluoro-2,3-dihydrobenzo[b][1,4]dioxin-2-yl)methanol

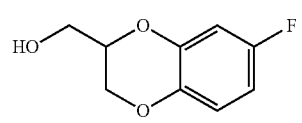

(21C)

To Intermediate 21B (1.3 g, 6.13 mmol) in MeOH (40 mL) was added potassium carbonate (2.79 g, 20.22 mmol). The mixture was stirred at room temperature for 5.0 h. HPLC and TLC indicated a completion of reaction. The mixture was treated with 1.0 N HCl (20 mL). Methanol was removed under vacuum. The residue was partitioned between EtOAc/water. The organic layer was washed with brine, dried over sodium sulfate. After evaporation of solvent, the crude product was dissolved in a small amount of chloroform and charged to a 24 g silica gel cartridge which was eluted with hexanes for 3 min, then a 15 min gradient from 0% to 40% EtOAc in hexanes. The desired fractions were combined and concentrated to give Intermediate 21C (1.1 g, 5.97 mmol, 97% yield) as colorless oil. $^1$H NMR (500 MHz, chloroform-d) δ 6.83 (dd, J=8.8, 5.5 Hz, 1H), 6.66 (dd, J=9.4, 3.0 Hz, 1H), 6.61-6.56 (m, 1H), 4.32-4.27 (m, 2H), 4.15-4.08 (m, 1H), 3.95-3.91 (m, 1H), 3.89-3.85 (m, 1H); $^{19}$F NMR (471 MHz, chloroform-d) δ -121.14 (s, 1F); LC-MS: method H, RT=1.45 min, MS (ESI) m/z: does not ionize

Intermediate 21D: (7-fluoro-2,3-dihydrobenzo[b][1,4]dioxin-2-yl)methyl acetate

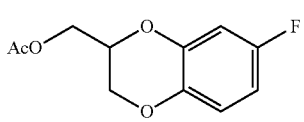

(21D)

To a solution of Intermediate 21C (1.1 g, 5.97 mmol) in THF (15 mL) at 0° C. was added TEA (2.081 mL, 14.93 mmol), followed by acetyl chloride (0.531 mL, 7.47 mmol). The mixture was stirred at 0° C. for 10 min, and at room temperature for 2.0 h. The reaction mixture was diluted with EtOAc, washed with water. The organic layer was washed with 1.0 N HCl, saturated sodium bicarbonate, brine and dried over sodium sulfate. After evaporation of solvent, the crude product was dissolved in a small amount of chloroform and charged to a 24 g silica gel cartridge which was eluted with hexanes for 3 min., then a 18 min gradient from 0% to 40% EtOAc in hexanes. The desired fractions were combined and concentrated to give Intermediate 21D (1.25 g, 5.53 mmol, 93% yield) as colorless oil. $^1$H NMR (500 MHz, chloroform-d) δ 6.83 (dd, J=8.8, 5.5 Hz, 1H), 6.67 (dd, J=9.2, 2.9 Hz, 1H), 6.59 (ddd, J=8.9, 8.1, 3.0 Hz, 1H), 4.44-4.40 (m, 1H), 4.33 (dd, J=6.9, 5.2 Hz, 2H), 4.28 (dd, J=11.6, 2.2 Hz, 1H), 4.05 (dd, J=11.6, 6.9 Hz, 1H), 2.14 (s, 3H); $^{19}$F NMR (471 MHz, CHLOROFORM-d) δ −120.90 (s, 1F); LC-MS: method H, RT=1.74 min, MS (ESI) m/z: 249.0 (M+Na)$^+$.

Intermediate 21E: (7-fluoro-6-nitro-2,3-dihydrobenzo[b][1,4]dioxin-2-yl)methyl acetate

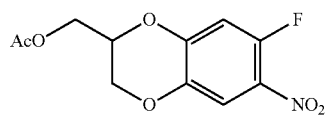

(21E)

To a solution of Intermediate 21D (1.25 g, 5.53 mmol) in acetic acid (2.0 mL) cooled at 0° C. with an ice-bath was added fuming nitric acid (1.032 mL, 22.10 mmol) dropwise. The mixture was stirred at 0° C. for 1.0 h. LCMS indicated a completion of the reaction. The reaction mixture was quenched with ice water/EtOAc. The aqueous was removed and the organic layer was washed with saturated sodium bicarbonate (3×), brine and dried over sodium sulfate. After evaporation of solvent, Intermediate 21E (1.4 g, 5.16 mmol, 93% yield) was obtained as a yellow solid that was used for the next step without further purification. $^1$H NMR (500 MHz, chloroform-d) δ 7.71 (d, J=7.2 Hz, 1H), 6.83 (d, J=11.6 Hz, 1H), 4.53 (dtd, J=7.3, 5.0, 2.5 Hz, 1H), 4.41-4.33 (m, 3H), 4.16-4.09 (m, 1H), 2.15 (s, 3H); $^{19}$F NMR (471 MHz, chloroform-d) δ −122.90 (s, 1F); LC-MS: method H, RT=1.73 min, MS (ESI) m/z: 294.0 (M+Na)$^+$.

Intermediate 21F: (6-amino-7-fluoro-2,3-dihydrobenzo[b][1,4]dioxin-2-yl)methyl acetate

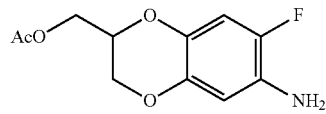

(21F)

To a solution of Intermediate 21E (1.2 g, 4.97 mmol, 96% yield) in ethyl acetate (15 mL) under argon was added 10% Pd/C (0.414 g, 5.16 mmol). The mixture was stirred under an atmosphere of hydrogen (balloon) at room temperature for 4.0 h. HPLC and TLC indicated a completion of reaction. Pd/C was removed by filtration. The filtrate was concentrated to give Intermediate 21F (1.2 g, 4.97 mmol, 96% yield) as colorless oil. $^1$H NMR (500 MHz, chloroform-d) δ 6.63 (d, J=11.3 Hz, 1H), 6.37 (d, J=8.5 Hz, 1H), 4.35-4.22 (m, 4H), 4.01 (dd, J=11.3, 6.9 Hz, 1H), 2.13 (s, 3H); $^{19}$F NMR (471 MHz, chloroform-d) δ −141.10 (s, 1F); LC-MS: method H, RT=0.94 min, MS (ESI) m/z: 242.0 (M+H)$^+$.

Intermediate 21G: (2-amino-4-fluoro-7,8-dihydro-[1,4]dioxino[2',3':3,4]benzo[1,2-d]thiazol-7-yl)methyl acetate

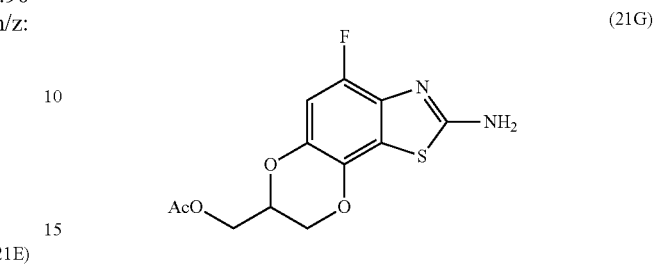

(21G)

To Intermediate 21F (147 mg, 0.609 mmol) in acetonitrile (2 mL) was added ammonium thiocyanate (69.6 mg, 0.914 mmol). The mixture was stirred at room temperature for 10 min. Benzyltrimethylammonium tribromide (238 mg, 0.609 mmol) in acetonitrile (1.5 mL) was added dropwise (5 min). The mixture was stirred at room temperature over night. HPLC and LCMS indicated a completion of reaction. The reaction mixture was diluted with EtOAc/saturated sodium bicarbonate. The insoluble material was removed by filtration. The organic layer of the filtrate was collected, washed with brine, dried over sodium sulfate. After evaporation of solvent, Intermediate 21G (165 mg, 0.553 mmol, 91% yield) was obtained as a yellow solid. It was used for the next step without further purification. $^1$H NMR (500 MHz, chloroform-d) δ 6.74 (d, J=10.7 Hz, 1H), 5.67 (br. s., 2H), 4.47-4.42 (m, 1H), 4.41-4.32 (m, 3H), 4.19-4.14 (m, 1H), 2.15 (s, 3H); $^{19}$F NMR (471 MHz, chloroform-d) δ −133.23 (s, 1F); LC-MS: method H, RT=1.38 min, MS (ESI) m/z: 299.0 (M+H)$^+$.

Intermediate 21H: (2-bromo-4-fluoro-7,8-dihydro-[1,4]dioxino[2',3':3,4]benzo[1,2-d]thiazol-7-yl)methyl acetate

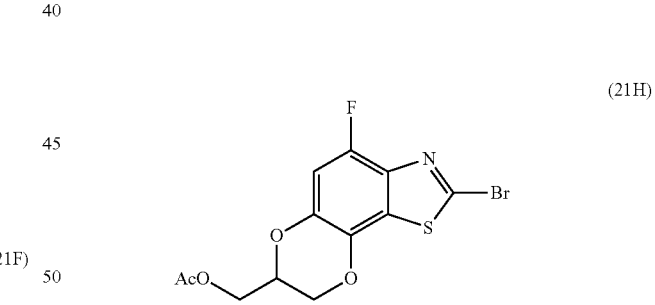

(21H)

tert-Butyl nitrite (0.806 mL, 6.10 mmol) was added to copper(II) bromide (1.324 g, 5.93 mmol) in acetonitrile (15 mL) under argon. The mixture was stirred at room temperature for 10 min. A suspension of Intermediate 21G (1.04 g, 3.49 mmol) in acetonitrile (15 mL) was added dropwise. The reaction mixture was stirred at room temperature for 1.5 h. Acetonitrile was removed under vacuum, the reaction mixture was diluted with EtOAc, quenched with 1.0 N HCl. The organic layer was washed with 0.5 N HCl (2×), saturated sodium bicarbonate, brine and dried over sodium sulfate. After evaporation of solvent, Intermediate 21H (1.26 g, 3.48 mmol, 100% yield) was obtained as a brown solid. It was used for next step without further purification. $^1$H NMR (500 MHz, chloroform-d) δ 6.87 (d, J=10.2 Hz, 1H), 4.52-4.47 (m, 1H), 4.44 (dd, J=11.4, 2.3 Hz, 1H), 4.42-4.36 (m, 2H), 4.19 (dd, J=11.6, 7.2 Hz, 1H), 2.15 (s, 3H); $^{19}$F NMR (471 MHz, chloroform-d) δ −128.77 (s, 1F); LC-MS: method H, RT=2.00 min, MS (ESI) m/z: 362.0 and 364.0 (M+H)$^+$.

Intermediate 21I: (2-bromo-4-fluoro-7,8-dihydro-[1,4]dioxino[2',3':3,4]benzo[1,2-d]thiazol-7-yl)methanol

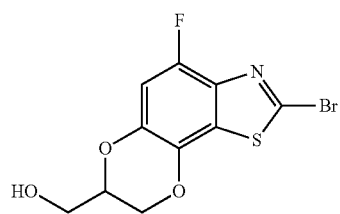

(21I)

To Intermediate 21H (1.15 g, 3.18 mmol) in THF (14 mL) cooled with an ice-bath was added 1.0 N NaOH (3.81 mL, 3.81 mmol). After 10 min stirring, MeOH (2.0 mL) was added. After another 20 min stirring at 0° C., 1.0 N HCl (6.0 mL) was added. The mixture was diluted with EtOAc/THF/water. The organic layer was collected, washed with saturated sodium bicarbonate, brine and dried over sodium sulfate. After evaporation of solvent, Intermediate 21I (1.07 g, 3.34 mmol, 105% yield) was obtained as a brown solid. $^1$H NMR (500 MHz, methanol-d$_4$) δ 6.84 (d, J=10.5 Hz, 1H), 4.45 (dd, J=11.4, 2.3 Hz, 1H), 4.31-4.28 (m, 1H), 4.19 (dd, J=11.4, 7.6 Hz, 1H), 3.86-3.78 (m, 2H); $^{19}$F NMR (471 MHz, methanol-d$_4$) δ −130.37 (s, 1F); LC-MS: method H, RT=1.80 min, MS (ESI) m/z: 320.0 and 322.0 (M+H)$^+$.

Intermediate 21J: tert-butyl N-({4-bromo-7-fluoro-10,13-dioxa-3-thia-5-azatricyclo[7.4.0.0^{2,6}]trideca-1(9), 2(6), 4,7-tetraen-11-yl}methyl)-N-[(tert-butoxy)carbonyl]carbamate

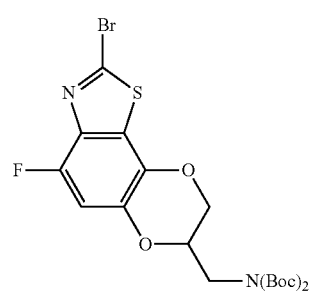

(21J)

A solution of DIAD (0.182 mL, 0.937 mmol) in THF (2 mL) was added to a solution of di-tert-butyl iminodicarboxylate (204 mg, 0.937 mmol), Intermediate 21I (100 mg, 0.312 mmol) and triphenylphosphine (246 mg, 0.937 mmol) in THF (3 mL). The reaction mixture was heated at 45° C. overnight. The mixture was diluted with DCM and saturated NaHCO$_3$, extracted with DCM, the combined organic layer was washed with brine, dried with MgSO$_4$ and concentrated. The crude sample was purified with a 40 g ISCO column eluted with 0-30% EtOAc in hexanes for 20 min. The desired fraction was collected to give Intermediate 21J (120 mg, 0.116 mmol, 37.0% yield). $^1$H NMR (500 MHz, chloroform-d) δ 7.90 (d, J=7.98 Hz, 1H), 7.45 (t, J=7.84 Hz, 1H), 7.30 (dd, J=0.83, 7.43 Hz, 1H), 4.98 (s, 2H), 1.41-1.46 (m, 18H). LC-MS: method C, RT=2.45 min, MS (ESI) m/z: 419 and 421 [M-Boc]$^+$.

Example 21

To Intermediate I-1 (38.8 mg, 0.116 mmol), Intermediate 21J (120 mg, 0.116 mmol) and PdCl$_2$(dppf)—CH$_2$Cl$_2$ adduct (4.72 mg, 5.78 μmol) was added toluene (0.75 mL), EtOH (0.25 mL) and sodium carbonate (0.116 mL, 2M, 0.231 mmol). The mixture was degassed with argon for 5 min. The reaction mixture was heated in a microwave reactor at 135° C. for 40 min. To the reaction mixture was added EtOAc/water/brine. The insoluble was removed by filtration with a pad of celite. The organic layers were collected, washed with brine, dried over sodium sulfate. After evaporation of solvent, the crude product was dissolved in a small amount of chloroform and charged to a 12 g ISCO column which was eluted with hexanes for 3 min, then a 20 min gradient from 0% to 75% dichloromethane in hexanes The desired fractions were combined and concentrated. The sample was further purified via preparative LC/MS (method D, 55-95% B over 10 min., then a 5-min hold at 100% B). Fractions containing the desired product were combined and dried via centrifugal evaporation to Example 21 (3.1 mg, 5.65 μmol, 4.89% yield). $^1$H NMR (500 MHz, Methanol-d$_4$) δ 8.71 (s, 1H), 8.64 (s, 1H), 7.77 (s, 1H), 7.83-7.49 (m, 2H), 6.84 (d, J=11.0 Hz, 1H), 4.47 (dd, J=11.6, 1.9 Hz, 1H), 4.37-4.29 (m, 1H), 4.22 (br. s., 1H), 4.10 (dd, J=11.0, 7.7 Hz, 1H), 3.47-3.42 (m, 2H), 2.65 (s, 3H), 1.45 (s, 9H). LC-MS: method C, RT=2.88 min, MS (ESI) m/z: 649.2 (M+H)$^+$. Analytical HPLC purity (method B): 100%.

Example 22

(2-(2-(difluoromethoxy)-7-methylquinoxalin-5-yl)-4-fluoro-7,8-dihydro-[1,4]dioxino[2',3':3,4]benzo[1,2-d]thiazol-8-yl)methanol

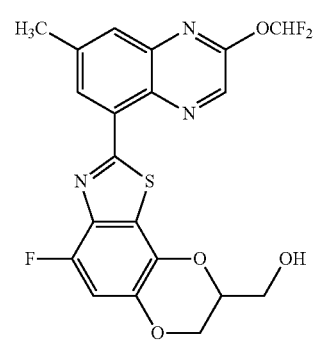

(22)

Intermediate 22A: 4-fluoro-2-(oxiran-2-ylmethoxy)benzaldehyde

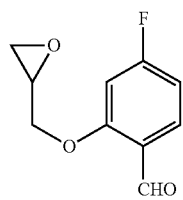

(22A)

To a solution of 4-fluoro-2-hydroxybenzaldehyde (1.9 g, 13.56 mmol) in DMF (30 mL) was added $Cs_2CO_3$ (9.72 g, 29.8 mmol) followed by 2-(bromomethyl)oxirane (2.090 mL, 24.41 mmol). The mixture was stirred at room temperature for 10 min then at 50° C. for 1.5 h. After it cooled to room temperature, the reaction mixture was diluted with EtOAc/water. The organic layer was collected, washed with brine, dried over sodium sulfate. After evaporation of solvent, the crude product was dissolved in a small amount of chloroform and charged to a 120 g silica gel cartridge which was eluted with hexanes for 3 min., then a 15 min gradient from 0% to 40% EtOAc in hexanes. The desired fractions were combined and concentrated to give Intermediate 22A (2.6 g, 13.25 mmol, 98% yield) as a white solid. $^1$H NMR (400 MHz, Methanol-$d_4$) δ 10.36 (d, J=0.5 Hz, 1H), 7.84 (dd, J=8.6, 6.8 Hz, 1H), 7.01 (dd, J=11.1, 2.3 Hz, 1H), 6.89-6.79 (m, 1H), 4.52 (dd, J=11.4, 2.3 Hz, 1H), 4.03 (dd, J=11.6, 6.3 Hz, 1H), 3.47-3.39 (m, 1H), 2.92 (dd, J=4.8, 4.3 Hz, 1H), 2.81 (dd, J=4.9, 2.7 Hz, 1H). LC-MS: method C, RT=1.42 min, MS (ESI) m/z: No (M+H)$^+$.

Intermediate 22B: 4-fluoro-2-(oxiran-2-ylmethoxy)phenyl formate

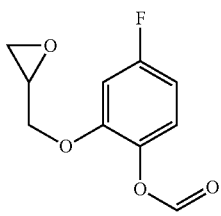

(22B)

To a stirred solution of Intermediate 22A (2.6 g, 13.25 mmol) in dichloromethane (50 mL) was added mCPBA (4.19 g, 18.22 mmol) followed by trifluoroacetic acid (1.021 mL, 13.25 mmol) in dichloromethane (5.0 mL). The mixture was stirred at room temperature for 3.0 h. TLC indicated a completion of reaction. 10% sodium thiosulfite (10.0 mL) was added to quench the reaction. Solvent was removed under vacuum. The residue was partitioned between EtOAc/saturated sodium bicarbonate. The organic layers were collected, washed with saturated sodium bicarbonate, brine, dried over sodium sulfate. After evaporation of solvent, the crude product was dissolved in a small amount of chloroform and charged to a 120 g silica gel cartridge which was eluted with hexanes for 3 min., then a 15 min gradient from 0% to 40% EtOAc in hexanes. The desired fractions were combined and concentrated to give Intermediate 22B (2.7 g, 11.45 mmol, 86% yield) as colorless oil. $^1$H NMR (400 MHz, methanol-$d_4$) δ 7.11 (dd, J=8.8, 5.8 Hz, 1H), 6.98 (dd, J=10.4, 2.8 Hz, 1H), 6.77-6.68 (m, 1H), 4.37 (dd, J=11.6, 2.3 Hz, 1H), 3.93 (dd, J=11.5, 6.2 Hz, 1H), 2.86 (t, J=4.5 Hz, 1H), 2.73 (dd, J=4.9, 2.7 Hz, 1H). $^{19}$F NMR (376 MHz, methanol-$d_4$) δ −117.05 (s, 1F). LC-MS: method C, RT=1.39 min, MS (ESI) m/z: 235 (M+Na)$^+$.

Intermediate 22C: (6-fluoro-2,3-dihydrobenzo[b][1,4]dioxin-2-yl)methanol

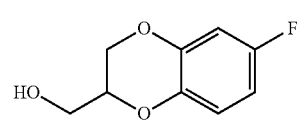

(22C)

To Intermediate 22B (2.7 g, 11.45 mmol) in MeOH (60 mL) was added potassium carbonate (5.22 g, 37.8 mmol). The mixture was stirred at room temperature overnight. TLC indicated a completion of reaction. The mixture was treated with 1.0 N HCl (40 mL). Methanol was removed under vacuum. The residual was partitioned between EtOAc/water. The organic layer was washed with brine, dried over sodium sulfate. After evaporation of solvent, the crude product was dissolved in a small amount of chloroform and charged to a 120 g silica gel cartridge which was eluted with hexanes for 3 min., then a 20 min gradient from 0% to 50% EtOAc in hexanes. The desired fractions were combined and concentrated to give Intermediate 22C (1.72 g, 9.34 mmol, 82% yield) as a white solid. $^1$H NMR (400 MHz, methanol-$d_4$) δ 6.83 (dd, J=9.0, 5.4 Hz, 1H), 6.63-6.51 (m, 2H), 4.32 (dd, J=11.4, 2.3 Hz, 1H), 4.18-4.09 (m, 1H), 4.07-4.00 (m, 1H), 3.75 (t, J=4.4 Hz, 2H). LC-MS: method C, RT=1.51 min, MS (ESI) m/z: No (M+H)$^+$.

Intermediate 22D: (6-fluoro-2,3-dihydrobenzo[b][1,4]dioxin-2-yl)methyl acetate

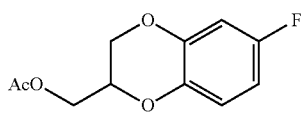

(22D)

To a solution of Intermediate 22C (1.72 g, 9.34 mmol) in THF (40 mL) at 0° C. was added TEA (3.25 mL, 23.35 mmol) followed by acetyl chloride (0.830 mL, 11.67 mmol). The mixture was stirred at 0° C. for 10 min then at room temperature for 2.0 h. The mixture was diluted with EtOAc, washed with water. The organic layer was washed with 1.0 N HCl, saturated sodium bicarbonate, brine, dried over sodium sulfate. After evaporation of solvent, the crude product was dissolved in a small amount of chloroform and charged to a 24 g silica gel cartridge which was eluted with hexanes for 3 min., then an 18 min gradient from 0% to 40% EtOAc in hexanes. The desired fractions were combined and concentrated to give Intermediate 22D (2.0 g, 8.84 mmol, 95% yield) as colorless oil. $^1$H NMR (400 MHz, chloroform-d) δ 6.84 (dd, J=8.8, 5.3 Hz, 1H), 6.70-6.48 (m, 2H), 4.43-4.23 (m, 4H), 4.05 (dd, J=11.5, 6.9 Hz, 1H), 2.12 (s, Intermediate 22E: (6-fluoro-7-nitro-2,3-dihydrobenzo[b][1,4]dioxin-2-yl)methyl acetate

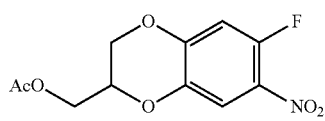

(22E)

To a solution of Intermediate 22D (2.0 g, 8.84 mmol) in acetic acid (2.0 mL) at 0° C. with an ice-bath was added fuming nitric acid (1.651 mL, 35.4 mmol) dropwise. The mixture was stirred at 0° C. for 1.0 h. HPLC indicated co-elution with starting material, but LCMS indicated a clean reaction. It was quenched with ice water. The aqueous layer was removed and the organic layer was washed with saturated sodium bicarbonate (3×), brine, dried over sodium sulfate. After evaporation of solvent, The crude sample was purified with a 120 g ISCO column eluted with 0-100% EtOAc in hexanes for 40 min. The desired fractions were collected and Intermediate 22E (2.2 g, 8.11 mmol, 92% yield) was obtained as a white solid. $^1$H NMR (500 MHz, chloroform-d) δ 7.73 (d, J=7.2 Hz, 1H), 6.80 (d, J=11.3 Hz, 1H), 4.43 (t, J=2.5 Hz, 1H), 4.41 (t, J=2.1 Hz, 1H), 4.35 (t, J=4.8 Hz, 2H), 4.15 (dd, J=12.1, 7.7 Hz, 1H), 2.14 (s, 3H). LC-MS: method C, RT=1.72 min, MS (ESI) m/z: 230 [M+1-Ac]$^+$.

Intermediate 22F: (7-amino-6-fluoro-2,3-dihydrobenzo[b][1,4]dioxin-2-yl)methyl acetate

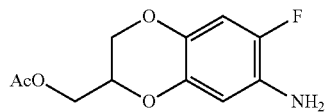

(22F)

To a solution of Intermediate 22E (2.2 g, 8.11 mmol) in ethyl acetate (30 mL) under argon was added 10% Pd/C (350 mg, 8.11 mmol). The mixture was stirred under an atmosphere of hydrogen (balloon) at room temperature for 3 h. IPLC and TLC indicated a completion of reaction. Pd/C was removed by filtration. The filtrate was concentrated to give Intermediate 22F (1.9 g, 7.88 mmol, 97% yield) as colorless oil. $^1$H NMR (400 MHz, chloroform-d) δ 6.59 (d, J=11.4 Hz, 1H), 6.35 (d, J=8.6 Hz, 1H), 4.45-4.18 (m, 4H), 4.04-3.92 (m, 1H), 3.45 (br. s., 2H), 2.11 (s, 3H). $^{19}$F NMR (376 MHz, chloroform-d) δ −136.37-152.99 (m, 2F). LC-MS: method C, RT=1.07 min, MS (ESI) m/z: 242 [M+1]$^+$.

Intermediate 22G: A (2-amino-4-fluoro-7,8-dihydro-[1,4]dioxino[2',3':3,4]benzo[1,2-d]thiazol-8-yl) methyl acetate

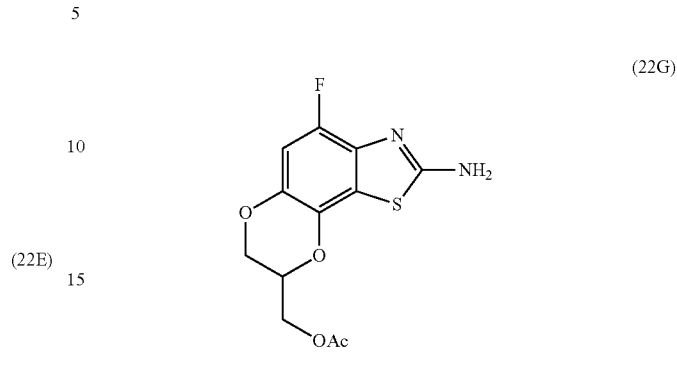

(22G)

To Intermediate 22F (1.7 g, 7.05 mmol) in acetonitrile (20 mL) was added ammonium thiocyanate (0.805 g, 10.57 mmol). The mixture was stirred at room temperature for 10 min. Benzyltrimethylammonium tribromide (2.75 g, 7.05 mmol) in acetonitrile (10 mL) was added dropwise (5 min). The mixture was stirred at room temperature overnight. The mixture was diluted with EtOAc/saturated sodium bicarbonate. The insoluble material was removed by filtration. The organic layer of the filtrate was collected, washed with brine, dried over sodium sulfate. After evaporation of solvent, Intermediate 22G (1.95 g, 6.54 mmol, 93% yield) was obtained as a yellow solid. $^1$H NMR (400 MHz, methanol-d$_4$) δ 6.65 (dd, J=11.1, 4.5 Hz, 1H), 4.59-4.46 (m, 1H), 4.43-4.27 (m, 3H), 4.11 (ddd, J=11.6, 6.9, 4.5 Hz, 1H), 2.09 (d, J=4.5 Hz, 3H). $^{19}$F NMR (376 MHz, methanol-d$_4$) δ −136.98 (br. s., 1F). LC-MS: method C, RT=1.45 min, MS (ESI) (m/z): 299 [M+1]$^+$.

Intermediate 22H: (2-bromo-4-fluoro-7,8-dihydro-[1,4]dioxino[2',3':3,4]benzo[1,2-d]thiazol-8-yl) methyl acetate

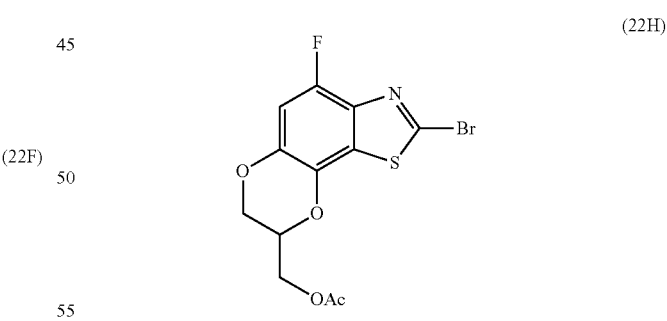

(22H)

tert-Butyl nitrite (1.706 mL, 12.91 mmol) was added to copper (II) bromide (2.80 g, 12.54 mmol) in dry acetonitrile (30 mL) under argon. The mixture was stirred at room temperature for 10 min. A suspension of Intermediate 22G (2.2 g, 7.38 mmol) in dry acetonitrile (30 mL) was added dropwise. The reaction mixture was stirred at room temperature for 1.5 h. IPLC and LCMS indicated a clean reaction. Acetonitrile was removed under vacuum, the reaction mixture was diluted with EtOAc, quenched with 1.0 N HCl. The organic layer was collected, washed with 0.5 N HCl (2×), saturated sodium bicarbonate, brine, dried over sodium sulfate. After evaporation of solvent, Intermediate 22H (2.33 g, 6.43 mmol, 87% yield) was obtained as brown oil. It was used for next step without further purification. $^1$H NMR (400 MHz, chloroform-d) δ 6.83 (d, J=10.4 Hz, 1H), 4.52 (dtd, J=7.1, 5.1, 2.4 Hz, 1H), 4.45-4.29 (m, 2H), 4.23-4.08 (m, 2H), 2.18-2.10 (m, 3H). $^{19}$F NMR (376 MHz, chloroform-d) δ −129.42 (s, 1F). LC-MS: method C, RT=2.00 min, MS (ESI) m/z: 361.9 and 363.9 [M+H]$^+$.

Example 22

To Intermediate I-1 (40 mg, 0.119 mmol), Intermediate 22H (44 mg, 0.121 mmol) and PdCl$_2$(dppf)—CH$_2$Cl$_2$ adduct (4.86 mg, 5.95 μmol) was added toluene (0.75 mL), EtOH (0.25 mL) and sodium carbonate (0.119 mL, 2M, 0.238 mmol). The mixture was degassed with argon for 5 min. The reaction mixture was heated in a microwave reactor at 135° C. for 40 min. To the reaction mixture was added EtOAc/water/brine. The insoluble was removed by filtration with a pad of celite. The organic layers were collected, washed with brine, dried over sodium sulfate. After evaporation of solvent, the crude product was dissolved in a small amount of DCM and charged to a 12 g ISCO column which was eluted with hexanes for 3 min., then a 20 min gradient from 0% to 75% dichloromethane in hexanes. The desired fractions were combined and concentrated. The sample was further purified via preparative LC/MS (method C, 40-75% B over 10 min., then a 5-min hold at 100% B). Fractions containing the desired product were combined and dried via centrifugal evaporation to give Example 22 (10.4 mg, 0.023 mmol, 19.45% yield). $^1$H NMR (500 MHz, DMSO-d$_6$) δ 8.18 (s, 1H), 7.89 (d, J=1.7 Hz, 1H), 7.09 (s, 1H), 7.25-6.86 (m, 1H), 6.28 (d, J=11.0 Hz, 1H), 4.37 (t, J=5.5 Hz, 1H), 3.67 (dd, J=11.6, 2.2 Hz, 1H), 3.55 (td, J=5.0, 2.5 Hz, 1H), 3.35 (dd, J=11.4, 7.6 Hz, 1H), 3.03-2.87 (m, 2H), 1.85 (s, 3H). LC-MS: method C, RT=2.35 min, MS (ESI) m/z: 450.0 (M+H)$^+$. Analytical HPLC purity (method B): 100%.

Example 23 tert-butyl ((2-(2-(difluoromethoxy)-7-methylquinoxalin-5-yl)-4-fluoro-7,8-dihydro-[1,4]dioxino[2',3':3,4]benzo[1,2-d]thiazol-8-yl)methyl)carbamate

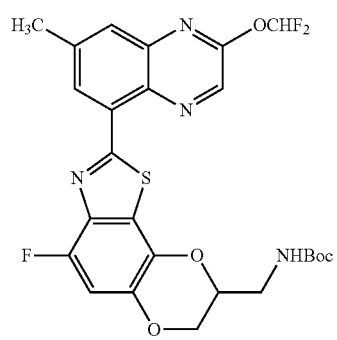

(23)

Intermediate 23A: (2-bromo-4-fluoro-7,8-dihydro-[1,4]dioxino[2',3':3,4]benzo[1,2-d]thiazol-8-yl)methanol

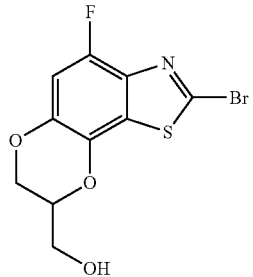

(23A)

To a solution of Intermediate 22H (2.3 g, 6.35 mmol) in THF (30 mL) cooled with an ice-bath was added 1.0 N NaOH (7.62 mL, 7.62 mmol). After 10 min stirring, MeOH (2.0 mL) was added. The mixture was stirred at room temperature for 1 h. 1.0 N HCl (6.0 mL) was added to quench the reaction. The mixture was diluted with EtOAc/THF/water. The organic layer was collected, washed with saturated sodium bicarbonate, brine, dried over sodium sulfate. After evaporation of solvent, Intermediate 23A (2 g, 6.25 mmol, 98% yield) was obtained as brown solid. $^1$H NMR (400 MHz, methanol-d$_4$) δ 6.81 (d, J=10.6 Hz, 1H), 4.44-4.23 (m, 2H), 4.15 (dd, J=11.5, 7.5 Hz, 1H), 3.88-3.77 (m, 2H). $^{19}$F NMR (376 MHz, methanol-d$_4$) δ −131.18 (s, 1F). LC-MS: method C, RT=1.82 min, MS (ESI) m/z: 319.9 and 321.9 (M+H)$^+$.

Intermediate 23B: tert-butyl ((2-bromo-4-fluoro-7,8-dihydro-[1,4]dioxino[2',3':3,4]benzo[1,2-d]thiazol-8-yl)methyl)carbamate

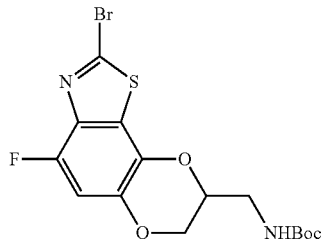

(23B)

DIAD (0.146 mL, 0.750 mmol) was added to a suspension of di-tert-butyl iminodicarboxylate (65.2 mg, 0.300 mmol). Intermediate 23A (80 mg, 0.250 mmol) and triphenylphosphine (197 mg, 0.750 mmol) in toluene (2 mL) was added to the above solution at 45° C. in 3h via syringe pump. The reaction mixture was stirred at 45° C. overnight. The mixture was diluted with DCM and saturated NaHCO$_3$, extracted with DCM, the combined organic layer was washed with brine, dried with MgSO$_4$ and concentrated. The crude sample was purified with a 12 g ISCO column eluted with 0-100% DCM/hexanes for 20 min, the desired fraction was collected to give Intermediate 23B (80 mg, 0.077 mmol, 30.8% yield) as a yellow solid. $^1$H NMR (400 MHz, chloroform-d) δ 6.82 (d, J=10.4 Hz, 1H), 4.52 (qd, J=6.1, 2.1 Hz, 1H), 4.35 (dd, J=11.9, 2.3 Hz, 1H), 4.13-4.04 (m, 2H), 3.85 (dd, J=14.5, 5.7 Hz, 1H), 1.51 (s, 18H). $^{19}$F NMR (376 MHz, chloroform-d) δ −129.89 (s, 1F). LC-MS: method C, RT=2.44 min, MS (ESI) m/z: 419 and 421 [M+1-Boc]$^+$.

Example 23

To Intermediate I-1 (25.9 mg, 0.077 mmol), Intermediate 23B (80 mg, 0.077 mmol) and PdCl$_2$(dppf)—CH$_2$Cl$_2$ adduct (3.14 mg, 3.85 µmol) was added toluene (0.75 mL), EtOH (0.25 mL) and sodium carbonate (0.077 mL, 2M, 0.154 mmol. The mixture was degassed with argon for 5 min. The reaction mixture was heated in a microwave reactor at 135° C. for 40 min. LCMS indicated a clean reaction. To the reaction mixture was added EtOAc/water/brine. The insoluble was removed by filtration with a pad of celite. The organic layers were collected, washed with brine, dried over sodium sulfate. After evaporation of solvent, the crude product was dissolved in a small amount of chloroform and charged to a 12 g ISCO column which was eluted with hexanes for 3 min., then a 20 min gradient from 0% to 75% dichloromethane in hexanes The desired fraction was collected and was further purified via preparative HPLC (method A, 30-100% B in 10 min.). The desired fractions were placed in a SpeedVac overnight to remove solvent, then lyophilized to give Example 23 (3 mg, 5.25 µmol, 6.82% yield). $^1$H NMR (400 MHz, acetonitrile-d$_3$) δ 8.89-8.61 (m, 2H), 7.84 (s, 1H), 8.00-7.45 (m, 1H), 6.94 (d, J=11.4 Hz, 1H), 5.66 (br. s., 1H), 4.49-4.36 (m, 2H), 4.11 (dd, J=11.9, 7.1 Hz, 1H), 3.58-3.33 (m, 2H), 2.70 (s, 3H), 1.44 (s, 9H). $^{19}$F NMR (376 MHz, acetonitrile-d$_3$) 6-90.54 (s, 2 F), −132.85 (br. s., 1F). LC-MS: method C, RT=2.42 min, MS (ESI) m/z: 542.9 (M+H)$^+$. Analytical HPLC purity (method A): 96%.

Example 24

(4-fluoro-2-(2-methoxy-7-methylquinoxalin-5-yl)-7,8-dihydro-[1,4]dioxino[2',3':3,4]benzo[1,2-d]thiazol-8-yl)methyl phenylcarbamate

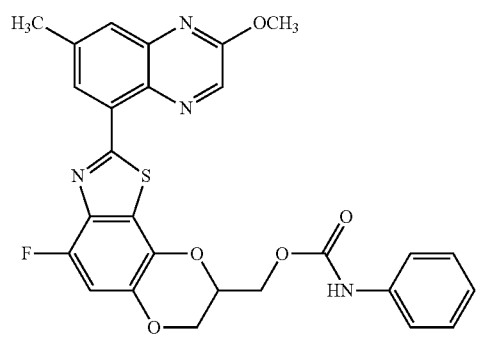

(24)

Intermediate 24A (4-fluoro-2-(2-methoxy-7-methylquinoxalin-5-yl)-7,8-dihydro-[1,4]dioxino[2',3':3,4]benzo[1,2-d]thiazol-8-yl)methanol

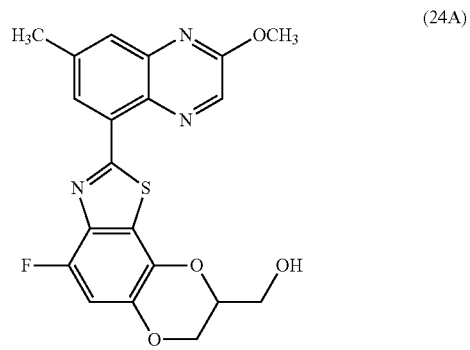 [SMILES: COc1cnc2c(-c3nc4c(F)cc5c(c4s3)OC(CO)CO5)cc(C)cc2n1]

(24A)

To a solution of Example 22 (334 mg, 0.743 mmol) in DMF (5 mL) was added sodium methoxide (4.46 mL, 0.5M, 2.230 mmol). The mixture was stirred at room temperature for 1 h. LCMS indicated a completion of the reaction. The mixture was diluted with EtOAc and water, extracted with EtOAc, the combined organic layer was washed with brine, dried with MgSO$_4$ and concentrated. The crude sample was purified with a 40 g ISCO column eluted with 0-100% EtOAc in hexanes for 20 min. The desired fractions were collected and concentrated to give Intermediate 24A (175 mg, 0.423 mmol, 57.0% yield) as a yellow solid. $^1$H NMR (500 MHz, DMSO-d$_6$) δ 8.80 (s, 1H), 8.60 (d, J=1.7 Hz, 1H), 7.89-7.79 (m, 1H), 7.11 (d, J=11.0 Hz, 1H), 5.18 (t, J=5.6 Hz, 1H), 4.48 (dd, J=11.7, 2.3 Hz, 1H), 4.41-4.32 (m, 1H), 4.17 (dd, J=11.6, 7.4 Hz, 1H), 4.08 (s, 3H), 3.74 (td, J=5.2, 2.8 Hz, 1H), 2.64 (s, 3H). LC-MS: method C, RT=2.38 min, MS (ESI) m/z: 414 (M+H)$^+$.

Intermediate 24B (4-fluoro-2-(2-methoxy-7-methylquinoxalin-5-yl)-7,8-dihydro-[1,4]dioxino[2',3':3,4]benzo[1,2-d]thiazol-8-yl)methyl carbonochloridate

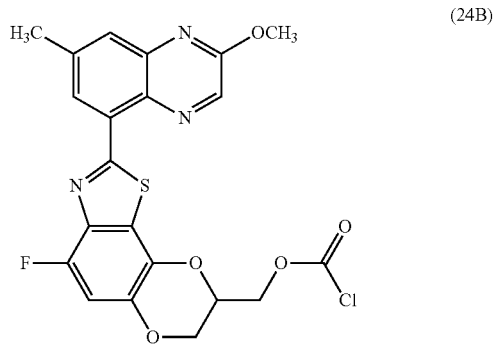 [SMILES: COc1cnc2c(-c3nc4c(F)cc5c(c4s3)OC(COC(=O)Cl)CO5)cc(C)cc2n1]

(24B)

To a solution of Intermediate 24A (60 mg, 0.145 mmol) in THF (5 mL) was added phosgene (0.614 mL, 20% in toluene, 1.161 mmol) and the mixture was stirred at room temperature for 1 h. LCMS indicated a completion of the reaction. Solvent was removed overnight to give Intermediate 24B (65 mg, 0.137 mmol, 94% yield) as a solid. The sample used for next step without purification. LC-MS: method C, RT=2.59 min, MS (ESI) m/z: 476 (M+H)+.

Example 24

To a solution of Intermediate 24B (10 mg, 0.021 mmol) in DCM (1 mL) was added aniline (5.87 mg, 0.063 mmol) and DIEA (0.037 mL, 0.210 mmol). The mixture was stirred at room temperature for 1 h, LCMS indicated a completion of the reaction. Solvent was removed, the residual was purified via preparative LC/MS (method D, 55-90% B over 10 min., then a 5-min hold at 100% B). Fractions containing the desired product were combined and dried via centrifugal evaporation to give Example 24 (3.9 mg, 7.32 µmol, 34.9% yield). $^1$H NMR (500 MHz, DMSO-$d_6$) δ 7.89 (s, 1H), 7.74 (d, J=1.9 Hz, 1H), 7.00 (dd, J=1.8, 1.0 Hz, 1H), 6.64 (d, J=7.7 Hz, 2H), 6.51-6.39 (m, 2H), 6.31 (d, J=11.0 Hz, 1H), 6.20-6.11 (m, 1H), 3.95-3.84 (m, 1H), 3.74 (dd, J=11.6, 2.2 Hz, 1H), 3.68-3.58 (m, 2H), 3.43 (dd, J=11.8, 7.2 Hz, 1H), 3.24 (s, 3H), 1.80 (s, 3H). LC-MS: method C, RT=2.59 min, MS (ESI) m/z: 533.3 (M+H)+. Analytical HPLC purity (method B): 100%.

Example 25

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (5-chloropyridin-3-yl)carbamate

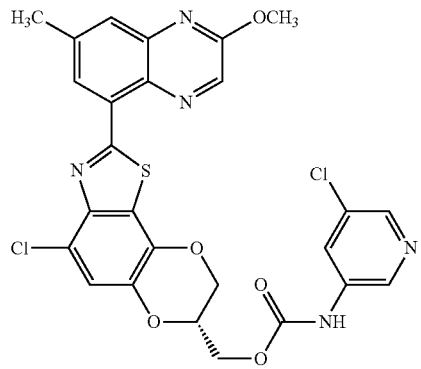

(25)

Intermediate 25A:
(R)-5-chloro-2-(oxiran-2-ylmethoxy)benzaldehyde

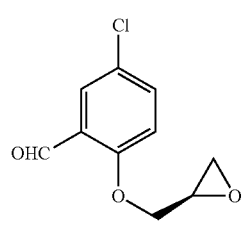

(25A)

To a solution of 5-chloro-2-hydroxybenzaldehyde (4 g, 25.5 mmol) in DMF (50 mL) was added (R)-oxiran-2-ylmethyl 3-nitrobenzenesulfonate (7.29 g, 28.1 mmol) and Cs$_2$CO$_3$ (24.97 g, 77 mmol). The mixture was stirred at room temperature overnight. LCMS indicated a completion of the reaction. The mixture was diluted with EtOAc and water, extracted with EtOAc, the combined organic layer was washed with saturated sodium bicarbonate, brine, dried over MgSO$_4$ and concentrated. The crude sample was purified with a 120 g ISCO column eluted with 0-100% EtOAc in hexane for 40 min. The desired fraction was collected and concentrated to Intermediate 25A (5 g, 23.52 mmol, 92% yield) as an off-white solid. $^1$H NMR (400 MHz, chloroform-d) δ 10.46 (s, 1H), 7.80 (d, J=2.6 Hz, 1H), 7.49 (dd, J=8.9, 2.8 Hz, 1H), 6.97 (d, J=9.0 Hz, 1H), 4.41 (dd, J=11.2, 2.6 Hz, 1H), 4.04 (dd, J=11.1, 5.8 Hz, 1H), 3.41 (ddt, J=5.8, 4.1, 2.8 Hz, 1H), 3.00-2.88 (m, 1H), 2.80 (dd, J=4.8, 2.6 Hz, 1H). LC-MS: method C, RT=1.64 min, MS (ESI) m/z: No (M+H)+.

Intermediate 25B: (S)-(7-chloro-2,3-dihydrobenzo[b][1,4]dioxin-2-yl)methanol

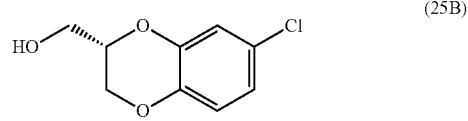 [SMILES: OC[C@H]1COc2ccc(Cl)cc2O1]

(25B)

To a stirred solution of Intermediate 25A (5.1 g, 24.46 mmol) in dichloromethane (100 mL) cooled with a water bath was added mCPBA (8.30 g, 36.1 mmol). Trifluoroacetic acid (1.884 mL, 24.46 mmol) in dichloromethane (10 mL) was added dropwise. The mixture was stirred at room temperature for 2.0 h. TLC indicated a completion of the reaction. The reaction was quenched by addition of saturated sodium bicarbonate, followed by 10% sodium thiosulfite (20.0 mL), extracted with dichloromethane. The organic layers were collected, washed with saturated sodium bicarbonate, brine and dried over sodium sulfate. After evaporation of solvent, the crude product was dissolved in a small amount of chloroform and charged to an 80 g silica gel cartridge which was eluted with hexanes for 2 min., then an 18 min gradient from 0% to 35% EtOAc in hexanes. The desired fractions were combined and concentrated to colorless oil. To the above oil (3 g, 13.12 mmol in MeOH (50 mL) was added potassium carbonate (5.44 g, 39.4 mmol). The mixture was stirred at room temperature overnight. IPLC indicated a completion of reaction. The mixture was treated with 1.0 N HCl (14 mL). Methanol was removed under vacuum. The residue was portioned between EtOAc/water. The organic layer was washed with brine, dried over sodium sulfate. After evaporation of solvent, the crude sample was purified by 120 g ISCO column eluted by 0-100% EtOAc/hex for 40 min. The desired fraction was collected and concentrated to Intermediate 25B (1.7 g, 8.47 mmol, 64.6% yield) as a white solid. $^1$H NMR (400 MHz, chloroform-d) δ 6.90-6.86 (m, 1H), 6.80 (d, J=1.5 Hz, 2H), 4.30-4.20 (m, 2H), 4.07 (dd, J=11.2, 7.3 Hz, 1H), 3.90-3.79 (m, 2H). LC-MS: method C, RT=1.72 min, MS (ESI) m/z: 223 (M+Na)+.

Intermediate 25C: (R)-(7-chloro-2,3-dihydrobenzo[b][1,4]dioxin-2-yl)methyl acetate

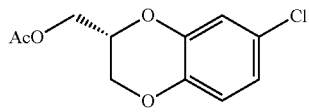

(25C)

To a solution of Intermediate 25B (1.7 g, 8.47 mmol) in THF (30 mL) at 0° C. was added TEA (2.95 mL, 21.18 mmol) followed by acetyl chloride (10.59 mL, 1M in DCM, 10.59 mmol) dropwise. The mixture was stirred at 0° C. for 10 min and at room temperature for 1.0 h. LCMS indicated a completion of the reaction. The mixture was diluted with EtOAc, washed with water. The organic layer was washed with 0.5 N HCl, saturated sodium bicarbonate, brine, dried over sodium sulfate. After evaporation of solvent, Intermediate 25C (1.92 g, 7.91 mmol, 93% yield) was obtained as oil. It was used for the next step without further purification. $^1$H NMR (400 MHz, chloroform-d) δ 6.92 (dd, J=2.0, 0.7 Hz, 1H), 6.85-6.68 (m, 2H), 4.47-4.36 (m, 1H), 4.34-4.23 (m, 3H), 4.05 (dd, J=11.6, 6.9 Hz, 1H), 2.12 (s, 3H). LC-MS: method C, RT=2.01 min, MS (ESI) m/z: 265 (M+Na)$^+$.

Intermediate 25D: (R)-(7-chloro-6-nitro-2,3-dihydrobenzo[b][1,4]dioxin-2-yl)methyl

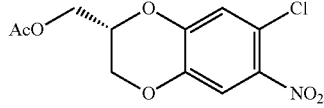

(25D)

To a solution of Intermediate 25C (1.9 g, 7.83 mmol) in acetic acid (20 mL) cooled at 0° C. with an ice-bath was added fuming nitric acid (1.827 mL, 39.2 mmol) dropwise. The mixture was stirred at 0° C. for 30 min. LCMS indicated a completion of the reaction. It was quenched with ice water. The aqueous was removed and the organic layer was washed with saturated sodium bicarbonate (3×), brine, dried over sodium sulfate. After evaporation of solvent, Intermediate 25D (2.25 g, 7.82 mmol, 100% yield) was obtained as a white solid which was used for the next step without further purification. $^1$H NMR (400 MHz, chloroform-d) δ 7.62 (s, 1H), 7.08 (s, 1H), 4.49 (dd, J=7.2, 2.3 Hz, 1H), 4.40-4.33 (m, 3H), 4.11 (dd, J=11.8, 7.2 Hz, 1H), 2.13 (s, 3H). LC-MS: method C, RT=1.90 min, MS (ESI) m/z: 310 (M+Na)$^+$.

Intermediate 25E: (R)-(6-amino-7-chloro-2,3-dihydrobenzo[b][1,4]dioxin-2-yl)methyl acetate

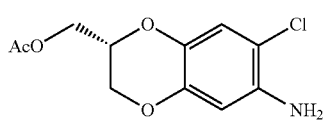

(25E)

To a solution of Intermediate 25D (2.25 g, 7.82 mmol) in MeOH (30 mL) and THF (30 mL) cooled with an water bath was added ammonium chloride (6.69 g, 125 mmol) and zinc dust (4.09 g, 62.6 mmol). The mixture was stirred at room temperature for 3.0 h. HPLC indicated a clean reaction. MeOH was removed under vacuum. The residue was diluted with EtOAc/saturated sodium bicarbonate and stirred at room temperature for 10 min. The mixture was filtered through a pad of wet celite to remove insoluble material. The filtrate was collected, organic layer was washed with brine, dried over sodium sulfate and concentrated to give Intermediate 25E (1.62 g, 6.29 mmol, 80% yield) as colorless oil. $^1$H NMR (400 MHz, methanol-d$_4$) δ 6.75 (s, 1H), 6.39 (s, 1H), 4.34-4.21 (m, 4H), 4.03-3.95 (m, 1H), 2.07 (s, 3H). LC-MS: method C, RT=1.28 min, MS (ESI) m/z: 258 (M+H)$^+$.

Intermediate 25F: (R)-(2-amino-4-chloro-7,8-dihydro-[1,4]dioxino[2',3':3,4]benzo[1,2-d]thiazol-7-yl)methyl acetate

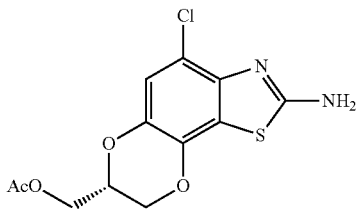

(25F)

To a solution of Intermediate 25E (1.6 g, 6.21 mmol) in acetonitrile (25 mL) was added ammonium thiocyanate (0.709 g, 9.31 mmol). The mixture was stirred at room temperature for 10 min. Benzyltrimethylammonium tribromide (2.54 g, 6.52 mmol) in acetonitrile (8 mL) was added dropwise (5 min). The mixture was stirred at room temperature overnight. IPLC and LCMS indicated a clean reaction. The mixture was diluted with EtOAc/THF/saturated sodium bicarbonate. The insoluble material was removed by filtration. The organic layer of the filtrate was collected, washed with brine, dried over sodium sulfate. After evaporation of solvent, Intermediate 25F (1.9 g, 6.04 mmol, 97% yield) was obtained as a yellow solid. It was used for the next step without further purification. $^1$H NMR (400 MHz, chloroform-d) δ 6.98 (s, 1H), 7.05-6.94 (m, 1H), 5.40 (br. s., 2H), 4.44-4.32 (m, 4H), 4.17 (dd, J=11.3, 7.2 Hz, 1H), 2.13 (s, 3H). LC-MS: method C, RT=1.58 min, MS (ESI) m/z: 315 (M+H)$^+$.

Intermediate 25G: (R)-(2-bromo-4-chloro-7,8-dihydro-[1,4]dioxino[2',3':3,4]benzo[1,2-d]thiazol-7-yl)methyl acetate

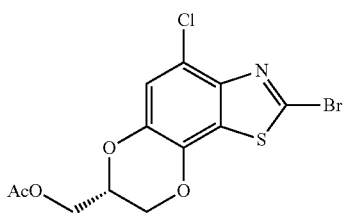

(25G)

tert-Butyl nitrite (0.367 mL, 2.78 mmol) was added to copper (II) bromide (603 mg, 2.70 mmol) in dry acetonitrile (5 mL) under argon. The mixture was stirred at room temperature for 10 min. A suspension of Intermediate 25F (500 mg, 1.589 mmol) in dry acetonitrile (5 mL) was added dropwise. The reaction mixture was stirred at room temperature for 2h. LCMS indicated completion of the reaction. Acetonitrile was removed under vacuum, the residual was diluted with EtOAc, quenched with 1.0 N HCl. The organic layer was collected, washed with 0.5 N HCl (2×), saturated sodium bicarbonate, brine, dried over sodium sulfate. After evaporation of solvent, the crude product was purified with flash chromatography (loading in chloroform, 0% to 70% EtOAc in hexanes over 20 min using a 40 g silica gel cartridge). The desired fractions were combined and concentrated to yield Intermediate 25G (550 mg, 1.453 mmol, 91% yield) as an off-white solid. $^1$H NMR (400 MHz, chloroform-d) δ 7.15 (s, 1H), 4.45 (dd, J=11.7, 2.0 Hz, 2H), 4.37-4.30 (m, 2H), 4.20 (d, J=4.2 Hz, 1H), 2.13 (s, 3H). LC-MS: method C, RT=2.13 min, MS (ESI) m/z: 377 and 379 (M+H)$^+$.

Intermediate 25H: (S)-(2-bromo-4-chloro-7,8-dihydro-[1,4]dioxino[2',3':3,4]benzo[1,2-d]thiazol-7-yl)methanol

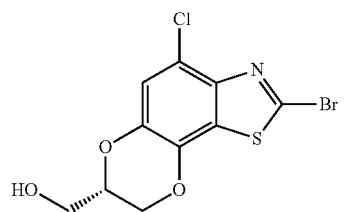

(25H)

To a solution of Intermediate 25G (550 mg, 1.453 mmol) in THF (5 mL) cooled with an ice-bath was added 1.0 N NaOH (2.18 mL, 12.18 mmol) and MeOH (2 mL). The mixture was stirred at 0° C. for 1 h. LCMS indicated a completion of the reaction. 1.0 N HCl (5.0 mL) was added to quench the reaction. The mixture was diluted with EtOAc/water. The organic layer was collected, washed with saturated sodium bicarbonate, brine, dried over sodium sulfate. After evaporation of solvent, Intermediate 25H (465 mg, 1.382 mmol, 95% yield) was obtained as off-white solid. $^1$H NMR (400 MHz, Methanol-d$_4$) δ 7.18 (s, 1H), 4.52 (dd, J=11.1, 2.1 Hz, 1H), 4.33-4.27 (m, 1H), 4.24 (d, J=11.2 Hz, 1H), 3.82 (d, J=5.1 Hz, 2H). LC-MS: method C, RT=1.98 min, MS (ESI) m/z: 335.9 and 337.9.(M+H)$^+$.

Intermediate 25I (S)-(4-chloro-2-(2-(difluoromethoxy)-7-methylquinoxalin-5-yl)-7,8-dihydro-[1,4]dioxino [2',3':3,4] benzo[1,2-d]thiazol-7-yl)methanol

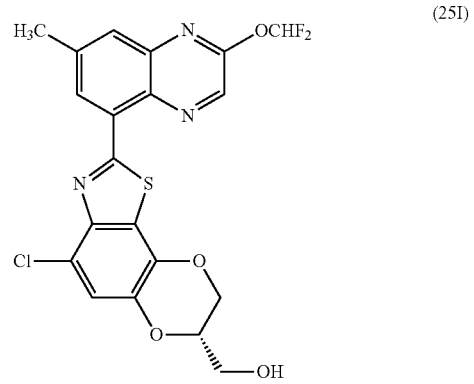 [SMILES: Cc1cc(-c2nc3c(Cl)cc4c(c3s2)OC[C@H](CO)O4)c2ncc(OC(F)F)nc2c1]

(25I)

To Intermediate I-1 (382 mg, 1.503 mmol), Intermediate 25H (460 mg, 1.367 mmol) and PdCl$_2$(dppf)—CH$_2$Cl$_2$ adduct (55.8 mg, 0.068 mmol) was added toluene (4.5 mL) and EtOH (1.5 mL). The mixture was sonicated for 1 min, and flushed with argon. To this was added sodium carbonate (1.367 mL, 2M, 2.73 mmol). The reaction mixture was heated in a microwave reactor at 130° C. for 30 min. The crude reaction mixture was directly loaded onto an ISCO column for purification without work up. The crude product was purified with flash chromatography (5% to 75% EtOAc in hexanes over 15 min using a 12 g silica gel cartridge). The desired fractions were combined and concentrated to Intermediate 25I (280 mg, 0.601 mmol, 44.0% yield) as a yellow solid. $^1$H NMR (400 MHz, chloroform-d) δ 8.88 (d, J=1.8 Hz, 1H), 8.68 (s, 1H), 8.03 (s, 1H), 7.80 (dd, J=1.9, 1.0 Hz, 1H), 7.87-7.45 (m, 1H), 7.22-7.16 (m, 1H), 4.53 (dd, J=11.0, 2.0 Hz, 1H), 4.44-4.29 (m, 2H), 4.07-3.92 (m, 2H), 2.70 (s, 3H). LC-MS: method C, RT=2.46 min, MS (ESI) m/z: 466 (M+H)$^+$.

Intermediate 25K (S)-(4-chloro-2-(2-methoxy-7-methylquinoxalin-5-yl)-7,8-dihydro-[1,4]dioxino[2',3':3,4]benzo[1,2-d]thiazol-7-yl)methanol

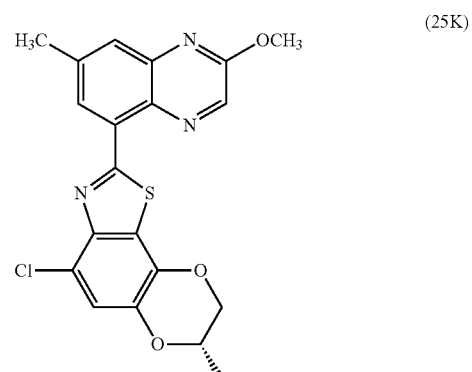

(25K)

To a solution of Intermediate 25I (280 mg, 0.601 mmol) in THF (3 mL) at room temperature was added 5.4 M sodium methoxide in MeOH (0.390 mL, 2.104 mmol). The reaction mixture was stirred at room temperature for 30 min. LCMS indicated a clean reaction. The reaction mixture was diluted with EtOAc, quenched with 0.5 N HCl (2.0 mL). The organic layer was washed with saturated sodium bicarbonate, brine, dried and concentrated to give Intermediate 25K (220 mg, 0.512 mmol, 85% yield) as a yellow solid. $^1$H NMR (500 MHz, DMSO-$d_6$) δ 8.75 (s, 1H), 8.56 (s, 1H), 7.84 (s, 1H), 7.27 (s, 1H), 5.15 (t, J=5.5 Hz, 1H), 4.57 (d, J=11.3 Hz, 1H), 4.33 (d, J=5.8 Hz, 1H), 4.27-4.18 (m, 1H), 4.08 (s, 3H), 3.71 (dt, J=10.8, 5.5 Hz, 2H), 2.64 (s, 3H). LC-MS: method C, RT=2.50 min, MS (ESI) m/z: 429.9 (M+H)$^+$.

Intermediate 25L (R)-(4-chloro-2-(2-methoxy-7-methylquinoxalin-5-yl)-7,8-dihydro-[1,4]dioxino[2',3':3,4]benzo[1,2-d]thiazol-7-yl)methyl carbonochloridate

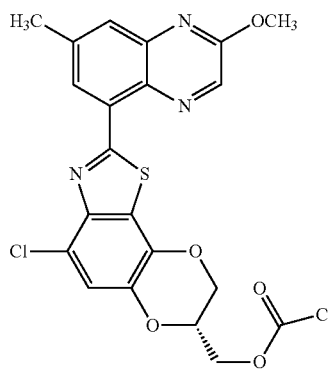

(25L)

To a solution of Intermediate 25K (90 mg, 0.209 mmol) in THF (3 mL) at room temperature was added 15% phosgene in toluene (0.738 mL, 1.047 mmol) and the mixture was stirred at room temperature overnight. LCMS indicated the reaction was complete. Solvent was removed under vacuum. Intermediate 25L was obtained as a yellow solid. It was used for the next step without any purification. LC-MS: method C, RT=2.81 min, MS (ESI) m/z: 493.9 (M+H)$^+$.

Example 25

To a solution of Intermediate 25L (20 mg, 0.041 mmol) in DCM (1 mL) and THF (0.5 mL) was added 5-chloropyridin-3-amine (18.28 mg, 0.142 mmol), followed by DIEA (0.071 mL, 0.406 mmol). The mixture was stirred at room temperature for 0.5 h. LCMS indicated a completion of reaction. The reaction was quenched by addition of a small amount of MeOH/water/0.1% TFA (HPLC solvent). Solvent was removed under vacuum. The residual was dissolved in 1 ml of DMF and purified via preparative LC/MS (method D, 55-95% B over 15 min., then a 5-min hold at 100% B). Fractions containing the desired product were combined and dried via centrifugal evaporation to give Example (7.9 mg, 33% yield). $^1$H NMR (500 MHz, DMSO-$d_6$) δ 10.35 (br. s., 1H), 8.77 (s, 1H), 8.58 (dd, J=7.7, 1.9 Hz, 2H), 8.28 (d, J=2.2 Hz, 1H), 8.03 (s, 1H), 7.86 (dd, J=1.8, 1.0 Hz, 1H), 7.32 (s, 1H), 4.80-4.69 (m, 1H), 4.65 (dd, J=11.4, 2.3 Hz, 1H), 4.59-4.44 (m, 2H), 4.34 (dd, J=11.6, 7.2 Hz, 1H), 4.09 (s, 3H), 2.65 (s, 3H). LC-MS: method C, RT=2.80 min, MS (ESI) m/z: 584.10 (M+H)$^+$. Analytical HPLC purity (method B): 99%.

Example 26

(R)-(4-chloro-2-(2-methoxy-7-methylquinoxalin-5-yl)-7,8-dihydro-[1,4]dioxino[2',3':3,4]benzo[1,2-d]thiazol-7-yl)methyl phenylcarbamate

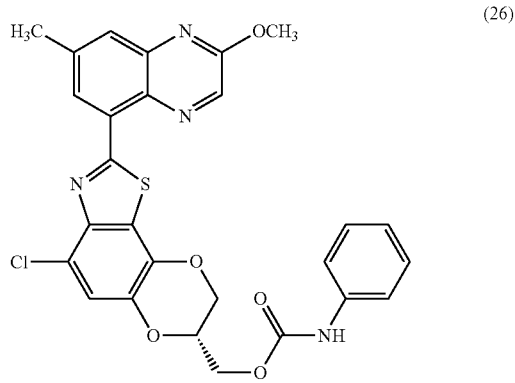

(26)

To a solution of Intermediate 25L (20 mg, 0.041 mmol) in DCM (1 mL) and THF (0.5 mL) was added aniline (13.24 mg, 0.142 mmol) followed by DIEA (0.071 mL, 0.406 mmol). The mixture was stirred at room temperature for 0.5 h. Solvent was removed under vacuum. The residual was purified via preparative LC/MS (method D, 60-100% B over 18 min., then a 5-min hold at 100% B). Fractions containing the desired product were combined and dried via centrifugal evaporation to give Example 26 (8.8 mg, 0.016 mmol, 39.5% yield). $^1$H NMR (500 MHz, DMSO-$d_6$) δ 9.84 (br. s., 1H), 8.54 (s, 1H), 7.82 (s, 1H), 7.48 (d, J=7.7 Hz, 2H), 7.33-7.26 (m, 3H), 7.01 (t, J=7.3 Hz, 1H), 4.75-4.61 (m, 2H), 4.52-4.39 (m, 2H), 4.35-4.25 (m, 1H), 4.07 (s, 3H), 2.63 (s, 3H). LC-MS: method C, RT=2.85 min, MS (ESI) m/z: 549.15 (M+H)$^+$. Analytical HPLC purity (method B): 100%.

Example 27

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (3-cyanophenyl)carbamate

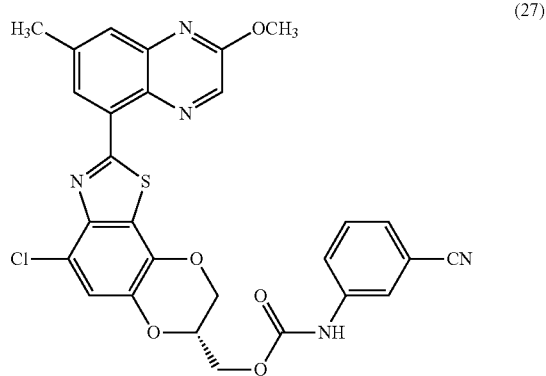

(27)

To a solution of Intermediate 25L (20 mg, 0.041 mmol) in DCM (1 mL) and THF (0.5 mL) was added 3-aminobenzonitrile (16.80 mg, 0.142 mmol) followed by DIEA (0.071 mL, 0.406 mmol). The mixture was stirred at room temperature for 0.5 h, quenched by addition of a small amount of MeOH/water/0.1% TFA (HPLC solvent). Solvent was removed under vacuum. The residual was purified via preparative LC/MS (method D, 60-100% B over 18 min., then a 5-min hold at 100% B). Fractions containing the desired product were combined and dried via centrifugal evaporation to give Example 27 (5.0 mg, 8.54 µmol, 21.01% yield). $^1$H NMR (500 MHz, DMSO-d$_6$) δ 10.25 (br. s., 1H), 8.69 (s, 1H), 8.52 (br. s., 1H), 7.88 (br. s., 1H), 7.79 (br. s., 1H), 7.74 (d, J=7.4 Hz, 1H), 7.56-7.43 (m, 2H), 7.28 (s, 1H), 4.73-4.61 (m, 2H), 4.53-4.40 (m, 2H), 4.36-4.28 (m, 1H), 4.06 (br. s., 3H), 2.62 (br. s., 3H). LC-MS: method C, RT=2.78 min, MS (ESI) m/z: 574.20(M+H)$^+$. Analytical IPLC purity (method B): 98%.

Example 28

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (5-fluoropyridin-3-yl)carbamate

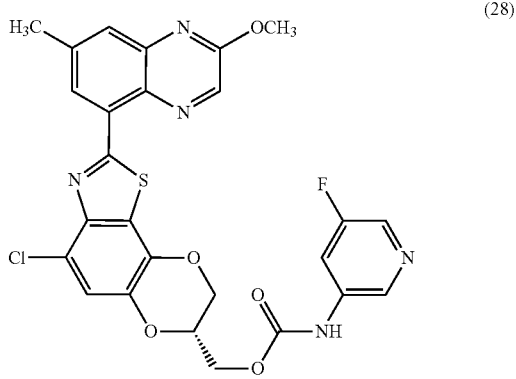 [SMILES: COc1cnc2c(-c3nc4c(Cl)cc5c(c4s3)OC[C@H](COC(=O)Nc3cncc(F)c3)O5)cc(C)cc2n1]

(28)

To a solution of Intermediate 25L (20 mg, 0.041 mmol) in DCM (1 mL) and THF (0.5 mL) was added 5-fluoropyridin-3-amine (15.94 mg, 0.142 mmol) followed by DIEA (0.071 mL, 0.406 mmol). The mixture was stirred at room temperature for 1.0 h. The reaction was quenched by addition of a small amount of MeOH/water/0.1% TFA (HPLC solvent). Solvent was removed under vacuum. The residual was purified via preparative LC/MS (method D, 60-100% B over 20 min., then a 5-min hold at 100% B). Fractions containing the desired product were combined and dried via centrifugal evaporation to give Example 28 (3.7 mg, 6.45 µmol, 15.88% yield). $^1$H NMR (500 MHz, DMSO-d$_6$) δ 10.39 (br. s., 1H), 8.76 (s, 1H), 8.58 (s, 1H), 8.48 (br. s., 1H), 8.24 (br. s., 1H), 7.88-7.76 (m, 2H), 7.32 (s, 1H), 4.71 (br. s., 1H), 4.66 (d, J=11.6 Hz, 1H), 4.57-4.44 (m, 2H), 4.38-4.29 (m, 1H), 4.08 (s, 3H), 2.65 (s, 3H). LC-MS: method C, RT=2.52 min, MS (ESI) m/z: 568.10 (M+H)$^+$. Analytical HPLC purity (method B): 99%.

Example 29

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (6-fluoropyridin-3-yl)carbamate

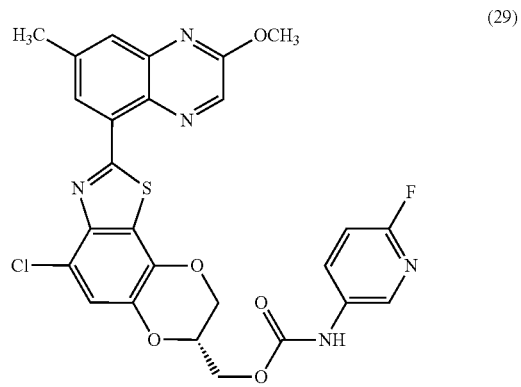 [SMILES: COc1cnc2c(-c3nc4c(Cl)cc5c(c4s3)OC[C@H](COC(=O)Nc3ccc(F)nc3)O5)cc(C)cc2n1]

(29)

To a solution of Intermediate 25L (20 mg, 0.041 mmol) in DCM (1 mL) and THF (0.5 mL) was added 6-fluoropyridin-3-amine (15.94 mg, 0.142 mmol) followed by DIEA (0.071 mL, 0.406 mmol). The mixture was stirred at room temperature for 1 h. The reaction was quenched by addition of a small amount of MeOH/water/0.1% TFA (HPLC solvent). Solvent was removed under vacuum. The residual was dissolved in 1 ml of DMSO and purified via preparative LC/MS (method D, 60-100% B over 18 min., then a 5-min hold at 100% B). Fractions containing the desired product were combined and dried via centrifugal evaporation to give Example 29 (6.6 mg, 0.012 mmol, 28.6% yield). $^1$H NMR (500 MHz, DMSO-d$_6$) δ 10.16 (br. s., 1H), 8.73 (s, 1H), 8.55 (s, 1H), 8.28 (br. s., 1H), 8.02 (d, J=9.1 Hz, 1H), 7.83 (s, 1H), 7.30 (s, 1H), 7.15 (d, J=8.5 Hz, 1H), 4.70 (br. s., 1H), 4.65 (d, J=11.3 Hz, 1H), 4.52-4.42 (m, 2H), 4.35-4.29 (m, 1H), 4.08 (s, 3H), 2.64 (s, 3H). LC-MS: method C, RT=22.69 min, MS (ESI) m/z: 568.15 (M+H)$^+$. Analytical HPLC purity (method B): 100%.

Example 30

(R)-(4-chloro-2-(2-methoxy-7-methylquinoxalin-5-yl)-7,8-dihydro-[1,4]dioxino[2',3':3,4]benzo[1,2-d]thiazol-7-yl)methyl pyridin-4-ylcarbamate

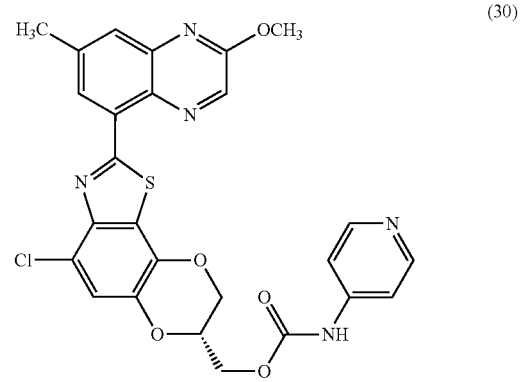 [SMILES: COc1cnc2c(-c3nc4c(Cl)cc5c(c4s3)OC[C@H](COC(=O)Nc3ccncc3)O5)cc(C)cc2n1]

(30)

To a solution of Intermediate 25L (20 mg, 0.041 mmol) in DCM (1 mL) and THF (0.5 mL) was added pyridin-4-amine (13.38 mg, 0.142 mmol) followed by DIEA (0.071 mL, 0.406 mmol). The mixture was stirred at room temperature for 0.5 h. LCMS indicated a completion of reaction. The reaction was quenched by addition of a small amount of MeOH/water/0.1% TFA (HPLC solvent). Solvent was removed under vacuum. The residual was dissolved in 1 ml of DMSO and purified via preparative LC/MS (method C, 35-70% B over 15 min., then a 5-min hold at 100% B). Fractions containing the desired product were combined and dried via centrifugal evaporation to give Example 30 (8.3 mg, 0.015 mmol, 36.4% yield). $^1$H NMR (500 MHz, DMSO-d$_6$) δ 11.23 (br. s., 1H), 8.74 (s, 1H), 8.62 (d, J=5.5 Hz, 2H), 8.56 (s, 1H), 7.86-7.79 (m, 3H), 7.30 (s, 1H), 4.74 (br. s., 1H), 4.66 (d, J=11.6 Hz, 1H), 4.61-4.47 (m, 2H), 4.35 (br. s., 1H), 4.08 (s, 3H), 2.64 (s, 3H). LC-MS: method C, RT=2.04 min, MS (ESI) m/z: 550.15 (M+H)$^+$. Analytical HPLC purity (method B): 98%.

Example 31

(R)-(4-chloro-2-(2-methoxy-7-methylquinoxalin-5-yl)-7,8-dihydro-[1,4]dioxino[2',3':3,4]benzo[1,2-d]thiazol-7-yl)methyl pyridin-3-ylcarbamate

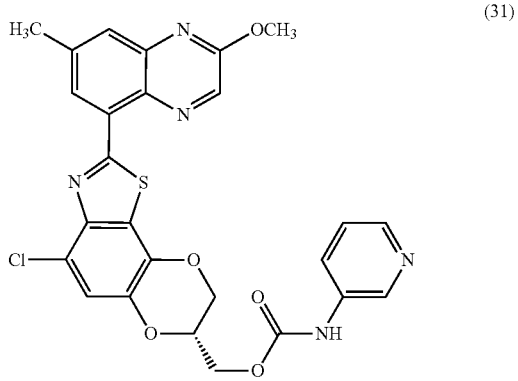 [SMILES: COc1cnc2c(-c3nc4c(Cl)cc5c(c4s3)OC[C@H](COC(=O)Nc3cccnc3)O5)cc(C)cc2n1]

(31)

To a solution of Intermediate 25L (95 mg, 0.193 mmol) in THF (3 mL) and toluene was added pyridin-3-amine (54.5 mg, 0.579 mmol) in DCM (2 mL) followed by DIEA (0.337 mL, 1.930 mmol). The mixture was stirred at room temperature overnight. LCMS indicated a completion of reaction. The reaction was quenched by addition of a small amount of MeOH/water/0.1% TFA (HPLC solvent). Solvent was removed under vacuum. The residual was dissolved in DMSO and purified by preparative HPLC (method A, 30 to 100% B followed by 100% B for 4 min). The desired fractions were placed in a SpeedVac overnight to remove solvent, then lyophilized to give Example 31 (50 mg, 0.075 mmol, 39.0% yield). $^1$H NMR (400 MHz, chloroform-d) δ 9.04 (br. s., 1H), 8.74 (br. s., 1H), 8.69 (d, J=1.8 Hz, 1H), 8.51 (s, 1H), 8.34 (d, J=5.1 Hz, 1H), 7.78-7.69 (m, 2H), 7.15 (s, 1H), 4.60-4.50 (m, 4H), 4.31 (dd, J=11.4, 6.4 Hz, 1H), 4.12 (s, 3H), 2.65 (s, 3H). $^{19}$F NMR (376 MHz, chloroform-d) δ −75.71 (s, 3F). LC-MS: method C, RT=2.33 min, MS (ESI) m/z: 550 (M+H)$^+$. Analytical IPLC purity (method A): 99%.

Example 32

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (6-chloropyridin-3-yl)carbamate

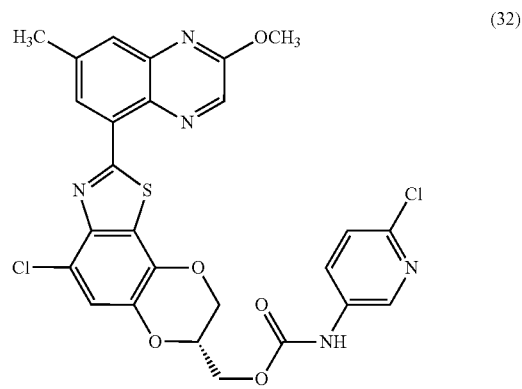 [SMILES: COc1cnc2c(-c3nc4c(Cl)cc5c(c4s3)OC[C@H](COC(=O)Nc3ccc(Cl)nc3)O5)cc(C)cc2n1]

(32)

To a solution of Intermediate 25L (20 mg, 0.041 mmol) in DCM (1 mL) and THF (0.5 mL) was added 6-chloropyridin-3-amine (18.28 mg, 0.142 mmol) followed by DIEA (0.071 mL, 0.406 mmol). The mixture was stirred at room temperature for 0.5 h. LCMS indicated a completion of reaction. The reaction was quenched by addition of MeOH/water/0.1% TFA (HPLC solvent). Solvent was removed under vacuum. The residual was dissolved in DMSO and purified via preparative LC/MS (method D, 55-95% B over 15 min., then a 5-min hold at 100% B). Fractions containing the desired product were combined and dried via centrifugal evaporation to give Example 32 (3.3 mg, 5.65 μmol, 13.90% yield). $^1$H NMR (500 MHz, DMSO-d$_6$) δ 10.25 (br. s., 1H), 8.73 (s, 1H), 8.55 (d, J=1.9 Hz, 1H), 8.49 (d, J=2.5 Hz, 1H), 7.97-7.92 (m, 1H), 7.88-7.77 (m, 1H), 7.46 (d, J=8.5 Hz, 1H), 7.31 (s, 1H), 4.74-4.69 (m, 1H), 4.65 (dd, J=11.6, 2.5 Hz, 1H), 4.51-4.42 (m, 2H), 4.32 (dd, J=11.6, 7.2 Hz, 1H), 4.08 (s, 3H), 2.64 (s, 3H). LC-MS: method C, RT=2.75 min, MS (ESI) m/z: 584.10 (M+H)$^+$. Analytical HPLC purity (method B): 100%.

Example 33

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (2-methylpyridin-4-yl)carbamate

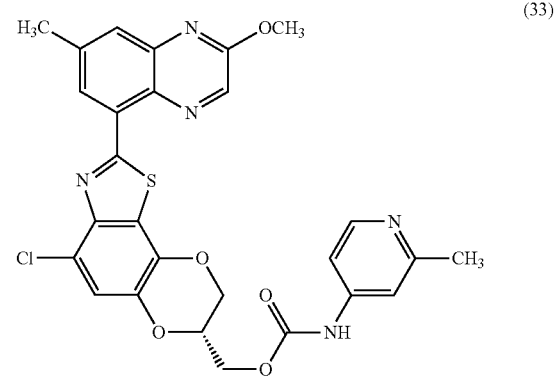 [SMILES: COc1cnc2c(-c3nc4c(Cl)cc5c(c4s3)OC[C@H](COC(=O)Nc3ccnc(C)c3)O5)cc(C)cc2n1]

(33)

To a solution of Intermediate 25L (20 mg, 0.041 mmol) in DCM (1 mL) and THF (0.5 mL) was added 2-methylpyridin-4-amine (15.38 mg, 0.142 mmol) and DIEA (0.071 mL, 0.406 mmol). The mixture was stirred at room temperature for 0.5 h. LCMS indicated a completion of reaction. The reaction was quenched by addition of a small amount of MeOH/water/0.1% TFA (HPLC solvent). Solvent was removed under vacuum. The residual was dissolved in DMSO and purified via preparative LC/MS (method C, 35-75% B over 18 min., then a 5-min hold at 100% B). Fractions containing the desired product were combined and dried via centrifugal evaporation to give Example 33 (11.8 mg, 0.021 mmol, 51.5% yield). $^1$H NMR (500 MHz, DMSO-$d_6$) δ 11.22 (br. s., 1H), 8.77 (s, 1H), 8.59 (d, J=1.7 Hz, 1H), 8.52 (d, J=6.6 Hz, 1H), 7.92-7.81 (m, 1H), 7.79-7.61 (m, 2H), 7.33 (s, 1H), 4.84-4.72 (m, 1H), 4.68 (dd, J=11.4, 2.3 Hz, 1H), 4.63-4.51 (m, 2H), 4.37 (dd, J=11.7, 7.0 Hz, 1H), 4.10 (s, 3H), 2.66 (s, 3H), 2.60 (s, 3H). LC-MS: method C, RT=2.22 min, MS (ESI) m/z: 564.20 (M+H)$^+$. Analytical HPLC purity (method B): 100%.

Example 34

(R)-(4-chloro-2-(2-methoxy-7-methylquinoxalin-5-yl)-7,8-dihydro-[1,4]dioxino[2',3':3,4]benzo[1,2-d]thiazol-7-yl)methyl pyridazin-4-ylcarbamate

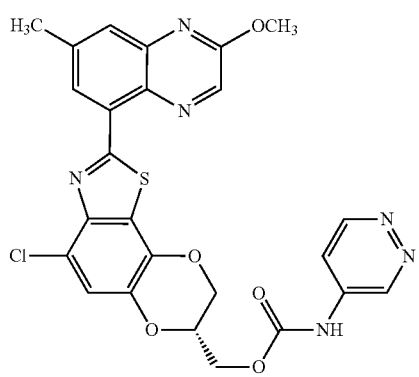

(34)

To a solution of Intermediate 25L (20 mg, 0.041 mmol) in DCM (1 mL) and THF (0.5 mL) was added pyridazin-4-amine (13.52 mg, 0.142 mmol) followed by DIEA (0.071 mL, 0.406 mmol). The mixture was stirred at room temperature overnight. The reaction was quenched by addition of a small amount of MeOH/water/0.1% TFA (HPLC solvent). Solvent was removed under vacuum. The residual was dissolved in DMSO and purified via preparative LC/MS (method C, 30-70% B over 12 min., then a 5-min hold at 100% B). Fractions containing the desired product were combined and dried via centrifugal evaporation to give Example 34 (3.8 mg, 6.76 μmol, 16.64% yield). $^1$H NMR (500 MHz, DMSO-$d_6$) δ 10.67 (br. s., 1H), 9.21 (br. s., 1H), 9.01 (d, J=5.5 Hz, 1H), 8.74 (s, 1H), 8.56 (s, 1H), 7.84 (s, 1H), 7.77 (br. s., 1H), 7.31 (s, 1H), 4.72 (br. s., 1H), 4.66 (d, J=11.6 Hz, 1H), 4.60-4.37 (m, 2H), 4.35 (d, J=9.1 Hz, 1H), 4.08 (s, 3H), 2.64 (s, 3H). LC-MS: method C, RT=2.13 min, MS (ESI) m/z: 551.15 (M+H)$^+$. Analytical HPLC purity (method B): 98%.

Example 35

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (6-cyanopyridin-3-yl)carbamate

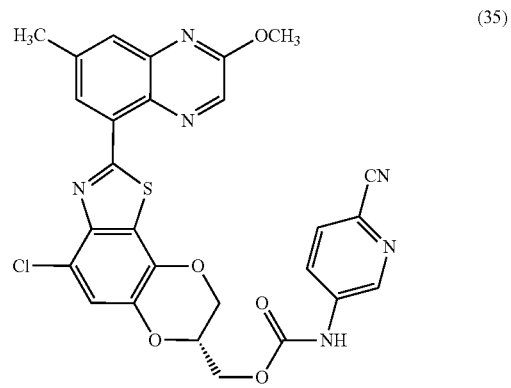 [SMILES: COc1cnc2c(-c3nc4c(Cl)cc5c(c4s3)OC[C@H](COC(=O)Nc3ccc(C#N)nc3)O5)cc(C)cc2n1]

(35)

Intermediate 35A: 6-cyanopyridin-3-ylcarbamic chloride

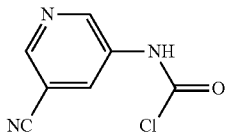

(35A)

To 5-aminopicolinonitrile (100 mg, 0.839 mmol), sodium bicarbonate (353 mg, 4.20 mmol) in DCM (5 ml) at 0° C. was added phosgene (15% in toluene) (1.776 ml, 2.52 mmol). The mixture was stirred for 15 min. TLC (MeOH quenched) indicated a clean conversion. The crude was filtered to a second flask and the solvent and excess of phosgene was removed under vacuum. The crude product Intermediate 35A was redissolved in DCM (5 ml), and was used for next step without purification. LC-MS: method C, RT=2.21 min, MS (ESI) m/z: 178 (M+H)$^+$ (methyl carbamate).

Example 35

To Intermediate 25K (20 mg, 0.047 mmol) in THF (0.3 mL) was added Intermediate 35A (33.8 mg, 0.186 mmol) in DCM (1 mL), followed by TEA (0.052 mL, 0.372 mmol). The mixture was stirred at room temperature for 30 min. LCMS indicated a completion of the reaction. The mixture was quenched by 10% water/acetonitrile with 0. 1% TFA. Solvent was removed, the residual was redissolved in DMSO and purified via preparative LC/MS (method D, 50-90% B over 10 min., then a 5-min hold at 100% B). Fractions containing the desired product were combined and dried via centrifugal evaporation to give Example 35 (6.3 mg, 10.74 µmol, 23.08% yield). ¹H NMR (500 MHz, DMSO-d₆) δ 10.64 (br. s., 1H), 8.76 (d, J=2.5 Hz, 1H), 8.72 (s, 1H), 8.55 (d, J=1.9 Hz, 1H), 8.10 (d, J=2.5 Hz, 1H), 8.09 (d, J=2.5 Hz, 1H), 7.97 (d, J=8.8 Hz, 1H), 7.83 (s, 1H), 7.30 (s, 1H), 4.80-4.70 (m, 1H), 4.65 (dd, J=11.6, 2.2 Hz, 1H), 4.58-4.45 (m, 2H), 4.33 (dd, J=11.6, 7.2 Hz, 1H), 4.07 (s, 3H). LC-MS: method C, RT=2.51 min, MS (ESI) m/z: 575.10 (M+H)⁺. Analytical IPLC purity (method B): 98%.

Example 36

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (2-methoxypyridin-4-yl)carbamate

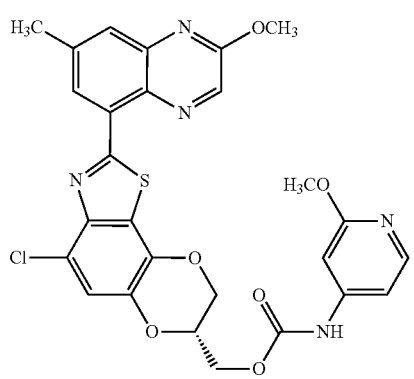

(36)

To a solution of Intermediate 25L (20 mg, 0.041 mmol) in DCM (1 mL) and THE (0.5 mL) was added 2-methoxypyridin-4-amine (17.65 mg, 0.142 mmol) followed by DIEA (0.071 mL, 0.406 mmol). The mixture was stirred at room temperature for 1 h. The reaction was quenched by addition of a small amount of MeOH/water/0.1% TFA (HPLC solvent). Solvent was removed under vacuum. The residual was dissolved in DMSO and purified via preparative LC/MS (method C, 40-75% B over 18 min., then a 5-min hold at 100% B). Fractions containing the desired product were combined and dried via centrifugal evaporation to give Example 36 (1.1 mg, 1.897 µmol, 4.67% yield). ¹H NMR (500 MHz, DMSO-d₆) δ 10.30 (s, 1H), 8.74 (s, 1H), 8.56 (d, J=1.7 Hz, 1H), 7.99 (d, J=5.8 Hz, 1H), 7.83 (s, 1H), 7.30 (s, 1H), 7.03 (dd, J=5.8, 1.7 Hz, 1H), 6.94 (d, J=1.7 Hz, 1H), 4.69 (dd, J=6.2, 3.2 Hz, 1H), 4.64 (dd, J=11.6, 2.2 Hz, 1H), 4.54-4.41 (m, 2H), 4.32 (dd, J=11.4, 7.3 Hz, 1H), 4.08 (s, 3H), 3.80 (s, 3H), 2.64 (s, 3H). LC-MS: method C, RT=2.24 min, MS (ESI) m/z: 580.10 (M+H)⁺. Analytical HPLC purity (method B): 100%.

Example 37

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (5-cyanopyridin-3-yl)carbamate

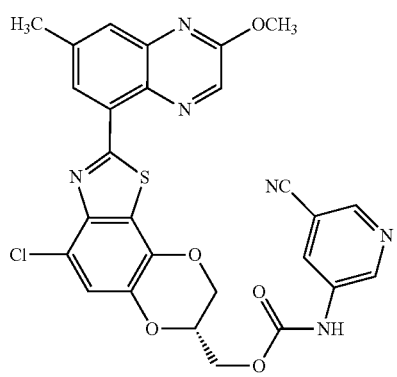

(37)

Intermediate 37A: 5-cyanopyridin-3-ylcarbamic chloride

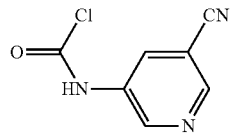

(37A)

To a solution of 5-aminonicotinonitrile (120 mg, 1.007 mmol) in DCM (8 ml) at 0° C. was added phosgene (15% in toluene) (3.55 ml, 5.04 mmol) followed by addition of DIEA (0.229 ml, 1.310 mmol) dropwise at 0° C. The mixture was stirred at 0° C. for 15 min, then slowly warmed up to room temperature. The mixture was bubbled with argon for 1 h to remove the extra phosgene. Intermediate 37A was used for next step without further purification. LC-MS: method C, RT=1.08 min, MS (ESI) m/z: 178 (M+H)⁺ (methyl carbamate).

Example 37

To a solution of Intermediate 25K (40 mg, 0.093 mmol) in THE (0.5 mL) was added a solution of Intermediate 37A (84 mg, 0.465 mmol) in DCM and toluene followed by DIEA (0.163 ml, 0.930 mmol) at room temperature. The mixture was stirred at room temperature for 30 min. LCMS indicated a completion of the reaction. The mixture was quenched with 10% water/acetonitrile with 0.1% TFA. Solvent was removed, the residual was purified with preparative IPLC (method A, 60-100% B in 8 min. Followed by 100% B for 4 min). The desired fractions were placed in a SpeedVac overnight to remove solvent, then lyophilized to give Example 37 (33 mg, 0.055 mmol, 58.6% yield). ¹H NMR (400 MHz, DMSO-d₆) δ 10.51 (br. s., 1H), 8.86 (d, J=2.4 Hz, 1H), 8.78 (s, 1H), 8.68 (d, J=1.8 Hz, 1H), 8.60 (d, J=1.8 Hz, 1H), 8.29 (s, 1H), 7.88 (s, 1H), 7.34 (s, 1H), 4.72 (br. s., 1H), 4.67 (dd, J=11.4, 2.4 Hz, 1H), 4.58-4.47 (m, 2H), 4.35 (dd, J=11.6, 7.2 Hz, 1H), 4.10 (s, 3H), 2.66 (s, 3H).

LC-MS: method C, RT=2.63 min, MS (ESI) m/z: 575.1 (M+H)⁺. Analytical IPLC purity (method A): 95%.

Example 38

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (6-cyanopyridin-3-yl)carbamate

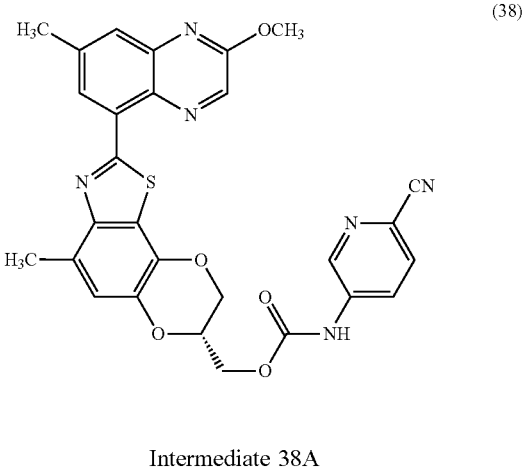

(38)

Intermediate 38A (R)-(2-(2-(difluoromethoxy)-7-methylquinoxalin-5-yl)-4-methyl-7,8-dihydro-[1,4]dioxin o[2',3':3,4]benzo[1,2-d]thiazol-7-yl)methyl acetate

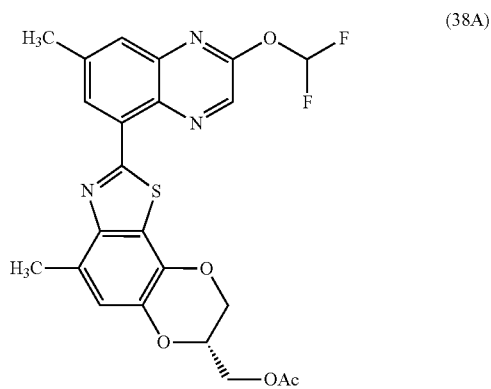 [SMILES: CC(=O)OC[C@H]1COc2c(cc(C)c3nc(-c4cc(C)cc5nc(OC(F)F)cnc45)sc23)O1]

(38A)

To Intermediate I-1 (401 mg, 1.192 mmol), Intermediate I-26 (340 mg, 1.084 mmol) and PdCl₂(dppf)—CH₂Cl₂ adduct (44.2 mg, 0.054 mmol) was added toluene (4.5 mL) and EtOH (1.5 mL). The mixture was sonicated for 1 min, and flushed with argon. To this was added sodium carbonate (1.084 mL, 2M, 2.167 mmol). The reaction mixture was heated in a microwave reactor at 130° C. for 40 min. LCMS indicated a completion of the reaction. The reaction mixture was directly loaded onto a 40 g ISCO column cartridge for purification. The crude product was purified by flash chromatography (0% to 100% EtOAc in hexanes over 20 min using a 40 g silica gel cartridge). The desired fractions were combined and concentrated to yield Intermediate 38A (620 mg, 1.081 mmol, 100% yield) as a yellow solid. NMR indicated ~85% pure. ¹H NMR (400 MHz, CHLOROFORM-d) δ 8.82 (d, J=1.8 Hz, 1H), 8.69 (s, 1H), 7.78 (dd, J=1.9, 1.0 Hz, 1H), 7.94-7.48 (m, 1H), 6.94 (d, J=0.7 Hz, 1H), 4.52-4.23 (m, 5H), 2.77 (d, J=0.9 Hz, 3H), 2.70 (s, 3H), 2.15 (s, 3H). ¹⁹F NMR (376 MHz, METHANOL-d₄) δ −90.63 (s, 2F). LC-MS: method C, RT=2.58 min, MS (ESI) m/z: 488.1 (M+H)⁺.

Intermediate 38B (S)-(2-(2-methoxy-7-methylquinoxalin-5-yl)-4-methyl-7,8-dihydro-[1,4]dioxino[2',3':3,4]benzo[1,2-d]thiazol-7-yl)methanol

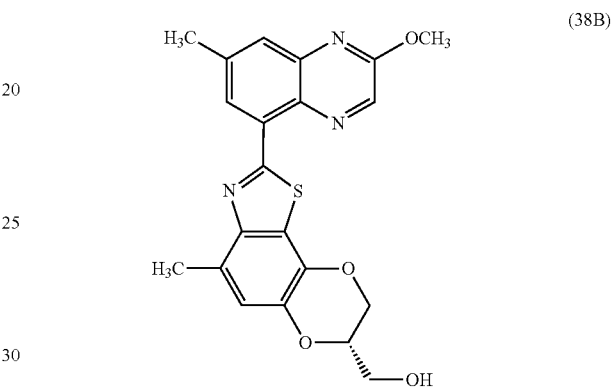

(38B)

To Intermediate 38A (526 mg, 1.08 mmol) dissolved in THF (5 mL) at room temperature was added 4.37 M sodium methoxide in MeOH (0.865 mL, 3.78 mmol). The reaction mixture was stirred at room temperature for 1 h. LCMS indicated a clean reaction. The reaction mixture was quenched with 1 N HCl (5.0 mL) and extracted by EtOAc (5×). The combined organic layer was washed with brine, dried over MgSO₄ and concentrated to give Intermediate 38B (540 mg, 1.055 mmol, 98% yield) as a yellow solid. ¹H NMR (400 MHz, chloroform-d) δ 8.67 (d, J=1.5 Hz, 1H), 8.55 (s, 1H), 7.74 (dd, J=1.9, 1.0 Hz, 1H), 6.92 (d, J=0.9 Hz, 1H), 4.49 (dd, J=11.1, 2.1 Hz, 1H), 4.38 (ddd, J=7.2, 4.2, 2.1 Hz, 1H), 4.34-4.27 (m, 1H), 4.13 (s, 3H), 4.03-3.91 (m, 2H), 2.78 (d, J=0.9 Hz, 3H), 2.67 (s, 3H). LC-MS: method C, RT=2.51 min, MS (ESI) m/z: 410.1 (M+H)⁺.

Example 38

To Intermediate 38B (20 mg, 0.039 mmol) in THF (0.5 mL) was added Intermediate 35A (21.29 mg, 0.117 mmol) in DCM (1 ml) followed by DIEA (0.068 ml, 0.391 mmol). The mixture was stirred at room temperature for 30 min. LCMS indicated a completion of the reaction. The mixture was quenched by 10% water/acetonitrile with 01% TFA. Solvent was removed and redissolved in DMSO and purified via preparative LC/MS (method D, 65-100% B over 20 min., then a 5-min hold at 100% B). Fractions containing the desired product were combined and dried via centrifugal evaporation to give Example 38 (7.6 mg, 0.014 mmol, 35.1% yield). ¹H NMR (500 MHz, chloroform-d) δ 8.67 (d, J=1.7 Hz, 1H), 8.58 (d, J=2.5 Hz, 1H), 8.55 (s, 1H), 8.27-8.16 (m, 2H), 7.75 (s, 1H), 7.69 (d, J=8.5 Hz, 1H), 6.92 (s, 1H), 4.61-4.55 (m, 3H), 4.52-4.49 (m, 1H), 4.30 (dd, J=11.4, 6.5 Hz, 1H), 4.13 (s, 3H), 2.77 (s, 3H), 2.67 (s, 3H).

LC-MS: method C, RT=2.63 min, MS (ESI) m/z: 555.20 (M+H)+. Analytical HPLC purity (method B): 100%.

Example 39

(R)-(4-chloro-2-(2-methoxy-7-methylquinoxalin-5-yl)-7,8-dihydro-[1,4]dioxino[2',3':3,4]benzo[1,2-d]thiazol-7-yl)methyl benzo[d]thiazol-5-ylcarbamate

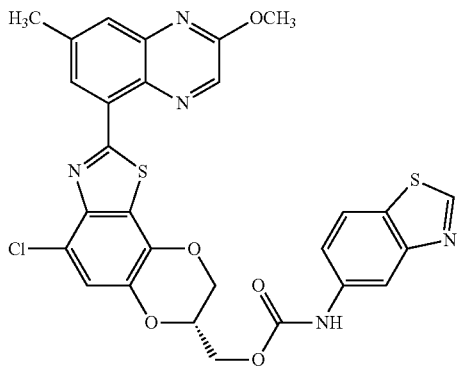
(39)

To a solution of Intermediate 25L (15 mg, 0.030 mmol) in DCM (1 mL) and THF (0.5 mL) was added benzo[d]thiazol-5-amine (13.73 mg, 0.091 mmol) followed by DIEA (0.053 mL, 0.305 mmol). The mixture was stirred at room temperature overnight. LCMS indicated a completion of reaction. The reaction was quenched by addition of a small amount of MeOH/water/0.1% TFA (HPLC solvent). Solvent was removed under vacuum. The residual was dissolved in DMSO and purified via preparative LC/MS (method D, 65-100% B over 22 min., then a 5-min hold at 100% B). Fractions containing the desired product were combined and dried via centrifugal evaporation to give Example 39 (7.0 mg, 0.011 mmol, 37.2% yield). $^1$H NMR (500 MHz, DMSO-$d_6$) δ 10.14 (br. s., 1H), 9.36 (s, 1H), 8.70 (s, 1H), 8.53 (d, J=1.7 Hz, 1H), 8.29 (s, 1H), 8.05 (d, J=8.8 Hz, 1H), 7.81 (s, 1H), 7.55 (d, J=8.5 Hz, 1H), 7.31 (s, 1H), 4.80-4.61 (m, 2H), 4.55-4.43 (m, 2H), 4.34 (dd, J=11.6, 7.2 Hz, 1H), 4.06 (s, 3H), 2.62 (s, 3H). LC-MS: method C, RT=2.66 min, MS (ESI) m/z: 606.10 (M+H)+. Analytical HPLC purity (method B): 98%.

Example 40

(R)-(4-chloro-2-(2-methoxy-7-methylquinoxalin-5-yl)-7,8-dihydro-[1,4]dioxino[2',3':3,4]benzo[1,2-d]thiazol-7-yl)methyl benzo[d]thiazol-6-ylcarbamate

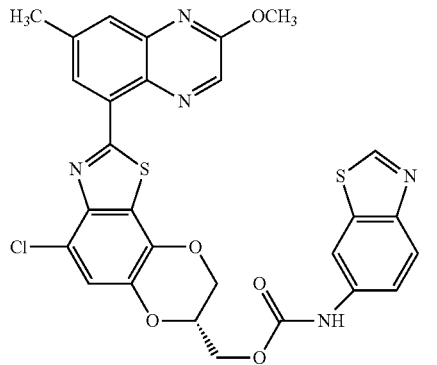
(40)

To a solution of Intermediate 25L (15 mg, 0.030 mmol) in DCM (1 mL) and THF (0.5 mL) was added benzo[d]thiazol-6-amine (13.73 mg, 0.091 mmol) followed by DIEA (0.053 mL, 0.305 mmol). The mixture was stirred at room temperature for 2 h. LCMS indicated a completion of reaction. The reaction was quenched by addition of a small amount of MeOH/water/0.1% TFA (HPLC solvent). Solvent was removed under vacuum. The residual was dissolved in DMSO and purified via preparative LC/MS (method D, 55-95% B over 10 min., then a 5-min hold at 100% B). Fractions containing the desired product were combined and dried via centrifugal evaporation to give Example (3.3 mg, 5.23 μmol, 17.16% yield). $^1$H NMR (500 MHz, DMSO-$d_6$) δ 10.18 (br. s., 1H), 9.24 (s, 1H), 8.74 (s, 1H), 8.56 (d, J=1.7 Hz, 1H), 8.31 (br. s., 1H), 8.00 (d, J=8.8 Hz, 1H), 7.84 (s, 1H), 7.56 (d, J=8.8 Hz, 1H), 7.33 (s, 1H), 4.81-4.59 (m, 1H), 4.55-4.44 (m, 1H), 4.34 (dd, J=11.4, 7.3 Hz, 1H), 4.07 (s, 1H), 2.64 (s, 1H). LC-MS: method C, RT=2.68 min, MS (ESI) m/z: 606.10 (M+H)+. Analytical HPLC purity (method B): 96%.

Example 41

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (6-fluoropyridin-3-yl)carbamate

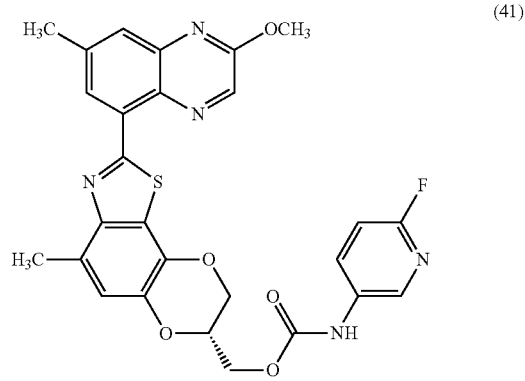 [SMILES: COc1cnc2c(-c3nc4c(C)cc5c(c4s3)OC[C@H](COC(=O)Nc3ccc(F)nc3)O5)cc(C)cc2n1]
(41)

Intermediate 41A (R)-(2-(2-methoxy-7-methylquinoxalin-5-yl)-4-methyl-7,8-dihydro-[1,4]dioxino[2',3':3,4]benzo[1,2-d]thiazol-7-yl)methyl carbonochloridate

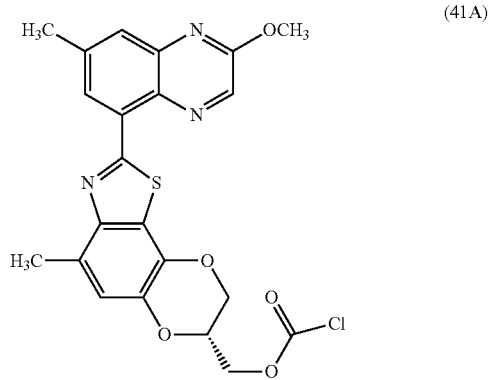 [SMILES: COc1cnc2c(-c3nc4c(C)cc5c(c4s3)OC[C@H](COC(=O)Cl)O5)cc(C)cc2n1]
(41A)

To a solution of Intermediate 38B (250 mg, 0.488 mmol) in THF (3 mL) at room temperature was added 15% phosgene in toluene (1.722 mL, 2.442 mmol). The reaction mixture was stirred at room temperature overnight. LCMS indicated the reaction was complete (methyl carbamate formation from MeOH quenching: LC-MS: method C, RT=2.81 min, MS (ESI) m/z 472.1). Solvent was removed under vacuum to give Intermediate 41A as a yellow solid. It was used for the next step without any purification.

Example 41

To a solution of Intermediate 41A (20 mg, 0.042 mmol) in DCM (1 mL) and THF (0.5 mL) was added 6-fluoropyridin-3-amine (16.63 mg, 0.148 mmol) followed by DIEA (0.074 mL, 0.424 mmol). The mixture was stirred at room temperature for 0.5 h. LCMS indicated a completion of reaction. The reaction was quenched with a small amount of MeOH/water/0.1% TFA (HPLC solvent). Solvent was removed under vacuum. The residual was dissolved in DMSO and purified via preparative LC/MS (method D, 70-100% B over 12 min., then a 5-min hold at 100% B). Fractions containing the desired product were combined and dried via centrifugal evaporation to give Example 41 (7.5 mg, 0.014 mmol, 32.3% yield). $^1$H NMR (500 MHz, DMSO-$d_6$) δ 10.19 (br. s., 1H), 8.72 (s, 1H), 8.56 (d, J=1.7 Hz, 1H), 8.28 (br. s., 1H), 8.03 (br. s., 1H), 7.80 (s, 1H), 7.16 (dd, J=8.8, 3.0 Hz, 1H), 6.98 (s, 1H), 4.68-4.62 (m, 1H), 4.59 (dd, J=11.3, 1.9 Hz, 1H), 4.52-4.38 (m, 2H), 4.27 (dd, J=11.4, 7.3 Hz, 1H), 4.07 (s, 3H), 2.66 (s, 3H), 2.62 (s, 3H). LC-MS: method C, RT=2.64 min, MS (ESI) m/z: 548.20 (M+H)$^+$. Analytical HPLC purity (method B): 100%.

Example 42

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (5-fluoropyridin-3-yl)carbamate

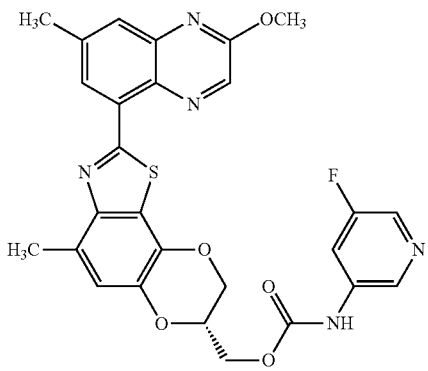

(42)

To a solution of Intermediate 41A (20 mg, 0.042 mmol) in DCM (1 mL) and THF (0.5 mL) was added 5-fluoropyridin-3-amine (16.63 mg, 0.148 mmol) followed by DIEA (0.074 mL, 0.424 mmol). The mixture was stirred at room temperature overnight. The reaction was quenched by addition of a small amount of MeOH/water/0.1% TFA. Solvent was removed under vacuum. The residual was dissolved in DMF and purified via preparative LC/MS (method C, 55-100% B over 10 min., then a 5-min hold at 100% B). Fractions containing the desired product were combined and dried via centrifugal evaporation to give Example 42 (1.5 mg, 2.68 μmol, 6.33% yield). $^1$H NMR (500 MHz, DMSO-$d_6$) δ 10.42 (br. s., 1H), 8.74 (s, 1H), 8.57 (s, 1H), 8.48 (s, 1H), 8.24 (d, J=2.5 Hz, 1H), 7.85 (d, J=11.3 Hz, 1H), 7.81 (s, 1H), 6.98 (s, 1H), 4.73-4.63 (m, 1H), 4.60-4.56 (m, 1H), 4.55-4.40 (m, 2H), 4.27 (dd, J=11.4, 7.3 Hz, 1H), 4.07 (s, 3H), 2.67 (s, 3H), 2.63 (s, 3H). LC-MS: method C, RT=2.54 min, MS (ESI) m/z: 548.20 (M+H)$^+$. Analytical HPLC purity (method B): 98%.

Example 43

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (5-methoxypyridin-3-yl)carbamate

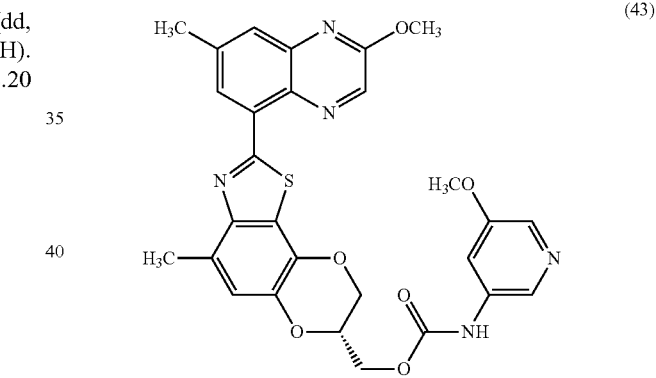

(43)

To a solution of Intermediate 41A (20 mg, 0.042 mmol) in DCM (1 mL) and THF (0.5 mL) was added 5-methoxypyridin-3-amine (18.41 mg, 0.148 mmol) followed by DIEA (0.074 mL, 0.424 mmol). The mixture was stirred at room temperature for 0.5 h. LCMS indicated a completion of reaction. The reaction was quenched by addition of a small amount of MeOH/water/0.1% TFA. Solvent was removed under vacuum. The residual was dissolved in DMSO and purified via preparative LC/MS (method D, 70-100% B over 12 min., then a 5-min hold at 100% B). Fractions containing the desired product were combined and dried via centrifugal evaporation to give Example 43 (5.1 mg, 8.84 μmol, 20.86% yield). $^1$H NMR (500 MHz, DMSO-$d_6$) δ 10.14 (br. s., 1H), 8.72 (s, 1H), 8.55 (d, J=1.7 Hz, 1H), 8.25 (s, 1H), 7.97 (d, J=2.5 Hz, 1H), 7.79 (s, 1H), 7.56 (br. s., 1H), 6.97 (s, 1H), 4.69-4.55 (m, 2H), 4.52-4.37 (m, 2H), 4.27 (dd, J=11.4, 7.3 Hz, 1H), 4.06 (s, 3H), 3.79 (s, 3H), 2.66 (s, 3H), 2.62 (s, 3H). LC-MS: method C, RT=2.18 min, MS (ESI) m/z: 560.20 (M+H)$^+$. Analytical HPLC purity (method B): 97%.

Example 44

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (2-methylpyridin-4-yl)carbamate

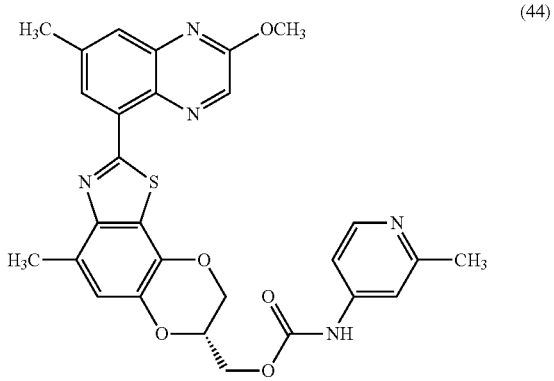

(44)

To a solution of Intermediate 41A (40 mg, 0.085 mmol) in DCM (2 mL) and THF (1 mL) was added 2-methylpyridin-4-amine (32.1 mg, 0.297 mmol) followed by DIEA (0.148 mL, 0.848 mmol). The mixture was stirred at room temperature for 0.5 h. LCMS indicated a completion of reaction. The reaction was quenched by addition of a small amount of MeOH/water/0.1% TFA (HPLC solvent). Solvent was removed under vacuum. The residual was dissolved in DMSO and purified with preparative HPLC (method A, 40-100% B in 8 min. Then 100% B in 4 min.). The desired fractions were placed in a SpeedVac overnight to remove solvent, then lyophilized to give Example 44 (17 mg, 0.030 mmol, 35.8% yield). $^1$H NMR (400 MHz, acetonitrile-$d_3$) δ 10.19 (s, 1H), 8.60 (d, J=1.3 Hz, 1H), 8.54-8.47 (m, 2H), 7.89-7.74 (m, 2H), 7.67 (s, 1H), 6.82 (s, 1H), 4.61-4.50 (m, 4H), 4.25 (dd, J=11.4, 6.6 Hz, 1H), 4.02 (s, 3H), 2.63 (s, 2H), 2.60 (s, 3H), 2.56 (s, 3H). LC-MS: method C, RT=2.34 min, MS (ESI) m/z: 544.2 (M+H)$^+$. Analytical HPLC purity (method A): 98%.

Example 45

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (2-methoxypyridin-4-yl)carbamate

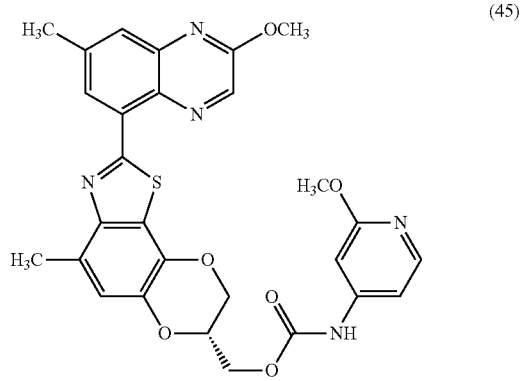 [SMILES: COc1cc(NC(=O)OC[C@H]2COc3c(cc(C)c4nc(-c5cc(C)cc6nc(OC)cnc56)sc34)O2)ccn1]

(45)

To a solution of Intermediate 41A (20 mg, 0.042 mmol) in DCM (1 mL) and THF (0.5 mL) was added 2-methoxypyridin-4-amine (18.41 mg, 0.148 mmol) followed by DIEA (0.074 mL, 0.424 mmol). The mixture was stirred at room temperature for 0.5 h. LCMS indicated a completion of reaction. The reaction was quenched by addition of a small amount of MeOH/water/0.1% TFA (HPLC solvent). Solvent was removed under vacuum. The residual was dissolved in DMSO and purified via preparative LC/MS (method D, 65-100% B over 20 min., then a 5-min hold at 100% B). Fractions containing the desired product were combined and dried via centrifugal evaporation to give Example (7.5 mg, 0.013 mmol, 30.4% yield). $^1$H NMR (500 MHz, DMSO-$d_6$) δ 10.31 (s, 1H), 8.72 (s, 1H), 8.56 (d, J=1.7 Hz, 1H), 7.99 (d, J=5.8 Hz, 1H), 7.79 (s, 1H), 7.03 (dd, J=5.8, 1.7 Hz, 1H), 6.97 (s, 1H), 6.94 (d, J=1.4 Hz, 1H), 4.70-4.62 (m, 1H), 4.59 (dd, J=11.4, 2.1 Hz, 1H), 4.52-4.45 (m, 1H), 4.44-4.36 (m, 1H), 4.26 (dd, J=11.4, 7.3 Hz, 1H), 4.06 (s, 3H), 3.80 (s, 3H), 2.66 (s, 3H), 2.62 (s, 3H). LC-MS: method C, RT=2.21 min, MS (ESI) m/z: 560.20 (M+H)$^+$. Analytical HPLC purity (method B): 96%.

Example 46

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (3-cyanophenyl)carbamate

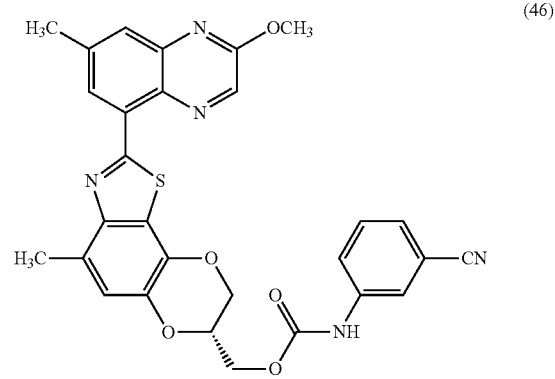 [SMILES: COc1cnc2c(-c3nc4c(C)cc5c(c4s3)OC[C@H](COC(=O)Nc3cccc(C#N)c3)O5)cc(C)cc2n1]

(46)

To a solution of Intermediate 41A (20 mg, 0.042 mmol) in DCM (1 mL) and THF (0.5 mL) was added 3-aminobenzonitrile (17.52 mg, 0.148 mmol) followed by DIEA (0.074 mL, 0.424 mmol). The mixture was stirred at room temperature for 1 h. LCMS indicated a completion of reaction. The reaction was quenched by addition of a small amount of MeOH/water/0.1% TFA (HPLC solvent). Solvent was removed under vacuum. The residual was dissolved in DMSO and purified via preparative LC/MS (method D, 65-100% B over 20 min., then a 5-min hold at 100% B). Fractions containing the desired product were combined and dried via centrifugal evaporation to give Example 46 (3.7 mg, 6.68 μmol, 15.77% yield). $^1$H NMR (500 MHz, DMSO-$d_6$) δ 10.29 (br. s., 1H), 8.72 (s, 1H), 8.55 (d, J=1.7 Hz, 1H), 7.89 (s, 1H), 7.79 (s, 1H), 7.74 (d, J=8.0 Hz, 1H), 7.57-7.41 (m, 2H), 6.97 (s, 1H), 4.64 (td, J=6.3, 3.2 Hz, 1H), 4.59 (dd, J=11.4, 2.1 Hz, 1H), 4.52-4.46 (m, 1H), 4.45-4.40 (m, 1H), 4.27 (dd, J=11.4, 7.3 Hz, 1H), 4.06 (s, 3H), 2.66 (s, 3H), 2.63-2.58 (m, 3H). LC-MS: method C, RT=2.74 min, MS (ESI) m/z: 554.20 (M+H)$^+$. Analytical HPLC purity (method B): 100%.

Example 47

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (6-chloropyridin-3-yl)carbamate

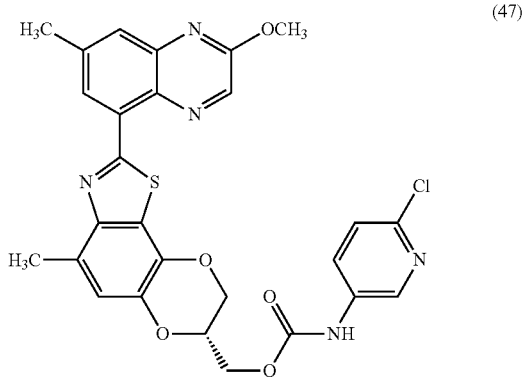 [SMILES: COc1cnc2c(-c3nc4c(C)cc5c(c4s3)OC[C@H](COC(=O)Nc3ccc(Cl)nc3)O5)cc(C)cc2n1]

(47)

To a solution of Intermediate 41A (20 mg, 0.042 mmol) in DCM (1 mL) and THF (0.5 mL) was added 6-chloropyridin-3-amine (19.07 mg, 0.148 mmol) followed by DIEA (0.074 mL, 0.424 mmol). The mixture was stirred at room temperature for 0.5 h. LCMS indicated a completion of reaction. The reaction was quenched by addition of a small amount of MeOH/water/0.1% TFA (HPLC solvent). Solvent was removed under vacuum. The residual was dissolved in DMSO and purified via preparative LC/MS (method D, 65-100% B over 20 min., then a 5-min hold at 100% B). Fractions containing the desired product were combined and dried via centrifugal evaporation to give Example 47 (5.8 mg, 10.08 µmol, 23.78% yield). $^1$H NMR (500 MHz, DMSO-d$_6$) δ 10.30 (br. s., 1H), 8.73 (s, 1H), 8.57 (d, J=1.7 Hz, 1H), 8.49 (d, J=2.2 Hz, 1H), 8.01-7.92 (m, 1H), 7.80 (s, 1H), 7.47 (d, J=8.8 Hz, 1H), 6.98 (s, 1H), 4.68-4.56 (m, 2H), 4.52-4.40 (m, 2H), 4.27 (dd, J=11.4, 7.3 Hz, 1H), 4.07 (s, 3H), 2.67 (s, 3H), 2.63 (s, 3H). LC-MS: method C, RT=2.74 min, MS (ESI) m/z: 564.15 (M+H)$^+$. Analytical HPLC purity (method B): 98%.

Example 48

(R)-(2-(2-methoxy-7-methylquinoxalin-5-yl)-4-methyl-7,8-dihydro-[1,4]dioxino[2',3':3,4]benzo[1,2-d]thiazol-7-yl)methyl pyridin-4-ylcarbamate

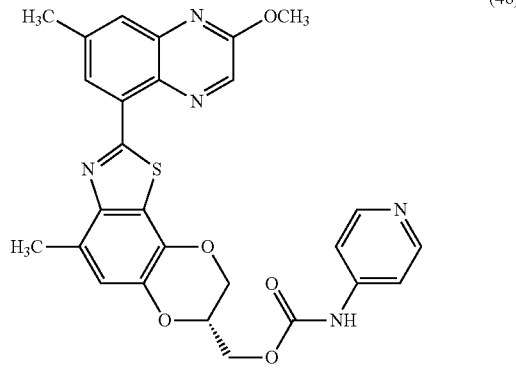

(48)

To a solution of Intermediate 41A (20 mg, 0.042 mmol) in DCM (1 mL) and THF (0.5 mL) was added pyridin-4-amine (13.96 mg, 0.148 mmol) followed by DIEA (0.074 mL, 0.424 mmol). The mixture was stirred at room temperature for 0.5 h. LCMS indicated a completion of reaction. The reaction was quenched by addition of a small amount of MeOH/water/0.1% TFA (HPLC solvent). Solvent was removed under vacuum. The residual was dissolved in DMF and purified via preparative LC/MS (method D, 30-70% B over 12 min., then a 5-min hold at 100% B). Fractions containing the desired product were combined and dried via centrifugal evaporation to give Example 48 (8.8 mg, 0.017 mmol, 39.2% yield). $^1$H NMR (500 MHz, DMSO-d$_6$) δ 11.12 (br. s., 1H), 8.74 (s, 1H), 8.64-8.41 (m, 3H), 7.84 (s, 1H), 7.77 (d, J=5.8 Hz, 2H), 6.98 (s, 1H), 4.73-4.65 (m, 1H), 4.64-4.53 (m, 2H), 4.53-4.43 (m, 1H), 4.29 (dd, J=11.3, 7.2 Hz, 1H), 4.07 (s, 3H), 2.67 (s, 3H), 2.63 (s, 3H). LC-MS: method C, RT=2.16 min, MS (ESI) m/z: 530.10 (M+H)$^+$. Analytical HPLC purity (method B): 100%.

Example 49

(R)-(2-(2-methoxy-7-methylquinoxalin-5-yl)-4-methyl-7,8-dihydro-[1,4]dioxino[2',3':3,4]benzo[1,2-d]thiazol-7-yl)methyl benzo[d]thiazol-5-ylcarbamate

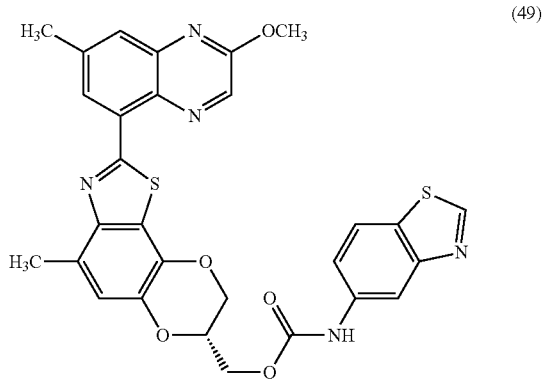 [SMILES: COc1cnc2c(-c3nc4c(C)cc5c(c4s3)OC[C@H](COC(=O)Nc3ccc4scnc4c3)O5)cc(C)cc2n1]

(49)

To a solution of Intermediate 41A (15 mg, 0.032 mmol) in DCM (1 mL) and THF (0.5 mL) was added benzo[d]thiazol-5-amine (14.32 mg, 0.095 mmol) followed by DIEA (0.056 mL, 0.318 mmol). The mixture was stirred at room temperature overnight. LCMS indicated a completion of reaction. The reaction was quenched by addition of a small amount of MeOH/water/0.1% TFA (HPLC solvent). Solvent was removed under vacuum. The residual was dissolved in DMSO and purified via preparative LC/MS (method D, 65-100% B over 20 min., then a 5-min hold at 100% B). Fractions containing the desired product were combined and dried via centrifugal evaporation to give Example 49 (3.0 mg, 4.92 µmol, 15.47% yield). $^1$H NMR (500 MHz, DMSO-d$_6$) δ 10.15 (br. s., 1H), 9.36 (s, 1H), 8.73 (s, 1H), 8.57 (d, J=1.7 Hz, 1H), 8.30 (s, 1H), 8.06 (d, J=8.5 Hz, 1H), 7.80 (s, 1H), 7.56 (d, J=8.5 Hz, 1H), 4.72-4.58 (m, 2H), 4.55-4.40 (m, 2H), 4.29 (dd, J=11.4, 7.3 Hz, 1H), 4.07 (s, 3H), 2.67 (s, 3H), 2.63 (s, 3H). LC-MS: method C, RT=2.66 min, MS (ESI) m/z: 586.15 (M+H)$^+$. Analytical HPLC purity (method B): 96%.

Example 50

(R)-(2-(2-methoxy-7-methylquinoxalin-5-yl)-4-methyl-7,8-dihydro-[1,4]dioxino[2',3':3,4]benzo[1,2-d]thiazol-7-yl)methyl benzo[d]thiazol-6-ylcarbamate

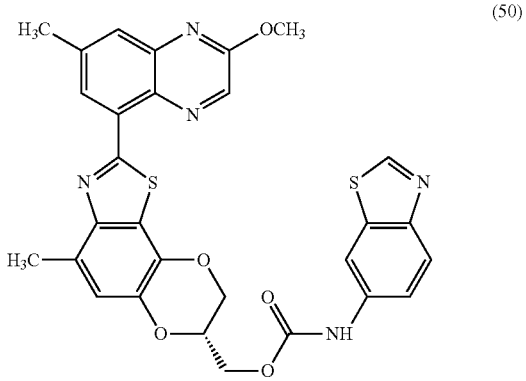 [SMILES: COc1cnc2c(-c3nc4c(C)cc5c(c4s3)OC[C@H](COC(=O)Nc3ccc4ncsc4c3)O5)cc(C)cc2n1]

(50)

To a solution of Intermediate 41A (15 mg, 0.032 mmol) in DCM (1 mL) and THF (0.5 mL) was added benzo[d]thiazol-6-amine (14.32 mg, 0.095 mmol) followed by DIEA (0.056 mL, 0.318 mmol). The mixture was stirred at room temperature for 1 h. The reaction was quenched by addition of a small amount of MeOH/water/0.1% TFA (HPLC solvent). Solvent was removed under vacuum. The residual was dissolved in DMSO and purified via preparative LC/MS (method D, 65-100% B over 20 min., then a 5-min hold at 100% B). Fractions containing the desired product were combined and dried via centrifugal evaporation to give Example 50 (2.3 mg, 3.85 µmol, 12.11% yield). $^1$H NMR (500 MHz, DMSO-$d_6$) δ 10.18 (br. s., 1H), 9.24 (s, 1H), 8.74 (s, 1H), 8.58 (d, J=1.7 Hz, 1H), 8.33 (s, 1H), 8.00 (d, J=8.8 Hz, 1H), 7.81 (s, 1H), 7.56 (d, J=8.8 Hz, 1H), 6.99 (s, 1H), 4.71-4.59 (m, 2H), 4.54-4.39 (m, 2H), 4.29 (dd, J=11.4, 7.3 Hz, 1H), 4.07 (s, 3H), 2.67 (s, 3H), 2.63 (s, 3H). LC-MS: method C, RT=2.68 min, MS (ESI) m/z: 586.15 (M+H)$^+$. Analytical HPLC purity (method B): 98%.

Example 51

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (5-cyanopyridin-3-yl)carbamate

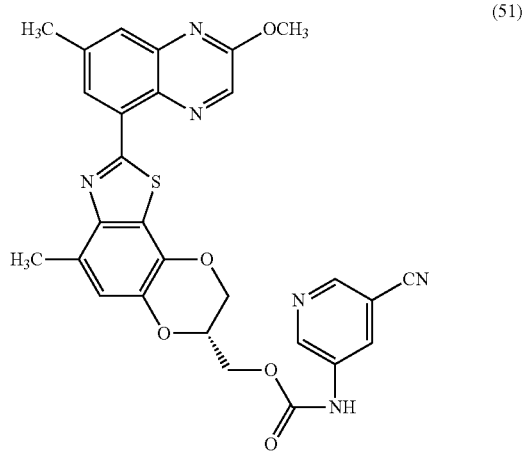 [SMILES: COc1cnc2c(-c3nc4c(C)cc5c(c4s3)OC[C@H](COC(=O)Nc3cncc(C#N)c3)O5)cc(C)cc2n1]

(51)

To a solution of Intermediate 38B (20 mg, 0.049 mmol) in THF (0.5 mL) was added a suspension of Intermediate 37A (44.3 mg, 0.244 mmol) in DCM (1 ml) followed by DIEA (0.085 ml, 0.488 mmol). The mixture was stirred at room temperature for 30 min. LCMS indicated a completion of the reaction. The mixture was quenched by a small amount of 10% water/acetonitrile with 0.01% TFA. Solvent was removed and the crude was purified via preparative LC/MS (method D, 50-95% B over 20 min., then a 5-min hold at 100% B). Fractions containing the desired product were combined and dried via centrifugal evaporation to give Example 51 (10.7 mg, 0.019 mmol, 39.1% yield). $^1$H NMR (500 MHz, DMSO-$d_6$) δ 10.53 (br. s., 1H), 8.85 (d, J=1.7 Hz, 1H), 8.75 (s, 1H), 8.67 (d, J=1.7 Hz, 1H), 8.58 (d, J=1.4 Hz, 1H), 8.29 (br. s., 1H), 7.82 (s, 1H), 6.99 (s, 1H), 4.72-4.63 (m, 1H), 4.60 (dd, J=11.4, 2.1 Hz, 1H), 4.56-4.43 (m, 2H), 4.28 (dd, J=11.6, 7.2 Hz, 1H), 4.07 (s, 3H), 2.67 (s, 3H), 2.63 (s, 3H). LC-MS: method C, RT=2.62 min, MS (ESI) m/z: 555.20 (M+H)$^+$. Analytical HPLC purity (method B): 99%.

Example 52

(R)-(2-(2,7-dimethylquinoxalin-5-yl)-4-methyl-7,8-dihydro-[1,4]dioxino[2',3':3,4]benzo[1,2-d]thiazol-7-yl)methyl (6-(dimethylamino)pyridin-3-yl) carbamate

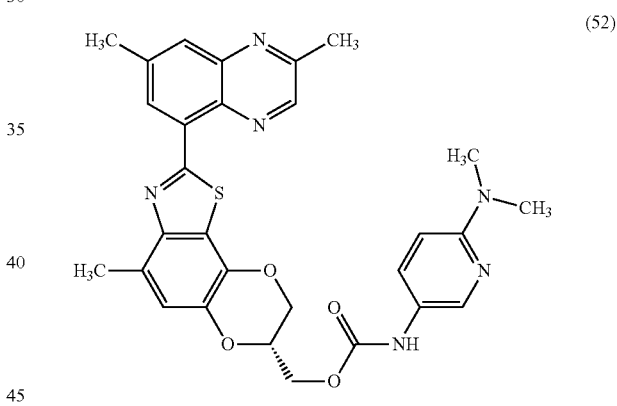

(52)

To a solution of Intermediate 41A (15 mg, 0.032 mmol) in THF (1 mL) was added $N_2,N_2$-dimethylpyridine-2,5-diamine (15.26 mg, 0.111 mmol) in DCM (1 mL) followed by DIEA (0.056 mL, 0.318 mmol). The mixture was stirred at room temperature overnight. LCMS indicated a completion of reaction. The reaction was quenched by addition of a small amount of MeOH/water/0.1% TFA (HPLC solvent). Solvent was removed under vacuum. The residual was dissolved in DMSO and purified via preparative LC/MS (method D, 65-100% B over 15 min., then a 5-min hold at 100% B). Fractions containing the desired product were combined and dried via centrifugal evaporation to give Example 52 (7.9 mg, 0.013 mmol, 42.1% yield). $^1$H NMR (500 MHz, DMSO-$d_6$) δ 9.59 (br. s., 1H), 8.73 (s, 1H), 8.56 (s, 1H), 8.14 (br. s., 1H), 7.80 (s, 1H), 7.63 (d, J=8.0 Hz, 1H), 6.98 (s, 1H), 6.68 (d, J=6.6 Hz, 1H), 4.58 (d, J=11.6 Hz, 2H), 4.46-4.33 (m, 2H), 4.30-4.20 (m, 1H), 4.07 (s, 3H), 2.98 (s, 6H), 2.67 (s, 3H), 2.63 (s, 3H). LC-MS: method C, RT=2.15 min, MS (ESI) m/z: 573.20 (M+H)$^+$. Analytical HPLC purity (method B): 97%.

Example 53

(R)-(2-(2-methoxy-7-methylquinoxalin-5-yl)-4-methyl-7,8-dihydro-[1,4]dioxino [2',3':3,4]benzo[1,2-d]thiazol-7-yl)methyl (6-(thiophen-2-yl)pyridin-3-yl)carbamate

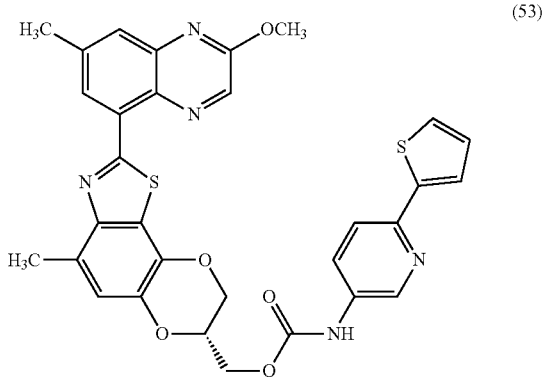 [SMILES: COc1cnc2c(-c3nc4c(C)cc5c(c4s3)OC[C@H](COC(=O)Nc3ccc(-c4cccs4)nc3)O5)cc(C)cc2n1]

(53)

To a solution of Intermediate 41A (15 mg, 0.032 mmol) in THF (1 mL) was added 6-(thiophen-2-yl)pyridin-3-amine (19.61 mg, 0.111 mmol) in DMC (1 ml) followed by DIEA (0.056 mL, 0.318 mmol). The mixture was stirred at room temperature overnight. LCMS indicated a completion of reaction. The reaction was quenched by addition of a small amount of MeOH/water/0.1% TFA (HPLC solvent). Solvent was removed under vacuum. The residual was dissolved in DMSO and purified via preparative LC/MS (method D, 70-100% B over 15 min., then a 5-min hold at 100% B). Fractions containing the desired product were combined and dried via centrifugal evaporation to give Example 53 (3.5 mg, 5.66 µmol, 17.82% yield). $^1$H NMR (500 MHz, DMSO-$d_6$) δ 10.20 (br. s., 1H), 8.73 (s, 1H), 8.64-8.54 (m, 2H), 7.97-7.92 (m, 1H), 7.88-7.84 (m, 1H), 7.80 (s, 1H), 7.66 (d, J=3.3 Hz, 1H), 7.56 (d, J=5.0 Hz, 1H), 7.13 (t, J=4.3 Hz, 1H), 6.99 (s, 1H), 4.65 (br. s., 1H), 4.60 (d, J=11.3 Hz, 1H), 4.53-4.41 (m, 2H), 4.28 (dd, J=11.4, 7.3 Hz, 1H), 4.07 (s, 3H), 2.67 (s, 3H), 2.63 (s, 3H). LC-MS: method C, RT=2.63 min, MS (ESI) m/z: 612.15 (M+H)$^+$. Analytical HPLC purity (method B): 99%.

Example 54

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (3-methyl-3H-imidazo[4,5-b]pyridin-6-yl)carbamate

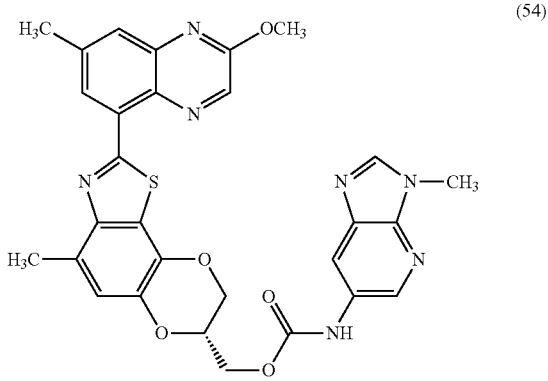

(54)

To a solution of Intermediate 41A (15 mg, 0.032 mmol) in DCM (1 mL) and THF (0.5 mL) was added 3-methyl-3H-imidazo[4,5-b]pyridin-6-amine (11.77 mg, 0.079 mmol) in DMC (1 ml) followed by DIEA (0.056 mL, 0.318 mmol). The mixture was stirred at room temperature overnight. LCMS indicated a completion of reaction. The reaction was quenched by addition of a small amount of MeOH/water/0.1% TFA (HPLC solvent). Solvent was removed under vacuum. The residual was dissolved in DMSO and purified via preparative LC/MS (method D, 45-95% B over 20 min., then a 5-min hold at 100% B). Fractions containing the desired product were combined and dried via centrifugal evaporation to give Example 54 (2.1 mg, 3.60 µmol, 11.32% yield). $^1$H NMR (500 MHz, DMSO-$d_6$) δ 10.06 (br. s., 1H), 8.76 (s, 1H), 8.59 (s, 1H), 8.43 (d, J=7.2 Hz, 2H), 8.20 (br. s., 1H), 7.83 (s, 1H), 7.04-6.93 (m, 1H), 4.70-4.57 (m, 2H), 4.53-4.37 (m, 2H), 4.34-4.23 (m, 1H), 4.08 (s, 3H), 3.81 (s, 3H), 2.68 (s, 3H), 2.64 (s, 3H). LC-MS: method C, RT=2.14 min, MS (ESI) m/z: 584.20 (M+H)$^+$. Analytical HPLC purity (method B): 100%.

Example 55

(R)-(2-(2-methoxy-7-methylquinoxalin-5-yl)-4-methyl-7,8-dihydro-[1,4]dioxino [2',3':3,4]benzo[1,2-d]thiazol-7-yl)methyl (6-(3-methyl-1H-1,2,4-triazol-1-yl)pyridin-3-yl)carbamate

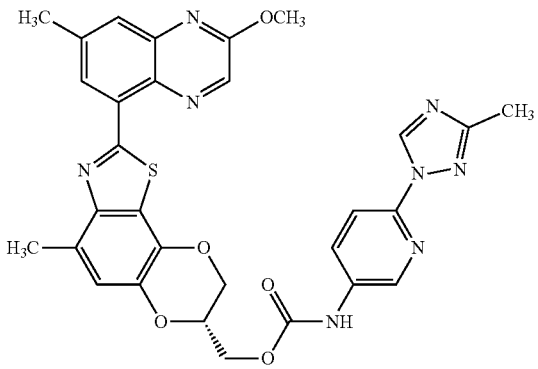

(55)

To a solution of Intermediate 41A (15 mg, 0.032 mmol) in toluene (0.5 mL) and THF (0.5 mL) was added 6-(3-methyl-1H-1,2,4-triazol-1-yl)pyridin-3-amine (19.49 mg, 0.111 mmol) in DCM (1 mL) followed by DIEA (0.056 mL, 0.318 mmol). The mixture was stirred at room temperature overnight. LCMS indicated a completion of reaction. The reaction was quenched by addition of a small amount of MeOH/water/0.1% TFA (HPLC solvent). Solvent was removed under vacuum. The residual was dissolved in DMSO and purified via preparative LC/MS (method D, 60-100% B over 25 min., then a 5-min hold at 100% B). Fractions containing the desired product were combined and dried via centrifugal evaporation to give Example 55 (1.9 mg, 3.02 µmol, 9.50% yield). $^1$H NMR (500 MHz, DMSO-$d_6$) δ 10.33 (br. s., 1H), 9.12 (s, 1H), 8.74 (s, 1H), 8.58 (s, 2H), 8.11 (d, J=6.3 Hz, 1H), 7.82 (s, 1H), 7.77 (d, J=8.8 Hz, 1H), 6.99 (s, 1H), 4.70-4.57 (m, 2H), 4.54-4.41 (m, 2H), 4.29 (dd, J=11.3, 7.2 Hz, 1H), 4.07 (s, 3H), 2.67 (s, 3H), 2.64 (s, 3H), 2.37 (s, 3H). LC-MS: method C, RT=2.51 min, MS (ESI) m/z: 611.25 (M+H)$^+$. Analytical HPLC purity (method B): 97%.

Example 56

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (6-methylpyridin-3-yl)carbamate

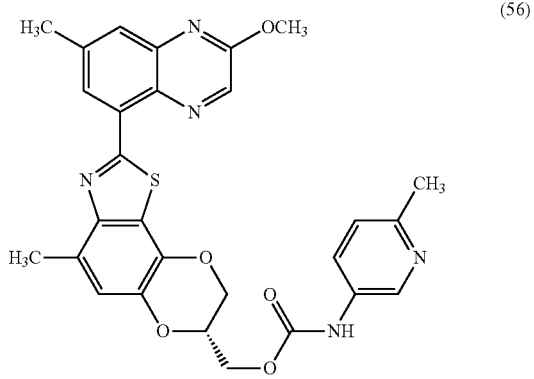

(56)

To a solution of Intermediate 41A (15 mg, 0.032 mmol) in DCM (1 mL) and THF (0.5 mL) was added 6-methylpyridin-3-amine (12.03 mg, 0.111 mmol) in DMC (1 ml) followed by DIEA (0.056 mL, 0.318 mmol). The mixture was stirred at room temperature for 30 min. The reaction was quenched by addition of a small amount of MeOH/water/0.1% TFA (HPLC solvent). Solvent was removed under vacuum. The residual was dissolved in DMSO and purified via preparative LC/MS (method D, 45-90% B over 15 min., then a 5-min hold at 100% B). Fractions containing the desired product were combined and dried via centrifugal evaporation to give Example 56 (6.7 mg, 0.012 mmol, 38.0% yield). $^1$H NMR (500 MHz, DMSO-$d_6$) δ 10.33 (br. s., 1H), 8.73 (s, 1H), 8.65 (br. s., 1H), 8.57 (s, 1H), 7.99 (d, J=7.7 Hz, 1H), 7.80 (s, 1H), 7.47 (d, J=8.3 Hz, 1H), 6.98 (s, 1H), 4.65 (br. s., 1H), 4.59 (d, J=11.6 Hz, 1H), 4.54-4.41 (m, 2H), 4.27 (dd, J=10.9, 7.6 Hz, 1H), 4.07 (s, 3H), 2.67 (s, 3H), 2.63 (s, 3H). LC-MS: method C, RT=2.1 min, MS (ESI) m/z: 544.2 (M+H)$^+$. Analytical HPLC purity (method B): 98%.

Example 57

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (5-methylpyridin-3-yl)carbamate

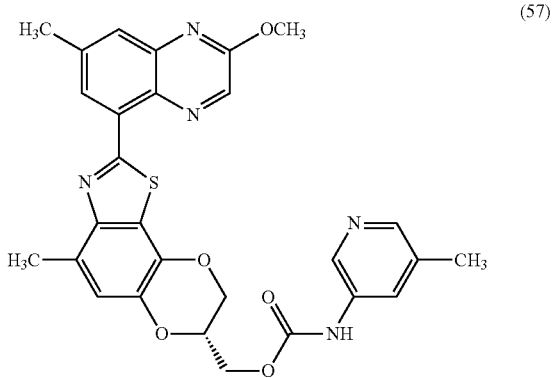

(57)

To a solution of Intermediate 41A (15 mg, 0.032 mmol) in DCM (1 mL) and THF (0.5 mL) was added 5-methylpyridin-3-amine (12.03 mg, 0.111 mmol) in DMC (1 ml) followed by DIEA (0.056 mL, 0.318 mmol). The mixture was stirred at room temperature overnight. LCMS indicated a completion of reaction. The reaction was quenched by addition of a small amount of MeOH/water/0.1% TFA (HPLC solvent). Solvent was removed under vacuum. The residual was dissolved in DMSO and purified via preparative LC/MS (method D, 65-100% B over 12 min., then a 5-min hold at 100% B). Fractions containing the desired product were combined and dried via centrifugal evaporation to give Example 57 (9.5 mg, 0.017 mmol, 53.9% yield). $^1$H NMR (500 MHz, DMSO-$d_6$) δ 10.08 (br. s., 1H), 8.73 (s, 1H), 8.57 (s, 1H), 8.47 (br. s., 1H), 8.09 (s, 1H), 7.80 (s, 1H), 7.75 (br. s., 1H), 6.98 (s, 1H), 4.64 (br. s., 1H), 4.59 (d, J=11.3 Hz, 1H), 4.51-4.39 (m, 2H), 4.27 (dd, J=11.1, 7.6 Hz, 1H), 4.07 (s, 3H), 2.67 (s, 3H), 2.63 (s, 3H), 2.27 (s, 3H). LC-MS: method C, RT=2.12 min, MS (ESI) m/z: 544.2 (M+H)$^+$. Analytical HPLC purity (method B): 98%.

Example 58

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (2-chloropyrimidin-5-yl)carbamate

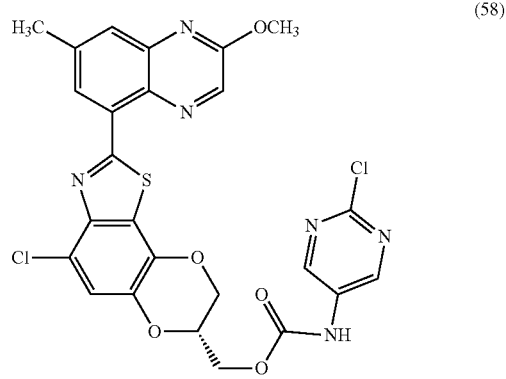 [SMILES: COc1cnc2c(-c3nc4c(Cl)cc5c(c4s3)OC[C@H](COC(=O)Nc3cnc(Cl)nc3)O5)cc(C)cc2n1]

(58)

Intermediate 58A: 2-chloropyrimidin-5-ylcarbamic chloride

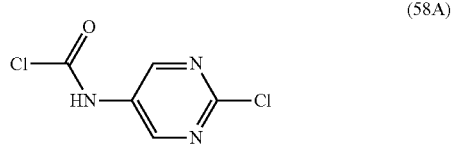 [SMILES: O=C(Cl)Nc1cnc(Cl)nc1]

(58A)

To a solution of 2-chloropyrimidin-5-amine (120 mg, 0.926 mmol) in DCM (8 ml) at 0° C. was added phosgene (15% in toluene) (3.27 ml, 4.63 mmol) followed by DIEA (0.210 ml, 1.204 mmol) dropwise at 0° C. The mixture was stirred at 0° C. for 15 min, then slowly warmed up to room temperature. Solvent was removed under vacuum to give Intermediate 58A, which was used for next step without further purification. LC-MS: method C, RT=1.08 min, MS (ESI) m/z: 188 (M+H)$^+$ (methyl carbamate).

Example 58

To Intermediate 25K (16 mg, 0.037 mmol) in THF (0.5 mL) was added Intermediate 58A (35.7 mg, 0.186 mmol) in DCM (1 ml) followed by DIEA (0.065 ml, 0.372 mmol). The mixture was stirred at room temperature overnight, quenched by a small amount of 10% water/acetonitrile with 0.1% TFA. Solvent was removed and the crude was purified via preparative LC/MS (method D, 65-100% B over 20 min., then a 5-min hold at 100% B). Fractions containing the desired product were combined and dried via centrifugal evaporation to give Example 58 (4.7 mg, 7.95 μmol, 21.35% yield) $^1$H NMR (500 MHz, DMSO-$d_6$) δ 10.50 (br. s., 1H), 8.81 (s, 2H), 8.69 (s, 1H), 8.51 (s, 1H), 7.79 (s, 1H), 7.29 (s, 1H), 4.70 (br. s., 1H), 4.64 (d, J=11.3 Hz, 1H), 4.56-4.45 (m, 2H), 4.31 (dd, J=11.3, 7.4 Hz, 1H), 4.06 (s, 3H), 2.62 (s, 3H). LC-MS: method C, RT=2.60 min, MS (ESI) m/z: 585.10 (M+H)$^+$. Analytical HPLC purity (method B): 99%.

Example 59

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (2-chloropyrimidin-5-yl)carbamate

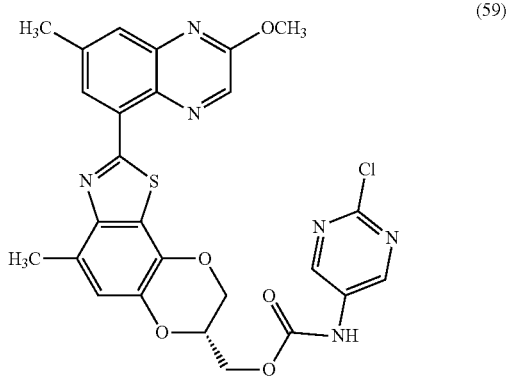 [SMILES: COc1cnc2c(-c3nc4c(C)cc5c(c4s3)OC[C@H](COC(=O)Nc3cnc(Cl)nc3)O5)cc(C)cc2n1]

(59)

To a solution of Intermediate 38B (15 mg, 0.037 mmol) in THF (1 mL) was added Intermediate 58A (35.2 mg, 0.183 mmol) in DCM (1 ml) followed by DIEA (0.064 ml, 0.366 mmol). The mixture was stirred at room temperature overnight, quenched by a small amount of 10% water/acetonitrile with 0.1% TFA. Solvent was removed, the residual was dissolved in DMSO and purified via preparative LC/MS (method C, 65-100% B over 15 min., then a 5-min hold at 100% B). Fractions containing the desired product were combined and dried via centrifugal evaporation to give Example 59 (3.2 mg, 5.44 μmol, 14.84% yield). $^1$H NMR (500 MHz, DMSO-$d_6$) δ 10.50 (br. s., 1H), 8.82 (br. s., 2H), 8.73 (s, 1H), 8.56 (s, 1H), 7.80 (s, 1H), 6.97 (s, 1H), 4.65 (br. s., 1H), 4.59 (d, J=11.6 Hz, 1H), 4.55-4.41 (m, 2H), 4.27 (dd, J=11.0, 7.4 Hz, 1H), 4.07 (s, 3H), 2.66 (s, 3H), 2.62 (s, 3H). LC-MS: method C, RT=2.62 min, MS (ESI) m/z: 565.10 (M+H)$^+$. Analytical HPLC purity (method B): 96%.

Example 60

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (5,6-dimethylpyridin-3-yl) carbamate

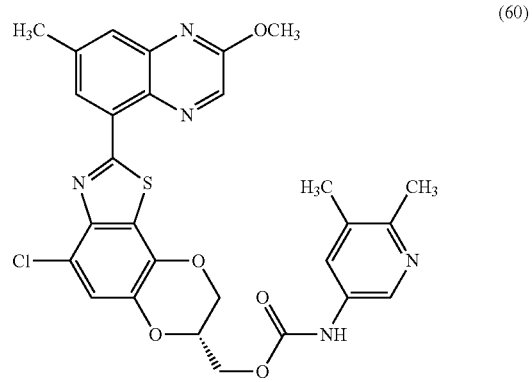 [SMILES: COc1cnc2c(-c3nc4c(Cl)cc5c(c4s3)OC[C@H](COC(=O)Nc3cnc(C)c(C)c3)O5)cc(C)cc2n1]

(60)

To a solution of 5,6-dimethylpyridin-3-amine (17.37 mg, 0.142 mmol) in DCM (1 mL) was added Intermediate 25L (20 mg, 0.041 mmol) in THF and toluene followed by DIEA (0.071 mL, 0.406 mmol). The mixture was stirred at room temperature overnight. The reaction was quenched by addition of a small amount of MeOH/water/0.1% TFA (HPLC solvent). Solvent was removed under vacuum. The residual was dissolved in DMSO and purified via preparative LC/MS (method C, 45-85% B over 15 min., then a 5-min hold at 100% B). Fractions containing the desired product were combined and dried via centrifugal evaporation to give Example 60 (9.8 mg, 0.016 mmol, 40.1% yield). $^1$H NMR (500 MHz, DMSO-$d_6$) δ 10.40 (br. s., 1H), 8.73 (s, 1H), 8.55 (s, 1H), 7.94 (d, J=12.7 Hz, 1H), 7.83 (s, 1H), 7.30 (s, 1H), 4.71 (br. s., 1H), 4.65 (d, J=11.6 Hz, 1H), 4.57-4.42 (m, 2H), 4.33 (dd, J=11.1, 7.3 Hz, 1H), 4.07 (s, 3H), 2.63 (s, 3H), 2.31 (s, 3H). LC-MS: method C, RT=2.14 min, MS (ESI) m/z: 578.1 (M+H)$^+$. Analytical HPLC purity (method B): 96%.

Example 61

(R)-(2-(2-methoxy-7-methylquinoxalin-5-yl)-4-methyl-7,8-dihydro-[1,4]dioxino [2',3':3,4]benzo[1,2-d]thiazol-7-yl)methyl (6-fluoro-5-methylpyridin-3-yl)carbamate

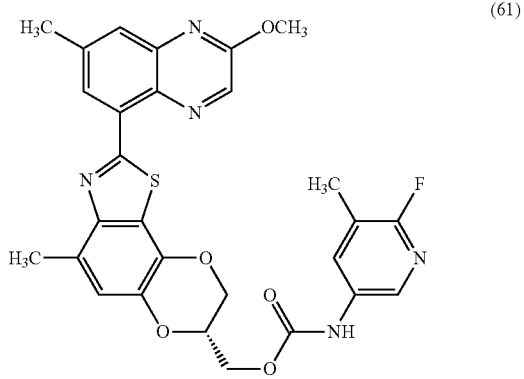 [SMILES: COc1cnc2c(-c3nc4c(C)cc5c(c4s3)OC[C@H](COC(=O)Nc3cnc(F)c(C)c3)O5)cc(C)cc2n1]

(61)

To a solution of Intermediate 41A (15 mg, 0.032 mmol) in DCM (1 mL) and THF (0.5 mL) was added 6-fluoro-5-methylpyridin-3-amine (14.03 mg, 0.111 mmol) in DMC (1 ml) followed by DIEA (0.056 mL, 0.318 mmol). The mixture was stirred at room temperature overnight. LCMS indicated a completion of reaction. The reaction was quenched by addition of a small amount of MeOH/water/0.1% TFA (HPLC solvent). Solvent was removed under vacuum. The residual was dissolved in DMSO and purified via preparative LC/MS (method C, 70-100% B over 15 min., then a 5-min hold at 100% B). Fractions containing the desired product were combined and dried via centrifugal evaporation to give Example 61 (4.1 mg, 7.30 µmol, 22.97% yield). $^1$H NMR (500 MHz, DMSO-$d_6$) δ 10.11 (br. s., 1H), 8.75 (s, 1H), 8.58 (s, 1H), 8.08 (br. s., 1H), 7.88 (d, J=8.0 Hz, 1H), 7.82 (s, 1H), 6.98 (s, 1H), 4.64 (br. s., 1H), 4.59 (d, J=11.3 Hz, 1H), 4.50-4.38 (m, 2H), 4.27 (dd, J=11.1, 7.3 Hz, 1H), 4.07 (s, 3H), 2.67 (s, 3H), 2.63 (s, 3H), 2.21 (s, 3H). LC-MS: method C, RT=2.686 min, MS (ESI) m/z: 562.15 (M+H)$^+$. Analytical HPLC purity (method B): 100%.

Example 62

(R)-(4-chloro-2-(2,7-dimethylquinoxalin-5-yl)-7,8-dihydro-[1,4]dioxino[2',3':3,4]benzo[1,2-d]thiazol-7-yl)methyl (6-methylpyridin-3-yl)carbamate

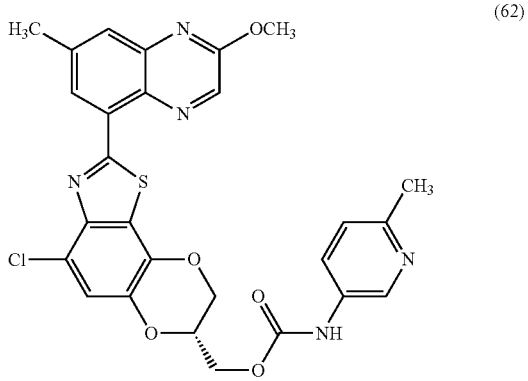 [SMILES: COc1cnc2c(-c3nc4c(Cl)cc5c(c4s3)OC[C@H](COC(=O)Nc3ccc(C)nc3)O5)cc(C)cc2n1]

(62)

To a solution of Intermediate 25L (20 mg, 0.041 mmol) in THE and toluene was added 6-methylpyridin-3-amine (15.38 mg, 0.142 mmol) in DCM (1 ml) followed by DIEA (0.071 mL, 0.406 mmol). The mixture was stirred at room temperature for 30 min. LCMS indicated a completion of reaction. The reaction was quenched by addition of a small amount of MeOH/water/0.1% TFA (HPLC solvent). Solvent was removed under vacuum. The residual was dissolved in DMSO and purified via preparative LC/MS (method C, 4 5-8 5% B over 15 min., then a 5-min hold at 100% B). Fractions containing the desired product were combined and dried via centrifugal evaporation to give Example 62 (11.2 mg, 0.020 mmol, 48.9% yield). $^1$H NMR (500 MHz, DMSO-$d_6$) δ 10.36 (br. s., 1H), 8.75 (s, 1H), 8.65 (br. s., 1H), 8.57 (s, 1H), 8.01 (d, J=6.3 Hz, 1H), 7.85 (s, 1H), 7.50 (d, J=8.0 Hz, 1H), 7.32 (s, 1H), 4.71 (br. s., 1H), 4.65 (d, J=11.6 Hz, 1H), 4.54-4.42 (m, 2H), 4.33 (dd, J=11.1, 7.6 Hz, 1H), 4.08 (s, 3H), 2.64 (s, 3H), 2.52 (s, 3H). LC-MS: method C, RT 2.08 min, MS (ESI) m/z: 564.10 (M+H)$^+$. Analytical HPLC purity (method B): 100%.

Example 63

(R)-(4-chloro-2-(2,7-dimethylquinoxalin-5-yl)-7,8-dihydro-[1,4]dioxino[2',3':3,4]benzo[1,2-d]thiazol-7-yl)methyl (5-methylpyridin-3-yl)carbamate

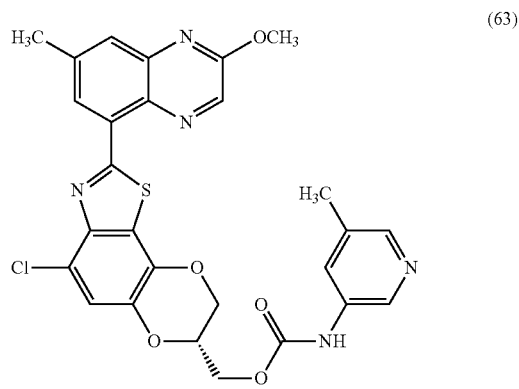

(63)

To 5-methylpyridin-3-amine (15.38 mg, 0.142 mmol) in DCM (1 mL) was added a solution of Intermediate 25L (20 mg, 0.041 mmol) in THF and toluene followed by DIEA (0.071 mL, 0.406 mmol). The mixture was stirred at room temperature for 30 min. LCMS indicated a completion of reaction. The reaction was quenched by addition of a small amount of MeOH/water/0.1% TFA (HPLC solvent). Solvent was removed under vacuum. The residual was dissolved in DMSO and purified via preparative LC/MS (method C, 45-85% B over 15 min., then a 5-min hold at 100% B). Fractions containing the desired product were combined and dried via centrifugal evaporation to give Example 63 (10.6 mg, 0.019 mmol, 46.3% yield). $^1$H NMR (500 MHz, DMSO-$d_6$) δ 10.66 (br. s., 1H), 8.69 (br. s., 1H), 8.51 (br. s., 1H), 8.11 (br. s., 1H), 7.79 (br. s., 1H), 7.28 (br. s., 1H), 4.85-4.60 (m, 2H), 4.52 (br. s., 2H), 4.32 (br. s., 1H), 4.06 (br. s., 3H), 2.62 (br. s., 3H), 2.42 (br. s., 3H). LC-MS: method C, RT=2.12 min, MS (ESI) m/z: 564.15 (M+H)$^+$. Analytical HPLC purity (method B): 100%.

Example 64

(R)-(4-chloro-2-(2-methoxy-7-methylquinoxalin-5-yl)-7,8-dihydro-[1,4]dioxino [2',3':3,4]benzo[1,2-d]thiazol-7-yl)methyl (6-fluoro-5-methylpyridin-3-yl)carbamate

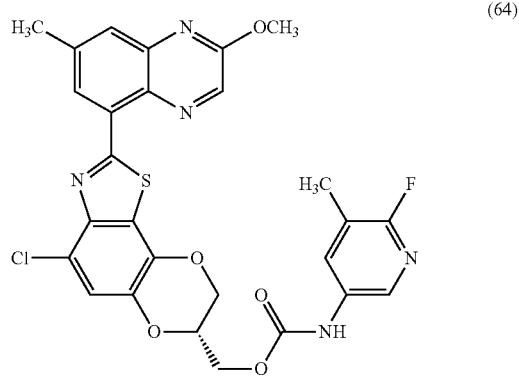 [SMILES: COc1cnc2c(-c3nc4c(Cl)cc5c(c4s3)OC[C@H](COC(=O)Nc3cnc(F)c(C)c3)O5)cc(C)cc2n1]

(64)

To 6-fluoro-5-methylpyridin-3-amine (17.93 mg, 0.142 mmol) in DCM (1 mL) was added a solution of Intermediate 25L (20 mg, 0.041 mmol) in THF and toluene followed by DIEA (0.071 mL, 0.406 mmol). The mixture was stirred at room temperature overnight. LCMS indicated a completion of reaction. The reaction was quenched by addition of a small amount of MeOH/water/0.1% TFA (HPLC solvent). Solvent was removed under vacuum. The residual was dissolved in DMSO and purified via preparative LC/MS (method D, 70-100% B over 12 min., then a 5-min hold at 100% B). Fractions containing the desired product were combined and dried via centrifugal evaporation to give Example 64 (5.6 mg, 9.53 μmol, 23.45% yield). $^1$H NMR (500 MHz, DMSO-d$_6$) δ 10.10 (br. s., 1H), 8.76 (s, 1H), 8.57 (s, 1H), 8.08 (br. s., 1H), 7.88-7.80 (m, 2H), 7.32 (s, 1H), 4.76-4.60 (m, 2H), 4.52-4.41 (m, 2H), 4.37-4.30 (m, 1H), 4.08 (s, 3H), 2.64 (s, 3H), 2.21 (s, 3H). LC-MS: method C, RT=2.62 min, MS (ESI) m/z: 582.15 (M+H)$^+$. Analytical HPLC purity (method B): 99%.

Example 65

(R)-(4-chloro-2-(2-methoxy-7-methylquinoxalin-5-yl)-7,8-dihydro-[1,4]dioxino [2',3':3,4]benzo[1,2-d]thiazol-7-yl)methyl (6-(dimethylamino)pyridin-3-yl)carbamate

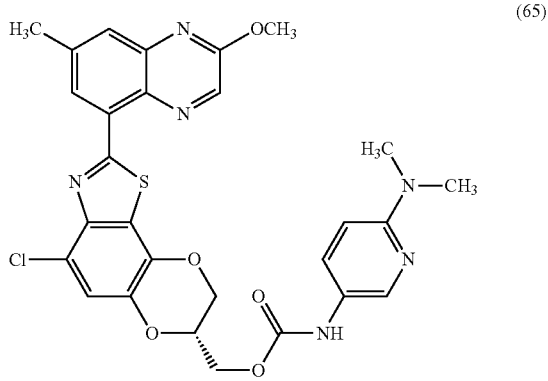 [SMILES: COc1cnc2c(-c3nc4c(Cl)cc5c(c4s3)OC[C@H](COC(=O)Nc3ccc(N(C)C)nc3)O5)cc(C)cc2n1]

(65)

To a solution of Intermediate 25L (20 mg, 0.041 mmol) in THF and toluene was added N2,N2-dimethylpyridine-2,5-diamine (19.50 mg, 0.142 mmol) in DCM (1 mL) followed by DIEA (0.071 mL, 0.406 mmol). The mixture was stirred at room temperature overnight. LCMS indicated a completion of reaction. The reaction was quenched by addition of a small amount of MeOH/water/0.1% TFA (HPLC solvent). Solvent was removed under vacuum. The residual was dissolved in DMSO and purified via preparative LC/MS (method D, 60-100% B over 20 min., then a 5-min hold at 100% B). Fractions containing the desired product were combined and dried via centrifugal evaporation to give Example 65 (10.1 mg, 0.017 mmol, 41.5% yield). $^1$H NMR (500 MHz, DMSO-d$_6$) δ 9.53 (br. s., 1H), 8.72 (s, 1H), 8.54 (s, 1H), 8.13 (br. s., 1H), 7.82 (s, 1H), 7.60 (d, J=8.3 Hz, 1H), 7.31 (s, 1H), 6.61 (d, J=9.1 Hz, 1H), 4.72-4.58 (m, 2H), 4.46-4.35 (m, 2H), 4.33-4.26 (m, 1H), 4.07 (s, 3H), 2.96 (s, 6H), 2.63 (s, 3H). LC-MS: method C, RT=2.13 min, MS (ESI) m/z: 593.15 (M+H)$^+$. Analytical HPLC purity (method B): 99%.

Example 66

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (2-oxo-2,3-dihydrobenzo[d]oxazol-6-yl)carbamate

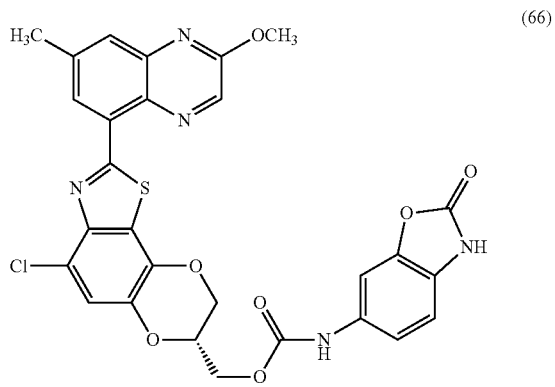 [SMILES: COc1cnc2c(-c3nc4c(Cl)cc5c(c4s3)OC[C@H](COC(=O)Nc3ccc4[nH]c(=O)oc4c3)O5)cc(C)cc2n1]

(66)

To a solution of 6-aminobenzo[d]oxazol-2(3H)-one (21.35 mg, 0.142 mmol) in DCM (1 mL) was added Intermediate 25L (20 mg, 0.041 mmol) in THF and toluene followed by DIEA (0.071 mL, 0.406 mmol). The mixture was stirred at room temperature overnight. LCMS indicated a completion of reaction. The reaction was quenched by addition of a small amount of MeOH/water/0.1% TFA (HPLC solvent). Solvent was removed under vacuum. The residual was dissolved in DMSO and purified via preparative LC/MS (method D, 60-100% B over 12 min., then a 5-min hold at 100% B). Fractions containing the desired product were combined and dried via centrifugal evaporation to give Example 66 (10.5 mg, 0.017 mmol, 42.2% yield). $^1$H NMR (500 MHz, DMSO-d$_6$) δ 9.91 (br. s., 1H), 8.72 (s, 1H), 8.53 (s, 1H), 7.81 (s, 1H), 7.48 (br. s., 1H), 7.30 (s, 1H), 7.15 (d, J=7.2 Hz, 1H), 7.00 (d, J=8.3 Hz, 1H), 4.70-4.61 (m, 2H), 4.50-4.38 (m, 2H), 4.31 (dd, J=11.1, 7.6 Hz, 1H), 4.07 (s, 3H), 2.63 (s, 3H). LC-MS: method C, RT=2.44 min, MS (ESI) m/z: 606.10 (M+H)$^+$. Analytical HPLC purity (method B): 99%.

Example 67

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (3-methyl-3H-imidazo[4,5-b]pyridin-6-yl)carbamate

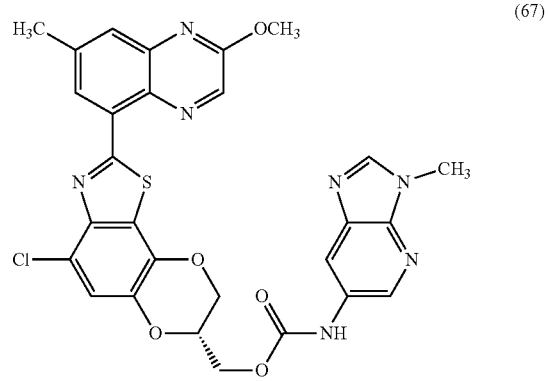 [SMILES: COc1cnc2c(-c3nc4c(Cl)cc5c(c4s3)OC[C@H](COC(=O)Nc3cnc4c(c3)ncn4C)O5)cc(C)cc2n1]

(67)

To a solution of 3-methyl-3H-imidazo[4,5-b]pyridin-6-amine (21.07 mg, 0.142 mmol) in DCM (1 mL) was added Intermediate 25L (20 mg, 0.041 mmol) in THF and toluene followed by DIEA (0.071 mL, 0.406 mmol). The mixture was stirred at room temperature overnight. LCMS indicated a completion of reaction. The reaction was quenched by addition of a small amount of MeOH/water/0.1% TFA (HPLC solvent). Solvent was removed under vacuum. The residual was dissolved in DMSO and purified with preparative HPLC (method A, 40-100% B in 10 min.). The desired fractions were placed in a SpeedVac overnight to remove solvent, then lyophilized to give Example 67 (7.0 mg, 0.011 mmol, 27.1% yield). $^1$H NMR (400 MHz, acetonitrile-d$_3$) δ 8.62 (d, J=2.0 Hz, 1H), 8.55 (s, 1H), 8.40 (s, 1H), 8.21 (br. s., 1H), 8.14 (s, 1H), 7.72 (dd, J=1.8, 0.9 Hz, 1H), 7.11 (s, 1H), 4.66-4.57 (m, 2H), 4.53-4.42 (m, 2H), 4.31 (dd, J=11.9, 7.5 Hz, 1H), 4.03 (s, 3H), 3.79 (s, 3H), 2.58 (s, 3H). LC-MS: method C, RT=2.38 min, MS (ESI) m/z: 604.1 (M+H)$^+$. Analytical HPLC purity (method B): 93%.

Example 68

(R)-(4-fluoro-2-(2-methoxy-7-methylquinoxalin-5-yl)-7,8-dihydro-[1,4]dioxino[2',3':3,4]benzo[1,2-d]thiazol-7-yl)methyl (6-methoxypyridin-3-yl)carbamate

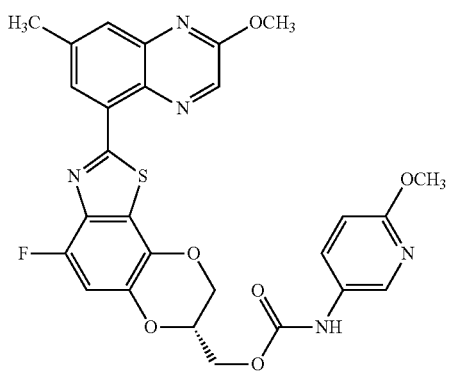

(68)

Intermediate 68A: (R)-5-fluoro-2-(oxiran-2-ylmethoxy)benzaldehyde

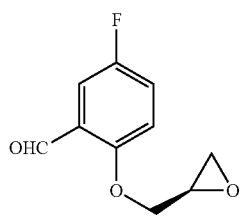

(68A)

To a solution of 5-fluoro-2-hydroxybenzaldehyde (4.1 g, 29.3 mmol) in DMF (80 mL) was added (R)-oxiran-2-ylmethyl 3-nitrobenzenesulfonate (8.34 g, 32.2 mmol) and Cs$_2$CO$_3$ (28.6 g, 88 mmol). The mixture was stirred at room temperature overnight. LCMS indicated a completion of the reaction. The mixture was diluted with EtOAc and water, extracted with EtOAc, the combined organic layer was washed with brine, dried with MgSO$_4$ and concentrated. The crude sample was purified with a 120 g ISCO column eluted with 0-100% EtOAc in hexanes for 40 min. The desired fraction was collected and concentrated to give Intermediate 68A (5.6 g, 28.5 mmol, 98% yield) as white solid. $^1$H NMR (400 MHz, chloroform-d) δ 10.48 (d, J=3.1 Hz, 1H), 7.53 (dd, J=8.1, 3.3 Hz, 1H), 7.34-7.13 (m, 1H), 7.00 (dd, J=9.1, 3.9 Hz, 1H), 4.40 (dd, J=11.1, 2.8 Hz, 1H), 4.04 (dd, J=11.2, 5.7 Hz, 1H), 3.41 (br. s., 1H), 2.96 (t, J=4.4 Hz, 1H), 2.80 (dd, J=4.8, 2.6 Hz, 1H). $^{19}$F NMR (376 MHz, chloroform-d) δ −121.53 (s, 1F). LC-MS: method C, RT=1.54 min, MS (ESI) m/z: No (M+H)$^+$.

Intermediate 68B: (S)-(7-fluoro-2,3-dihydrobenzo[b][1,4]dioxin-2-yl)methanol

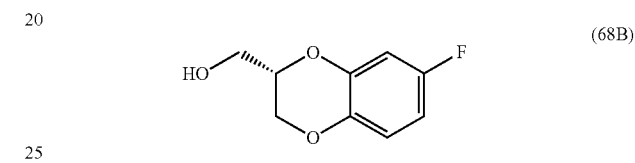

(68B)

To a stirred solution of Intermediate 68A (5.6 g, 28.5 mmol) in dichloromethane (100 mL) cooled with an ice bath was added mCPBA (9.69 g, 42.1 mmol). Trifluoroacetic acid (2.199 mL, 28.5 mmol) in dichloromethane (20 mL) was added dropwise. Ice bath was removed and the mixture was stirred at room temperature for 1.0 h. The reaction was quenched by addition of saturated sodium bicarbonate, followed by 10% sodium thiosulfite (50.0 mL), extracted with dichloromethane. The organic layers were collected, washed with saturated sodium bicarbonate, brine, dried over sodium sulfate. After evaporation of solvent, the crude product was dissolved in 100 ml of MeOH, and K$_2$CO$_3$ (11.84 g, 86 mmol) was added. The mixture was stirred at room temperature for 3 h. TLC indicated a completion of the reaction. Solvent was removed, the residual was diluted with EtOAc and water, extracted with EtOAc, the combined organic layer was washed with brine, dried with MgSO$_4$ and concentrated. The crude sample was dissolved in a small amount of DCM and MeOH and purified with a 120 g ISCO column eluted with 0-100% EtOAc in hexanes for 40 min. The desired fractions were combined and concentrated to Intermediate 68B (4.6 g, 24.98 mmol, 87% yield) as yellow oil. $^1$H NMR (400 MHz, chloroform-d) δ 6.82 (dd, J=8.8, 5.5 Hz, 1H), 6.65 (dd, J=9.4, 3.0 Hz, 1H), 6.60-6.52 (m, 1H), 4.32-4.24 (m, 2H), 4.13-4.05 (m, 2H), 3.95-3.80 (m, 2H). $^{19}$F NMR (376 MHz, chloroform-d) δ −121.14 (s, 1F). LC-MS: method C, RT=1.43 min, MS (ESI) m/z: No (M+H)$^+$.

Intermediate 68C: (R)-(7-fluoro-2,3-dihydrobenzo[b][1,4]dioxin-2-yl)methyl acetate

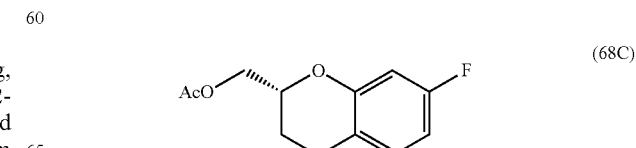

(68C)

To a solution of Intermediate 68B (4.6 g, 24.98 mmol) in THF (100 mL) at 0° C. was added TEA (8.70 mL, 62.4 mmol) followed by acetyl chloride in DCM (31.2 mL, 1M, 31.2 mmol) dropwise. The mixture was stirred at 0° C. for 10 min, then at room temperature for 1.0 h. LCMS indicated a clean reaction. The mixture was diluted with EtOAc and water. The organic layer was washed with 0.5 N HCl, saturated sodium bicarbonate, brine, dried over sodium sulfate. After evaporation of solvent, Intermediate 68C (5.45 g, 24.09 mmol, 96% yield) was obtained as yellow oil. It was used for the next step without further purification. $^1$H NMR (400 MHz, chloroform-d) δ 6.82 (dd, J=8.9, 5.4 Hz, 1H), 6.65 (dd, J=9.4, 3.0 Hz, 1H), 6.61-6.53 (m, 1H), 4.44-4.38 (m, 1H), 4.32 (t, J=5.0 Hz, 2H), 4.29-4.24 (m, 1H), 4.03 (dd, J=11.7, 6.8 Hz, 1H), 2.12 (s, 3H). $^{19}$F NMR (376 MHz, chloroform-d) δ -120.89 (s, 1F). LC-MS: method C, RT=1.80 min, MS (ESI) m/z: 249 (M+Na)$^+$.

Intermediate 68D: (R)-(7-fluoro-6-nitro-2,3-dihydrobenzo[b][1,4]dioxin-2-yl)methyl

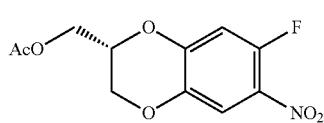

(68D)

To a solution of Intermediate 68C (5.45 g, 24.09 mmol) in acetic acid (50 mL) cooled at 0° C. with an ice-bath was added fuming nitric acid (5.62 mL, 120 mmol) dropwise. The mixture was stirred at 0° C. C for 1 h, then at room temperature for 4 h. It was quenched with ice water and diluted with EtOAc. The aqueous was removed and the organic layer was washed with saturated sodium bicarbonate (3×), brine, dried over sodium sulfate. After evaporation of solvent, the crude sample was purified with a 120 g ISCO column eluted with 0-100% EtOAc in hexane for 20 min. The desired fraction was collected and concentrated to give Intermediate 68D (3.4 g, 12.54 mmol, 52.0% yield) as an off-white solid. $^1$H NMR (400 MHz, chloroform-d) δ 7.69 (d, J=7.3 Hz, 1H), 6.80 (d, J=11.4 Hz, 1H), 4.61-4.47 (m, 1H), 4.43-4.29 (m, 3H), 4.09 (dd, J=11.9, 7.0 Hz, 1H), 2.12 (s, 3H). LC-MS: method C, RT=1.73 min, MS (ESI) m/z: 294 (M+Na)$^+$.

Intermediate 68E: (R)-(6-amino-7-fluoro-2,3-dihydrobenzo[b][1,4]dioxin-2-yl)methyl acetate

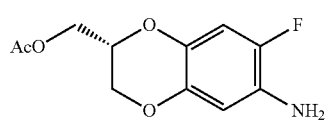

(68E)

To a solution of Intermediate 68D (4.3 g, 15.86 mmol) in MeOH (50 mL) and THF (50 mL) cooled with an ice bath was added ammonium chloride (13.57 g, 254 mmol) and zinc dust (8.29 g, 127 mmol). The mixture was stirred at 0° C. for 30 min, then at room temperature for 1.0 h. IPLC indicated a completion of the reaction. MeOH and THF were removed under vacuum. The residual was diluted with EtOAc/saturated sodium bicarbonate and stirred at room temperature for 3 min. The mixture was filtered through a pad of wet celite to remove insoluble material. The filtrate was collected, organic layer was washed with brine, dried over sodium sulfate, concentrated to give Intermediate 68E (3.8 g, 15.75 mmol, 99% yield) as yellow oil. The crude sample was used for next step without purification. $^1$H NMR (400 MHz, chloroform-d) δ 6.61 (d, J=11.2 Hz, 1H), 6.33 (d, J=8.6 Hz, 1H), 4.35-4.25 (m, 3H), 4.24-4.20 (m, 1H), 4.00 (dd, J=11.4, 6.6 Hz, 1H), 2.11 (s, 3H). $^{19}$F NMR (376 MHz, chloroform-d) δ -141.30 (s, 1F). LC-MS: method C, RT=0.90 min, MS (ESI) m/z: 242 (M+H)$^+$.

Intermediate 68F: (R)-(2-amino-4-fluoro-7,8-dihydro-[1,4]dioxino[2',3':3,4]benzo[1,2-d]thiazol-7-yl)methyl acetate

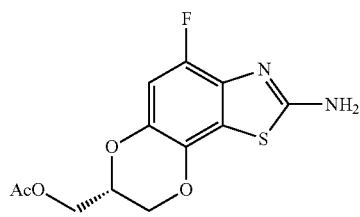

(68F)

To Intermediate 68E (3.8 g, 15.75 mmol) dissolved in acetonitrile (50 mL) was added ammonium thiocyanate (1.799 g, 23.63 mmol). The mixture was stirred at room temperature for 10 min. Benzyltrimethylammonium tribromide (6.45 g, 16.54 mmol) in acetonitrile (8 mL) was added dropwise (5 min). The mixture was stirred at room temperature overnight. HPLC and LCMS indicated a clean reaction. The mixture was diluted with EtOAc/THF/saturated sodium bicarbonate. The insoluble material was removed by filtration. The organic layer of the filtrate was collected, washed with brine, dried over sodium sulfate. After evaporation of solvent, Intermediate 68F (4.6 g, 15.42 mmol, 98% yield) was obtained as a yellow solid. $^1$H NMR (400 MHz, chloroform-d) δ 6.72 (d, J=10.8 Hz, 1H), 5.44 (br. s., 2H), 4.52-4.26 (m, 4H), 4.15 (dd, J=11.4, 7.0 Hz, 1H), 2.13 (s, 3H). $^{19}$F NMR (376 MHz, chloroform-d) δ -133.26 (s, 1F). LC-MS: method C, RT=1.58 min, MS (ESI) m/z: 299 (M+H)$^+$.

Intermediate 68G: (R)-(2-bromo-4-fluoro-7,8-dihydro-[1,4]dioxino[2',3':3,4]benzo[1,2-d]thiazol-7-yl)methyl acetate

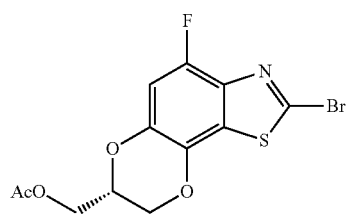

(68G)

tert-Butyl nitrite (3.57 mL, 27.0 mmol) was added to copper (II) bromide (5.86 g, 26.2 mmol) in dry acetonitrile (15 mL) under argon. The mixture was stirred at room temperature for 10 min. A suspension of Intermediate 68F (4.6 g, 15.42 mmol) in dry acetonitrile (10 mL) was added dropwise. The reaction mixture was stirred at room temperature for 3 h. LCMS indicated a completion of the reaction. Acetonitrile was removed under vacuum, the reaction mixture was diluted with EtOAc, quenched with 1.0 N HCl. The organic layer was collected, washed with 0.5 N HCl (2×), saturated sodium bicarbonate, brine, dried over sodium sulfate. After evaporation of solvent. Intermediate 68G (5 g, 13.81 mmol, 90% yield) was obtained as brown solid. The sample was used without further purification. $^1$H NMR (400 MHz, chloroform-d) δ 6.85 (d, J=10.6 Hz, 1H), 4.50-4.32 (m, 4H), 4.18 (dd, J=11.6, 7.2 Hz, 1H), 2.13 (s, 3H). $^{19}$F NMR (376 MHz, chloroform-d) δ −128.77 (s, 1F). LC-MS: method C, RT=2.14 min, MS (ESI) m/z: 361.9 and 363.9 (M+H)$^+$.

Intermediate 68H (R)-(2-(2-(difluoromethoxy)-7-methylquinoxalin-5-yl)-4-fluoro-7,8-dihydro-[1,4]dioxino [2',3':3,4] benzo[1,2-d]thiazol-7-yl)methyl acetate

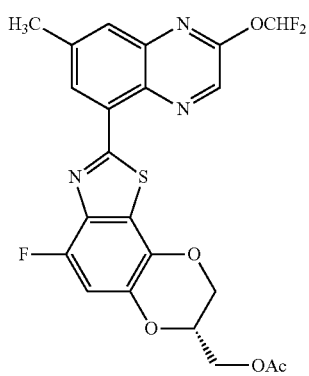

To Intermediate I-1 (350 mg, 1.041 mmol), Intermediate 68G (377 mg, 1.041 mmol) and PdCl$_2$(dppf)—CH$_2$Cl$_2$ adduct (42.5 mg, 0.052 mmol) was added toluene (3 mL) and EtOH (1 mL). The mixture was sonicated for 1 min, and flushed with argon. To this was added sodium carbonate (1.041 mL, 2M, 2.082 mmol). The reaction mixture was heated in a microwave reactor at 130° C. for 40 min. LCMS indicated completion of the reaction. The crude reaction mixture was diluted with EtOAc and NaHCO$_3$, extracted with EtOAc. The combined organic layer was washed with brine and concentrated. The crude product was purified with flash chromatography (0% to 100% EtOAc in hexanes over 20 min using a 40 g silica gel cartridge followed by 0-20% MeOH in DCM for 20 min). The desired fractions were combined and concentrated to yield Intermediate 68H (750 mg, 0.992 mmol, 95% yield) as a yellow solid. $^1$H NMR (400 MHz, chloroform-d) δ 8.78 (d, J=1.8 Hz, 1H), 8.62 (s, 1H), 7.74 (d, J=0.9 Hz, 1H), 7.82-7.43 (m, 1H), 6.84 (d, J=10.6 Hz, 1H), 4.53-4.48 (m, 1H), 4.44 (dd, J=11.4, 2.2 Hz, 1H), 4.36 (t, J=5.0 Hz, 2H), 4.21 (dd, J=11.4, 7.0 Hz, 1H), 2.63 (s, 3H), 2.11 (s, 3H). $^{19}$F NMR (376 MHz, chloroform-d) δ −89.72 (s, 2F), −129.81 (s, 1F). LC-MS: method C, RT=2.50 min, MS (ESI) m/z: 492 (M+H)$^+$.

Intermediate 68I (S)-(4-fluoro-2-(2-methoxy-7-methylquinoxalin-5-yl)-7,8-dihydro-[1,4]dioxino[2',3':3,4]benzo[1,2-d]thiazol-7-yl)methanol

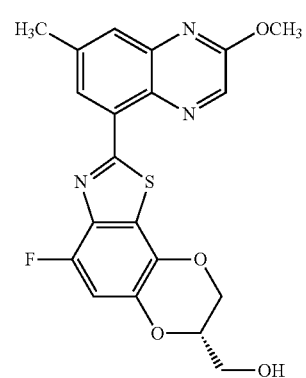

To Intermediate 68H (511 mg, 1.04 mmol) in THF (5 mL) was added 4.37 M sodium methoxide in MeOH (0.833 mL, 3.64 mmol) at room temperature. The reaction mixture was stirred at room temperature for 1 h. LCMS indicated a clean reaction. The reaction mixture was quenched with 1 N HCl (5.0 mL) and extracted with EtOAc (5×). The combined organic layer was washed with brine, dried with MgSO$_4$ and concentrated to give Intermediate 68I (390 mg, 0.943 mmol, 91% yield) as a yellow solid. $^1$H NMR (400 MHz, chloroform-d) δ 8.72 (d, J=1.5 Hz, 1H), 8.54 (s, 1H), 7.76 (dd, J=1.9, 1.0 Hz, 1H), 6.87 (d, J=10.6 Hz, 1H), 4.50 (dd, J=11.2, 2.2 Hz, 1H), 4.39 (ddd, J=10.8, 4.8, 2.2 Hz, 2H), 4.33-4.26 (m, 2H), 4.14 (br. s., 3H), 2.64 (s, 3H). LC-MS: method C, RT=2.41 min, MS (ESI) m/z: 414 (M+H)$^+$.

Intermediate 68J (R)-(4-fluoro-2-(2-methoxy-7-methylquinoxalin-5-yl)-7,8-dihydro-[1,4]dioxino[2',3':3,4]benzo[1,2-d]thiazol-7-yl)methyl carbonochloridate

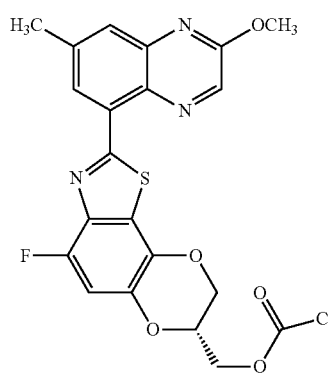

To a solution of Intermediate 68I in THF (3 mL) was added 15% phosgene in toluene (1.024 mL, 1.451 mmol) and the mixture was stirred at room temperature overnight. The solution of Intermediate 68J was bubble with argon for 1 h and was used for the next step without any purification. LC-MS: method C, RT=2.63 min, MS (ESI) m/z: 476 (M+H)⁺.

Example 68

To a solution of Intermediate 68J (15 mg, 0.032 mmol) in toluene and THF (0.5 mL) was added 6-methoxypyridin-3-amine (13.70 mg, 0.110 mmol) in DCM (1 mL) followed by DIEA (0.055 mL, 0.315 mmol). The mixture was stirred at room temperature for 0.5 h. LCMS indicated a completion of reaction. The reaction was quenched by addition of a small amount of MeOH/water/0.1% TFA (HPLC solvent). Solvent was removed under vacuum. The residual was dissolved in DMSO and purified via preparative LC/MS (method D, 55-100% B over 20 min., then a 5-min hold at 100% B). Fractions containing the desired product were combined and dried via centrifugal evaporation to give Example 68 (4.2 mg, 7.45 µmol, 23.64% yield). ¹H NMR (500 MHz, DMSO-d₆) δ 9.83 (br. s., 1H), 8.75 (br. s., 1H), 8.57 (br. s., 1H), 8.23 (br. s., 1H), 7.84 (br. s., 1H), 7.79 (br. s., 1H), 7.14 (d, J=10.5 Hz, 1H), 6.79 (d, J=8.3 Hz, 1H), 4.73-4.57 (m, 2H), 4.45 (br. s., 2H), 4.29 (d, J=8.8 Hz, 1H), 4.08 (br. s., 3H), 3.80 (br. s., 3H), 2.63 (br. s., 3H). LC-MS: method C, RT=2.49 min, MS (ESI) m/z: 563.15 (M+H)⁺. Analytical HPLC purity (method B): 100%.

Example 69

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (6-(3-methyl-1H-1,2,4-triazol-1-yl)pyridin-3-yl) carbamate

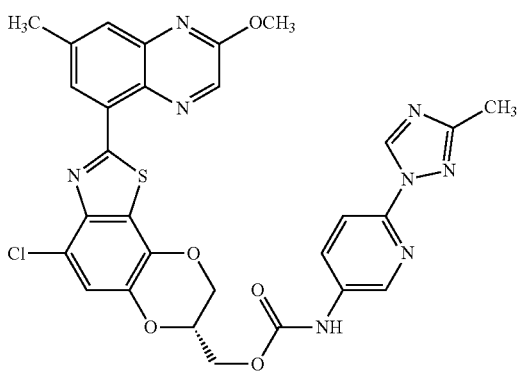

(69)

To a solution of Intermediate 25L (20 mg, 0.041 mmol) in THF and toluene was added 6-(3-methyl-1H-1,2,4-triazol-1-yl)pyridin-3-amine (24.91 mg, 0.142 mmol) in DCM (1 mL) followed by DIEA (0.071 mL, 0.406 mmol). The mixture was stirred at room temperature overnight. The reaction was quenched by addition of a small amount of MeOH/water/0.1% TFA (HPLC solvent). Solvent was removed under vacuum. The residual was dissolved in DMSO and purified via preparative LC/MS (method C, 60-100% B over 20 min., then a 5-min hold at 100% B). Fractions containing the desired product were combined and dried via centrifugal evaporation to give Example 69 (1.5 mg, 2.282 µmol, 5.62% yield). ¹H NMR (500 MHz, DMSO-d₆) δ 10.32 (br. s., 1H), 9.11 (s, 1H), 8.76 (s, 1H), 8.63-8.52 (m, 2H), 8.11 (br. s., 1H), 7.86 (s, 1H), 7.76 (d, J=8.8 Hz, 1H), 7.34 (s, 1H), 4.72 (br. s., 1H), 4.66 (d, J=11.3 Hz, 1H), 4.50 (br. s., 2H), 4.35 (dd, J=11.0, 7.4 Hz, 1H), 4.08 (s, 3H), 2.65 (s, 3H), 2.37 (s, 3H). LC-MS: method C, RT=2.52 min, MS (ESI) m/z: 631.15 (M+H)⁺. Analytical HPLC purity (method B): 96%.

Example 70

(R)-(4-fluoro-2-(2-methoxy-7-methylquinoxalin-5-yl)-7,8-dihydro-[1,4]dioxino[2',3':3,4]benzo[1,2-d]thiazol-7-yl)methyl pyridin-3-ylcarbamate

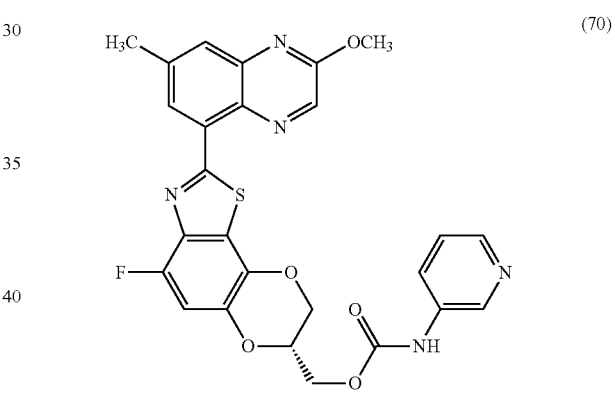

(70)

To a solution of Intermediate 68J (15 mg, 0.032 mmol) in toluene and THF (0.5 mL) was added pyridin-3-amine (10.38 mg, 0.110 mmol) in DCM (1 mL) followed by DIEA (0.055 mL, 0.315 mmol). The mixture was stirred at room temperature for 0.5 h. The reaction was quenched by addition of a small amount of MeOH/water/0.1% TFA (HPLC solvent). Solvent was removed under vacuum. The residual was dissolved in DMSO and purified via preparative LC/MS (method D, 55-95% B over 18 min., then a 5-min hold at 100% B). Fractions containing the desired product were combined and dried via centrifugal evaporation to give Example 70 (2.6 mg, 4.82 µmol, 15.31% yield). ¹H NMR (500 MHz, DMSO-d₆) δ 10.12 (br. s., 1H), 8.74 (br. s., 1H), 8.65 (br. s., 1H), 8.56 (br. s., 1H), 8.23 (br. s., 1H), 7.90 (d, J=5.8 Hz, 1H), 7.83 (br. s., 1H), 7.37-7.29 (m, 1H), 7.14 (d, J=9.1 Hz, 1H), 4.70 (br. s., 1H), 4.63 (d, J=11.3 Hz, 1H), 4.53-4.41 (m, 2H), 4.29 (t, J=8.3 Hz, 1H), 4.07 (br. s., 3H), 2.63 (br. s., 3H). LC-MS: method C, RT=2.00 min, MS (ESI) m/z: 534.15 (M+H)⁺. Analytical HPLC purity (method B): 99%.

Example 71

(R)-(4-fluoro-2-(2-methoxy-7-methylquinoxalin-5-yl)-7,8-dihydro-[1,4]dioxino[2',3':3,4]benzo[1,2-d]thiazol-7-yl)methyl (6-fluoropyridin-3-yl)carbamate

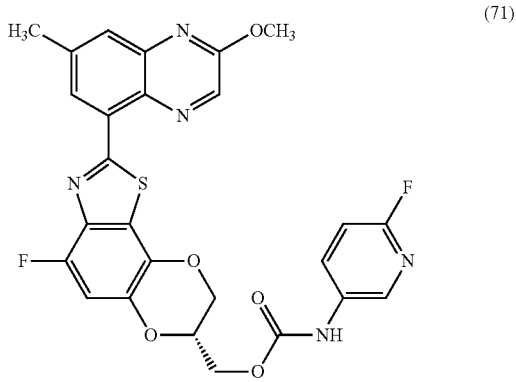 [SMILES: COc1cnc2c(-c3nc4c(F)cc5c(c4s3)OC[C@H](COC(=O)Nc3ccc(F)nc3)O5)cc(C)cc2n1]

(71)

To a solution of Intermediate 68J (15 mg, 0.032 mmol) in toluene and THF (0.5 mL) was added 6-fluoropyridin-3-amine (12.37 mg, 0.110 mmol) in DCM (1 mL) followed by DIEA (0.055 mL, 0.315 mmol). The mixture was stirred at room temperature for 1 h. The reaction was quenched by addition of a small amount of MeOH/water/0.1% TFA (HPLC solvent). Solvent was removed under vacuum. The residual was dissolved in DMSO and purified via preparative LC/MS (method D, 55-100% B over 18 min., then a 5-min hold at 100% B). Fractions containing the desired product were combined and dried via centrifugal evaporation to give Example 71 (3.3 mg, 5.98 µmol, 18.98% yield). $^1$H NMR (500 MHz, DMSO-$d_6$) δ 10.20 (br. s., 1H), 8.72 (s, 1H), 8.54 (s, 1H), 8.28 (br. s., 1H), 8.03 (br. s., 1H), 7.81 (s, 1H), 7.15 (t, J=11.1 Hz, 2H), 4.69 (br. s., 1H), 4.63 (d, J=11.6 Hz, 1H), 4.53-4.40 (m, 2H), 4.31-4.25 (m, 1H), 4.07 (s, 3H), 2.62 (s, 3H). LC-MS: method C, RT=2.57 min, MS (ESI) m/z: 552.1 (M+H)$^+$. Analytical HPLC purity (method B): 100%.

Example 72

(R)-(4-fluoro-2-(2-methoxy-7-methylquinoxalin-5-yl)-7,8-dihydro-[1,4]dioxino[2',3':3,4]benzo[1,2-d]thiazol-7-yl)methyl (3-cyanophenyl)carbamate

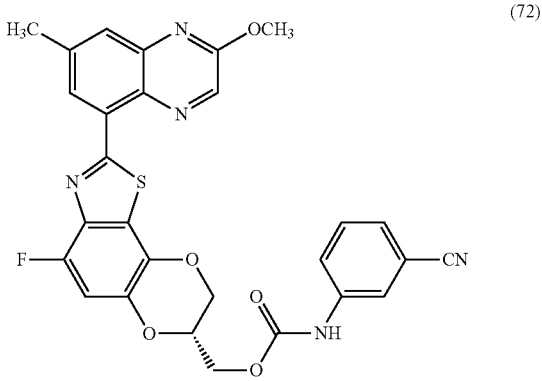 [SMILES: COc1cnc2c(-c3nc4c(F)cc5c(c4s3)OC[C@H](COC(=O)Nc3cccc(C#N)c3)O5)cc(C)cc2n1]

(72)

To a solution of Intermediate 68J (15 mg, 0.032 mmol) in toluene and THF (0.5 mL) was added 3-aminobenzonitrile (13.03 mg, 0.110 mmol) in DCM (1 mL) followed by DIEA (0.055 mL, 0.315 mmol). The mixture was stirred at room temperature for 0.5 h. The reaction was quenched by addition of a small amount of MeOH/water/0.1% TFA (HPLC solvent). Solvent was removed under vacuum. The residual was dissolved in DMSO and purified via preparative LC/MS (method D, 60-100% B over 20 min., then a 5-min hold at 100% B). Fractions containing the desired product were combined and dried via centrifugal evaporation to give Example 72 (2.1 mg, 3.73 µmol, 11.83% yield). $^1$H NMR (500 MHz, DMSO-$d_6$) δ 10.29 (br. s., 1H), 8.73 (s, 1H), 8.55 (s, 1H), 8.03-7.71 (m, 3H), 7.56-7.45 (m, 2H), 7.14 (d, J=11.0 Hz, 1H), 4.70 (br. s., 1H), 4.63 (d, J=11.3 Hz, 1H), 4.55-4.40 (m, 2H), 4.35-4.23 (m, 1H), 4.07 (s, 3H), 2.62 (s, 3H). LC-MS: method C, RT=2.57 min, MS (ESI) m/z: 558.20 (M+H)$^+$. Analytical HPLC purity (method B): 99%.

Example 73

(R)-(4-fluoro-2-(2-methoxy-7-methylquinoxalin-5-yl)-7,8-dihydro-[1,4]dioxino[2',3':3,4]benzo[1,2-d]thiazol-7-yl)methyl pyridin-4-ylcarbamate

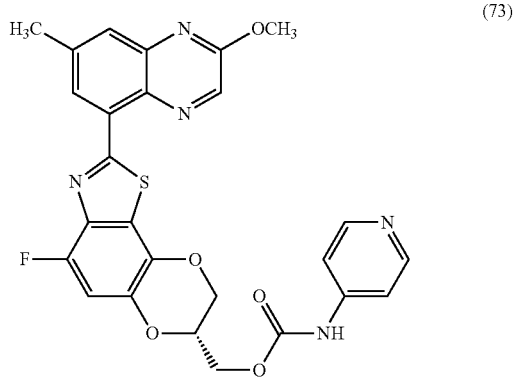 [SMILES: COc1cnc2c(-c3nc4c(F)cc5c(c4s3)OC[C@H](COC(=O)Nc3ccncc3)O5)cc(C)cc2n1]

(73)

To a solution of Intermediate 68J (15 mg, 0.032 mmol) in toluene and THF (0.5 mL) was added pyridin-4-amine (10.38 mg, 0.110 mmol) in DCM (1 mL) followed by DIEA (0.055 mL, 0.315 mmol). The mixture was stirred at room temperature for 1 h, quenched by addition of a small amount of MeOH/water/0.1% TFA (HPLC solvent). Solvent was removed under vacuum. The residual was dissolved in DMSO and purified via preparative LC/MS (method D, 55-95% B over 20 min., then a 5-min hold at 100% B). Fractions containing the desired product were combined and dried via centrifugal evaporation to give Example 73 (2.7 mg, 5.06 µmol, 16.05% yield). $^1$H NMR (500 MHz, DMSO-$d_6$) δ 10.53 (br. s., 1H), 8.76 (s, 1H), 8.57 (s, 1H), 8.44 (br. s., 2H), 7.85 (s, 1H), 7.52 (d, J=4.4 Hz, 2H), 7.15 (d, J=10.7 Hz, 1H), 4.71 (br. s., 1H), 4.64 (d, J=11.6 Hz, 1H), 4.56-4.44 (m, 2H), 4.35-4.24 (m, 1H), 4.08 (s, 3H), 2.63 (s, 3H). LC-MS: method C, RT=2.00 min, MS (ESI) m/z: 534.15 (M+H)$^+$. Analytical HPLC purity (method B): 100%.

Example 74

(4-(difluoromethyl)-2-(2-methoxy-7-methylquinoxalin-5-yl)-7,8-dihydro-[1,4]dioxino[2',3':3,4]benzo[1,2-d]thiazol-7-yl)methyl (2-methylpyridin-4-yl)carbamate

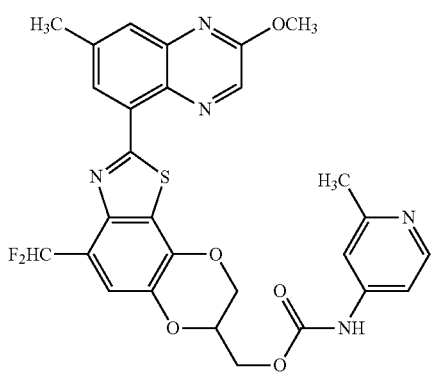

(74)

Intermediate 74A 2-bromo-7-(((tert-butyldimethylsilyl)oxy)methyl)-4-methyl-7,8-dihydro-[1,4]dioxino[2',3':3,4]benzo[1,2-d]thiazole

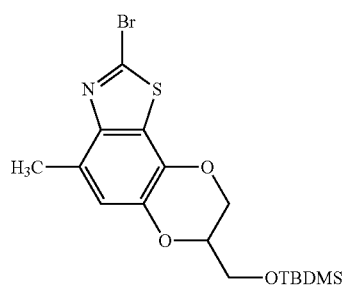

(74A)

To a stirred solution of Intermediate I-7I (1.17 g, 3.70 mmol) in DMF (10 mL) was added TBDMS-Cl (0.781 g, 5.18 mmol) and imidazole (0.441 g, 6.48 mmol). The reaction mixture was left stirring at room temperature for 1.0 h. The mixture was partitioned between EtOAc/water. The organic layer was washed with brine, dried over sodium sulfate. After evaporation of solvent, the crude product was dissolved in a small amount of chloroform and charged to a 40 g ISCO column which was eluted with hexanes for 3 min., then a 30 min gradient from 0% to 50% EtOAc in hexanes. The desired fractions were combined and concentrated to give Intermediate 74A (1.6 g, 3.72 mmol, 100% yield) as off-white solid. $^1$H NMR (400 MHz, chloroform-d) δ 6.84 (d, J=0.9 Hz, 1H), 4.44 (dd, J=11.0, 2.0 Hz, 1H), 4.30-4.23 (m, 1H), 4.22-4.15 (m, 1H), 3.94 (dd, J=10.8, 4.4 Hz, 1H), 3.85-3.72 (m, 1H), 2.59 (d, J=0.9 Hz, 3H), 0.93-0.90 (m, 9H), 0.10 (d, J=3.5 Hz, 6H). LC-MS: method C, RT=2.13 min, MS (ESI) m/z: 430 and 432 (M+H)$^+$.

Intermediate 74B 2-bromo-7-(((tert-butyldimethylsilyl)oxy)methyl)-4-(dibromomethyl)-7,8-dihydro-[1,4]dioxino[2',3':3,4]benzo[1,2-d]thiazole

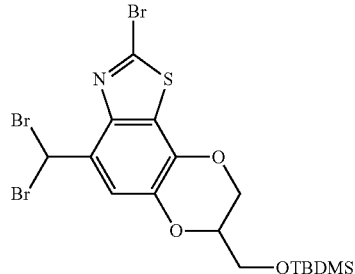

(74B)

To a solution of Intermediate 74A (300 mg, 0.697 mmol) in CCl$_4$ (5 mL) was added NBS (273 mg, 1.533 mmol) and benzoic peroxide (16.88 mg, 0.070 mmol). The mixture was heated up to reflux (90° C. oil bath) for 3 h. LCMS indicated a completion of the reaction. The mixture was cooled to room temperature and filtered. The filtrate was concentrated to yield Intermediate 74B (410 mg, 0.697 mmol, 100% yield) as a yellow solid. The sample was used for next step without purification. $^1$H NMR (400 MHz, chloroform-d) δ 7.59 (s, 1H), 7.52 (s, 1H), 4.50 (dd, J=10.9, 1.9 Hz, 1H), 4.34-4.21 (m, 2H), 4.00-3.96 (m, 1H), 3.85 (dd, J=10.9, 6.5 Hz, 1H), 2.78 (s, 1H), 0.93-0.91 (m, 9H), 0.13-0.09 (m, 6H). LC-MS: method C, RT=1.80 and 1.93 min, MS (ESI) m/z: No (M+H)$^+$.

Intermediate 74C: 2-bromo-7-(hydroxymethyl)-7,8-dihydro-[1,4]dioxino[2',3':3,4]benzo[1,2-d]thiazole-4-carbaldehyde

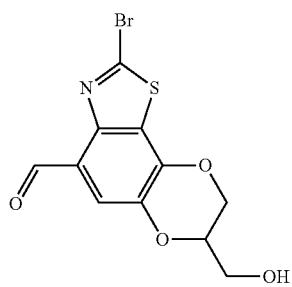

(74C)

To a solution of Intermediate 74B (410 mg, 0.697 mmol) in ethanol (3 mL) was slowly added silver nitrate (1.2 g, 6.97 mmol) in water (3 mL) dropwise. White precipitate was formed and the mixture was heated up to reflux (oil bath 100° C.) for 1 h. The mixture was cooled to room temperature and pour to 100 ml of water. The mixture was filtered and the filter cake was washed with CHCl$_3$ (3×). The combined filtrate was extracted with CHCl$_3$ and the organic layer was combined, washed with NaHCO$_3$, brine, dried with MgSO$_4$ and concentrated. The crude sample was purified with a 12 g ISCO column eluted with 0-100% EtOAc in hexanes for 15 min, the desired fraction was concentrated to give Intermediate 74C (140 mg, 0.424 mmol, 60.8% yield) as yellow oil. $^1$H NMR (400 MHz, chloroform-d) δ 10.68 (s, 1H), 7.60 (s, 1H), 4.60-4.51 (m, 1H), 4.41-4.33 (m, 2H), 4.05-3.89 (m, 2H). LC-MS: method C, RT=1.80 min, MS (ESI) m/z: 330 and 332 (M+H)$^+$.

Intermediate 74D (2-bromo-4-formyl-7,8-dihydro-[1,4]dioxino[2',3':3,4]benzo[1,2-d]thiazol-7-yl)methyl acetate

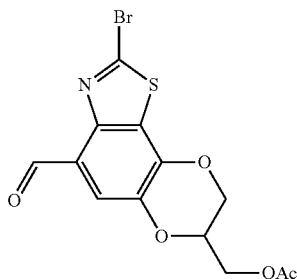

(74D)

To a solution of Intermediate 74C (230 mg, 0.697 mmol) in THF (5 mL) at room temperature was added TEA (0.243 mL, 1.742 mmol), followed by acetyl chloride in DCM (0.871 mL, 0.871 mmol) dropwise. The mixture was stirred at room temperature for 2.0 h. LCMS indicated a clean reaction. The mixture was diluted with EtOAc, washed with water. The organic layer was washed with 0.5 N HCl, saturated sodium bicarbonate, brine, dried over sodium sulfate. After evaporation of solvent, the crude sample was purified with a 12 g ISCO column eluted with 0-100% EtOAc in hexanes for 15 min. The desired fraction was collected and concentrated to give Intermediate 74D (160 mg, 0.430 mmol, 61.7% yield) as white solid. $^1$H NMR (400 MHz, chloroform-d) δ 10.74 (s, 1H), 7.69 (s, 1H), 4.59-4.47 (m, 2H), 4.45-4.33 (m, 2H), 4.32-4.22 (m, 1H), 2.13 (s, 3H). LC-MS: method C, RT=2.12 min, MS (ESI) m/z: 372 and 374 (M+H)$^+$.

Intermediate 74E: (2-bromo-4-(difluoromethyl)-7,8-dihydro-[1,4]dioxino[2',3':3,4]benzo[1,2-d]thiazol-7-yl)methyl acetate

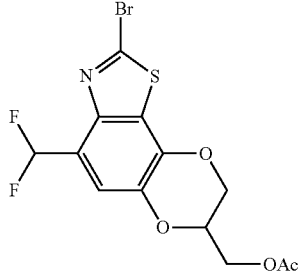

(74E)

To a solution of Intermediate 74D (110 mg, 0.296 mmol) in DCM (5 mL) was added DAST (0.4 mL, 3.0 mmol) dropwise at room temperature. The mixture was stirred at room temperature overnight. LCMS indicated a completion of the reaction. The reaction was quenched with ice water, extracted with EtOAc. The combined organic layer was washed with NaHCO$_3$ and brine, dried with MgSO$_4$ and concentrated. The crude sample was purified with a 12 g ISCO column eluted with 0-100% EtOAc for 15 min. The desired fraction was collected and concentrated to give Intermediate 74E (80 mg, 0.203 mmol, 68.7% yield) was a white solid. $^1$H NMR (400 MHz, chloroform-d) δ 7.39 (s, 1H), 7.51-7.14 (m, 1H), 4.56-4.46 (m, 2H), 4.38 (dd, J=5.1, 2.9 Hz, 2H), 4.29-4.19 (m, 1H), 2.14 (s, 3H). $^{19}$F NMR (376 MHz, chloroform-d) δ −111.81 (s, 2F). LC-MS: method C, RT=2.16 min, MS (ESI) m/z: 393.9 and 395.9 (M+H)$^+$.

Intermediate 74F (2-(2-(difluoromethoxy)-7-methylquinoxalin-5-yl)-4-(difluoromethyl)-7,8-dihydro-[1,4]dioxino[2',3':3,4]benzo[1,2-d]thiazol-7-yl)methyl acetate

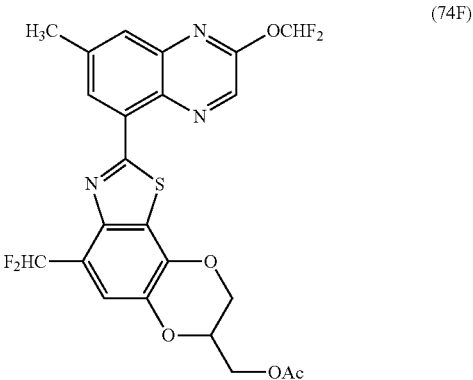 [SMILES: CC(=O)OCC1COc2c(cc(C(F)F)c3nc(-c4cc(C)cc5nc(OC(F)F)cnc45)sc23)O1]

(74F)

To Intermediate I-1 (74.1 mg, 0.292 mmol), Intermediate 74E (115 mg, 0.292 mmol) and PdCl$_2$(dppf)—CH$_2$Cl$_2$ adduct (11.91 mg, 0.015 mmol) was added toluene (4.5 mL) and EtOH (1.5 mL). The mixture was sonicated for 1 min, and flushed with argon. To this was added sodium carbonate (0.292 mL, 2M, 0.583 mmol). The reaction mixture was heated in a microwave reactor at 130° C. for 40 min. The crude reaction mixture was directly loaded onto a 40 g ISCO column cartridge for purification. The crude product was purified with flash chromatography (0% to 100% EtOAc in hexanes over 20 min using a 40 g silica gel cartridge). The desired fractions were combined and concentrated to yield Intermediate 74F (153 mg, 0.292 mmol, 100% yield) as a yellow solid. $^1$H NMR (400 MHz, chloroform-d) δ 8.81 (d, J=1.8 Hz, 1H), 8.68 (s, 1H), 7.80 (dd, J=1.9, 1.0 Hz, 1H), 7.86-7.47 (m, 2H), 7.44 (s, 1H), 4.57-4.52 (m, 2H), 4.42 (dd, J=5.0, 1.7 Hz, 2H), 4.30 (dd, J=11.8, 7.6 Hz, 1H), 2.70 (s, 3H), 2.16 (s, 3H). $^{19}$F NMR (376 MHz, chloroform-d) δ −89.75 (s, 2F), −111.58 (s, 2 F). LC-MS: method C, RT=2.59 min, MS (ESI) m/z: 524 (M+H)$^+$.

Intermediate 74G (4-(difluoromethyl)-2-(2-methoxy-7-methylquinoxalin-5-yl)-7,8-dihydro-[1,4]dioxino[2',3':3,4]benzo[1,2-d]thiazol-7-yl)methanol

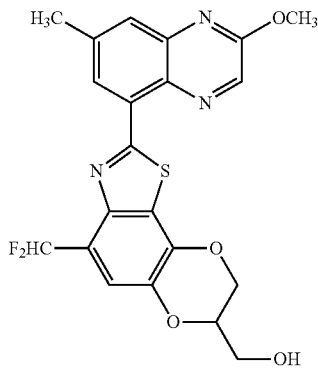

(74G)

To a solution of Intermediate 74F (153 mg, 0.292 mmol) in THF (5 mL) was added sodium methoxide in MeOH (0.31 mL, 4.7 M, 1.5 mmol. The reaction mixture was stirred at room temperature overnight. The reaction mixture was quenched with 1 N HCl (5.0 mL) and extracted with DCM. The combined organic layer was washed with brine, dried with $MgSO_4$ and concentrated to give Intermediate 74G (120 mg, 0.269 mmol, 92% yield) as a yellow solid. $^1$H NMR (400 MHz, Chloroform-d) δ 8.71-8.65 (m, 1H), 8.55 (s, 1H), 7.77 (dd, J=1.8, 0.9 Hz, 1H), 7.76-7.47 (m, 1H), 7.42 (s, 1H), 4.55 (dd, J=10.7, 1.7 Hz, 1H), 4.44-4.33 (m, 2H), 4.14 (s, 3H), 4.06-3.91 (m, 2H), 2.67 (s, 3H). $^{19}$F NMR (376 MHz, chloroform-d) δ −111.42 (d, J=10.3 Hz, 2F). LC-MS: method C, RT=2.51 min, MS (ESI) m/z: 446.1 (M+H)$^+$.

Intermediate 74H (4-(difluoromethyl)-2-(2-methoxy-7-methylquinoxalin-5-yl)-7,8-dihydro-[1,4]dioxino[2',3':3,4]benzo[1,2-d]thiazol-7-yl)methyl carbonochloridate

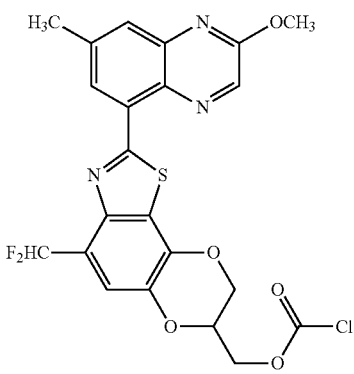

(74H)

To a solution of Intermediate 74G (83 mg, 0.186 mmol) in THF (3 mL) at room temperature was added 15% phosgene in toluene (0.657 mL, 0.932 mmol). The mixture was stirred at room temperature overnight. The solution of Intermediate 74H was bubble with argon for 2 h. And was used for the next step without any purification. LC-MS: method C, RT=2.77 min, MS (ESI) m/z: 508 (M+H)$^+$.

Example 74

To a solution of 2-methylpyridin-4-amine (9.69 mg, 0.090 mmol) in DCM (0.5 mL) was added DIEA (0.045 mL, 0.256 mmol) followed by a solution of Intermediate 74H (13 mg, 0.026 mmol) in toluene and THF (0.5 mL). The mixture was stirred at room temperature for 0.5 h. The reaction was quenched by addition of a small amount of MeOH/water/0.1% TFA (HPLC solvent) and concentrated. The residual was dissolved in DMSO and purified via preparative LC/MS (method D, 55-95% B over 30 min., then a 5-min hold at 100% B). Fractions containing the desired product were combined and dried via centrifugal evaporation to give Example 74 (7.6 mg, 0.013 mmol, 50.2% yield). H NMR (500 MHz, DMSO-$d_6$) δ 10.78 (br. s., 1H), 8.75 (br. s., 1H), 8.62 (br. s., 1H), 8.39 (br. s., 1H), 7.85 (br. s., 1H), 7.78-7.46 (m, 3H), 7.35 (br. s., 1H), 4.81-4.64 (m, 2H), 4.61-4.46 (m, 2H), 4.40 (d, J=8.3 Hz, 1H), 4.08 (br. s., 3H), 2.64 (br. s., 3H). LC-MS: method C, RT=2.18 min, MS (ESI) m/z: 580.15 (M+H)$^+$. Analytical HPLC purity (method B): 98%.

Example 75

(R)-(4-fluoro-2-(2-methoxy-7-methylquinoxalin-5-yl)-7,8-dihydro-[1,4]dioxino[2',3':3,4]benzo[1,2-d]thiazol-7-yl)methyl (2-methylpyridin-4-yl)carbamate

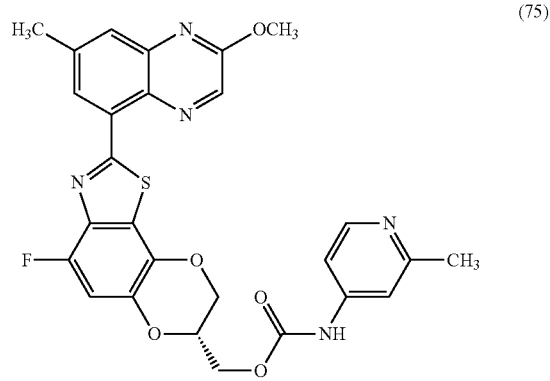 [SMILES: COc1cnc2c(-c3nc4c(F)cc5c(c4s3)OC[C@H](COC(=O)Nc3ccnc(C)c3)O5)cc(C)cc2n1]

(75)

To a solution of Intermediate 68J (15 mg, 0.032 mmol) in toluene and THF (0.5 mL) was added 2-methylpyridin-4-amine (11.93 mg, 0.110 mmol) in DCM (1 mL) followed by DIEA (0.055 mL, 0.315 mmol). The mixture was stirred at room temperature for 1 h. The reaction was quenched by addition of a small amount of MeOH/water/0.1% TFA (HPLC solvent). Solvent was removed under vacuum. The residual was dissolved in DMSO and purified via preparative LC/MS (method C, 35-70% B over 20 min., then a 5-min hold at 100% B). Fractions containing the desired product were combined and dried via centrifugal evaporation to give Example 75 (1 mg, 1.735 µmol, 5.50% yield). $^1$H NMR (500 MHz, DMSO-$d_6$) δ 11.25 (br. s., 1H), 8.76 (br. s., 1H), 8.58 (br. s., 1H), 8.51 (d, J=5.5 Hz, 1H), 7.85 (br. s., 1H), 7.75-7.60 (m, 2H), 7.29-6.97 (m, 2H), 4.74 (br. s., 1H), 4.65-4.51 (m, 3H), 4.32 (t, J=8.9 Hz, 1H), 4.08 (br. s., 3H), 2.64 (br. s., 3H), 2.58 (br. s., 3H). LC-MS: method C, RT=2.17 min, MS (ESI) m/z: 548.15 (M+H)⁺. Analytical HPLC purity (method B): 95%.

Example 76

(R)-(4-fluoro-2-(2-methoxy-7-methylquinoxalin-5-yl)-7,8-dihydro-[1,4]dioxino[2',3':3,4]benzo[1,2-d]thiazol-7-yl)methyl (6-methylpyridin-3-yl)carbamate

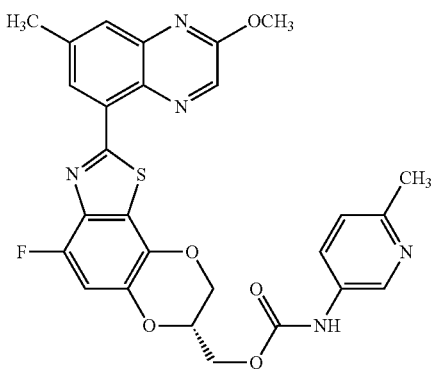

(76)

To a solution of Intermediate 68J (57.6 mg, 0.121 mmol) in DCM (1 mL) was added 6-methylpyridin-3-amine (26.2 mg, 0.242 mmol) in DCM (1 mL) followed by DIEA (0.211 mL, 1.210 mmol). The mixture was stirred at room temperature for 0.5 h. LCMS indicated a completion of reaction. The reaction was quenched by addition of a small amount of MeOH/water/0.1% TFA (HPLC solvent). Solvent was removed under vacuum. The residual was dissolved in DMSO and purified with preparative HPLC (method A, 30-100% B in 10 min.). The desired fractions were placed in a SpeedVac overnight to remove solvent, then lyophilized to give Example 76 (21 mg, 0.031 mmol, 25.7% yield). ¹⁹F NMR (376 MHz, acetonitrile-d₃) δ −76.31 (s, 1F), −131.97 (s, 1F). ¹H NMR (400 MHz, acetonitrile-d₃) δ 8.82 (s, 1H), 8.62 (d, J=1.8 Hz, 1H), 8.59 (s, 1H), 8.36 (br. s., 1H), 8.11 (d, J=8.4 Hz, 1H), 7.81-7.76 (m, 1H), 7.51 (d, J=8.6 Hz, 1H), 6.95 (d, J=11.0 Hz, 1H), 4.65-4.59 (m, 1H), 4.58-4.51 (m, 3H), 4.32 (dd, J=11.7, 6.6 Hz, 1H), 4.11 (s, 3H), 2.66 (s, 3H), 2.60 (s, 3H). LC-MS: method C, RT=2.14 min, MS (ESI) m/z: 548.2 (M+H)⁺. Analytical HPLC purity (method A): 99%.

Example 77

(2-(2-methoxy-7-methylquinoxalin-5-yl)-4-methyl-7,8-dihydro-[1,4]dioxino [2',3':3,4]benzo[1,2-d]thiazol-7-yl)methyl (5-carbamoylpyridin-3-yl)carbamate

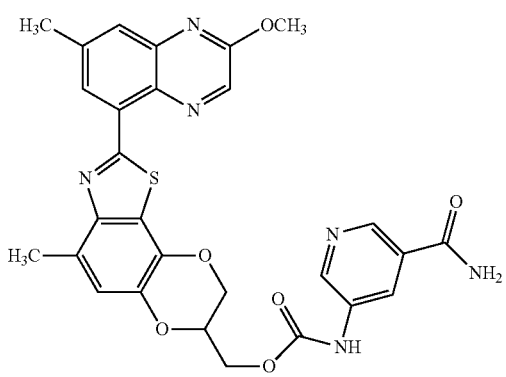

(77)

Intermediate 77A: 5-carbamoylpyridin-3-ylcarbamic chloride

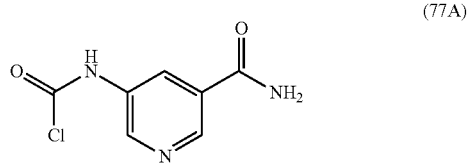 [SMILES: NC(=O)c1cncc(NC(=O)Cl)c1]

(77A)

To a suspension of 5-aminonicotinamide (83 mg, 0.605 mmol) in DCM (3 ml) at 0° C. was added phosgene (15% in toluene) (2.134 ml, 3.03 mmol) followed by addition of DIEA (0.137 ml, 0.787 mmol) dropwise at 0° C. The mixture was stirred at 0° C. for 15 min, then warmed up to room temperature overnight. Solvent was removed under vacuum to give Intermediate 77A as a yellow solid which was used for next step without further purification. LC-MS: method C, RT=0.23 min, MS (ESI) m/z: 196 (M+H)⁺ (methyl carbamate).

Example 77

To a solution of Intermediate I-7 (12 mg, 0.029 mmol) in THF (0.5 mL) was added a suspension of Intermediate 77A (17.55 mg, 0.088 mmol) in DCM (1 ml) followed by DIEA (0.051 ml, 0.293 mmol). The mixture was stirred at room temperature overnight, quenched by a drop of 10% water/acetonitrile with 01% TFA. Solvent was removed, the residual was dissolved in DMSO and purified via preparative LC/MS (method C, 35-70% B over 15 min., then a 5-min hold at 100% B). Fractions containing the desired product were combined and dried via centrifugal evaporation to give Example 77 (4.2 mg, 6.75 μmol, 23.03% yield). ¹H NMR (500 MHz, DMSO-d₆) δ 10.24 (br. s., 1H), 8.73 (d, J=9.4 Hz, 2H), 8.69 (br. s., 1H), 8.56 (br. s., 1H), 8.33 (br. s., 1H), 8.13 (br. s., 1H), 7.80 (br. s., 1H), 7.57 (br. s., 1H), 6.98 (br. s., 1H), 4.65 (br. s., 1H), 4.60 (d, J=11.6 Hz, 1H), 4.54-4.41 (m, 2H), 4.29 (d, J=8.3 Hz, 1H), 4.07 (br. s., 3H), 2.67 (br. s., 3H), 2.63 (br. s., 3H). LC-MS: method C, RT=2.07 min, MS (ESI) m/z: 574.2 (M+H)⁺. Analytical IPLC purity (method B): 92%.

Example 78

(2-(2-methoxy-7-methylquinoxalin-5-yl)-4-methyl-7,8-dihydro-[1,4]dioxino[2',3':3,4]benzo[1,2-d]thiazol-7-yl)methyl (1-oxo-1,2,3,4-tetrahydroisoquinolin-7-yl)carbamate

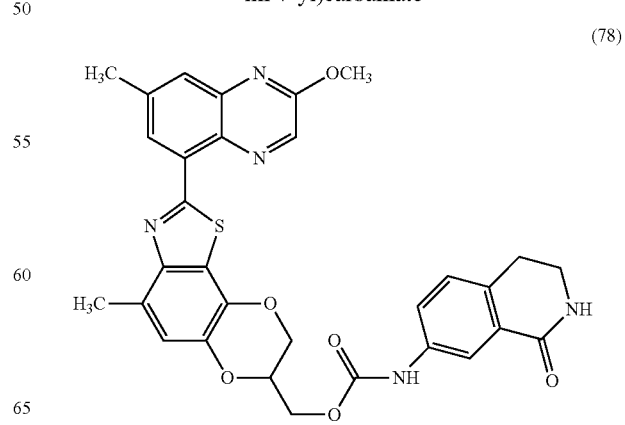

(78)

Intermediate 78A (2-(2-methoxy-7-methylquinoxalin-5-yl)-4-methyl-7,8-dihydro-[1,4]dioxino[2',3':3,4]benzo[1,2-d]thiazol-7-yl)methyl carbonochloridate

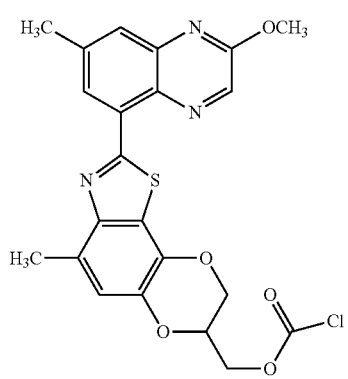

(78A)

To a suspension of Intermediate I-7 (100 mg, 0.244 mmol) in THF (3 mL) at room temperature was added 15% phosgene in toluene (0.861 mL, 1.221 mmol) and the mixture was stirred at room temperature overnight. LCMS indicated a completion of reaction. Solvent was removed under vacuum to give Intermediate 78A as a yellow solid. It was used for the next step without any purification. LC-MS: method C, RT=2.78 min, MS (ESI) m/z: 472 (M+H)$^+$.

Example 78

To a solution of 7-amino-3,4-dihydroisoquinolin-1(2H)-one (12.03 mg, 0.074 mmol) in DCM (1 mL) was added a suspension of Intermediate 78A (10 mg, 0.021 mmol) in THF followed by DIEA (0.037 mL, 0.212 mmol). The mixture was stirred at room temperature for 2 h. The reaction was quenched by addition of a small amount of MeOH/water/0.1% TFA (HPLC solvent). Solvent was removed under vacuum. The residual was dissolved in DMSO and purified via preparative LC/MS (method D, 55-100% B over 20 min., then a 5-min hold at 100% B). Fractions containing the desired product were combined and dried via centrifugal evaporation to give Example 78 (4.5 mg, 7.53 µmol, 35.5% yield). $^1$H NMR (500 MHz, DMSO-d$_6$) δ 9.93 (br. s., 1H), 8.74 (br. s., 1H), 8.57 (br. s., 1H), 8.00 (br. s., 1H), 7.89 (br. s., 1H), 7.81 (br. s., 1H), 7.55 (d, J=6.6 Hz, 1H), 7.22 (d, J=7.4 Hz, 1H), 6.99 (br. s., 1H), 4.70-4.55 (m, 2H), 4.43 (d, J=11.0 Hz, 2H), 4.27 (br. s., 1H), 4.07 (br. s., 3H), 2.83 (br. s., 2H), 2.67 (br. s., 3H), 2.63 (br. s., 3H). LC-MS: method C, RT=2.50 min, MS (ESI) m/z: 598.2 (M+H)$^+$. Analytical HPLC purity (method B): 100%.

Example 79

(2-(2-methoxy-7-methylquinoxalin-5-yl)-4-methyl-7,8-dihydro-[1,4]dioxino[2',3':3,4]benzo[1,2-d]thiazol-7-yl)methyl (2-methylpyrimidin-5-yl)carbamate

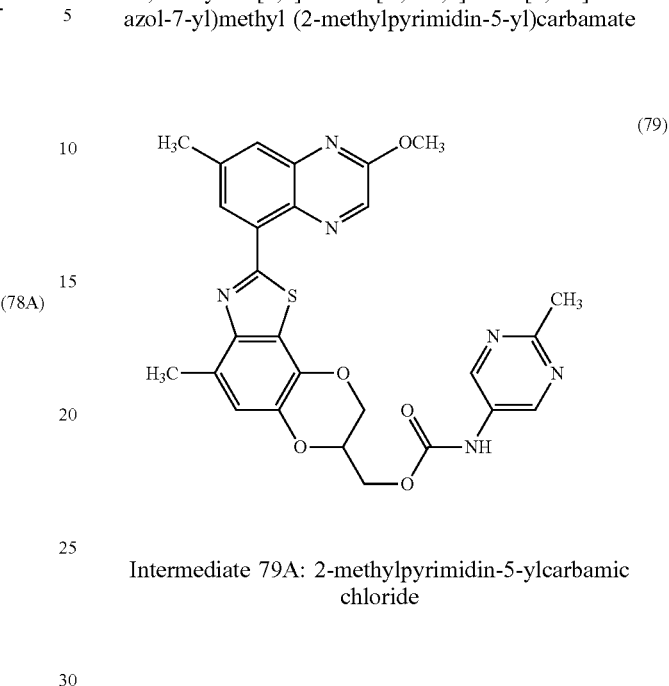

(79)

Intermediate 79A: 2-methylpyrimidin-5-ylcarbamic chloride (79A)

To a suspension of 2-methylpyrimidin-5-amine (68 mg, 0.623 mmol) in DCM (10 ml) was added phosgene (15% in toluene) (2.197 ml, 3.12 mmol) followed by addition of DIEA (0.163 ml, 0.935 mmol) dropwise. The mixture was stirred at room temperature overnight. Solvent was removed under vacuum to give Intermediate 79A as a yellow solid. It was used for next step without further purification. LC-MS: method C, RT=0.57 min, MS (ESI) m/z: 154 (M+H)$^+$ (methyl carbamate).

Example 79

To a solution of Intermediate I-7 (10 mg, 0.024 mmol) in THF (0.5 mL) was added suspension of Intermediate 79A (20.95 mg, 0.122 mmol) in DCM (2 ml) followed by DIEA (0.043 ml, 0.244 mmol). The mixture was stirred at room temperature for 30 min. Another portion of Intermediate 79A (20.95 mg, 0.122 mmol) was added to the mixture was stirred at room temperature overnight. The mixture was quenched by 10% water/acetonitrile with 0.1% TFA (HPLC solvent). Solvent was removed, the residual was dissolved in DMSO and purified via preparative LC/MS (method C, 50-80% B over 25 min., then a 5-min hold at 100% B). Fractions containing the desired product were combined and dried via centrifugal evaporation to give Example 79 (4.2 mg, 7.40 µmol, 30.3% yield). $^1$H NMR (500 MHz, DMSO-d$_6$) δ 10.16 (br. s., 1H), 8.75 (br. s., 2H), 8.70 (br. s., 1H), 8.55 (br. s., 1H), 7.78 (br. s., 1H), 6.97 (br. s., 1H), 4.69-4.55 (m, 2H), 4.53-4.39 (m, 2H), 4.27 (br. s., 1H), 4.06 (br. s., 3H), 2.66 (br. s., 3H), 2.62 (br. s., 3H), 2.55 (br. s., 3H).

LC-MS: method H, RT=2.4 min, MS (ESI) m/z: 545.25 (M+H)⁺. Analytical HPLC purity (method B): 96%.

Example 80

(R)-(4-(difluoromethyl)-2-(2-methoxy-7-methylquinoxalin-5-yl)-7,8-dihydro-[1,4]dioxino[2',3':3,4]benzo[1,2-d]thiazol-7-yl)methyl (6-methylpyridin-3-yl)carbamate

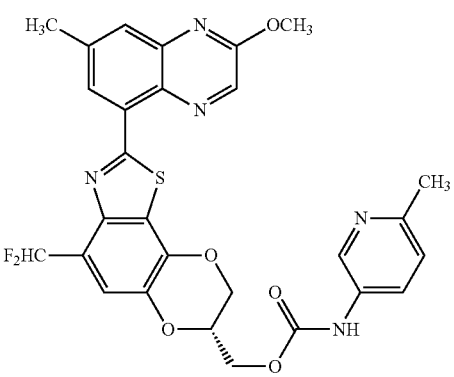

Intermediate 80A: (R)-(2-chloro-4-(dibromomethyl)-7,8-dihydro-[1,4]dioxino[2',3':3,4]benzo[1,2-d]thiazol-7-yl)methyl acetate

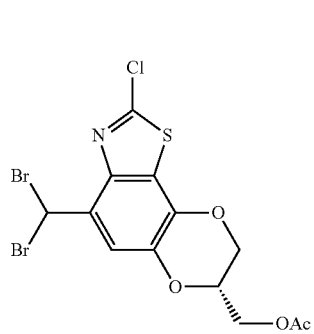

To a solution of Intermediate I-26 (350 mg, 1.116 mmol) in CCl₄ (8 mL) was added NBS (437 mg, 2.454 mmol) and benzoic peroxide (27.0 mg, 0.112 mmol). The mixture was heated up to reflux (90° C. oil bath) for 3.5 h. LCMS indicated a completion of the reaction. The mixture was cooled to room temperature and filtered. The filtrate was concentrated to give Intermediate 80A (526 mg, 1.115 mmol, 100% yield) as a yellow solid. The sample was used for next step without purification.

Intermediate 80B: (S)-2-chloro-7-(hydroxymethyl)-7,8-dihydro-[1,4]dioxino[2',3':3,4]benzo[1,2-d]thiazole-4-carbaldehyde

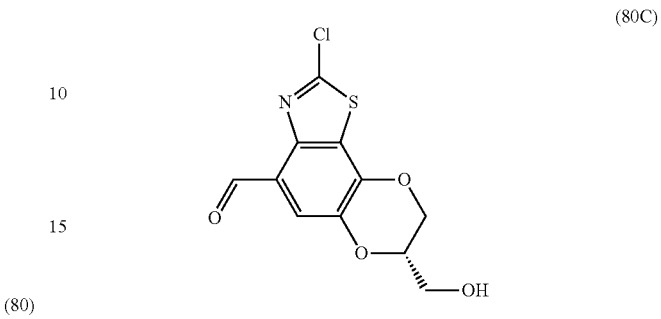

To a solution of Intermediate 80A (526 mg, 1.116 mmol) in ethanol (3 mL) was added silver nitrate (1896 mg, 11.16 mmol) in water (3 mL) dropwise. White precipitate was formed, and the mixture was heated to reflux (oil bath 100° C.) for 1 h. The mixture was cooled to room temperature and poured to 100 ml of water. The mixture was filtered, and the filter cake was washed with CHCl₃ (3×). The combined filtrate was extracted with CHCl₃ and the organic layer was combined, washed with NaHCO₃, brine, dried over MgSO₄. The crude sample was purified by a 12 g ISCO column eluted with 0-100% EtOAc in hexanes for 15 min to give Intermediate 80B (250 mg, 0.875 mmol, 78% yield). ¹H NMR (400 MHz, methanol-d₄) δ 10.58 (s, 1H), 7.62 (s, 1H), 4.70-4.55 (m, 1H), 4.39-4.24 (m, 2H), 3.86 (d, J=4.4 Hz, 2H). LC-MS: method H, RT=1.78 min, MS (ESI) m/z: 286.0 (M+H)⁺.

Intermediate 80C: (R)-(2-chloro-4-formyl-7,8-dihydro-[1,4]dioxino[2',3':3,4]benzo[1,2-d]thiazol-7-yl)methyl acetate

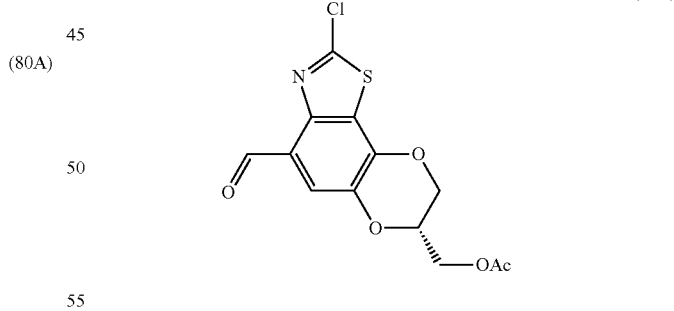

To a solution of Intermediate 80B (290 mg, 1.015 mmol) in THF (5 mL) was added TEA (0.354 mL, 2.54 mmol), followed by acetyl chloride in DCM (1.269 mL, 1.269 mmol) dropwise. The mixture was stirred at room temperature overnight, diluted with EtOAc, washed with water. The organic layer was washed with 0.5 N HCl, saturated sodium bicarbonate, brine and dried over sodium sulfate. After evaporation of solvent, the crude sample was purified with a 24 g ISCO column eluted with 0-100% EtOAc in hexanes for 15 min. The desired fractions were combined and concentrated to give Intermediate 80C (258 mg, 0.787 mmol, 78% yield) as white solid. ¹H NMR (400 MHz, chloroform-d) δ 10.69 (s, 1H), 7.68 (s, 1H), 4.58-4.48 (m, 2H), 4.39 (dd, J=7.6, 5.2 Hz, 2H), 4.32-4.25 (m, 1H), 2.13 (s, 3H). LC-MS: method H, RT=1.97 min, MS (ESI) m/z: 328.0 (M+H)+.

Intermediate 80D: (R)-(2-chloro-4-(difluoromethyl)-7,8-dihydro-[1,4]dioxino[2',3':3,4]benzo[1,2-d]thiazol-7-yl)methyl acetate

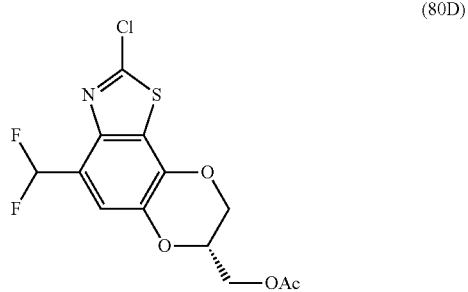 [SMILES: CC(=O)OC[C@H]1COc2c(cc(C(F)F)c3nc(Cl)sc23)O1]
(80D)

To a solution of Intermediate 80C (250 mg, 0.763 mmol) in DCM (5 mL) was added DAST (1.008 mL, 7.63 mmol) dropwise. The mixture was stirred at room temperature for 30 min. LCMS indicated a small conversion. Another portion of DAST (1.008 mL, 7.63 mmol) was added, and the mixture was continued stirring at room temperature overnight. The reaction was quenched by ice water, extracted with EtOAc. The combined organic layer was washed with NaHCO$_3$, brine, dried over MgSO$_4$ and concentrated. The crude sample was purified with a 12 g ISCO column eluted with 0-100% EtOAc in hexanes for 15 min. The desired fraction was collected and concentrated to give Intermediate 80D (220 mg, 0.629 mmol, 82% yield) as a white solid. $^{19}$F NMR (376 MHz, chloroform-d) δ −111.85 (s, 2F). $^1$H NMR (400 MHz, chloroform-d) δ 7.41-7.38 (m, 1H), 7.42 (s, 1H), 4.58-4.45 (m, 2H), 4.43-4.36 (m, 2H), 4.29-4.19 (m, 1H), 2.14 (s, 3H). LC-MS: method H, RT=2.14 min, MS (ESI) m/z: 350.0 (M+H)+.

Intermediate 80E (R)-(2-(2-(difluoromethoxy)-7-methylquinoxalin-5-yl)-4-(difluoromethyl)-7,8-dihydro-[1,4]dioxino[2',3':3,4]benzo[1,2-d]thiazol-7-yl)methyl acetate

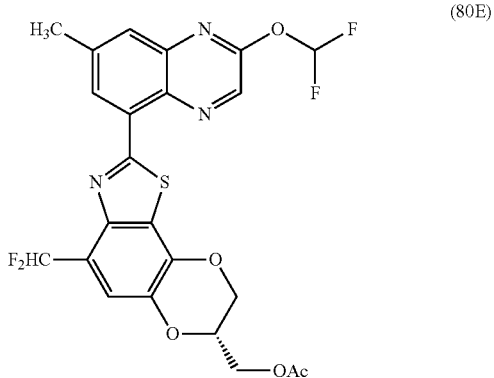 [SMILES: CC(=O)OC[C@H]1COc2c(cc(C(F)F)c3nc(-c4cc(C)cc5nc(OC(F)F)cnc45)sc23)O1]
(80E)

To Intermediate I-1 (202 mg, 0.600 mmol), Intermediate 80D (210 mg, 0.600 mmol) and PdCl$_2$(dppf)—CH$_2$Cl$_2$ adduct (24.52 mg, 0.030 mmol) was added toluene (4.5 mL) and EtOH (1.5 mL). The mixture was sonicated for 1 min, and flushed with argon. To this was added sodium carbonate (0.600 mL, 2M, 1.201 mmol). The reaction mixture was heated in a microwave reactor at 130° C. for 40 min. The crude reaction mixture was directly loaded onto a 40 g ISCO column cartridge for purification. The crude product was purified by flash chromatography (0% to 100% EtOAc in hexane over 20 min using a 40 g silica gel cartridge). The desired fractions were combined and concentrated to yield Intermediate 80E (314 mg, 0.600 mmol, 100% yield) as a yellow solid. $^{19}$F NMR (376 MHz, chloroform-d) δ −89.75 (s, 2F), −111.50 (s, 2F). LC-MS: method H, RT=2.59 min, MS (ESI) m/z: 524.1 (M+H)+.

Intermediate 80F (S)-(4-(difluoromethyl)-2-(2-methoxy-7-methylquinoxalin-5-yl)-7,8-dihydro-[1,4]dioxino [2',3':3,4] benzo[1,2-d]thiazol-7-yl)methanol

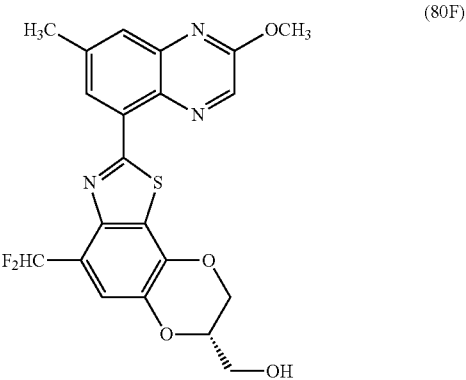 [SMILES: COc1cnc2c(-c3nc4c(C(F)F)cc5c(c4s3)OC[C@H](CO)O5)cc(C)cc2n1]
(80F)

To Intermediate 80E (314 mg, 0.600 mmol) dissolved in THF (5 mL) at room temperature was added 4.37 M sodium methoxide in MeOH (2.100 mmol). The reaction mixture was stirred at room temperature overnight, quenched with 1 N HCl (5.0 mL) and extracted with DCM (5×). The combined organic layer was washed with brine, dried over MgSO$_4$ and concentrated to give Intermediate 80F (200 mg, 0.449 mmol, 74.9% yield) as a yellow solid. $^1$H NMR (400 MHz, chloroform-d) δ 8.71 (d, J=1.5 Hz, 1H), 8.58 (s, 1H), 7.80 (dd, J=1.9, 1.0 Hz, 1H), 7.78-7.50 (m, 1H), 7.45 (s, 1H), 4.60-4.56 (m, 1H), 4.45-4.36 (m, 2H), 4.16 (s, 3H), 3.98 (br. s., 2H), 2.70 (s, 3H). $^{19}$F NMR (376 MHz, chloroform-d) δ −111.42 (d, J=11.4 Hz, 2F). LC-MS: method H, RT=2.51 min, MS (ESI) m/z: 446.1 (M+H)+.

Intermediate 80G (R)-(4-(difluoromethyl)-2-(2-methoxy-7-methylquinoxalin-5-yl)-7,8-dihydro-[1,4]dioxino[2',3':3,4]benzo[1,2-d]thiazol-7-yl)methyl carbonochloridate

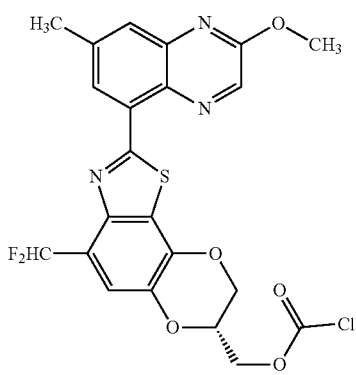

(80G)

To a solution of Intermediate 80F (70 mg, 0.157 mmol) in THF (3 mL) at room temperature was added 15% phosgene in toluene (0.554 mL, 0.786 mmol). The mixture was stirred at room temperature overnight. The mixture containing Intermediate 80G was bubble with argon for 3 h. The sample used for the next step without any purification. LC-MS: method H, RT=2.76 min, MS (ESI) m/z: 508.1 (M+H)+ for methyl carbamate.

Example 80

To a solution of 6-methylpyridin-3-amine (11.18 mg, 0.103 mmol) in DCM (0.5 mL) was added DIEA (0.052 mL, 0.295 mmol) followed by Intermediate 80G (15 mg, 0.030 mmol) in THF (0.5 mL). The mixture was stirred at room temperature for 1 h. The reaction was quenched by addition of a small amount of MeOH/water/0.1% TFA (HPLC solvent) and concentrated. The residual was dissolved in DMSO and purified via preparative LC/MS (method C, 45-85% B over 15 min., then a 5-min hold at 100% B). Fractions containing the desired product were combined and dried via centrifugal evaporation to give Example 80 (4.5 mg, 7.76 μmol, 26.3% yield). $^1$H NMR (500 MHz, DMSO-$d_6$) δ 10.25 (br. s., 1H), 8.74 (br. s., 1H), 8.60 (br. s., 2H), 7.93 (br. s., 1H), 7.84 (br. s., 1H), 7.78-7.51 (m, 1H), 7.42-7.32 (m, 2H), 4.78-4.64 (m, 2H), 4.57-4.42 (m, 2H), 4.37 (br. s., 1H), 4.07 (br. s., 3H), 2.63 (br. s., 3H), 2.54 (br. s., 3H), 2.47 (br. s., 3H). LC-MS: method C, RT=2.09 min, MS (ESI) m/z: 580.2 (M+H)+. Analytical HPLC purity (method B): 100%.

Example 81

(R)-(4-(difluoromethyl)-2-(2-methoxy-7-methylquinoxalin-5-yl)-7,8-dihydro-[1,4]dioxino[2',3':3,4]benzo[1,2-d]thiazol-7-yl)methyl (6-methoxypyridin-3-yl)carbamate

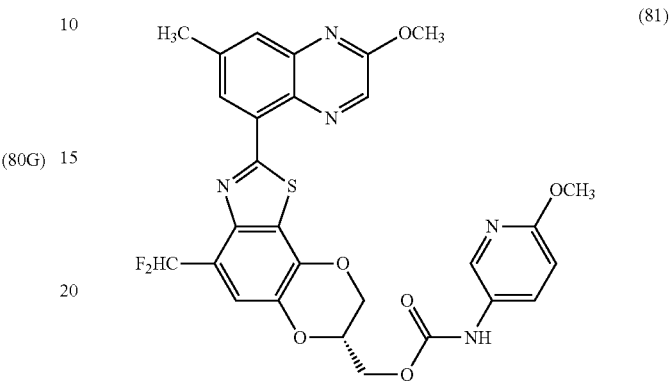

(81)

To a solution of 6-methoxypyridin-3-amine (12.83 mg, 0.103 mmol) in DCM (0.5 mL) was added DIEA (0.052 mL, 0.295 mmol) followed by Intermediate 80G (15 mg, 0.030 mmol) in THF (0.5 mL). The mixture was stirred at room temperature for 1 h. LCMS indicated the formation of the desired product. The reaction was quenched by addition of a small amount of MeOH/water/0.1% TFA (HPLC solvent) and concentrated. The residual was dissolved in DMSO and purified via preparative LC/MS (method D, 60-100% B over 20 min., then a 5-min hold at 100% B). Fractions containing the desired product were combined and dried via centrifugal evaporation to give Example 81 (7.8 mg, 0.013 mmol, 44.3% yield). $^1$H NMR (500 MHz, DMSO-$d_6$) δ 9.81 (br. s., 1H), 8.74 (s, 1H), 8.61 (d, J=1.7 Hz, 1H), 8.23 (br. s., 1H), 7.84 (s, 1H), 7.79-7.53 (m, 2H), 7.36 (s, 1H), 6.79 (d, J=8.8 Hz, 1H), 4.75-4.66 (m, 2H), 4.51-4.40 (m, 2H), 4.36 (dd, J=11.4, 7.3 Hz, 1H), 4.07 (s, 3H), 3.80 (s, 3H), 2.63 (s, 3H). LC-MS: method C, RT=2.49 min, MS (ESI) m/z: 596.25 (M+H)+. Analytical HPLC purity (method B): 100%.

Example 82

(2-(2-methoxy-7-methylquinoxalin-5-yl)-4-methyl-7,8-dihydro-[1,4]dioxino[2',3':3,4]benzo[1,2-d]thiazol-7-yl)methyl benzo[d]oxazol-5-ylcarbamate

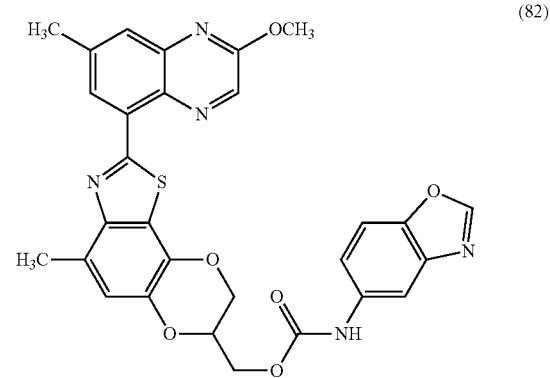 [SMILES: COc1cnc2c(-c3nc4c(C)cc5c(c4s3)OCC(COC(=O)Nc3ccc4ocnc4c3)O5)cc(C)cc2n1]

(82)

To a solution of benzo[d]oxazol-5-amine (9.95 mg, 0.074 mmol) in DCM (1 mL) was added a suspension of Intermediate 78A (10 mg, 0.021 mmol) in THF and toluene followed by DIEA (0.037 mL, 0.212 mmol). The mixture was stirred at room temperature overnight. The reaction was quenched by addition of a small amount of MeOH/water/0.1% TFA (HPLC solvent). Solvent was removed under vacuum. The residual was dissolved in DMSO and purified via preparative LC/MS (method D, 55-95% B over 20 min., then a 5-min hold at 100% B). Fractions containing the desired product were combined and dried via centrifugal evaporation to give Example 82 (5.0 mg, 7.46 μmol, 35.2% yield). LC-MS: method C, RT=2.53 min, MS (ESI) m/z: 570.20 (M+H)+. Analytical HPLC purity (method B): 85%.

Example 83

(R)-(4-fluoro-2-(7-(hydroxymethyl)-2-methoxyquinoxalin-5-yl)-7,8-dihydro-[1,4]dioxino [2',3':3,4]benzo[1,2-d]thiazol-7-yl)methyl pyridin-3-ylcarbamate

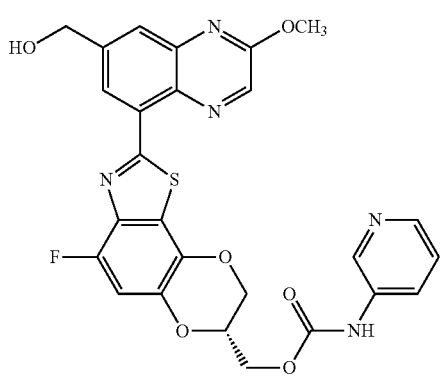

(83)

Intermediate 83A (S)-(2-(7-(((tert-butyldimethylsilyl)oxy)methyl)-2-methoxyquinoxalin-5-yl)-4-fluoro-7,8-dihydro-[1,4]dioxino[2',3':3,4]benzo[1,2-d]thiazol-7-yl)methanol

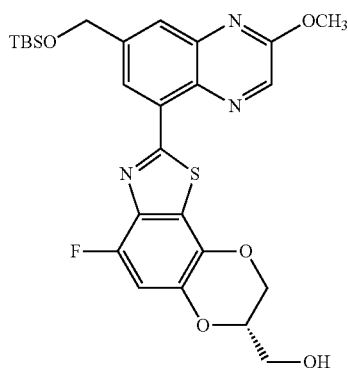

(83A)

To Intermediate I-27 (100 mg, 0.232 mmol), Intermediate 68G (84 mg, 0.232 mmol) and PdCl2(dppf)—CH2Cl2 adduct (9.49 mg, 0.012 mmol) was added toluene (3 mL) and EtOH (1 mL). The mixture was sonicated for 1 min, and flushed with argon. To this was added sodium carbonate (0.232 mL, 2M, 0.465 mmol). The reaction mixture was heated in a microwave reactor at 130° C. for 30 min. The crude product was purified with flash chromatography (0% to 100% EtOAc in hexanes over 20 min using a 40 g silica gel cartridge followed by 0-20% MeOH in DCM for 20 min). The desired fractions were combined and concentrated to yield (R)-(2-(7-(((tert-butyldimethylsilyl)oxy)methyl)-2-methoxyquinoxalin-5-yl)-4-fluoro-7,8-dihydro-[1,4]dioxino[2',3':3,4]benzo[1,2-d]thiazol-7-yl)methyl acetate as a yellow solid. LC-MS: method C, RT=3.28 min, MS (ESI) m/z: 586.3 (M+H)+. The sample was dissolved in THF (2 ml) and treated with NaOH (0.348 mL, 0.697 mmol). The mixture was stirred at room temperature for 1 h. The reaction mixture was diluted with EtOAc and NaHCO3, extracted with EtOAc. The combined organic layer was washed with brine and concentrated. The crude sample was purified with a 40 g ISCO column eluted with 0-100% EtOAc in hexanes for 20 min. The desired fraction was collected and concentrated to give Intermediate 83A (50 mg, 0.074 mmol, 31.7% yield). 1H NMR (400 MHz, chloroform-d) δ 8.73 (d, J=2.0 Hz, 1H), 8.56 (s, 1H), 8.07-7.88 (m, 1H), 6.85 (d, J=10.6 Hz, 1H), 5.03 (s, 2H), 4.49 (dd, J=11.1, 2.1 Hz, 1H), 4.42-4.37 (m, 1H), 4.33-4.26 (m, 2H), 4.15 (s, 3H), 4.00-3.90 (m, 2H), 1.03-1.01 (m, 9H), 0.20-0.18 (m, 6H), 19F NMR (376 MHz, chloroform-d) δ −130.18 (s, 1F). LC-MS: method C, RT=2.99 min, MS (ESI) m/z: 544.3 (M+H)+.

Intermediate 83B (R)-(2-(7-(((tert-butyldimethylsilyl)oxy)methyl)-2-methoxyquinoxalin-5-yl)-4-fluoro-7,8-dihydro-[1,4]dioxino[2',3':3,4]benzo[1,2-d]thiazol-7-yl)methyl carbonochloridate

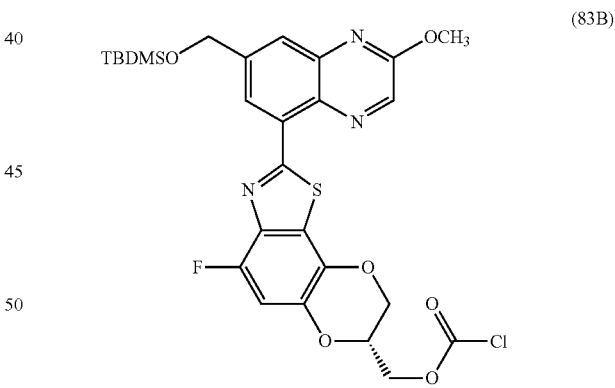

(83B)

To a solution of Intermediate 83A (45 mg, 0.083 mmol) and DIEA (0.072 ml, 0.414 mmol) in THF (1 mL) was added to 15% phosgene in toluene (0.175 ml, 0.248 mmol). The reaction mixture was stirred at room temperature for 2 h. The mixture was concentrated and dried under vacuum to give Intermediate 83B as a yellow solid. The sample was used for next step without further purification. LC-MS: method C, RT=3.43 min, MS (ESI) m/z: 606 (M+H)+.

Example 83

To a solution of Intermediate 83B (10 mg, 0.016 mmol) in THF (0.5 mL) was added pyridin-3-amine (4.66 mg, 0.049 mmol) and DIEA (0.029 mL, 0.165 mmol) in DCM (1 mL). The mixture was stirred at room temperature for 1 h. TBAF (0.165 mL, 0.165 mmol) was added, and the mixture and stirred at room temperature overnight. LCMS indicated a completion of the reaction. The reaction was quenched by addition of a small amount of MeOH/water/0.1% TFA (HPLC solvent). Solvent was removed under vacuum. The residual was dissolved in DMSO and purified via preparative LC/MS (method C, 15-55% B over 20 min., then a 5-min hold at 100% B). Fractions containing the desired product were combined and dried via centrifugal evaporation to give Example 83 (4.0 mg, 6.84 μmol, 41.5% yield). LC-MS: method C, RT=1.56 min, MS (ESI) m/z: 550.10 (M+H)+. Analytical HPLC purity (method B): 94%.

Example 84

(R)-(2-(7-(difluoromethyl)-2-methoxyquinoxalin-5-yl)-4-methyl-7,8-dihydro-[1,4]dioxin o[2',3':3,4]benzo[1,2-d]thiazol-7-yl)methyl (2-methylpyridin-4-yl)carbamate

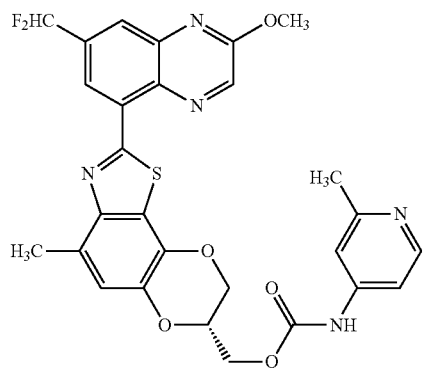

(84)

Intermediate 84A: 5-bromo-7-(difluoromethyl)-2-methoxyquinoxaline

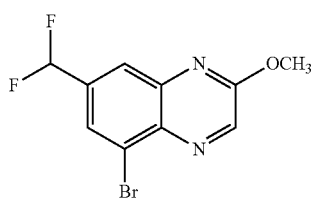

(84A)

To a solution of Intermediate I-27A (100 mg, 0.374 mmol) in DCM (3 mL) was added DAST (0.495 mL, 3.74 mmol) at −78° C. The reaction mixture was slowly warmed up to room temperature and continued stirring overnight. The mixture was diluted with EtOAc and water, extracted with EtOAc. The combined organic layer was washed with NaHCO₃, brine, dried with MgSO₄ and concentrated. The crude was purified with a 12 g ISCO column eluted with 0-100% EtOAc in hexanes for 15 min. The desired fraction was collected and concentrated to give Intermediate 84A (65 mg, 0.225 mmol, 60.1% yield) as a white solid, 1H NMR (400 MHz, chloroform-d) δ 8.62 (s, 1H), 7.99 (dd, J=11.8, 1.4 Hz, 2H), 7.00-6.57 (m, 1H), 4.14 (s, 3H). ¹⁹F NMR (376 MHz, chloroform-d) 6-111.58 (s, 1F). LC-MS: method C, RT=2.08 min, MS (ESI) m/z: 289 and 291 (M+H)+.

Intermediate 84B 7-(difluoromethyl)-2-methoxy-5-(4,4,5,5-tetramethyl-1,3,2-dioxaborolan-2-yl)quinoxalin e

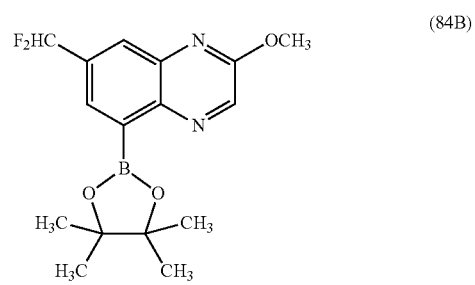 [SMILES: COc1cnc2c(B3OC(C)(C)C(C)(C)O3)cc(C(F)F)cc2n1]

(84B)

A mixture of Intermediate 84A (65 mg, 0.225 mmol), bis(pinacolato)diboron (86 mg, 0.337 mmol), potassium acetate (55.2 mg, 0.562 mmol) in dioxane (5 mL) was degassed with argon for 5 min, then PdCl₂(dppf)—CH₂Cl₂ adduct (9.18 mg, 0.011 mmol) was added. The mixture was sealed and heated in microwave reactor at 130° C. for 30 min. The mixture was diluted with EtOAc/water, insoluble material was removed by filtration. The filtrate was extracted with EtOAc, washed with brine, dried over sodium sulfate. After evaporation of solvent, the crude product was dissolved in a small amount of toluene and charged to a 12 g silica gel cartridge which was eluted with 5% EtOAc in hexanes for 3 min., then a 18 min gradient from 5% to 75% EtOAc in hexanes. The desired fractions were combined, concentrated and lyophilized to give Intermediate 84B (40 mg, 0.119 mmol, 52.9% yield) as a pale solid. LC-MS: method C, RT=1.94 min, MS (ESI) m/z: 255 (M+H)+ (boronic acid).

Intermediate 84C (S)-(2-(7-(difluoromethyl)-2-methoxyquinoxalin-5-yl)-4-methyl-7,8-dihydro-[1,4]dioxino [2',3':3,4]benzo[1,2-d]thiazol-7-yl)methanol

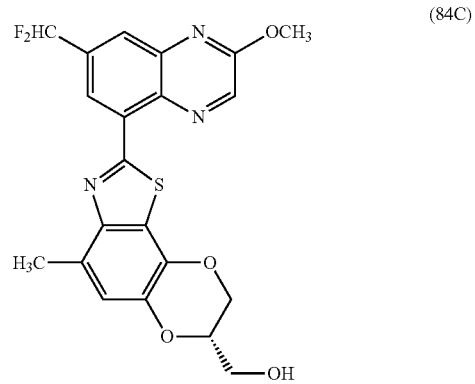 [SMILES: COc1cnc2c(-c3nc4c(C)cc5c(c4s3)OC[C@H](CO)O5)cc(C(F)F)cc2n1]

(84C)

To Intermediate 84B (40 mg, 0.119 mmol), Intermediate I-26 (37.3 mg, 0.119 mmol) and PdCl₂(dppf)—CH₂Cl₂ adduct (4.86 mg, 5.95 μmol) was added toluene (4.5 mL) and EtOH (1.5 mL). The mixture was sonicated for 1 min, and flushed with argon. To this was added sodium carbonate (0.119 mL, 2M, 0.238 mmol). The reaction mixture was heated in a microwave reactor at 130° C. for 40 min. The crude reaction mixture was directly loaded onto an 40 g ISCO column which was eluted with 0-100% EtOAc in hexanes for 20 min. The desired fractions were combined and concentrated to yield (R)-(2-(7-(difluoromethyl)-2-methoxyquinoxalin-5-yl)-4-methyl-7,8-dihydro-[1,4]dioxino[2',3':3,4]benzo[1,2-d]thiazol-7-yl)methyl acetate as a yellow solid. LC-MS: method C, RT=2.60 min, MS (ESI) m/z: 488(M+H)⁺. The intermediate was redissolved in THF (2 ml) and treated with sodium methoxide (0.054 mL, 4.37M, 0.238 mmol). The mixture was stirred at room temperature for 1 h. LCMS indicated a completion of the reaction. The mixture was diluted with EtOAc and water, extracted with EtOAc, the combined organic layer was washed with water and brine, dried with MgSO₄ and concentrated. The sample was purified with a 40 g ISCO column eluted with 0-100% EtOAc in hexane for 20 min. The desired fraction was collected and concentrated to give Intermediate 84C (45 mg, 0.081 mmol, 67.9% yield). ¹H NMR (400 MHz, chloroform-d) δ 8.82 (d, J=1.8 Hz, 1H), 8.69 (s, 1H), 7.78 (dd, J=1.9, 1.0 Hz, 1H), 7.94-7.48 (m, 1H), 6.94 (d, J=0.7 Hz, 1H), 4.52-4.23 (m, 5H), 2.77 (d, J=0.9 Hz, 3H), 2.70 (s, 3H), 2.15 (s, 3H). ¹⁹F NMR (376 MHz, chloroform-d) δ −111.57 (s, 2F). LC-MS: method C, RT=2.25 min, MS (ESI) m/z: 446 (M+H)⁺.

Intermediate 84D (R)-(2-(7-(difluoromethyl)-2-methoxyquinoxalin-5-yl)-4-methyl-7,8-dihydro-[1,4]dioxino[2',3':3,4]benzo[1,2-d]thiazol-7-yl)methyl carbonochloridate

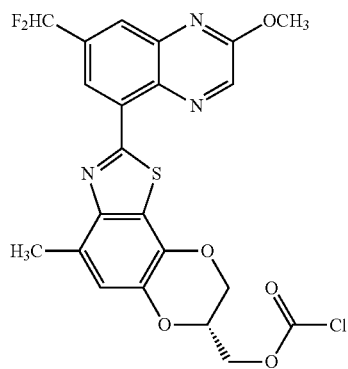

(84D)

To a solution of Intermediate 84C (40 mg, 0.090 mmol) in THF (2 ml) was added to 15% phosgene in toluene (0.317 ml, 0.449 mmol) and the mixture was stirred at room temperature overnight. The mixture was concentrated and dried under vacuum to give Intermediate 84D as a yellow solid. The sample was used for next step without further purification. LC-MS: method C, RT=2.56 min, MS (ESI) m/z: 508 (M+H)⁺.

Example 84

To a solution of 2-methylpyridin-4-amine (7.45 mg, 0.069 mmol) in DCM (0.5 mL) was added DIEA (0.034 mL, 0.197 mmol) followed by Intermediate 84D (10 mg, 0.020 mmol) in THF (0.5 mL). The mixture was stirred at room temperature for 1 h. The reaction was quenched by addition of a small amount of MeOH/water/0.1% TFA (HPLC solvent) and concentrated. The residual was dissolved in DMSO and purified via preparative LC/MS (method C, 40-80% B over 20 min., then a 5-min hold at 100% B). Fractions containing the desired product were combined and dried via centrifugal evaporation to give Example 84 (1.2 mg, 1.946 μmol, 9.88% yield). ¹H NMR (500 MHz, DMSO-d₆) δ 8.92 (s, 1H), 8.86 (d, J=1.7 Hz, 1H), 8.46 (d, J=6.3 Hz, 1H), 8.19 (s, 1H), 7.62 (br. s., 1H), 7.59 (br. s., 1H), 7.53-7.28 (m, 1H), 7.02-6.99 (m, 1H), 4.69 (d, J=3.9 Hz, 1H), 4.61 (dd, J=11.4, 2.3 Hz, 1H), 4.58-4.46 (m, 2H), 4.30 (dd, J=11.4, 7.3 Hz, 1H), 4.12 (s, 3H), 2.69 (s, 3H), 2.55 (s, 3H). LC-MS: method C, RT=2.14 min, MS (ESI) m/z: 580.15 (M+H)⁺. Analytical HPLC purity (method B): 94%.

Example 85

(R)-(4-fluoro-2-(7-(hydroxymethyl)-2-methoxyquinoxalin-5-yl)-7,8-dihydro-[1,4]dioxino[2',3':3,4]benzo[1,2-d]thiazol-7-yl)methyl (2-methylpyridin-4-yl)carbamate

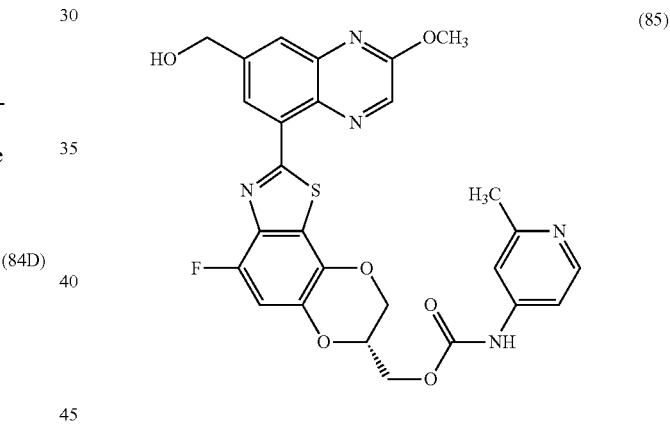

(85)

To a solution of Intermediate 83B (10 mg, 0.016 mmol) in THF (1 mL) was added 2-methylpyridin-4-amine (5.35 mg, 0.049 mmol) and DIEA (0.029 mL, 0.165 mmol) in DCM (1 mL). The mixture was stirred at room temperature for 2 h. TBAF (0.165 mL, 0.165 mmol) was added and the mixture was stirred at room temperature overnight. The reaction was quenched by addition of a small amount of MeOH/water/0.1% TFA (HPLC solvent). Solvent was removed under vacuum. The residual was dissolved in DMSO and purified via preparative LC/MS (method D, 30-70% B over 20 min., then a 5-min hold at 100% B). Fractions containing the desired product were combined and dried via centrifugal evaporation to give Example 85 (0.8 mg, 1.420 μmol, 8.60% yield). ¹H NMR (500 MHz, DMSO-d₆) δ 8.81 (s, 1H), 8.75 (d, J=1.7 Hz, 1H), 8.35 (d, J=5.8 Hz, 1H), 7.95 (s, 1H), 7.50-7.39 (m, 2H), 7.15 (d, J=11.0 Hz, 1H), 5.65 (br. s., 1H), 4.83 (d, J=3.6 Hz, 2H), 4.71 (br. s., 1H), 4.64 (dd, J=11.6, 2.2 Hz, 1H), 4.57-4.44 (m, 2H), 4.31 (dd, J=11.6, 7.2 Hz, 1H), 4.10 (s, 3H), 2.46 (s, 3H). LC-MS: method C, RT=1.48 min, MS (ESI) m/z: 564.10 (M+H)⁺. Analytical HPLC purity (method B): 100%.

Example 86

(2-(2-methoxy-7-vinylquinoxalin-5-yl)-4-methyl-7,8-dihydro-[1,4]dioxino[2',3':3,4]benzo[1,2-d]thiazol-7-yl)methyl (6-methoxypyridin-3-yl)carbamate

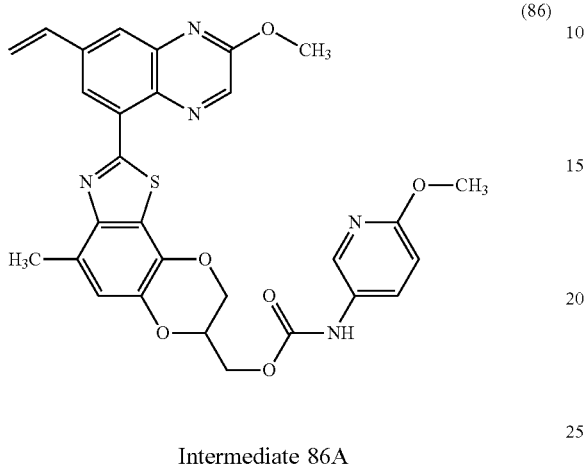

(86)

Intermediate 86A (2-(7-chloro-2-methoxyquinoxalin-5-yl)-4-methyl-7,8-dihydro-[1,4]dioxino[2',3':3,4]benzo[1,2-d]thiazol-7-yl)methanol

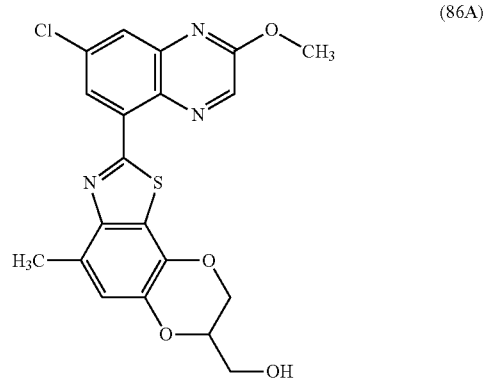

(86A)

To Intermediate I-28 (500 mg, 2.097 mmol), Intermediate I-71 (729 mg, 2.307 mmol) and PdCl$_2$(dppf)—CH$_2$Cl$_2$ (86 mg, 0.105 mmol) were added toluene (12.00 mL) and EtOH (4 mL). The mixture was sonicated for 1 min, and flushed with N$_2$ for 5 minutes, and sodium carbonate (1.722 mL, 3.44 mmol) was added. The reaction mixture was heated at 100° C. for 30 min. After cooling to room temperature, the precipitated solid was filtered, washed with water and a small amount of EtOAc, and dried in vacuo to give the product as a yellow solid. The filtrate was extracted with EtOAc, dried over Na$_2$SO$_4$, and concentrated on a rotary evaporator. The residue was purified by flash chromatography (40 g column, 0-100% EtOAc/Hexane gradient) to give additional product. Combined products gave Intermediate 86A (812 mg, 1.89 mmol, 90%). $^1$H NMR (400 MHz, DMSO-d$_6$) δ 8.78 (s, 1H), 8.58 (d, J=2.4 Hz, 1H), 8.00 (d, J=2.4 Hz, 1H), 6.95 (d, J=0.9 Hz, 1H), 5.12 (s, 1H), 4.52 (dd, J=11.2, 2.2 Hz, 1H), 4.33-4.24 (m, 1H), 4.18 (dd, J=11.3, 7.6 Hz, 1H), 4.08 (s, 3H), 3.70 (dt, J=9.8, 5.0 Hz, 2H), 2.64 (s, 3H); LC-MS: method J, RT=1.24 min, MS (ESI) m/z: 430.0 (M+H)$^+$.

Intermediate 86B (2-(2-methoxy-7-vinylquinoxalin-5-yl)-4-methyl-7,8-dihydro-[1,4]dioxino[2',3':3,4]benzo[1,2-d]thiazol-7-yl)methanol

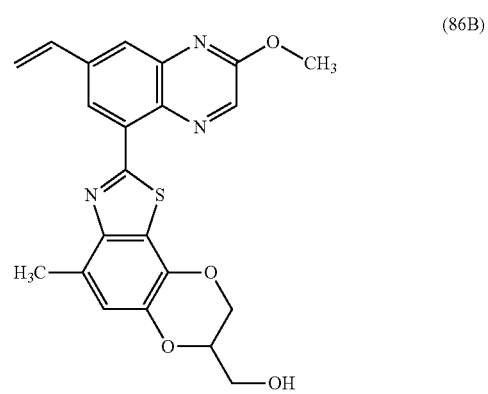 [SMILES: C=Cc1cc(-c2nc3c(C)cc4c(c3s2)OCC(CO)O4)c2ncc(OC)nc2c1]

(86B)

To a vial with a stirring bar was added Intermediate 86A (300 mg, 0.698 mmol), potassium trifluoro(vinyl)borate (187 mg, 1.396 mmol), cesium carbonate (682 mg, 2.094 mmol), (S)-2,2'-bis(diphenylphosphino)-1,1'-binaphthalene (43.5 mg, 0.070 mmol), diacetoxypalladium (7.83 mg, 0.035 mmol) and DMF (10 mL). After degassing with bubbling N$_2$ for 10 minutes, the vial was sealed and was stirred at room temperature for 10 minutes, then heated at 120° C. for 2 hours. After cooling to room temperature, the reaction mixture was diluted by adding 50 mL of EtOAc and was washed with water and brine, and dried over Na$_2$SO$_4$. Filtration and concentration in vacuo gave crude product Intermediate 86B (363 mg, 123%) that was used in the next step without purification. LC-MS: method J, RT=0.92 min, MS (ESI) m/z: 422.2 (M+H)$^+$.

Intermediate 86C (2-(2-methoxy-7-vinylquinoxalin-5-yl)-4-methyl-7,8-dihydro-[1,4]dioxino[2',3':3,4]benzo[1,2-d]thiazol-7-yl)methyl carbonochloridate

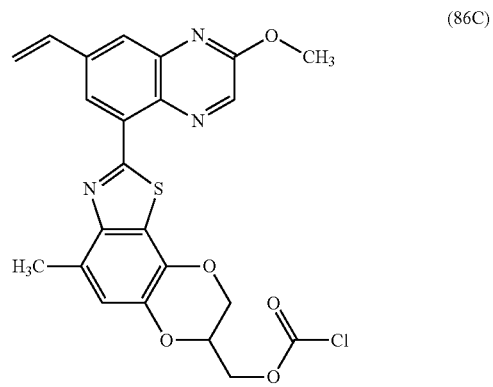 [SMILES: C=Cc1cc(-c2nc3c(C)cc4c(c3s2)OCC(COC(=O)Cl)O4)c2ncc(OC)nc2c1]

(86C)

Intermediate 86B (0.294 g, 0.698 mmol) was suspended in anhydrous THF (20 mL). Phosgene (1.836 mL, 3.49 mmol) in toluene was added. The mixture was stirred for 1 hour at room temperature and another 5 eq. of phosgene (1.836 mL, 3.49 mmol) was added. The mixture was stirred at room temperature overnight. On the next day, the solvent was removed and the residue was dried in vacuo for 2 h. The crude product was used in the next step without purification. LC-MS: method J, RT=1.26 min, MS (ESI) m/z: 484.0 (M+H)$^+$.

Example 86

Intermediate 86C (65 mg, 0.134 mmol) was dissolved in DCM (mL) and mixed with 6-methoxypyridin-3-amine (66.7 mg, 0.537 mmol). DIEA (0.117 mL, 0.672 mmol) was added, and the mixture was stirred at room temperature for 4 h. The solvent was removed on a rotary evaporator and the residue was purified by flash chromatography (12 g column, 0-50% EtOAc/Hexane) to afford Example 86 (51 mg, 0.089 mmol, 66.4% yield) as a yellow solid. $^1$H NMR (500 MHz, DMSO-$d_6$) δ 9.81 (br s, 1H), 8.82 (d, J=1.9 Hz, 1H), 8.76 (s, 1H), 8.24 (br s, 1H), 8.07 (d, J=1.9 Hz, 1H), 7.86-7.71 (m, 1H), 7.08 (dd, J=17.6, 11.0 Hz, 1H), 6.99 (d, J=0.5 Hz, 1H), 6.79 (d, J=8.8 Hz, 1H), 6.20 (d, J=17.6 Hz, 1H), 5.58 (d, J=11.0 Hz, 1H), 4.69-4.56 (m, 2H), 4.50-4.37 (m, 2H), 4.27 (dd, J=11.3, 7.2 Hz, 1H), 4.09 (s, 3H), 3.80 (s, 3H), 2.69 (s, 3H); LC-MS: method L, RT=2.636 min, MS (ESI) m/z: 572.2 (M+H)$^+$.

Example 87

(2-(7-(hydroxymethyl)-2-methoxyquinoxalin-5-yl)-4-methyl-7,8-dihydro-[1,4]dioxino[2',3':3,4]benzo[1,2-d]thiazol-7-yl)methyl (6-methoxypyridin-3-yl)carbamate

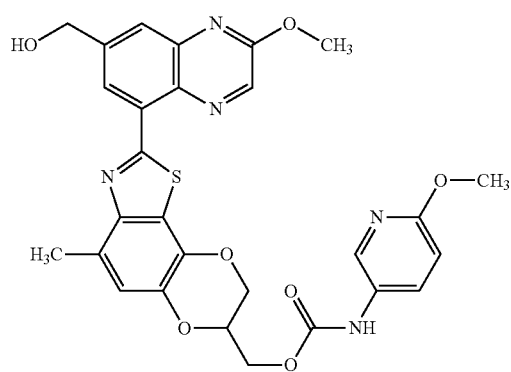

(87)

Intermediate 87A (2-(7-formyl-2-methoxyquinoxalin-5-yl)-4-methyl-7,8-dihydro-[1,4]dioxino[2',3':3,4]benzo[1,2-d]thiazol-7-yl)methyl (6-methoxypyridin-3-yl)carbamate

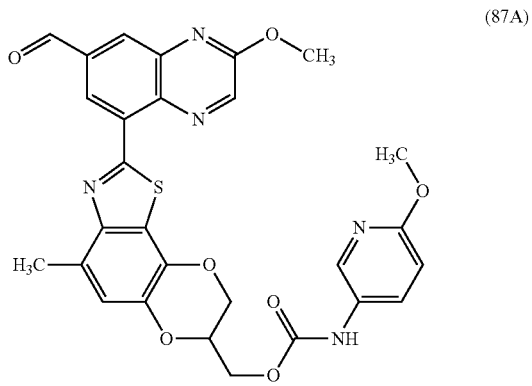 [SMILES: COc1ccc(NC(=O)OCC2COc3c(cc(C)c4nc(-c5cc(C=O)cc6nc(OC)cnc56)sc34)O2)cn1]

(87A)

To a solution of Example 86 (50 mg, 0.087 mmol) and osmium tetroxide (0.011 mL, 1.749 μmol) in THF (3 mL) and water (1 mL) was added sodium periodate (56.1 mg, 0.262 mmol). The mixture was stirred at room temperature for 6 hours. 20 mL of water and 30 mL of EtOAc were added, the aqueous layer was extracted with ethyl acetate (20 mL), and the combined organic phases were washed with saturated aqueous sodium thiosulfate solution and brine, dried over sodium sulfate, filtered and concentrated to give Intermediate 87A as a yellow solid (52.7 mg, 0.092 mmol, 105% yield). LC-MS: method J, RT=1.04 min, MS (ESI) m/z: 574.1 (M+H)$^+$.

Example 87

Intermediate 87A (25 mg, 0.044 mmol) was dissolved in THF (1 mL)/MeOH (1 mL) and treated with NaBH$_4$ (3.30 mg, 0.087 mmol) at room temperature for 30 minutes. 2 mL of saturated NH$_4$Cl (aq.) was added to quench the reaction. The reaction mixture containing the product was purified via preparative LC/MS with condition D, and dried via centrifugal evaporation to yield Example 87 (7.1 mg, 0.012 mmol, 26.9% yield). $^1$H NMR (500 MHz, DMSO-$d_6$) δ 9.81 (br s, 1H), 8.78 (s, 1H), 8.73 (d, J=1.7 Hz, 1H), 8.23 (br s, 1H), 7.93-7.90 (m, 1H), 7.78 (d, J=7.4 Hz, 1H), 6.99 (d, J=0.8 Hz, 1H), 6.79 (d, J=9.1 Hz, 1H), 5.62 (t, J=5.8 Hz, 1H), 4.83 (d, J=5.5 Hz, 2H), 4.66-4.56 (m, 2H), 4.47-4.37 (m, 2H), 4.27 (dd, J=11.3, 7.2 Hz, 1H), 4.09 (s, 3H), 3.80 (s, 3H), 2.68 (s, 3H); LC-MS: method L, RT=1.92 min, MS (ESI) m/z: 576.0 (M+H)$^+$.

Example 88

(2-(7-(1-hydroxyethyl)-2-methoxyquinoxalin-5-yl)-4-methyl-7,8-dihydro-[1,4]dioxino[2',3':3,4]benzo[1,2-d]thiazol-7-yl)methyl (6-methoxypyridin-3-yl)carbamate (88)

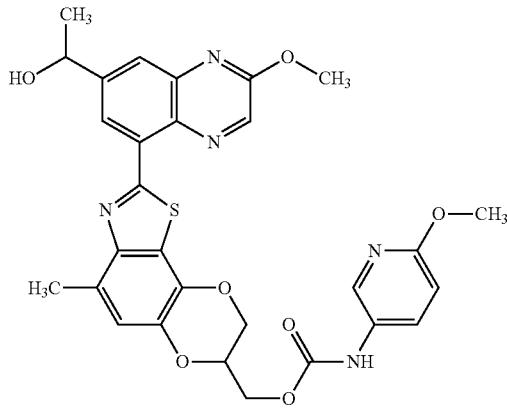

Intermediate 87A (25 mg, 0.044 mmol) was dissolved in anhydrous THF (2 mL) under $N_2$ and cooled to −78° C. Methylmagnesium bromide (3.0 M in ether) (0.058 mL, 0.174 mmol) was added dropwise. The reaction mixture was slowly warmed to room temperature. HCl (1 mL, 1M aq.) was added to quench the reaction, followed by EtOAc and water. The aqueous layer was extracted with EtOAc. The combined organic phases were washed with saturated aqueous NaCl, passed through $Na_2SO_4$ and concentrated on a rotary evaporator. The residue was purified via preparative LC/MS with condition D, and dried via centrifugal evaporation to yield Example 88 (5.3 mg, 19.6% yield). $^1$H NMR (500 MHz, DMSO-$d_6$) δ 9.81 (br s, 1H), 8.79 (d, J=1.7 Hz, 1H), 8.78 (s, 1H), 8.23 (br s, 1H), 7.93 (d, J=1.7 Hz, 1H), 7.78 (d, J=8.3 Hz, 1H), 6.99 (d, J=0.6 Hz, 1H), 6.79 (d, J=9.1 Hz, 1H), 5.69-5.50 (m, 1H), 5.06 (q, J=6.5 Hz, 1H), 4.67-4.54 (m, 2H), 4.49-4.35 (m, 2H), 4.27 (dd, J=11.3, 7.2 Hz, 1H), 4.09 (s, 3H), 3.80 (s, 3H), 2.69 (s, 3H), 1.49 (d, J=6.6 Hz, 3H); LC-MS: method L, RT=2.019 min, MS (ESI) m/z: 590.2 (M+H)$^+$.

Example 89

(2-(2-methoxy-7-vinylquinoxalin-5-yl)-4-methyl-7,8-dihydro-[1,4]dioxino[2',3':3,4]benzo[1,2-d]thiazol-7-yl)methyl pyridin-3-ylcarbamate (89)

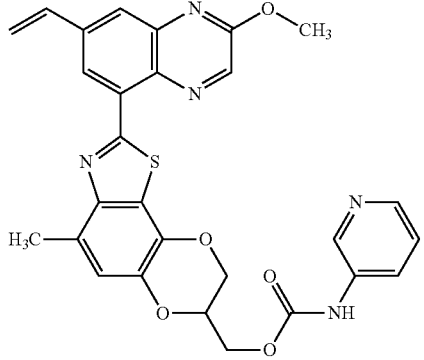

Example 89 was made by following the procedure in Example 86. $^1$H NMR (500 MHz, DMSO-$d_6$) δ 10.28 (br s, 1H), 8.81 (s, 1H), 8.74 (s, 2H), 8.32 (br s, 1H), 8.07-8.00 (m, 2H), 7.50 (br s, 1H), 7.07 (dd, J=17.5, 10.9 Hz, 1H), 6.98 (s, 1H), 6.19 (d, J=17.6 Hz, 1H), 5.57 (d, J=10.7 Hz, 1H), 4.65 (br s, 1H), 4.60 (d, J=11.6 Hz, 1H), 4.53-4.41 (m, 2H), 4.32-4.25 (m, 1H), 4.09 (s, 3H), 2.68 (s, 3H)); LC-MS: method L, RT=2.248 min, MS (ESI) m/z: 542.2 (M+H)$^+$.

Example 90

(2-(7-(hydroxymethyl)-2-methoxyquinoxalin-5-yl)-4-methyl-7,8-dihydro-[1,4]dioxino[2',3':3,4]benzo[1,2-d]thiazol-7-yl)methyl pyridin-3-ylcarbamate (90)

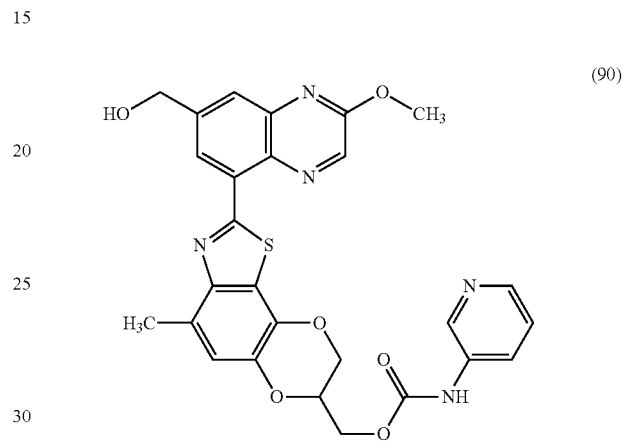

Example 90 was made from Example 89 by following procedure in Example 87. $^1$H NMR (500 MHz, DMSO-$d_6$) δ 10.13 (br s, 1H), 8.79 (s, 1H), 8.73 (d, J=1.7 Hz, 1H), 8.65 (d, J=2.2 Hz, 1H), 8.23 (dd, J=4.7, 1.4 Hz, 1H), 7.94-7.88 (m, 2H), 7.34 (dd, J=8.3, 4.7 Hz, 1H), 7.00 (s, 1H), 5.66 (br s, 1H), 4.83 (br s, 2H), 4.65 (tt, J=6.3, 3.2 Hz, 1H), 4.60 (dd, J=11.3, 2.2 Hz, 1H), 4.52-4.39 (m, 2H), 4.28 (dd, J=11.4, 7.3 Hz, 1H), 4.09 (s, 3H), 2.68 (s, 3H); LC-MS: method K, RT=1.847 min, MS (ESI) m/z: 546.2 (M+H)$^+$.

Example 91

(R)-(2-(7-cyano-2-methoxyquinoxalin-5-yl)-4-methyl-7,8-dihydro-[1,4]dioxino[2',3':3,4]benzo[1,2-d]thiazol-7-yl)methyl (6-methylpyridin-3-yl)carbamate (91)

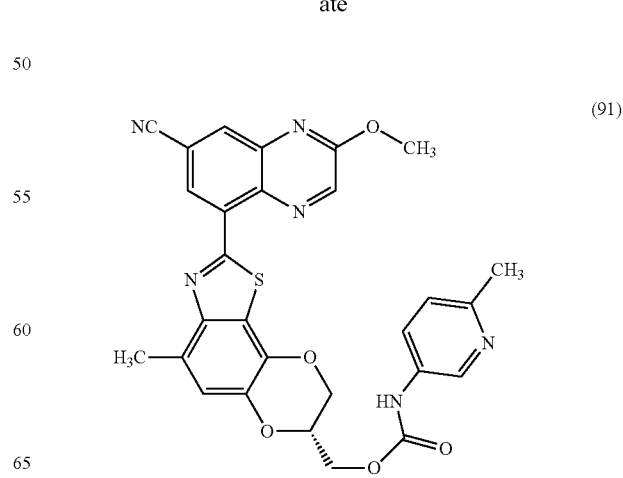

Intermediate 91A (R)-(2-(7-cyano-2-methoxyquinoxalin-5-yl)-4-methyl-7,8-dihydro-[1,4]dioxino[2',3':3,4]benzo[1,2-d]thiazol-7-yl)methyl (6-methylpyridin-3-yl)carbamate

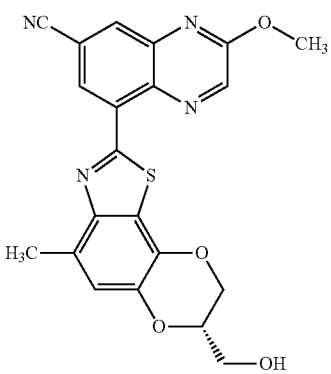
(91A)

Intermediate I-26 (123 mg, 0.393 mmol) was mixed with Intermediate I-38 (102 mg, 0.328 mmol) in 1,4-dioxane (2 mL). $Na_2CO_3$ (2 mL, 4.00 mmol) was added, followed by $PdCl_2(dppf)$—$CH_2Cl_2$ adduct (13.39 mg, 0.016 mmol). The mixture was stirred at 120° C. on microwave for 60 minutes. The reaction mixture was cooled to room temperature, and diluted by adding 20 mL of EtOAc and 10 mL of water. After shaking and separation, the aqueous layer was extracted with EtOAc (10 mL×2). The combined organic phases were washed with brine, dried over $Na_2SO_4$, filtered and concentrated to give crude product. The crude product was purified by flash chromatography (24 g silica gel column, 0-100% EtOAc EtOAc/Hexane) to give Intermediate 91A. LC-MS: method J, RT=1.08 min, MS (ESI) m/z: 421.1 (M+H)$^+$.

Intermediate 91B ((R)-(2-(7-cyano-2-methoxyquinoxalin-5-yl)-4-methyl-7,8-dihydro-[1,4]dioxino[2',3':3,4]benzo[1,2-d]thiazol-7-yl)methyl carbonochloridate

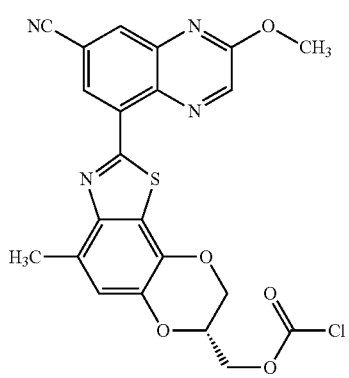
(91B)

Intermediate 91B was made from Intermediate 91A by following the procedure in Intermediate 86C. LC-MS: method H, RT=1.08 min, MS (ESI) m/z: 483.1 (M+H)$^+$.

Example 91

Example 91 was made from Intermediate 91B by following procedure described in Example 86. $^1$H NMR (500 MHz, DMSO-$d_6$) δ 10.28 (br s, 1H), 8.88 (s, 1H), 8.78 (s, 1H), 8.64 (br s, 1H), 8.44 (s, 1H), 7.98 (d, J=7.7 Hz, 1H), 7.46 (d, J=8.5 Hz, 1H), 6.98 (s, 1H), 4.72-4.40 (m, 4H), 4.28 (dd, J=11.6, 7.4 Hz, 1H), 4.10 (s, 3H), 2.65 (s, 3H), 2.54 (s, 3H); LC-MS: method L, RT=1.90 min, MS (ESI) m/z: 555.20 (M+H)$^+$.

Examples 92 to 97 were prepared according to the general preparation process of Example 91.

Example 92

(R)-(2-(7-cyano-2-methoxyquinoxalin-5-yl)-4-methyl-7,8-dihydro-[1,4]dioxino[2',3':3,4]benzo[1,2-d]thiazol-7-yl)methyl (2-methylpyridin-4-yl)carbamate

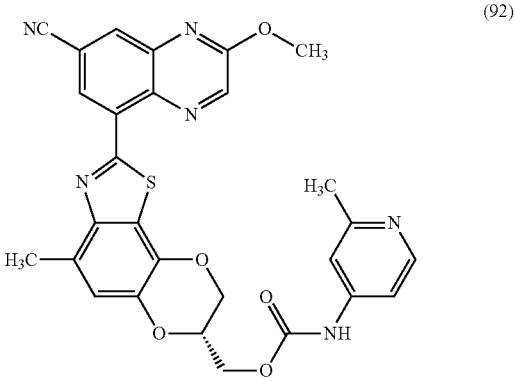 [SMILES: COc1cnc2c(-c3nc4c(C)cc5c(c4s3)OC[C@H](COC(=O)Nc3ccnc(C)c3)O5)cc(C#N)cc2n1]
(92)

$^1$H NMR (500 MHz, DMSO-$d_6$) δ 11.17 (br s, 1H), 8.92 (s, 1H), 8.83 (s, 1H), 8.55-8.44 (m, 2H), 7.75-7.60 (m, 2H), 7.00 (s, 1H), 4.71 (br s, 1H), 4.66-4.48 (m, 3H), 4.38-4.27 (m, 1H), 4.12 (s, 3H), 2.67 (s, 3H), 2.59 (s, 3H); LC-MS: method L, RT=1.94 min, MS (ESI) m/z: 555.20 (M+H)$^+$.

Example 93

(R)-(2-(7-cyano-2-methoxyquinoxalin-5-yl)-4-methyl-7,8-dihydro-[1,4]dioxino[2',3':3,4]benzo[1,2-d]thiazol-7-yl)methyl pyridin-3-ylcarbamate

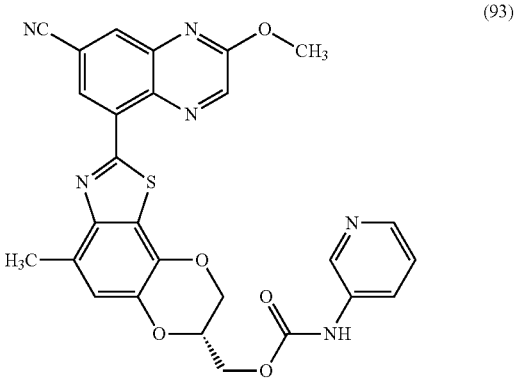 [SMILES: COc1cnc2c(-c3nc4c(C)cc5c(c4s3)OC[C@H](COC(=O)Nc3cccnc3)O5)cc(C#N)cc2n1]
(93)

¹H NMR (500 MHz, chloroform-d) δ 9.04 (d, J=1.9 Hz, 1H), 8.69 (s, 1H), 8.59 (s, 1H), 8.36 (d, J=4.4 Hz, 1H), 8.22 (d, J=1.7 Hz, 1H), 8.07 (br s, 1H), 7.35 (dd, J=8.3, 5.0 Hz, 1H), 7.14 (br s, 1H), 6.96 (s, 1H), 4.62-4.56 (m, 1H), 4.55-4.48 (m, 3H), 4.29 (dd, J=11.3, 6.9 Hz, 1H), 4.17 (s, 3H), 2.76 (s, 3H)); LC-MS: method L, RT=1.87 min, MS (ESI) m/z: 541.20 (M+H)⁺.

Example 94

(R)-(2-(7-cyano-2-methoxyquinoxalin-5-yl)-4-methyl-7,8-dihydro-[1,4]dioxino[2',3':3,4]benzo[1,2-d]thiazol-7-yl)methyl (6-methoxypyridin-3-yl)carbamate

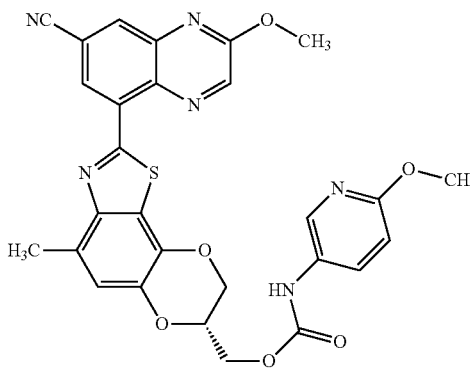

(94)

¹H NMR (500 MHz, chloroform-d) δ 9.02 (d, J=1.7 Hz, 1H), 8.69 (s, 1H), 8.21 (d, J=1.7 Hz, 1H), 8.10 (br s, 1H), 7.79 (br s, 1H), 6.95 (s, 1H), 6.75 (d, J=8.8 Hz, 1H), 6.70 (br s, 1H), 4.60-4.54 (m, 1H), 4.50 (dd, J=4.8, 2.1 Hz, 3H), 4.33-4.23 (m, 1H), 4.17 (s, 3H), 3.92 (s, 3H), 2.76 (s, 3H); LC-MS: method L, RT=2.347 min, MS (ESI) m/z: 571.20 (M+H)⁺.

Example 95

(2-(7-chloro-2-methoxyquinoxalin-5-yl)-4-methyl-7,8-dihydro-[1,4]dioxino[2',3':3,4]benzo[1,2-d]thiazol-7-yl)methyl pyridin-3-ylcarbamate

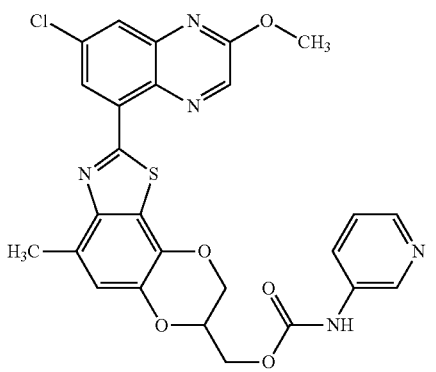

(95)

¹H NMR (400 MHz, chloroform-d) δ 8.74 (d, J=2.4 Hz, 1H), 8.51 (s, 1H), 8.45 (d, J=2.4 Hz, 1H), 8.28 (dd, J=4.6, 1.3 Hz, 1H), 7.91 (br s, 1H), 7.85 (d, J=2.4 Hz, 1H), 7.25-7.21 (m, 1H), 6.87 (d, J=0.9 Hz, 1H), 6.70 (br s, 1H), 4.45 (d, J=4.6 Hz, 4H), 4.21 (dd, J=11.3, 6.7 Hz, 1H), 4.06 (s, 3H), 2.69 (d, J=0.7 Hz, 3H); LC-MS: method H, RT=1.32 min, MS (ESI) m/z: 550.1 (M+H)⁺.

Example 96

(2-(7-chloro-2-methoxyquinoxalin-5-yl)-4-methyl-7,8-dihydro-[1,4]dioxino[2',3':3,4]benzo[1,2-d]thiazol-7-yl)methyl (6-fluoropyridin-3-yl)carbamate

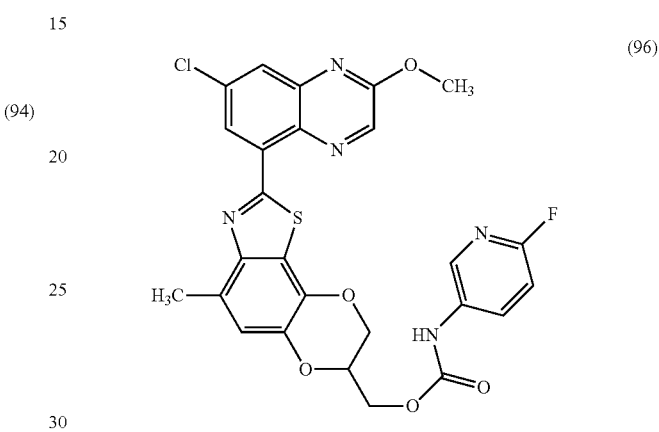

(96)

¹H NMR (500 MHz, DMSO-d₆) δ 10.15 (br s, 1H), 8.82 (s, 1H), 8.63 (s, 1H), 8.29 (br s, 1H), 8.04 (br s, 2H), 7.15 (d, J=8.5 Hz, 1H), 7.00 (s, 1H), 4.75-4.55 (m, 2H), 4.53-4.35 (m, 2H), 4.33-4.21 (m, 1H), 4.09 (s, 3H), 2.67 (s, 3H); LC-MS: method L, RT=2.805 min, MS (ESI) m/z: 568.1 (M+H)⁺.

Example 97

(2-(7-chloro-2-methoxyquinoxalin-5-yl)-4-methyl-7,8-dihydro-[1,4]dioxino[2',3':3,4]benzo[1,2-d]thiazol-7-yl)methyl (6-methylpyridin-3-yl)carbamate

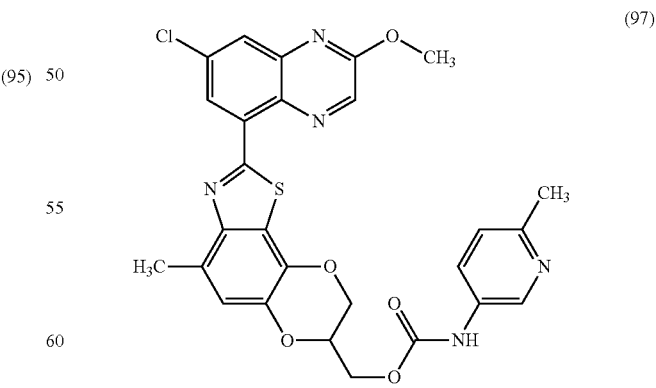

(97)

¹H NMR (500 MHz, DMSO-d₆) δ 10.29 (br s, 1H), 8.73 (s, 1H), 8.65 (br s, 1H), 8.53 (s, 1H), 7.99 (d, J=8.0 Hz, 1H), 7.96 (br s, 1H), 7.46 (d, J=8.5 Hz, 1H), 6.96 (s, 1H), 4.65 (br s, 1H), 4.60 (d, J=11.3 Hz, 1H), 4.54-4.47 (m, 1H), 4.47-4.40

(m, 2H), 4.27 (dd, J=10.7, 7.7 Hz, 2H), 4.06 (s, 4H), 2.63 (s, 3H); LC-MS: method L, RT=2.382 min, MS (ESI) m/z: 564.2 (M+H)⁺.

Example 98

(R)-(2-(7-(hydroxymethyl)-2-methoxyquinoxalin-5-yl)-4-methyl-7,8-dihydro-[1,4]dioxin o[2',3':3,4]benzo[1,2-d]thiazol-7-yl)methyl (6-methoxypyridin-3-yl)carbamate

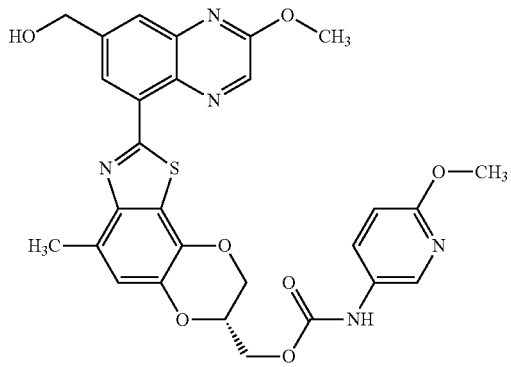

(98)

Intermediate 98A (R)-(2-chloro-4-methyl-7,8-dihydro-[1,4]dioxino[2',3':3,4]benzo[1,2-d]thiazol-7-yl)methy 1lcarbonochloridate

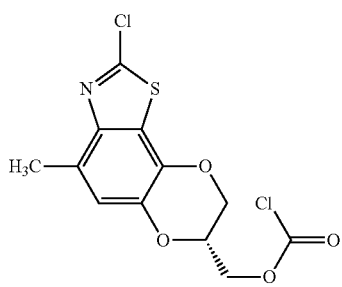

(98A)

Intermediate I-26 (34 mg, 0.125 mmol) was suspended in THF (2 mL) and was treated with phosgene (0.413 mL, 0.626 mmol) at room temperature for 5 h. The solvent was removed on a rotary evaporator and the residue was dried in vacuo for 10 minutes. The crude product was used in the next step without further purification. LC-MS: method H, RT=1.12 min, MS (ESI) m/z: 334.0 (M+H)⁺.

Intermediate 98B (R)-(2-chloro-4-methyl-7,8-dihydro-[1,4]dioxino[2',3':3,4]benzo[1,2-d]thiazol-7-yl)methy 1 (6-methoxypyridin-3-yl)carbamate

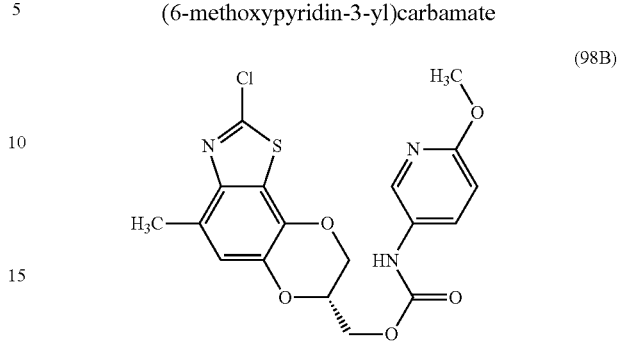

(98B)

Intermediate 98A (41.8 mg, 0.125 mmol) was dissolved in anhydrous DCM (2 mL) and was mixed with 6-methoxypyridin-3-amine (62.1 mg, 0.500 mmol), followed by DIEA (0.109 mL, 0.625 mmol). The mixture was stirred at room temperature overnight. On the next day, solvent was removed on a rotary evaporator and the residue was purified by flash chromatography (24 g column, 0-100% EtOAc/hexane gradient) to give Intermediate 98B (40 mg, 0.095 mmol, 76% yield) as a yellow solid. LC-MS: method H, RT=1.03 min, MS (ESI) m/z: 422.1 (M+H)⁺.

Example 98

Example 98 was made from Intermediate 98B and Intermediate I-35 by following the procedure in Intermediate 86A. ¹H NMR (500 MHz, DMSO-d₆) δ 9.81 (br s, 1H), 8.77 (s, 1H), 8.72 (d, J=1.7 Hz, 1H), 8.23 (br s, 1H), 7.91 (s, 1H), 7.78 (d, J=8.3 Hz, 1H), 6.99 (s, 1H), 6.79 (d, J=8.8 Hz, 1H), 5.62 (t, J=5.8 Hz, 1H), 4.82 (d, J=5.8 Hz, 2H), 4.65-4.56 (m, 2H), 4.47-4.37 (m, 2H), 4.27 (dd, J=11.3, 7.2 Hz, 1H), 4.09 (s, 3H), 3.80 (s, 3H), 2.67 (s, 3H); LC-MS: method L, RT=1.89 min, MS (ESI) m/z: 576.20 (M+H)⁺.

Examples 99 to 101 were synthesized according to the general procedure described for Example 98.

Example 99

(R)-(2-(7-(hydroxymethyl)-2-methoxyquinoxalin-5-yl)-4-methyl-7,8-dihydro-[1,4]dioxin o[2',3':3,4]benzo[1,2-d]thiazol-7-yl)methyl (2-methylpyridin-4-yl)carbamate

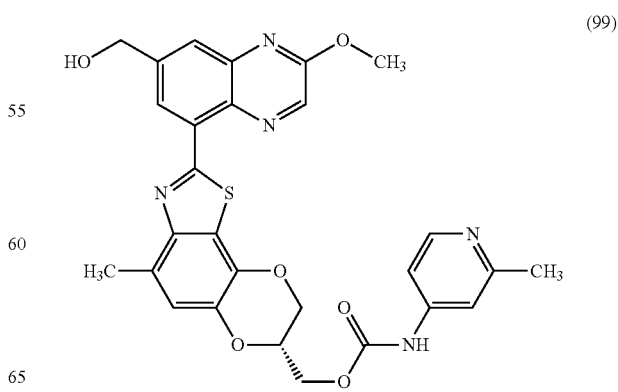

(99)

¹H NMR (500 MHz, DMSO-d₆) δ 10.52 (br s, 1H), 8.79 (s, 1H), 8.74 (s, 1H), 8.34 (d, J=5.5 Hz, 1H), 7.93 (s, 1H), 7.51-7.33 (m, 2H), 7.00 (s, 1H), 5.64 (br s, 1H), 4.84 (d, J=3.0 Hz, 2H), 4.67 (br s, 1H), 4.61 (d, J=11.0 Hz, 1H), 4.57-4.40 (m, 2H), 4.30 (dd, J=11.3, 7.2 Hz, 1H), 4.10 (s, 3H), 2.69 (s, 3H), 2.46 (s, 3H); LC-MS: method L, RT=1.545 min, MS (ESI) m/z: 560.20 (M+H)⁺.

Example 100

(R)-(2-(7-(hydroxymethyl)-2-methoxyquinoxalin-5-yl)-4-methyl-7,8-dihydro-[1,4]dioxino[2',3':3,4]benzo[1,2-d]thiazol-7-yl)methyl (6-methylpyridin-3-yl)carbamate

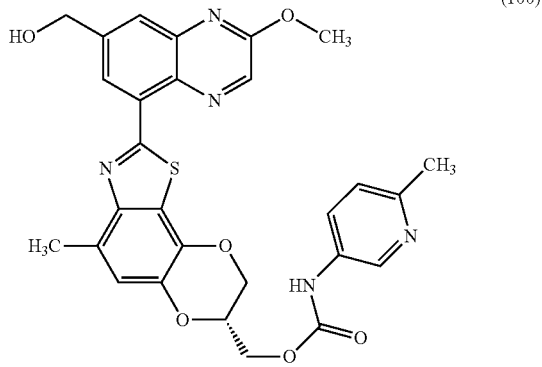

(100)

¹H NMR (500 MHz, DMSO-d₆) δ 10.00 (s., 1H), 8.75 (s., 1H), 8.71 (s., 1H), 8.53 (s., 1H), 7.90 (s., 1H), 7.80 (s., 1H), 7.22 (d, J=8.0 Hz, 1H), 6.97 (s., 1H), 5.62 (s., 1H), 4.82 (s., 2H), 4.68-4.55 (m, 2H), 4.50-4.34 (m, 2H), 4.28 (d, J=9.6 Hz, 1H), 4.08 (s., 3H), 2.67 (s., 3H), 2.41 (s., 3H); LC-MS: method L, RT=1.507 min, MS (ESI) m/z: 560.20 (M+H)⁺.

Example 101

(R)-(2-(7-(hydroxymethyl)-2-methoxyquinoxalin-5-yl)-4-methyl-7,8-dihydro-[1,4]dioxino[2',3':3,4]benzo[1,2-d]thiazol-7-yl)methyl pyridin-3-ylcarbamate

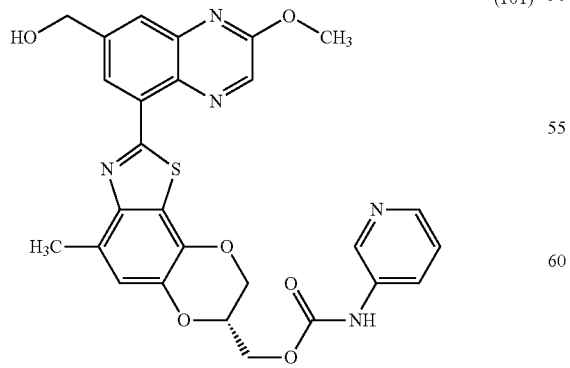

(101)

¹H NMR (500 MHz, DMSO-d₆) δ 10.12 (br s, 1H), 8.77 (s, 1H), 8.72 (s, 1H), 8.66 (br s, 1H), 8.24 (d, J=4.4 Hz, 1H), 8.01-7.86 (m, 2H), 7.36 (dd, J=8.3, 4.7 Hz, 1H), 6.98 (s, 1H), 5.62 (br s, 1H), 4.82 (s, 2H), 4.70-4.55 (m, 2H), 4.52-4.39 (m, 2H), 4.28 (dd, J=11.4, 7.3 Hz, 1H), 4.09 (s, 3H), 2.67 (s, 3H); LC-MS: method L, RT=1.485 min, MS (ESI) m/z: 546.20 (M+H)⁺.

Example 102

(R)-(2-(2-methoxy-7-methylquinoxalin-5-yl)-7,8-dihydro-[1,4]dioxino[2',3':3,4]benzo[1,2-d]thiazol-7-yl)methyl (6-methylpyridin-3-yl)carbamate

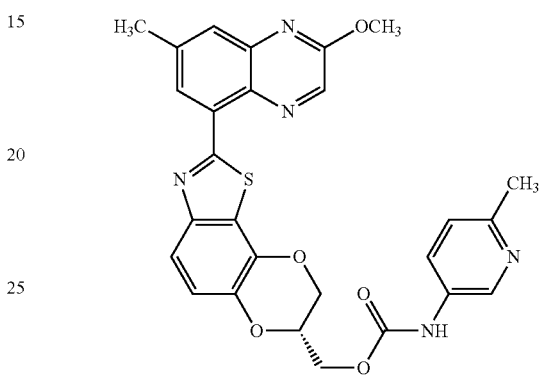

Intermediate 102A (S)-(2-(2-methoxy-7-methylquinoxalin-5-yl)-7,8-dihydro-[1,4]dioxino[2',3':3,4]benzo[1,2-d]thiazol-7-yl)methanol

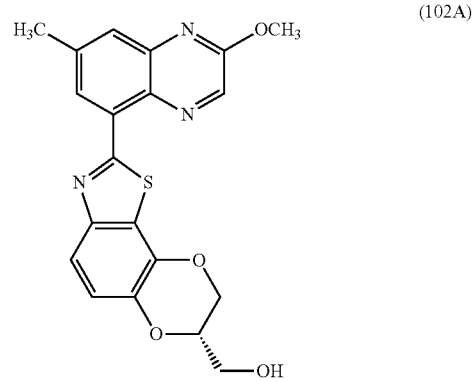 [SMILES: COc1cnc2c(-c3nc4ccc5c(c4s3)OC[C@H](CO)O5)cc(C)cc2n1]

(102A)

Pd(OAc)₂ (10.45 mg, 0.047 mmol), 2-(di-tert-butylphosphino)biphenyl (27.8 mg, 0.093 mmol) and sodium formate (39.6 mg, 0.582 mmol) were sealed in microwave vial. MeOH (5 mL) was added to the mixture and degassed with argon for 3 min. The mixture was stirred at room temperature for 10 min, followed by addition of Intermediate 25K (50 mg, 0.116 mmol) in THF (1 mL). The mixture was heated at 135° C. for 1.5 h. After evaporation of solvent, the crude reaction mixture was loaded to a 40 g ISCO column eluted with EtOAc in DCM from 0-100% for 20 min. The desired fraction was collected and concentrated to yield Intermediate 102A (24 mg, 0.061 mmol, 52.2% yield). $^1$H NMR (400 MHz, chloroform-d) δ 8.63 (d, J=2.0 Hz, 1H), 8.56 (s, 1H), 7.76 (dd, J=1.8, 0.9 Hz, 1H), 7.68 (d, J=8.8 Hz, 1H), 7.12 (d, J=8.8 Hz, 1H), 4.52 (dd, J=11.0, 2.0 Hz, 1H), 4.40 (dd, J=4.7, 1.7 Hz, 1H), 4.36-4.30 (m, 1H), 4.13 (s, 3H), 4.04-3.91 (m, 2H), 2.65 (s, 3H). LC-MS: method C, RT=2.45 min, MS (ESI) m/z: 396.1 (M+H)$^+$.

Intermediate 102B: (6-methylpyridin-3-yl)carbamic chloride

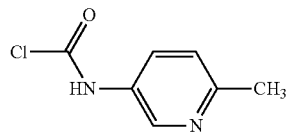

To a solution of phosgene (15% in toluene, 1.630 ml, 2.312 mmol) in CH$_2$Cl$_2$ (2 ml) was added 6-methylpyridin-3-amine (50 mg, 0.462 mmol), followed by addition of DIEA (0.089 ml, 0.509 mmol) dropwise. The reaction mixture was stirred at room temperature for 1 h, at which time LCMS indicated a completion of reaction. Solvent was completely removed and the residue was dried under vacuum for 1 h to give Intermediate 102B. It was used for next step without purification. LC-MS: method C, RT=0.45 min, MS (ESI) m/z: 167.1 (M+H)$^+$.

Example 102

To a solution of Intermediate 102A (24 mg, 0.061 mmol) in CH$_2$Cl$_2$ (1 ml) was added Intermediate 102B (31.1 mg, 0.182 mmol) in CH$_2$Cl$_2$ (2 ml), followed by addition of DIEA (0.053 ml, 0.303 mmol) dropwise. The reaction mixture was stirred at room temperature for 30 min, at which time LCMS indicated a completion of reaction. Solvent was removed. The crude was dissolved in DMSO and purified via preparative LC/MS (method A, 10-100% B over 10 minutes, then a 2-minute hold at 100% B). Fractions containing the desired product were combined and dried via centrifugal evaporation to yield Example 102 (11.5 mg, 0.021 mmol, 34.0% yield) as a solid. $^1$H NMR (400 MHz, THF) δ 9.04 (br. s., 1H), 8.73 (d, J=2.0 Hz, 1H), 8.58 (s, 1H), 8.43 (br. s., 1H), 7.88 (d, J=7.0 Hz, 1H), 7.76 (dd, J=1.9, 1.0 Hz, 1H), 7.59 (d, J=8.6 Hz, 1H), 7.12-7.03 (m, 2H), 4.60-4.54 (m, 2H), 4.46 (d, J=4.6 Hz, 2H), 4.28 (dd, J=11.7, 7.9 Hz, 1H), 4.11 (s, 3H), 2.64 (s, 3H), 2.41 (s, 3H). LC-MS: method C, RT=0.45 min, MS (ESI) m/z: 530.1 (M+H)$^+$. Analytical HPLC purity (method A): 95%.

Example 103

(R)-(2-(2-methoxy-7-methylquinoxalin-5-yl)-7,8-dihydro-[1,4]dioxino [2',3':3,4]benzo[1,2-d]thiazol-7-yl)methyl (2-methylpyrimidin-5-yl)carbamate

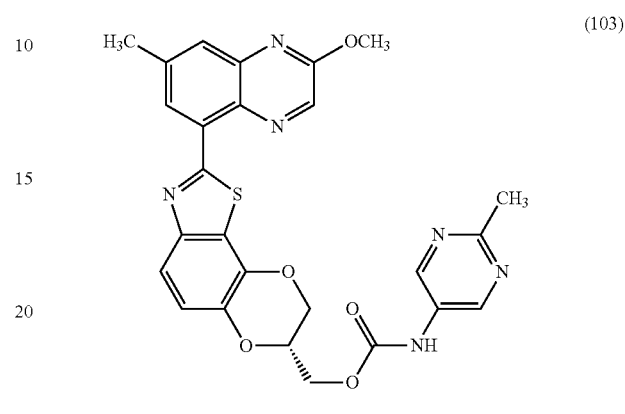

Intermediate 103A (R)-(2-(2-methoxy-7-methylquinoxalin-5-yl)-7,8-dihydro-[1,4]dioxino[2',3':3,4]benzo[1,2-d]thiazol-7-yl)methyl carbonochloridate

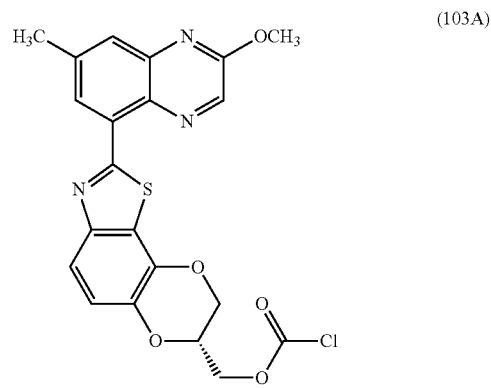 [SMILES: COc1cnc2c(-c3nc4ccc5c(c4s3)OC[C@H](COC(=O)Cl)O5)cc(C)cc2n1]

To the solution of Intermediate 102A (170 mg, 0.353 mmol) in THF (3 ml) was added 15% phosgene in toluene (0.995 ml, 1.410 mmol), followed by DIEA (0.185 ml, 1.058 mmol). The reaction mixture was stirred at room temperature for 30 min, at which time LCMS indicated a completion of reaction. Solvent and excess of phosgene was completely removed under vacuum to give Intermediate 103A which was used for the next step without purification. LC-MS: method C, RT=2.37 min, MS (ESI) m/z: 458.1 (M+H)$^+$.

Example 103

Intermediate 103A (170 mg) in DCM (2 mL) was added to 2-methylpyrimidin-5-amine (46.2 mg, 0.423 mmol) in DCM (1 mL), followed by addition of pyridine (0.14 mL, 1.76 mmol). The reaction mixture was stirred at room temperature for 1h, at which time LCMS indicated a completion of reaction. The reaction mixture was diluted with EtOAc, washed with 0.5 N HCl. The organic layer was washed with brine, dried over sodium sulfate and concentrated. The crude was dissolved in DMSO and purified via preparative LC/MS (method A, 50-100% B over 10 minutes, then a 2-minute hold at 100% B). Fractions containing the desired product were combined and dried via centrifugal evaporation to yield Example 103 (80 mg, 43% yield) as a solid. $^1$H NMR (400 MHz, chloroform-d) δ 8.78 (s, 2H), 8.63 (d, J=1.5 Hz, 1H), 8.56 (s, 1H), 7.77 (d, J=0.9 Hz, 1H), 7.69 (d, J=8.6 Hz, 1H), 7.13 (d, J=8.8 Hz, 1H), 4.64-4.49 (m, 4H), 4.32 (dd, J=11.4, 6.6 Hz, 1H), 4.14 (s, 3H), 2.73 (s, 3H), 2.66 (s, 3H). LC-MS: method C, RT=2.37 min, MS (ESI) m/z: 531.1 (M+H)$^+$. Analytical HPLC purity: 95%.

Example 104

(R)-(2-(2-methoxy-7-methylquinoxalin-5-yl)-7,8-dihydro-[1,4]dioxino[2',3':3,4]benzo[1,2-d]thiazol-7-yl)methyl (6-methoxypyridin-3-yl)carbamate

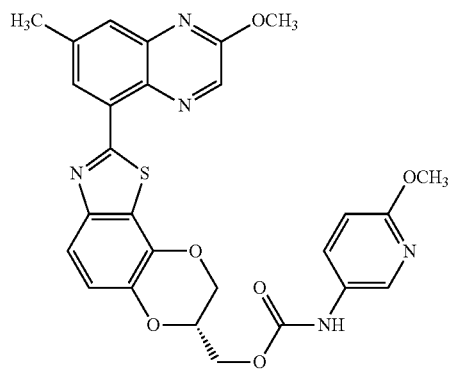

(104)

A solution of Intermediate 103A (12 mg, 0.026 mmol) in DCM (1.5 mL) was added to 6-methoxypyridin-3-amine (9.76 mg, 0.079 mmol) in DCM (0.5 mL). The reaction mixture was stirred at room temperature for 1 h, at which time LCMS indicated a completion of reaction. The crude was dissolved in DMSO and purified via preparative LC/MS (method C, 50-100% B over 20 minutes, then a 5-minute hold at 100% B). Fractions containing the desired product were combined and dried via centrifugal evaporation to yield Example 104 (3.9 mg, 27.3% yield). $^1$H NMR (500 MHz, DMSO-d$_6$) δ 9.78 (br. s., 1H), 8.68 (s, 1H), 8.52 (s, 1H), 8.18 (br. s., 1H), 7.81-7.72 (m, 2H), 7.63 (d, J=8.5 Hz, 1H), 7.14 (d, J=8.5 Hz, 1H), 6.78 (d, J=8.9 Hz, 1H), 4.66-4.55 (m, 2H), 4.48-4.35 (m, 2H), 4.28 (br. s., 1H), 4.05 (s, 3H), 3.72 (s, 3H), 2.59 (s, 3H). LC-MS: method C, RT=2.46 min, MS (ESI) m/z: 546.1 (M+H)$^+$. Analytical IPLC purity (method B): 100%.

Example 105

(R)-(2-(2-methoxy-7-methylquinoxalin-5-yl)-7,8-dihydro-[1,4]dioxino[2',3':3,4]benzo[1,2-d]thiazol-7-yl)methyl (6-cyanopyridin-3-yl)carbamate

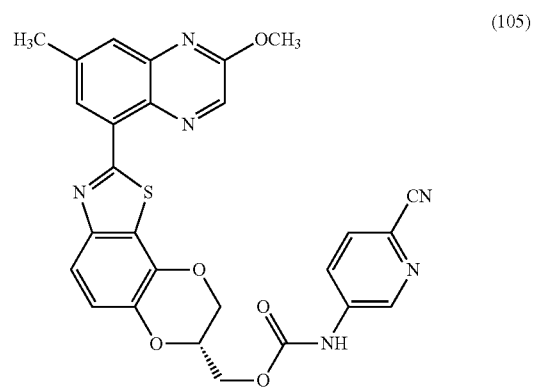

(105)

Intermediate 105A: (6-cyanopyridin-3-yl)carbamic chloride

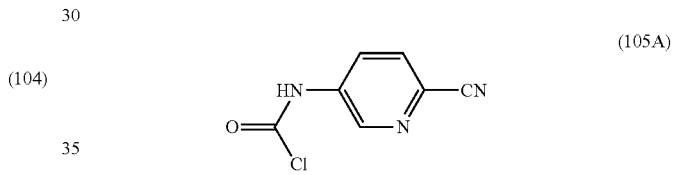

(105A)

To a solution of phosgene (15% in toluene, 2.96 mL, 4.20 mmol) in DCM (2 ml) was added 5-aminopicolinonitrile (100 mg, 0.839 mmol), followed by addition of DIEA (0.161 mL, 0.923 mmol) dropwise. The reaction mixture was stirred at room temperature for 30 min. Solvent was removed under vacuum to yield Intermediate 105A which was used for next step without further purification. LC-MS: method C, RT=1.18 min, MS (ESI) m/z: 178 (M+H)$^+$.

Example 105

To a solution of Intermediate 102A (22 mg, 0.056 mmol) in CH$_2$Cl$_2$ (1 ml) was added Intermediate 105A (30.3 mg, 0.167 mmol) in CH$_2$Cl$_2$ (2 ml), followed by addition of DIEA (0.032 ml, 0.184 mmol) dropwise. The reaction mixture was stirred at room temperature for 30 min, at which time LCMS indicated a completion of reaction. Solvent was removed. The crude was dissolved in DMSO and purified via preparative LC/MS (method A, 10-100% B over 10 minutes, then a 2-minute hold at 100% B). Fractions containing the desired product were combined and dried via centrifugal evaporation to yield Example 105 (15 mg, 0.026 mmol, 47.4% yield) as a solid. $^1$H NMR (400 MHz, chloroform-d) δ 8.62 (d, J=1.5 Hz, 1H), 8.58 (d, J=2.4 Hz, 1H), 8.56 (s, 1H), 8.19 (d, J=7.0 Hz, 1H), 7.78 (d, J=0.9 Hz, 1H), 7.72-7.68 (m, 2H), 7.13 (d, J=8.8 Hz, 1H), 7.08 (s, 1H), 4.64-4.52 (m, 4H), 4.33 (dd, J=11.4, 6.6 Hz, 1H), 4.14 (s, 3H), 2.66 (s, 3H). LC-MS: method C, RT=1.18 min, MS (ESI) m/z: 541.0 (M+H)$^+$. Analytical HPLC purity (method A): 96%.

Example 106

(R)-(2-(2-methoxy-7-methylquinoxalin-5-yl)-7,8-dihydro-[1,4]dioxino[2',3':3,4]benzo [1,2-d]thiazol-7-yl)methyl (2-oxo-2,3-dihydrobenzo[d]oxazol-6-yl) carbamate

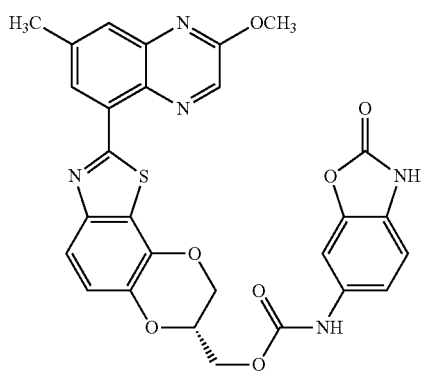

(106)

A solution of Intermediate 103A (12 mg, 0.026 mmol) in DCM (1.5 mL) was added to a suspension of 6-aminobenzo[d]oxazol-2(3H)-one (11.80 mg, 0.079 mmol) in DCM (0.5 mL). The reaction mixture was stirred at room temperature for 1 h, at which time LCMS indicated a completion of reaction. After evaporation of solvent, the crude was dissolved in DMSO and purified via preparative LC/MS (method C, 45-100% B over 20 minutes, then a 5-minute hold at 100% B). Fractions containing the desired product were combined and dried via centrifugal evaporation to yield Example 106 (1.6 mg, 10% yield). $^1$H NMR (500 MHz, DMSO-$d_6$) δ 9.86 (br. s., 1H), 8.68 (br. s., 1H), 8.51 (br. s., 1H), 7.77 (br. s., 1H), 7.62 (d, J=8.5 Hz, 1H), 7.45 (br. s., 1H), 7.14 (d, J=8.5 Hz, 2H), 7.00 (d, J=8.5 Hz, 1H), 4.68-4.56 (m, 2H), 4.47-4.36 (m, 2H), 4.28 (dd, J=11.6, 7.6 Hz, 1H), 4.05 (s, 3H), 2.59 (s, 3H). LC-MS: method C, RT=2.28 min, MS (ESI) m/z: 572.15 (M+H)$^+$. Analytical HPLC purity (method B): 93%.

Example 107

(R)-(2-(2-methoxy-7-methylquinoxalin-5-yl)-7,8-dihydro-[1,4]dioxino[2',3':3,4]benzo [1,2-d]thiazol-7-yl)methyl 1H-pyrrolo[2,3-b]pyridin-5-ylcarbamate

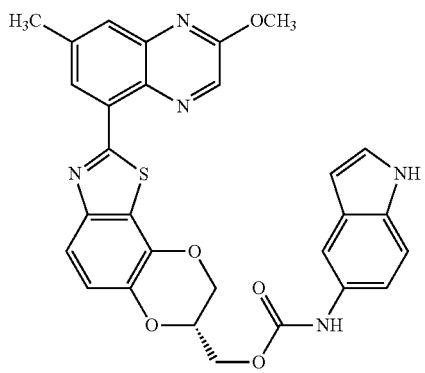

(107)

A solution of Intermediate 103A (12 mg, 0.026 mmol) in DCM (1.5 mL) was added to a suspension of 1H-pyrrolo[2,3-b]pyridin-5-amine (10.47 mg, 0.079 mmol) in DCM (0.5 mL) and DIEA (0.046 mL, 0.262 mmol). The reaction mixture was stirred at room temperature for 1 h, at which time LCMS indicated a completion of reaction. After evaporation of solvent, the crude was dissolved in DMSO and purified via preparative LC/MS (method C, 45-100% B over 20 minutes, then a 5-minute hold at 100% B). Fractions containing the desired product were combined and dried via centrifugal evaporation to yield Example 107 (4.5 mg, 29.1% yield). $^1$H NMR (500 MHz, DMSO-$d_6$) δ 11.52 (br. s., 1H), 9.79 (br. s., 1H), 8.59 (s, 1H), 8.44 (s, 1H), 8.23 (br. s., 1H), 8.06 (br. s., 1H), 7.70 (s, 1H), 7.59 (d, J=8.8 Hz, 1H), 7.42 (br. s., 1H), 7.13 (d, J=8.5 Hz, 1H), 6.41 (br. s., 1H), 4.69-4.51 (m, 2H), 4.48-4.36 (m, 2H), 4.28 (br. s., 1H), 4.01 (s, 3H), 2.55 (s, 3H). LC-MS: method C, RT=2.30 min, MS (ESI) m/z: 555.15 (M+H)$^+$. Analytical HPLC purity (method B): 94%.

Example 108

(R)-(2-(2-methoxy-7-methylquinoxalin-5-yl)-7,8-dihydro-[1,4]dioxino[2',3':3,4]benzo[1,2-d]thiazol-7-yl)methyl pyridin-3-ylcarbamate

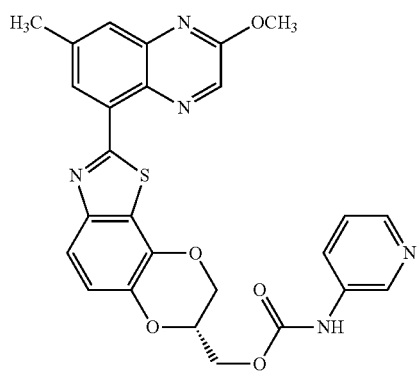

(108)

A solution of Intermediate 103A (12 mg, 0.026 mmol) in THF (1 mL) was added to a solution of pyridin-3-amine (4.76 mg, 0.051 mmol) in DCM (0.5 mL) and DIEA (0.044 ml, 0.253 mmol). The reaction mixture was stirred at room temperature for 1 h, at which time LCMS indicated a completion of reaction. After evaporation of solvent, the crude was dissolved in DMSO and purified via preparative LC/MS (method C, 45-100% B over 20 minutes, then a 5-minute hold at 100% B). Fractions containing the desired product were combined and dried via centrifugal evaporation to yield Example 108 (1.9 mg, 14.1% yield). $^1$H NMR (500 MHz, DMSO-$d_6$) δ 10.09 (br. s., 1H), 8.74 (s, 1H), 8.64 (br. s., 1H), 8.57 (s, 1H), 8.23 (d, J=3.7 Hz, 1H), 7.90 (d, J=7.0 Hz, 1H), 7.82 (s, 1H), 7.65 (d, J=8.8 Hz, 1H), 7.34 (dd, J=8.1, 4.7 Hz, 1H), 7.16 (d, J=8.5 Hz, 1H), 4.64 (d, J=11.0 Hz, 2H), 4.54-4.40 (m, 2H), 4.31 (dd, J=11.3, 7.3 Hz, 1H), 4.07 (s, 3H), 2.62 (s, 3H). LC-MS: method C, RT=2.28 min, MS (ESI) m/z: 517.10 (M+H)$^+$. Analytical HPLC purity (method B): 97%.

Example 109

(R)-(2-(2-methoxy-7-methylquinoxalin-5-yl)-7,8-dihydro-[1,4]dioxino[2',3':3,4]benzo[1,2-d]thiazol-7-yl)methyl (6-bromopyridin-3-yl)carbamate

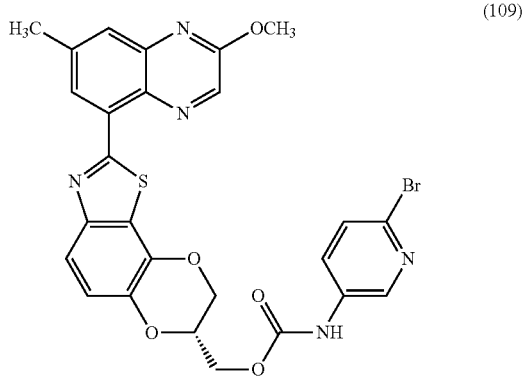 [SMILES: COc1cnc2c(-c3nc4ccc5c(c4s3)OC[C@H](COC(=O)Nc3ccc(C#N)nc3)O5)cc(C)cc2n1]

(109)

Intermediate 109A: (6-bromopyridin-3-yl)carbamic chloride

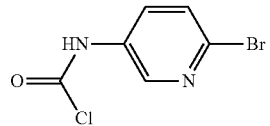

(109A)

To a solution of phosgene (15% in toluene, 2.0 ml, 2.89 mmol) in CH$_2$Cl$_2$ (2 ml) was added 6-bromopyridin-3-amine (100 mg, 0.578 mmol) in CH$_2$Cl$_2$ (2 mL). The reaction mixture was stirred at room temperature for 30 min, at which time LCMS indicated a completion of the reaction. Solvent was removed under vacuum to yield Intermediate 109A which was used for next step without further purification. LC-MS: method C, RT=1.91 min, MS (ESI) m/z: 230 and 232.10 (methyl carbamate M+H)$^+$.

Example 109

To a solution of Intermediate 102A (36 mg, 0.091 mmol) in DCM (0.5 mL) was added Intermediate 109A (42.9 mg, 0.137 mmol) in DCM (0.5 mL), followed by addition of DIEA (0.159 mL, 0.910 mmol) dropwise. The reaction mixture was stirred at room temperature for 30 min, at which time LCMS indicated a completion of reaction. Solvent was removed under vacuum. The crude was loaded to a 12 g ISCO column which was eluted with 0-100% EtOAc in dichloromethane. The fractions containing the desired product were combined and concentrated to yield a solid product (50 mg, 0.084 mmol, 92% yield). A small amount (5 mg) was further purified via preparative LC/MS (method C, 45-100% B over 20 minutes, then a 5-minute hold at 100% B). Fractions containing the desired product were combined and dried via centrifugal evaporation to yield Example 109 (3.0 mg). $^1$H NMR (400 MHz, chloroform-d) δ 8.63 (d, J=1.8 Hz, 1H), 8.57-8.54 (m, 1H), 8.33 (d, J=2.9 Hz, 1H), 7.87 (d, J=6.6 Hz, 1H), 7.76 (dd, J=1.8, 0.9 Hz, 1H), 7.68 (d, J=8.6 Hz, 1H), 7.45 (d, J=8.6 Hz, 1H), 7.12 (d, J=8.8 Hz, 1H), 6.89 (br. s., 1H), 4.63-4.55 (m, 1H), 4.55-4.50 (m, 3H), 4.30 (dd, J=11.3, 6.7 Hz, 1H), 4.13 (s, 3H), 2.65 (s, 3H). LC-MS: method C, RT=2.57 min, MS (ESI) m/z: 594.05 and 596.05 (M+H)$^+$. Analytical HPLC purity (method B): 100%.

Example 110

(R)-(2-(2-methoxy-7-methylquinoxalin-5-yl)-7,8-dihydro-[1,4]dioxino[2',3':3,4]benzo[1,2-d]thiazol-7-yl)methyl (6-vinylpyridin-3-yl)carbamate

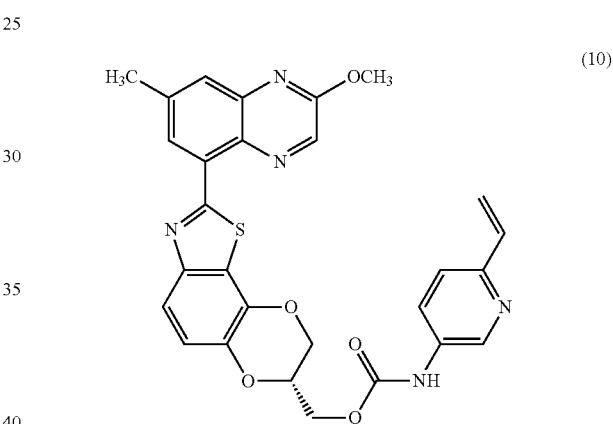

(10)

A solution of Example 109 (50 mg, 0.084 mmol) in toluene (1 mL) was added to a sealed microwave vial containing Pd(Ph$_3$P)$_4$ (9.72 mg, 8.41 μmol). The mixture was degassed with argon for 3 min. Tributyl(vinyl)stannane (0.246 mL, 0.841 mmol) was added, and the reaction mixture was heated in a microwave reactor at 120° C. for 1 h. After it cooled to room temperature, the reaction mixture was loaded to a 40 g ISCO column eluted with 0-100% EtOAc in dichloromethane for 20 min. The desired fractions were combined and concentrated to give a solid product (20 mg, 0.037 mmol, 43.9% yield). A small amount (3 mg) was further purified via preparative LC/MS (method C, 30-100% B over 20 minutes, then a 5-minute hold at 100% B). Fractions containing the desired product were combined and dried via centrifugal evaporation to yield Example 110 (1.6 mg). $^1$H NMR (500 MHz, DMSO-d$_6$) δ 8.76 (s, 1H), 8.61 (s, 1H), 8.58 (s, 1H), 7.88 (d, J=8.2 Hz, 1H), 7.83 (s, 1H), 7.66 (d, J=8.8 Hz, 1H), 7.46 (d, J=8.5 Hz, 1H), 7.17 (d, J=8.9 Hz, 1H), 6.74 (dd, J=17.4, 11.0 Hz, 1H), 6.08 (d, J=18.0 Hz, 1H), 5.35 (d, J=11.3 Hz, 1H), 4.65 (d, J=11.3 Hz, 2H), 4.54-4.40 (m, 2H), 4.31 (dd, J=11.0, 7.6 Hz, 1H), 4.08 (s, 3H), 2.63 (s, 3H). LC-MS: method C, RT=2.02 min, MS (ESI) m/z: 542.10 (M+H)$^+$. Analytical HPLC purity (method B): 98%.

Example 111

((R)-2-(2-methoxy-7-methylquinoxalin-5-yl)-7,8-dihydro-[1,4]dioxino[2',3':3,4]benzo [1,2-d]thiazol-7-yl)methyl (6-((S)-1,2-dihydroxyethyl)pyridin-3-yl)carbamate

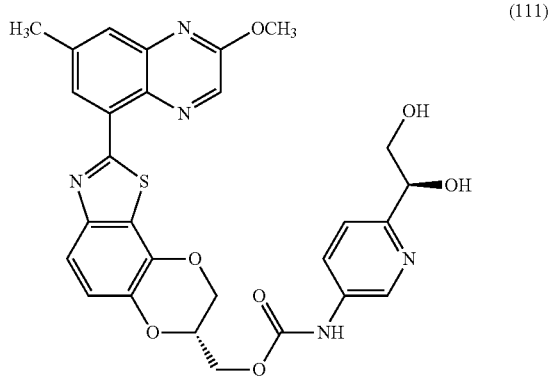 [SMILES: COc1cnc2c(-c3nc4ccc5c(c4s3)OC[C@H](COC(=O)Nc3ccc([C@H](O)CO)nc3)O5)cc(C)cc2n1]
(111)

To a solution of Example 110 (15 mg, 0.028 mmol) in THF (1 mL) and water (0.3 mL) was added AD-mix-α (20 mg, 0.028 mmol). The reaction mixture was sonicated for 2 h. Another portion of AD-mix-α (20 mg, 0.028 mmol) was added, and the reaction was continued at room temperature overnight. The mixture was diluted with EtOAc and water. The organic layer was washed with brine, dried over sodium sulfate and concentrated. The crude was purified via preparative LC/MS (method C, 10-100% B over 20 minutes, then a 5-minute hold at 100% B). Fractions containing the desired product were combined and dried via centrifugal evaporation to yield Example 111 (1.8 mg, 11% yield). $^1$H NMR (500 MHz, DMSO-$d_6$) δ 9.96 (br. s., 1H), 8.54 (br. s., 1H), 8.49 (br. s., 1H), 8.39 (s, 1H), 7.82 (d, J=7.0 Hz, 1H), 7.68 (s, 1H), 7.56 (d, J=8.5 Hz, 1H), 7.40 (d, J=8.5 Hz, 1H), 7.10 (d, J=8.9 Hz, 1H), 4.63-4.51 (m, 3H), 4.48-4.36 (m, 2H), 4.25 (dd, J=11.1, 7.2 Hz, 1H), 3.99 (s, 1H), 3.93 (s, 3H), 3.62 (dd, J=11.1, 4.1 Hz, 1H), 3.47 (dd, J=11.0, 6.7 Hz, 1H), 2.53 (s, 3H). LC-MS: method C, RT=2.05 min, MS (ESI) m/z: 576.05 (M+H)$^+$. Analytical HPLC purity (method B): 94%.

Example 112

(R)-2-(2-methoxy-7-methylquinoxalin-5-yl)-7,8-dihydro-[1,4]dioxino[2',3':3,4]benzo[1,2-d]thiazol-7-yl)methyl (6-fluoropyridin-3-yl)carbamate

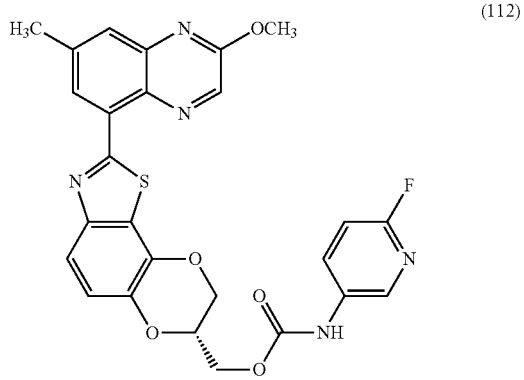 [SMILES: COc1cnc2c(-c3nc4ccc5c(c4s3)OC[C@H](COC(=O)Nc3ccc(F)nc3)O5)cc(C)cc2n1]
(112)

A solution of Intermediate 103A (12 mg, 0.026 mmol) in THF (1 mL) was added to a solution of 6-fluoropyridin-3-amine (12.76 mg, 0.114 mmol) in DCM (0.5 mL) and DIEA (0.020 ml, 0.114 mmol). The reaction mixture was stirred at room temperature for 1 h, at which time LCMS indicated a completion of reaction. After evaporation of solvent, the crude was dissolved in DMSO and purified via preparative LC/MS (method C, 20-100% B over 20 minutes, then a 5-minute hold at 100% B). Fractions containing the desired product were combined and dried via centrifugal evaporation to yield Example 112 (1.2 mg, 2.204 μmol, 6% yield). $^1$H NMR (500 MHz, DMSO-$d_6$) δ 10.17 (br. s., 1H), 8.74 (s, 1H), 8.57 (d, J=1.7 Hz, 1H), 8.29 (br. s., 1H), 8.03 (t, J=6.7 Hz, 1H), 7.82 (s, 1H), 7.65 (d, J=8.5 Hz, 1H), 7.20-7.10 (m, 2H), 4.76-4.59 (m, 2H), 4.55-4.40 (m, 2H), 4.31 (dd, J=11.4, 7.3 Hz, 1H), 4.08 (s, 3H), 2.62 (s, 3H). LC-MS: method C, RT=2.40 min, MS (ESI) m/z: 534.10 (M+H)$^+$. Analytical HPLC purity (method B): 98%.

Example 113

(R)-(2-(2-methoxy-7-methylquinoxalin-5-yl)-7,8-dihydro-[1,4]dioxino[2',3':3,4]benzo[1,2-d]thiazol-7-yl)methyl (5-cyanopyridin-3-yl)carbamate

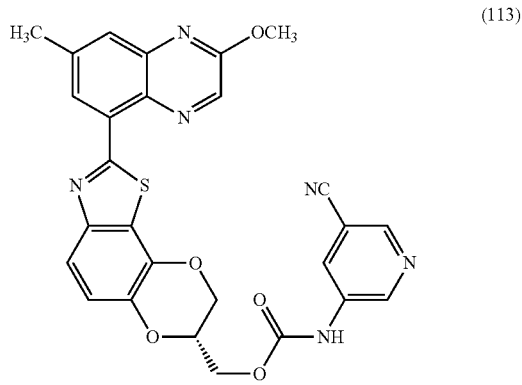 [SMILES: COc1cnc2c(-c3nc4ccc5c(c4s3)OC[C@H](COC(=O)Nc3cncc(C#N)c3)O5)cc(C)cc2n1]
(113)

Intermediate 103A (30 mg, 0.076 mmol) in DCM (2 mL) was added to a solution of 5-amino-3-pyridinecarbonitrile (18.08 mg, 0.152 mmol) in DCM (1 mL), followed by addition of pyridine (0.061 ml, 0.759 mmol). The reaction mixture was stirred at room temperature for 1h, at which time LCMS indicated a completion of reaction. The reaction mixture was diluted with EtOAc, washed with 0.5 N HCl. The organic layer was washed with brine, dried over sodium sulfate and concentrated. The crude was dissolved in DMSO and purified via preparative LC/MS (method C, 40-80% B over 20 min, then a 2-min hold at 100% B). Fractions containing the desired product were combined and dried via centrifugal evaporation to yield Example 113 (10 mg, 23% yield) as a solid. $^1$H NMR (500 MHz, DMSO-$d_6$) δ 10.50 (br. s., 1H), 8.85 (s, 1H), 8.73 (s, 1H), 8.66 (s, 1H), 8.56 (s, 1H), 8.28 (br. s., 1H), 7.81 (s, 1H), 7.64 (d, J=8.9 Hz, 1H), 7.16 (d, J=8.5 Hz, 1H), 4.77-4.61 (m, 2H), 4.57-4.43 (m, 2H), 4.31 (dd, J=11.1, 7.2 Hz, 1H), 4.07 (s, 3H), 2.62 (s, 3H). LC-MS: method C, RT=2.34 min, MS (ESI) m/z: 541.10 (M+H)$^+$. Analytical HPLC purity (method B): 95%.

Example 114

(R)-(2-(2-methoxy-7-methylquinoxalin-5-yl)-7,8-dihydro-[1,4]dioxino[2',3':3,4]benzo [1,2-d]thiazol-7-yl)methyl (4-(morpholine-4-carbonyl)phenyl)carbamate

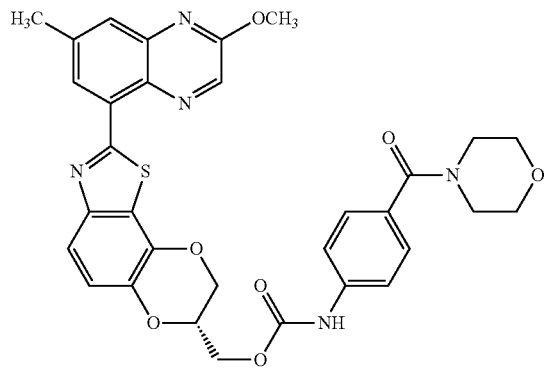

Intermediate 114A: (4-(morpholine-4-carbonyl)phenyl)carbamic chloride

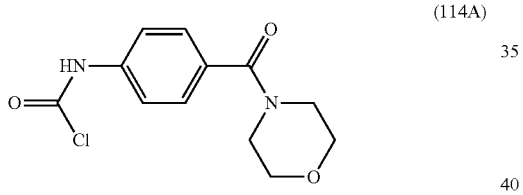

To a solution of phosgene (15% in toluene, 0.342 ml, 0.485 mmol) in CH₂Cl₂ (2 ml) was added 4-aminophenyl)(morpholino)methanone (20 mg, 0.097 mmol) in CH₂Cl₂ (2 mL), followed by addition of DIEA (0.019 ml, 0.107 mmol) dropwise. The reaction mixture was stirred at room temperature for 15 min, at which time LCMS indicated a completion of the reaction. Solvent was removed under vacuum to yield Intermediate 114A which was used for next step without further purification. LC-MS: method C, RT=0.40 min, MS (ESI) m/z: 268 (M+H)⁺.

Example 114

To a solution of Intermediate 102A (15 mg, 0.030 mmol) in CH₂Cl₂ (1 ml) was added Intermediate 114A (30.3 mg, 0.167 mmol) in CH₂Cl₂ (2 ml), followed by addition of DIEA (0.032 ml, 0.184 mmol) dropwise. The reaction mixture was stirred at room temperature for 2 h, at which time LCMS indicated a completion of reaction. Solvent was removed. The crude was dissolved in DMSO and purified via preparative LC/MS (method A, 25-100% B over 10 minutes, then a 2-minute hold at 100% B). Fractions containing the desired product were combined and dried via centrifugal evaporation to yield Example 114 (8.4 mg, 0.013 mmol, 43% yield) as a solid. ¹H NMR (500 MHz, DMSO-d₆) δ 10.15 (s, 1H), 8.77 (s, 1H), 8.60 (s, 1H), 7.85 (s, 1H), 7.70 (d, J=8.5 Hz, 1H), 7.61 (d, J=8.2 Hz, 2H), 7.43 (d, J=8.2 Hz, 2H), 7.22 (d, J=8.5 Hz, 1H), 4.75-4.66 (m, 2H), 4.60-4.46 (m, 2H), 4.43-4.30 (m, 1H), 4.13 (s, 3H), 3.65 (bro, 8H), 2.67 (s, 3H). LC-MS: method C, RT=2.34 min, MS (ESI) m/z: 628.10 (M+H)⁺. Analytical IPLC purity (method B): 97%.

The general procedures described below pertain to the experimental procedure for Example 115 to 142.

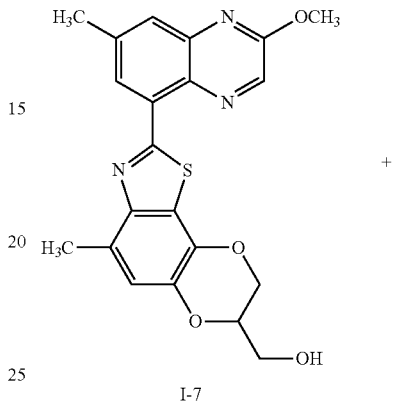

I-7

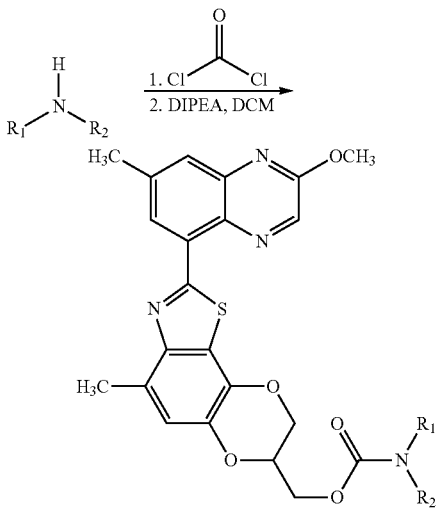

Intermediate I-7 (12 mg, 0.029 mmol) in THF (0.4 mL) was added into a Wheaton tube (16×100 mm) with a stir bar. Phosgene (46.3 μl, 1.9 molar, 0.94 g/mL, 20%) in toluene was added, and the mixture was stirred at room temperature overnight. 10 μl of reaction solution was taken from the reaction and dissolved in 250 μl MeOH for LCMS analysis. The analysis showed that the intermediate as methyl carbamate was formed and starting material Intermediate I-7 was consumed. The solvent and excess phosgene were removed by a stream of nitrogen. The solid was dissolved in DCM (1 mL) and added into corresponding amine. All reactions were placed on 24-well plate and stirred at room temperature for 5 hours. LCMS analysis of the reaction found the desired mass of the product. All samples were dried by a stream of nitrogen and re-dissolved in DMF (1 mL) and purified by IPLC (Method D).

Example 115 to Example 142

| Ex. No. | Structure | LCMS [M + H]+ m/z | Purity | HPLC Method |
|---|---|---|---|---|
| 115 | 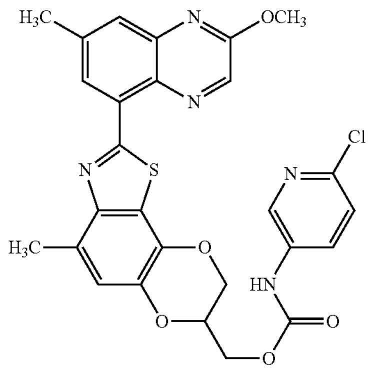 [SMILES: COc1cnc2c(-c3nc4c(C)cc5c(c4s3)OCC(COC(=O)Nc3ccc(Cl)nc3)O5)cc(C)cc2n1] | 564.2 | 99 | B |
| 116 | 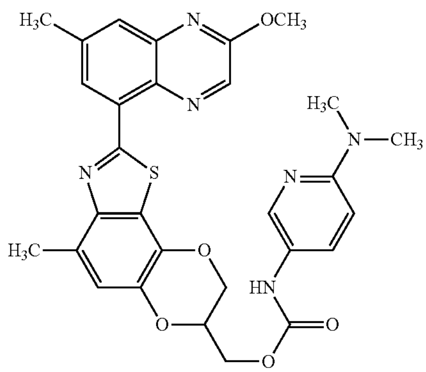 | 573.4 | 100.0 | A |
| 117 | 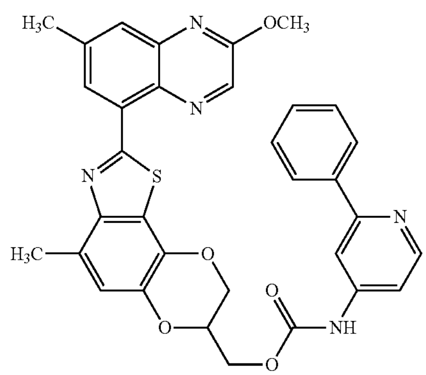 [SMILES: COc1cnc2c(-c3nc4c(C)cc5c(c4s3)OCC(COC(=O)Nc3ccnc(-c4ccccc4)c3)O5)cc(C)cc2n1] | 606.4 | 99.5 | A |
| 118 | 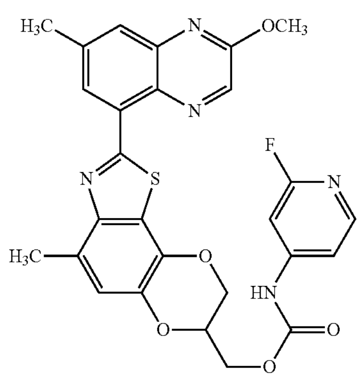 [SMILES: COc1cnc2c(-c3nc4c(C)cc5c(c4s3)OCC(COC(=O)Nc3ccnc(F)c3)O5)cc(C)cc2n1] | 548.3 | 100.0 | A |

-continued

| Ex. No. | Structure | LCMS [M + H]+ m/z | Purity | HPLC Method |
|---|---|---|---|---|
| 119 | 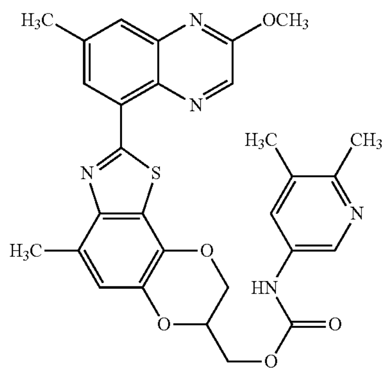 | 558.3 | 97.6 | B |
| 120 | 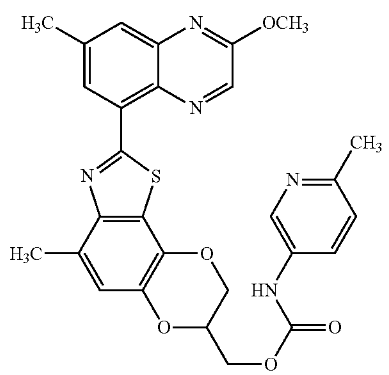 | 544.3 | 95.8 | A |
| 121 | 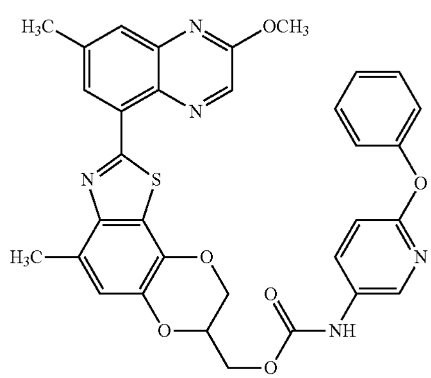 [SMILES: COc1cnc2c(-c3nc4c(C)cc5c(c4s3)OCC(COC(=O)Nc3ccc(Oc4ccccc4)nc3)O5)cc(C)cc2n1] | 622.3 | 93.0 | A |
| 122 | 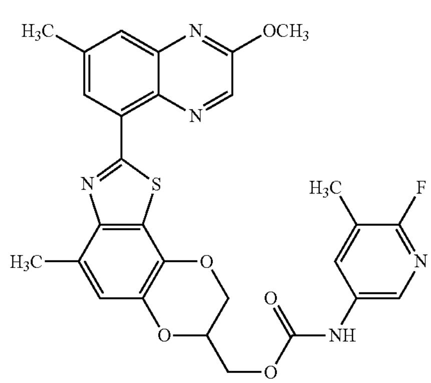 [SMILES: COc1cnc2c(-c3nc4c(C)cc5c(c4s3)OCC(COC(=O)Nc3cnc(F)c(C)c3)O5)cc(C)cc2n1] | 562.4 | 95.2 | A |

-continued

| Ex. No. | Structure | LCMS [M + H]+ m/z | Purity | HPLC Method |
|---|---|---|---|---|
| 123 | 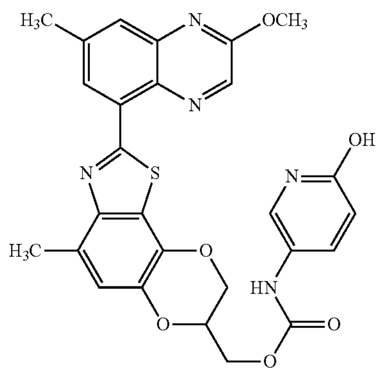 [SMILES: COc1cnc2c(-c3nc4c(C)cc5c(c4s3)OCC(COC(=O)Nc3ccc(O)nc3)O5)cc(C)cc2n1] | 546.3 | 100.0 | A |
| 124 | 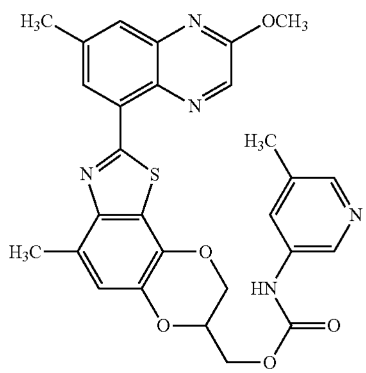 [SMILES: COc1cnc2c(-c3nc4c(C)cc5c(c4s3)OCC(COC(=O)Nc3cncc(C)c3)O5)cc(C)cc2n1] | 544.3 | 97.1 | B |
| 125 | 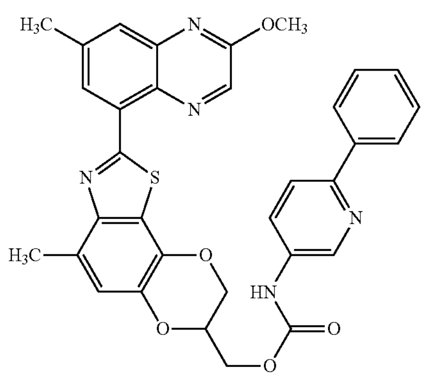 [SMILES: COc1cnc2c(-c3nc4c(C)cc5c(c4s3)OCC(COC(=O)Nc3ccc(-c4ccccc4)nc3)O5)cc(C)cc2n1] | 606.3 | 96.1 | A |
| 126 | 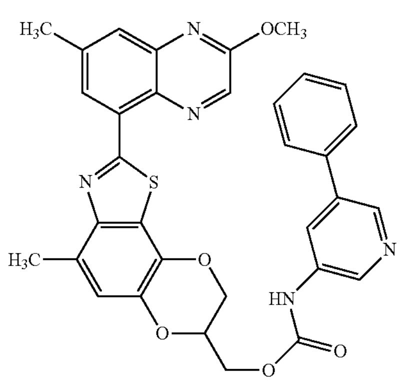 [SMILES: COc1cnc2c(-c3nc4c(C)cc5c(c4s3)OCC(COC(=O)Nc3cncc(-c4ccccc4)c3)O5)cc(C)cc2n1] | 606.4 | 95.7 | A |

-continued

| Ex. No. | Structure | LCMS [M + H]+ m/z | Purity | HPLC Method |
|---|---|---|---|---|
| 127 | 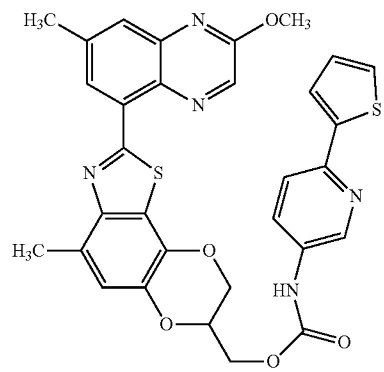 [SMILES: COc1cnc2c(-c3nc4c(C)cc5c(c4s3)OCC(COC(=O)Nc3ccc(-c4cccs4)nc3)O5)cc(C)cc2n1] | 612.3 | 95.0 | B |
| 128 | 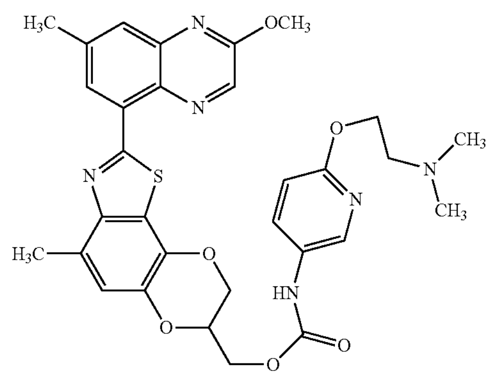 | 617.4 | 89.7 | B |
| 129 | 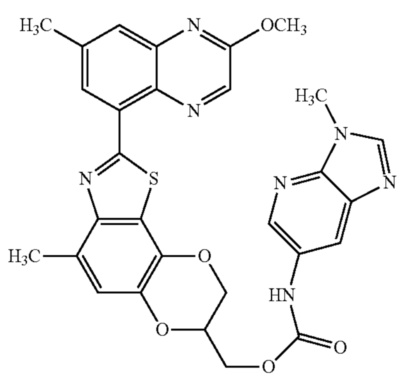 [SMILES: COc1cnc2c(-c3nc4c(C)cc5c(c4s3)OCC(COC(=O)Nc3cnc4c(c3)ncn4C)O5)cc(C)cc2n1] | 584.4 | 86.1 | B |
| 130 | 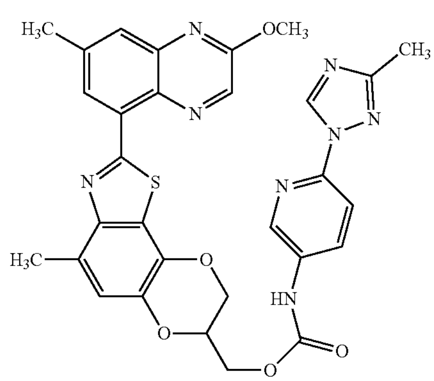 | 611.3 | 95.6 | B |

-continued

| Ex. No. | Structure | LCMS [M + H]+ m/z | Purity | HPLC Method |
|---|---|---|---|---|
| 131 | 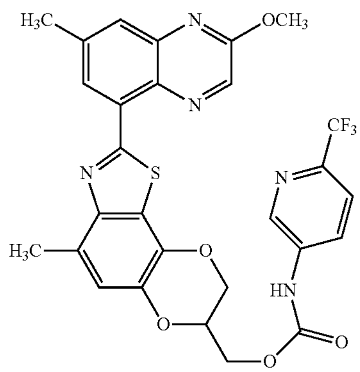 [SMILES: COc1cnc2c(-c3nc4c(C)cc5c(c4s3)OCC(COC(=O)Nc3ccc(C(F)(F)F)nc3)O5)cc(C)cc2n1] | 598.3 | 95.5 | A |
| 132 | 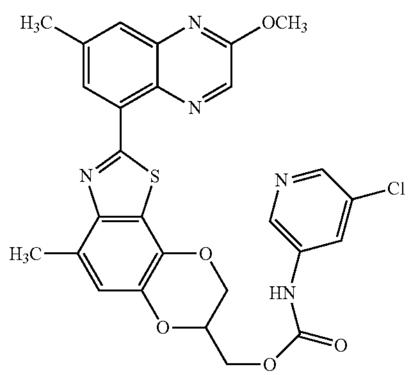 [SMILES: COc1cnc2c(-c3nc4c(C)cc5c(c4s3)OCC(COC(=O)Nc3cncc(Cl)c3)O5)cc(C)cc2n1] | 564.3 | 100.0 | A |
| 133 | 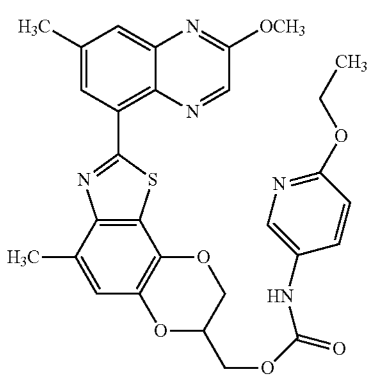 [SMILES: CCOc1ccc(NC(=O)OCC2COc3c(cc(C)c4nc(-c5cc(C)cc6nc(OC)cnc56)sc34)O2)cn1] | 574.3 | 98.6 | B |
| 134 | 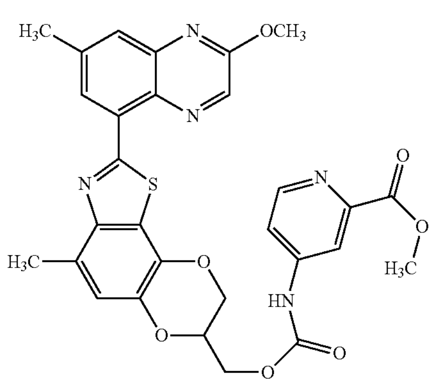 [SMILES: COC(=O)c1cc(NC(=O)OCC2COc3c(cc(C)c4nc(-c5cc(C)cc6nc(OC)cnc56)sc34)O2)ccn1] | 588.2 | 94.8 | B |

| Ex. No. | Structure | LCMS [M + H]+ m/z | Purity | HPLC Method |
|---|---|---|---|---|
| 135 | 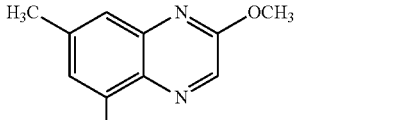 | 598.3 | 98.0 | A |
| 136 | 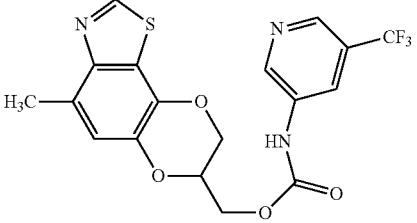 | 714.6 | 97.9 | B |
| 137 | 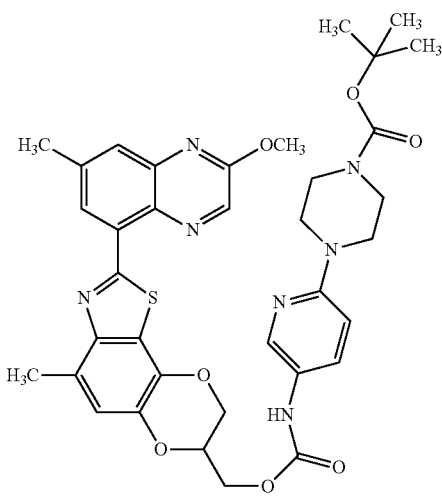 [SMILES: COc1cnc2c(-c3nc4c(C)cc5c(c4s3)OCC(COC(=O)Nc3ccc(N4CCN(C(=O)OC(C)(C)C)CC4)nc3)O5)cc(C)cc2n1] | 599.4 | 97.8 | B |
| | 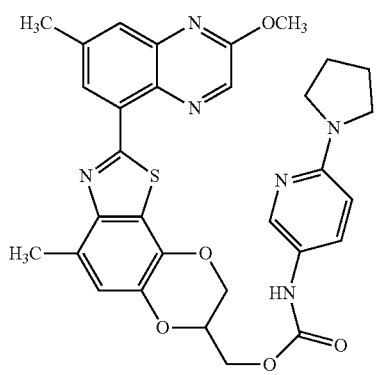 [SMILES: COc1cnc2c(-c3nc4c(C)cc5c(c4s3)OCC(COC(=O)Nc3ccc(N4CCCC4)nc3)O5)cc(C)cc2n1] | | | |

-continued

| Ex. No. | Structure | LCMS [M + H]+ m/z | Purity | HPLC Method |
|---|---|---|---|---|
| 138 | 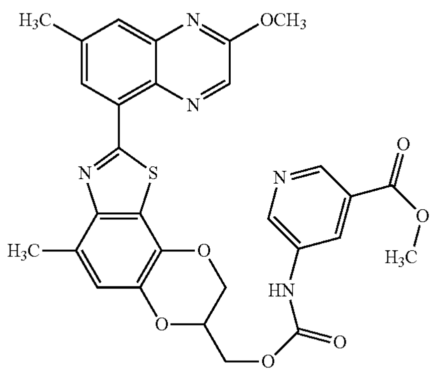 [SMILES: COC(=O)c1cncc(NC(=O)OCC2COc3c(cc(C)c4nc(-c5cc(C)cc6nc(OC)cnc56)sc34)O2)c1] | 586.5 | 95.1 | B |
| 139 | 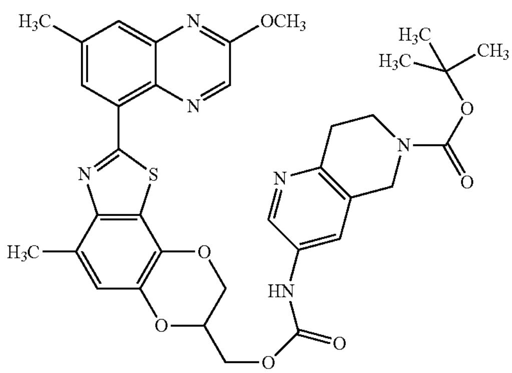 [SMILES: COc1cnc2c(-c3nc4c(C)cc5c(c4s3)OCC(COC(=O)Nc3cnc4c(c3)CN(C(=O)OC(C)(C)C)CC4)O5)cc(C)cc2n1] | 685.4 | 99.5 | A |
| 140 | 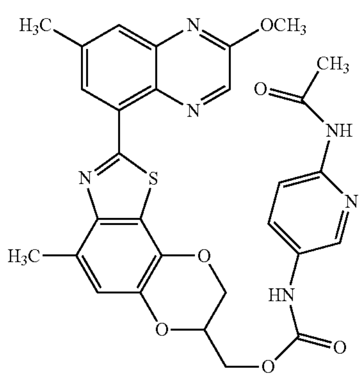 [SMILES: COc1cnc2c(-c3nc4c(C)cc5c(c4s3)OCC(COC(=O)Nc3ccc(NC(C)=O)nc3)O5)cc(C)cc2n1] | 587.4 | 99.0 | B |
| 141 | 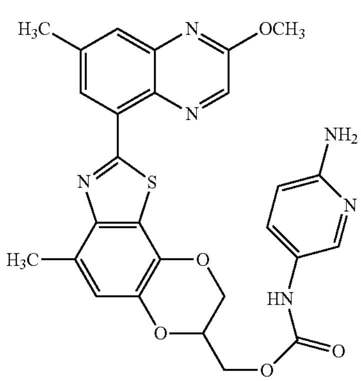 [SMILES: COc1cnc2c(-c3nc4c(C)cc5c(c4s3)OCC(COC(=O)Nc3ccc(N)nc3)O5)cc(C)cc2n1] | 545.4 | 93.6 | A |

| Ex. No. | Structure | LCMS [M + H]+ m/z | Purity | HPLC Method |
|---|---|---|---|---|
| 142 | 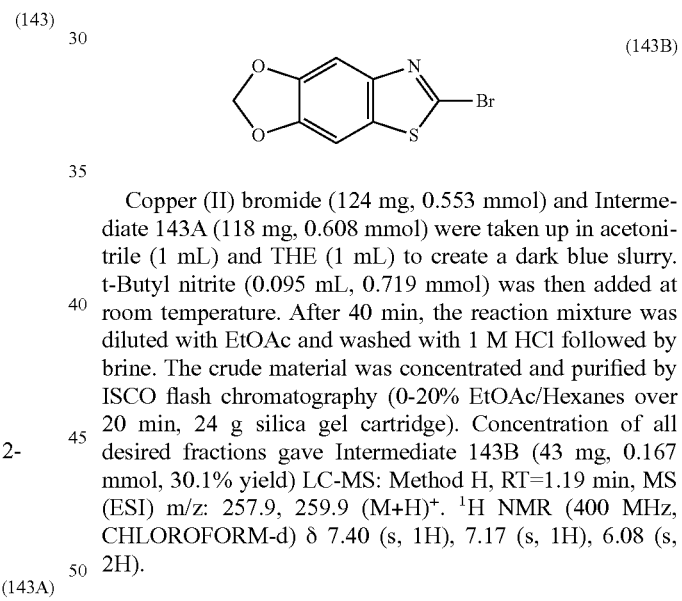 | 569.4 | 98.3 | A |

Example 143

6-(2-(methoxymethyl)-7-methylquinoxalin-5-yl)-[1,3]dioxolo[4',5':4,5]benzo[1,2-d]thiazole

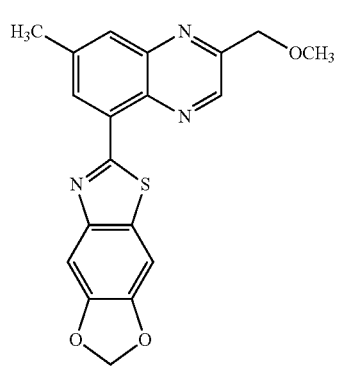

Intermediate 143A: [1,3]dioxolo[4',5':4,5]benzo[1,2-d]thiazol-6-amine

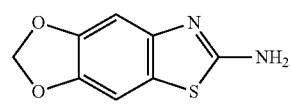

To benzo[d][1,3]dioxol-5-amine (200 mg, 1.458 mmol) in acetonitrile (7.292 mL) was added ammonium thiocyanate (167 mg, 2.188 mmol) followed by benzyltrimethylammonium tribromide (569 mg, 1.458 mmol). The reaction mixture was allowed to stir at room temperature overnight. After 15 hours, the reaction mixture was diluted with $CH_2Cl_2$ and washed with saturated $NaHCO_3$ followed by brine. The organic phase was concentrated to give Intermediate 143A (118 mg, 0.608 mmol, 41.7% yield) as a dark brown solid. This crude product was taken on to the next reaction without further purification. LC-MS: Method H, RT=0.72 min, MS (ESI) m/z: 195.0 (M+H)+. $^1$H NMR (400 MHz, METHANOL-$d_4$) δ 7.27 (s, 1H), 7.02 (s, 1H), 6.08 (s, 2H).

Intermediate 143B: 6-bromo-[1,3]dioxolo[4',5':4,5]benzo[1,2-d]thiazole

Copper (II) bromide (124 mg, 0.553 mmol) and Intermediate 143A (118 mg, 0.608 mmol) were taken up in acetonitrile (1 mL) and THF (1 mL) to create a dark blue slurry. t-Butyl nitrite (0.095 mL, 0.719 mmol) was then added at room temperature. After 40 min, the reaction mixture was diluted with EtOAc and washed with 1 M HCl followed by brine. The crude material was concentrated and purified by ISCO flash chromatography (0-20% EtOAc/Hexanes over 20 min, 24 g silica gel cartridge). Concentration of all desired fractions gave Intermediate 143B (43 mg, 0.167 mmol, 30.1% yield) LC-MS: Method H, RT=1.19 min, MS (ESI) m/z: 257.9, 259.9 (M+H)+. $^1$H NMR (400 MHz, CHLOROFORM-d) δ 7.40 (s, 1H), 7.17 (s, 1H), 6.08 (s, 2H).

Example 143

Intermediate I-2 (29.2 mg, 0.046 mmol), $PdCl_2(dppf)$—$CH_2Cl_2$ adduct (2.53 mg, 3.10 µmol) and Intermediate 143B (10 mg, 0.039 mmol) were solvated in DMF (1 mL). Sodium carbonate (2 M in $H_2O$) (100 µL, 0.200 mmol) was added, and the solution was degassed with argon for 10 min. The vial was then sealed and heated to 100° C. in the microwave for 30 min. The crude solution was filtered and purified by preparative HPLC (Method D, 45-85% over 10 minutes) to yield Example 143 (3.2 mg, 0.006 mmol, 15.8% yield). $^1$H NMR (500 MHz, DMSO-$d_6$) δ 9.08 (s, 1H), 8.78 (s, 1H), 8.01 (s, 1H), 7.72 (s, 1H), 7.61 (s, 1H), 6.17 (s, 2H), 4.81 (s, 2H), 3.47 (s, 3H), 2.68 (s, 3H). LC-MS: Method H, RT=1.35 min, MS (ESI) m/z: 366.1 (M+H)+. Analytical HPLC purity (method B): 95%.

Example 144

(R)-(2-(2-methoxy-7-methylquinoxalin-5-yl)-7,8-dihydrobenzofuro[5,4-d]thiazol-7-yl)methyl (2-methylpyrimidin-5-yl)carbamate

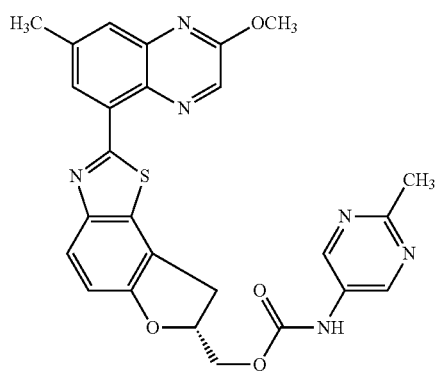

(144)

Intermediate 144A: 2-chlorobenzo[d]thiazol-6-ol

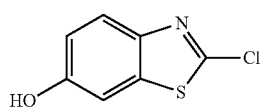

(144A)

To 2-chloro-6-methoxybenzo[d]thiazole (8.4 g, 42.1 mmol) and tetrabutylammonium iodide (16.32 g, 44.2 mmol) in dichloromethane (150 ml) at −78° C. was added 1.0 M boron trichloride in heptane (99 ml, 99 mmol) dropwise. The mixture was slowly warmed up by removing the cooling bath and stirred at room temperature overnight. HPLC and LCMS indicated a clean reaction. The mixture was poured into 1.5 M potassium phosphate and ice, stirred for 20 min, extracted with EtOAc. The organic layers were collected, washed with 10% Na₂S₂O₃, water, brine and dried over sodium sulfate. The crude product was purified by flash chromatography (loading in chloroform/THF, 5% to 60% EtOAc in hexane over 15 min using a 220 g silica gel cartridge). The desired fractions were combined and concentrated to yield Intermediate 144A (7.4 g, 39.9 mmol, 95% yield) as a white sold. $^1$H NMR (400 MHz, METHANOL-d₄) δ 7.70 (d, J=8.8 Hz, 1H), 7.25 (d, J=2.4 Hz, 1H), 7.00 (dd, J=8.9, 2.5 Hz, 1H).

Intermediate 144B: 6-(allyloxy)-2-chlorobenzo[d]thiazole

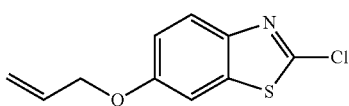

(144B)

To a solution of Intermediate 144A (7.4 g, 39.9 mmol) in DMF (100 mL) was added 3-bromoprop-1-ene (4.74 mL, 54.8 mmol), cesium carbonate (39.0 g, 120 mmol) and the mixture was stirred at room temperature for 5 h, at which time HPLC and TLC indicated completion of the reaction. The reaction mixture was diluted with EtOAc and water (20 mL), neutralized with 1.0 N HCl (40 mL), and extracted with ethyl acetate (X3). The organic layer was washed with brine (2×), dried over Na₂SO₄ and concentrated. The crude product was purified by flash chromatography (loading in chloroform, 0% to 60% EtOAc in hexane over 20 min using a 120 g silica gel cartridge). The desired fractions were combined and concentrated to yield Intermediate 144B (8.6 g, 38.1 mmol, 96% yield) as white solid. $^1$H NMR (500 MHz, CHLOROFORM-d) δ 7.83 (d, J=9.1 Hz, 1H), 7.25 (d, J=2.5 Hz, 1H), 7.11 (dd, J=9.1, 2.5 Hz, 1H), 6.08 (ddt, J=17.3, 10.6, 5.3 Hz, 1H), 5.45 (dq, J=17.2, 1.6 Hz, 1H), 5.34 (dq, J=10.5, 1.4 Hz, 1H), 4.60 (dt, J=5.3, 1.5 Hz, 2H). LC-MS: Method H, 2 to 98% B. RT=0.94 min, MS (ESI) m/z: 225.90 and 227.90 (M+H)⁺.

Intermediate 144C: 7-allyl-2-chlorobenzo[d]thiazol-6-ol

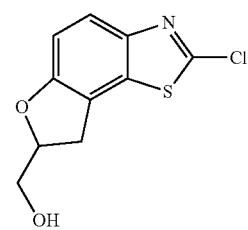

(144C)

A solution of Intermediate 144B (6.4 g, 28.4 mmol) in N,N-diethyl aniline (40 ml) was heated at 200° C. (oil bath) under argon for 2 h. After cooling to room temperature, the reaction mixture was diluted with EtOAc, washed with 3.0 N HCl (3×50 mL), brine (2×). The organic layer was dried over sodium sulfate and concentrated. The crude product was purified by flash chromatography (loading in chloroform, 0% to 50% EtOAc in hexane over 30 min using a 330 g silica gel cartridge). The desired fractions were combined and concentrated to yield Intermediate 144C (3.20 g, 14.18 mmol, 50% yield) as a white solid. $^1$H NMR (500 MHz, CHLOROFORM-d) δ 7.72 (d, J=8.8 Hz, 1H), 7.01 (d, J=8.5 Hz, 1H), 5.99 (ddt, J=17.4, 9.9, 6.3 Hz, 1H), 5.30 (s, 1H), 5.25-5.22 (m, 1H), 5.20 (dq, J=3.0, 1.6 Hz, 1H), 3.59 (dt, J=6.3, 1.5 Hz, 2H).). LC-MS: Method H, 2 to 98% B. RT=0.86 min, MS (ESI) m/z: 225.95 and 227.90 (M+H)⁺.

Intermediate 144D: (2-chloro-7,8-dihydrobenzofuro[5,4-d]thiazol-7-yl)methanol

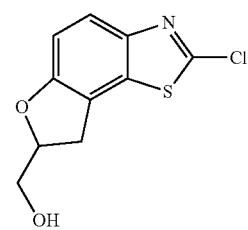

(144D)

To a suspension of Intermediate 144C (3.9 g, 17.28 mmol) in dichloromethane (120 mL) was added sodium bicarbonate (2.032 g, 24.19 mmol), followed by mCPBA (6.20 g, 27.6 mmol). The reaction mixture was stirred overnight at room temperature. Solvent was removed under vacuum. The residue was retaken into THF (80 mL), K$_2$CO$_3$ (7.88 g, 57.0 mmol) was added, followed by addition of water (10 mL) and MeOH (10 mL). The reaction mixture was stirred at room temperature for 30 min. TLC indicated a completion of reaction. The reaction mixture was diluted with EtOAc (100 mL), washed with water (100 mL), saturated sodium bicarbonate (3×), brine (2×). The organic layer was dried over sodium sulfate and concentrated. The crude product was purified by flash chromatography (loading in chloroform, 5% to 60% EtOAc in hexane over 20 min using a 220 g silica gel cartridge). The desired fractions were combined and concentrated to yield Intermediate 144D (3.17 g, 13.12 mmol, 76% yield) as a white solid. $^1$H NMR (500 MHz, CHLOROFORM-d) δ 7.75-7.71 (m, 1H), 6.98 (d, J=8.5 Hz, 1H), 5.11 (dddd, J=9.7, 7.0, 6.0, 3.2 Hz, 1H), 4.00-3.93 (m, 1H), 3.83 (dt, J=12.0, 5.8 Hz, 1H), 3.37 (dd, J=15.7, 9.6 Hz, 1H), 3.20 (dd, J=15.7, 7.4 Hz, 1H), 1.97 (t, J=6.3 Hz, 1H). LC-MS: Method H, 2 to 98% B. RT=0.71 min, MS (ESI) m/z: 241.95 and 243.90 (M+H)$^+$.

Intermediate 144E: (R)-(2-chloro-7,8-dihydrobenzofuro[5,4-d]thiazol-7-yl)methanol

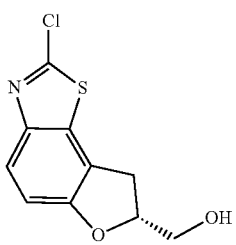

(144E)

Intermediate 144D (3.1 g) was subject to chiral SFC for separation using the following conditions: Instrument: Berger SFC MGII; Column: Chiralpak AS-H, 30×250 mm, 5 micron; Mobile Phase: 10% EtOH/ACN(1:1)/90% CO$_2$; Flow Conditions: 75 mL/min, 150 Bar, 40° C.; Detector wavelength: 220 nm. Injection Details: 0.7 mL of 35 mg/mL in ACN/EtOH. The first eluting fractions (first peak, RT=9 min) were concentrated to give Intermediate 144E (1.45 g): $^1$H NMR (500 MHz, chloroform-d) δ 7.67 (d, J=8.5 Hz, 1H), 6.92 (d, J=8.8 Hz, 1H), 5.11-5.03 (m, 1H), 3.93 (dd, J=12.1, 2.5 Hz, 1H), 3.80 (dd, J=12.0, 5.6 Hz, 1H), 3.31 (dd, J=15.4, 9.6 Hz, 1H), 3.20-3.12 (m, 1H), 2.44 (br. s., 1H). LC-MS: Method H, 2 to 98% B. RT=0.75 min, MS (ESI) m/z: 241.9 and 243.9 (M+H)$^+$.

Intermediate 144 F (R)-(2-(2-methoxy-7-methylquinoxalin-5-yl)-7,8-dihydrobenzofuro[5,4-d]thiazol-7-yl)methanol

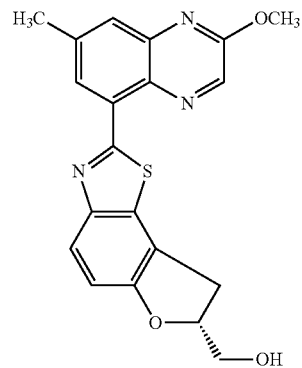

(144F)

A solution of Intermediate I-9 (349 mg, 1.601 mmol) and Intermediate 144E (387 mg, 1.601 mmol) in toluene/EtOH (3:1) (12 mL) was added to PdCl$_2$(dppf)—CH$_2$Cl$_2$ adduct (65.4 mg, 0.080 mmol). The mixture was flushed with argon for 1 min. To this was added 1.5 M Na$_2$CO$_3$ (2.94 mL, 4.40 mmol). The reaction mixture was heated in a microwave reactor at 140° C. for 45 min, at which time HPLC indicated a completion of reaction. Toluene was removed by blowing a stream of nitrogen overnight. The crude was treated with wet MeOH/water (ca 15 mL, 4:1), sonicated. The precipitate was collected by filtration, washed with water, and MeOH until no color in the MeOH washing. The precipitate was air dried first, then under high vacuum to give a dark green solid. The dark green solid was dissolved in THF (60 mL), treated with 0.7 g SilaMetS Thiol resin (from Silicycle, R51030B, 1.28 mmol/g) at 55° C. for 3.0 h. The mixture was diluted with EtOAc (20 mL), filtered through a 12 g silica gel cartridge, rinsed with 100 mL of THF/EtOAc (1:1). The filtrate was concentrated to give Intermediate 144F (465 mg, 1.23 mmol, 77% yield) as a yellow solid. $^1$H NMR (400 MHz, chloroform-d) δ 8.62 (d, J=1.5 Hz, 1H), 8.56 (s, 1H), 7.93 (d, J=8.8 Hz, 1H), 7.75 (s, 1H), 7.03 (d, J=8.6 Hz, 1H), 5.18-5.09 (m, 1H), 4.13 (s, 3H), 4.01-3.92 (m, 1H), 3.89-3.80 (m, 1H), 3.48 (dd, J=15.4, 9.5 Hz, 1H), 3.26 (dd, J=15.6, 7.3 Hz, 1H), 2.65 (s, 3H), 1.98 (br. s., 1H); LC-MS: Method H; 2 to 98% B. RT=0.94 min, MS (ESI) m/z: 380.0 (M+H)$^+$. Analytical IPLC purity (method B): 91%.

Intermediate 144G (R)-(2-(2-methoxy-7-methylquinoxalin-5-yl)-7,8-dihydrobenzofuro[5,4-d]thiazol-7-yl)methyl carbonochloridate

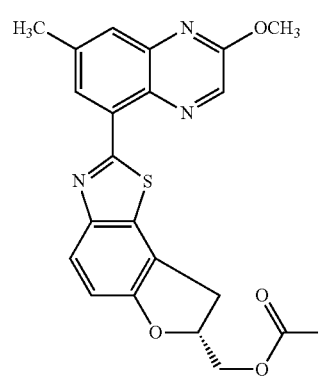

(144G)

To a suspension of Intermediate 144F (465 mg, 1.226 mmol) in THF (20 mL) at room temperature was added 15% phosgene in toluene (3.50 mL, 4.90 mmol). The reaction mixture was left stirring at room temperature for 2 min, DIEA (0.642 mL, 3.68 mmol) was added. The reaction was continued at room temperature for 30 min, at which time IPLC and LCMS indicated the reaction was completed. Solvent was removed under high vacuum to give Intermediate 144G (542 mg, 1.227 mmol, 100% yield) as a slightly yellow solid. It was used for the next step without any purification. LC-MS: Method H, 2 to 98% B. RT=1.19 min, MS (ESI) m/z: 442.05 and 444.05 (M+H)$^+$.

Example 144

Intermediate 144G (540 mg, 1.222 mmol) in dichloromethane (12 mL) was added to a solution of 2-methylpyrimidin-5-amine (267 mg, 2.444 mmol) and pyridine (0.791 mL, 9.78 mmol) in dichloromethane (8 mL) dropwise. The reaction mixture was stirred at room temperature for 1 h, at which time LCMS and IPLC indicated a completion of reaction. The reaction mixture was diluted with dichloromethane (20 mL) and quenched with 0.5 N HCl (20 mL). After stirring at room temperature for 10 min, the mixture was extracted with dichloromethane (3×50 mL). The organic layer was washed with brine, dried over sodium sulfate. After evaporation of solvent, the crude product was triturated with EtOAc, the precipitate was collected by filtration, rinsed with EtOAc, dried under vacuum to give 410 mg product. The filtrate was concentrated, purified by flash chromatography (loading in chloroform/THF, 30% to 100% EtOAc in hexane over 10 min using a 12 g silica gel cartridge). The desired fractions were combined and concentrated to yield additional 80 mg product. The products were combined and lyophilized to give Example 144 (483 mg, 0.920 mmol, 75% yield) as a yellow lyophilate. $^1$H NMR (500 MHz, DMSO-d$_6$) δ 10.09 (br. s., 1H), 8.74 (s, 3H), 8.58 (d, J=1.4 Hz, 1H), 7.91 (d, J=8.8 Hz, 1H), 7.81 (s, 1H), 7.08 (d, J=8.5 Hz, 1H), 5.35-5.26 (m, 1H), 4.51 (dd, J=12.1, 2.8 Hz, 1H), 4.38 (dd, J=12.1, 6.9 Hz, 1H), 4.08 (s, 3H), 3.57 (dd, J=15.7, 9.6 Hz, 1H), 3.29-3.25 (m, 1H), 2.63 (s, 3H), 2.53 (br. s., 3H). LC-MS::Method H, 2 to 98% B. RT=0.95 min, MS (ESI) m/z: 515.10(M+H)$^+$. Analytical HPLC purity (method B): 98%.

Example 145

(R)-(5-fluoro-2-(2-methoxy-7-methylquinoxalin-5-yl)-7,8-dihydrobenzofuro[5,4-d]thiazo l-7-yl)methyl (2-methylpyrimidin-5-yl)carbamate

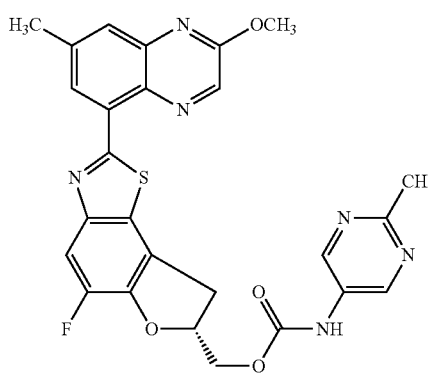

(145)

Intermediate 145A: 6-(allyloxy)-2-bromo-5-fluorobenzo[d]thiazole

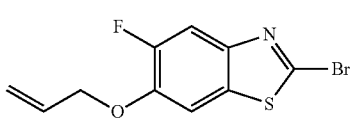

(145A)

To a solution of 2-bromo-5-fluorobenzo[d]thiazol-6-ol (5.0 g, 20.16 mmol) in DMF (40 mL) was added 3-bromoprop-1-ene (2.4 mL, 27.7 mmol), Cs$_2$CO$_3$ (18.39 g, 56.4 mmol). The reaction mixture was stirred at room temperature for 4.0 h, at which time HPLC and TLC indicated a completion of reaction. The reaction mixture was diluted with EtOAc, quenched with 0.5 N HCl (40 mL), and extracted with ethyl acetate (3×). The organic layer was washed with brine, dried over Na$_2$SO$_4$ and concentrated. The crude product was purified by flash chromatography (loading in chloroform, 0% to 50% EtOAc in hexane over 10 min using a 120 g silica gel cartridge). The desired fractions were combined and concentrated to yield Intermediate 145A (5.33 g, 18.50 mmol, 92% yield) as a slightly yellow solid. $^1$H NMR (500 MHz, CHLOROFORM-d) δ 7.71 (d, J=11.0 Hz, 1H), 7.33 (d, J=7.4 Hz, 1H), 6.10 (ddt, J=17.3, 10.5, 5.2 Hz, 1H), 5.48 (dq, J=17.3, 1.4 Hz, 1H), 5.37 (dq, J=10.5, 1.3 Hz, 1H), 4.68 (dt, J=5.4, 1.4 Hz, 2H). $^{19}$F NMR (376 MHz, CHLOROFORM-d) δ −132.86 (s, 1F). LC-MS: Method H, 2 to 98% B. RT=0.95 min, MS (ESI) m/z: 287.90 and 289.90 (M+H)$^+$.

Intermediate 145B: 7-allyl-2-bromo-5-fluorobenzo[d]thiazol-6-ol

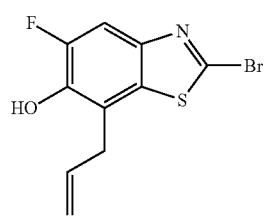

(145B)

A solution of Intermediate 145A (3.7 g, 12.84 mmol) in N,N-diethyl aniline (16 mL) was heated in a round bottom flask under argon at 190° C. (oil bath) for 2 h, at which time TLC indicated a completion of reaction. The mixture was cooled and diluted with EtOAc, washed with 4.0 N HCl (2×30 mL), brine (2×), dried over sodium sulfate and concentrated. The crude product was purified by flash chromatography (loading in chloroform/MeOH, 0% to 50% EtOAc in hexane over 18 min using an 80 g silica gel cartridge). The desired fractions were combined and concentrated to yield Intermediate 145B (3.43 g, 11.31 mmol, 88% yield) as a white solid. $^1$H NMR (500 MHz, CHLOROFORM-d) δ 7.62 (d, J=10.2 Hz, 1H), 5.92 (dd, J=16.8, 10.5 Hz, 1H), 5.57 (d, J=5.5 Hz, 1H), 5.20-5.16 (m, 1H), 5.15 (t, J=1.5 Hz, 1H), 3.61 (dt, J=6.3, 1.4 Hz, 2H). 19F NMR (376 MHz, CHLOROFORM-d) δ −139.11 (s, 1F). LC-MS: Method H, 2 to 98% B. RT=0.89 min, MS (ESI) m/z: 287.90 and 289.90 (M+H)$^+$.

Intermediate 145C: (2-bromo-5-fluoro-7,8-dihydrobenzofuro[5,4-d]thiazol-7-yl)methanol

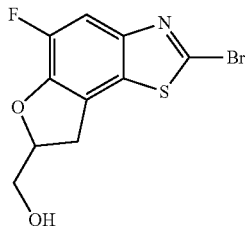

(145C)

To a suspension of Intermediate 145B (240 mg, 0.833 mmol) in dichloromethane (10 mL) was added mCPBA (299 mg, 1.333 mmol). The reaction mixture was stirred at room temperature over the weekend (total 90 h). Solvent was removed under vacuum. The residue was retaken into THF (10 mL), $K_2CO_3$ (403 mg, 2.92 mmol) in water (2 mL) was added, followed by addition of MeOH (2 mL). The reaction mixture was stirred at room temperature for 40 min. TLC indicated a completion of reaction. The reaction mixture was diluted with EtOAc and washed with water, saturated sodium bicarbonate (2×), brine. The organic layer was dried over sodium sulfate and concentrated. The crude product was purified by flash chromatography (loading in chloroform, 0% to 60% EtOAc in hexane over 12 min using a 12 g silica gel cartridge). The desired fractions were combined and concentrated to yield Intermediate 145C (180 mg, 0.592 mmol, 71.1% yield) as a white solid. $^1$H NMR (500 MHz, CHLOROFORM-d) δ 7.58 (d, J=10.5 Hz, 1H), 5.23-5.16 (m, 1H), 4.02 (dd, J=12.4, 3.0 Hz, 1H), 3.84 (dd, J=12.4, 5.2 Hz, 1H), 3.44-3.37 (m, 1H), 3.34-3.26 (m, 1H). $^{19}$F NMR (471 MHz, CHLOROFORM-d) 6-137.96 (s, 1F). LC-MS: Method H, 2 to 98% B. RT=0.75 min, MS (ESI) m/z: 303.9 and 305.9 (M+H)$^+$.

Intermediate 145D: (R)-(2-bromo-5-fluoro-7,8-dihydrobenzofuro[5,4-d]thiazol-7-yl) methanol

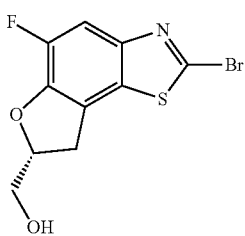

(145D)

Intermediate 145C (1.4 g) was subject to chiral SFC for separation using the following conditions: Instrument: PIC Solution Prep SFC; Column: Lux Cellulose-4, 30× 250 mm, 5 micron; Mobile Phase: 20% MeOH/80% $CO_2$; Flow Conditions: 100 mL/min, 150 Bar, 40° C.; Detector Wavelength: 220 nm. Injection Details: 2 mL of ~20 mg/ml in MeOH. The slower eluting fractions (second peak, RT=10.7 min) were concentrated to give Intermediate 145D (0.6 g). $^1$H NMR (500 MHz, CHLOROFORM-d) δ 7.58 (d, J=10.5 Hz, 1H), 5.23-5.16 (m, 1H), 4.02 (dd, J=12.4, 3.0 Hz, 1H), 3.84 (dd, J=12.4, 5.2 Hz, 1H), 3.44-3.37 (m, 1H), 3.34-3.26 (m, 1H). $^{19}$F NMR (471 MHz, CHLOROFORM-d) 6-137.96 (s, 1F). LC-MS: Method H, 2 to 98% B. RT=0.75 min, MS (ESI) m/z: 303.9 and 305.9 (M+H)$^+$.

Intermediate 145E (R)-(5-fluoro-2-(2-methoxy-7-methylquinoxalin-5-yl)-7,8-dihydrobenzofuro[5,4-d]thiazo 1-7-yl)methanol

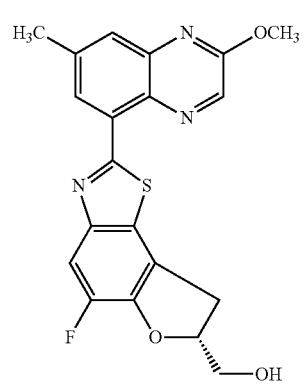

(145E)

A solution of Intermediate I-9 (146 mg, 0.669 mmol) and Intermediate 145D (226 mg, 0.743 mmol) in dioxane (7 mL) and toluene (1.5 mL) was added to $PdCl_2$(dppf)—$CH_2Cl_2$ adduct. The mixture was flushed with argon for 1 min. To this was added 1.5 M $Na_2CO_3$ (1.362 mL, 2.043 mmol). The reaction mixture was heated in a microwave reactor at 140° C. for 45 min. IPLC indicated a completion of reaction. Toluene was removed under vacuum. The mixture was treated with MeOH, sonicated. The precipitate was collected by filtration, washed with water, MeOH and dried under house vacuum and then under high vacuum to give 180 mg of crude product. The crude product was dissolved in THF (20 mL). SilaMeta Thiol resin (200 mg) was added. The mixture was stirred at 50° C. overnight. After cooled to room temperature, the mixture was filtered through a 12 g silica gel, washed with THF and EtOAc. The filtrated was concentrated to give Intermediate 145E (159 mg, 50% yield). $^1$H NMR (500 MHz, THF) δ 8.60 (d, J=1.7 Hz, 1H), 8.45 (s, 1H), 7.64 (dd, J=1.9, 1.1 Hz, 1H), 7.52 (d, J=11.0 Hz, 1H), 5.03-4.97 (m, 1H), 3.99 (s, 3H), 3.74-3.68 (m, 1H), 3.66-3.60 (m, 1H), 3.39-3.26 (m, 2H), 2.53 (s, 3H); $^{19}$F NMR (471 MHz, THF) δ −140.72 (s, 1F); LC-MS: Method H, 2 to 98% B. RT=1.03 min, MS (ESI) m/z: 398.10 (M+H)$^+$. Analytical IPLC purity (method B): 93%.

Intermediate 145F (R)-(5-fluoro-2-(2-methoxy-7-methylquinoxalin-5-yl)-7,8-dihydrobenzofuro[5,4-d]thiazo 1-7-yl)methyl carbonochloridate

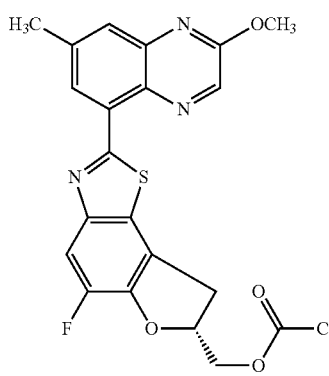
(145F)

To a suspension of Intermediate 145E (280 mg, 0.705 mmol) in THF (14 mL) at room temperature was added 15% phosgene in toluene (2.011 mL, 2.82 mmol). The reaction mixture was stirred for 2 min, DIEA (0.369 mL, 2.114 mmol) was added. The reaction was continued at room temperature for 40 min, at which time IPLC and LCMS indicated completion of reaction. Solvent was removed under high vacuum to give Intermediate 145F (324 mg, 0.705 mmol, 100% yield) as a slightly yellow solid. It was used for the next step without any purification. LC-MS: Method H, 2 to 98% B. RT=1.12 min, MS (ESI) m/z: 460.00 and 462.05 (M+H)$^+$.

Example 145

Intermediate 145F (324 mg, 0.705 mmol) in dichloromethane (6 mL) was added to a solution of 2-methylpyrimidin-5-amine (154 mg, 1.409 mmol) and pyridine (0.456 mL, 5.64 mmol) in dichloromethane (3 mL) dropwise. The reaction mixture was stirred at room temperature for 0.5 h, at which time LCMS and HPLC indicated a completion of reaction. The reaction mixture was quenched with 0.5 N HCl (10 mL). Dichloromethane was removed under vacuum. The suspension was poured into a stirred solution of isopropanol. The precipitate formed was collected by filtration, washed with water and isopropanol and dried under house vacuum overnight. The product was further triturated in MeOH, sonicated, centrifuged. MeOH was removed and the solid was collected to give Example 145 (278 mg, 0.512 mmol, 72.6% yield) as a pale yellow solid. $^1$H NMR (500 MHz, THF) δ 9.05 (br. s., 1H), 8.61 (d, J=1.4 Hz, 3H), 8.44 (s, 1H), 7.66 (dd, J=1.8, 1.0 Hz, 1H), 7.57 (d, J=11.0 Hz, 1H), 5.29-5.21 (m, 1H), 4.45 (dd, J=12.1, 3.0 Hz, 1H), 4.33 (dd, J=12.2, 6.2 Hz, 1H), 3.99 (s, 3H), 3.56-3.50 (m, 1H), 3.26 (dd, J=15.5, 7.6 Hz, 1H), 2.53 (s, 3H), 2.43 (s, 3H). $^{19}$F NMR (471 MHz, THF) δ -140.57 (s, 1F). LC-MS: Method H, 0 to 100% B. RT=1.97 min, MS (ESI) m/z: 533.2 (M+H)$^+$. Analytical HPLC purity (method B): 98%.

Example 146

(S)-(5-fluoro-2-(2-methoxy-7-methylquinoxalin-5-yl)-7,8-dihydrobenzofuro[5,4-d]thiazol-7-yl)methanol

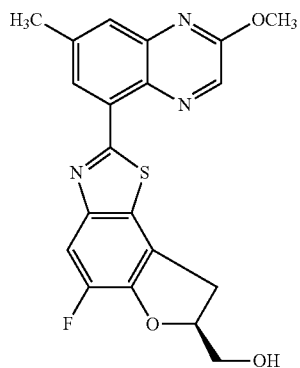
(146)

Intermediate 146A: (S)-(2-bromo-5-fluoro-7,8-dihydrobenzofuro[5,4-d]thiazol-7-yl) methanol

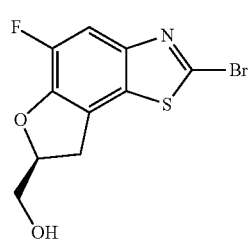
(146A)

Intermediate 145C (1.4 g) was subject to chiral SFC for separation using the following conditions: Instrument: PIC Solution Prep SFC; Column: Lux Cellulose-4, 30× 250 mm, 5 micron; Mobile Phase: 20% MeOH/80% CO$_2$; Flow Conditions: 100 mL/min, 150 Bar, 40° C.; Detector Wavelength: 220 nm. Injection Details: 2 mL of −20 mg/ml in MeOH. The faster eluting fractions (first peak, RT=8.2 min) were concentrated to give Intermediate 146A (0.65 g). $^1$H NMR (500 MHz, CHLOROFORM-d) δ 7.58 (d, J=10.5 Hz, 1H), 5.23-5.16 (m, 1H), 4.02 (dd, J=12.4, 3.0 Hz, 1H), 3.84 (dd, J=12.4, 5.2 Hz, 1H), 3.44-3.37 (m, 1H), 3.34-3.26 (m, 1H). $^{19}$F NMR (471 MHz, CHLOROFORM-d) δ −137.96 (s, 1F). LC-MS: Method H, 2 to 98% B. RT=0.75 min, MS (ESI) m/z: 303.9 and 305.9 (M+H)$^+$.

Example 146

A solution of Intermediate I-9 (35.4 mg, 0.162 mmol) and Intermediate 146A (52 mg, 0.171 mmol) in toluene/EtOH (3:1) (2.0 mL) was added to PdCl$_2$(dppf)—CH$_2$Cl$_2$ adduct (6.98 mg, 8.55 µmol). The mixture was flushed with argon for 1 min. To this was added 1.5 M Na$_2$CO$_3$ (0.313 mL, 0.470 mmol). The reaction mixture was heated in a microwave reactor at 140° C. for 45 min. HPLC indicated a completion of reaction. The reaction mixture was transferred to a round bottom flask, and the toluene was removed under vacuum. The mixture was treated with MeOH, sonicated. The precipitate was collected by filtration, washed with water, MeOH and dried under vacuum. The crude solid product (45 mg) was dissolved in 1:1 THF/DMSO (total 9 mL), and was purified via preparative HPLC (method A, 60-100% B over 10 min). The desired fractions were placed in a Speedvac over night to remove solvent, then dissolved in EtOAc/THF, washed with sat sodium bicarbonate, dried over sodium sulfate, concentrated and lyophilized to Example 146 (36 mg, 0.086 mmol, 50.3% yield) as a yellow lyophilate. $^1$H NMR (500 MHz, TIF) δ 8.76-8.73 (m, 1H), 8.59 (s, 1H), 7.79 (d, J=0.8 Hz, 1H), 7.66 (d, J=11.0 Hz, 1H), 5.18-5.11 (m, 1H), 4.32 (t, J=6.2 Hz, 1H), 4.14 (s, 3H), 3.89-3.83 (m, 1H), 3.81-3.75 (m, 1H), 3.54-3.40 (m, 2H), 2.67 (s, 3H). $^{19}$F NMR (471 MHz, THF) 6-140.72 (s, 1F LC-MS: Method H, 2 to 98% B. RT=0.97 min, MS (ESI) m/z: 398.10 (M+H)$^+$. Analytical HPLC purity (method B): 93%.

Example 147

(S)-(4-chloro-2-(2-methoxy-7-methylquinoxalin-5-yl)-7,8-dihydrobenzofuro[5,4-d]thiazo 1-7-yl)methyl (6-methylpyridin-3-yl)carbamate

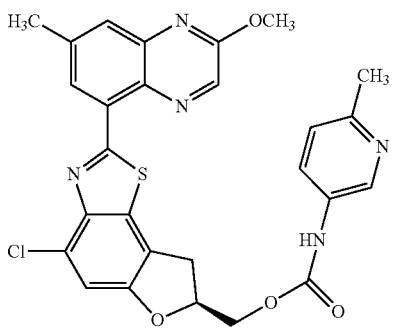

(147)

Intermediate 20B (73 mg, 0.133 mmol) was subject to chiral SFC for separation using the following conditions: Instrument: Burger Multigram II SFC; Column: Chiralpak IB, 30×250 mm, 5 micron; Mobile Phase: 40% MeOH/60% CO$_2$; Flow Conditions: 85 mL/min, 150 Bar, 40° C.; Detector Wavelength: 220 nm Injection Details: 1 mL of 12 mg/mL in MeOH/THF 1:1. The slow eluting fractions (second peak, RT=17.8 min) were concentrated and lyophilized to give Example 147 (28 mg): $^1$H NMR (500 MHz, THF) δ 8.99 (br. s., 1H), 8.74 (d, J=1.7 Hz, 1H), 8.49 (s, 1H), 8.40 (br. s., 1H), 7.85 (br. s., 1H), 7.73 (s, 1H), 7.04 (s, 2H), 5.31-5.21 (m, 1H), 4.50-4.43 (m, 1H), 4.43-4.36 (m, 1H), 4.09 (s, 3H), 3.49 (dd, J=15.5, 9.8 Hz, 1H), 3.25 (dd, J=15.7, 7.4 Hz, 1H), 2.64 (s, 3H), 2.38 (s, 3H); LC-MS: Method H, 2 to 98% B. RT=1.91 min, MS (ESI) m/z: 548.3 (M+H)$^+$. Analytical HPLC purity (method A): 98%.

Example 148

(4-chloro-2-(7-(hydroxymethyl)-2-methoxyquinoxalin-5-yl)-7,8-dihydrobenzofuro[5,4-d]thiazol-7-yl)methyl (6-methylpyridin-3-yl)carbamate

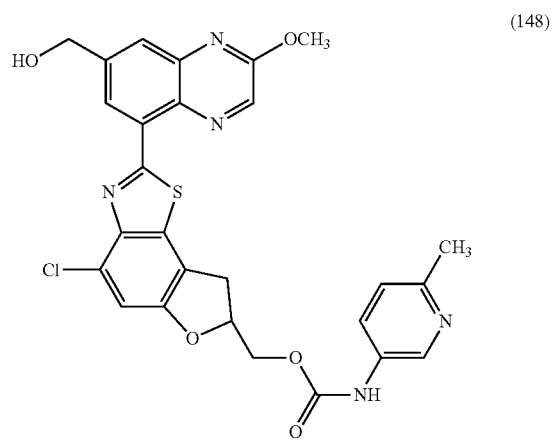 [SMILES: COc1cnc2c(-c3nc4c(Cl)cc5c(c4s3)CC(COC(=O)Nc3ccc(C)nc3)O5)cc(CO)cc2n1]

(148)

To Intermediate I-27 (15 mg, 0.035 mmol), Intermediate 20A (15.85 mg, 0.035 mmol) and PdCl$_2$(dppf)—CH$_2$Cl$_2$ adduct (1.423 mg, 1.742 μmol) was added toluene (0.75 mL) and EtOH (0.25 mL). The mixture was sonicated for 1 min, and flushed with argon. To this was added sodium carbonate (0.035 mL, 2M, 0.070 mmol). The reaction mixture was heated in a microwave at 120° C. for 40 min. LCMS indicated completion of the reaction. The reaction mixture was directly loaded to 12 g ISCO column which was eluted with hexanes for 3 min, then a 15 min gradient from 0% to 100% EtOAc in hexanes. The desired fractions were combined and concentrated to a yellow solid. The yellow solid was dissolved in DCM (2 mL) then TBAF (0.174 mL, 0.174 mmol) was added. The mixture was stirred at room temperature for 2 h. The reaction was quenched by addition of a small amount of MeOH/water/0.1% TFA (HPLC solvent). Solvent was removed under vacuum. The residual was dissolved in DMSO and was purified via preparative LC/MS (Method D: Gradient: 35-75% B over 15 minutes, then a 5-minute hold at 100% B then Method C: Gradient: 15-55% B over 20 minutes, then a 5-minute hold at 100% B). Fractions containing the desired product were combined and dried via centrifugal evaporation to yield Example 148 (0.7 mg, 1.204 μmol, 3.45% yield). $^1$H NMR (500 MHz, DMSO-d$_6$) δ 8.78 (s, 1H), 8.75 (d, J=1.7 Hz, 1H), 8.48 (br. s., 1H), 7.94 (d, J=0.8 Hz, 1H), 7.75 (br. s., 1H), 7.26 (s, 1H), 7.15 (br. s., 1H), 5.65 (t, J=5.8 Hz, 1H), 5.41-5.27 (m, 1H), 4.84 (d, J=5.5 Hz, 2H), 4.48 (dd, J=12.4, 2.8 Hz, 1H), 4.35 (dd, J=12.4, 6.9 Hz, 1H), 4.09 (s, 3H), 3.62-3.55 (m, 1H), 3.27-3.20 (m, 1H), 2.37 (br. s., 3H). LC-MS: method C, RT=1.96 min, MS (ESI) m/z: 564.3 (M+H)$^+$. Analytical HPLC purity (method B): 97%.

Example 149

(S)-(2-(2-methoxy-7-methylquinoxalin-5-yl)-7,8-dihydrobenzofuro[5,4-d]thiazol-7-yl)methanol

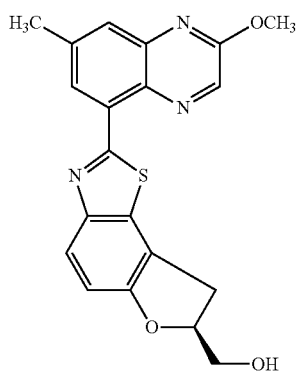
(149)

Intermediate 149A: (S)-(2-chloro-7,8-dihydrobenzofuro[5,4-d]thiazol-7-yl)methanol

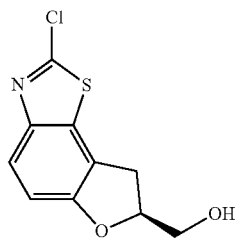
(149A)

Intermediate 144D (3.1 g) was subject to chiral SFC for separation using the following conditions: Instrument: Berger SFC MGII; Column: Chiralpak AS-H, 30×250 mm, 5 micron; Mobile Phase: 10% EtOH/ACN(1:1)/90% $CO_2$; Flow Conditions: 75 mL/min, 150 Bar, 40° C.; Detector Wavelength: 220 nm. Injection Details: 0.7 mL of 35 mg/mL in ACN/EtOH. The second eluting fractions (second peak, RT=11.2 min) were concentrated to give Intermediate 149A (1.4 g): $^1$H NMR (500 MHz, CHLOROFORM-d) δ 7.68 (d, J=8.8 Hz, 1H), 6.92 (d, J=8.5 Hz, 1H), 5.11-5.02 (m, 1H), 3.98-3.88 (m, 1H), 3.85-3.75 (m, 1H), 3.32 (dd, J=15.4, 9.6 Hz, 1H), 3.16 (dd, J=15.4, 7.4 Hz, 1H), 2.37 (br. s., 1H). LC-MS: Method H, 2 to 98% B. RT=0.75 min, MS (ESI) m/z: 241.9 and 243.9 (M+H)$^+$.

Example 149

A solution of I-9 (35.2 mg, 0.161 mmol) and Intermediate 149A (39 mg, 0.161 mmol) in toluene/EtOH (3:1) (2.0 mL) was added to PdCl$_2$(dppf)—CH$_2$Cl$_2$ adduct (6.59 mg, 8.07 μmol). The mixture was flushed with argon for 1 min. To this was added 1.5 M Na$_2$CO$_3$ (0.296 mL, 0.444 mmol). The reaction mixture was heated in a microwave reactor at 140° C. for 45 min, at which time HPLC indicated a completion of reaction. The reaction mixture was diluted with EtOAc/brine. The organic layer was collected, washed with brine, dried over sodium sulfate and concentrated. The crude residue was purified via preparative LC/MS (method A, 40-100% B over 10 minutes, then a 2-minute hold at 100% B). Fractions containing the desired product were combined and dried via centrifugal evaporation to yield the Example 149 (47 mg, 0.124 mmol, 77% yield) as a yellow solid. $^1$H NMR (400 MHz, chloroform-d) δ 8.62 (d, J=1.5 Hz, 1H), 8.56 (s, 1H), 7.93 (d, J=8.8 Hz, 1H), 7.75 (s, 1H), 7.03 (d, J=8.6 Hz, 1H), 5.18-5.09 (m, 1H), 4.13 (s, 3H), 4.01-3.92 (m, 1H), 3.89-3.80 (m, 1H), 3.48 (dd, J=15.4, 9.5 Hz, 1H), 3.26 (dd, J=15.6, 7.3 Hz, 1H), 2.65 (s, 3H), 1.98 (br. s., 1H); LC-MS: Method H; 2 to 98% B. RT=0.94 min, MS (ESI) m/z: 380.0 (M+H)$^+$. Analytical HPLC purity (method B): 95%.

Example 150

(S)-(2-(2-methoxy-7-methylquinoxalin-5-yl)-7,8-dihydrobenzofuro[5,4-d]thiazol-7-yl)methyl (2-methylpyrimidin-5-yl)carbamate

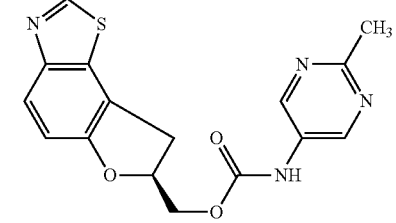
(150)

Intermediate 150A (S)-(2-(2-methoxy-7-methylquinoxalin-5-yl)-7,8-dihydrobenzofuro[5,4-d]thiazol-7-yl)methyl chloroformate

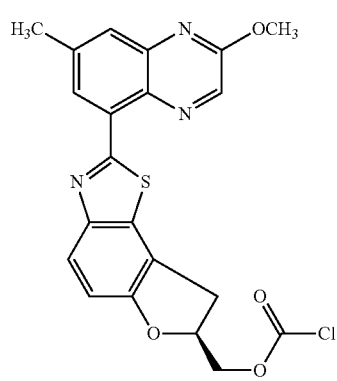
(150A)

To a suspension of Example 149 (47 mg, 0.124 mmol) in THF (3.0 mL) at room temperature was added 15% phosgene in toluene (0.354 mL, 0.495 mmol). The reaction mixture was left stirring at room temperature for 2 min, DIEA (0.065 mL, 0.372 mmol) was added. The reaction was continued at room temperature for 30 min, at which time IPLC and LCMS indicated the reaction was completed. Solvent was removed under high vacuum to give Intermediate 150A (54 mg, 0.122 mmol, 99% yield) as a slightly yellow solid. It was used for the next step without any purification. LC-MS: Method H, 2 to 98% B. RT=1.19 min, MS (ESI) m/z: 442.05 and 444.05 (M+H)$^+$.

Example 150

Intermediate 150A (54 mg, 0.122 mmol) in dichloromethane (2 mL) was added to a solution of 2-methylpyrimidin-5-amine (26.7 mg, 0.244 mmol) and pyridine (0.079 mL, 0.978 mmol) in dichloromethane (1.0 mL) dropwise. The reaction mixture was stirred at room temperature for 1 h, at which time LCMS and HPLC indicated a completion of reaction. The reaction mixture was diluted with dichloromethane (20 mL) and quenched with 0.5 N HCl (2 mL). After stirring at room temperature for 10 min, the mixture was extracted with dichloromethane. The organic layer was washed with brine, dried over sodium sulfate. After evaporation of solvent, the crude product was purified via preparative LC/MS (method A, 55-100% B over 10 minutes, then a 2-minute hold at 100% B). Fractions containing the desired product were combined and dried via centrifugal evaporation, then lyophilized to yield the Example 150 (31 mg, 0.059 mmol, 48.3% yield) as a yellow lyophilate. $^1$H NMR (500 MHz, acetone) δ 9.85 (br. s., 1H), 8.71 (br. s., 2H), 8.57 (s, 1H), 8.55 (d, J=1.9 Hz, 1H), 7.80 (d, J=8.8 Hz, 1H), 7.70 (s, 1H), 6.96 (d, J=8.8 Hz, 1H), 5.29-5.22 (m, 1H), 4.47 (dd, J=12.1, 3.0 Hz, 1H), 4.35 (dd, J=12.0, 6.5 Hz, 1H), 4.02 (s, 3H), 3.53 (dd, J=15.7, 9.9 Hz, 1H), 3.27 (dd, J=15.7, 7.4 Hz, 1H), 2.56 (s, 3H), 2.43 (s, 3H). LC-MS: Method H, 2 to 98% B. RT=2.08 min, MS (ESI) m/z: 515.2 (M+H)$^+$. Analytical HPLC purity (method B): 98%.

Example 151

(S)-(5-fluoro-2-(2-methoxy-7-methylquinoxalin-5-yl)-7,8-dihydrobenzofuro[5,4-d]thiazol-7-yl)methyl (2-methylpyrimidin-5-yl)carbamate

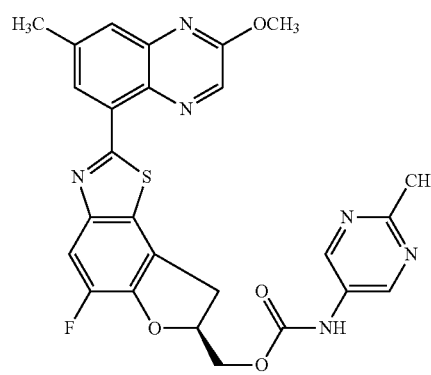
(151)

Intermediate 151A (S)-(2-bromo-5-fluoro-7,8-dihydrobenzofuro[5,4-d]thiazol-7-yl)methanol

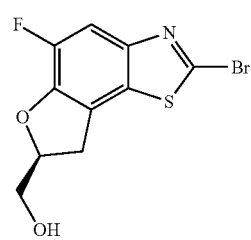
(151A)

Intermediate 145C (5.3 g) was subject to chiral SFC for separation using the following conditions: Instrument: PIC Solution Prep SFC; Column: Lux Cellulose-4, 30× 250 mm, 5 micron; Mobile Phase: 20% MeOH/80% CO$_2$; Flow Conditions: 100 mL/min, 150 Bar, 40° C.; Detector Wavelength: 220 nm. Injection Details: 2 mL of ~20 mg/ml in MeOH. The faster eluting fractions (first peak, RT=8.2 min) were concentrated to give Intermediate 151A (2.24 g). $^1$H NMR (500 MHz, CHLOROFORM-d) δ 7.58 (d, J=10.7 Hz, 1H), 5.20 (dddd, J=9.4, 7.8, 5.2, 3.2 Hz, 1H), 4.05-3.99 (m, 1H), 3.88-3.80 (m, 1H), 3.44-3.37 (m, 1H), 3.33-3.26 (m, 1H), 1.98 (t, J=6.1 Hz, 1H). $^{19}$F NMR (471 MHz, CHLOROFORM-d) δ −137.96 (s, 1F). LC-MS: Method H, 2 to 98% B. RT=0.75 min, MS (ESI) m/z: 303.9 and 305.9 (M+H)$^+$.

Intermediate 151B (S)-(5-fluoro-2-(2-methoxy-7-methylquinoxalin-5-yl)-7,8-dihydrobenzofuro[5,4-d]thiazol-7-yl)methanol

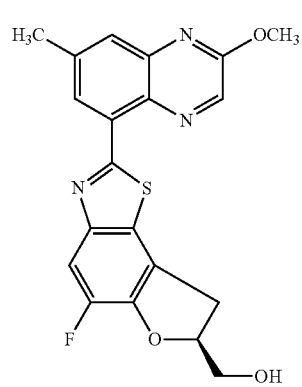
(151B)

A solution of I-9 (32.3 mg, 0.148 mmol) and Intermediate 151A (50 mg, 0.164 mmol) in toluene/EtOH (3:1) (1.5 mL) was added to PdCl$_2$(dppf)—CH$_2$Cl$_2$ adduct (6.71 mg, 8.22 μmol). The mixture was flushed with argon for 1 min. To this was added 1.5 M Na$_2$CO$_3$ (0.301 mL, 0.452 mmol). The reaction mixture was heated in a microwave reactor at 140° C. for 45 min. HPLC indicated a completion of reaction. The mixture was directly loaded on to a 40 g ISCO column and eluted with 0-100% EtOAc/DCM for 20 min. The desired fraction was collected and concentrated to yield Intermediate 151B (60 mg, 0.149 mmol, 91% yield). $^1$H NMR (500 MHz, CHLOROFORM-d) δ 8.63 (d, J=5.0 Hz, 1H), 8.57 (d, J=6.1 Hz, 1H), 7.77 (br. s., 1H), 7.73 (dd, J=11.1, 5.4 Hz, 1H), 5.24 (br. s., 1H), 4.15 (d, J=5.8 Hz, 3H), 4.02 (br. s., 1H), 3.90 (br. s., 1H), 3.62-3.47 (m, 1H), 3.44-3.27 (m, 1H), 2.66 (d, J=5.8 Hz, 3H). $^{19}$F NMR (471 MHz, THF) δ −140.72 (s, 1F); LC-MS: Method H, 2 to 98% B. RT=1.03 min, MS (ESI) m/z: 398.15 (M+H)$^+$.

Intermediate 151C (S)-(5-fluoro-2-(2-methoxy-7-methylquinoxalin-5-yl)-7,8-dihydrobenzofuro[5,4-d]thiazol-7-yl)methyl chloroformate

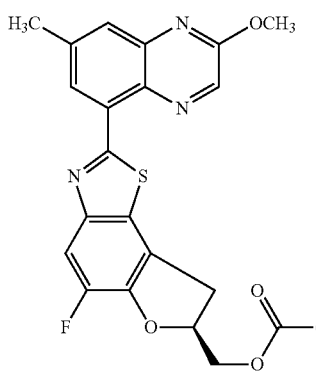

(151C)

To a suspension of Intermediate 151B (60 mg, 0.136 mmol) in THF (2 ml) at room temperature was added 15% phosgene in toluene (0.383 ml, 0.544 mmol). The reaction mixture was stirred for 2 min, DIEA (0.142 ml, 0.815 mmol) was added. The reaction was continued at room temperature for 40 min, at which time HPLC and LCMS indicated completion of reaction. Solvent was removed under high vacuum to give Intermediate 151C (63 mg, 0.136 mmol, 100% yield) as a slightly yellow solid. It was used for the next step without any purification. LC-MS: Method H, 2 to 98% B. RT=1.12 min, MS (ESI) m/z: 460.00 and 462.05 (M+H)$^+$.

Example 151

Intermediate 151C (63 mg, 0.136 mmol) in dichloromethane (2 mL) was added to a solution of 2-methylpyrimidin-5-amine (22.24 mg, 0.204 mmol) and pyridine (0.088 ml, 1.087 mmol) in dichloromethane (2 mL) dropwise. The reaction mixture was stirred at room temperature for 0.5 h, at which time LCMS and HPLC indicated a completion of reaction. The reaction mixture was quenched with 0.5 N HCl (2 mL) and extracted with DCM. The combined organic layer was washed with 1N HCl, NaHCO$_3$ and brine, dried with MgSO$_4$ and concentrated. The crude was purified with a 40 g ISCO column eluted with 0-100% EtOAc/DCM for 20 min. The desired fractions were collected and concentrated to give 20 mg of desired product. The product was further purified using a preparative HPLC (method A, 55-100% B over 10 minutes, then a 2-minute hold at 100% B). Fractions containing the desired product were combined and dried via centrifugal evaporation, then lyophilized to yield the Example 151 (17 mg) as a yellow lyophilate. $^1$H NMR (500 MHz, THF) δ 9.16 (br. s., 1H), 8.72 (s, 3H), 8.56 (s, 1H), 7.77 (s, 1H), 7.68 (d, J=11.0 Hz, 1H), 5.41-5.31 (m, 1H), 4.60-4.39 (m, 2H), 4.10 (s, 3H), 3.68-3.61 (m, 1H), 3.38 (dd, J=15.7, 7.4 Hz, 1H), 2.64 (s, 3H), 2.53 (s, 3H). $^{19}$F NMR (376 MHz, CHLOROFORM-d) δ −142.43 (s, 1F). LC-MS: Method H, 0 to 100% B. RT=1.02 min, MS (ESI) m/z: 533.15 (M+H)$^+$. Analytical HPLC purity (method B): 99% purity.

Example 152

(S)-(2-(2-ethoxy-7-methylquinoxalin-5-yl)-5-fluoro-7,8-dihydrobenzofuro[5,4-d]thiazol-7-yl)methanol

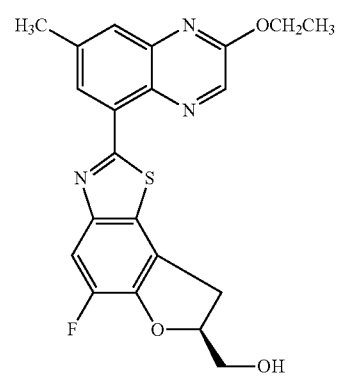

(152)

Intermediate 152A (S)-(2-(2-(difluoromethoxy)-7-methylquinoxalin-5-yl)-5-fluoro-7,8-dihydrobenzofuro[5,4-d]thiazol-7-yl)methanol

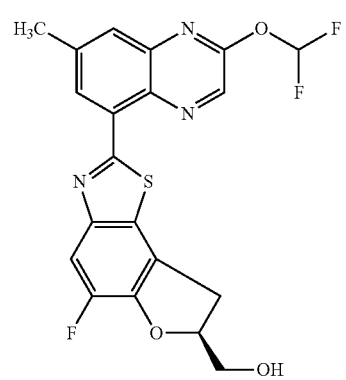

(152A)

A solution of I-1 (34.9 mg, 0.137 mmol) and Intermediate 151A (44 mg, 0.145 mmol) in toluene/EtOH (3:1) (2.0 mL) was added to PdCl$_2$(dppf)—CH$_2$Cl$_2$ adduct (5.91 mg, 7.23 μmol). The mixture was flushed with argon for 1 min. To this was added 1.5 M Na$_2$CO$_3$ (0.212 mL, 0.318 mmol). The reaction mixture was heated in a microwave at 130° C. for 45 min. IPLC indicated a completion of reaction. The reaction mixture was transferred to a round bottom flask, and toluene was removed under vacuum. The mixture was treated with MeOH, sonicated. The precipitate was collected by filtration, washed with water, MeOH and dried under vacuum. The crude solid product (ca 40 mg) was dissolved in THF (2.0 mL), treated with SilaMeta Thiol resin (70 mg) at room temperature overnight. The mixture was filtered through a 4.0 g Silica gel cartridge, rinsed with THF. After evaporation of solvent, Intermediate 152A (38 mg, 0.088 mmol, 60.6% yield) was obtained as a bright yellow solid. LC-MS: Method H, 2 to 98% B. RT=1.00 min, MS (ESI) m/z: 434.06 (M+H)$^+$.

Example 152

To a solution of Intermediate 152A (38 mg, 0.088 mmol) dissolved in THF (1.6 mL) and EtOH (0.8 mL) was added 21% sodium ethoxide in EtOH (0.131 mL, 0.351 mmol). The reaction mixture was stirred at room temperature overnight, at which time HPLC and LCMS indicated a completion of the reaction. The reaction was quenched by addition of 0.3 mL 1.0 N HCl, purified via preparative LC/MS (method C, 40-100% B over 20 minutes, then a 5-minute hold at 100% B). Fractions containing the desired product were combined and dried via centrifugal evaporation to yield Example 152 (15 mg, 40% yield). $^1$H NMR (500 MHz, DMSO-d$_6$) δ 8.72 (s, 1H), 8.57 (s, 1H), 7.85 (d, J=11.1 Hz, 1H), 7.81 (s, 1H), 5.24-5.19 (m, 1H), 4.57-4.49 (m, 2H), 3.31 (dd, J=15.7, 7.2 Hz, 1H), 1.45 (t, J=7.1 Hz, 3H). LC-MS: Method H, 2 to 98% B. RT=2.39 min, MS (ESI) m/z: 412.20 (M+H)$^+$. Analytical HPLC purity (method B): 98% purity.

Example 153

(R)-(2-(2-ethoxy-7-methylquinoxalin-5-yl)-5-fluoro-7,8-dihydrobenzofuro[5,4-d]thiazol-7-yl)methyl (2-methylpyrimidin-5-yl)carbamate

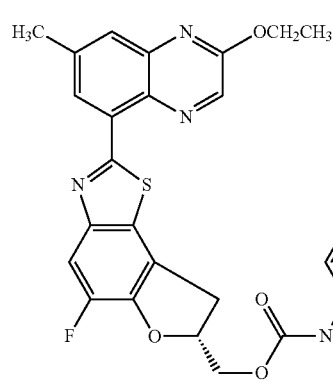

(153)

Intermediate 153A (R)-(2-(2-(difluoromethoxy)-7-methylquinoxalin-5-yl)-5-fluoro-7,8-dihydrobenzofuro[5,4-d]thiazol-7-yl)methanol

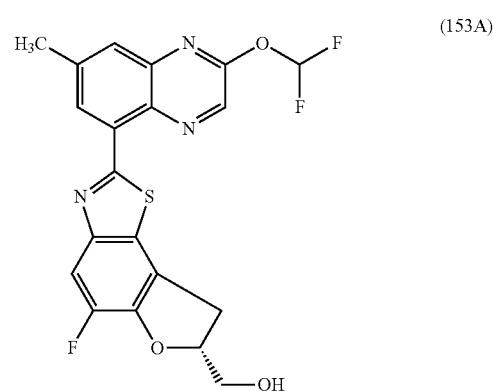 [SMILES: Cc1cc(-c2nc3cc(F)c4c(c3s2)C[C@H](CO)O4)c2ncc(OC(F)F)nc2c1]

(153A)

A solution of I-1 (336 mg, 1.324 mmol) and Intermediate 145D (424 mg, 1.394 mmol) in toluene/EtOH (3:1) (10 mL) was added to PdCl$_2$(dppf)—CH$_2$Cl$_2$ adduct (50.1 mg, 0.061 mmol). The mixture was flushed with argon for 1 min. To this was added 1.5 M Na$_2$CO$_3$ (1.859 mL, 2.79 mmol). The reaction mixture was heated in a microwave reactor at 125° C. for 45 min. HPLC indicated a completion of reaction. The reaction mixture was transferred to a round bottom flask, and the toluene was removed under vacuum. The mixture was treated with MeOH, sonicated. The precipitate was collected by filtration, washed with water, MeOH and dried under vacuum. The crude solid product (630 mg) was dissolved in THF (18 mL) and treated with SilaMeta Thiol resin (570 mg) at 50° C. for 6 h. After cooling to rt, the reaction mixture was filtered through a 12 g Silica gel cartridge, washed with THF and EtOAc. The filtrate was concentrated to give Intermediate 153A (380 mg, 0.877 mmol, 62.9% yield) as a yellow solid. LC-MS: Method H, 2 to 98% B. RT=0.97 min, MS (ESI) m/z: 434.00 (M+H)$^+$.

Intermediate 153B (R)-(2-(2-ethoxy-7-methylquinoxalin-5-yl)-5-fluoro-7,8-dihydrobenzofuro[5,4-d]thiazol-7-yl)methanol

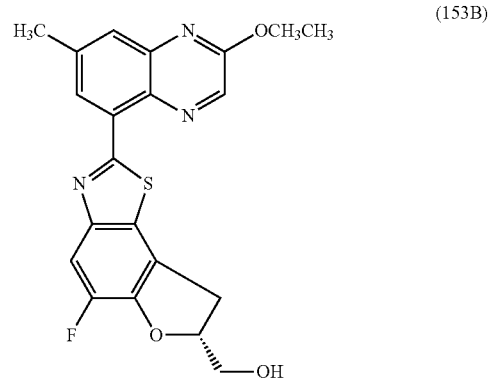

(153B)

To a solution of Intermediate 153A (30 mg, 0.069 mmol) dissolved in THF (1.5 mL) and EtOH (0.7 mL) was added 21% sodium ethoxide in EtOH (0.103 mL, 0.277 mmol). The reaction mixture was stirred at 50° C. for 1.0 h and then at room temperature overnight, at which time HPLC and LCMS indicated a completion of the reaction. Solvent was removed under vacuum, and the crude was triturated with MeOH. The precipitate was collected by filtration, rinsed with MeOH, chased with toluene and dried to give Intermediate 153B (27 mg, 0.066 mmol, 95% yield) as a yellow solid. LC-MS: Method H, 2 to 98% B. RT=1.0 min, MS (ESI) m/z:412.05 (M+H)⁺.

Intermediate 153C (R)-(2-(2-ethoxy-7-methylquinoxalin-5-yl)-5-fluoro-7,8-dihydrobenzofuro[5,4-d]thiazol-7-yl)methyl chloroformate

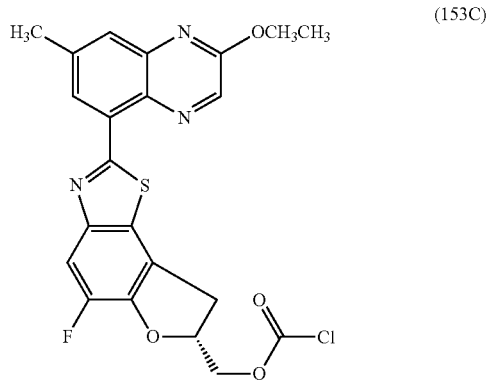

(153C)

To a suspension of Intermediate 153B (27 mg, 0.066 mmol) in THF (1.8 mL) at room temperature was added 15% phosgene in toluene (0.187 mL, 0.262 mmol). The reaction mixture was left stirring at room temperature for 2 min, DIEA (0.034 mL, 0.197 mmol) was added. The reaction was continued at room temperature for 30 min, at which time IPLC and LCMS indicated the reaction was complete and clean. Solvent was completely removed under high vacuum to give Intermediate 153C (30 mg, 0.063 mmol, 96% yield) as a slightly yellow solid. It was used for the next step without any purification. LC-MS: Method H, 2 to 98% B. RT=1.13 min, MS (ESI) m/z: 474.05 and 476.05 (M+H)⁺.

Example 153

Intermediate 153C (30 mg, 0.063 mmol) in dichloromethane (1.0 mL) was added to a solution of 2-methylpyrimidin-5-amine (13.82 mg, 0.127 mmol) and pyridine (0.041 mL, 0.506 mmol) in dichloromethane (1.0 mL) dropwise. The reaction mixture was stirred at room temperature for 1 h, at which time LCMS and IPLC indicated a completion of reaction. The reaction mixture was quenched with 0.5 N HCl (5 mL) and extracted with dichloromethane. The organic layer was washed with brine, dried over sodium sulfate and concentrated. The crude product was triturated with MeOH (2×), spun in a centrifuge. The liquid was removed and the solid was collected, dried and lyophilized to give Example 153 (20 mg, 0.034 mmol, 53.8% yield) as a slightly yellow lyophilate. ¹H NMR (500 MHz, THF) δ 8.60 (d, J=1.7 Hz, 3H), 8.44-8.40 (m, 1H), 7.63 (d, J=0.8 Hz, 1H), 7.57 (d, J=10.7 Hz, 1H), 5.29-5.22 (m, 1H), 4.49-4.42 (m, 3H), 4.33 (dd, J=12.2, 6.2 Hz, 1H), 3.56-3.51 (m, 1H), 3.27 (dd, J=15.1, 7.4 Hz, 1H), 2.53 (s, 3H), 2.43 (s, 3H), 1.37 (t, J=7.0 Hz, 3H); LC-MS: Method A, 40 to 100% B. RT=2.21 min, MS (ESI) m/z: 547.2(M+H)⁺. Analytical IPLC purity (method B): 93% purity.

Example 154

(R)-(5-fluoro-2-(2-methoxy-7-methylquinoxalin-5-yl)-7,8-dihydrobenzofuro[5,4-d]thiazol-7-yl)methyl (5-cyanopyridin-3-yl)carbamate

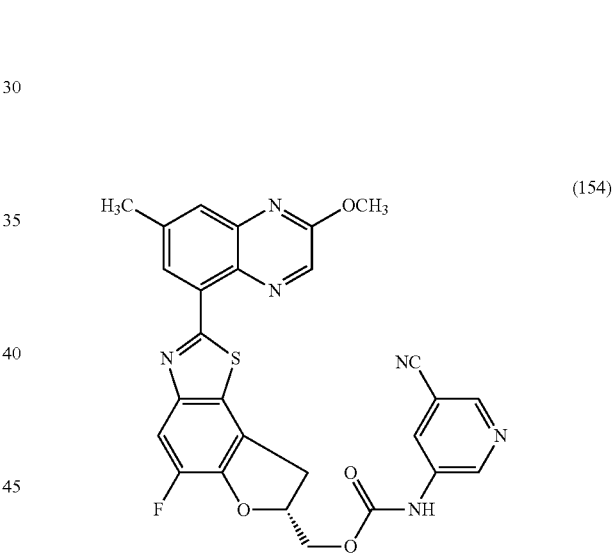

(154)

5-Aminonicotinonitrile (19.49 mg, 0.164 mmol) and pyridine (0.060 mL, 0.748 mmol) were dissolved in DCM (1.0 mL). Intermediate 145F (43 mg, 0.094 mmol) in DCM (2 mL) was added dropwise and the reaction mixture was stirred at room temperature for 30 minutes. The reaction was quenched by addition of 1.0 N HCl (0.7 mL). Dichloromethane was removed. The mixture was triturated with MeOH, centrifuged and the precipitate was collected to give 60 mg crude. The crude was dissolved in DMSO and purified via preparative LC/MS (method C, 45-95% B over 20 min, then a 5-min hold at 100% B). Fractions containing the desired product were combined and dried via centrifugal evaporation to yield the Example 154 (40.1 mg, 78% yield). ¹H NMR (500 MHz, CHLOROFORM-d) δ 8.58 (br. s., 1H), 8.51 (s, 1H), 8.46 (br. s., 1H), 8.43 (s, 1H), 8.28 (br. s., 1H), 7.82 (br. s., 1H), 7.69 (s, 1H), 7.62 (d, J=11.0 Hz, 1H), 5.27 (br. s., 1H), 4.57 (d, J=11.8 Hz, 1H), 4.39 (dd, J=12.1, 6.3 Hz, 1H), 4.06 (s, 3H), 3.54 (dd, J=15.3, 9.8 Hz, 1H), 3.24 (dd, J=15.5, 7.6 Hz, 1H), 2.57 (s, 3H); LC-MS: method C, 2 to 98% B. RT=2.38 min, MS (ESI) m/z: 543.1 (M+H)+. Analytical HPLC purity (method B): 99%.

Example 155

(R)-(5-fluoro-2-(2-methoxy-7-methylquinoxalin-5-yl)-7,8-dihydrobenzofuro[5,4-d]thiazo 1-7-yl)methyl (2-(2-hydroxyethyl)pyrimidin-5-yl)carbamate

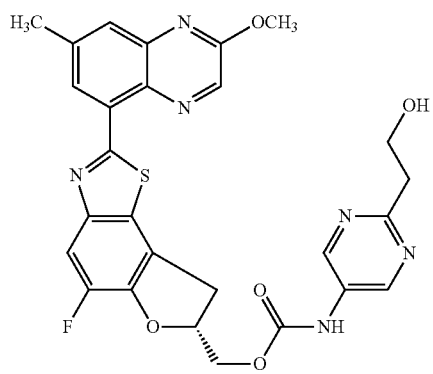

(155)

Intermediate I-54 (50 mg, 0.132 mmol) was dissolved in DCM (1.0 mL) along with pyridine (0.061 mL, 0.757 mmol). Intermediate 145F (43.5 mg, 0.095 mmol) in DCM (2 mL) was added dropwise. The reaction mixture was stirred at room temperature for 30 minutes, then quenched with 1.0 N HCl (0.7 mL). Solvent was removed under vacuum. The crude was dried under high vacuum overnight, then treated with THF (2.0 mL) and 4 mL of 20:1 MeOH/ concentrated HCl overnight. HPLC and LCMS indicated a complete deprotection of the silyl group. Solvent was removed under vacuum. The crude was dissolved in DMF (3.0 mL), neutralized with 0.1 mL DIEA, filtered and purified via preparative LC/MS (method C, 40-80% B over 20 min, then a 5-min hold at 100% B). Fractions containing the desired product were combined and dried via centrifugal evaporation to yield Example 155 (17.6 mg, 0.031 mmol, 33.1% yield): ¹H NMR (500 MHz, DMSO-d₆) δ 8.74 (br. s., 1H), 8.64 (s, 1H), 8.50 (s, 1H), 7.81 (d, J=11.3 Hz, 1H), 7.77 (s, 1H), 5.40 (d, J=7.9 Hz, 1H), 4.54 (d, J=11.6 Hz, 1H), 4.41 (dd, J=12.4, 6.6 Hz, 1H), 4.05 (s, 3H), 3.70 (s, 3H), 3.60 (dd, J=15.9, 10.1 Hz, 1H), 3.30 (dd, J=15.7, 7.8 Hz, 1H), 2.94 (br. s., 2H), 2.59 (s, 3H), LC-MS: method C, 2 to 98% B. RT=2.07 min, MS (ESI) m/z: 563.15 (M+H)+. Analytical HPLC purity (method B): 100%.

Example 156

(S)-methyl 2-(2-methoxy-7-methylquinoxalin-5-yl)-7,8-dihydrobenzofuro[5,4-d]thiazole-7-carboxyla te

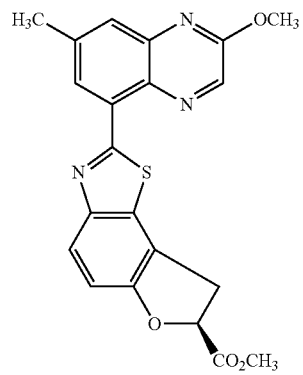

(156)

Intermediate 156A: (S)-2-chloro-7,8-dihydrobenzofuro[5,4-d]thiazole-7-carboxylic acid

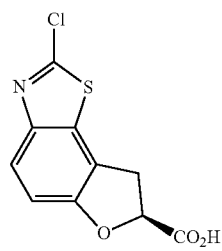

(156A)

An aqueous solution of 1.0 M NaBr (0.077 mL, 0.077 mmol), 1.0 M tetrabutylammonium bromide (0.077 mL, 0.077 mmol), TEMPO (28.7 mg, 0.184 mmol) and saturated aqueous solution of NaHCO₃(4 mL, 1.531 mmol) were added to a solution of Intermediate 149A (370 mg, 1.531 mmol) in dichloromethane (16 mL) and water (4 mL) cooled with an ice-water bath. The resulting mixture was treated with an aqueous solution of sodium hypochlorite (chlorine content 10-14%) (2.374 mL, 4.59 mmol) and continuously stirred for 2.0 h as the temperature increased from 0° C. to rt, at which time LCMS indicated a completion of the reaction. The reaction media was neutralized with HCl (1.0 N, 8 mL) to pH 3, diluted with water, and extracted with dichloromethane. The organic layer was washed with brine, dried over sodium sulfate and concentrated to give Intermediate 156A (391 mg, 1.529 mmol, 100% yield). It was used for the next step without further purification. LC-MS: method H, 2 to 98% B. RT=0.723 min, MS (ESI) m/z: 255.95 and 257.95 (M+H)+.

Intermediate 156B: (S)-methyl 2-chloro-7,8-dihydrobenzofuro[5,4-d]thiazole-7-carboxylate

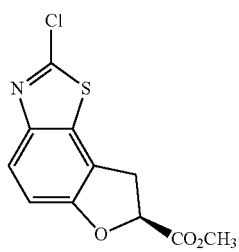

(156B)

To a solution of Intermediate 156A (380 mg, 1.486 mmol) in CH$_2$Cl$_2$ (10 mL) and MeOH (4 mL) at room temperature was added (diazomethyl)trimethylsilane 2.0 M in diethyl ether (1.486 mL, 2.97 mmol). The mixture was stirred at room temperature for 1.0 h, at which time HPLC and LCMS indicated a completion of reaction. Solvent was removed under vacuum. The crude product was purified by flash chromatography (loading in chloroform, 0% to 35% EtOAc in hexane over 15 min using a 12 g silica gel cartridge). The desired fractions were combined and concentrated to yield Intermediate 156B (350 mg, 1.298 mmol, 87% yield) as oil. $^1$H NMR (500 MHz, CHLOROFORM-d) δ 7.74 (d, J=8.8 Hz, 1H), 7.06 (d, J=8.8 Hz, 1H), 5.37 (dd, J=10.7, 6.6 Hz, 1H), 3.83 (s, 3H), 3.65 (dd, J=16.0, 10.7 Hz, 1H), 3.49 (dd, J=15.8, 6.5 Hz, 1H). LC-MS: method H, 2 to 98% B. RT=0.83 min, MS (ESI) m/z: 269.90 and 271.90 (M+H)$^+$.

Intermediate 156C (S)-2-(2-methoxy-7-methylquinoxalin-5-yl)-7,8-dihydrobenzofuro[5,4-d]thiazole-7-carboxylic acid

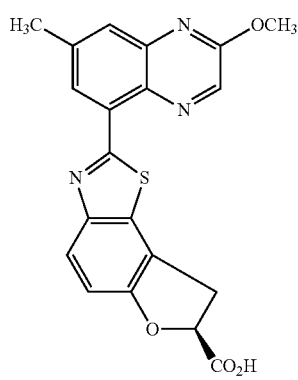

(156C)

A solution of I-9 (30.7 mg, 0.141 mmol) and Intermediate 156B (38 mg, 0.141 mmol) in toluene/MeOH (3:1) (2.0 mL) was added to PdCl$_2$(dppf)—CH$_2$Cl$_2$ adduct (5.75 mg, 7.04 μmol). The mixture was flushed with argon for 1 min. To this was added 1.5 M Na$_2$CO$_3$ (0.207 mL, 0.310 mmol). The reaction mixture was heated in a microwave at 125° C. for 45 min. HPLC and LCMS indicated a completion of reaction. The reaction mixture was transferred to a round bottom flask, toluene was removed under vacuum. The mixture was treated with MeOH, sonicated. The precipitate was dissolved in DMSO and purified via preparative LC/MS (method C, 30-80% B over 14 min, then a 5-min hold at 100% B). Fractions containing the desired product were combined and dried via centrifugal evaporation to yield Intermediate 156C (29.1 mg, 0.074 mmol, 52.5% yield) $^1$H NMR (500 MHz, DMSO-d$_6$) δ 8.61 (s, 1H), 8.48 (s, 1H), 7.90 (d, J=8.9 Hz, 1H), 7.72 (s, 1H), 7.12 (d, J=8.9 Hz, 1H), 5.43 (dd, J=10.4, 6.1 Hz, 1H), 4.04 (s, 3H), 3.45 (dd, J=15.9, 5.8 Hz, 1H), 2.57 (br. s., 3H), LC-MS: method C, 2 to 98% B. RT=2.18 min, MS (ESI) m/z: 394.15 (M+H)$^+$. Analytical HPLC purity (method B): 100%.

Example 156

To a solution of Intermediate 156C (12 mg, 0.031 mmol) in THF (2 mL) and MeOH (0.8 mL) at room temperature was added (diazomethyl)trimethylsilane 2.0 M in hexanes (0.061 mL, 0.122 mmol). The mixture was stirred at room temperature for 4 h, at which time HPLC and LCMS indicated a completion of reaction. Solvent was removed under vacuum. The crude was dissolved in DMSO and purified via preparative LC/MS (method C, 35-100% B over 20 min, then a 5-min hold at 100% B). Fractions containing the desired product were combined and dried via centrifugal evaporation to yield Example 156 (1.4 mg, 2.96 μmol, 9.69% yield). $^1$H NMR (500 MHz, CHLOROFORM-d) δ 8.55 (s, 1H), 8.48 (s, 1H), 7.88 (d, J=8.8 Hz, 1H), 7.68 (s, 1H), 7.06 (d, J=8.5 Hz, 1H), 5.34 (dd, J=10.7, 6.6 Hz, 1H), 4.05 (s, 3H), 3.71 (dd, J=15.7, 10.7 Hz, 1H), 3.55 (dd, J=15.7, 6.6 Hz, 1H), 2.57 (s, 3H); LC-MS: method C, 2 to 98% B. RT=2.40 min, MS (ESI) m/z: 408.30 (M+H)$^+$. Analytical HPLC purity (method B): 86%.

Example 157

(R)-(5-fluoro-2-(2-methoxy-7-methylquinoxalin-5-yl)-7,8-dihydrobenzofuro[5,4-d]thiazo 1-7-yl)methyl pyridin-3-ylcarbamate

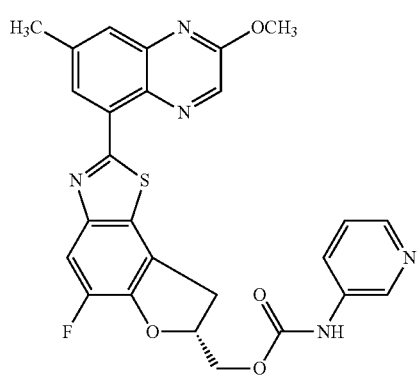

(157)

Pyridin-3-amine (13.10 mg, 0.139 mmol) was dissolved in DCM (1.0 mL) along with pyridine (0.045 mL, 0.557 mmol). Intermediate 145F (32 mg, 0.070 mmol) in DCM (2 mL) was added dropwise. The reaction mixture was stirred at room temperature for 30 minutes, then quenched by addition of 1.0 N HCl (0.6 mL). Dichloromethane was removed under vacuum. The mixture was dissolved in THF/DMSO (1:1, 7 mL), and purified with preparative HPLC (method A, 40-100% B in 8 min. Then 100% B in 4 min.). The desired fractions were placed in a SpeedVac overnight to remove solvent, then lyophilized to give Example 157 (25.6 mg, 0.048 mmol, 69.0% yield) as a yellow lyophilate. $^1$H NMR (500 MHz, TIF) δ 9.18 (br. s., 1H), 8.72 (d, J=1.7 Hz, 1H), 8.56 (s, 1H), 8.20 (br. s, 1H), 8.00 (br. s., 1H), 7.77 (dd, J=1.8, 1.0 Hz, 1H), 7.71-7.66 (d, J=11.0 Hz, 1H), 7.20 (br. s., 1H), 5.41-5.33 (m, 1H), 4.55 (dd, J=12.2, 3.2 Hz, 1H), 4.43 (dd, J=12.1, 6.3 Hz, 1H), 4.12-4.09 (s, 3H), 3.66-3.61 (m, 1H), 3.38 (dd, J=15.4, 7.4 Hz, 1H), 2.64 (s, 3H); $^{19}$F NMR (471 MHz, THF) δ −142.41 (s, 1F); LC-MS: method H, 2 to 98% B. RT=0.85 min, MS (ESI) m/z: 518.15 (M+H)$^+$. Analytical HPLC purity (method A): 97% purity.

Example 158

(R)-(5-fluoro-2-(2-methoxy-7-methylquinoxalin-5-yl)-7,8-dihydrobenzofuro[5,4-d]thiazo 1-7-yl)methyl pyridazin-4-ylcarbamate

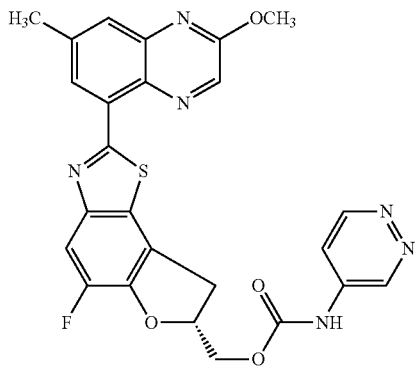

(158)

Pyridazin-4-amine (13.24 mg, 0.139 mmol) was dissolved in DCM (1.0 mL) along with pyridine (0.045 mL, 0.557 mmol). Intermediate 145F (32 mg, 0.070 mmol) in DCM (2.0 mL) was added dropwise. The reaction mixture was stirred at room temperature for 30 minutes, then quenched by addition of 1.0 N HCl (0.6 mL). Dichloromethane was removed under vacuum. The mixture was dissolved in THF/DMSO (1:1, 7 mL), and purified using a preparative preparative HPLC (method A, 35-100% B in 8 min. Then 100% B in 4 min.). The desired fractions were placed in a SpeedVac overnight to remove solvent, then lyophilized to give Example 158 (6.7 mg, 0.013 mmol, 18.01% yield) as a yellow solid. $^1$H NMR (500 MHz, THF) δ 9.70 (br. s., 1H), 9.09 (br. s., 1H), 8.92 (br. s., 1H), 8.72 (s, 1H), 8.56 (s, 1H), 7.82 (br. s., 1H), 7.78 (s, 1H), 7.72 (d, J=11.0 Hz, 1H), 5.39 (d, J=6.9 Hz, 1H), 4.60 (d, J=9.1 Hz, 1H), 4.48 (dd, J=11.7, 6.2 Hz, 1H), 4.11 (s, 3H), 3.65 (dd, J=14.9, 9.9 Hz, 1H), 3.45-3.35 (m, 1H), 2.65 (s, 3H); $^{19}$F NMR (471 MHz, THF) δ −142.43 (s, 1F); LC-MS: method H, 2 to 98% B. RT=0.87 min, MS (ESI) m/z: 519.15(M+H)$^+$. Analytical HPLC purity (method A): 97% purity.

Example 159

(R)-(5-fluoro-2-(2-methoxy-7-methylquinoxalin-5-yl)-7,8-dihydrobenzofuro[5,4-d]thiazol-7-yl)methyl (6-methylpyridin-3-yl)carbamate

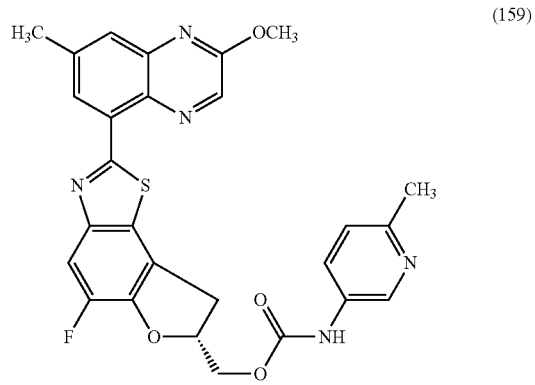

(159)

6-Methylpyridin-3-amine (15.05 mg, 0.139 mmol) was dissolved in DCM (1.0 mL) along with pyridine (0.045 mL, 0.557 mmol). Intermediate 145F (32 mg, 0.070 mmol) in DCM (2 mL) was added dropwise. The reaction mixture was stirred at room temperature for 30 minutes, then quenched by addition of 1.0 N HCl (0.6 mL). Dichloromethane was removed under vacuum. The mixture was dissolved in THF/DMSO (1:1, 7 mL), and purified with preparative HPLC (method A, 40-100% B in 8 min. Then 100% B in 4 min.). The desired fractions were placed in a SpeedVac overnight to remove solvent, then dissolved in a mixture of THF/EtOAc, washed with saturated sodium bicarbonate, brine, dried over sodium sulfate and concentrated. The final product was lyophilized to give Example 159 (29.7 mg, 0.054 mmol, 78% yield) as a yellow solid. $^1$H NMR (500 MHz, THF) δ 9.04 (br. s, 1H), 8.72 (d, J=1.7 Hz, 1H), 8.56 (s, 1H), 8.42 (br. s., 1H), 7.87 (br. s., 1H), 7.77 (dd, J=1.9, 0.8 Hz, 1H), 7.70-7.65 (d, J=11.0 Hz, 1H), 7.05 (d, J=7.4 Hz, 1H), 5.40-5.31 (m, 1H), 4.53 (dd, J=12.2, 3.2 Hz, 1H), 4.41 (dd, J=12.2, 6.2 Hz, 1H), 4.10 (s, 3H), 3.65-3.62 (m, 1H), 3.38 (dd, J=15.4, 7.4 Hz, 1H), 2.64 (s, 3H), 2.47 (s, 3H); $^{19}$F NMR (471 MHz, THF) δ −142.41 (s, 1F); LC-MS: method H, 2 to 98% B. RT=0.85 min, MS (ESI) m/z:532.15 (M+H)$^+$. Analytical HPLC purity (method A): 97% purity.

Example 160

(R)-(5-fluoro-2-(2-methoxy-7-methylquinoxalin-5-yl)-7,8-dihydrobenzofuro[5,4-d]thiazol-7-yl)methyl (2-methylpyridin-4-yl)carbamate

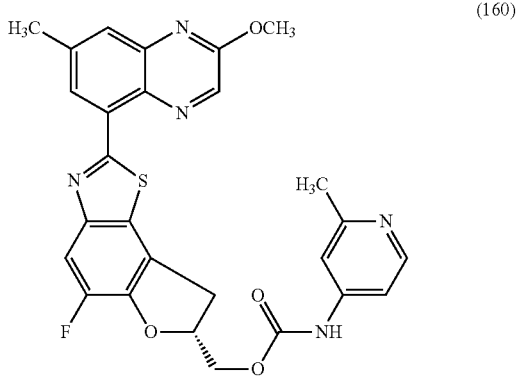 [SMILES: COc1cnc2c(-c3nc4cc(F)c5c(c4s3)C[C@H](COC(=O)Nc3cncc(C#N)c3)O5)cc(C)cc2n1]

(160)

2-Methylpyridin-4-amine (15.05 mg, 0.139 mmol) was dissolved in DCM (1.0 mL) along with pyridine (0.045 mL, 0.557 mmol). Intermediate 145F (32 mg, 0.070 mmol) in DCM (2 mL) was added dropwise and the reaction stirred at room temperature for 30 minutes. LCMS analysis showed complete consumption of the starting materials and formation of desired product as the major component of the mixture. The reaction was quenched by addition of 1.0 N HCl (0.6 mL). Dichloromethane was removed under vacuum. The mixture was dissolved in THF/DMSO (1:1, 7 mL), and was purified with preparative HPLC (method A, 35-100% B in 8 min. Then 100% B in 4 min.). The desired fractions were placed in a SpeedVac overnight to remove solvent, then dissolved in a mixture of THF/EtOAc, washed with saturated sodium bicarbonate, brine, dried over sodium sulfate and concentrated. The final product was lyophilized to give Example 160 (25.8 mg, 0.047 mmol, 67.0% yield) as a yellow lyophilate. $^1$H NMR (500 MHz, THF) δ 9.28 (s, 1H), 8.72 (d, J=1.7 Hz, 1H), 8.55 (s, 1H), 8.26 (br. s., 1H), 7.77 (dd, J=1.8, 1.0 Hz, 1H), 7.71 (d, J=11.0 Hz, 1H), 7.34 (br. s, 1H), 7.17 (br. s, 1H), 5.40-5.31 (m, 1H), 4.55 (dd, J=12.1, 3.0 Hz, 1H), 4.43 (dd, J=12.1, 6.3 Hz, 1H), 4.10 (s, 3H), 3.67-3.61 (m, 1H), 3.37 (dd, J=15.7, 7.7 Hz, 1H), 2.64 (s, 3H), 2.40 (s, 3H); $^{19}$F NMR (471 MHz, THF) δ-140.56 (s, 1F); LC-MS: method H, 2 to 98% B. RT=0.87 min, MS (ESI) m/z: 532.15 (M+H)$^+$. Analytical HPLC purity (method A): 96% purity.

Example 161

(R)-(5-fluoro-2-(2-methoxy-7-methylquinoxalin-5-yl)-7,8-dihydrobenzofuro[5,4-d]thiazol-7-yl)methyl (5-fluoropyridin-3-yl)carbamate

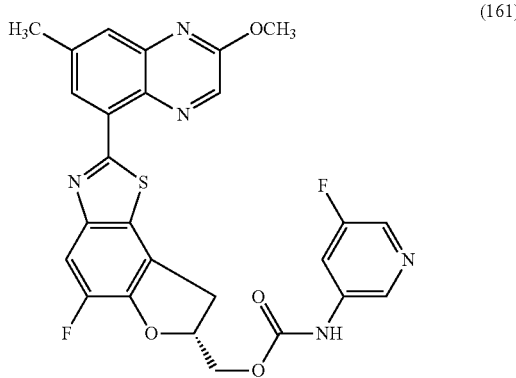 [SMILES: COc1cnc2c(-c3nc4cc(F)c5c(c4s3)C[C@H](COC(=O)Nc3cncc(F)c3)O5)cc(C)cc2n1]

(161)

5-Fluoropyridin-3-amine (15.60 mg, 0.139 mmol) was dissolved in DCM (1.0 mL) along with pyridine (0.045 mL, 0.557 mmol). Intermediate 145F (32 mg, 0.070 mmol) in DCM (2 mL) was added dropwise and the reaction stirred at room temperature for 30 minutes. LCMS analysis showed complete consumption of the starting materials and formation of desired product as the major component of the mixture. The reaction was quenched by addition of 1.0 N HCl (0.6 mL). Dichloromethane was removed under vacuum. The mixture was dissolved in THF/DMSO (1:1, 7 mL), and was purified with preparative HPLC (method A, 65-100% B in 8 min. Then 100% B in 4 min.). The desired fractions were placed in a SpeedVac overnight to remove solvent, then dissolved in a mixture of THF/EtOAc, washed with saturated sodium bicarbonate, brine, dried over sodium sulfate and concentrated. The final product was lyophilized to give Example 161 (28.6 mg, 0.050 mmol, 72.1% yield) as a yellow solid. $^1$H NMR (500 MHz, THF) δ 9.46 (br. s, 1H), 8.72 (d, J=1.9 Hz, 1H), 8.56 (s, 1H), 8.31 (s, 1H), 8.08 (d, J=2.5 Hz, 1H), 7.95 (d, J=11.0 Hz, 1H), 7.77 (dd, J=1.9, 0.8 Hz, 1H), 7.69 (d, J=11.0 Hz, 1H), 5.41-5.34 (m, 1H), 4.57 (dd, J=12.4, 3.0 Hz, 1H), 4.45 (dd, J=12.2, 6.2 Hz, 1H), 4.11 (s, 3H), 3.67-3.61 (m, 1H), 3.38 (dd, J=15.4, 7.2 Hz, 1H), 2.64 (s, 3H); $^{19}$F NMR (471 MHz, THF) δ -128.57 (s, 1F), -140.56 (s, 1F); LC-MS: method H, 2 to 98% B. RT=1.02 min, MS (ESI) m/z: 536.15 (M+H)$^+$. Analytical HPLC purity (method A): 94% purity.

Example 162

(R)-(5-fluoro-2-(2-methoxy-7-methylquinoxalin-5-yl)-7,8-dihydrobenzofuro[5,4-d]thiazol-7-yl)methyl (3-cyanophenyl)carbamate

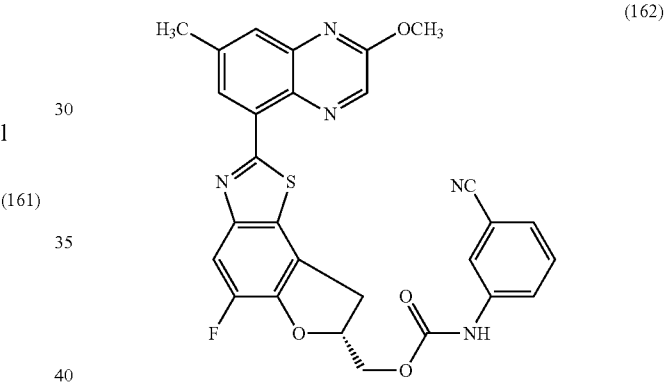

(162)

3-Aminobenzonitrile (12.84 mg, 0.109 mmol) was dissolved in DCM (1.0 mL) along with pyridine (0.035 mL, 0.435 mmol) and DIEA (0.028 mL, 0.163 mmol). Intermediate 145F (25 mg, 0.054 mmol) in DCM (2 mL) was added dropwise and the reaction stirred at room temperature for 30 minutes. LCMS analysis showed complete consumption of the starting materials and formation of desired product as the major component of the mixture. The reaction was quenched by addition of 1.0 N HCl (0.6 mL). Dichloromethane was removed under vacuum. The mixture was dissolved in THF/DMSO (1:1, 7 mL), and was purified with preparative HPLC (method A, 80-100% B in 8 min. Then 100% B in 4 min.). The desired fractions were placed in a SpeedVac overnight to remove solvent, then lyophilized to give Example 162 (16.2 mg, 0.029 mmol, 53.9% yield) as a yellow lyophilate. $^1$H NMR (500 MHz, THF) δ 9.33 (br. s., 1H), 8.72 (d, J=1.9 Hz, 1H), 8.55 (s, 1H), 7.88 (s, 1H), 7.77 (dd, J=1.9, 1.1 Hz, 1H), 7.72-7.65 (m, 2H), 7.39 (t, J=8.0 Hz, 1H), 7.30 (dt, J=7.7, 1.2 Hz, 1H), 5.40-5.33 (m, 1H), 4.56 (dd, J=12.1, 3.0 Hz, 1H), 4.44 (dd, J=12.2, 6.2 Hz, 1H), 4.12 (s, 3H), 3.66-3.61 (m, 1H), 3.37 (dd, J=15.4, 7.7 Hz, 1H), 2.64 (s, 3H); $^{19}$F NMR (471 MHz, THF) δ -142.42 (s, 1F); LC-MS: method H, 2 to 98% B. RT=1.08 min, MS (ESI) m/z: 542.15 (M+H)$^+$. Analytical HPLC purity (method A): 98% purity.

Example 163

(R)-(5-fluoro-2-(2-methoxy-7-methylquinoxalin-5-yl)-7,8-dihydrobenzofuro[5,4-d]thiazol-7-yl)methyl (2-methoxypyridin-4-yl)carbamate

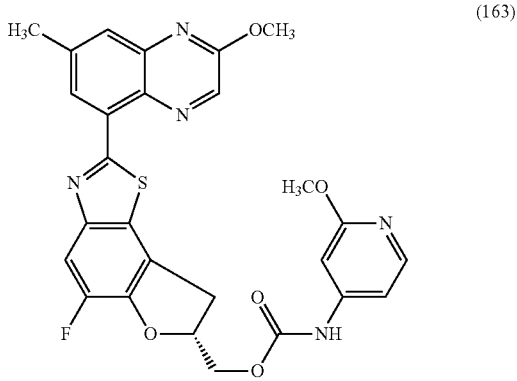

(163)

2-Methoxypyridin-4-amine (13.50 mg, 0.109 mmol) was dissolved in DCM (1.0 mL) along with pyridine (0.035 mL, 0.435 mmol) and DIEA (0.028 mL, 0.163 mmol). Intermediate 145F (25 mg, 0.054 mmol) in DCM (2 mL) was added dropwise and the reaction stirred at room temperature for 30 minutes. LCMS analysis showed complete consumption of the starting materials and formation of desired product as the major component of the mixture. The reaction was quenched by addition of 1.0 N HCl (0.6 mL). Dichloromethane was removed under vacuum. The mixture was dissolved in THF/DMSO (1:1, 7 mL), and was purified with preparative HPLC (method A, 50-100% B in 8 min. Then 100% B in 4 min.). The desired fractions were placed in a SpeedVac overnight to remove solvent, then lyophilized to give Example 163 (13.3 mg, 0.023 mmol, 42.4% yield) as a yellow lyophilate. $^1$H NMR (500 MHz, THF) δ 9.29 (s, 1H), 8.73 (d, J=1.7 Hz, 1H), 8.56 (s, 1H), 7.90 (d, J=5.8 Hz, 1H), 7.77 (s, 1H), 7.68 (d, J=11.0 Hz, 1H), 6.94 (dd, J=5.8, 1.7 Hz, 1H), 6.91 (s, 1H), 5.40-5.32 (m, 1H), 4.55 (dd, J=12.1, 3.0 Hz, 1H), 4.42 (dd, J=12.2, 6.2 Hz, 1H), 4.11 (s, 3H), 3.82 (s, 3H), 3.64 (d, J=9.9 Hz, 1H), 3.37 (dd, J=15.7, 7.7 Hz, 1H), 2.64 (s, 3H); $^{19}$F NMR (471 MHz, THF) δ -140.56 (s, 1F); LC-MS: method H, 2 to 98% B. RT=0.90 min, MS (ESI) m/z: 548.15 (M+H)$^+$. Analytical HPLC purity (method A): 95% purity.

Example 164

(R)-(5-fluoro-2-(2-methoxy-7-methylquinoxalin-5-yl)-7,8-dihydrobenzofuro[5,4-d]thiazol-7-yl)methyl (6-methoxypyridin-3-yl)carbamate

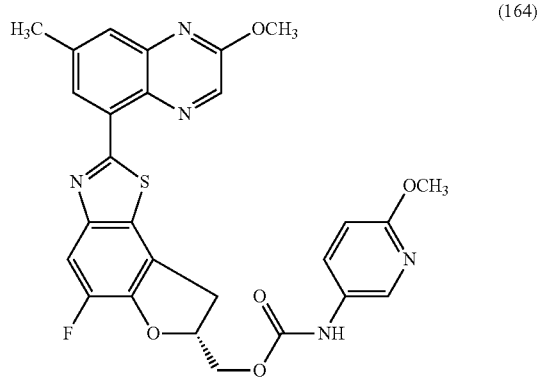

(164)

6-Methoxypyridin-3-amine (13.50 mg, 0.109 mmol) was dissolved in DCM (1.0 mL) along with pyridine (0.035 mL, 0.435 mmol) and DIEA (0.028 mL, 0.163 mmol). Intermediate 145F (25 mg, 0.054 mmol) in DCM (2 mL) was added dropwise and the reaction stirred at room temperature for 30 minutes. LCMS analysis showed complete consumption of the starting materials and formation of desired product. The reaction was quenched by addition of 1.0 N HCl (0.6 mL). Dichloromethane was removed under vacuum. The mixture was dissolved in THF/DMSO (1:1, 7 mL), and was purified with preparative HPLC (method A, 75-100% B in 8 min. Then 100% B in 4 min.). The desired fractions were placed in a SpeedVac overnight to remove solvent, then lyophilized to give Example 164 (9.8 mg, 0.017 mmol, 30.6% yield) as a yellow lyophilate. $^1$H NMR (500 MHz, TIF) δ 8.93 (br. s., 1H), 8.76 (d, J=1.7 Hz, 1H), 8.59 (s, 1H), 8.18 (br. s., 1H), 7.86 (d, J=7.7 Hz, 1H), 7.80 (dd, J=1.9, 0.8 Hz, 1H), 7.74-7.68 (m, 1H), 6.67 (d, J=8.8 Hz, 1H), 5.42-5.35 (m, 1H), 4.55 (dd, J=12.1, 3.3 Hz, 1H), 4.43 (dd, J=12.4, 6.1 Hz, 1H), 4.15 (s, 3H), 3.84 (br s, 3H), 3.68-3.64 (m, 1H), 3.41 (dd, J=15.5, 7.6 Hz, 1H), 2.68 (s, 3H); $^{19}$F NMR (471 MHz, TIF) δ -140.56 (s, 1F); LC-MS: method H, 2 to 98% B. RT=1.03 min, MS (ESI) m/z: 548.15 (M+H)$^+$. Analytical HPLC purity (method A): 93% purity.

Example 165

(R)-(5-fluoro-2-(2-methoxy-7-methylquinoxalin-5-yl)-7,8-dihydrobenzofuro[5,4-d]thiazol-7-yl)methyl (6-(2-hydroxyethoxy)pyridin-3-yl)carbamate

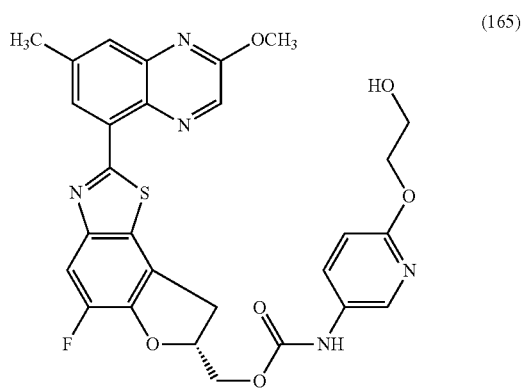 [SMILES: COc1cnc2c(-c3nc4cc(F)c5c(c4s3)C[C@H](COC(=O)Nc3ccc(OCCO)nc3)O5)cc(C)cc2n1]

(165)

Intermediate I-55 (22 mg, 0.082 mmol) was dissolved in DCM (1.0 mL) along with pyridine (0.035 mL, 0.435 mmol) and DIEA (0.028 mL, 0.163 mmol). Intermediate 145F (25 mg, 0.054 mmol) in DCM (2 mL) was added dropwise and the reaction stirred at room temperature for 30 minutes. LCMS analysis showed complete consumption of the starting materials and formation of desired product. The reaction was quenched by addition of 1.0 N HCl (0.6 mL). Dichloromethane was removed under vacuum. The crude was dried under high vacuum for 1 h, then treated with THE (1.5 mL) and 4 mL of 20:1 MeOH/concentrated HCl at room temperature for 1.5 h. HPLC and LCMS indicated a complete deprotection of silyl group. Solvent was removed under vacuum. The mixture was dissolved in THF/DMSO (1:1, 7 mL), and was purified with preparative HPLC (method A, 60-100% B in 8 min. Then 100% B in 4 min.). The desired fractions were placed in a SpeedVac overnight to remove solvent, then lyophilized to give Example 165 (22.9 mg, 0.037 mmol, 68.2% yield) as a yellow lyophilate. $^1$H NMR (500 MHz, THF) δ 9.64 (br. s., 1H), 8.70 (d, J=1.7 Hz, 1H), 8.63 (s, 1H), 8.27 (br. s., 1H), 7.86 (d, J=6.9 Hz, 1H), 7.80 (dd, J=1.9, 0.8 Hz, 1H), 7.72 (d, J=11.3 Hz, 1H), 6.66 (d, J=8.3 Hz, 1H), 5.45-5.37 (m, 1H), 4.55 (dd, J=12.4, 3.0 Hz, 1H), 4.40 (dd, J=12.2, 6.7 Hz, 1H), 4.24 (t, J=5.2 Hz, 2H), 4.11 (s, 3H), 3.74-3.69 (m, 2H), 3.66 (dd, J=15.8, 9.8 Hz, 1H), 3.45-3.36 (m, 1H), 2.65 (s, 3H); $^{19}$F NMR (471 MHz, THF) δ -140.17 (s, 1F); LC-MS: method H, 2 to 98% B. RT=0.95 min, MS (ESI) m/z: 578.15 (M+H)$^+$. Analytical HPLC purity (method A): 94% purity.

Example 166

(R)-(5-fluoro-2-(2-methoxy-7-methylquinoxalin-5-yl)-7,8-dihydrobenzofuro[5,4-d]thiazo 1-7-yl)methyl (6-(2,2-difluoro-3-hydroxypropoxy)pyridin-3-yl) carbamate

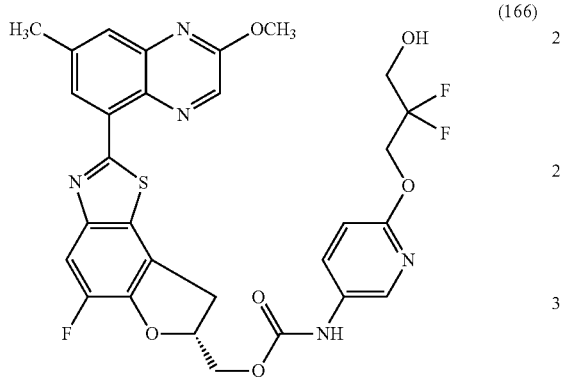

(166)

Intermediate I-56 (10 mg, 0.031 mmol) was dissolved in DCM (1.0 mL) along with pyridine (0.017 mL, 0.209 mmol) and DIEA (0.014 mL, 0.079 mmol). Intermediate 145F (12.03 mg, 0.026 mmol) in DCM (2 mL) was added dropwise and the reaction stirred at room temperature for 50 minutes. LCMS analysis showed complete consumption of the starting materials and formation of desired product. The reaction was quenched by addition of 1.0 N HCl (0.5 mL). Dichloromethane was removed under vacuum. The crude was dried under high vacuum for 1 h, then treated with THF (1.5 mL) and 4 mL of 20:1 MeOH/concentrated HCl at room temperature for 1.5 h. HPLC and LCMS indicated a complete deprotection of silyl group. Solvent was removed under vacuum. The mixture was dissolved in THF/DMSO (1:1, 5 mL) and was purified with preparative HPLC (method A, 70-100% B in 8 min. Then 100% B in 4 min.). The desired fractions were placed in a SpeedVac overnight to remove solvent, then lyophilized to give Example 166 (6.3 mg, 9.54 μmol, 36.4% yield) as a yellow lyophilate. $^1$H NMR (500 MHz, THF) δ 8.99 (br. s., 1H), 8.72 (d, J=1.7 Hz, 1H), 8.56 (s, 1H), 8.17 (br. s., 1H), 7.89 (br. s., 1H), 7.77 (dd, J=1.8, 1.0 Hz, 1H), 7.70 (d, J=11.0 Hz, 1H), 6.75 (d, J=8.0 Hz, 1H), 5.40-5.32 (m, 1H), 4.58-4.49 (m, 3H), 4.41 (dd, J=12.1, 6.1 Hz, 1H), 4.11 (s, 3H), 3.75 (t, J=12.9 Hz, 2H), 3.63 (d, J=9.9 Hz, 1H), 3.37 (dd, J=15.5, 7.6 Hz, 1H), 2.64 (s, 3H); $^{19}$F NMR (471 MHz, THF) δ -118.29 (s, 2F), -142.42 (s, 1F); LC-MS: method H, 2 to 98% B. RT=1.02 min, MS (ESI) m/z: 628.15 (M+H)$^+$. Analytical HPLC purity (method A): 95% purity.

Example 167

(5-fluoro-2-(2-methoxy-7-methylquinoxalin-5-yl)-7-methyl-7,8-dihydrobenzofuro[5,4-d]thiazol-7-yl)methanol

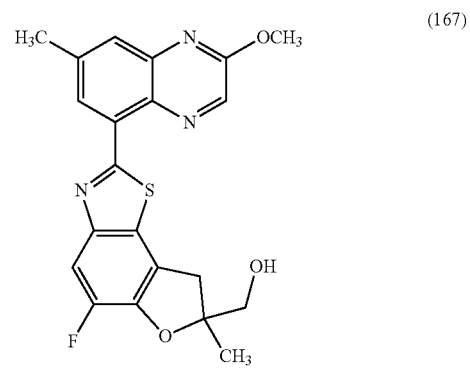 [SMILES: COc1cnc2c(-c3nc4cc(F)c5c(c4s3)CC(C)(CO)O5)cc(C)cc2n1]

(167)

Intermediate 167A: 2-chloro-5-fluoro-6-((2-methylallyl)oxy)benzo[d]thiazole

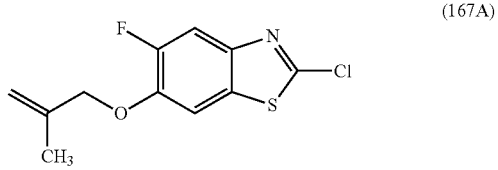 [SMILES: C=C(C)COc1cc2sc(Cl)nc2cc1F]

(167A)

To a solution of 2-chloro-5-fluorobenzo[d]thiazol-6-ol (4.1 g, 20.14 mmol) in DMF (50 mL) was added 3-bromo-2-methylprop-1-ene (2.79 mL, 27.7 mmol) and Cs$_2$CO$_3$ (14.43 g, 44.3 mmol). The reaction mixture was stirred at room temperature for 2.0 h. TLC and LCMS indicated completion of the reaction. The reaction mixture was diluted with water, extracted with ethyl acetate (3×). The organic layer was dried over Na$_2$SO$_4$ and concentrated under reduced pressure. The crude product was purified by flash chromatography (loading in chloroform, 0% to 35% EtOAc in hexane over 12 min using a 120 g silica gel cartridge). The desired fractions were combined and concentrated to yield Intermediate 167A (5.1 g, 19.79 mmol, 98% yield) as a slightly yellow solid. $^1$H NMR (500 MHz, CHLOROFORM-d) δ 7.63 (d, J=11.0 Hz, 1H), 7.25 (d, J=6.6 Hz, 1H), 5.11 (s, 1H), 5.02 (s, 1H), 4.54 (s, 2H), 1.84 (s, 3H); $^{19}$F NMR (376 MHz, CHLOROFORM-d) δ -132.81 (s, 1F); LC-MS: method H, 2 to 98% B. RT=1.07 min, MS (ESI) m/z: 258.3 and 260.3 (M+H)$^+$.

Intermediate 167B: 2-chloro-5-fluoro-7-(2-methylallyl)benzo[d]thiazol-6-ol

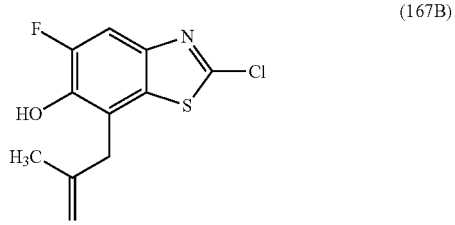 [SMILES: C=C(C)Cc1c(O)c(F)cc2nc(Cl)sc12]

(167B)

A solution of Intermediate 167A (2.55 g, 9.89 mmol) in diphenyl ether (19.79 ml) was placed in a pre-heated oil bath (180° C.). The reaction mixture was heated at 190° C. (oil bath) for 3 h. TLC indicated completion of reaction. After cooling to room temperature, the reaction mixture was diluted with EtOAc, extracted with 1.0 N NaOH (3×20 mL). The aqueous solution was diluted with EtOAc and acidified with 3.0 N HCl. The organic layer was washed with brine, dried over sodium sulfate and concentrated. The crude product was purified by flash chromatography (loading in chloroform/TiF, 5% to 50% EtOAc in hexane over 15 min using a 120 g silica gel cartridge). The desired fractions were combined and concentrated to yield Intermediate 167B (1.530 g, 5.94 mmol, 60% yield): $^1$H NMR (500 MHz, CHLOROFORM-d) δ 7.59 (d, J=10.2 Hz, 1H), 5.50 (d, J=5.5 Hz, 1H), 4.92 (s, 1H), 4.81 (d, J=0.8 Hz, 1H), 3.58 (s, 2H), 1.74 (s, 3H); $^{19}$F NMR (471 MHz, CHLOROFORM-d) δ −138.80 (s, 1F); LC-MS: method H, 0 to 100% B. RT=2.12 min, MS (ESI) m/z:258.0 and 260.0 (M+H)$^+$.

Intermediate 167C (2-chloro-5-fluoro-7-methyl-7,8-dihydrobenzofuro[5,4-d]thiazol-7-yl)methanol

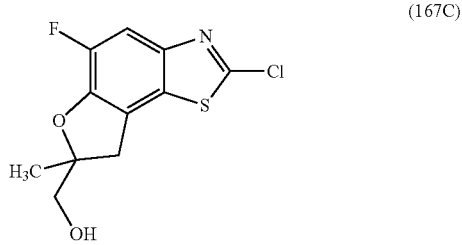 [SMILES: CC1(CO)Cc2c(c(F)cc3nc(Cl)sc23)O1]

(167C)

To a solution of Intermediate 167B (3.2 g, 12.42 mmol) in CH$_2$Cl$_2$ (70 mL) was added mCPBA (4.17 g, 18.63 mmol). The reaction mixture was stirred at room temperature for 2 h, at which time TLC, HPLC and LCMS indicated a clean conversion to the epoxide. PTSA monohydrate (0.709 g, 3.73 mmol) was added, and the reaction mixture was stirred at room temperature for 4 h. The reaction was quenched by addition of 8% Na$_2$S$_2$O$_3$ (30 mL), stirred at room temperature for 10 min. The organic layer was collected, the aqueous was extracted with CH$_2$Cl$_2$. The combined organic layer was washed with saturated sodium bicarbonate, brine, dried over sodium sulfate and concentrated. The crude product was purified by flash chromatography (loading in chloroform/TiF, 5% to 50% EtOAc in hexane over 15 min using a 120 g silica gel cartridge). The desired fractions were combined and concentrated to yield Intermediate 167C (2.71 g, 9.90 mmol, 80% yield) as a white solid. $^1$H NMR (500 MHz, CHLOROFORM-d) δ 7.55 (d, J=10.7 Hz, 1H), 3.85 (dd, J=12.1, 4.7 Hz, 1H), 3.70 (dd, J=12.1, 7.2 Hz, 1H), 3.50 (dd, J=15.7, 0.8 Hz, 1H), 3.04 (dd, J=15.7, 0.6 Hz, 1H), 1.98 (t, J=6.5 Hz, 1H), 1.55 (s, 3H); $^{19}$F NMR (471 MHz, CHLOROFORM-d) δ −138.01 (s, 1F); LC-MS: method H, 2 to 98% B. RT=0.86 min, MS (ESI) m/z: 274.3 and 276.3 (M+H)$^+$.

Example 167

To Intermediate I-9 (63.7 mg, 0.292 mmol), Intermediate 167C (100 mg, 0.292 mmol) and PdCl$_2$(dppf)—CH$_2$Cl$_2$ adduct (11.93 mg, 0.015 mmol) was added toluene (1.2 mL) and EtOH (0.4 mL). The mixture was sonicated for 1 min, and flushed with argon. To this was added sodium carbonate (0.536 mL, 2M, 0.804 mmol). The reaction mixture was heated in a microwave at 140° C. for 45 min. LCMS indicated completion of the reaction. The reaction mixture was directly loaded to 40 g ISCO column which was eluted with hexanes for 3 min, then a 20 min gradient from 0% to 100% EtOAc in hexanes. The desired fractions were combined and concentrated. The compound was dissolved in DMSO and was further purified via preparative LC/MS (Method A: Gradient: 50-100% B over 10 minutes, then a 2-minute hold at 100% B). Fractions containing the desired product were combined and dried via centrifugal evaporation to Example 167 (100 mg, 0.231 mmol, 79% yield). $^1$H NMR (400 MHz, DMSO-d$_6$) δ 8.75 (s, 1H), 8.58 (d, J=1.8 Hz, 1H), 7.88-7.79 (m, 2H), 5.20 (t, J=5.8 Hz, 1H), 4.08 (s, 3H), 3.65-3.48 (m, 3H), 3.18 (d, J=15.6 Hz, 1H), 2.63 (s, 3H), 1.48 (s, 3H). $^{19}$F NMR (376 MHz, DMSO-d$_6$) δ −138.85 (s, 1F). LC-MS: method B, RT=4.43 min, MS (ESI) m/z: 412.0 (M+H)$^+$. Analytical HPLC purity (method A): 95%.

Example 168

(R)-(5-fluoro-2-(2-methoxy-7-methylquinoxalin-5-yl)-7,8-dihydrobenzofuro[5,4-d]thiazo 1-7-yl)methyl (5-methoxypyridin-3-yl)carbamate

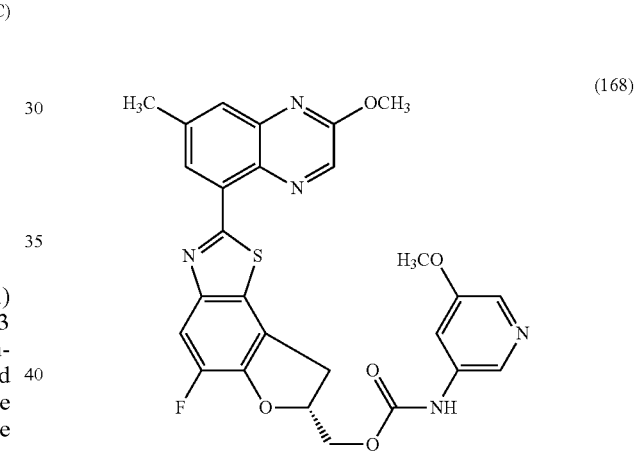

(168)

5-Methoxypyridin-3-amine (13.50 mg, 0.109 mmol) was dissolved in DCM (1.0 mL) along with pyridine (0.035 mL, 0.435 mmol) and DIEA (0.028 mL, 0.163 mmol). Intermediate 145F (25 mg, 0.054 mmol) in DCM (2 mL) was added dropwise and the reaction stirred at room temperature for 30 minutes. LCMS analysis showed complete consumption of the starting materials and formation of desired product. The reaction was quenched by addition of 1.0 N HCl (0.6 mL). Dichloromethane was removed under vacuum. The mixture was dissolved in THF/DMSO (1:1, 7 mL), and was purified via preparative LC/MS (method C, 35-100% B over 15 min, then a 0.75-min hold at 100% B). Fractions containing the desired product were combined and dried via centrifugal evaporation to yield Example 168 (11.9 mg, 0.022 mmol, 39.6% yield). $^1$H NMR (500 MHz, DMSO-d$_6$) δ 8.68 (s, 1H), 8.53 (s, 1H), 8.24 (br. s., 1H), 7.96 (br. s., 1H), 7.84 (d, J=11.0 Hz, 1H), 7.78 (s, 1H), 7.55 (br. s., 1H), 5.46-5.36 (m, 1H), 4.54 (dd, J=12.2, 2.4 Hz, 1H), 4.41 (dd, J=12.2, 7.0 Hz, 1H), 4.07 (s, 3H), 3.80 (s, 3H), 3.66-3.56 (m, 1H), 2.61 (s, 3H); $^{19}$F NMR (471 MHz, DMSO-d$_6$) δ −138.95 (s, 1F); LC-MS: method C, 2 to 98% B. RT=2.04 min, MS (ESI) m/z: 548.30 (M+H)$^+$. Analytical HPLC purity (method B): 99%.

Example 169

(R)-(5-fluoro-2-(2-methoxy-7-methylquinoxalin-5-yl)-7,8-dihydrobenzofuro[5,4-d]thiazol-7-yl)methyl (4-(morpholine-4-carbonyl)phenyl)carbamate (169)

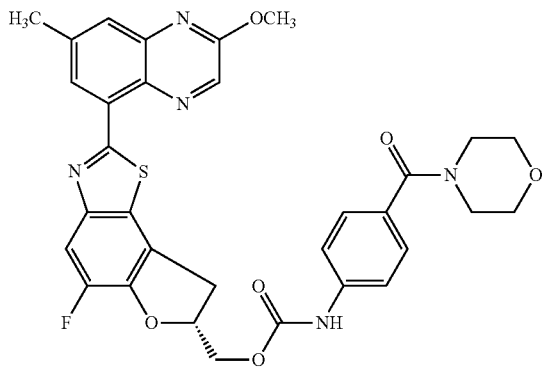

(4-Aminophenyl)(morpholino)methanone (22.42 mg, 0.109 mmol) was dissolved in DCM (1.0 mL) along with pyridine (0.035 mL, 0.435 mmol) and DIEA (0.028 mL, 0.163 mmol). Intermediate 145F (25 mg, 0.054 mmol) in DCM (2 mL) was added dropwise and the reaction stirred at room temperature for 30 minutes. LCMS analysis showed complete consumption of the starting materials and formation of desired product. The reaction was quenched by addition of 1.0 N HCl (0.6 mL). Dichloromethane was removed under vacuum. The mixture was dissolved in THF/DMSO (1:1, 7 mL), and was purified via preparative LC/MS (method C, 35-100% B over 15 min, then a 5-min hold at 100% B). Fractions containing the desired product were combined and dried via centrifugal evaporation to yield Example 169 (27.7 mg, 0.043 mmol, 79% yield). $^1$H NMR (500 MHz, DMSO-$d_6$) δ 8.79-8.72 (m, 1H), 8.59 (s, 1H), 7.93-7.87 (m, 1H), 7.84 (s, 1H), 7.52 (br. s., 2H), 7.34 (d, J=7.9 Hz, 2H), 5.44 (d, J=7.9 Hz, 1H), 4.63-4.51 (m, 1H), 4.41 (dd, J=12.1, 6.9 Hz, 1H), 4.09 (s, 3H), 3.67 (dd, J=15.9, 9.8 Hz, 1H), 3.57 (br. s., 4H), 3.34 (br. s, 4H), 2.64 (s, 3H); $^{19}$F NMR (471 MHz, DMSO-$d_6$) δ −138.85 (s, 1F); LC-MS: method C, 2 to 98% B. RT=2.34 min, MS (ESI) m/z: 630.30 (M+H)$^+$. Analytical HPLC purity (method B): 98%.

Example 170

(R)-(5-fluoro-2-(2-methoxy-7-methylquinoxalin-5-yl)-7,8-dihydrobenzofuro[5,4-d]thiazo 1-7-yl)methyl (6-fluoropyridin-3-yl)carbamate (170)

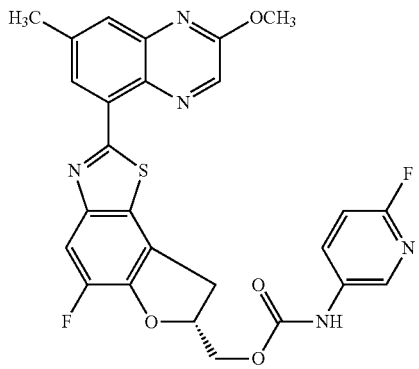

6-Fluoropyridin-3-amine (12.19 mg, 0.109 mmol) was dissolved in DCM (1.0 mL) along with pyridine (0.035 mL, 0.435 mmol) and DIEA (0.028 mL, 0.163 mmol). Intermediate 145F (25 mg, 0.054 mmol) in DCM (2 mL) was added dropwise and the reaction stirred at room temperature for 30 minutes. LCMS analysis showed complete consumption of the starting materials and formation of desired product. The reaction was quenched by addition of 1.0 N HCl (0.6 mL). Dichloromethane was removed under vacuum. The mixture was dissolved in THF/DMSO (1:1, 7 mL), and was purified via preparative LC/MS (method C, 35-100% B over 15 min, then a 5-min hold at 100% B). Fractions containing the desired product were combined and dried via centrifugal evaporation to yield Example 170 (12.1 mg, 0.022 mmol, 41.1% yield). $^1$H NMR (500 MHz, CHLOROFORM-d) δ 8.60 (d, J=1.7 Hz, 1H), 8.52 (s, 1H), 8.12 (br. s., 1H), 7.76 (d, J=0.8 Hz, 1H), 7.71 (d, J=11.0 Hz, 1H), 7.26 (s, 2H), 6.90 (br. s., 1H), 5.39-5.32 (m, 1H), 4.60 (dd, J=12.1, 3.0 Hz, 1H), 4.45 (dd, J=12.1, 6.3 Hz, 1H), 4.13 (s, 3H), 3.61 (dd, J=15.7, 9.9 Hz, 1H), 3.31 (dd, J=15.7, 7.2 Hz, 1H), 2.65 (s, 3H); $^{19}$F NMR (471 MHz, CHLOROFORM-d) δ −136.54 (s, 1F), −138.73 (br. s., 1F); LC-MS: method C, 2 to 98% B. RT=2.50 min, MS (ESI) m/z: 536.10 (M+H)$^+$. Analytical HPLC purity (method B): 99%.

Example 171

(2-(2-methoxy-7-methylquinoxalin-5-yl)-7-methyl-7,8-dihydrobenzofuro[5,4-d]thiazol-7-yl)methanol (171)

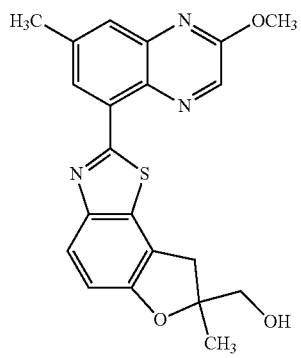

Intermediate 171A: 2-chloro-6-((2-methylallyl)oxy)benzo[d]thiazole (171A)

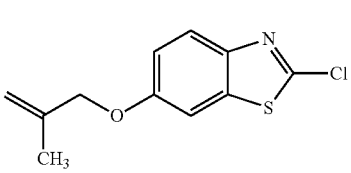

To a solution of Intermediate 144A (1.0 g, 5.39 mmol) in DMF (20 mL) was added 3-bromo-2-methylprop-1-ene (0.652 mL, 6.46 mmol) and Cs$_2$CO$_3$ (4.39 g, 13.47 mmol). The reaction mixture was stirred at room temperature for 5 h, at which time LCMS and TLC indicated completion of the reaction. The reaction mixture was diluted with EtOAc and water (20 mL), neutralized with 1.0 N HCl (40 mL), and extracted with ethyl acetate. The organic layer was washed with brine, dried over Na$_2$SO$_4$ and concentrated. The crude product was purified by flash chromatography (loading in chloroform, 0% to 70% EtOAc in hexane over 20 min using a 80 g silica gel cartridge). The desired fractions were combined and concentrated to yield Intermediate 171A (1.29 g, 5.38 mmol, 100% yield) as white solid. $^1$H NMR (400 MHz, CHLOROFORM-d) δ 7.83 (d, J=9.0 Hz, 1H), 7.25 (d, J=2.4 Hz, 1H), 7.11 (dd, J=8.9, 2.5 Hz, 1H), 5.12 (s, 1H), 5.03 (s, 1H), 4.50 (s, 2H), 1.86 (s, 3H). LC-MS: method C, RT=2.25 min, MS (ESI) m/z: 240.0 (M+H)$^+$.

Intermediate 171B: 2-chloro-7-(2-methylallyl)benzo[d]thiazol-6-ol

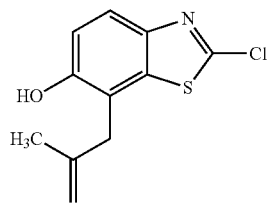

(171B)

A solution of Intermediate 171A (1.29 g, 5.38 mmol) in N,N-diethyl aniline (7 ml) was heated at 190° C. (oil bath) under argon for 2 h. After cooling to room temperature, the reaction mixture was diluted with EtOAc, washed with 3.0 N HCl (3×50 mL), brine (2×). The organic layer was dried over sodium sulfate and concentrated. The crude product was purified by flash chromatography (loading in chloroform, 0% to 50% EtOAc in hexane over 30 min using a 120 g silica gel cartridge). The desired fractions were combined and concentrated to yield Intermediate 171B (590 mg, 2.461 mmol, 45.7% yield) as a white solid. $^1$H NMR (400 MHz, CHLOROFORM-d) δ 7.71 (d, J=8.6 Hz, 1H), 7.01 (d, J=8.6 Hz, 1H), 5.40 (s, 1H), 4.96 (s, 1H), 4.88 (d, J=0.7 Hz, 1H), 3.54 (s, 2H), 1.76 (s, 3H). LC-MS: Method C, RT=2.15 min, MS (ESI) m/z: 240.0 (M+H)$^+$. Starting material 171A (0.7 g, 2.92 mmol, 54.3% yield) was recovered.

Intermediate 171C (2-chloro-7-methyl-7,8-dihydrobenzofuro[5,4-d]thiazol-7-yl)methanol

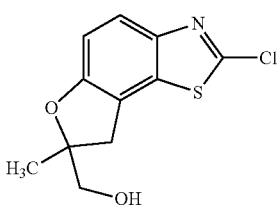

(171C)

To a solution of Intermediate 171B (212 mg, 0.884 mmol) in Dichloromethane (5 mL) was added mCPBA (297 mg, 1.327 mmol). The reaction mixture was stirred at room temperature for 3 h. PTSA (33.6 mg, 0.177 mmol) was added and the reaction mixture was stirred at room temperature overnight. The mixture was diluted with EtOAc, 8% Na$_2$S$_2$O$_3$ and extracted with EtOAc. The combined organic layer was washed with saturated sodium bicarbonate, brine, dried over sodium sulfate and concentrated. The crude product was purified by flash chromatography (loading in chloroform, 0% to 60% EtOAc in hexane over 20 min using a 40 g silica gel cartridge). The desired fractions were combined and concentrated to yield Intermediate 171C (180 mg, 0.704 mmol, 80% yield) as a white solid. $^1$H NMR (400 MHz, CHLOROFORM-d) δ 7.72 (d, J=8.6 Hz, 1H), 6.93 (d, J=8.8 Hz, 1H), 3.85-3.73 (m, 1H), 3.71-3.63 (m, 1H), 3.40 (d, J=15.6 Hz, 1H), 2.99 (d, J=15.6 Hz, 1H), 1.90 (dd, J=7.5, 5.7 Hz, 1H), 1.51 (s, 3H). LC-MS: Method C, RT=1.85 min, MS (ESI) m/z: 256.0 (M+H)$^+$.

Example 171

To Intermediate I-9 (49.9 mg, 0.229 mmol), Intermediate 171C (65 mg, 0.254 mmol) and PdCl$_2$(dppf)—CH$_2$Cl$_2$ adduct (10.38 mg, 0.013 mmol) was added toluene (1.2 mL) and EtOH (0.4 mL). The mixture was sonicated for 1 min, and flushed with argon. To this was added sodium carbonate (0.466 mL, 2M, 0.699 mmol). The reaction mixture was heated in a microwave at 140° C. for 45 min. LCMS indicated completion of the reaction. The reaction mixture was directly loaded to 40 g ISCO column which was eluted with hexanes for 3 min, then a 20 min gradient from 0% to 100% EtOAc in hexanes. The desired fractions were combined and concentrated. The crude was dissolved in DMSO and was further purified via preparative LC/MS (Method D: 40-95% B over 10 minutes, then a 5-minute hold at 100% B). Fractions containing the desired product were combined and dried via centrifugal evaporation to Example 171 (67 mg, 0.170 mmol, 74.4% yield). $^1$H NMR (500 MHz, DMSO-d$_6$) δ 8.75 (s, 1H), 8.58 (s, 1H), 7.88 (d, J=8.9 Hz, 1H), 7.81 (s, 1H), 7.00 (d, J=8.9 Hz, 1H), 5.15 (t, J=5.8 Hz, 1H), 4.08 (s, 3H), 3.65-3.34 (m, 2H), 3.08 (d, J=15.9 Hz, 1H), 2.63 (s, 3H). LC-MS: method L, RT=2.26 min, MS (ESI) m/z: 394.00 (M+H)$^+$. Analytical HPLC purity (method B): 99%.

Example 172

(S)-(5-fluoro-2-(2-methoxy-7-methylquinoxalin-5-yl)-7-methyl-7,8-dihydrobenzofuro[5,4-d]thiazol-7-yl)methanol

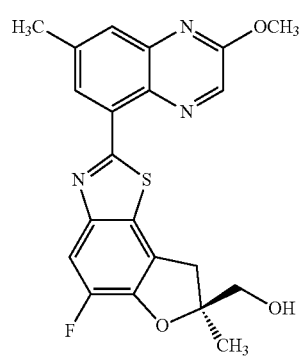

(172)

Intermediate 172A (S)-(2-chloro-5-fluoro-7-methyl-7,8-dihydrobenzo-furo[5,4-d]thiazol-7-yl)methanol

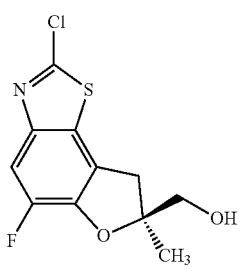

(172A)

Intermediate 167C (3.06 g, 11.18 mmol) was subject to chiral SFC for separation using the following conditions: Instrument: Berger II Prep SFC; Chiralpak ID, 4.6×250 mm, 5 micron; Mobile Phase: 8% MeOH/92% $CO_2$; Flow Conditions: 2 mL/min, 150 Bar, 40° C.; Detector Wavelength: 220 nm. Injection Details: 1 mL of ~30 mg/ml in MeOH. The first eluting fractions (first peak, RT=2.7 min) were concentrated to give Intermediate 172A (1.2 g, 4.38 mmol, 39.2% yield): LC-MS: method H, 2 to 98% B. RT=0.86 min, MS (ESI) m/z: 274.3 and 276.3 (M+H)$^+$. e.e. >99%.

Example 172

To Intermediate I-9 (405 mg, 1.856 mmol), Intermediate 172A (508 mg, 1.856 mmol) and $PdCl_2(dppf)$—$CH_2Cl_2$ adduct (68.2 mg, 0.084 mmol) was added toluene (9 mL) and EtOH (3 mL). The mixture was sonicated for 1 min, and flushed with argon. To this was added $Na_2CO_3$ (2M, 2.475 mL, 3.71 mmol). The reaction mixture was heated in a microwave at 145° C. for 50 min, at which time HPLC and TLC indicated a completion of reaction. The reaction mixture was diluted in EtOAc/THF/brine, sonicated, and filtered through a pad of wet celite. The organic layer was collected, washed with brine, dried over sodium sulfate and concentrated. The crude solid was triturated with MeOH. The solid was collected by filtration to give crude product (800 mg). The crude product was triturated with MeOH (3×), sonicated and centrifuged. The liquid was separated from the solid. The solid was lyophilized to give Example 172 (401 mg, 0.965 mmol, 52% yield). The liquid was concentrated. HPLC indicated ca 20-30% of product. The residual was dissolved in DMSO and purified with preparative HPLC (method A, 500-100% B in 8 min. Then 100% B in 4 min.). The desired fractions were placed in a SpeedVac overnight to remove solvent, then lyophilized to give additional Example 172 (60 mg). $^1$H NMR (500 MHz, THF) δ 8.70 (d, J=1.9 Hz, 1H), 8.55 (s, 1H), 7.74 (d, J=0.8 Hz, 1H), 7.63 (d, J=11.3 Hz, 1H), 4.36 (t, J=6.3 Hz, 1H), 4.10 (s, 3H), 3.72-3.67 (m, 1H), 3.63-3.60 (m, 1H), 3.12 (d, J=15.4 Hz, 1H), 2.45 (d, J=15.4 Hz, 1H), 2.63 (s, 3H), 1.52 (s, 3H); $^1$H NMR (500 MHz, CHLOROFORM-d) δ 8.57 (d, J=1.9 Hz, 1H), 8.55 (s, 1H), 7.78 (d, J=0.8 Hz, 1H), 7.75 (d, J=10.7 Hz, 1H), 4.14 (s, 3H), 3.88 (d, J=12.1 Hz, 1H), 3.76 (d, J=12.4 Hz, 1H), 3.59 (d, J=15.4 Hz, 1H), 3.17 (d, J=15.4 Hz, 1H), 2.65 (s, 3H), 1.59 (s, 3H); $^{19}$F NMR (471 MHz, THF) δ −140.69 (s, 1F); LC-MS: method H, 2 to 98% B. RT=1.14 min, MS (ESI) m/z: 412.4 (M+H)$^+$. Analytical HPLC purity (method A): 99.9% purity.

Example 173

(R)-(5-fluoro-2-(2-methoxy-7-methylquinoxalin-5-yl)-7,8-dihydrobenzofuro[5,4-d]thiazo 1-7-yl)methyl (2-(2-hydroxyethoxy)pyrimidin-5-yl)carbamate

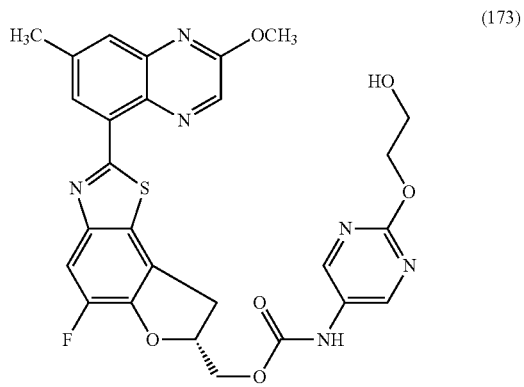 [SMILES: COc1cnc2c(-c3nc4cc(F)c5c(c4s3)C[C@H](COC(=O)Nc3cnc(OCCO)nc3)O5)cc(C)cc2n1]

(173)

Intermediate I-57 (27.9 mg, 0.104 mmol) was dissolved in DCM (1.0 mL) along with pyridine (0.039 mL, 0.487 mmol) and DIEA (0.032 mL, 0.183 mmol). Intermediate 145F (28 mg, 0.061 mmol) in 2 mL of DCM was added dropwise, and the reaction mixture was stirred at room temperature for 50 minutes. The reaction was quenched with 1.0 N HCl (0.5 mL). All solvent was removed under vacuum. The crude was dried under high vacuum for 1 h, then treated with THF (1.5 mL) and 3 mL of 20:1 MeOH/concentrated HCl at room temperature for 1.5 h. HPLC and LCMS indicated a complete deprotection of the silyl group. Solvent was removed under vacuum. The crude was dissolved in THF/DMSO (1:1, 7 mL), purified using a preparative HPLC (method A, 50-100% B in 8 min. Then 100% B in 4 min.). The desired fractions were placed in a SpeedVac overnight to remove solvent, then lyophilized to give Example 173 (24 mg, 0.040 mmol, 65.4% yield) as a yellow lyophilate. $^1$H NMR (500 MHz, THF) δ 8.73 (d, J=1.9 Hz, 1H), 8.60 (br. s., 1H), 8.57 (s, 1H), 8.07 (s, 3H), 7.78 (dd, J=1.8, 1.0 Hz, 1H), 7.68 (d, J=11.0 Hz, 1H), 5.36 (ddd, J=10.3, 4.7, 2.3 Hz, 1H), 4.65 (s, 3H), 4.55 (dd, J=12.2, 3.2 Hz, 1H), 4.43 (dd, J=12.1, 6.1 Hz, 1H), 4.28 (t, J=5.0 Hz, 2H), 3.75 (br. s., 3H), 3.67-3.62 (m, 1H), 3.38 (dd, J=15.7, 7.4 Hz, 1H), 2.65 (s, 3H); $^{19}$F NMR (471 MHz, THF) δ −142.43 (s, 1F); LC-MS: method H, 2 to 98% B. RT=0.93 min, MS (ESI) m/z: 579.15 (M+H)$^+$. Analytical HPLC purity (method A): 96% purity.

Example 174

(S)-(5-fluoro-2-(2-methoxy-7-methylquinoxalin-5-yl)-7-methyl-7,8-dihydrobenzofuro[5,4-d]thiazol-7-yl)methyl (2-methylpyrimidin-5-yl)carbamate

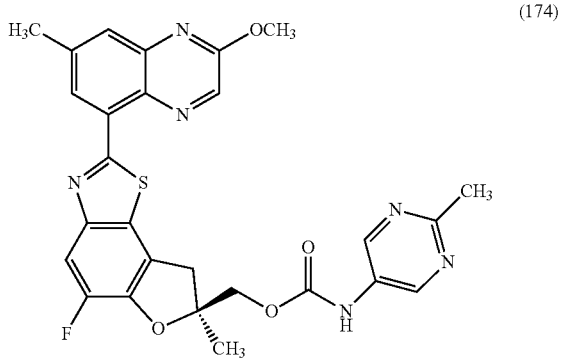

(174)

Intermediate 174A (S)-(5-fluoro-2-(2-methoxy-7-methylquinoxalin-5-yl)-7-methyl-7,8-dihydrobenzofuro[5,4-d]thiazol-7-yl)methyl chloroformate

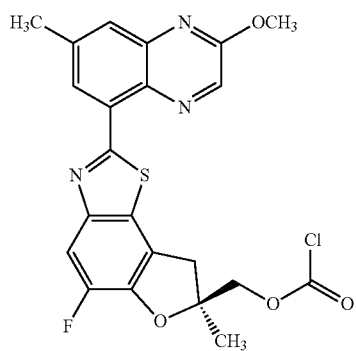

(174A)

To the solution of Example 172 (30 mg, 0.073 mmol) in THF (2 ml) was added 15% phosgene in toluene (0.206 ml, 0.292 mmol), followed by DIEA (0.076 ml, 0.437 mmol). The reaction mixture was stirred at room temperature for 30 min, at which time LCMS indicated a completion of reaction. Solvent and excess of phosgene was completely removed under vacuum to give Intermediate 174A which was used for the next step without purification. LC-MS: method C, RT=2.65 min, MS (ESI) m/z: 474.0 (M+H)$^+$.

Example 174

Intermediate 174A (10 mg, 0.021 mmol) in dichloromethane (1 mL) was added to a solution of 2-methylpyrimidin-5-amine (4.61 mg, 0.042 mmol) and pyridine (0.017 ml, 0.211 mmol) in dichloromethane (0.5 mL) dropwise. The reaction mixture was stirred at room temperature for 0.5 h, at which time LCMS and HPLC indicated a completion of reaction. The reaction mixture was diluted with EtOAc, washed with 0.5 N HCl. The organic layer was washed with brine, dried over sodium sulfate and concentrated. The crude was dissolved in DMSO and purified via preparative LC/MS (Method D: Gradient: 45-90% B over 10 minutes, then a 5-minute hold at 100% B). Fractions containing the desired product were combined and dried via centrifugal evaporation to Example 174 (7.8 mg, 0.014 mmol, 67.6% yield). $^1$H NMR (500 MHz, DMSO-d$_6$) δ 10.02 (br. s., 1H), 8.72 (s, 3H), 8.56 (s, 1H), 7.85 (d, J=11.3 Hz, 1H), 7.81 (s, 1H), 4.49-4.32 (m, 2H), 4.07 (s, 3H), 3.57-3.29 (m, 2H), 2.62 (s, 3H), 2.54 (s, 3H), 1.60 (s, 3H). LC-MS: Method L, 0 to 100% B. RT=2.27 min, MS (ESI) m/z: 547.15 (M+H)$^+$. Analytical HPLC purity (method B): 100%.

Example 175

(S)-(5-fluoro-2-(2-methoxy-7-methylquinoxalin-5-yl)-7-methyl-7,8-dihydrobenzofuro[5,4-d]thiazol-7-yl)methyl pyridin-3-ylcarbamate

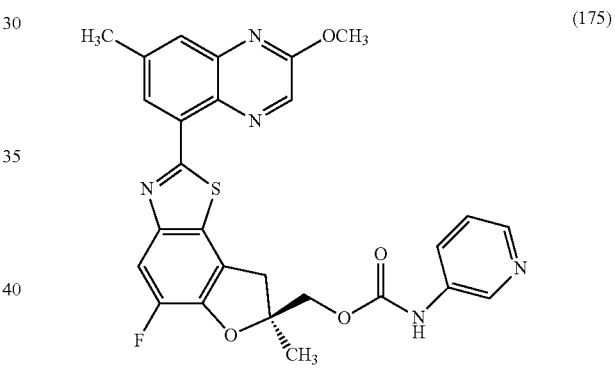

(175)

Intermediate 174A (10 mg, 0.021 mmol) in dichloromethane (1 mL) was added to a solution of pyridin-3-amine (3.97 mg, 0.042 mmol) and pyridine (0.017 ml, 0.211 mmol) in dichloromethane (0.5 mL) dropwise. The reaction mixture was stirred at room temperature for 0.5 h, at which time LCMS and HPLC indicated a completion of reaction. The reaction mixture was diluted with EtOAc, washed with 0.5 N HCl. The organic layer was washed with brine, dried over sodium sulfate and concentrated. The crude was dissolved in DMSO and purified via preparative LC/MS (Method D: Gradient: 45-90% B over 10 minutes, then a 5-minute hold at 100% B). Fractions containing the desired product were combined and dried via centrifugal evaporation to Example 175 (7.7 mg, 0.014 mmol, 68.6% yield). $^1$H NMR (500 MHz, DMSO-d$_6$) δ 10.00 (br. s., 1H), 8.72 (s, 1H), 8.62 (br. s., 1H), 8.56 (s, 1H), 8.21 (br. s., 1H), 7.98-7.75 (m, 3H), 7.33 (br. s., 1H), 4.45-4.33 (m, 2H), 4.07 (s, 3H), 3.62-3.30 (m, 1H), 2.62 (s, 3H), 1.60 (s, 3H). LC-MS: Method L, RT=2.02 min, MS (ESI) m/z: 532.15 (M+H)$^+$. Analytical HPLC purity (method B): 100%.

Example 176

(S)-(5-fluoro-2-(2-methoxy-7-methylquinoxalin-5-yl)-7-methyl-7,8-dihydrobenzofuro[5,4-d]thiazol-7-yl)methyl (3-cyanophenyl)carbamate

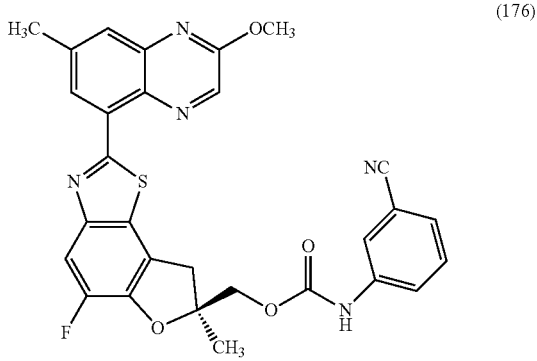 [SMILES: COc1cnc2c(-c3nc4cc(F)c5c(c4s3)C[C@@](C)(COC(=O)Nc3cccc(C#N)c3)O5)cc(C)cc2n1]
(176)

Intermediate 174A (10 mg, 0.021 mmol) in dichloromethane (1 mL) was added to a solution of 3-aminobenzonitrile (4.99 mg, 0.042 mmol) and pyridine (0.017 ml, 0.211 mmol) in dichloromethane (0.5 mL) dropwise. The reaction mixture was stirred at room temperature for 0.5 h, at which time LCMS and HPLC indicated a completion of reaction. The reaction mixture was diluted with EtOAc, washed with 0.5 N HCl. The organic layer was washed with brine, dried over sodium sulfate and concentrated. The crude was dissolved in DMSO and purified via preparative LC/MS (Method D: Gradient: 50-100% B over 12 minutes, then a 5-minute hold at 100% B). Fractions containing the desired product were combined and dried via centrifugal evaporation to Example 176 (7.7 mg, 0.014 mmol, 68.6% yield). $^1$H NMR (500 MHz, DMSO-$d_6$) δ 8.71 (s, 1H), 8.55 (s, 1H), 7.90-7.78 (m, 3H), 7.69 (br. s., 1H), 7.53-7.26 (m, 2H), 4.51-4.25 (m, 2H), 4.06 (s, 3H), 3.61-3.25 (m, 2H), 2.61 (s, 3H), 1.60 (s, 3H). LC-MS: Method L, RT=2.63 min, MS (ESI) m/z: 556.20 (M+H)$^+$. Analytical HPLC purity (method B): 100%.

Example 177

(R)-(5-fluoro-2-(2-methoxy-7-methylquinoxalin-5-yl)-7,8-dihydrobenzofuro[5,4-d]thiazol-7-yl)methyl (2-methoxypyrimidin-5-yl)carbamate

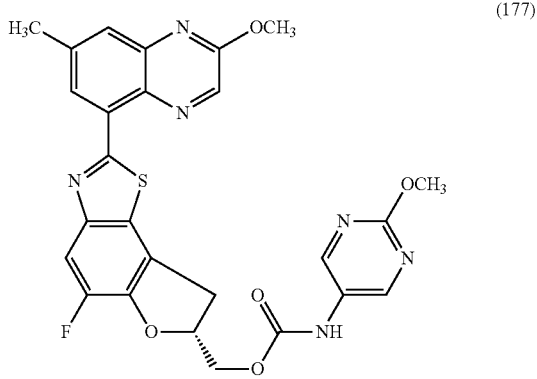 [SMILES: COc1cnc2c(-c3nc4cc(F)c5c(c4s3)C[C@H](COC(=O)Nc3cnc(OC)nc3)O5)cc(C)cc2n1]
(177)

2-Methoxypyrimidin-5-amine (12.95 mg, 0.104 mmol) was dissolved in DCM (1.0 mL) along with pyridine (0.039 mL, 0.487 mmol) and DIEA (0.032 mL, 0.183 mmol). Intermediate 145F (28 mg, 0.061 mmol) in 2 mL of DCM was added dropwise, and the reaction mixture was stirred at room temperature for 50 minutes. The reaction was quenched with 1.0 N HCl (0.5 mL). All solvent was removed under vacuum. The crude was dissolved in DMSO/THF (2:1, 6 mL) and purified via preparative LC/MS (method C, 50-100% B over 18 min, then a 5-min hold at 100% B). Fractions containing the desired product were combined and dried via centrifugal evaporation to yield Example 177 (21.4 mg, 64% yield). $^1$H NMR (500 MHz, DMSO-$d_6$) δ 8.72 (s, 1H), 8.63 (br. s., 2H), 8.56 (s, 1H), 7.87 (d, J=11.0 Hz, 1H), 7.82 (s, 1H), 5.42 (d, J=7.3 Hz, 1H), 4.53 (d, J=11.9 Hz, 1H), 4.40 (dd, J=12.1, 6.6 Hz, 1H), 4.08 (s, 3H), 3.65 (dd, J=15.7, 9.9 Hz, 1H), 3.42-3.32 (m, 1H), 2.63 (s, 3H), 2.55 (s, 3H); LC-MS: method C, 2 to 98% B. RT=2.32 min, MS (ESI) m/z: 549.15 (M+H)$^+$. Analytical HPLC purity (method B): 100%.

Example 178

(R)-(5-fluoro-2-(2-methoxy-7-methylquinoxalin-5-yl)-7,8-dihydrobenzofuro[5,4-d]thiazo1-7-yl)methyl (3-oxoisoindolin-5-yl)carbamate

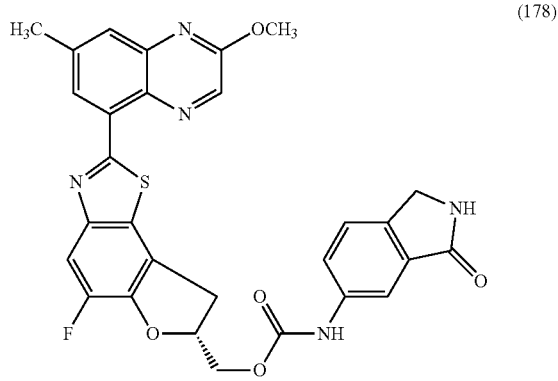 [SMILES: COc1cnc2c(-c3nc4cc(F)c5c(c4s3)C[C@H](COC(=O)Nc3ccc4c(c3)C(=O)NC4)O5)cc(C)cc2n1]
(178)

6-Aminoisoindolin-1-one (15.34 mg, 0.104 mmol) was dissolved in DCM (1.0 mL) along with pyridine (0.039 mL, 0.487 mmol) and DIEA (0.032 mL, 0.183 mmol). Intermediate 145F (28 mg, 0.061 mmol) in 2 mL of DCM was added dropwise, and the reaction mixture was stirred at room temperature for 50 minutes. The reaction was quenched with 1.0 N HCl (0.5 mL). All solvent was removed under vacuum. The crude was dissolved in DMSO/THF (2:1, 6 mL) and purified via preparative LC/MS (method C, 40-100% B over 18 min, then a 5-min hold at 100% B). Fractions containing the desired product were combined and dried via centrifugal evaporation to yield Example 178 (10.7 mg, 31% yield). $^1$H NMR (500 MHz, DMSO-$d_6$) δ 8.72 (s, 1H), 8.56 (s, 1H), 8.51 (br. s., 1H), 7.86 (d, J=10.7 Hz, 2H), 7.81 (br. s., 2H), 7.61 (br. s., 1H), 7.46 (d, J=5.8 Hz, 1H), 5.48-5.38 (m, 1H), 4.54 (d, J=12.2 Hz, 1H), 4.41 (dd, J=12.1, 7.2 Hz, 1H), 4.29 (s, 2H), 4.08 (s, 3H), 3.64 (dd, J=15.9, 9.8 Hz, 1H), 3.36 (d, J=13.7 Hz, 1H), 2.62 (s, 3H); LC-MS: method C, 2 to 98% B. RT=2.21 min, MS (ESI) m/z: 572.30 (M+H)$^+$. Analytical HPLC purity (method B): 100%.

Example 179

(R)-(5-fluoro-2-(2-methoxy-7-methylquinoxalin-5-yl)-7,8-dihydrobenzofuro[5,4-d]thiazo 1-7-yl)methyl (3-cyano-5-fluorophenyl)carbamate

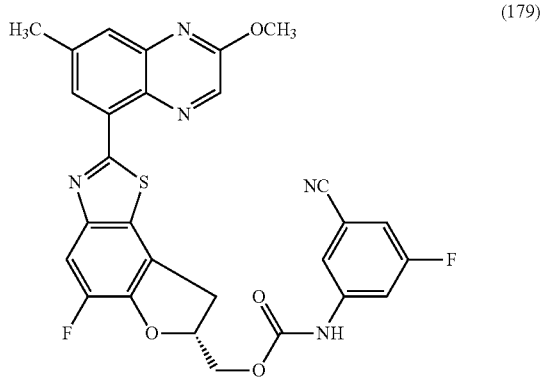 [SMILES: COc1cnc2c(-c3nc4cc(F)c5c(c4s3)C[C@H](COC(=O)Nc3cc(F)cc(C#N)c3)O5)cc(C)cc2n1]

(179)

3-Amino-5-fluorobenzonitrile (11.10 mg, 0.082 mmol) was dissolved in DCM (1.0 mL) along with pyridine (0.039 mL, 0.487 mmol) and DIEA (0.032 mL, 0.183 mmol). Intermediate 145F (25 mg, 0.054 mmol) in 2 mL of DCM was added dropwise, and the reaction mixture was stirred at room temperature for 50 minutes. The reaction was quenched with 1.0 N HCl (0.5 mL). All solvent was removed under vacuum. The crude was dissolved in DMSO/THF (2:1, 6 mL) and purified via preparative LC/MS (method C, 60-100% B over 10 min, then a 5-min hold at 100% B). Fractions containing the desired product were combined and dried via centrifugal evaporation to yield Example 179 (8.1 mg, 26% yield). $^1$H NMR (500 MHz, DMSO-$d_6$) δ 8.76 (s, 1H), 8.60 (s, 1H), 7.95-7.88 (m, 1H), 7.85 (s, 1H), 7.65 (br. s., 2H), 7.46 (d, J=7.9 Hz, 1H), 5.52-5.40 (m, 1H), 4.56 (d, J=12.8 Hz, 1H), 4.44 (dd, J=12.2, 7.3 Hz, 1H), 4.09 (s, 3H), 3.68 (dd, J=15.6, 9.5 Hz, 1H), 2.64 (s, 3H); LC-MS: method C, 2 to 98% B. RT=2.63 min, MS (ESI) m/z: 560.15 (M+H)$^+$. Analytical HPLC purity (method B): 98%.

Example 180

(R)-(5-fluoro-2-(2-methoxy-7-methylquinoxalin-5-yl)-7,8-dihydrobenzofuro[5,4-d]thiazol-7-yl)methyl (3-carbamoylphenyl)carbamate

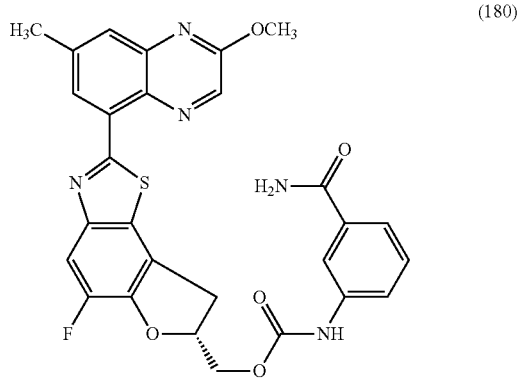 [SMILES: COc1cnc2c(-c3nc4cc(F)c5c(c4s3)C[C@H](COC(=O)Nc3cccc(C(N)=O)c3)O5)cc(C)cc2n1]

(180)

3-Aminobenzamide (11.10 mg, 0.082 mmol) was dissolved in DCM (1.0 mL) along with pyridine (0.039 mL, 0.487 mmol) and DIEA (0.032 mL, 0.183 mmol). Intermediate 145F (25 mg, 0.054 mmol) in 2 mL of DCM was added dropwise, and the reaction mixture was stirred at room temperature for 50 minutes. The reaction was quenched with 1.0 N HCl (0.5 mL). All solvent was removed under vacuum. The crude was dissolved in DMSO/THF (2:1, 6 mL) and purified via preparative LC/MS (method C, 45-90% B over 10 min, then a 5-min hold at 100% B). Fractions containing the desired product were combined and dried via centrifugal evaporation to yield Example 180 (18 mg, 58% yield). $^1$H NMR (500 MHz, DMSO-$d_6$) δ 8.72 (s, 1H), 8.56 (s, 1H), 7.95 (br. s., 1H), 7.87 (d, J=11.3 Hz, 2H), 7.81 (s, 1H), 7.58 (br. s., 1H), 7.48 (d, J=7.3 Hz, 1H), 7.36-7.28 (m, 2H), 5.42 (d, J=7.9 Hz, 1H), 4.53 (d, J=11.9 Hz, 1H), 4.41 (dd, J=12.1, 6.9 Hz, 1H), 4.08 (s, 3H), 3.69-3.60 (m, 1H), 3.40-3.32 (m, 1H), 2.62 (s, 3H); LC-MS: method C, 2 to 98% B. RT=2.22 min, MS (ESI) m/z: 560.15 (M+H)$^+$. Analytical HPLC purity (method B): 98%.

Example 181

(R)-(5-fluoro-2-(2-methoxy-7-methylquinoxalin-5-yl)-7-methyl-7,8-dihydrobenzofuro[5, 4-d]thiazol-7-yl)methanol

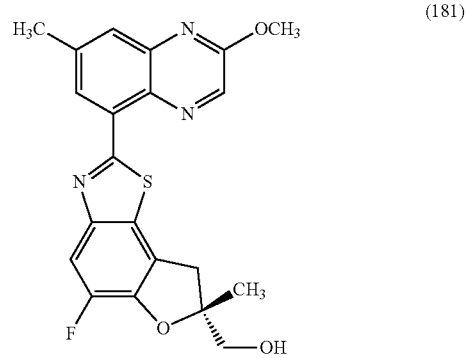 [SMILES: COc1cnc2c(-c3nc4cc(F)c5c(c4s3)C[C@](C)(CO)O5)cc(C)cc2n1]

(181)

Intermediate 181A (R)-(2-chloro-5-fluoro-7-methyl-7,8-dihydrobenzofuro[5,4-d]thiazol-7-yl)methanol

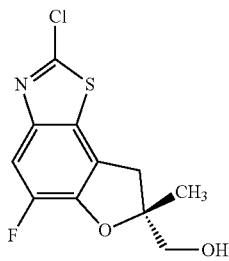

(181A)

Intermediate 167C (3.06 g, 11.18 mmol) was subject to chiral SFC for separation using the following conditions: Instrument: Berger II Prep SFC; Chiralpak ID, 4.6×250 mm, 5 micron; Mobile Phase: 8% MeOH/92% CO$_2$; Flow Conditions: 2 mL/min, 150 Bar, 40° C.; Detector Wavelength: 220 nm. Injection Details: 1 mL of ~30 mg/ml in MeOH. The second eluting fractions (second peak, RT=3.6 min) were concentrated to give Intermediate 181A (1.2 g, 4.38 mmol, 39.2% yield): LC-MS: method H, 2 to 98% B. RT=0.86 min, MS (ESI) m/z: 274.3 and 276.3 (M+H)$^+$. e.e. >99%.

Example 181

To Intermediate I-9 (40 mg, 0.183 mmol), Intermediate 181A (50.2 mg, 0.183 mmol) and PdCl$_2$(dppf)—CH$_2$Cl$_2$ adduct (7.49 mg, 9.17 µmol) was added toluene (2 mL) and EtOH (0.7 mL). The mixture was sonicated for 1 min, and flushed with argon. To this was added Na$_2$CO$_3$ (2M, 0.183 mL, 0.367 mmol). The reaction mixture was heated in a microwave at 135° C. for 45 min, at which time HPLC and TLC indicated a completion of reaction. The reaction mixture was directly loaded on an ISCO column, purified by flash chromatography (loading in chloroform, 0% to 85% EtOAc in CH$_2$Cl$_2$ over 10 min using a 12 g silica gel cartridge). The desired fractions were combined and concentrated to yield the crude product (72 mg). HPLC and LCMS indicated ca 75% purity. 35 mg of the crude was purified via preparative LC/MS (method C, 50-100% B over 22 min, then a 5-min hold at 100% B). Fractions containing the desired product were combined and dried via centrifugal evaporation to yield Example 181 (23 mg). $^1$H NMR (500 MHz, DMSO-d$_6$) δ 8.68 (s, 1H), 8.52 (s, 1H), 7.83-7.75 (m, 2H), 4.06 (s, 3H), 3.60 (d, J=5.8 Hz, 1H), 3.58-3.51 (m, 1H), 3.48 (d, J=15.9 Hz, 1H), 3.15 (d, J=16.2 Hz, 1H), 2.60 (s, 3H), 1.47 (s, 3H); LC-MS: method C, 2 to 98% B. RT=2.32 min, MS (ESI) m/z: 412.30 (M+H)$^+$. Analytical HPLC purity (method B): 100%.

Example 182

(R)-(5-fluoro-2-(2-methoxy-7-methylquinoxalin-5-yl)-7-methyl-7,8-dihydrobenzofuro[5,4-d]thiazol-7-yl)methyl (2-methylpyrimidin-5-yl)carbamate

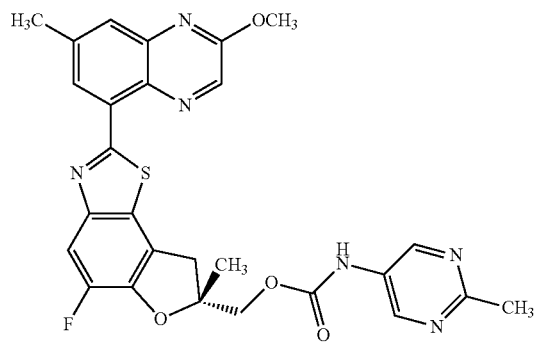

(182)

Intermediate 182A (R)-(5-fluoro-2-(2-methoxy-7-methylquinoxalin-5-yl)-7-methyl-7,8-dihydrobenzofuro[5,4-d]thiazol-7-yl)methyl chloroformate

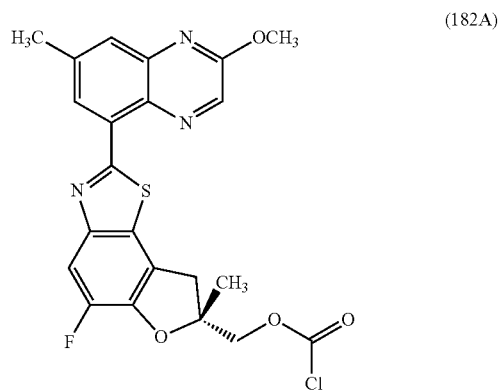 [SMILES: COc1cnc2c(-c3nc4cc(F)c5c(c4s3)C[C@](C)(COC(=O)Cl)O5)cc(C)cc2n1]

(182A)

To the solution of Example 181 (30 mg, 0.073 mmol) in THF (2 ml) was added 15% phosgene in toluene (0.206 ml, 0.292 mmol), followed by DIEA (0.076 ml, 0.437 mmol). The reaction mixture was stirred at room temperature for 30 min, at which time LCMS (quenched with MeOH) indicated a completion of reaction. Solvent and excess of phosgene was completely removed under vacuum to give Intermediate 182A which was used for the next step without purification. LC-MS: method C, RT=2.56 and 2.63 min, MS (ESI) m/z: 470.0 (M+H)$^+$ (methyl carbamate).

Example 182

Intermediate 182A (10 mg, 0.021 mmol) in dichloromethane (1 mL) was added to a solution of 2-methylpyrimidin-5-amine (4.61 mg, 0.042 mmol) and pyridine (0.017 ml, 0.211 mmol) in dichloromethane (0.5 mL) dropwise. The reaction mixture was stirred at room temperature for 0.5 h, at which time LCMS and HPLC indicated a completion of reaction. The reaction mixture was diluted with EtOAc, washed with 0.5 N HCl. The organic layer was washed with brine, dried over sodium sulfate and concentrated. The crude was dissolved in DMSO and purified via preparative LC/MS (Method D: Gradient: 45-90% B over 10 minutes, then a 5-minute hold at 100% B). Fractions containing the desired product were combined and dried via centrifugal evaporation to Example 182 (8.4 mg, 0.015 mmol, 72.8% yield). $^1$H NMR (500 MHz, DMSO-d$_6$) δ 8.73 (s, 3H), 8.56 (s, 1H), 7.94-7.72 (m, 2H), 4.53-4.29 (m, 2H), 4.07 (s, 3H), 3.63-3.19 (m, 1H), 2.62 (s, 3H), 1.60 (s, 3H). LC-MS: Method L, 0 to 100% B. RT=2.27 min, MS (ESI) m/z: 547.15 (M+H)$^+$. Analytical HPLC purity (method B): 100%.

Example 183

(R)-(5-fluoro-2-(2-methoxy-7-methylquinoxalin-5-yl)-7-methyl-7,8-dihydrobenzofuro[5,4-d]thiazol-7-yl)methyl pyridin-3-ylcarbamate

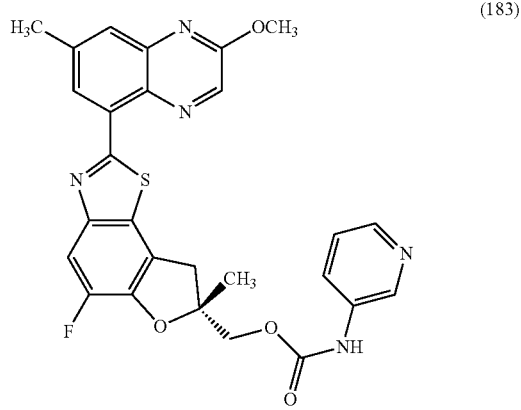 [SMILES: COc1cnc2c(-c3nc4cc(F)c5c(c4s3)C[C@](C)(COC(=O)Nc3cccnc3)O5)cc(C)cc2n1]

(183)

Intermediate 182A (10 mg, 0.021 mmol) in dichloromethane (1 mL) was added to a solution of pyridin-3-amine (3.97 mg, 0.042 mmol) and pyridine (0.017 ml, 0.211 mmol) in dichloromethane (0.5 mL) dropwise. The reaction mixture was stirred at room temperature for 0.5 h, at which time LCMS and HPLC indicated a completion of reaction. The reaction mixture was diluted with EtOAc, washed with 0.5 N HCl. The organic layer was washed with brine, dried over sodium sulfate and concentrated. The crude was dissolved in DMSO and purified via preparative LC/MS (Method D: Gradient: 45-90% B over 10 minutes, then a 5-minute hold at 100% B). Fractions containing the desired product were combined and dried via centrifugal evaporation to Example 183 (5.9 mg, 0.011 mmol, 52.6% yield). $^1$H NMR (500 MHz, DMSO-$d_6$) δ 10.09 (br. s., 1H), 8.71 (s, 1H), 8.66 (br. s., 1H), 8.55 (s, 1H), 8.25 (br. s., 1H), 7.95 (br. s., 1H), 7.85 (d, J=11.3 Hz, 1H), 7.80 (s, 1H), 7.40 (br. s., 1H), 4.48-4.25 (m, 2H), 4.06 (s, 3H), 3.58-3.23 (m, 1H), 2.61 (s, 3H), 1.61 (s, 3H). LC-MS: Method L, RT=2.04 min, MS (ESI) m/z: 532.15 (M+H)$^+$. Analytical HPLC purity (method B): 100%.

Example 184

(R)-(5-fluoro-2-(2-methoxy-7-methylquinoxalin-5-yl)-7-methyl-7,8-dihydrobenzofuro[5,4-d]thiazol-7-yl)methyl (3-cyanophenyl)carbamate

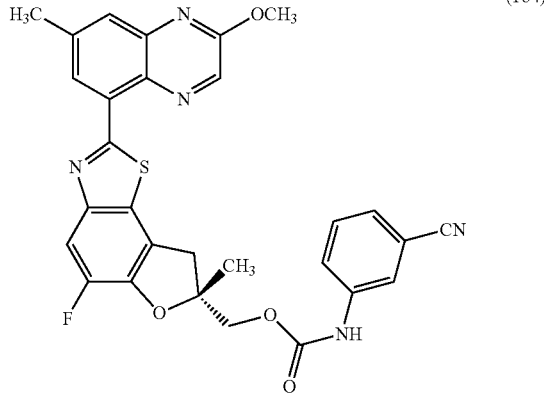

(184)

Intermediate 182A (10 mg, 0.021 mmol) in dichloromethane (1 mL) was added to a solution of 3-aminobenzonitrile (4.99 mg, 0.042 mmol) and pyridine (0.017 ml, 0.211 mmol) in dichloromethane (0.5 mL) dropwise. The reaction mixture was stirred at room temperature for 0.5 h, at which time LCMS and HPLC indicated a completion of reaction. The reaction mixture was diluted with EtOAc, washed with 0.5 N HCl. The organic layer was washed with brine, dried over sodium sulfate and concentrated. The crude was dissolved in DMSO and purified via preparative LC/MS (Method D: Gradient: 50-100% B over 12 minutes, then a 5-minute hold at 100% B). Fractions containing the desired product were combined and dried via centrifugal evaporation to Example 184 (9.6 mg, 0.017 mmol, 82% yield). $^1$H NMR (500 MHz, DMSO-$d_6$) δ 10.11 (br. s., 1H), 8.72 (s, 1H), 8.55 (s, 1H), 7.95-7.79 (m, 3H), 7.69 (br. s., 1H), 7.50-7.17 (m, 2H), 4.56-4.23 (m, 2H), 4.07 (s, 3H), 3.60-3.23 (m, 2H), 2.62 (s, 3H), 1.60 (s, 3H). LC-MS: Method L, RT=2.63 min, MS (ESI) m/z: 556.20 (M+H)$^+$. Analytical HPLC purity (method B): 100%.

Example 185

(R)-(5-fluoro-2-(2-methoxy-7-methylquinoxalin-5-yl)-7,8-dihydrobenzofuro[5,4-d]

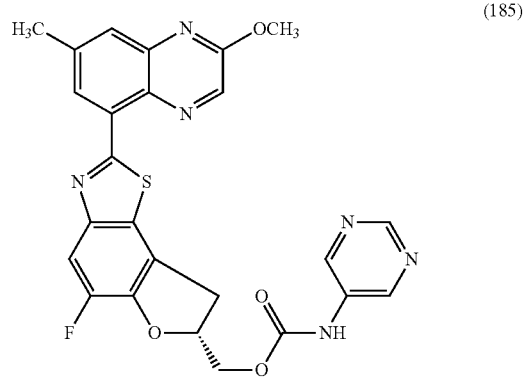 [SMILES: COc1cnc2c(-c3nc4cc(F)c5c(c4s3)C[C@H](COC(=O)Nc3cncnc3)O5)cc(C)cc2n1]

(185)

Pyrimidin-5-amine (9.84 mg, 0.104 mmol) was dissolved in DCM (1.0 mL) along with pyridine (0.039 mL, 0.487 mmol) and DIEA (0.032 mL, 0.183 mmol). Intermediate 145F (28 mg, 0.061 mmol) in 2 mL of DCM was added dropwise, and the reaction mixture was stirred at room temperature for 50 minutes. The reaction was quenched with 1.0 N HCl (0.5 mL). All solvent was removed under vacuum. The crude material was dissolved in DMSO/THF (2:1, 6 mL) and purified via preparative LC/MS (method C, 45-70% B over 30 min, then a 5-min hold at 100% B). Fractions containing the desired product were combined and dried via centrifugal evaporation to yield Example 185 (1.6 mg, 4.3% yield). $^1$H NMR (500 MHz, DMSO-$d_6$) δ 8.86 (m, 3H), 8.76 (s, 1H), 8.60 (s, 1H), 7.90 (d, J=11.0 Hz, 1H), 7.85 (br. s., 1H), 5.45 (d, J=7.9 Hz, 1H), 4.57 (d, J=12.2 Hz, 1H), 4.45 (dd, J=12.2, 6.7 Hz, 1H), 4.09 (s, 3H), 3.68 (dd, J=15.9, 9.8 Hz, 1H), 3.33 (d, J=12.2 Hz, 1H), 2.64 (s, 3H); LC-MS: method C, 2 to 98% B. RT=2.14 min, MS (ESI) m/z: 519.30 (M+H)$^+$. Analytical HPLC purity (method B): >86%.

Example 186

2-(2-methoxy-7-methylquinoxalin-5-yl)-7,7-dimethyl-7,8-dihydrobenzofuro[5,4-d]thiazole

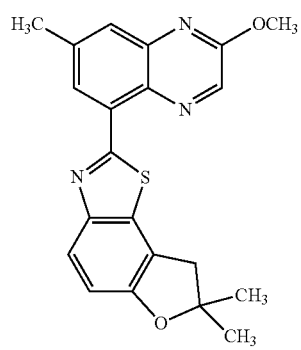

(186)

Intermediate 186A: 2-chloro-7,7-dimethyl-7,8-dihydrobenzofuro[5,4-d]thiazole

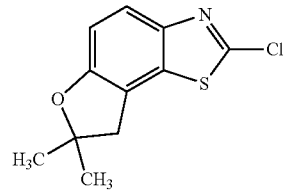

(186A)

To a solution of Intermediate 171B (51 mg, 0.213 mmol) in dichloromethane (1 mL) was added PTSA (24.28 mg, 0.128 mmol). The reaction mixture was stirred at room temperature overnight. TLC indicated a completion of the reaction. The crude mixture was directly loaded on 12 g ISCO column for purification (loading in chloroform, 0% to 100% EtOAc in hexane over 15 min). The desired fraction was collected and concentrated to yield Intermediate 186A (35 mg, 0.146 mmol, 68.6% yield) as a white solid. $^1$H NMR (400 MHz, CHLOROFORM-d) δ 7.71 (d, J=8.6 Hz, 1H), 6.91 (d, J=8.6 Hz, 1H), 3.11 (s, 2H), 1.55 (s, 6H). LC-MS: method C, RT=2.17 min, MS (ESI) m/z: 240 (M+H)$^+$.

Example 186

To Intermediate I-9 (24.56 mg, 0.113 mmol), Intermediate 186A (30 mg, 0.125 mmol) and PdCl$_2$(dppf)—CH$_2$Cl$_2$ adduct ((5.11 mg, 6.26 μmol) was added toluene (0.75 mL) and EtOH (0.25 mL). The mixture was sonicated for 1 min, and flushed with argon. To this was added sodium carbonate (229 μl, 1.5M, 0.344 mmol). The reaction mixture was heated in a microwave at 140° C. for 45 min. LCMS indicated completion of the reaction. The reaction mixture was directly loaded to 40 g ISCO column which was eluted with hexanes for 3 min, then a 20 min gradient from 0% to 100% EtOAc in hexanes. The desired fractions were combined and concentrated. The crude was dissolved in DMSO and further purified via preparative LC/MS for two times (Method D: Gradient: 60-100% B over 20 minutes, then a 5-minute hold at 100% B then Method D 75-100% B over 25 minutes, then a 7-minute hold at 100% B). Fractions containing the desired product were combined and dried via centrifugal evaporation to Example 186 (5.8 mg, 0.015 mmol, 12.28% yield). $^1$H NMR (500 MHz, CHLOROFORM-d) δ 8.61 (d, J=1.9 Hz, 1H), 8.56 (s, 1H), 7.93 (d, J=8.5 Hz, 1H), 7.79-7.66 (m, 1H), 6.98 (d, J=8.5 Hz, 1H), 4.13 (s, 3H), 3.30-3.19 (m, 2H), 2.65 (s, 3H), 1.58 (s, 6H). LC-MS: method L, RT=2.72 min, MS (ESI) m/z: 378.15 (M+H)$^+$. Analytical HPLC purity (method B): 100%.

Example 187

(S)-(2-(2-methoxy-7-methylquinoxalin-5-yl)-7-methyl-7,8-dihydrobenzofuro[5,4-d]thiazo 1-7-yl)methanol

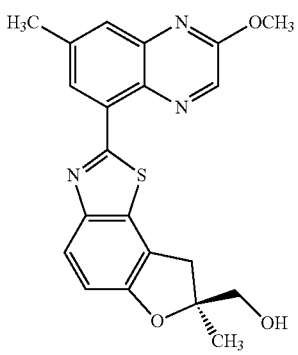

(187)

Example 171 (60 mg, 0.152 mmol) was separated via Berger preparative SFC (Chiralcel OJ, 21×250 mm, 5 micron, Mobile Phase: 20% MeOH/80% CO$_2$ Flow Conditions: 45 mL/min, 150 Bar, 40° C., Detector Wavelength: 220 nm, Injection Details: 3 ml/injection of (~2.5 mg/mL) in MeOH:ACN+5% THF). Fractions from the first peak (RT=11.2 min) were combined and dried via centrifugal evaporation to yield Example 187 (22 mg, 0.053 mmol, 34.8% yield). $^1$H NMR (400 MHz, CHLOROFORM-d) δ 8.61 (d, J=1.8 Hz, 1H), 8.56 (s, 1H), 7.93 (d, J=8.6 Hz, 1H), 7.75 (d, J=0.7 Hz, 1H), 7.00 (d, J=8.8 Hz, 1H), 4.13 (s, 3H), 3.83-3.68 (m, 2H), 3.49 (d, J=15.4 Hz, 1H), 3.13 (d, J=15.6 Hz, 1H), 2.65 (s, 3H), 1.99 (t, J=6.6 Hz, 1H), 1.55 (s, 3H). LC-MS: Method C, RT=2.39 min, MS (ESI) m/z: 394.0 (M+H)$^+$. Analytical HPLC purity (method A): 95%.

Example 188

(R)-(2-(2-methoxy-7-methylquinoxalin-5-yl)-7-methyl-7,8-dihydrobenzofuro[5,4-d]thiazol-7-yl)methanol

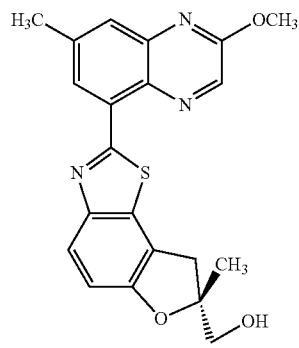

(188)

Example 171 (60 mg, 0.152 mmol) was separated via Berger preparative SFC (Chiralcel OJ, 21×250 mm, 5 micron, Mobile Phase: 20% MeOH/80% CO$_2$ Flow Conditions: 45 mL/min, 150 Bar, 40° C., Detector Wavelength: 220 nm, Injection Details: 3 ml/injection of (~2.5 mg/mL) in MeOH:ACN+5% THF). Fractions from the second peak (RT=17.2 min) were combined and dried via centrifugal evaporation to yield Example 188 (30 mg, 0.072 mmol, 47.5% yield). $^1$H NMR (400 MHz, CHLOROFORM-d) δ 8.62 (d, J=2.0 Hz, 1H), 8.57 (s, 1H), 7.93 (d, J=8.6 Hz, 1H), 7.80-7.63 (m, 1H), 7.00 (d, J=8.8 Hz, 1H), 4.14 (s, 3H), 3.76 (dd, J=13.1, 6.5 Hz, 2H), 3.49 (d, J=15.6 Hz, 1H), 3.13 (d, J=15.4 Hz, 1H), 2.66 (s, 3H), 1.95 (t, J=6.6 Hz, 1H), 1.55 (s, 3H). LC-MS: Method C, RT=2.39 min, MS (ESI) m/z: 394.0 (M+H)$^+$. Analytical HPLC purity (method A): 95%.

Example 189

(2-(2-methoxy-7-methylquinoxalin-5-yl)-8-methyl-7,8-dihydrobenzofuro[5,4-d]thiazol-7-yl)methanol

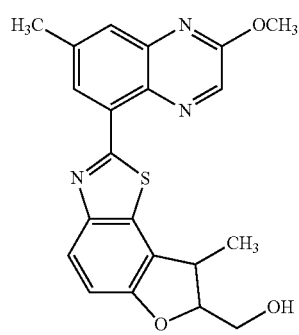

(189)

Intermediate 189A: (E)-6-(but-2-en-1-yloxy)-2-chlorobenzo[d]thiazole

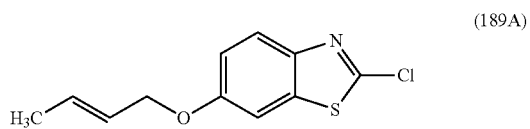

(189A)

To a solution of Intermediate 144A (220 mg, 1.185 mmol) in DMF (5 mL) was added (E)-1-bromobut-2-ene (0.147 mL, 1.422 mmol) and cesium carbonate (965 mg, 2.96 mmol). The mixture was stirred at room temperature for 4 hours, at which time LCMS and TLC indicated completion of the reaction. The reaction mixture was diluted with EtOAc and water (5 mL), neutralized with 1.0 N HCl (10 mL), and extracted with ethyl acetate. The organic layer was washed with brine, dried over Na$_2$SO$_4$ and concentrated. The crude product was purified by flash chromatography (loading in chloroform, 0% to 70% EtOAc in hexane over 20 min using a 40 g silica gel cartridge). The desired fractions were combined and concentrated to yield Intermediate 189A (280 mg, 1.168 mmol, 99% yield) as white solid. $^1$H NMR (400 MHz, CHLOROFORM-d) δ 7.81 (d, J=9.0 Hz, 1H), 7.23 (d, J=2.6 Hz, 1H), 7.08 (dd, J=8.9, 2.5 Hz, 1H), 5.97-5.70 (m, 2H), 4.52-4.48 (m, 2H), 1.78 (dd, J=6.5, 1.2 Hz, 3H). LC-MS: method C, RT=2.25 min, MS (ESI) m/z: 240.0 (M+H)$^+$.

Intermediate 189B: 7-(but-3-en-2-yl)-2-chlorobenzo[d]thiazol-6-ol

A solution of Intermediate 189A (60 mg, 0.250 mmol) in N,N-diethyl aniline (0.5 ml) was heated at 240° C. in a microwave reactor for 45 min. After cooling to room temperature, the reaction mixture was diluted with EtOAc, washed with 3.0 N HCl (3×10 mL), brine (2×). The organic layer was dried over sodium sulfate and concentrated. The crude product was purified by flash chromatography (loading in chloroform, 0% to 50% EtOAc in hexane over 15 min using a 40 g silica gel cartridge). The desired fractions were combined and concentrated to yield Intermediate 189B (60 mg, 0.250 mmol, 100% yield) as a white solid. $^1$H NMR (400 MHz, CHLOROFORM-d) δ 7.68 (d, J=8.6 Hz, 1H), 6.99 (d, J=8.6 Hz, 1H), 6.21 (ddd, J=17.1, 10.9, 4.6 Hz, 1H), 5.37 (d, J=2.2 Hz, 1H), 5.35-5.30 (m, 1H), 3.95 (ddt, J=7.0, 4.6, 2.2 Hz, 1H), 1.48 (d, J=7.0 Hz, 3H). LC-MS: Method C, RT=2.17 min, MS (ESI) m/z: 240.0 (M+H)$^+$.

369

Intermediate 189C: (2-chloro-8-methyl-7,8-dihydrobenzofuro[5,4-d]thiazol-7-yl) methanol

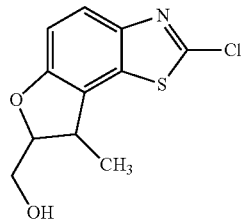

(189C)

To a solution of Intermediate 189B (60 mg, 0.250 mmol) in dichloromethane (3 mL) was added mCPBA (84 mg, 0.375 mmol). The reaction mixture was stirred at room temperature for 2 h. PTSA (9.52 mg, 0.050 mmol) was added, and the reaction mixture was stirred at room temperature overnight. The mixture was diluted with EtOAc and 8% $Na_2S_2O_3$, extracted with EtOAc, the combined organic layer was washed with saturated sodium bicarbonate, brine and dried over sodium sulfate and concentrated. The crude product was purified by flash chromatography (loading in chloroform, 0% to 60% EtOAc in hexane over 20 min using a 40 g silica gel cartridge). The desired fractions were combined and concentrated to yield Intermediate 189C (45 mg, 0.176 mmol, 70.3% yield) as a white solid. LC-MS: Method C, RT=1.87 min, MS (ESI) m/z: 256.0 $(M+H)^+$.

Example 189

To Intermediate I-9 (34.5 mg, 0.158 mmol), Intermediate 189C (45 mg, 0.176 mmol) and $PdCl_2(dppf)$—$CH_2Cl_2$ adduct (7.19 mg, 8.80 μmol) was added toluene (1.2 mL) and EtOH (0.4 mL). The mixture was sonicated for 1 min, and flushed with argon. To this was added sodium carbonate (0.323 mL, 1.5 M, 0.484 mmol). The reaction mixture was heated in a microwave at 140° C. for 45 min. LCMS indicated completion of the reaction. The reaction mixture was directly loaded to 40 g ISCO column which was eluted with hexanes for 3 min, then a 20 min gradient from 0% to 100% EtOAc in hexanes. The desired fractions were combined and concentrated. The compound was dissolved in DMSO and was further purified via preparative LC/MS (Method A: 30-100% B over 10 minutes, then a 2-minute hold at 100% B). Fractions containing the desired product were combined and dried via centrifugal evaporation to Example 189 (12 mg, 0.029 mmol, 16.46% yield). $^1$H NMR (400 MHz, CHLOROFORM-d) δ 8.59 (s, 1H), 8.56 (s, 1H), 7.98 (d, J=8.8 Hz, 1H), 7.79 (s, 1H), 7.06 (dd, J=8.7, 4.5 Hz, 1H), 5.08-4.99 (m, 0.5H), 4.61 (td, J=6.6, 3.1 Hz, 0.5H), 4.14 (s, 3H), 4.08-3.62 (m, 3H), 2.65 (s, 4H), 1.59 (d, J=6.8 Hz, 1.5H), 1.47 (d, J=7.3 Hz, 1.5 H). LC-MS: method B, RT=4.22 min, MS (ESI) m/z: 394.0 $(M+H)^+$. Analytical HPLC purity (method A): 98%.

370

Example 190

(S)-2-(2-methoxy-7-methylquinoxalin-5-yl)-7,8-dihydrobenzofuro[5,4-d]thiazol-7-yl) ethanol

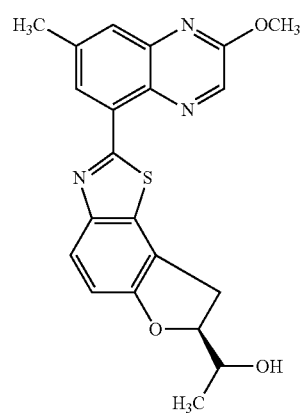

(190)

Intermediate 190A: (S)-2-chloro-7,8-dihydrobenzofuro[5,4-d]thiazole-7-carbaldehyde

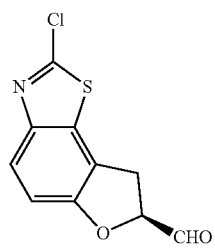

(190A)

A solution of oxalyl chloride (0.206 mL, 2.358 mmol) in dichloromethane (4.0 mL) at −78° C. was treated dropwise with DMSO (0.335 mL, 4.72 mmol) in dichloromethane (0.5 mL) and stirred for 15 min. A solution of Intermediate 149A (285 mg, 1.179 mmol) in dichloromethane (3.0 mL) was added and the mixture was stirred for 45 min. TEA (0.986 mL, 7.08 mmol) in dichloromethane (0.5 mL) was added dropwise, and the reaction mixture was stirred at −78° C. for 1.0 h before being allowed to slowly warm to room temperature. After 2 h, the reaction mixture was diluted with dichloromethane, quenched by addition of water. The organic layer was collected, washed with 1.0 N HCl, saturated sodium bicarbonate, brine, dried over sodium sulfate and concentrated to give Intermediate 190A (300 mg, 100%). The crude was dried over night at high vacuum and used for the next step without further purification. $^1$H NMR (500 MHz, CHLOROFORM-d) δ 9.90 (d, J=0.5 Hz, 1H), 7.80 (d, J=8.8 Hz, 1H), 7.11 (d, J=8.8 Hz, 1H), 5.25 (ddd, J=10.9, 5.9, 0.8 Hz, 1H), 3.62-3.54 (m, 1H), 3.52-3.46 (m, 1H); LC-MS: method H, 2 to 98% B. RT=0.67 min, MS (ESI) m/z: 257.95 and 259.95 $(M+H)^+$.

Intermediate 190B: (S)-2-chloro-7,8-dihydrobenzo-furo[5,4-d]thiazol-7-yl)ethanol

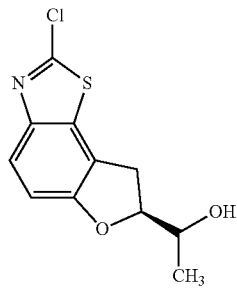

(190B)

To a solution of Intermediate 190A (300 mg, 1.164 mmol) in THF (6 mL) at −10° C. was added methyl magnesium bromide (3.0 M in diethyl ether, 1.164 mL, 3.49 mmol). The reaction mixture was stirred between −10° C. and 0° C. for 40 min, and then at room temperature for 1.0 h. The reaction was quenched at 0° C. with 1.0 M HCl (2.0 mL), diluted with EtOAc/brine. After stirring at room temperature for 15 min, the organic layer was washed with saturated sodium carbonate, brine, dried over sodium sulfate and concentrated. The crude product was purified by flash chromatography (loading in chloroform, 0% to 50% EtOAc in hexane over 18 min using a 40 g silica gel cartridge). The desired fractions were combined and concentrated to yield Intermediate 190B (90 mg, 0.352 mmol, 30.2% yield) as a mixture of diastereoisomers. $^1$H NMR (500 MHz, CHLOROFORM-d) δ 7.64-7.57 (m, 1H), 6.89-6.82 (m, 1H), 4.82-4.65 (m, 1H), 4.17-3.80 (m, 1H), 3.33-3.19 (m, 1H), 3.16-2.98 (m, 1H), 1.27 and 1.16 (d, J=6.33 Hz, 3H); LC-MS: method H, 2 to 98% B. RT=0.77 min, MS (ESI) m/z: 255.95 and 258.00 (M+H)$^+$.

Intermediate 190C s(S)-2-(2-(difluoromethoxy)-7-methylquinoxalin-5-yl)-7,8-dihydrobenzofuro[5,4-d]thiazo 1-7-yl)ethanol

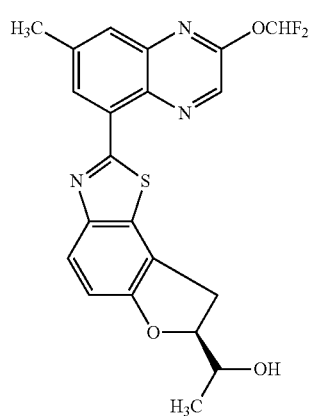

(190C)

A solution of I-1 (113 mg, 0.446 mmol) and Intermediate 190B (120 mg, 0.469 mmol) in toluene/EtOH (3:1) (4 mL) was added to PdCl$_2$(dppf)—CH$_2$Cl$_2$ adduct (19.16 mg, 0.023 mmol). The mixture was flushed with argon for 1 min. To this was added 1.5 M Na$_2$CO$_3$ (0.688 mL, 1.032 mmol). The reaction mixture was heated in a microwave at 140° C. for 45 min. IPLC indicated a completion of reaction. The reaction mixture was transferred to a round bottom flask, and the toluene/EtOH was removed under vacuum. The crude was treated with MeOH, sonicated. The precipitate was collected by filtration, washed with water, MeOH and dried under vacuum to yield Intermediate 190C (115 mg, 0.268 mmol, 57.1% yield) as a yellow solid. LC-MS: method H, 2 to 98% B. RT=0.98 min, MS (ESI) m/z: 430.05 (M+H)$^+$.

Example 190

To Intermediate 190C (115 mg, 0.268 mmol) dissolved in THF (4 mL) and MeOH (4 mL) at room temperature was added 4.0 M sodium methoxide in MeOH (0.268 mL, 1.071 mmol). The reaction mixture was stirred at 50° C. for 2.5 h. Solvent was removed under vacuum, and the crude was triturated with MeOH. The precipitate was collected by filtration, rinsed with MeOH, chased with toluene/TIF (1:1, 20 mL) and dried under high vacuum to give crude product (105 mg) as a yellow solid. 15 mg was dissolved in DMSO and purified via preparative LC/MS (method C, 45-90% B over 20 min, then a 5-min hold at 100% B). Fractions containing the desired product were combined and dried via centrifugal evaporation to yield Example 190 (5.3 mg). $^1$HNMR indicated a mixture of diastereoisomers in a ratio of 1:5. The major isomer: $^1$H NMR (500 MHz, CHLOROFORM-d) δ 8.61 (s, 1H), 8.57-8.53 (m, 1H), 7.94-7.89 (m, 1H), 7.74 (s, 1H), 7.04-6.98 (m, 1H), 4.95-4.76 (m, 1H), 4.28-4.21 (m, 1H), 4.13 (s, 3H), 3.51-3.42 (m, 1H), 3.37-3.17 (m, 1H), 2.61 (s, 3H), 1.36-1.28 (m, 3H); LC-MS: method C, 2 to 98% B. RT=0.98 min, MS (ESI) m/z: 394.10 (M+H)$^+$. Analytical HPLC purity (method B): 100%.

Example 191

Methyl ((2-(2-methoxy-7-methylquinoxalin-5-yl)-7,8-dihydrobenzofuro[5,4-d]thiazol-7-yl)methy 1)carbamate

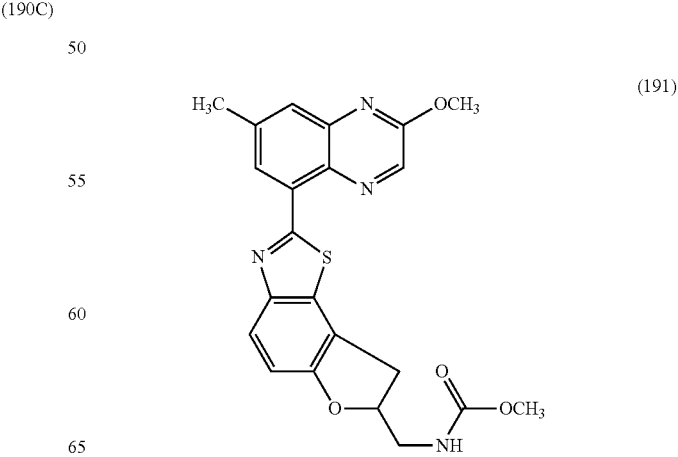

(191)

Intermediate 191A (2-(2-methoxy-7-methylquinoxalin-5-yl)-7,8-dihydrobenzofuro[5,4-d]thiazol-7-yl)methan ol

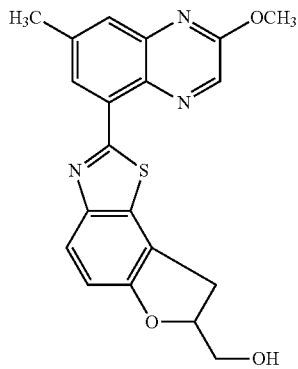
(191A)

To a solution of Intermediate I-9 (273 mg, 1.250 mmol) and Intermediate 144D (318 mg, 1.316 mmol) in toluene (7.5 mL) and EtOH (2.5 mL) was added to PdCl$_2$(dppf)—CH$_2$Cl$_2$ adduct (47.3 mg, 0.058 mmol). The mixture was flushed with argon for 1 min. To this was added sodium carbonate (1.754 mL, 1.5 M, 2.63 mmol). The reaction mixture was heated in a microwave reactor at 140° C. for 45 min, at which time HPLC indicated a completion of reaction. Toluene was removed by blowing a stream of nitrogen overnight. The crude was treated with wet MeOH/water (ca 15 mL, 4:1), sonicated. The precipitate was collected by filtration, washed with water, and MeOH until no color in the MeOH washing. The precipitate was air dried first, then under high vacuum to give a dark green solid. The dark green solid was dissolved in THF (60 mL), treated with 450 mg SilaMetS Thiol resin (from Silicycle, R51030B, 1.28 mmol/g) at 55° C. for 3.0 h. The mixture was diluted with EtOAc (20 mL), filtered through a 12 g silica gel cartridge, rinsed with 100 mL of THF/EtOAc (1:1). The filtrate was concentrated to give Intermediate 191A (350 mg, 0.922 mmol, 78% yield) as a yellow solid. $^1$H NMR (400 MHz, CHLOROFORM-d) δ 8.62 (d, J=2.0 Hz, 1H), 8.56 (s, 1H), 7.93 (d, J=8.6 Hz, 1H), 7.75 (s, 1H), 7.03 (d, J=8.6 Hz, 1H), 5.21-5.06 (m, 1H), 4.13 (s, 3H), 4.01-3.91 (m, 1H), 3.84 (dt, J=12.0, 6.1 Hz, 1H), 3.48 (dd, J=15.4, 9.7 Hz, 1H), 3.26 (dd, J=15.2, 7.3 Hz, 1H), 2.65 (s, 3H), 1.96 (t, J=6.4 Hz, 1H). LC-MS: Method C; RT=2.33 min, MS (ESI) m/z: 380.0 (M+H)$^+$.

Intermediate 191B (2-(2-methoxy-7-methylquinoxalin-5-yl)-7,8-dihydrobenzofuro[5,4-d]thiazol-7-yl)methyl methanesulfonate

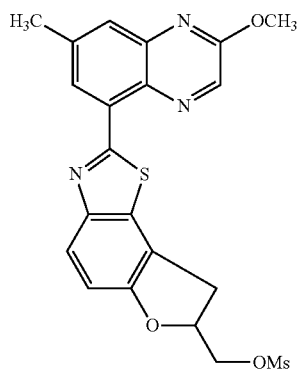
(191B)

To a suspension of Intermediate 191A (90 mg, 0.237 mmol) in CH$_2$Cl$_2$ (2 mL) was added methanesulfonyl chloride (0.028 mL, 0.356 mmol), followed by triethylamine (0.165 mL, 1.186 mmol). The mixture was stirred at room temperature for 1 h. The reaction was quenched by 1N HCl and extracted with CH$_2$Cl$_2$. The combined organic layer was washed with brine, dried over MgSO$_4$ and concentrated to Intermediate 191B (109 mg, 0.238 mmol, 100% yield) as a yellow solid. This material was used directly for the next step without any purification. $^1$H NMR (400 MHz, CHLOROFORM-d) δ 8.64 (d, J=1.8 Hz, 1H), 8.57 (s, 1H), 7.96 (d, J=8.8 Hz, 1H), 7.77 (d, J=0.9 Hz, 1H), 7.04 (d, J=8.6 Hz, 1H), 5.33-5.21 (m, 1H), 4.57-4.44 (m, 2H), 4.14 (s, 3H), 3.60 (dd, J=15.6, 9.7 Hz, 1H), 3.31 (dd, J=15.7, 6.9 Hz, 1H), 3.08 (s, 3H), 2.66 (s, 3H). LC-MS: Method C; RT=2.31 min, MS (ESI) m/z: 458.0 (M+H)$^+$.

Intermediate 191C 7-(azidomethyl)-2-(2-methoxy-7-methylquinoxalin-5-yl)-7,8-dihydrobenzofuro[5,4-d]thia zole

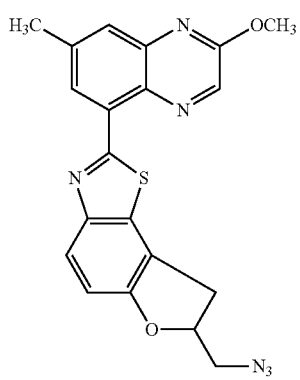
(191C)

To a suspension of Intermediate 191B (109 mg, 0.238 mmol) in DMF (2 mL) and THF (2 mL) was added sodium azide (31.0 mg, 0.476 mmol). The mixture was heated at 75° C. for 6 hours, at which TLC and LCMS indicated completion of the reaction. The mixture was cooled, diluted with EtOAc and water, extracted with EtOAc. The combined organic layer was washed with brine, dried with MgSO$_4$ and concentrated to Intermediate 191C (96 mg, 0.237 mmol, 100% yield) as a yellow solid. The sample was used for next step without purification. $^1$H NMR (400 MHz, CHLOROFORM-d) δ 8.63 (d, J=1.8 Hz, 1H), 8.57 (s, 1H), 7.95 (d, J=8.6 Hz, 1H), 7.77 (d, J=0.9 Hz, 1H), 7.07 (d, J=8.8 Hz, 1H), 5.30-5.12 (m, 1H), 4.14 (s, 3H), 3.67-3.52 (m, 3H), 3.25 (dd, J=15.5, 6.7 Hz, 1H), 2.66 (s, 3H). LC-MS: Method C; RT=2.57 min, MS (ESI) m/z: 405.0 (M+H)$^+$.

Intermediate 191D (2-(2-methoxy-7-methylquinoxalin-5-yl)-7,8-dihydrobenzofuro[5,4-d]thiazol-7-yl)methan amine

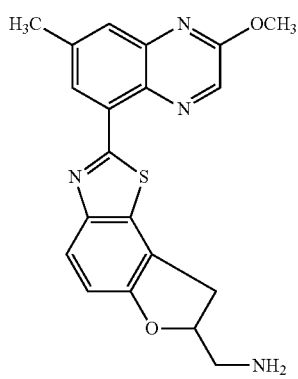

(191D)

To a solution of Intermediate 191C (96 mg, 0.237 mmol) in THF/water (9/1, 2 mL) was added triphenylphosphine (187 mg, 0.712 mmol). The mixture was stirred at room temperature overnight. TLC and LCMS indicated completion of the reaction. The mixture was diluted with EtOAc and water, extracted with EtOAc, the combined organic layer was washed saturated sodium bicarbonate, brine and dried over sodium sulfate and concentrated. The compound was dissolved in DMSO and further purified via preparative LC/MS (Method A: 0-100% B over 10 minutes, then a 2-minute hold at 100% B). Fractions containing the desired product were combined and dried via centrifugal evaporation to Intermediate 191D (44 mg, 0.085 mmol, 35.8% yield) as a yellow solid. H NMR (400 MHz, METHANOL-d$_4$) δ 8.58 (d, J=1.8 Hz, 1H), 8.57 (s, 1H), 7.93 (d, J=8.6 Hz, 1H), 7.81 (d, J=0.9 Hz, 1H), 7.12 (d, J=8.8 Hz, 1H), 5.34-5.16 (m, 1H), 4.14 (s, 3H), 3.68 (dd, J=15.8, 9.7 Hz, 1H), 3.42-3.36 (m, 1H), 3.28-3.20 (m, 2H), 2.66 (s, 3H). LC-MS: method C, RT=2.0 min, MS (ESI) m/z: 397.0 (M+H)$^+$. Analytical HPLC purity (method A): 94%.

Example 191

To a solution of Intermediate 191D (9.2 mg, 0.019 mmol) and pyridine (0.023 mL, 0.280 mmol) in dichloromethane (1 mL) was added methyl chloroformate (5.30 mg, 0.056 mmol). The reaction mixture was stirred at room temperature for 0.5 h, then quenched with 1N HCl and extracted with EtOAc. The combined organic layer was washed with saturated sodium bicarbonate, brine, dried over sodium sulfate and concentrated. The crude was dissolved in DMSO and purified via preparative LC/MS (Method D: 45-90% B over 20 minutes, then a 10-minute hold at 100% B). Fractions containing the desired product were combined and dried via centrifugal evaporation to Example 191 (5.4 mg, 0.012 mmol, 66.2% yield). $^1$H NMR (500 MHz, DMSO-d$_6$) δ 8.75 (s, 1H), 8.58 (s, 1H), 7.89 (d, J=8.5 Hz, 1H), 7.82 (br. s., 1H), 7.47 (br. s., 1H), 7.04 (d, J=8.5 Hz, 1H), 5.04 (br. s., 1H), 4.08 (s, 3H), 3.50 (d, J=16.2 Hz, 2H), 3.36-3.11 (m, 2H), 2.63 (s, 3H). LC-MS: method L, RT=2.23 min, MS (ESI) m/z: 437.23 (M+H)$^+$. Analytical HPLC purity (method B): 100%.

Example 192

Phenyl ((2-(2-methoxy-7-methylquinoxalin-5-yl)-7,8-dihydrobenzofuro[5,4-d]thiazol-7-yl)methy 1)carbamate

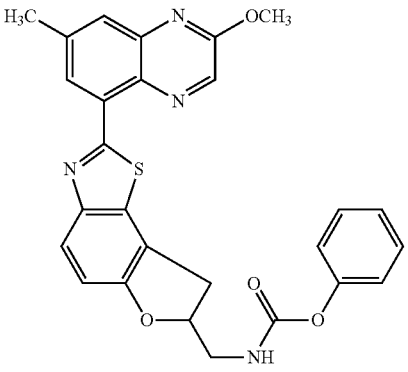

(192)

To a solution of Intermediate 191D (11.0 mg, 0.022 mmol) and pyridine (0.027 mL, 0.335 mmol) in CH$_2$Cl$_2$ (1 mL) was added phenyl chloroformate (10.49 mg, 0.067 mmol). The mixture was stirred at room temperature for 0.5 h, at which TLC and LCMS indicated completion of the reaction. The reaction was quenched with 1N HCl, extracted with EtOAc, the combined organic layer was washed with saturated sodium bicarbonate, brine, dried over sodium sulfate and concentrated. The crude was dissolved in DMSO and purified via preparative LC/MS (Method D: 45-100% B over 15 minutes, then a 5-minute hold at 100% B). Fractions containing the desired product were combined and dried via centrifugal evaporation to afford Example 192 (5.5 mg, 10.48 μmol, 46.9% yield). $^1$H NMR (500 MHz, DMSO-d$_6$) δ 8.74 (s, 1H), 8.58 (br. s., 1H), 8.10 (br. s., 1H), 7.91 (d, J=8.2 Hz, 1H), 7.81 (br. s., 1H), 7.37 (t, J=7.2 Hz, 2H), 7.24-7.17 (m, 1H), 7.08 (d, J=4.0 Hz, 3H), 5.12 (br. s., 1H), 4.07 (s, 3H), 3.66-3.39 (m, 2H), 3.35-3.16 (m, 2H), 2.62 (s, 3H). LC-MS: method L, RT=2.50 min, MS (ESI) m/z: 499.30 (M+H)$^+$. Analytical IPLC purity (method B): 96%.

Example 193

Benzyl ((2-(2-methoxy-7-methylquinoxalin-5-yl)-7,8-dihydrobenzofuro[5,4-d]thiazol-7-yl)methy 1)carbamate

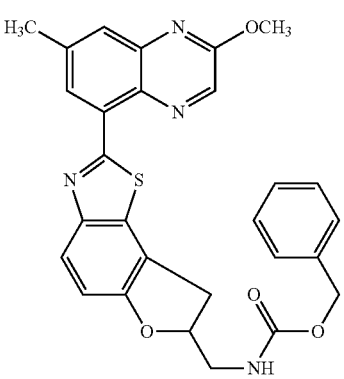

(193)

To a solution of Intermediate 191D (9.2 mg, 0.019 mmol) and pyridine (0.023 mL, 0.280 mmol) in dichloromethane (1 mL) was added benzyl chloroformate (9.56 mg, 0.056 mmol). The mixture was stirred at room temperature for 0.5 h, at which TLC and LCMS indicated completion of the reaction. The reaction was quenched with 1N HCl, extracted with EtOAc, the combined organic layer was washed with saturated sodium bicarbonate, brine, dried over sodium sulfate and concentrated. The crude was dissolved in DMSO and purified via preparative LC/MS (Method D: 45-100% B over 13 minutes, then a 6-minute hold at 100% B). Fractions containing the desired product were combined and dried via centrifugal evaporation to Example 193 (4.1 mg, 7.52 µmol, 40.2% yield). $^1$H NMR (500 MHz, DMSO-$d_6$) δ 8.75 (s, 1H), 8.59 (br. s., 1H), 7.89 (d, J=8.5 Hz, 1H), 7.82 (br. s., 1H), 7.61 (br. s., 1H), 7.33 (br. s., 5H), 7.04 (d, J=8.2 Hz, 1H), 5.04 (br. s., 3H), 4.08 (s, 3H), 3.80-2.85 (m, 4H), 2.63 (br. s., 3H). LC-MS: method L, RT=2.56 min, MS (ESI) m/z: 513.35 (M+H)$^+$. Analytical HPLC purity (method B): 94%.

Example 194

(R)-(2-(2-methoxy-7-methylquinoxalin-5-yl)-7-methyl-7,8-dihydrobenzofuro[5,4-d]thiazol-7-yl) methyl (2-methylpyrimidin-5-yl)carbamate

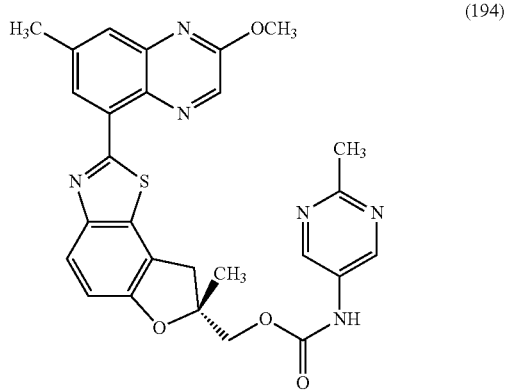 [SMILES: COc1cnc2c(-c3nc4ccc5c(c4s3)C[C@](C)(COC(=O)Nc3cnc(C)nc3)O5)cc(C)cc2n1]

Intermediate 194A (R)-(2-(2-methoxy-7-methylquinoxalin-5-yl)-7-methyl-7,8-dihydrobenzofuro[5,4-d]thiazol-7-yl) methyl chloroformate

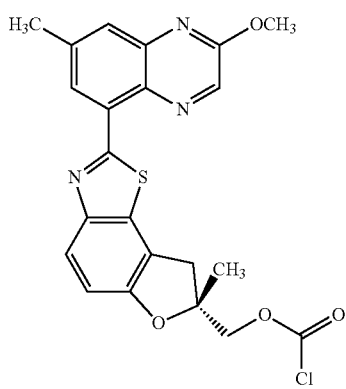

To the solution of Example 188 (30 mg, 0.076 mmol) in THF (2 ml) was added 15% phosgene in toluene (0.215 mL, 0.305 mmol), followed by DIEA (0.080 mL, 0.457 mmol). The reaction mixture was stirred at room temperature for 30 min, at which time LCMS (quenched with MeOH) indicated a completion of reaction. Solvent and excess of phosgene was completely removed under vacuum to give Intermediate 194A which was used for the next step without purification. LC-MS: method C, RT=2.61 min, MS (ESI) m/z: 456.0 (M+H)$^+$ (methyl carbamate).

Example 194

To Intermediate 194A (10 mg, 0.022 mmol) in dichloromethane (1 mL) was added to a solution of 2-methylpyrimidin-5-amine (4.79 mg, 0.044 mmol) and pyridine (0.018 ml, 0.219 mmol) in dichloromethane (0.5 mL) dropwise. The reaction mixture was stirred at room temperature for 0.5 h, at which time LCMS and HPLC indicated a completion of reaction. The reaction mixture was diluted with EtOAc, washed with 0.5 N HCl. The organic layer was washed with brine, dried over sodium sulfate and concentrated. The crude was dissolved in DMSO and purified via preparative LC/MS (Method D: Gradient: 45-90% B over 20 minutes, then a 5-minute hold at 100% B). Fractions containing the desired product were combined and dried via centrifugal evaporation to Example 194 (4.0 mg, 7.57 µmol, 34.5% yield). $^1$H NMR (500 MHz, DMSO-$d_6$) δ 10.01 (br. s., 1H), 8.73 (br. s., 3H), 8.57 (br. s., 1H), 7.90 (d, J=8.2 Hz, 1H), 7.80 (br. s., 1H), 7.04 (d, J=8.5 Hz, 1H), 4.48-4.27 (m, 2H), 4.07 (s, 3H), 3.56-3.15 (m, 2H), 2.62 (s, 3H), 2.54 (s, 3H), 1.55 (s, 3H). LC-MS: Method L, 0 to 100% B. RT=2.20 min, MS (ESI) m/z: 529.35 (M+H)$^+$. Analytical HPLC purity (method B): 100%.

Example 195

(R)-(2-(2-methoxy-7-methylquinoxalin-5-yl)-7-methyl-7,8-dihydrobenzofuro[5,4-d]thiazol-7-yl) methyl pyridin-3-ylcarbamate

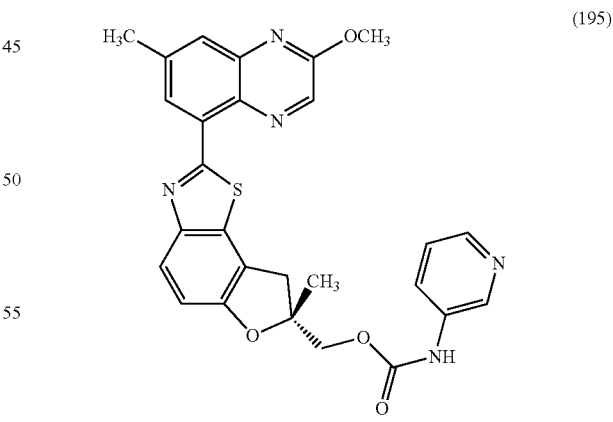

To Intermediate 194A (10 mg, 0.022 mmol) in dichloromethane (1 mL) was added to a solution of pyridin-3-amine (4.13 mg, 0.044 mmol) and pyridine (0.018 ml, 0.219 mmol) in dichloromethane (0.5 mL) dropwise. The reaction mixture was stirred at room temperature for 0.5 h, at which time LCMS and HPLC indicated a completion of reaction. The reaction mixture was diluted with EtOAc, washed with 0.5 N HCl. The organic layer was washed with brine, dried over sodium sulfate and concentrated. The crude was dissolved in DMSO and purified via preparative LC/MS (Method D: Gradient: 50-100% B over 20 minutes, then a 5-minute hold at 100% B). Fractions containing the desired product were combined and dried via centrifugal evaporation to Example 195 (4.4 mg, 8.57 µmol, 39.1% yield). $^1$H NMR (500 MHz, DMSO-$d_6$) δ 10.03 (br. s., 1H), 8.74 (s, 1H), 8.65 (br. s., 1H), 8.58 (br. s., 1H), 8.23 (br. s., 1H), 7.91 (d, J=8.5 Hz, 2H), 7.81 (br. s., 1H), 7.36 (br. s., 1H), 7.05 (d, J=8.5 Hz, 1H), 4.45-4.27 (m, 2H), 4.07 (s, 3H), 3.55-2.95 (m, 2H), 2.63 (s, 3H), 2.54 (s, 3H), 1.56 (br. s., 3H). LC-MS: Method L, 0 to 100% B. RT=2.01 min, MS (ESI) m/z: 514.05 (M+H)$^+$. Analytical HPLC purity (method B): 100%.

Example 196

(R)-(2-(2-methoxy-7-methylquinoxalin-5-yl)-7-methyl-7,8-dihydrobenzofuro[5,4-d]thiazol-7-yl) methyl (3-cyanophenyl)carbamate

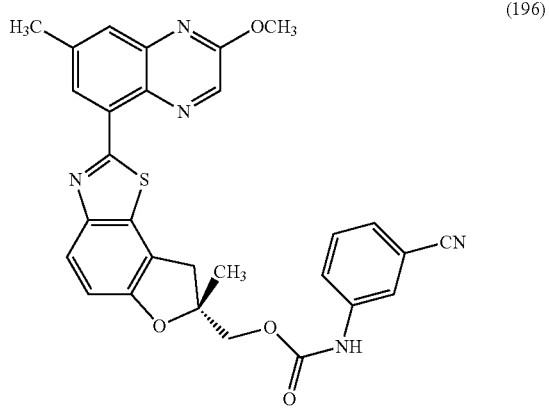 [SMILES: COc1cnc2c(-c3nc4ccc5c(c4s3)C[C@](C)(COC(=O)Nc3cccc(C#N)c3)O5)cc(C)cc2n1]

(196)

To Intermediate 194A (10 mg, 0.022 mmol) in dichloromethane (1 mL) was added to a solution of 3-aminobenzonitrile (5.18 mg, 0.044 mmol)) and pyridine (0.018 ml, 0.219 mmol) in dichloromethane (0.5 mL) dropwise. The reaction mixture was stirred at room temperature for 0.5 h, at which time LCMS and HPLC indicated a completion of reaction. The reaction mixture was diluted with EtOAc, washed with 0.5 N HCl. The organic layer was washed with brine, dried over sodium sulfate and concentrated. The crude was dissolved in DMSO and purified via preparative LC/MS (Method D: Gradient: 60-100% B over 22 minutes, then a 5-minute hold at 100% B). Fractions containing the desired product were combined and dried via centrifugal evaporation to Example 196 (7.2 mg, 0.013 mmol, 61.1% yield). $^1$H NMR (500 MHz, DMSO-$d_6$) δ 10.11 (br. s., 1H), 8.74 (s, 1H), 8.58 (br. s., 1H), 7.91 (d, J=8.5 Hz, 1H), 7.86 (br. s., 1H), 7.82 (br. s., 1H), 7.70 (br. s., 1H), 7.52-7.41 (m, 2H), 7.05 (d, J=8.2 Hz, 1H), 4.43-4.30 (m, 2H), 4.08 (s, 3H), 3.90 (s, 1H), 3.51-3.21 (m, 1H), 2.63 (br. s., 3H), 1.56 (br. s., 3H). LC-MS: Method L, 0 to 100% B. RT=2.60 min, MS (ESI) m/z: 538.20 (M+H)$^+$. Analytical HPLC purity (method B): 100%.

Example 197

Ethyl ((2-(2-methoxy-7-methylquinoxalin-5-yl)-7,8-dihydrobenzofuro[5,4-d]thiazol-7-yl) methyl)carbamate

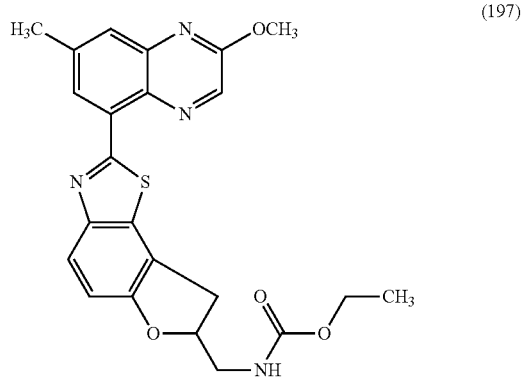 [SMILES: CCOC(=O)NCC1Cc2c(ccc3nc(-c4cc(C)cc5nc(OC)cnc45)sc23)O1]

(197)

To a solution of Intermediate 191D (6.0 mg, 0.012 mmol) and pyridine (0.015 mL, 0.183 mmol) in CH$_2$Cl$_2$ (1 mL) was added ethyl chloroformate (3.97 mg, 0.037 mmol). The mixture was stirred at room temperature for 0.5 h, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: 50-100% B over 20 minutes, then a 10-minute hold at 100% B). Fractions containing the desired product were combined and dried via centrifugal evaporation to Example 197 (3.7 mg, 8.21 µmol, 67.4% yield). $^1$H NMR (500 MHz, DMSO-$d_6$) δ 8.74 (br. s., 1H), 8.57 (br. s., 1H), 7.89 (d, J=8.2 Hz, 1H), 7.81 (br. s., 1H), 7.41 (br. s., 1H), 7.04 (d, J=8.2 Hz, 1H), 5.03 (br. s., 1H), 4.07 (br. s., 3H), 4.00 (d, J=6.1 Hz, 2H), 3.63-3.44 (m, 2H), 3.37-3.10 (m, 2H), 2.62 (br. s., 3H), 1.15 (br. s., 3H). LC-MS: method L, RT=2.41 min, MS (ESI) m/z: 451.30 (M+H)$^+$. Analytical HPLC purity (method B): 100%.

Example 198

Isobutyl ((2-(2-methoxy-7-methylquinoxalin-5-yl)-7,8-dihydrobenzofuro[5,4-d]thiazol-7-yl)methyl)carbamate

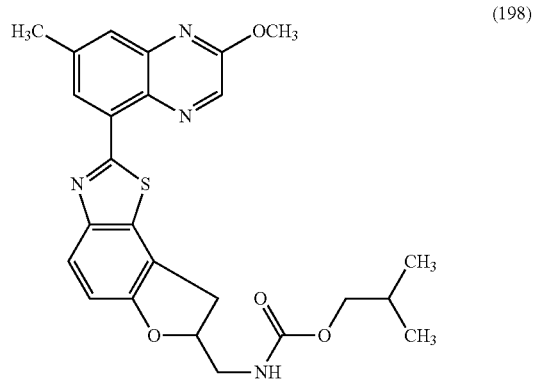 [SMILES: COc1cnc2c(-c3nc4ccc5c(c4s3)CC(CNC(=O)OCC(C)C)O5)cc(C)cc2n1]

(198)

To a solution of Intermediate 191D (6.0 mg, 0.012 mmol) and pyridine (0.015 mL, 0.183 mmol) in DCM (1 mL) was added isobutyl chloroformate (4.99 mg, 0.037 mmol). The mixture was stirred at room temperature for 0.5 h, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 60-100% B over 20 minutes, then a 10-minute hold at 100% B). Fractions containing the desired product were combined and dried via centrifugal evaporation to Example 198 (3.6 mg, 7.52 µmol, 61.7% yield). $^1$H NMR (500 MHz, DMSO-$d_6$) δ 8.75 (br. s., 1H), 8.58 (br. s., 1H), 7.89 (d, J=8.2 Hz, 1H), 7.82 (br. s., 1H), 7.43 (br. s., 1H), 7.04 (d, J=8.5 Hz, 1H), 5.04 (br. s., 1H), 4.08 (br. s., 3H), 3.75 (br. s., 2H), 3.56-2.93 (m, 4H), 2.63 (br. s., 3H), 1.81 (br. s., 1H), 0.85 (br. s., 6H). LC-MS: method L, RT=2.58 min, MS (ESI) m/z: 479.05 (M+H)$^+$. Analytical HPLC purity (method B): 100%.

Example 199 cis-5-fluoro-2-(2-methoxy-7-methylquinoxalin-5-yl)-8-methyl-7,8-dihydrobenzofuro[5,4-d]thiazol-7-yl)methanol

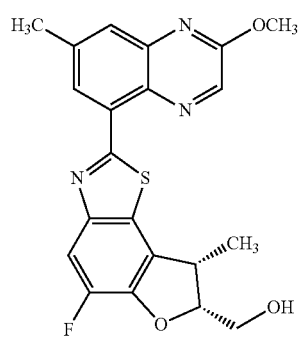

(199)

Intermediate 199A: (E)-6-(but-2-en-1-yloxy)-2-chloro-5-fluorobenzo[d]thiazole

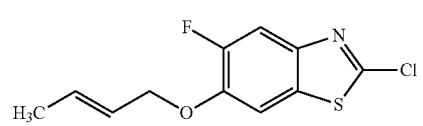

(199A)

To a solution of 2-chloro-5-fluorobenzo[d]thiazol-6-ol (5 g, 24.56 mmol) in DMF (60 mL) was added (E)-1-bromobut-2-ene (3.57 mL, 29.5 mmol), cesium carbonate (20.00 g, 61.4 mmol). The mixture was stirred at room temperature for 2 h, at which time LCMS and TLC indicated completion of the reaction. The reaction mixture was diluted with EtOAc and water (100 mL), neutralized with 1.0 N HCl (100 mL), and extracted with ethyl acetate. The organic layer was washed with brine, dried over Na$_2$SO$_4$ and concentrated to yield Intermediate 199A (6.1 g, 23.67 mmol, 96% yield) as white solid. $^1$H NMR (400 MHz, CHLORO-FORM-d) δ 7.66 (d, J=11.2 Hz, 1H), 7.29 (d, J=7.7 Hz, 1H), 5.98-5.86 (m, 1H), 5.81-5.69 (m, 1H), 4.58 (d, J=6.2 Hz, 2H), 1.78 (dd, J=6.4, 1.1 Hz, 3H). $^{19}$F NMR (376 MHz, CHLOROFORM-d) δ -132.83 (s, 1F). LC-MS: method C, RT=2.24 min, MS (ESI) m/z: 258.0 (M+H)$^+$. Intermediate 199B: 7-(but-3-en-2-yl)-2-chloro-5-fluorobenzo[d]thiazol-6-ol

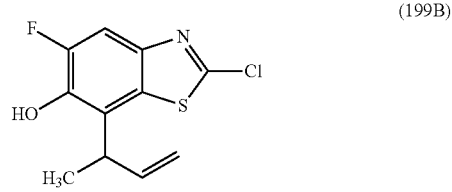 [SMILES: C=CC(C)c1c(O)c(F)cc2nc(Cl)sc12]

(199B)

A solution of Intermediate 199A (4.8 g, 18.63 mmol) in N,N-diethyl aniline (70 ml) was heated at 190° C. (oil bath) under argon for 2 h. After cooling to room temperature, the reaction mixture was diluted with EtOAc, washed with 3.0 N HCl (3×200 mL), brine (2×). The organic layer was dried over sodium sulfate and concentrated to yield Intermediate 199B (4.65 g, 18.04 mmol, 97% yield) as an off-white solid. $^1$H NMR (400 MHz, CHLOROFORM-d) δ 7.57 (d, J=10.1 Hz, 1H), 6.12 (ddd, J=17.1, 10.6, 5.2 Hz, 1H), 5.53 (d, J=5.9 Hz, 1H), 5.30 (t, J=1.8 Hz, 1H), 5.26 (dt, J=9.8, 1.4 Hz, 1H), 4.31-3.94 (m, 1H), 1.46 (d, J=7.3 Hz, 3H). $^{19}$F NMR (376 MHz, CHLOROFORM-d) δ -138.88 (s, 1F). LC-MS: Method C, RT=2.20 min, MS (ESI) m/z: 257.9 (M+H)$^+$.

Intermediate 199C trans-2-chloro-5-fluoro-8-methyl-7,8-dihydrobenzofuro[5,4-d]thiazol-7-yl)methanol and Intermediate 199D cis-2-chloro-5-fluoro-8-methyl-7,8-dihydrobenzofuro[5,4-d]thiazol-7-yl)methanol

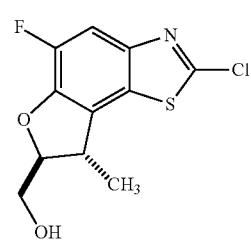

(199C)

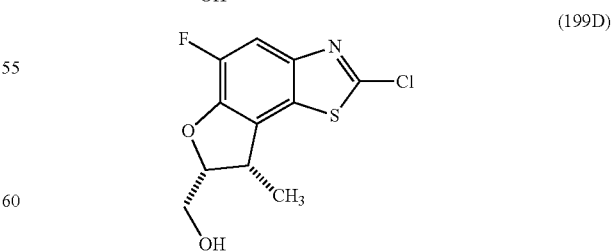

(199D)

To a solution of Intermediate 199B (400 mg, 1.552 mmol) in dichloromethane (15 mL) was added mCPBA (696 mg, 3.10 mmol), followed PTSA (59.0 mg, 0.310 mmol). The mixture was stirred at 45° C. overnight. The mixture was diluted with EtOAc and 8% Na₂S₂O₃, extracted with EtOAc, the combined organic layer was washed with saturated sodium bicarbonate, brine, dried over sodium sulfate and concentrated. The crude product was purified by flash chromatography (loading in chloroform, 0% to 70% EtOAc in hexane over 30 min using a 120 g silica gel cartridge). Two fractions were obtained. The 1$^{st}$ fraction, Intermediate 199 C (140 mg, 0.511 mmol, 33.0% yield) was obtained as a white solid. $^1$H NMR (400 MHz, CHLOROFORM-d) δ 7.56 (d, J=10.6 Hz, 1H), 4.67 (ddd, J=7.9, 4.8, 3.1 Hz, 1H), 4.11-4.01 (m, 1H), 3.87 (dd, J=12.4, 5.0 Hz, 1H), 3.69 (quin, J=7.2 Hz, 1H), 1.48 (d, J=7.0 Hz, 3H). $^{19}$F NMR (376 MHz, CHLOROFORM-d) 6-138.04 (s, 1F). LC-MS: Method C, RT=1.94 min, MS (ESI) m/z: 273.9 (M+H)⁺. The second fraction, Intermediate 199D (150 mg, 0.548 mmol, 35.3% yield) was obtained as a white solid. $^1$H NMR (400 MHz, CHLOROFORM-d) δ 7.55 (d, J=10.6 Hz, 1H), 5.08 (ddd, J=9.0, 6.8, 4.2 Hz, 1H), 4.07-3.92 (m, 2H), 3.90-3.76 (m, 1H), 1.38 (d, J=7.3 Hz, 3H). $^{19}$F NMR (376 MHz, CHLOROFORM-d) δ -137.85 (s, 1F). LC-MS: Method C, RT=1.94 min, MS (ESI) m/z: 273.9 (M+H)⁺.

Example 199

To Intermediate I-9 (17.92 mg, 0.082 mmol), intermediate 199D (25 mg, 0.091 mmol) and PdCl₂(dppf)—CH₂Cl₂ adduct (3.73 mg, 4.57 μmol) was added toluene (0.6 mL) and EtOH (0.2 mL). The mixture was sonicated for 1 min, and flushed with argon. To this was added sodium carbonate (0.167 mL, 1.5M, 0.251 mmol). The reaction mixture was heated in a microwave at 140° C. for 40 min. LCMS indicated completion of the reaction. The reaction mixture was directly loaded to 40 g ISCO column which was eluted with hexanes for 3 min, then a 20 min gradient from 0% to 100% EtOAc in hexanes. The desired fractions were combined and concentrated. The crude was dissolved in DMSO and purified via preparative LC/MS (Method D: Gradient: 45-90% B over 20 minutes, then a 8-minute hold at 100% B). Fractions containing the desired product were combined and dried via centrifugal evaporation to Example 199 (6.7 mg, 0.016 mmol, 19.81% yield). $^1$H NMR (500 MHz, DMSO-d₆) δ 8.74 (br. s., 1H), 8.55 (br. s., 1H), 7.83 (d, J=11.3 Hz, 1H), 7.80 (br. s., 1H), 5.06 (br. s., 1H), 5.01 (d, J=4.9 Hz, 1H), 4.07 (br. s., 3H), 3.93 (t, J=6.9 Hz, 1H), 2.61 (br. s., 3H), 1.35 (d, J=6.1 Hz, 3H). LC-MS: method L, RT=2.30 min, MS (ESI) m/z: 412.30 (M+H)⁺. Analytical HPLC purity (method B): 100%.

Example 200

5-fluoro-2-(2-methoxy-7-methylquinoxalin-5-yl)-7,7-dimethyl-7,8-dihydrobenzofuro[5,4-d]thiazole

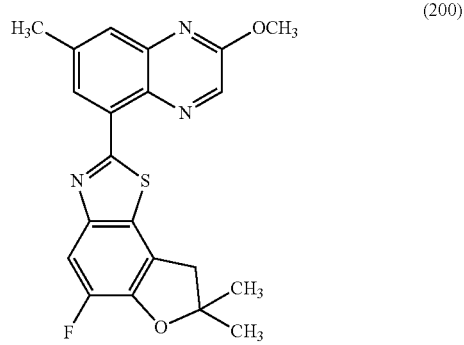 [SMILES: COc1cnc2c(-c3nc4cc(F)c5c(c4s3)CC(C)(C)O5)cc(C)cc2n1]

(200)

Intermediate 200A: 2-chloro-5-fluoro-7,7-dimethyl-7,8-dihydrobenzofuro[5,4-d]thiazole

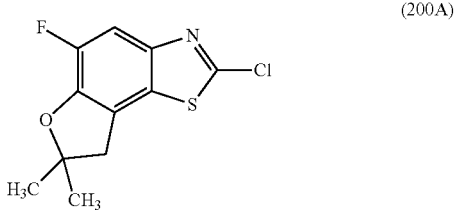 [SMILES: CC1(C)Cc2c(c(F)cc3nc(Cl)sc23)O1]

(200A)

To a solution of Intermediate 167B (20 mg, 0.078 mmol) in dichloromethane (1 mL) was added TFA (0.598 mL, 7.76 mmol). The reaction mixture was stirred at 45° C. overnight. The reaction mixture was diluted with EtOAc and saturated sodium bicarbonate, extracted with EtOAc, the combined organic layer was washed with saturated sodium bicarbonate, brine, dried over sodium sulfate and concentrated. The crude product was purified by flash chromatography (loading in chloroform, 0% to 100% EtOAc in hexane over 15 min using a 12 g silica gel cartridge). The desired fraction was collected and concentrated to Intermediate 200A (15 mg, 0.058 mmol, 75.0% yield) as a white solid. $^1$H NMR (400 MHz, CHLOROFORM-d) δ 7.54 (d, J=10.6 Hz, 1H), 3.16 (d, J=0.7 Hz, 2H), 1.60 (s, 6H). $^{19}$F NMR (376 MHz, CHLOROFORM-d) 6-138.29 (s, 1F). LC-MS: method C, RT=2.22 min, MS (ESI) m/z: 258.0 (M+H)⁺.

Example 200

To Intermediate I-9 (11.42 mg, 0.052 mmol), Intermediate 200A (15 mg, 0.058 mmol) and PdCl₂(dppf)—CH₂Cl₂ adduct (2.377 mg, 2.91 μmol) was added toluene (0.3 mL) and EtOH (0.1 mL). The mixture was sonicated for 1 min, and flushed with argon. To this was added sodium carbonate (0.107 mL, 1.5M, 0.160 mmol). The reaction mixture was heated in a microwave at 140° C. for 45 min. LCMS indicated completion of the reaction. The reaction mixture was directly loaded to 12 g ISCO column which was eluted with hexanes for 3 min, then a 20 min gradient from 0% to 100% EtOAc in hexanes. The desired fractions were combined and concentrated. The crude was dissolved in DMSO and purified via preparative LC/MS (Method D: Gradient: 60-100% B over 22 minutes, then a 5-minute hold at 100% B). Fractions containing the desired product were combined and dried via centrifugal evaporation to Example 200 (3.8 mg, 9.61 μmol, 18.34% yield). $^1$H NMR (500 MHz, DMSO-d₆) δ 8.76 (br. s., 1H), 8.59 (br. s., 1H), 7.96-7.67 (m, 2H), 4.08 (br. s., 3H), 3.32 (d, J=4.6 Hz, 2H), 2.63 (br. s., 3H), 1.56 (br. s., 6H). LC-MS: method L, RT=2.81 min, MS (ESI) m/z: 396.30 (M+H)⁺. Analytical HPLC purity (method B): 100%.

Example 201 trans-5-fluoro-2-(2-methoxy-7-methylquinoxalin-5-yl)-8-methyl-7,8-dihydrobenzofuro[5,4-d]thiazol-7-yl)methanol

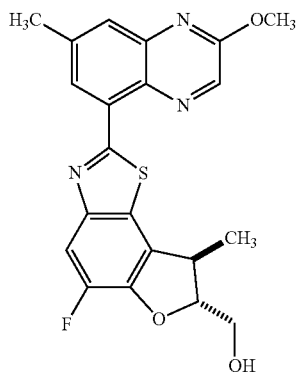

(201)

To Intermediate I-9 (21.51 mg, 0.099 mmol), 199C (30 mg, 0.110 mmol) and PdCl$_2$(dppf)—CH$_2$Cl$_2$ adduct (4.48 mg, 5.48 µmol) was added toluene (0.75 mL) and EtOH (0.25 mL). The mixture was sonicated for 1 min, and flushed with argon. To this was added sodium carbonate (0.201 mL, 1.5M, 0.301 mmol). The reaction mixture was heated in a microwave at 140° C. for 40 min. LCMS indicated completion of the reaction. The reaction mixture was directly loaded to 40 g ISCO column which was eluted with hexanes for 3 min, then a 20 min gradient from 0% to 100% EtOAc in hexanes. The desired fractions were combined and concentrated. The crude was dissolved in DMSO and purified via preparative LC/MS (Method D: Gradient: 45-90% B over 22 minutes, then a 5-minute hold at 100% B). Fractions containing the desired product were combined and dried via centrifugal evaporation to Example 201 (2.6 mg, 6.32 µmol, 6.41% yield). $^1$H NMR (500 MHz, DMSO-d$_6$) δ 8.77 (br. s., 1H), 8.58 (br. s., 1H), 7.87 (d, J=11.0 Hz, 1H), 7.84 (br. s., 1H), 5.15 (br. s., 1H), 4.64 (br. s., 1H), 4.08 (br. s., 4H), 3.78 (br. s., 1H), 3.33 (d, J=6.4 Hz, 1H), 2.63 (br. s., 4H), 1.50 (d, J=5.8 Hz, 3H). LC-MS: method L, RT=2.13 min, MS (ESI) m/z: 412.30 (M+H)$^+$. Analytical HPLC purity (method B): 100%.

Example 202

(S)-tert-butyl ((5-fluoro-2-(2-methoxy-7-methylquinoxalin-5-yl)-7,8-dihydrobenzofuro[5,4-d]thiazol-7-yl)methyl)carbamate

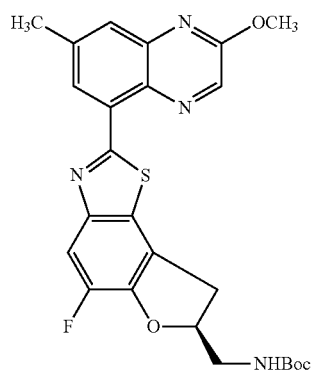

(202)

Intermediate 202A (S)-(5-fluoro-2-(2-methoxy-7-methylquinoxalin-5-yl)-7,8-dihydrobenzofuro[5,4-d]thiazol-7-yl)methyl methanesulfonate

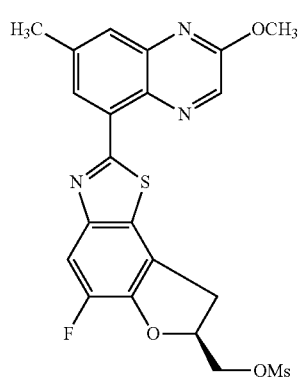

(202A)

To a suspension of Intermediate 151B (75 mg, 0.189 mmol) in DCM (2 mL) was added methanesulfonyl chloride (0.022 mL, 0.283 mmol), followed triethylamine (0.132 mL, 0.944 mmol). The mixture was stirred at room temperature for 1 h. The reaction was quenched by 1N HCl and extracted with DCM. The combined organic layer was washed with brine, dried over MgSO$_4$ and concentrated to Intermediate 202A (90 mg, 0.189 mmol, 100% yield) as a yellow solid. This material was used directly for the next step without any purification. $^1$H NMR (400 MHz, CHLOROFORM-d) δ 8.62 (d, J=1.8 Hz, 1H), 8.55 (s, 1H), 7.77 (d, J=0.9 Hz, 1H), 7.75-7.71 (m, 1H), 5.41-5.32 (m, 1H), 4.60-4.47 (m, 2H), 4.14 (s, 3H), 3.64 (dd, J=15.8, 9.7 Hz, 1H), 3.40-3.34 (m, 1H), 3.11 (s, 3H), 2.66 (s, 3H). $^{19}$F NMR (376 MHz, CHLOROFORM-d) δ −138.92 (s, 1F). LC-MS Method C; RT=2.34 min, MS (ESI) m/z: 476.0 (M+H)$^+$.

Intermediate 202B (S)-7-(azidomethyl)-5-fluoro-2-(2-methoxy-7-methylquinoxalin-5-yl)-7,8-dihydrobenzofuro[5,4-d]thiazole

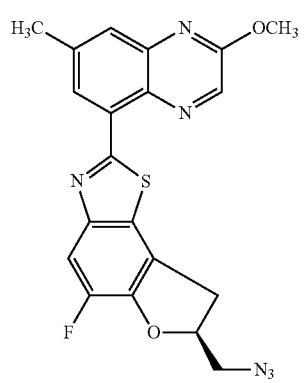

(202B)

To a suspension of Intermediate 202A (90 mg, 0.189 mmol) in DMF (2 mL) and THF (2 mL) was added sodium azide (24.61 mg, 0.379 mmol). The mixture was heated up to 75° C. for 8 hours, at which time TLC and LCMS indicated completion of the reaction. The mixture was cooled and diluted with EtOAc and water, extracted with EtOAc. The combined organic layer was washed with brine, dried with MgSO$_4$ and concentrated to Intermediate 202B (80 mg, 0.189 mmol, 100% yield) as a yellow solid. The sample was used for next step without purification. LC-MS: Method C; RT=2.57 min, MS (ESI) m/z: 423.0 (M+H)$^+$.

Intermediate 202C (S)-(5-fluoro-2-(2-methoxy-7-methylquinoxalin-5-yl)-7,8-dihydrobenzofuro[5,4-d]thiazol-7-yl)methanamine

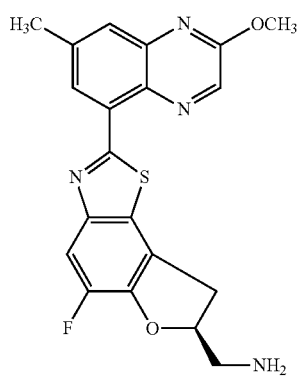

(202C)

To a solution of Intermediate 202B (140 mg, 0.332 mmol) in THF/water (9/1) (3 mL) was added PPh$_3$ (174 mg, 0.664 mmol). The mixture was stirred at room temperature overnight. TLC and LCMS indicated the completion of the reaction. The mixture was diluted with EtOAc and water, extracted with EtOAc, the combined organic layer was washed with saturated sodium bicarbonate, brine, dried over sodium sulfate and concentrated. The compound was dissolved in DMSO and purified via preparative LC/MS (Method A: 20-100% B over 10 minutes, then a 2-minute hold at 100% B). Fractions containing the desired product were combined and dried via centrifugal evaporation to Intermediate 202C (55 mg, 0.102 mmol, 30.8% yield) as a yellow solid. H NMR (400 MHz, METHANOL-d$_4$) δ 8.59 (d, J=1.8 Hz, 1H), 8.55 (s, 1H), 7.80 (d, J=0.9 Hz, 1H), 7.73 (d, J=11.2 Hz, 1H), 5.50-5.22 (m, 1H), 4.13 (s, 3H), 3.73 (dd, J=16.0, 9.8 Hz, 1H), 3.52-3.35 (m, 3H), 2.65 (s, 3H). $^{19}$F NMR (376 MHz, METHANOL-d$_4$) δ −77.03 (s, 3F), −140.24 (s, 1F). LC-MS: method C, RT=2.06 min, MS (ESI) m/z: 397.0 (M+H)$^+$. Analytical HPLC purity (method A): 95%.

Example 202

To a solution of Intermediate 202B (127 mg, 0.3 mmol) in THF/water (9/1) (2 mL) was added PPh$_3$ (236 mg, 0.900 mmol). The mixture was stirred at room temperature overnight. TLC and LCMS indicated the completion of the reaction. The mixture was diluted with EtOAc and water, extracted with EtOAc, the combined organic layer was washed with saturated sodium bicarbonate, brine, dried over sodium sulfate and concentrated. The crude sample was dissolved in DCM (2 mL), then pyridine (0.121 mL, 1.500 mmol) and BOC-anhydride (0.225 mL, 0.450 mmol) was added. The mixture was stirred at room temperature for 1 hour. The reaction mixture was diluted with EtOAc and saturated sodium bicarbonate, extracted with EtOAc, the combined organic layer was washed with saturated sodium bicarbonate, brine, dried over sodium sulfate and concentrated. The crude product was purified by flash chromatography (loading in chloroform, 0% to 70% EtOAc in hexane over 20 min using a 40 g silica gel cartridge). Fractions containing the desired product were concentrated and further purified via preparative LC/MS (Method D: Gradient: 60-100% B over 20 minutes, then a 5-minute hold at 100% B). Fractions containing the desired product were combined and dried via centrifugal evaporation to Example 202 (40 mg, 0.081 mmol, 26.9% yield). $^1$H NMR (500 MHz, DMSO-d$_6$) δ 8.68 (br. s., 1H), 8.52 (br. s., 1H), 7.88-7.73 (m, 2H), 7.15 (br. s., 1H), 5.12 (br. s., 1H), 4.05 (br. s., 3H), 3.49 (br. s., 2H), 3.32 (br. s., 1H), 3.26-3.17 (m, 1H), 2.60 (br. s., 3H), 1.36 (br. s., 9H). LC-MS: method L, RT=2.68 min, MS (ESI) m/z: 397.0 (M+H)$^+$. Analytical HPLC purity (method B): 100%.

Example 203

(R)-(5-fluoro-2-(2-methoxy-7-methylquinoxalin-5-yl)-7,8-dihydrobenzofuro[5,4-d]thiazo 1-7-yl)methyl (3-(dimethylcarbamoyl)phenyl)carbamate

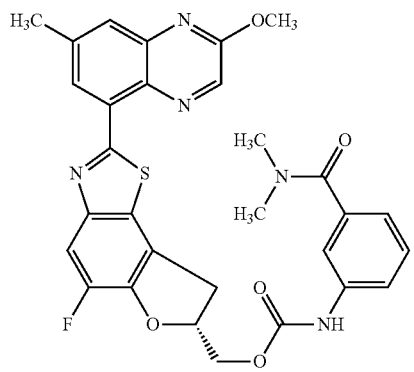

(203)

3-Amino-N,N-dimethylbenzamide (16.07 mg, 0.098 mmol) was dissolved in DCM (1.0 mL) along with pyridine (0.021 mL, 0.261 mmol) and DIEA (0.017 mL, 0.098 mmol). Intermediate 145F (15 mg, 0.033 mmol) in 2 mL of DCM was added dropwise, and the reaction mixture was stirred at room temperature for 50 minutes. The reaction was quenched with 1.0 N HCl (0.5 mL). All solvent was removed under vacuum. The crude was dissolved in DMSO/THF (2:1, 6 mL) and purified via preparative LC/MS (method C, 50-95% B over 20 min, then a 5-min hold at 100% B). Fractions containing the desired product were combined and dried via centrifugal evaporation to yield Example 203 (9.8 mg, 50% yield). $^1$H NMR (500 MHz, DMSO-d$_6$) δ 9.95 (br. s., 1H), 8.72 (s, 1H), 8.56 (d, J=1.5 Hz, 1H), 7.87 (d, J=11.3 Hz, 1H), 7.81 (s, 1H), 7.51 (br. s., 2H), 7.33 (br. s., 1H), 7.01 (d, J=7.6 Hz, 1H), 5.46-5.38 (m, 1H), 4.52 (dd, J=12.2, 2.7 Hz, 1H), 4.40 (dd, J=12.4, 6.9 Hz, 1H), 4.08 (s, 3H), 3.68-3.60 (m, 1H), 3.39-3.31 (m, 1H), 2.97 (br. s., 3H), 2.88 (br. s., 3H), 2.55 (s, 3H); LC-MS: method C, 2 to 98% B. RT=2.32 min, MS (ESI) m/z: 588.25 (M+H)$^+$. Analytical HPLC purity (method B): 97%.

Example 204

(R)-(5-fluoro-2-(2-methoxy-7-methylquinoxalin-5-yl)-7,8-dihydrobenzofuro[5,4-d]thiazo l-7-yl)methyl (4-(dimethylcarbamoyl)phenyl)carbamate

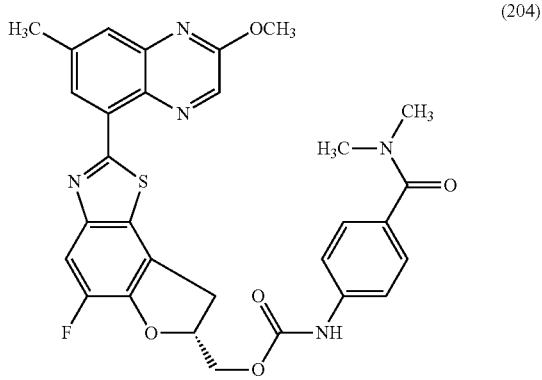 [SMILES: COc1cnc2c(-c3nc4cc(F)c5c(c4s3)C[C@H](COC(=O)Nc3ccc(C(=O)N(C)C)cc3)O5)cc(C)cc2n1]
(204)

4-Amino-N,N-dimethylbenzamide (16.07 mg, 0.098 mmol) was dissolved in DCM (1.0 mL) along with pyridine (0.021 mL, 0.261 mmol) and DIEA (0.017 mL, 0.098 mmol). Intermediate 145F (15 mg, 0.033 mmol) in 2 mL of DCM was added dropwise, and the reaction mixture was stirred at room temperature for 50 minutes. The reaction was quenched with 1.0 N HCl (0.5 mL). All solvent was removed under vacuum. The crude was dissolved in DMSO/THF (2:1, 6 mL) and purified via preparative LC/MS (method C, 40-90% B over 10 min, then a 5-min hold at 100% B). Fractions containing the desired product were combined and dried via centrifugal evaporation to yield Example 204 (11.8 mg, 62% yield). $^1$H NMR (500 MHz, DMSO-$d_6$) δ 10.00 (br. s., 1H), 8.68 (s, 1H), 8.53 (d, J=1.2 Hz, 1H), 7.84 (d, J=11.0 Hz, 1H), 7.78 (s, 1H), 7.50 (br. s., 2H), 7.33 (br. s., 2H), 5.46-5.37 (m, 1H), 4.53 (dd, J=12.4, 2.6 Hz, 1H), 4.40 (dd, J=12.2, 7.0 Hz, 1H), 4.06 (s, 3H), 3.66-3.58 (m, 1H), 3.33 (dd, J=15.9, 7.6 Hz, 1H), 2.92 (br. s., 6H), 2.61 (s, 3H); LC-MS: method C, 2 to 98% B. RT=2.36 min, MS (ESI) m/z: 588.30 (M+H)$^+$. Analytical HPLC purity (method B): 100%.

Example 205

(R)-(5-fluoro-2-(2-methoxy-7-methylquinoxalin-5-yl)-7,8-dihydrobenzofuro[5,4-d]thiazo l-7-yl)methyl (5-carbamoylpyridin-3-yl)carbamate

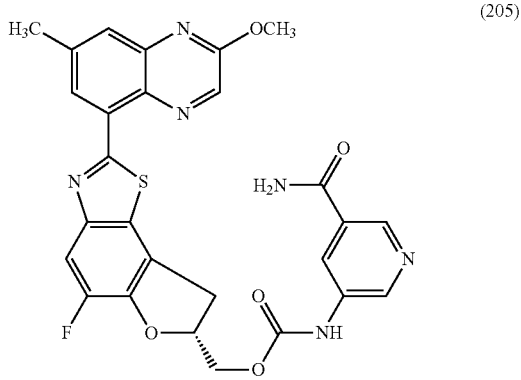 [SMILES: COc1cnc2c(-c3nc4cc(F)c5c(c4s3)C[C@H](COC(=O)Nc3cncc(C(N)=O)c3)O5)cc(C)cc2n1]
(205)

5-Aminonicotinamide (13.42 mg, 0.098 mmol) was dissolved in DCM (1.0 mL) along with pyridine (0.021 mL, 0.261 mmol) and DIEA (0.017 mL, 0.098 mmol). Intermediate 145F (15 mg, 0.033 mmol) in 2 mL of DCM was added dropwise, and the reaction mixture was stirred at room temperature for 50 minutes. The reaction was quenched with 1.0 N HCl (0.5 mL). All solvent was removed under vacuum. The crude was dissolved in DMSO/THF (2:1, 6 mL) and purified via preparative LC/MS (method C, 40-80% B over 16 min, then a 5-min hold at 100% B). Fractions containing the desired product were combined and dried via centrifugal evaporation to yield Example 205 (7.1 mg, 38% yield). $^1$H NMR (500 MHz, DMSO-$d_6$) δ 10.13 (br. s., 1H), 8.69-8.64 (m, 2H), 8.61 (s, 1H), 8.49 (d, J=1.5 Hz, 1H), 8.25 (br. s., 1H), 8.06 (br. s., 1H), 7.80 (d, J=11.3 Hz, 1H), 7.75 (s, 1H), 7.50 (br. s., 1H), 5.41-5.32 (m, 1H), 4.49 (dd, J=12.4, 2.6 Hz, 1H), 4.37 (dd, J=12.5, 7.0 Hz, 1H), 4.01 (s, 3H), 3.63-3.53 (m, 1H), 3.33-3.20 (m, 1H), 2.48 (s, 3H); LC-MS: method C, 2 to 98% B. RT=2.08 min, MS (ESI) m/z: 561.30(M+H)$^+$. Analytical HPLC purity (method B): 98%.

Example 206

(R)-(5-fluoro-2-(2-methoxy-7-methylquinoxalin-5-yl)-8,8-dimethyl-7,8-dihydrobenzofur o[5,4-d]thiazol-7-yl)methanol

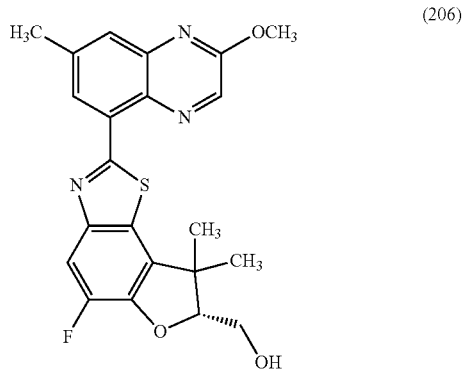 [SMILES: COc1cnc2c(-c3nc4cc(F)c5c(c4s3)C(C)(C)[C@H](CO)O5)cc(C)cc2n1]
(206)

Intermediate 206A: 2-chloro-5-fluoro-6-((3-methylbut-2-en-1-yl)oxy)benzo[d]thiazole

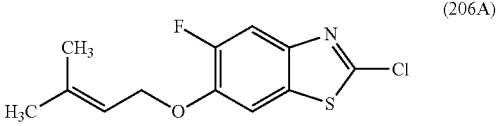 [SMILES: CC(C)=CCOc1cc2sc(Cl)nc2cc1F]
(206A)

To a solution of 2-chloro-5-fluorobenzo[d]thiazol-6-ol (204 mg, 0.902 mmol) in DMF (5 mL) was added 1-bromo-3-methylbut-2-ene (0.123 mL, 1.082 mmol), cesium carbonate (734 mg, 2.254 mmol). The reaction mixture was stirred at room temperature overnight, at which time LCMS and TLC indicated completion of the reaction. The mixture was diluted with EtOAc and water (5 mL), neutralized with 1.0 N HCl (10 mL), and extracted with ethyl acetate (X3). The organic layer was washed with brine (2×), dried over Na$_2$SO$_4$ and concentrated. The crude product was purified by flash chromatography (loading in chloroform, 0% to 70% EtOAc in hexane over 20 min using a 40 g silica gel cartridge). The desired fractions were combined and concentrated to yield Intermediate 206A (245 mg, 0.902 mmol, 100% yield) as colorless oil. ¹H NMR (400 MHz, CHLOROFORM-d) δ 7.65 (d, J=11.2 Hz, 1H), 7.30 (d, J=7.7 Hz, 1H), 5.56-5.50 (m, 1H), 4.64 (d, J=6.6 Hz, 2H), 1.82 (s, 3H), 1.77 (s, 3H); ¹⁹F NMR (376 MHz, CHLOROFORM-d) δ −132.81 (s, 1F). LC-MS: method C, RT=2.24 min, MS (ESI) m/z: 258.0 (M+H)⁺.

Intermediate 206B: 2-chloro-5-fluoro-7-(2-methylbut-3-en-2-yl)benzo[d]thiazol-6-ol

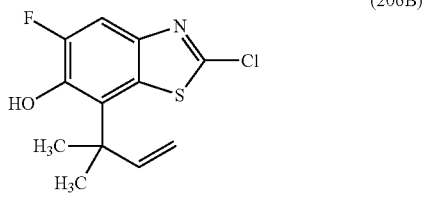

(206B)

To a solution of Intermediate 206A (55 mg, 0.202 mmol) in N,N-diethyl aniline (0.5 ml) was added hexamethyldisilazane (0.424 mL, 2.024 mmol). The mixture was heated at 250° C. in a microwave reactor for 45 min. After cooling to room temperature, the reaction mixture was diluted with EtOAc, washed with 3.0 N HCl (3×10 mL), brine (2×). The organic layer was dried over sodium sulfate and concentrated. The crude product was purified by flash chromatography (loading in chloroform, 0% to 50% EtOAc in hexane over 15 min using a 40 g silica gel cartridge). The desired fractions were combined and concentrated to yield Intermediate 206B (50 mg, 0.184 mmol, 91% yield) as a white solid. ¹H NMR (400 MHz, CHLOROFORM-d) δ 7.59 (d, J=9.9 Hz, 1H), 6.37 (dd, J=17.6, 10.6 Hz, 1H), 5.79 (d, J=6.4 Hz, 1H), 5.44-5.27 (m, 2H), 1.66 (s, 6H). ¹⁹F NMR (376 MHz, CHLOROFORM-d) δ −137.85 (s, 1F). LC-MS: Method C, RT=2.29 min, MS (ESI) m/z: 272.0 (M+H)⁺.

Intermediate 206C (2-chloro-5-fluoro-8,8-dimethyl-7,8-dihydrobenzofuro[5,4-d]thiazol-7-yl)methanol

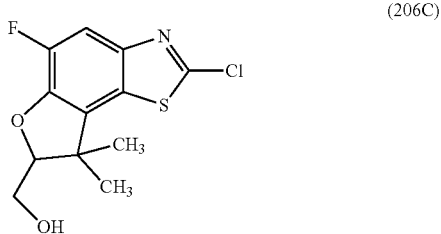 [SMILES: CC1(C)c2c(c(F)cc3nc(Cl)sc23)OC1CO]

(206C)

To a solution of Intermediate 206B (50 mg, 0.184 mmol) in dichloromethane (4 mL) was added mCPBA (59.4 mg, 0.265 mmol), followed by PTSA (6.72 mg, 0.035 mmol). The reaction mixture was stirred at 45° C. overnight. The mixture was diluted with EtOAc and 8% Na₂S₂O₃, extracted with EtOAc, the combined organic layer was washed with saturated sodium bicarbonate, brine, dried over sodium sulfate and concentrated. The crude product was purified by flash chromatography (loading in chloroform, 0% to 100% EtOAc in hexane over 20 min using a 40 g silica gel cartridge). The desired fractions were combined and concentrated to yield Intermediate 206C (30 mg, 0.104 mmol, 59.0% yield) as a white solid. ¹H NMR (400 MHz, CHLOROFORM-d) δ 7.56 (d, J=10.6 Hz, 1H), 4.64 (dd, J=7.5, 3.7 Hz, 1H), 4.06-3.99 (m, 1H), 3.97-3.90 (m, 1H), 1.52 (s, 3H), 1.34 (s, 3H). ¹⁹F NMR (376 MHz, CHLOROFORM-d) δ −137.84 (s, 1F). LC-MS: Method C, RT=2.04 min, MS (ESI) m/z: 288.0 (M+H)⁺.

Intermediate 206D (5-fluoro-2-(2-methoxy-7-methylquinoxalin-5-yl)-8,8-dimethyl-7,8-dihydrobenzofuro[5,4-d]thiazol-7-yl)methanol

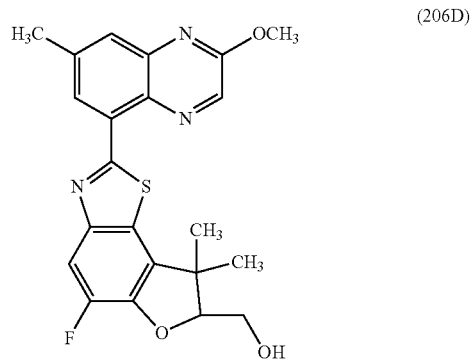 [SMILES: COc1cnc2c(-c3nc4cc(F)c5c(c4s3)C(C)(C)C(CO)O5)cc(C)cc2n1]

(206D)

To Intermediate I-9 (20.46 mg, 0.094 mmol), Intermediate 206C (30 mg, 0.104 mmol) and PdCl₂(dppf)—CH₂Cl₂ adduct (4.26 mg, 5.21 μmol) was added toluene (0.6 mL) and EtOH (0.2 mL). The mixture was sonicated for 1 min, and flushed with argon. To this was added sodium carbonate (0.191 mL, 1.5M, 0.287 mmol). The reaction mixture was heated at 95° C. for 10 hours. LCMS indicated completion of the reaction. The reaction mixture was directly loaded to 40 g ISCO column which was eluted with hexanes for 3 min, then a 20 min gradient from 0% to 100% EtOAc in hexanes. The desired fractions were combined and concentrated to Intermediate 206D (35 mg, 0.082 mmol, 88% yield). ¹H NMR (400 MHz, CHLOROFORM-d) δ 8.62 (d, J=1.8 Hz, 1H), 8.59 (s, 1H), 7.77 (d, J=0.9 Hz, 1H), 7.73 (d, J=10.8 Hz, 1H), 4.68 (dd, J=7.8, 3.6 Hz, 1H), 4.14 (s, 3H), 4.11-4.04 (m, 1H), 3.99-3.94 (m, 1H), 2.66 (s, 3H), 1.67 (s, 4H), 1.45 (s, 3H). ¹⁹F NMR (376 MHz, CHLOROFORM-d) δ −139.05 (s, 1F). LC-MS: method L, RT=2.47 min, MS (ESI) m/z: 426.0 (M+H)⁺.

Intermediate 206E (S)-(5-fluoro-2-(2-methoxy-7-methylquinoxalin-5-yl)-8,8-dimethyl-7,8-dihydrobenzofuro [5,4-d]thiazol-7-yl)methanol

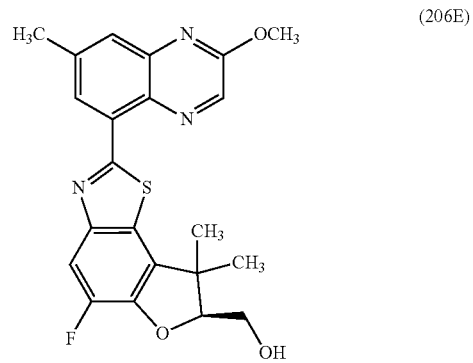 [SMILES: COc1cnc2c(-c3nc4cc(F)c5c(c4s3)C(C)(C)[C@@H](CO)O5)cc(C)cc2n1]

(206E)

Intermediate 206D (30 mg, 0.071 mmol) was separated via PIC Solution SFC (Column: Chiralcel AD-H, 21×250 mm, 5 micron, Mobile Phase: 30% MeOH/70% CO$_2$, Flow Conditions: 45 mL/min, 150 Bar, 40° C., Detector Wavelength: 220 nm, Injection Details: 0.4 mL of 3.6 mg/mL in MeOH/ACN 2:3). Fractions from the first peak (RT=9.0 min) were combined and dried via centrifugal evaporation to yield Intermediate 206E (5 mg, 0.011 mmol, 15.83% yield). $^1$H NMR (400 MHz, CHLOROFORM-d) δ 8.62 (s, 1H), 8.59 (s, 1H), 7.78 (s, 1H), 7.73 (d, J=11.0 Hz, 1H), 4.68 (dd, J=7.8, 3.6 Hz, 1H), 4.14 (s, 3H), 4.12-4.02 (m, 1H), 4.00-3.88 (m, 1H), 2.66 (s, 3H), 1.99 (dd, J=8.3, 4.3 Hz, 1H), 1.67 (s, 4H), 1.46 (s, 3H). $^{19}$F NMR (376 MHz, CHLOROFORM-d) δ −139.06 (br. s., 1F). LC-MS: Method C, RT=2.44 min, MS (ESI) m/z: 426.0 (M+H)$^+$. Analytical HPLC purity (method A): 95%.

Example 206

Intermediate 206D (30 mg, 0.071 mmol) was separated via PIC Solution SFC (Column: Chiralcel AD-H, 21×250 mm, 5 micron, Mobile Phase: 30% MeOH/70% CO$_2$, Flow Conditions: 45 mL/min, 150 Bar, 40° C., Detector Wavelength: 220 nm, Injection Details: 0.4 mL of 3.6 mg/mL in MeOH/ACN 2:3). Fractions from the second peak (RT=11.0 min) were combined and dried via centrifugal evaporation to yield Example 206 (6 mg, 0.013 mmol, 18.00% yield). $^1$H NMR (400 MHz, CHLOROFORM-d) δ 8.62 (d, J=1.5 Hz, 1H), 8.59 (s, 1H), 7.77 (s, 1H), 7.73 (d, J=10.8 Hz, 1H), 4.68 (dd, J=7.7, 3.5 Hz, 1H), 4.14 (s, 3H), 4.11-4.03 (m, 1H), 3.97 (d, J=12.1 Hz, 1H), 2.66 (s, 3H), 2.06 (br. s., 1H), 1.67 (s, 3H), 1.46 (s, 3H). $^{19}$F NMR (376 MHz, CHLOROFORM-d) δ −139.06 (br. s., 1F). LC-MS: Method C, RT=2.46 min, MS (ESI) m/z: 426.0 (M+H)$^+$. Analytical HPLC purity (method A): 90%.

Example 207

(R)-(5-fluoro-2-(2-methoxy-7-methylquinoxalin-5-yl)-7,8-dihydrobenzofuro[5,4-d]thiazo 1-7-yl)methyl (4-(oxazol-2-yl)phenyl)carbamate

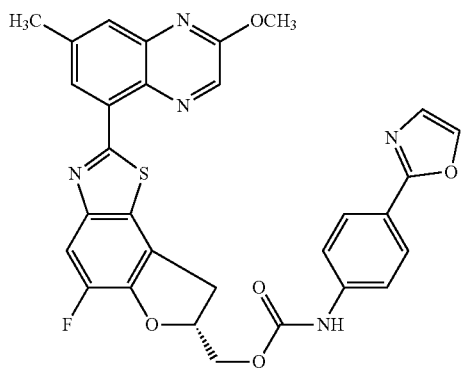

(207)

4-(Oxazol-2-yl)aniline (15.67 mg, 0.098 mmol) was dissolved in DCM (1.0 mL) along with pyridine (0.021 mL, 0.261 mmol) and DIEA (0.017 mL, 0.098 mmol). Intermediate 145F (15 mg, 0.033 mmol) in 2 mL of DCM was added dropwise, and the reaction mixture was stirred at room temperature for 50 minutes. The reaction was quenched with 1.0 N HCl (0.5 mL). All solvent was removed under vacuum. The crude was dissolved in DMSO/THF (2:1, 6 mL) and purified via preparative LC/MS (method C, 55-100% B over 20 min, then a 5-min hold at 100% B). Fractions containing the desired product were combined and dried via centrifugal evaporation to yield Example 207 (7.5 mg, 39% yield). $^1$H NMR (500 MHz, DMSO-d$_6$) δ 8.72 (s, 1H), 8.57 (d, J=1.5 Hz, 1H), 8.15-8.10 (m, 1H), 7.90-7.85 (m, 3H), 7.81 (s, 2H), 7.62 (br. s., 1H), 7.33-7.28 (m, 1H), 5.48-5.40 (m, 1H), 4.55 (dd, J=12.4, 2.6 Hz, 1H), 4.42 (dd, J=12.4, 6.9 Hz, 1H), 4.08 (s, 3H), 3.66 (dd, J=15.9, 9.8 Hz, 1H), 2.55 (s, 3H); LC-MS: method C, 2 to 98% B. RT=2.54 min, MS (ESI) m/z: 584.25 (M+H)$^+$. Analytical HPLC purity (method B): 100%.

Example 208

(R)-(5-fluoro-2-(2-methoxy-7-methylquinoxalin-5-yl)-7,8-dihydrobenzofuro[5,4-d]thiazo 1-7-yl)methyl (4-(methylcarbamoyl)phenyl)carbamate

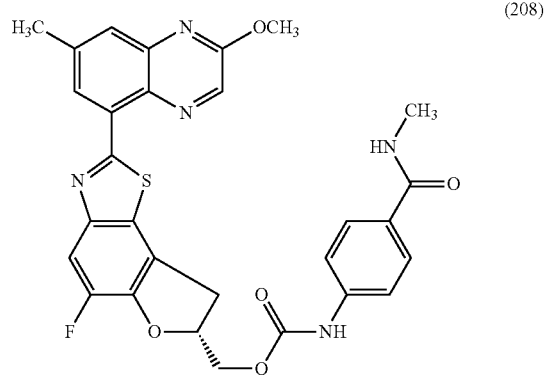 [SMILES: CNC(=O)c1ccc(NC(=O)OC[C@H]2Cc3c(c(F)cc4nc(-c5cc(C)cc6nc(OC)cnc56)sc34)O2)cc1]

(208)

4-Amino-N-methylbenzamide (14.70 mg, 0.098 mmol) was dissolved in DCM (1.0 mL) along with pyridine (0.021 mL, 0.261 mmol) and DIEA (0.017 mL, 0.098 mmol). Intermediate 145F (15 mg, 0.033 mmol) in 2 mL of DCM was added dropwise, and the reaction mixture was stirred at room temperature for 50 minutes. The reaction was quenched with 1.0 N HCl (0.5 mL). All solvent was removed under vacuum. The crude was dissolved in DMSO/THF (2:1, 6 mL) and purified via preparative LC/MS (method C, 55-100% B over 20 min, then a 5-min hold at 100% B). Fractions containing the desired product were combined and dried via centrifugal evaporation to yield Example 208 (3.7 mg, 19% yield). $^1$H NMR (500 MHz, DMSO-d$_6$) δ 8.75 (s, 1H), 8.59 (d, J=1.2 Hz, 1H), 8.26 (d, J=4.3 Hz, 1H), 7.89 (d, J=11.3 Hz, 1H), 7.84 (s, 1H), 7.75 (d, J=8.5 Hz, 2H), 7.52 (d, J=8.2 Hz, 2H), 5.47-5.39 (m, 1H), 4.54 (dd, J=12.5, 2.7 Hz, 1H), 4.41 (dd, J=12.2, 7.0 Hz, 1H), 4.09 (s, 3H), 3.67 (dd, J=15.9, 9.8 Hz, 1H), 2.76 (d, J=4.3 Hz, 3H), 2.64 (s, 3H); LC-MS: method C, 2 to 98% B. RT=2.28 min, MS (ESI) m/z: 574.30 (M+H)$^+$. Analytical HPLC purity (method B): 96%.

Example 209

(S)-N-((5-fluoro-2-(2-methoxy-7-methylquinoxalin-5-yl)-7,8-dihydrobenzofuro[5,4-d]thiazol-7-yl)methyl)acetamide

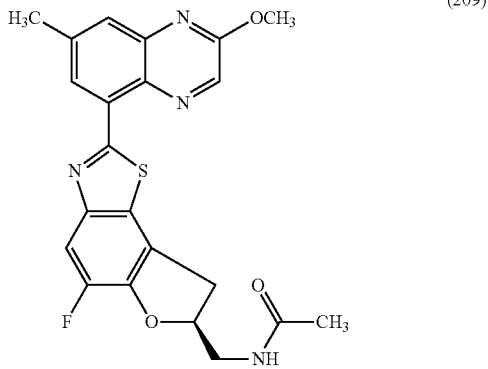

(209)

To a solution of Intermediate 202C (7 mg, 0.014 mmol) and pyridine (0.017 mL, 0.206 mmol) in DCM (1 mL) was added acetyl chloride (3.23 mg, 0.041 mmol). The mixture was stirred at room temperature for 0.5 h, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 40-80% B over 20 minutes, then a 5-minute hold at 100% B). Fractions containing the desired product were combined and dried via centrifugal evaporation to Example 209 (1.7 mg, 3.88 μmol, 28.3% yield). $^1$H NMR (500 MHz, DMSO-$d_6$) δ 8.75 (s, 1H), 8.58 (d, J=1.5 Hz, 1H), 8.24 (t, J=5.6 Hz, 1H), 7.86 (d, J=11.3 Hz, 1H), 7.84 (s, 1H), 5.25-5.10 (m, 1H), 4.08 (s, 3H), 3.63-3.44 (m, 2H), 3.38-3.20 (m, 2H), 2.63 (s, 4H), 1.84 (s, 3H). LC-MS: method C, RT=2.34 min, MS (ESI) m/z: 439.1 (M+H)$^+$. Analytical HPLC purity (method B): 100%.

Example 210

(S)-methyl ((5-fluoro-2-(2-methoxy-7-methylquinoxalin-5-yl)-7,8-dihydrobenzofuro[5,4-d]thiazol-7-yl)methyl)carbamate

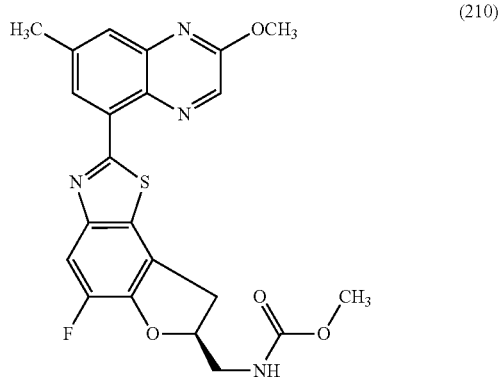

(210)

To a solution of Intermediate 202C (7 mg, 0.014 mmol) and pyridine (0.017 mL, 0.206 mmol) in DCM (1 mL) was added methyl chloroformate (3.89 mg, 0.041 mmol). The mixture was stirred at room temperature for 0.5 h, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 45-95% B over 15 minutes, then a 5-minute hold at 100% B). Fractions containing the desired product were combined and dried via centrifugal evaporation to Example 210 (3.7 mg, 8.14 μmol, 59.4% yield). $^1$H NMR (500 MHz, DMSO-$d_6$) δ 8.72 (s, 1H), 8.55 (d, J=1.5 Hz, 1H), 7.84 (d, J=11.3 Hz, 1H), 7.81 (s, 1H), 7.52 (br. s., 1H), 5.22-5.05 (m, 1H), 4.07 (s, 3H), 3.62-3.51 (m, 3H), 3.42-3.20 (m, 2H), 2.62 (s, 3H), 2.54 (s, 3H). LC-MS: method L, RT=2.33 min, MS (ESI) m/z: 455.1 (M+H)$^+$. Analytical HPLC purity (method B): 100%.

Example 211

(S)-benzyl ((5-fluoro-2-(2-methoxy-7-methylquinoxalin-5-yl)-7,8-dihydrobenzofuro[5,4-d]thiazol-7-yl)methyl)carbamate

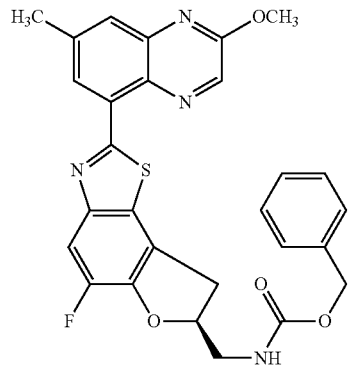

(211)

To a solution of Intermediate 202C (7 mg, 0.014 mmol) and pyridine (0.017 mL, 0.206 mmol) in DCM (1 mL) was added benzyl chloroformate (7.02 mg, 0.041 mmol). The mixture was stirred at room temperature for 0.5 h, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 50-100% B over 15 minutes, then a 5-minute hold at 100% B). Fractions containing the desired product were combined and dried via centrifugal evaporation to Example 211 (5.4 mg, 10.08 μmol, 73.5% yield). $^1$H NMR (500 MHz, DMSO-$d_6$) δ 8.73 (s, 1H), 8.56 (s, 1H), 7.84 (d, J=11.3 Hz, 1H), 7.82 (s, 1H), 7.65 (br. s., 1H), 7.38-7.23 (m, 4H), 5.18 (br. s., 1H), 5.04 (s, 2H), 4.07 (s, 3H), 3.68-3.18 (m, 4H), 2.62 (s, 3H). LC-MS: method L, RT=2.59 min, MS (ESI) m/z: 531.1 (M+H)$^+$. Analytical HPLC purity (method B): 99%.

Example 212

(S)-phenyl ((5-fluoro-2-(2-methoxy-7-methylquinoxalin-5-yl)-7,8-dihydrobenzofuro[5,4-d]thiazol-7-yl)methyl)carbamate

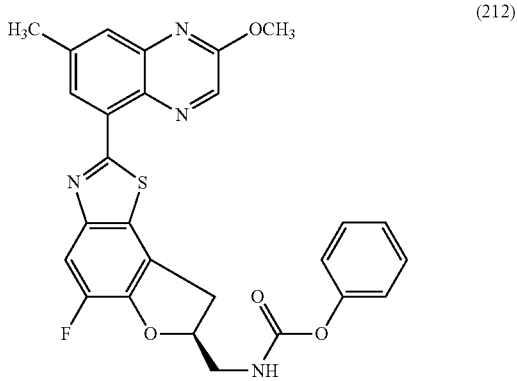 [SMILES: COc1cnc2c(-c3nc4cc(F)c5c(c4s3)C[C@@H](CNC(=O)Oc3ccccc3)O5)cc(C)cc2n1]

(212)

To a solution of Intermediate 202C (7 mg, 0.014 mmol) and pyridine (0.017 mL, 0.206 mmol) in DCM (1 mL) was added phenyl chloroformate (6.44 mg, 0.041 mmol). The mixture was stirred at room temperature overnight, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 60-100% B over 18 minutes, then a 5-minute hold at 100% B). Fractions containing the desired product were combined and dried via centrifugal evaporation to Example 212 (4 mg, 6.97 µmol, 50.8% yield). $^1$H NMR (500 MHz, DMSO-$d_6$) δ 8.73 (s, 1H), 8.56 (d, J=1.5 Hz, 1H), 8.14 (t, J=5.6 Hz, 1H), 7.87 (d, J=11.3 Hz, 1H), 7.82 (s, 1H), 7.37 (t, J=7.8 Hz, 2H), 7.25-7.18 (m, 1H), 7.08 (d, J=7.9 Hz, 2H), 5.33-5.14 (m, 1H), 4.08 (s, 3H), 3.68-3.57 (m, 1H), 3.54-3.28 (m, 3H), 2.62 (s, 3H). LC-MS: method L, RT=2.58 min, MS (ESI) m/z: 517.3 (M+H)$^+$. Analytical HPLC purity (method B): 100%.

Example 213

(S)-p-tolyl ((5-fluoro-2-(2-methoxy-7-methylquinoxalin-5-yl)-7,8-dihydrobenzofuro[5,4-d]thiazol-7-yl)methyl)carbamate

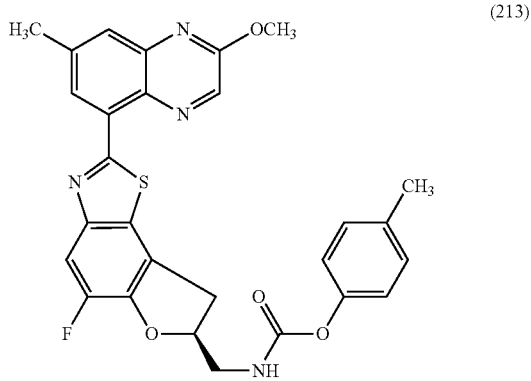

(213)

To a solution of Intermediate 202C (7 mg, 0.014 mmol) and pyridine (0.017 mL, 0.206 mmol) in DCM (1 mL) was added p-tolyl chloroformate (7.02 mg, 0.041 mmol). The mixture was stirred at room temperature overnight, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 60-100% B over 15 minutes, then a 5-minute hold at 100% B). Fractions containing the desired product were combined and dried via centrifugal evaporation to Example 213 (4.3 mg, 8.10 µmol, 59.1% yield). $^1$H NMR (500 MHz, DMSO-$d_6$) δ 8.74 (s, 1H), 8.57 (d, J=1.5 Hz, 1H), 8.08 (t, J=5.6 Hz, 1H), 7.87 (d, J=11.0 Hz, 1H), 7.83 (s, 1H), 7.15 (d, J=8.2 Hz, 2H), 6.95 (d, J=8.2 Hz, 2H), 5.23 (dd, J=8.7, 6.3 Hz, 1H), 4.08 (s, 3H), 3.67-3.59 (m, 1H), 3.49 (d, J=5.8 Hz, 1H), 3.36-3.24 (m, 1H), 2.62 (s, 3H), 2.27 (s, 3H). LC-MS: method L, RT=2.67 min, MS (ESI) m/z: 531.25 (M+H)$^+$. Analytical HPLC purity (method B): 100%.

Example 214

(S)-4-chlorophenyl ((5-fluoro-2-(2-methoxy-7-methylquinoxalin-5-yl)-7,8-dihydrobenzofuro[5,4-d]thiazol-7-yl)methyl)carbamate

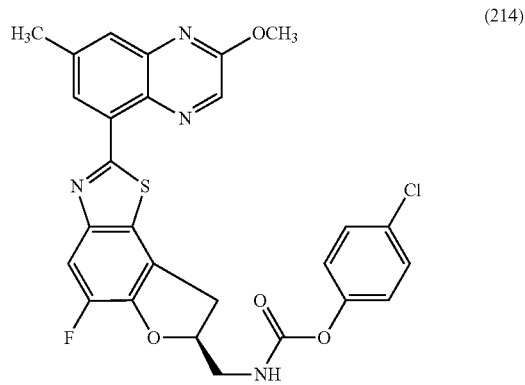 [SMILES: COc1cnc2c(-c3nc4cc(F)c5c(c4s3)C[C@@H](CNC(=O)Oc3ccc(Cl)cc3)O5)cc(C)cc2n1]

(214)

To a solution of Intermediate 202C (7 mg, 0.014 mmol) and pyridine (0.017 mL, 0.206 mmol) in DCM (1 mL) was added 4-chlorophenyl chloroformate (7.86 mg, 0.041 mmol). The mixture was stirred at room temperature overnight, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 50-100% B over 18 minutes, then a 5-minute hold at 100% B). Fractions containing the desired product were combined and dried via centrifugal evaporation to Example 214 (4.2 mg, 7.62 µmol, 55.6% yield). $^1$H NMR (500 MHz, DMSO-$d_6$) δ 8.76 (s, 1H), 8.59 (br. s., 1H), 7.92-7.82 (m, 2H), 7.18 (d, J=8.9 Hz, 2H), 6.76 (d, J=8.9 Hz, 2H), 5.24-5.12 (m, 1H), 4.08 (s, 3H), 3.79-3.63 (m, 4H), 2.63 (s, 3H). LC-MS: method L, RT=2.70 min, MS (ESI) m/z: 551.25 (M+H)$^+$. Analytical HPLC purity (method B): 100%.

Example 215

(S)-2,2,2-trifluoro-N-((5-fluoro-2-(2-methoxy-7-methylquinoxalin-5-yl)-7,8-dihydrobenzofuro[5,4-d]thiazol-7-yl)methyl)acetamide

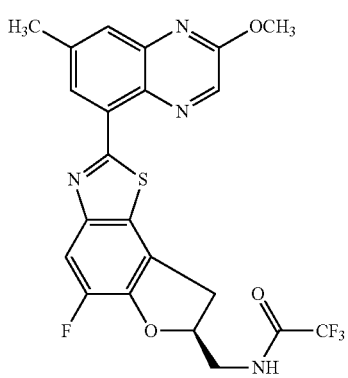

(215)

Example 215 (2.4 mg, 4.87 μmol, 35.5% yield) was obtained as a side product from the preparation of Example 214. It was presumably generated from the reaction of Intermediate 202C with trace amount of trifluoroacetic anhydride in the lyophilizer. $^1$H NMR (500 MHz, DMSO-$d_6$) δ 8.74 (s, 1H), 8.57 (d, J=1.2 Hz, 1H), 7.87 (d, J=11.3 Hz, 1H), 7.83 (s, 1H), 5.46-5.13 (m, 1H), 4.08 (s, 3H), 3.79-3.63 (m, 4H), 2.62 (s, 3H). LC-MS: method L, RT=2.45 min, MS (ESI) m/z: 493.25 (M+H)$^+$. Analytical HPLC purity (method B): 100%.

Example 216

(S)-4-methoxyphenyl ((5-fluoro-2-(2-methoxy-7-methylquinoxalin-5-yl)-7,8-dihydrobenzofuro[5,4-d]thiazol-7-yl)methyl)carbamate

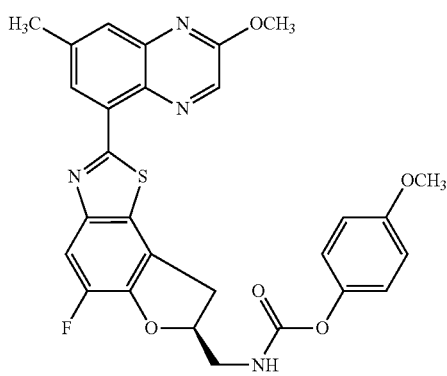

(216)

To a solution of Intermediate 202C (7 mg, 0.014 mmol) and pyridine (0.017 mL, 0.206 mmol) in DCM (1 mL) was added 4-methoxyphenyl chloroformate (7.68 mg, 0.041 mmol). The mixture was stirred at room temperature overnight, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 60-100% B over 19 minutes, then a 5-minute hold at 100% B). Fractions containing the desired product were combined and dried via centrifugal evaporation to Example 216 (4.6 mg, 8.42 μmol, 61.4% yield). $^1$H NMR (500 MHz, DMSO-$d_6$) δ 8.76 (s, 1H), 8.59 (d, J=1.5 Hz, 1H), 8.05 (t, J=6.0 Hz, 1H), 7.89 (d, J=11.3 Hz, 1H), 7.84 (s, 1H), 6.98 (d, J=8.9 Hz, 2H), 6.89 (d, J=9.2 Hz, 2H), 5.31-5.13 (m, 1H), 4.08 (s, 3H), 3.72 (s, 3H), 3.68-3.43 (m, 2H), 3.33 (br. s., 2H), 2.63 (s, 3H) LC-MS: method L, RT=2.56 min, MS (ESI) m/z: 547.30 (M+H)$^+$. Analytical HPLC purity (method B): 100%.

Example 217

(R)-N-((5-fluoro-2-(2-methoxy-7-methylquinoxalin-5-yl)-7,8-dihydrobenzofuro[5,4-d]thiazol-7-yl)methyl)-2-phenylacetamide

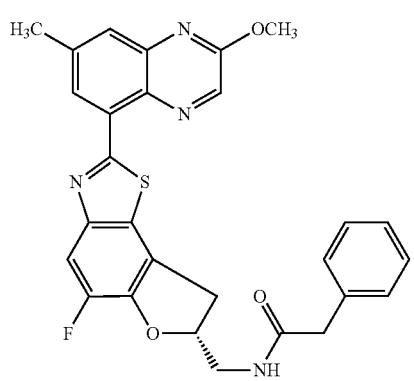

(217)

Intermediate 217A (R)-(5-fluoro-2-(2-methoxy-7-methylquinoxalin-5-yl)-7,8-dihydrobenzofuro[5,4-d]thiazol-7-yl)methyl methanesulfonate

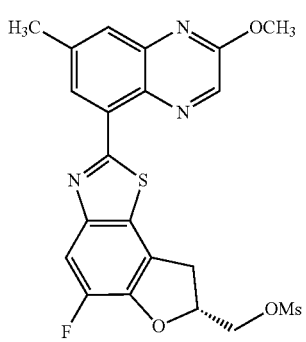

(217A)

To a suspension of Intermediate 145E (190 mg, 0.478 mmol) in DCM (5 mL) and THF (1 mL) was added methanesulfonyl chloride (0.056 mL, 0.717 mmol), followed triethylamine (0.333 mL, 2.390 mmol). The mixture was stirred at room temperature for 45 min. The reaction was quenched by 1N HCl and extracted with DCM. The combined organic layer was washed with brine, dried over MgSO$_4$ and concentrated to Intermediate 217A (227 mg, 0.477 mmol, 100% yield) as a yellow solid. This material was used directly for the next step without any purification. LC-MS: Method C; RT=2.36 min, MS (ESI) m/z: 476.0 (M+H)$^+$.

Intermediate 217B (R)-7-(azidomethyl)-5-fluoro-2-(2-methoxy-7-methylquinoxalin-5-yl)-7,8-dihydrobenzofuro[5,4-d]thiazole

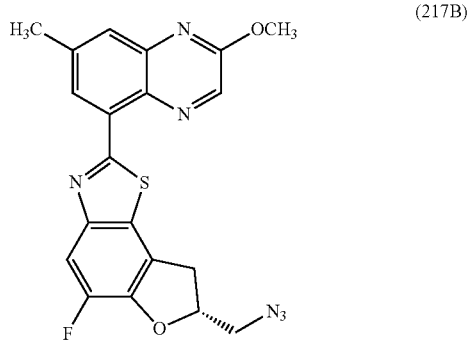 [SMILES: COc1cnc2c(-c3nc4cc(F)c5c(c4s3)C[C@H](CN=[N+]=[N-])O5)cc(C)cc2n1]

(217B)

To a suspension of Intermediate 217A (0.197 g, 0.478 mmol) in DMF (5 mL) was added NaN$_3$ (0.062 g, 0.956 mmol). The mixture was heated at 75° C. for 6.5 hours, at which time TLC and LCMS indicated the completion of the reaction. The mixture was cooled and diluted with EtOAc and water, extracted with EtOAc. The combined organic layer was washed with brine, dried with MgSO$_4$ and concentrated to Intermediate 217B (0.202 g, 0.478 mmol, 100% yield) as a yellow solid. The sample was used for next step without purification. LC-MS: Method C; RT=2.57 min, MS (ESI) m/z: 423.0 (M+H)$^+$.

Intermediate 217C (R)-(5-fluoro-2-(2-methoxy-7-methylquinoxalin-5-yl)-7,8-dihydrobenzofuro[5,4-d]thiazo 1-7-yl)methanamine

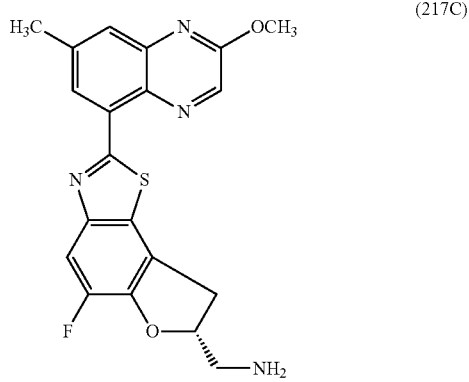 [SMILES: COc1cnc2c(-c3nc4cc(F)c5c(c4s3)C[C@H](CN)O5)cc(C)cc2n1]

(217C)

To a solution of Intermediate 217B (202 mg, 0.478 mmol) in THF/water (9/1) (5 mL) was added PPh$_3$ (251 mg, 0.956 mmol). The mixture was stirred at room temperature overnight. TLC and LCMS indicated the completion of the reaction. The mixture was diluted with EtOAc and water, extracted with EtOAc, the combined organic layer was washed with saturated sodium bicarbonate, brine, dried over sodium sulfate and concentrated. The compound was dissolved in DMSO (10 mL) and 1N HCl (0.956 mL, 0.956 mmol). The mixture was stirred at 45° C. for 30 min before purified via preparative LC/MS (Method A: 30-100% B over 10 minutes, then a 2-minute hold at 100% B). Fractions containing the desired product were combined and dried via centrifugal evaporation to Intermediate 217C (70 mg, 0.130 mmol, 27.3% yield) as a yellow solid. $^1$H NMR (400 MHz, METHANOL-d$_4$) δ 8.55 (d, J=2.0 Hz, 1H), 8.49 (s, 1H), 7.76 (d, J=0.9 Hz, 1H), 7.69 (d, J=11.0 Hz, 1H), 5.40-5.30 (m, 1H), 4.12 (s, 3H), 3.69 (dd, J=16.0, 9.6 Hz, 1H), 3.49-3.35 (m, 2H), 3.29-3.20 (m, 1H), 2.64 (s, 3H). $^{19}$F NMR (376 MHz, METHANOL-d$_4$) δ −76.98 (s, 3F), −140.25 (s, 1F). LC-MS: method C, RT=2.07 min, MS (ESI) m/z: 397.0 (M+H)$^+$. Analytical HPLC purity (method A): 95%.

Example 217

To a solution of Intermediate 217C (8 mg, 0.016 mmol) and pyridine (0.019 mL, 0.235 mmol) in DCM (1 mL) was added 2-phenylacetyl chloride (2.423 mg, 0.016 mmol). The mixture was stirred at room temperature for 30 min, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 60-100% B over 25 minutes, then a 5-minute hold at 100% B). Fractions containing the desired product were combined and dried via centrifugal evaporation to Example 217 (5.9 mg, 0.011 mmol, 73.2% yield). $^1$H NMR (500 MHz, DMSO-d$_6$) δ 8.74 (s, 1H), 8.59 (s, 1H), 8.45-8.38 (m, 1H), 8.01-7.82 (m, 2H), 7.43-7.05 (m, 5H), 5.20 (br. s., 1H), 4.08 (s, 3H), 3.69-3.15 (m, 6H), 2.63 (s, 3H). LC-MS: method L, RT=2.42 min, MS (ESI) m/z: 515.30 (M+H)$^+$. Analytical HPLC purity (method B): 100%.

Example 218

(R)-methyl ((5-fluoro-2-(2-methoxy-7-methylquinoxalin-5-yl)-7,8-dihydrobenzofuro[5,4-d]thiazol-7-yl)methyl) carbamate

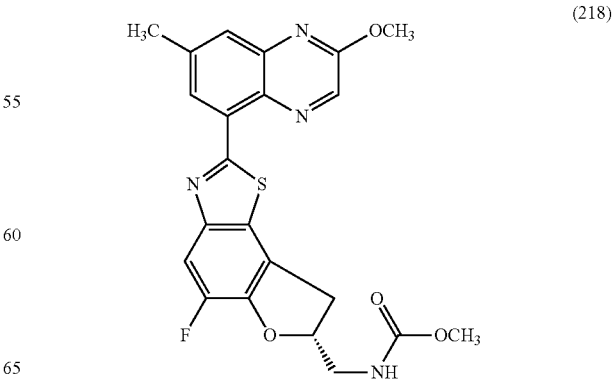

(218)

To a solution of Intermediate 217C (8 mg, 0.016 mmol) and pyridine (0.019 mL, 0.235 mmol) in DCM (1 mL) was added methyl chloroformate (4.44 mg, 0.047 mmol). The mixture was stirred at room temperature for 30 min, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 50-100% B over 18 minutes, then a 5-minute hold at 100% B). Fractions containing the desired product were combined and dried via centrifugal evaporation to Example 218 (6.3 mg, 0.014 mmol, 88% yield). $^1$H NMR (500 MHz, DMSO-$d_6$) δ 8.74 (s, 1H), 8.57 (d, J=1.5 Hz, 1H), 7.85 (d, J=11.3 Hz, 1H), 7.82 (s, 1H), 7.52 (br. s., 1H), 5.30-5.00 (m, 1H), 4.07 (s, 3H), 3.62-3.56 (m, 4H), 3.41-3.20 (m, 3H), 2.62 (s, 3H). LC-MS: method L, RT=2.34 min, MS (ESI) m/z: 455.25 (M+H)$^+$. Analytical HPLC purity (method B): 100%.

Example 219

(R)-N-((5-fluoro-2-(2-methoxy-7-methylquinoxalin-5-yl)-7,8-dihydrobenzofuro[5,4-d]thiazol-7-yl)methyl)acetamide

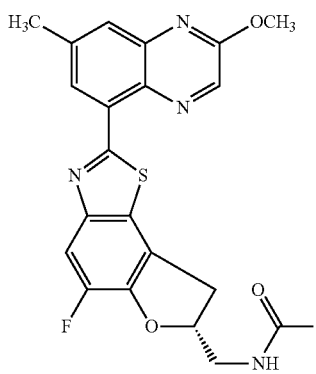

(219)

To a solution of Intermediate 217C (10 mg, 0.020 mmol) and pyridine (0.024 mL, 0.294 mmol) in DCM (1 mL) was added acetyl chloride (4.61 mg, 0.059 mmol). The mixture was stirred at room temperature for 30 min, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 45-90% B over 10 minutes, then a 5-minute hold at 100% B). Fractions containing the desired product were combined and dried via centrifugal evaporation to Example 219 (6.4 mg, 0.015 mmol, 74.5% yield). $^1$H NMR (500 MHz, DMSO-$d_6$) δ 8.75 (s, 1H), 8.58 (d, J=1.5 Hz, 1H), 8.24 (t, J=5.6 Hz, 1H), 7.87 (d, J=11.0 Hz, 1H), 7.84 (s, 1H), 5.27-5.02 (m, 1H), 4.08 (s, 3H), 3.64-3.14 (m, 4H), 2.63 (s, 3H), 1.84 (s, 3H). LC-MS: method L, RT=2.13 min, MS (ESI) m/z: 439.35 (M+H)$^+$. Analytical HPLC purity (method B): 100%.

Example 220

(R)-phenyl ((5-fluoro-2-(2-methoxy-7-methylquinoxalin-5-yl)-7,8-dihydrobenzofuro[5,4-d]thiazol-7-yl)methyl)carbamate

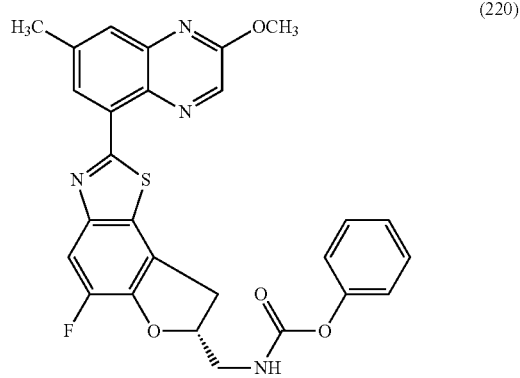

(220)

To a solution of Intermediate 217C (8 mg, 0.016 mmol) and pyridine (0.019 mL, 0.235 mmol) in DCM (1 mL) was added phenyl chloroformate (7.36 mg, 0.047 mmol). The mixture was stirred at room temperature for 30 min, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 55-100% B over 18 minutes, then a 10-minute hold at 100% B). Fractions containing the desired product were combined and dried via centrifugal evaporation to Example 220 (5.1 mg, 9.87 μmol, 63.0% yield). $^1$H NMR (500 MHz, DMSO-$d_6$) δ 8.74 (s, 1H), 8.57 (s, 1H), 8.13 (t, J=5.8 Hz, 1H), 7.88 (s, 1H), 7.83 (s, 1H), 7.36 (t, J=7.8 Hz, 2H), 7.24-7.10 (m, 2H), 6.74 (d, J=8.5 Hz, 1H), 5.25 (br. s., 1H), 4.07 (s, 3H), 3.71-3.45 (m, 2H), 3.41-3.27 (m, 2H), 2.62 (s, 3H). LC-MS: method L, RT=2.58 min, MS (ESI) m/z: 517.30 (M+H)$^+$. Analytical HPLC purity (method B): 100%.

Example 221

(R)-benzyl ((5-fluoro-2-(2-methoxy-7-methylquinoxalin-5-yl)-7,8-dihydrobenzofuro[5,4-d]thiazol-7-yl)methyl)carbamate

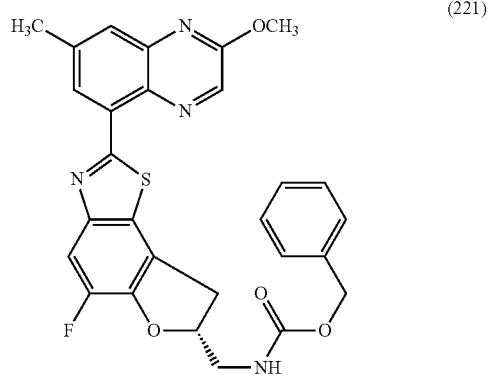 [SMILES: COc1cnc2c(-c3nc4cc(F)c5c(c4s3)C[C@H](CNC(=O)OCc3ccccc3)O5)cc(C)cc2n1]

(221)

To a solution of Intermediate 217C (8 mg, 0.016 mmol) and pyridine (0.019 mL, 0.235 mmol) in DCM (1 mL) was added benzyl chloroformate (8.02 mg, 0.047 mmol). The mixture was stirred at room temperature for 30 min, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 60-100% B over 18 minutes, then a 7-minute hold at 100% B). Fractions containing the desired product were combined and dried via centrifugal evaporation to Example 221 (7.3 mg, 0.014 mmol, 88% yield). $^1$H NMR (500 MHz, DMSO-$d_6$) δ 8.74 (s, 1H), 8.57 (s, 1H), 7.85 (d, J=11.3 Hz, 1H), 7.82-7.79 (m, 1H), 7.65 (t, J=5.5 Hz, 1H), 7.46-7.23 (m, 5H), 5.31-5.14 (m, 1H), 5.04 (s, 2H), 4.07 (s, 3H), 3.70-3.08 (m, 4H), 2.62 (s, 3H); LC-MS: method L, RT=2.64 min, MS (ESI) m/z: 531.30 (M+H)$^+$. Analytical HPLC purity (method B): 100%.

Example 222

(R)-2,2,2-trifluoro-N-((5-fluoro-2-(2-methoxy-7-methylquinoxalin-5-yl)-7,8-dihydrobenzofuro[5,4-d]thiazol-7-yl)methyl)acetamide

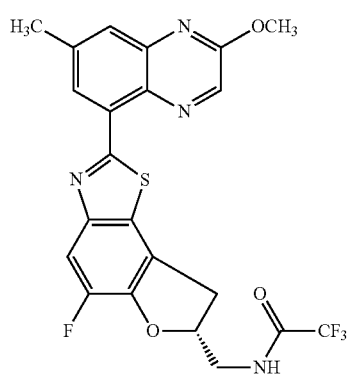

(222)

Example 222 (4.9 mg, 9.95 µmol, 50.8% yield) was obtained as a side product, presumably from the reaction of Intermediate 217C with a trace amount of trifluoroacetic anhydride in the lyophilizer. $^1$H NMR (500 MHz, DMSO-$d_6$) δ 8.72 (s, 1H), 8.56 (d, J=1.5 Hz, 1H), 7.85 (d, J=11.0 Hz, 1H), 7.81 (s, 1H), 5.37-5.17 (m, 1H), 4.07 (s, 3H), 3.69-3.53 (m, 3H), 3.38-3.19 (m, 1H), 2.62 (s, 3H). LC-MS: method L, RT=2.41 min, MS (ESI) m/z: 493.25 (M+H)$^+$. Analytical HPLC purity (method B): 100%.

Example 223

(R)-tert-butyl ((5-fluoro-2-(2-methoxy-7-methylquinoxalin-5-yl)-7,8-dihydrobenzofuro[5,4-d]thiazol-7-yl)methyl)carbamate

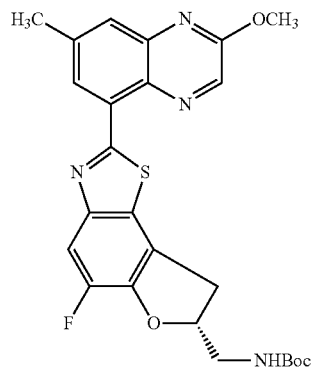

(223)

To a solution of Intermediate 217C (10 mg, 0.020 mmol) and pyridine (0.024 mL, 0.294 mmol) in DCM (1 mL) was added di-tert-butyl dicarbonate (0.049 mL, 0.098 mmol). The mixture was stirred at room temperature for 30 min, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 50-100% B over 18 minutes, then a 5-minute hold at 100% B). Fractions containing the desired product were combined and dried via centrifugal evaporation to Example 223 (4.1 mg, 8.26 µmol, 42.1% yield). $^1$H NMR (500 MHz, DMSO-$d_6$) δ 8.72 (s, 1H), 8.56 (s, 1H), 7.87-7.79 (m, 2H), 7.17 (br. s., 1H), 5.28-5.07 (m, 1H), 4.07 (s, 3H), 3.60-3.15 (m 4H), 2.62 (s, 3H), 1.37 (s, 9H). LC-MS: method L, RT=2.67 min, MS (ESI) m/z: 497.30 (M+H)$^+$. Analytical HPLC purity (method B): 100%.

Example 224

(S)-isobutyl ((2-(2-methoxy-7-methylquinoxalin-5-yl)-7,8-dihydrobenzofuro[5,4-d]thiazol-7-yl)methyl)carbamate

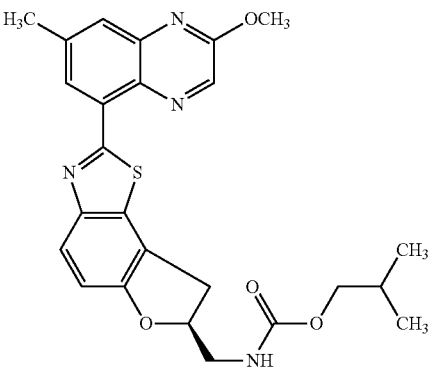

(224)

Intermediate 224A (S)-(2-(2-methoxy-7-methylquinoxalin-5-yl)-7,8-dihydrobenzofuro[5,4-d]thiazol-7-yl)methyl methanesulfonate

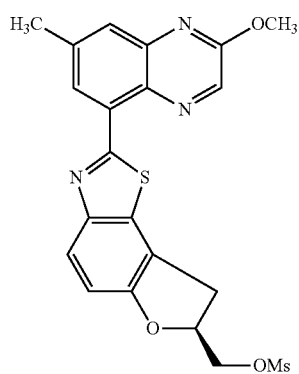

(224A)

To a suspension of Example 149 (100 mg, 0.264 mmol) in DCM (3 mL) was added methanesulfonyl chloride (0.031 mL, 0.395 mmol 1), followed by triethylamine (0.184 mL, 1.318 mmol). The mixture was stirred at room temperature for 1 hour. The reaction was quenched by 1N HCl and extracted with DCM. The combined organic layer was washed with brine, dried over $MgSO_4$ and concentrated to Intermediate 224A (121 mg, 0.264 mmol, 100% yield) as a yellow solid. This material was used directly for the next step without any purification. $^1$H NMR (400 MHz, CHLOROFORM-d) δ 8.64 (d, J=1.8 Hz, 1H), 8.57 (s, 1H), 7.95 (d, J=8.6 Hz, 1H), 7.77 (d, J=0.9 Hz, 1H), 7.04 (d, J=8.8 Hz, 1H), 5.37-5.11 (m, 1H), 4.62-4.36 (m, 2H), 4.14 (s, 3H), 3.60 (dd, J=15.5, 9.8 Hz, 1H), 3.31 (dd, J=15.7, 6.9 Hz, 1H), 3.08 (s, 3H), 2.66 (s, 3H). LC-MS: Method C; RT=2.33 min, MS (ESI) m/z: 458.0 (M+H)$^+$.

Intermediate 224B (S)-7-(azidomethyl)-2-(2-methoxy-7-methylquinoxalin-5-yl)-7,8-dihydrobenzofuro[5,4-d]thiazole

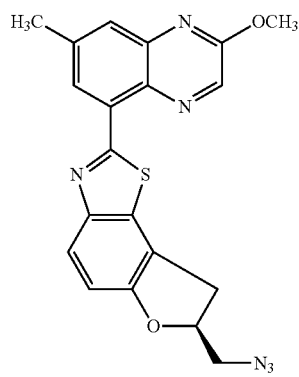

(224B)

To a suspension of Intermediate 224A (0.121 g, 0.264 mmol) in DMF (3 mL) was added $NaN_3$ (0.051 g, 0.792 mmol). The mixture was heated at 75° C. for 4 hours, at which time TLC and LCMS indicated the completion of the reaction. The mixture was cooled and diluted with EtOAc and water, extracted with EtOAc. The combined organic layer was washed with brine, dried with $MgSO_4$ and concentrated to Intermediate 224B (0.107 g, 0.264 mmol, 100% yield) as a yellow solid. The sample was used for next step without purification. LC-MS: Method C; RT=2.49 min, MS (ESI) m/z: 404.0 (M+H)$^+$.

Intermediate 224C (S)-(2-(2-methoxy-7-methylquinoxalin-5-yl)-7,8-dihydrobenzofuro[5,4-d]thiazol-7-yl)methanamine

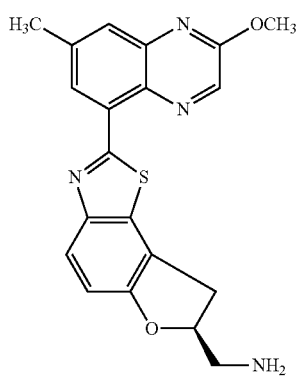

(224C)

To a suspension of Intermediate 224B (0.107 g, 0.264 mmol, 100% yield) in THF/water/EtOH (1:1:1) (3 mL) was added Zinc dust (51.8 mg, 0.792 mmol) then ammonium chloride (70.6 mg, 1.320 mmol). The mixture was stirred at room temperature overnight. TLC and LCMS indicated the completion of the reaction. The mixture was diluted with EtOAc and water, extracted with EtOAc, the combined organic layer was washed with saturated sodium bicarbonate, brine, dried over sodium sulfate and concentrated to Intermediate 224C (0.10 g, 0.264 mmol, 100% yield). The sample was used for next step without purification. LC-MS: Method C, RT=2.06 min, MS (ESI) m/z: 397.0 (M+H)$^+$.

Example 224

To a solution of Intermediate 224C (25 mg, 0.066 mmol) and pyridine (0.080 mL, 0.991 mmol) in DCM (1 mL) was added isobutyl chloroformate (27.1 mg, 0.198 mmol). The mixture was stirred at room temperature for 30 min, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 60-100% B over 22 minutes, then a 5-minute hold at 100% B). Fractions containing the desired product were combined and dried via centrifugal evaporation to Example 224 (6.5 mg, 0.014 mmol, 20.56% yield). $^1$H NMR (500 MHz, DMSO-$d_6$) δ 8.75 (s, 1H), 8.59 (s, 1H), 7.89 (d, J=8.9 Hz, 1H), 7.82 (s, 1H), 7.43 (br. s., 1H), 7.04 (d, J=8.5 Hz, 1H), 5.03 (d, J=9.5 Hz, 1H), 4.08 (s, 3H), 3.74 (d, J=6.7 Hz, 2H), 3.50 (dd, J=15.7, 9.0 Hz, 1H), 3.41-3.37 (m, 2H), 3.18 (dd, J=16.0, 6.6 Hz, 1H), 2.63 (s, 3H), 1.87-1.68 (m, 1H), 0.84 (d, J=6.7 Hz, 6H). LC-MS: method L, RT=2.58 min, MS (ESI) m/z: 479.35 (M+H)$^+$. Analytical HPLC purity (method B): 100%.

Example 225

(S)-benzyl ((2-(2-methoxy-7-methylquinoxalin-5-yl)-7,8-dihydrobenzofuro[5,4-d]thiazol-7-yl)methyl)carbamate

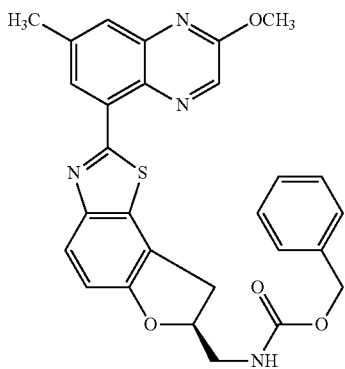

(225)

To a solution of Intermediate 224C (25 mg, 0.066 mmol) and pyridine (0.080 mL, 0.991 mmol) in DCM (1 mL) was added benzyl chloroformate (33.8 mg, 0.198 mmol). The mixture was stirred at room temperature for 1 hour, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 60-100% B over 22 minutes, then a 5-minute hold at 100% B). Fractions containing the desired product were combined and dried via centrifugal evaporation to Example 225 (4.5 mg, 8.78 μmol, 13.29% yield). $^1$H NMR (500 MHz, DMSO-$d_6$) δ 8.71 (s, 1H), 8.56 (s, 1H), 7.88 (d, J=8.5 Hz, 1H), 7.80 (s, 1H), 7.59 (br. s., 1H), 7.47-7.21 (m, 5H), 7.03 (d, J=8.5 Hz, 1H), 5.02 (s, 3H), 4.06 (s, 3H), 3.48-3.41 (m, 1H), 3.38 (br. s., 2H), 3.24-3.10 (m, 1H), 2.61 (s, 3H). LC-MS: method L, RT=2.53 min, MS (ESI) m/z: 513.15 (M+H)$^+$. Analytical HPLC purity (method B): 100%.

Example 226

(S)-methyl ((2-(2-methoxy-7-methylquinoxalin-5-yl)-7,8-dihydrobenzofuro[5,4-d]thiazol-7-yl)methyl)carbamate

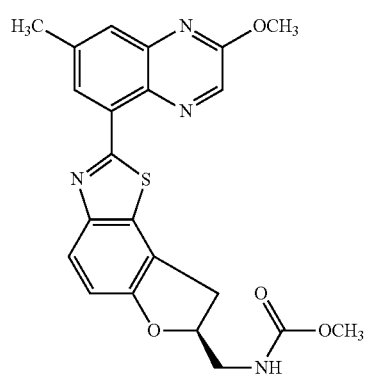

(226)

To a solution of Intermediate 224C (25 mg, 0.066 mmol) and pyridine (0.080 mL, 0.991 mmol) in DCM (1 mL) was added methyl chloroformate (18.73 mg, 0.198 mmol). The mixture was stirred at room temperature for 1 hour, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 45-90% B over 22 minutes, then a 5-minute hold at 100% B). Fractions containing the desired product were combined and dried via centrifugal evaporation to Example 226 (5.7 mg, 0.013 mmol, 19.37% yield). $^1$H NMR (500 MHz, DMSO-$d_6$) δ 8.66 (s, 1H), 8.51 (s, 1H), 7.86 (d, J=8.9 Hz, 1H), 7.74 (s, 1H), 7.46 (br. s., 1H), 7.02 (d, J=8.5 Hz, 1H), 5.15-4.89 (m, 1H), 4.04 (s, 3H), 3.47-3.30 (m, 3H), 3.17-3.06 (m, 1H), 2.58 (s, 3H). LC-MS: method L, RT=2.24 min, MS (ESI) m/z: 437.30 (M+H)$^+$. Analytical HPLC purity (method B): 98%.

Example 227

(S)-tetrahydro-2H-pyran-4-yl ((2-(2-methoxy-7-methylquinoxalin-5-yl)-7,8-dihydrobenzofuro[5,4-d]thiazol-7-yl)methyl)carbamate

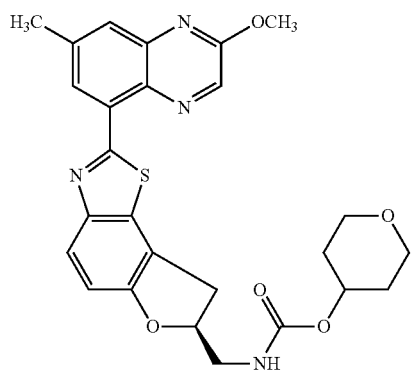

(227)

Intermediate 227A: (S)-4-nitrophenyl ((2-(2-methoxy-7-methylquinoxalin-5-yl)-7,8-dihydrobenzofuro[5,4-d]thiazol-7-yl)methyl)carbamate

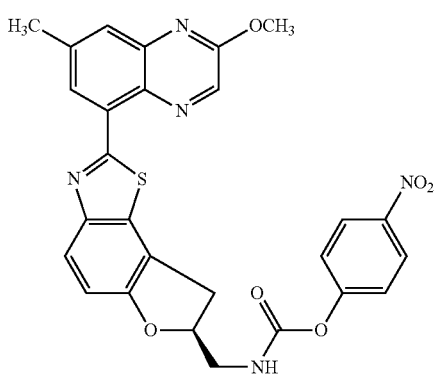

(227A)

To a solution of Intermediate 224C (0.023 g, 0.06 mmol) and pyridine (9.71 µl, 0.120 mmol) in DCM (1 mL) was added 4-nitrophenyl chloroformate (0.013 g, 0.066 mmol). The mixture was stirred at room temperature for 30 min, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated to Intermediate 227A (0.033 g, 0.060 mmol, 100% yield). LC-MS: method C, RT=2.55 min, MS (ESI) m/z 544.0 (M+H)$^+$.

Example 227

To a solution of Intermediate 227A (32.6 mg, 0.06 mmol) in THF (1 mL) was added tetrahydro-2H-pyran-4-ol (61.3 mg, 0.600 mmol) and KHDMS (0.120 mL, 1 M, 0.120 mmol). The mixture was stirred at room temperature for 30 min. TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 45-90% B over 20 minutes, then a 5-minute hold at 100% B). Fractions containing the desired product were combined and dried via centrifugal evaporation to Example 227 (1.3 mg, 2.464 µmol, 4.11% yield). $^1$H NMR (500 MHz, CHLOROFORM-d) δ 8.62 (s, 1H), 8.55 (s, 1H), 7.93 (d, J=8.8 Hz, 1H), 7.75 (s, 1H), 7.01 (d, J=8.5 Hz, 1H), 5.23-5.06 (m, 2H), 4.86 (br. s., 1H), 4.13 (s, 3H), 3.99-3.80 (m, 2H), 3.70 (br. s., 1H), 3.57-3.45 (m, 4H), 3.17 (dd, J=15.4, 6.9 Hz, 1H), 2.65 (s, 3H). LC-MS: method L, RT=2.24 min, MS (ESI) m/z: 507.15 (M+H)$^+$. Analytical HPLC purity (method B): 96%.

Example 228

(S)-N-((2-(2-methoxy-7-methylquinoxalin-5-yl)-7,8-dihydrobenzofuro[5,4-d]thiazol-7-yl) methyl)methanesulfonamide

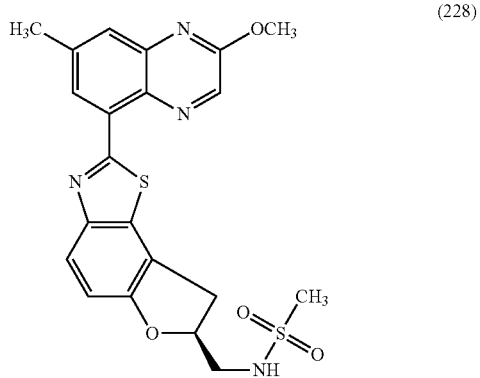 [SMILES: COc1cnc2c(-c3nc4ccc5c(c4s3)C[C@@H](CNS(C)(=O)=O)O5)cc(C)cc2n1]

(228)

To a suspension of Intermediate 224C (22.71 mg, 0.06 mmol) in DCM (1 mL) was added methanesulfonyl chloride (6.97 µl, 0.090 mmol) and triethylamine (0.042 mL, 0.300 mmol). The mixture was stirred at room temperature for 30 min, at which time TLC and LCMS indicated completion of the reaction. The reaction was quenched with MeOH and solvent was removed under vacuum. The residual was dissolved in DMSO and purified via preparative LC/MS (Method D: Gradient: 40-80% B over 20 minutes, then a 5-minute hold at 100% B). Fractions containing the desired product were combined and dried via centrifugal evaporation to Example 228 (1.2 mg, 0.00263 mmol, 4.38% yield). $^1$H NMR (500 MHz, DMSO-d$_6$) δ 8.67 (s, 1H), 8.52 (s, 1H), 7.87 (d, J=8.9 Hz, 1H), 7.76 (s, 1H), 7.38 (t, J=6.3 Hz, 1H), 7.04 (d, J=8.9 Hz, 1H), 5.18-4.98 (m, 1H), 4.04 (s, 3H), 3.50-3.42 (m, 1H), 3.38-3.25 (m, 2H), 3.23-3.17 (m, 1H), 2.93 (s, 3H), 2.59 (s, 3H). LC-MS: method L, RT=2.06 min, MS (ESI) m/z: 457.10 (M+H)$^+$. Analytical HPLC purity (method B): 100%.

Example 229

(Tetrahydrofuran-3-yl)methyl (((S)-2-(2-methoxy-7-methylquinoxalin-5-yl)-7,8-dihydrobenzofuro[5,4-d]thiazol-7-yl)m ethyl)carbamate

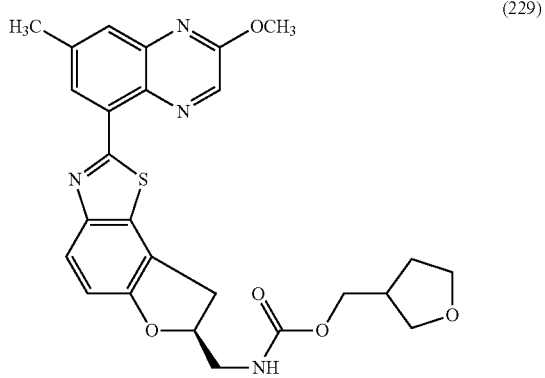 [SMILES: COc1cnc2c(-c3nc4ccc5c(c4s3)C[C@@H](CNC(=O)OCC3CCOC3)O5)cc(C)cc2n1]

(229)

To a solution of Intermediate 227A (32.6 mg, 0.06 mmol) in THF (1 mL) was added (tetrahydrofuran-3-yl)methanol (30.6 mg, 0.300 mmol) and KHDMS (0.120 mL, 1M, 0.120 mmol). The mixture was stirred at room temperature for 30 min. TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and was purified via preparative LC/MS (Method D: Gradient: 45-90% B over 20 minutes, then a 7-minute hold at 100% B). Fractions containing the desired product were combined and dried via centrifugal evaporation to Example 229 (1.2 mg, 1.919 μmol, 3.20% yield). LC-MS: method L, RT=2.25 min, MS (ESI) m/z: 507.30 (M+H)⁺. Analytical HPLC purity (method B): 81%.

Example 230

(R)-tetrahydrofuran-3-yl (((S)-2-(2-methoxy-7-methylquinoxalin-5-yl)-7,8-dihydrobenzofuro[5,4-d]thiazol-7-yl)m ethyl)carbamate

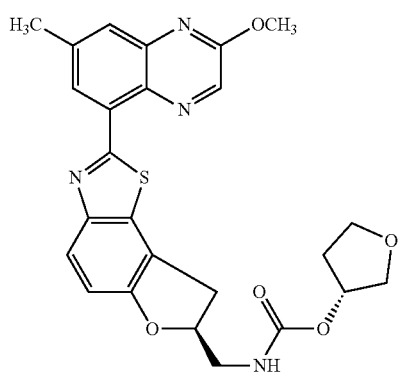

(230)

To a solution of Intermediate 227A (32.6 mg, 0.06 mmol) in THF (1 mL) was added (R)-tetrahydrofuran-3-ol (52.9 mg, 0.600 mmol) and KHDMS (0.120 mL, 1M, 0.120 mmol). The mixture was stirred at room temperature for 30 min. TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 45-90% B over 20 minutes, then a 5-minute hold at 100% B). Fractions containing the desired product were combined and dried via centrifugal evaporation to Example 230 (2.4 mg, 4.78 μmol, 7.96% yield). ¹H NMR (500 MHz, DMSO-d₆) δ 8.69 (s, 1H), 8.53 (s, 1H), 7.87 (d, J=8.9 Hz, 1H), 7.78 (s, 1H), 7.49 (br. s., 1H), 7.02 (d, J=8.5 Hz, 1H), 5.10 (br. s., 1H), 5.02 (br. s., 1H), 4.05 (s, 3H), 3.70 (d, J=5.5 Hz, 2H), 3.46 (dd, J=15.6, 9.5 Hz, 1H), 3.34 (br. s., 2H), 3.18-3.11 (m, 1H), 2.60 (s, 3H), 2.08 (dd, J=14.2, 6.9 Hz, 1H), 1.83 (d, J=7.0 Hz, 1H). LC-MS: method L, RT=2.22 min, MS (ESI) m/z: 493.30 (M+H)⁺. Analytical HPLC purity (method B): 98%.

Example 231

(S)-3-cyanobenzyl ((2-(2-methoxy-7-methylquinoxalin-5-yl)-7,8-dihydrobenzofuro[5,4-d]thiazol-7-yl)methy 1)carbamate

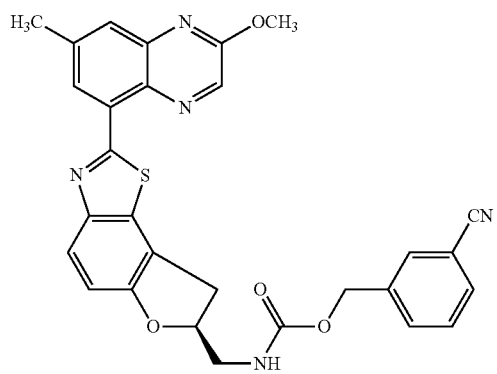

(231)

To a solution of Intermediate 227A (32.6 mg, 0.06 mmol) in THF (1 mL) was added 3-(hydroxymethyl)benzonitrile (80 mg, 0.600 mmol) and KHDMS (0.120 mL, 1M, 0.120 mmol). The mixture was stirred at room temperature for 45 min. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 50-100% B over 20 minutes, then a 5-minute hold at 100% B). Fractions containing the desired product were combined and dried via centrifugal evaporation to Example 231(1.6 mg, 2.95 μmol, 4.91% yield). ¹H NMR (500 MHz, DMSO-d₆) δ 8.67 (s, 1H), 8.51 (s, 1H), 7.86 (d, J=8.5 Hz, 1H), 7.79-7.60 (m, 5H), 7.57-7.46 (m, 1H), 7.01 (d, J=8.5 Hz, 1H), 5.13-4.98 (m, 3H), 4.04 (s, 3H), 3.51-3.27 (m, 3H), 3.13 (dd, J=15.9, 6.4 Hz, 1H), 2.59 (s, 3H). LC-MS: method L, RT=2.45 min, MS (ESI) m/z: 538.30 (M+H)⁺. Analytical HPLC purity (method B): 99%.

Example 232

(S)-pyridin-3-ylmethyl ((2-(2-methoxy-7-methylquinoxalin-5-yl)-7,8-dihydrobenzofuro[5,4-d]thiazol-7-yl)methy 1)carbamate

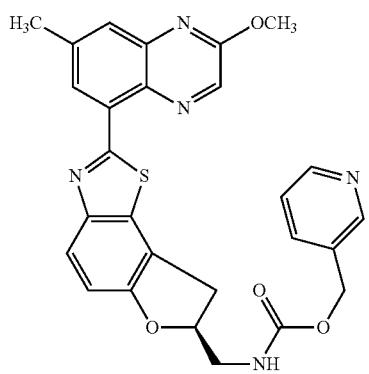

(232)

To a solution of Intermediate 227A (32.6 mg, 0.06 mmol) in THF (1 mL) was added pyridin-3-ylmethanol (65.5 mg, 0.600 mmol) and KHDMS (0.120 mL, 1M, 0.120 mmol). The mixture was stirred at room temperature for 30 min. TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 45-90% B over 20 minutes, then a 7-minute hold at 100% B). Fractions containing the desired product were combined and dried via centrifugal evaporation to Example 232 (2.1 mg, 4.01 µmol, 6.68% yield). $^1$H NMR (500 MHz, DMSO-d$_6$) δ 8.64 (s, 1H), 8.53 (br. s., 1H), 8.50-8.45 (m, 2H), 7.85 (d, J=8.5 Hz, 1H), 7.76-7.70 (m, 2H), 7.64 (br. s., 1H), 7.40-7.34 (m, 1H), 7.00 (d, J=8.5 Hz, 1H), 5.06 (s, 2H), 5.02 (br. s., 1H), 4.03 (s, 3H), 3.47-3.34 (m, 3H), 3.11 (dd, J=15.6, 6.7 Hz, 1H), 2.58 (s, 3H). LC-MS: method L, RT=1.83 min, MS (ESI) m/z: 514.30 (M+H)$^+$. Analytical HPLC purity (method B): 98.5%.

Example 233

(S)-pyridin-4-ylmethyl ((2-(2-methoxy-7-methylquinoxalin-5-yl)-7,8-dihydrobenzofuro[5,4-d]thiazol-7-yl)methyl)carbamate

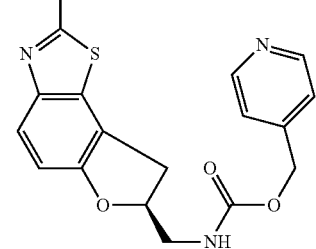

(233)

To a solution of Intermediate 227A (32.6 mg, 0.06 mmol) in THF (1 mL) was added pyridin-4-ylmethanol (65.5 mg, 0.600 mmol) and KHDMS (0.120 mL, 1M, 0.120 mmol). The mixture was stirred at room temperature for 45 min. TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 30-70% B over 20 minutes, then a 5-minute hold at 100% B). Fractions containing the desired product were combined and dried via centrifugal evaporation to Example 233 (2.3 mg, 4.21 µmol, 7.02% yield). $^1$H NMR (500 MHz, DMSO-d$_6$) δ 8.65 (s, 1H), 8.49 (d, J=12.5 Hz, 3H), 7.86 (d, J=8.5 Hz, 1H), 7.75 (br. s., 2H), 7.25 (br. s., 2H), 7.19-7.04 (m, 1H), 7.02 (d, J=8.5 Hz, 1H), 5.07 (br. s., 3H), 4.04 (s, 3H), 3.49-3.32 (m, 3H), 3.17-3.08 (m, 1H), 2.58 (s, 3H). LC-MS: method K, RT=2.22 min, MS (ESI) m/z: 514.35 (M+H)$^+$. Analytical HPLC purity (method B): 94.4%.

Example 234

Tetrahydro-2H-pyran-3-yl (((S)-2-(2-methoxy-7-methylquinoxalin-5-yl)-7,8-dihydrobenzofuro[5,4-d]thiazol-7-yl)methyl)carbamate

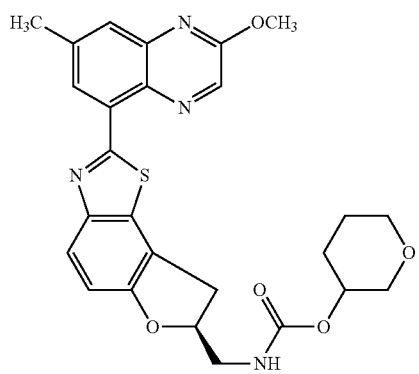

(234)

To a solution of Intermediate 227A (32.6 mg, 0.06 mmol) in THF (1 mL) was added tetrahydro-2H-pyran-3-ol (61.3 mg, 0.600 mmol) and KHDMS (0.120 mL, 1M, 0.120 mmol). The mixture was stirred at room temperature for 1 hour. TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 45-90% B over 20 minutes, then a 5-minute hold at 100% B). Fractions containing the desired product were combined and dried via centrifugal evaporation to Example 234 (1.6 mg, 3.00 µmol, 5.00% yield). $^1$H NMR (500 MHz, DMSO-d$_6$) δ 8.67 (s, 1H), 8.52 (s, 1H), 7.86 (d, J=8.9 Hz, 1H), 7.77 (s, 1H), 7.72-7.42 (m, 2H), 7.02 (d, J=8.8 Hz, 1H), 5.02 (br. s., 1H), 4.49 (br. s., 1H), 4.04 (s, 3H), 3.53-3.41 (m, 3H), 3.34 (br. s., 2H), 3.18-3.09 (m, 1H), 2.59 (s, 3H), 1.83 (br. s., 1H), 1.66 (br. s., 1H), 1.57 (br. s., 1H), 1.42 (br. s., 1H). LC-MS: method L, RT=2.32 min, MS (ESI) m/z: 507.30 (M+H)$^+$. Analytical HPLC purity (method B): 95%.

Example 235

(Tetrahydro-2H-pyran-2-yl)methyl (((S)-2-(2-methoxy-7-methylquinoxalin-5-yl)-7,8-dihydrobenzofuro[5,4-d]thiazol-7-yl)methyl)carbamate

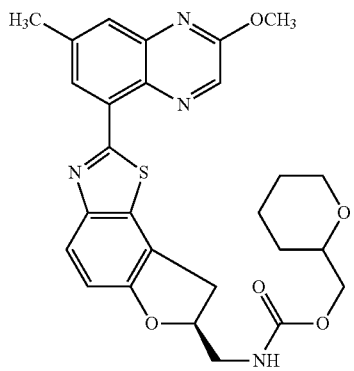

(235)

To a solution of Intermediate 227A (32.6 mg, 0.06 mmol) in THF (1 mL) was added (tetrahydro-2H-pyran-2-yl)methanol (69.7 mg, 0.600 mmol) and KHDMS (0.120 mL, 1M, 0.120 mmol). The mixture was stirred at room temperature for 1 hour. TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 50-100% B over 20 minutes, then a 7-minute hold at 100% B). Fractions containing the desired product were combined and dried via centrifugal evaporation to Example 235 (1.7 mg, 3.27 µmol, 5.44% yield). $^1$H NMR (500 MHz, DMSO-$d_6$) δ 8.66 (s, 1H), 8.51 (s, 1H), 7.86 (d, J=8.5 Hz, 1H), 7.76 (s, 1H), 7.48 (br. s., 1H), 7.01 (d, J=8.5 Hz, 1H), 5.11-4.91 (m, 1H), 4.04 (s, 3H), 3.87 (br. s., 2H), 3.78 (d, J=11.9 Hz, 1H), 3.46-3.31 (m, 4H), 3.24 (d, J=10.7 Hz, 1H), 3.18-3.08 (m, 1H), 2.59 (s, 3H), 1.70 (br. s., 1H), 1.50-1.34 (m, 4H), 1.22-1.11 (m, 1H). LC-MS: method L, RT=2.43 min, MS (ESI) m/z: 521.30 (M+H)$^+$. Analytical HPLC purity (method B): 100%.

Example 236

(S)-tetrahydrofuran-3-yl (((S)-2-(2-methoxy-7-methylquinoxalin-5-yl)-7,8-dihydrobenzofuro[5,4-d]thiazol-7-yl)m ethyl)carbamate

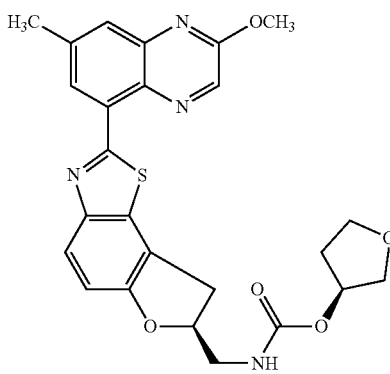

(236)

To a solution of Intermediate 227A (32.6 mg, 0.06 mmol) in THF (1 mL) was added (S)-tetrahydrofuran-3-ol (52.9 mg, 0.600 mmol) and KHDMS (0.120 mL, 1M, 0.120 mmol). The mixture was stirred at room temperature for 1 hour. TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 45-90% B over 20 minutes, then a 7-minute hold at 100% B). Fractions containing the desired product were combined and dried via centrifugal evaporation to Example 236 (1.6 mg, 3.18 µmol, 5.31% yield). $^1$H NMR (500 MHz, DMSO-$d_6$) δ 8.74 (s, 1H), 8.58 (s, 1H), 7.89 (d, J=8.9 Hz, 1H), 7.82 (s, 1H), 7.51 (br. s., 1H), 7.04 (d, J=8.9 Hz, 1H), 5.11 (br. s., 1H), 5.03 (br. s., 1H), 4.07 (s, 3H), 3.79-3.60 (m, 3H), 3.34 (br. s., 2H), 3.16 (br. s., 1H), 2.62 (s, 3H), 2.39-2.30 (m, 1H), 2.14-2.03 (m, 1H), 1.84 (br. s., 1H), 1.22 (br. s., 1H). LC-MS: method L, RT=2.21 min, MS (ESI) m/z: 493.30 (M+H)$^+$. Analytical HPLC purity (method B): 100%.

Example 237

(S)-(5-fluoro-2-(2-methoxy-7-methylquinoxalin-5-yl)-7-methyl-7,8-dihydrobenzofuro[5,4-d]thiazol-7-yl)methyl dihydrogen phosphate

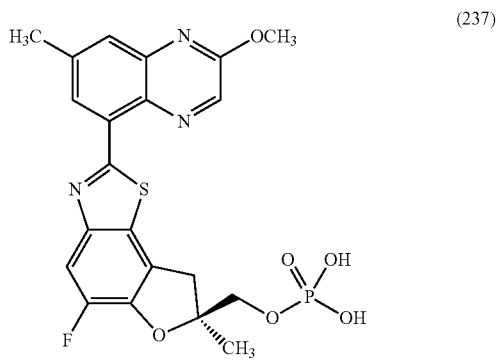 [SMILES: COc1cnc2c(-c3nc4cc(F)c5c(c4s3)C[C@@](C)(COP(=O)(O)O)O5)cc(C)cc2n1]

(237)

Intermediate 237A (S)-(5-fluoro-2-(2-methoxy-7-methylquinoxalin-5-yl)-7-methyl-7,8-dihydrobenzofuro[5,4-d]thiazol-7-yl)methyl bis(2-(trimethylsilyl)ethyl) phosphate

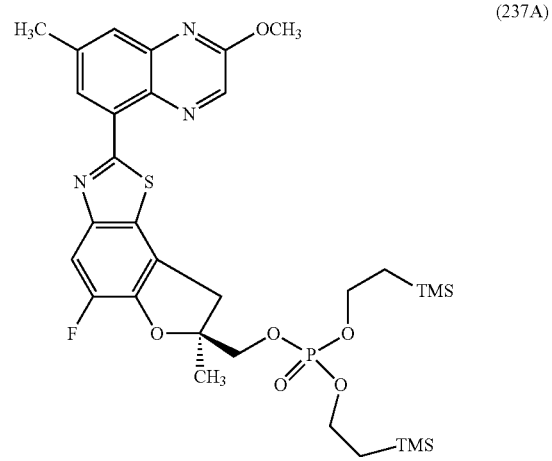 [SMILES: COc1cnc2c(-c3nc4cc(F)c5c(c4s3)C[C@@](C)(COP(=O)(OCC[Si](C)(C)C)OCC[Si](C)(C)C)O5)cc(C)cc2n1]

(237A)

To a suspension of Example 172 (20 mg, 0.049 mmol) in $CH_2Cl_2$ (4.0 mL) was added bis(2-(trimethylsilyl)ethyl)diisopropylphosphoramidite (178 mg, 0.486 mmol), followed by 1H-tetrazole (34.1 mg, 0.486 mmol) at room temperature. The reaction mixture was stirred for 4 hours and the suspension turned to a clear solution. The reaction mixture was cooled at 0° C. and hydrogen peroxide (30% wt. in $H_2O$, 0.149 mL, 1.458 mmol) was added. The reaction mixture was allowed to stir at room temperature for 30 minutes, at which time IPLC and LCMS indicated a completion of reaction. Dichloromethane was removed under vacuum. The reaction mixture was diluted with EtOAc, and washed with saturated $Na_2S_2O_3$. The organic phase was dried over $Na_2SO_4$, and concentrated to give Intermediate 237A (33.6 mg, 0.049 mmol, 100% yield). LC-MS: method H, 2 to 98% B. RT=1.43 min, MS (ESI) m/z: 692.5 (M+H)$^+$.

Example 237

To Intermediate 237A (33 mg, 0.048 mmol) in dichloromethane (3.0 mL) was added TFA (0.367 mL, 4.77 mmol) at room temperature. The reaction mixture was stirred at room temperature for 25 min. LCMS indicated completion of reaction. Solvent was removed under vacuum. The crude was dissolved in DMSO/CH$_3$CN (1:1, 3 mL) and purified with preparative HPLC (method A, 40-100% B in 8 min. Then 100% B in 4 min.). The desired fractions were placed in a SpeedVac overnight to remove solvent, then lyophilized to give Example 237 (21 mg, 0.042 mmol, 89% yield). $^1$H NMR (500 MHz, THF) δ 8.66 (d, J=1.4 Hz, 1H), 8.52 (s, 1H), 7.71 (s, 1H), 7.62 (d, J=11.3 Hz, 1H), 4.15-4.10 (m, 2H), 4.09 (s, 3H), 3.64 (d, J=15.7 Hz, 1H), 3.19 (d, J=15.7 Hz, 1H), 2.61 (s, 3H), 1.59 (s, 3H); $^{19}$F NMR (471 MHz, THF) δ −142.29 (s, 1F); $^{31}$P NMR (202 MHz, THF) δ −0.8 (br. s., 1P); LC-MS: method H, 2 to 98% B. RT=0.89 min, MS (ESI) m/z:492.00 (M+H)$^+$. Analytical HPLC purity (method A): 99% purity.

Example 238

((7S,8S)-5-fluoro-2-(2-methoxy-7-methylquinoxalin-5-yl)-8-methyl-7,8-dihydrobenzofuro[5,4-d]thiazol-7-yl)methanol

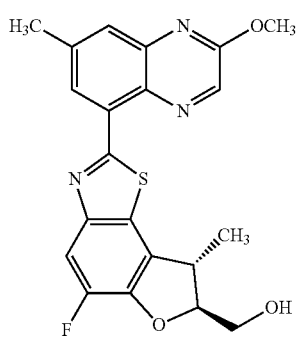

(238)

Intermediate 238A: ((7R,8R)-2-chloro-5-fluoro-8-methyl-7,8-dihydrobenzofuro[5,4-d]thiazol-7-yl)methanol and Intermediate 238B ((7S,8S)-2-chloro-5-fluoro-8-methyl-7,8-dihydrobenzofuro[5,4-d]thiazol-7-yl)methanol

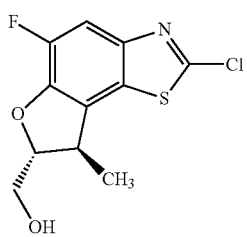

(238A)

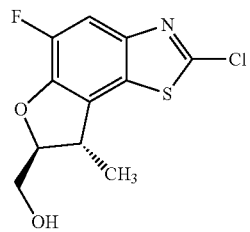

(238B)

Intermediate 199C (600 mg, 2.192 mmol) was separated via Berger preparative SFC (Column: Chiralpak AD-H, 21×250 mm, 5 micron, Mobile Phase: 10% MeOH/90% CO$_2$, Flow Conditions: 45 mL/min, 150 Bar, 40° C., Detector Wavelength: 220 nm, Injection Details: 1 mL of a 30 mg/mL soln. in methanol). Fractions containing the first peak (RT=6.8 min) were combined and dried via centrifugal evaporation to yield Intermediate 238A (180 mg, 0.658 mmol, 30.0% yield). Fractions containing the second peak (RT=9.7 min) were combined and dried via centrifugal evaporation to yield Intermediate 238B (2$^{nd}$ peak, 180 mg, 0.658 mmol, 30.0% yield).

Example 238

To Intermediate I-9 (18.32 mg, 0.084 mmol), Intermediate 238B (23 mg, 0.084 mmol) and PdCl$_2$(dppf)—CH$_2$Cl$_2$ adduct (3.02 mg, 3.70 μmol) was added dioxane (1 mL). The mixture was sonicated for 1 min, and flushed with argon. To this was added sodium carbonate (0.168 mL, 1.5M, 0.252 mmol). The reaction mixture was heated in a microwave at 100° C. for 45 min. LCMS indicated completion of the reaction. The reaction mixture was directly loaded to 40 g ISCO column which was eluted with hexanes for 3 min, then a 20 min gradient from 0% to 100% EtOAc in hexanes. The desired fractions were combined and concentrated. The compound was dissolved in DMSO and purified via preparative LC/MS (Method D: Gradient: 50-100% B over 20 minutes, then a 5-minute hold at 100% B). Fractions containing the desired product were combined and dried via centrifugal evaporation to Example 238 (32 mg, 0.076 mmol, 91% yield). $^1$H NMR (500 MHz, DMSO-d$_6$) δ 8.71 (s, 1H), 8.53 (s, 1H), 7.83 (d, J=11.3 Hz, 1H), 7.79 (s, 1H), 5.24 (t, J=5.3 Hz, 1H), 4.63 (d, J=3.7 Hz, 1H), 4.07 (s, 3H), 3.84-3.68 (m, 3H), 2.61 (s, 3H), 2.70-2.58 (m, 3H), 1.48 (d, J=6.7 Hz, 3H). LC-MS: method L, RT=2.28 min, MS (ESI) m/z: 412.09 (M+H)$^+$. Analytical HPLC purity (method B): 98%.

Example 239

((7R,8R)-5-fluoro-2-(2-methoxy-7-methylquinoxalin-5-yl)-8-methyl-7,8-dihydrobenzofuro[5,4-d]thiazol-7-yl)methanol

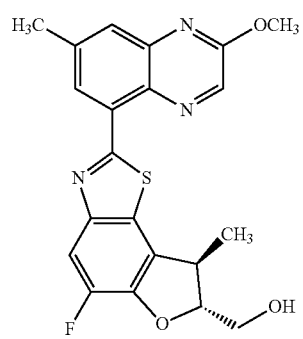

(239)

To Intermediate I-9 (21.51 mg, 0.099 mmol), Intermediate 238A (27 mg, 0.099 mmol) and PdCl$_2$(dppf)—CH$_2$Cl$_2$ adduct (3.54 mg, 4.34 µmol) was added dioxane (1 mL). The mixture was sonicated for 1 min, and flushed with argon. To this was added sodium carbonate (0.197 mL, 1.5 M, 0.296 mmol). The reaction mixture was heated in a microwave at 100° C. for 45 min. LCMS indicated completion of the reaction. The reaction mixture was directly loaded to 40 g ISCO column which was eluted with hexanes for 3 min, then a 20 min gradient from 0% to 100% EtOAc in hexanes. The desired fractions were combined and concentrated. The compound was dissolved in DMSO and purified via preparative LC/MS (Method D: Gradient: 50-100% B over 20 minutes, then a 5-minute hold at 100% B). Fractions containing the desired product were combined and dried via centrifugal evaporation to Example 239 (35 mg, 0.083 mmol, 84% yield). $^1$H NMR (500 MHz, DMSO-d$_6$) δ 8.73 (s, 1H), 8.54 (s, 1H), 7.84 (d, J=11.3 Hz, 1H), 7.80 (s, 1H), 5.16 (t, J=5.3 Hz, 1H), 4.68-4.54 (m, 1H), 4.06 (s, 3H), 3.82-3.66 (m, 3H), 2.68-2.58 (m, 3H), 2.61 (s, 3H), 1.48 (d, J=6.7 Hz, 3H). LC-MS: method L, RT=2.28 min, MS (ESI) m/z: 412.10 (M+H)$^+$. Analytical HPLC purity (method B): 97%.

Example 240

(S)-methyl ((5-fluoro-2-(2-methoxy-7-methylquinoxalin-5-yl)-7-methyl-7,8-dihydrobenzofuro[5,4-d]thiazol-7-yl)methyl)carbamate Intermediate 240A (S)-(5-fluoro-2-(2-methoxy-7-methylquinoxalin-5-yl)-7-methyl-7,8-dihydrobenzofuro[5,4-d]thiazol-7-yl)methyl methanesulfonate

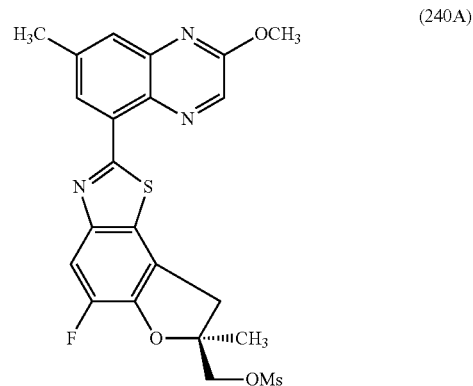 [SMILES: COc1cnc2c(-c3nc4cc(F)c5c(c4s3)C[C@@](C)(COS(C)(=O)=O)O5)cc(C)cc2n1]

(240A)

To a suspension of Example 172 (115 mg, 0.279 mmol) in DCM (3 mL) was added methanesulfonyl chloride (0.032 mL, 0.419 mmol), followed by triethylamine (0.195 mL, 1.397 mmol). The mixture was stirred at room temperature for 30 min. The reaction was quenched by 1N HCl and extracted with DCM. The combined organic layer was washed with brine, dried over MgSO$_4$ and concentrated to Intermediate 240A (137 mg, 0.280 mmol, 100% yield) as a yellow solid. This material was used directly for the next step without any purification. $^1$H NMR (400 MHz, CHLOROFORM-d) δ 8.62 (d, J=2.0 Hz, 1H), 8.56 (s, 1H), 7.77 (d, J=0.7 Hz, 1H), 7.74 (d, J=11.0 Hz, 1H), 4.41 (s, 2H), 4.14 (s, 3H), 3.56 (d, J=15.8 Hz, 1H), 3.28 (d, J=15.8 Hz, 1H), 3.07 (s, 3H), 2.66 (s, 3H), 1.69 (s, 3H). $^{19}$F NMR (376 MHz, CHLOROFORM-d) δ −139.08 (s, 1F). LC-MS: Method B; RT=4.44 min, MS (ESI) m/z: 490.1 (M+H)$^+$.

Intermediate 240B (S)-7-(azidomethyl)-5-fluoro-2-(2-methoxy-7-methylquinoxalin-5-yl)-7-methyl-7,8-dihyd robenzofuro[5,4-d]thiazole

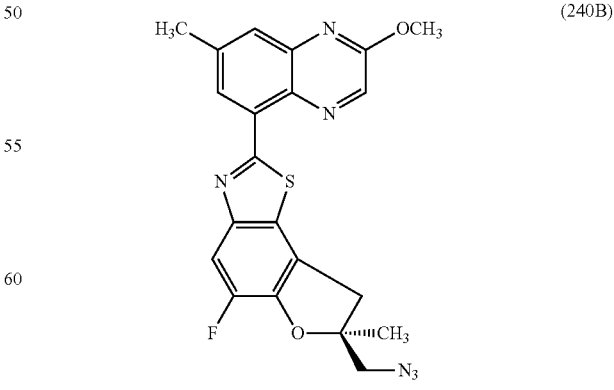

(240B)

To a suspension of Intermediate 240A (137 mg, 0.279 mmol) in DMF (4 mL) was added NaN$_3$ (108.8 mg, 1.674 mmol). The mixture was heated at 120° C. for 15 hours. The mixture was cooled, diluted with EtOAc and water, extracted with EtOAc. The combined organic layer was washed with brine, dried with MgSO$_4$ and concentrated. The crude product was purified by flash chromatography (loading in chloroform, 0% to 100% EtOAc in hexane over 20 min using a 40 g silica gel cartridge). The desired fractions were combined and concentrated to Intermediate 240B (50 mg, 0.115 mmol, 41.1% yield) as a yellow solid. $^1$H NMR (400 MHz, CHLOROFORM-d) δ 8.62 (d, J=1.5 Hz, 1H), 8.56 (s, 1H), 7.77 (d, J=0.9 Hz, 1H), 7.74 (d, J=10.8 Hz, 1H), 4.14 (s, 3H), 3.64 (d, J=12.8 Hz, 1H), 3.56-3.43 (m, 2H), 3.23 (d, J=15.6 Hz, 1H), 2.66 (s, 3H), 1.66 (s, 3H). 19F NMR (376 MHz, CHLOROFORM-d) δ −138.97 (s, 1F). LC-MS: Method C; RT=2.66 min, MS (ESI) m/z: 437.1 (M+H)$^+$.

Intermediate 240C (S)-(5-fluoro-2-(2-methoxy-7-methylquinoxalin-5-yl)-7-methyl-7,8-dihydrobenzofuro[5,4-d]thiazol-7-yl)methanamine

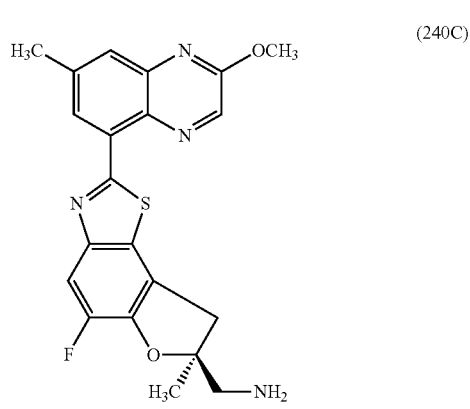 [SMILES: COc1cnc2c(-c3nc4cc(F)c5c(c4s3)C[C@@](C)(CN)O5)cc(C)cc2n1]

To a suspension of Intermediate 240B (50 mg, 0.115 mmol) in THF/water/EtOH (1:1:1) (3 mL) was added Zinc dust (22.47 mg, 0.344 mmol) then NH$_4$Cl (30.6 mg, 0.573 mmol). The mixture was stirred at room temperature overnight, then at 65° C. for 45 min. TLC and LCMS indicated completion of the reaction. The mixture was diluted with EtOAc and water, extracted with EtOAc, the combined organic layer was washed with saturated sodium bicarbonate, brine, dried over sodium sulfate and concentrated to Intermediate 240C (47.2 mg, 0.115 mmol, 100% yield). The sample was used for next step without purification. LC-MS: Method C, RT=2.15 min, MS (ESI) m/z: 411.1 (M+H)$^+$.

Example 240

To a solution of Intermediate 240C (15 mg, 0.037 mmol) and pyridine (0.044 mL, 0.548 mmol) in DCM (1 mL) was added methyl chloroformate (10.36 mg, 0.110 mmol). The mixture was stirred at room temperature for 30 min, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 45-100% B over 20 minutes, then a 5-minute hold at 100% B). Fractions containing the desired product were combined and dried via centrifugal evaporation to Example 240 (4.6 mg, 9.82 μmol, 26.9% yield). $^1$H NMR (500 MHz, DMSO-d$_6$) δ 8.75 (s, 1H), 8.58 (s, 1H), 7.97-7.77 (m, 2H), 7.52 (br. s., 1H), 4.09 (s, 3H), 3.45-3.41 (m, 6H), 3.27-3.18 (m, 1H), 2.64 (s, 3H), 1.51 (s, 3H). LC-MS: method L, RT=2.45 min, MS (ESI) m/z: 469.35 (M+H)$^+$. Analytical IPLC purity (method B): 100%.

Example 241

(S)-isobutyl ((5-fluoro-2-(2-methoxy-7-methylquinoxalin-5-yl)-7-methyl-7,8-dihydrobenzofuro[5,4-d]thiazol-7-yl)methyl)carbamate

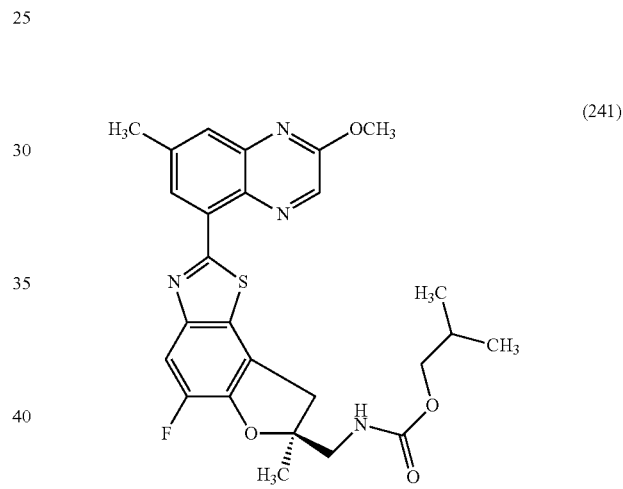

To a solution of Intermediate 240C (15 mg, 0.037 mmol) and pyridine (0.044 mL, 0.548 mmol) in DCM (1 mL) was added isobutyl chloroformate (14.97 mg, 0.110 mmol). The mixture was stirred at room temperature for 30 min, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 70-100% B over 16 minutes, then a 5-minute hold at 100% B). Fractions containing the desired product were combined and dried via centrifugal evaporation to Example 241 (5.1 mg, 9.79 μmol, 26.8% yield). $^1$H NMR (500 MHz, DMSO-d$_6$) δ 8.74 (s, 1H), 8.56 (s, 1H), 7.87-7.81 (m, 2H), 7.46 (br. s., 1H), 4.07 (s, 3H), 3.69 (d, J=4.9 Hz, 2H), 3.49 (d, J=15.9 Hz, 1H), 3.26-3.14 (m, 1H), 2.62 (s, 3H), 2.54 (s, 2H), 1.80-1.67 (m, 1H), 1.50 (s, 3H), 0.85 (br. s., 1H), 0.76 (d, J=6.1 Hz, 6H). LC-MS: method L, RT=2.74 min, MS (ESI) m/z: 511.05 (M+H)$^+$. Analytical HPLC purity (method B): 98%.

Example 242

(S)-tert-butyl ((5-fluoro-2-(2-methoxy-7-methylquinoxalin-5-yl)-7-methyl-7,8-dihydrobenzofuro[5,4-d]thiazol-7-yl)methyl)carbamate

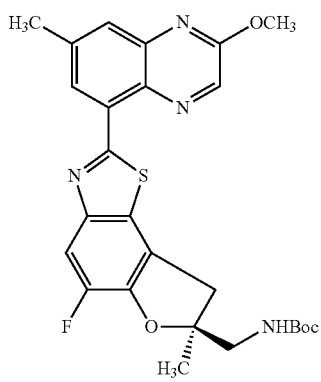
(242)

To a solution of Intermediate 240C (15 mg, 0.037 mmol) and pyridine (0.044 mL, 0.548 mmol) in DCM (1 mL) was added BOC-anhydride (0.110 mL, 1N, 0.110 mmol). The mixture was stirred at room temperature for 30 min, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 70-100% B over 16 minutes, then a 5-minute hold at 100% B). Fractions containing the desired product were combined and dried via centrifugal evaporation to Example 242 (3.6 mg, 6.70 μmol, 18.33% yield). $^1$H NMR (500 MHz, DMSO-$d_6$) δ 8.75 (s, 1H), 8.57 (s, 1H), 7.86-7.80 (m, 2H), 7.16 (br. s., 1H), 4.07 (s, 3H), 3.48 (d, J=16.2 Hz, 1H), 3.30 (br. s., 1H), 3.25-3.13 (m, 2H), 2.62 (s, 3H), 1.33 (s, 9H). LC-MS: method L, RT=2.76 min, MS (ESI) m/z: 511.05 (M+H)$^+$. Analytical HPLC purity (method B): 95%.

Example 243

(R)-1-((S)-2-(2-methoxy-7-methylquinoxalin-5-yl)-7,8-dihydrobenzofuro[5,4-d]thiazol-7-yl)ethanol

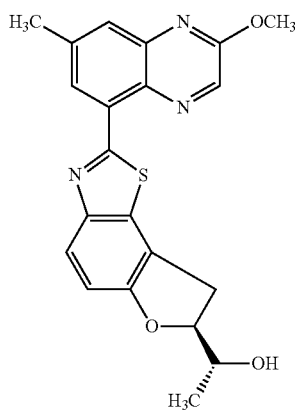
(243)

Example 190 (90 mg, 0.229 mmol) was subject to chiral SFC for separation using the following conditions: Instrument: Berger II Prep SFC; Chiralpak ID, 4.6×250 mm, 5 micron; Mobile Phase: 8% MeOH/92% $CO_2$; Flow Conditions: 2 mL/min, 150 Bar, 40° C.; Detector Wavelength: 220 nm. Injection Details: 1 mL of ~30 mg/ml in MeOH. The first eluting fractions (first peak, RT=8 min) were concentrated to give Example 243 (20 mg, 0.050 mmol, 22% yield). $^1$H NMR (500 MHz, THF) δ 8.71 (d, J=1.7 Hz, 1H), 8.55 (s, 1H), 7.80 (d, J=8.5 Hz, 1H), 7.73 (d, J=0.8 Hz, 1H), 6.92 (d, J=8.8 Hz, 1H), 4.74 (ddd, J=9.4, 7.8, 5.1 Hz, 1H), 4.14 (d, J=4.7 Hz, 1H), 4.10 (s, 3H), 3.97-3.91 (m, 1H), 3.49-3.43 (m, 1H), 3.37-3.31 (m, 1H), 2.63 (s, 3H), 1.24 (d, J=6.3 Hz, 3H); LC-MS: method H, 2 to 98% B. RT=1.03 min, MS (ESI) m/z: 394.05 (M+H)$^+$. Analytical HPLC purity (method A): 99% purity.

Example 244

(S)-tert-butyl ((2-(2-methoxy-7-methylquinoxalin-5-yl)-7,8-dihydrobenzofuro[5,4-d]thiazol-7-yl)methyl)carbamate

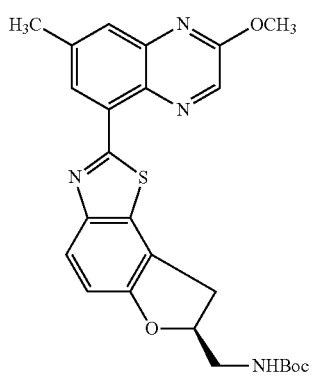
(244)

To a solution of Intermediate 224C (37.8 mg, 0.1 mmol) and pyridine (0.121 mL, 1.500 mmol) in DCM (1 mL) was added BOC-anhydride (0.150 mL, 2N, 0.300 mmol). The mixture was stirred at room temperature for 30 min, at which time TLC and LCMS indicated completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 60-100% B over 20 minutes, then a 5-minute hold at 100% B). Fractions containing the desired product were combined and dried via centrifugal evaporation to Example 244 (0.7 mg, 1.463 μmol, 1.463% yield). $^1$H NMR (500 MHz, DMSO-$d_6$) δ 8.76 (s, 1H), 8.59 (s, 1H), 7.90 (d, J=8.5 Hz, 1H), 7.83 (s, 1H), 7.13 (br. s., 1H), 7.04 (d, J=8.5 Hz, 1H), 5.01 (br. s., 1H), 4.08 (s, 3H), 3.54-3.43 (m, 1H), 3.22-3.12 (m, 1H), 2.63 (s, 3H), 1.38 (s, 9H). LC-MS: method L, RT=2.59 min, MS (ESI) m/z: 479.1(M+H)$^+$. Analytical HPLC purity (method B): 100%.

Example 245

(S)-tetrahydro-2H-pyran-4-yl ((5-fluoro-2-(2-methoxy-7-methylquinoxalin-5-yl)-7,8-dihydrobenzofuro[5,4-d]thiazol-7-yl)methyl)carbamate

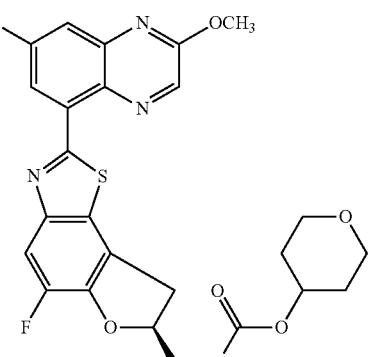

Intermediate 245A: (S)-4-nitrophenyl ((5-fluoro-2-(2-methoxy-7-methylquinoxalin-5-yl)-7,8-dihydrobenzofuro[5,4-d]thiazol-7-yl)methyl)carbamate

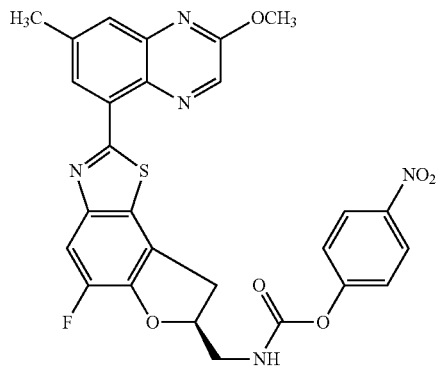

To a solution of Intermediate 202C (20 mg, 0.050 mmol) and pyridine (8.16 µl, 0.101 mmol) in DCM (1 mL) was added 4-nitrophenyl chloroformate (11.19 mg, 0.055 mmol). The mixture was stirred at room temperature overnight, at which time TLC and LCMS indicated the completion of the reaction. The reaction was quenched with 1N HCl, extracted with EtOAc, the combined organic layer was washed with saturated sodium bicarbonate, brine, dried over sodium sulfate and concentrated to Intermediate 245A (28.2 mg, 0.050 mmol, 100% yield). LC-MS: method C, RT=2.44 min, MS (ESI) m/z: 562.0 (M+H)+.

Example 245

To a solution of Intermediate 245A (28.1 mg, 0.05 mmol) in THF (1 mL) was added tetrahydro-2H-pyran-4-ol (51.1 mg, 0.500 mmol) and KHDMS (0.10 mL, 1M, 0.10 mmol). The mixture was stirred at room temperature for 30 min. TLC and LCMS indicated the completion of the reaction. The reaction was quenched with 1N HCl, extracted with EtOAc, the combined organic layer was washed with saturated sodium bicarbonate, brine, dried over sodium sulfate and concentrated. The compound was dissolved in DMSO and purified via preparative LC/MS (Method D: Gradient: 50-100% B over 22 minutes, then a 5-minute hold at 100% B). Fractions containing the desired product were combined and dried via centrifugal evaporation to Example 245 (0.7 mg, 1.334 µmol, 2.67% yield). $^1$H NMR (500 MHz, DMSO-$d_6$) δ 8.74 (s, 1H), 8.57 (s, 1H), 7.88-7.82 (m, 2H), 7.50 (br. s., 1H), 5.17 (br. s., 1H), 4.70 (br. s., 1H), 4.08 (s, 3H), 3.73 (d, J=17.1 Hz, 2H), 3.61 (br. s., 2H), 3.40 (br. s., 2H), 3.35-3.14 (m, 2H), 2.63 (s, 3H), 1.82 (br. s., 2H), 1.45 (br. s., 2H). LC-MS: method L, RT=2.37 min, MS (ESI) m/z: 525.0 (M+H)+. Analytical HPLC purity (method B): 100%.

Example 246

(S)-isobutyl ((5-fluoro-2-(2-methoxy-7-methylquinoxalin-5-yl)-7,8-dihydrobenzofuro[5,4-d]thiazol-7-yl)methyl)carbamate

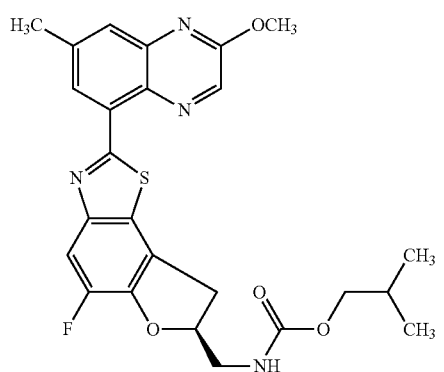

To a solution of Intermediate 202B (22.3 mg, 0.053 mmol) in THF (1 mL) was added PMe$_3$ in toluene (0.055 mL, 1N, 0.055 mmol) dropwise. The mixture was stirred at room temperature for 1 hour. TLC and LCMS indicated completion of the reduction. Isobutyl chloroformate (8.65 mg, 0.063 mmol) was added to the mixture dropwise and the mixture was stirred at room temperature for 1 hour. The reaction was quenched with phosphate buffer (pH 7), extracted with EtOAc. The combined organic layer was washed with saturated sodium bicarbonate, brine, dried over sodium sulfate and concentrated. The crude was dissolved in DMSO and purified via preparative LC/MS (Method D: Gradient: 60-100% B over 22 minutes, then a 5-minute hold at 100% B). Fractions containing the desired product were combined and dried via centrifugal evaporation to Example 246 (7.2 mg, 0.014 mmol, 27.5% yield). $^1$H NMR (500 MHz, DMSO-$d_6$) δ 8.66 (s, 1H), 8.50 (br. s., 1H), 7.87-7.78 (m, 1H), 7.76 (s, 1H), 7.48 (br. s., 1H), 5.16 (d, J=6.4 Hz, 1H), 4.05 (s, 3H), 3.74 (d, J=6.4 Hz, 1H), 3.89-3.64 (m, 1H), 3.62-3.46 (m, 1H), 3.39-3.30 (m, 2H), 3.27-3.17 (m, 1H), 2.59 (s, 3H), 1.95-1.68 (m, 1H), 0.83 (d, J=6.4 Hz, 6H). LC-MS: method L, RT=2.71 min, MS (ESI) m/z: 497.1 (M+H)+. Analytical HPLC purity (method B): 100%.

Example 247

(S)-2-fluoroethyl ((5-fluoro-2-(2-methoxy-7-methylquinoxalin-5-yl)-7,8-dihydrobenzofuro[5,4-d]thiazol-7-yl)methyl) carbamate

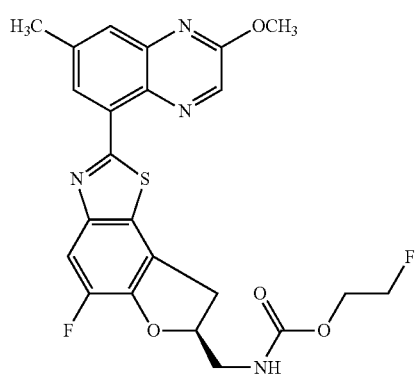

(247)

To a solution of Intermediate 202B (17.0 mg, 0.04 mmol) in THF (1 mL) was added PMe₃ in toluene (0.06 mL, 1N, 0.06 mmol) dropwise. The mixture was stirred at room temperature for 1 hour. TLC and LCMS indicated completion of the reduction. 2-Fluoroethyl chloroformate (7.59 mg, 0.060 mmol) was added to the mixture dropwise and the mixture was stirred at room temperature for 1 hour. The reaction was quenched with phosphate buffer (pH 7), extracted with EtOAc. The combined organic layer was washed with saturated sodium bicarbonate, brine, dried over sodium sulfate and concentrated. The crude was dissolved in DMSO and purified via preparative LC/MS (Method D: Gradient: 60-100% B over 22 minutes, then a 5-minute hold at 100% B). Fractions containing the desired product were combined and dried via centrifugal evaporation to Example 247 (5.6 mg, 0.012 mmol, 28.8% yield). ¹H NMR (500 MHz, DMSO-d₆) δ 8.70 (s, 1H), 8.54 (s, 1H), 7.95-7.71 (m, 2H), 7.66 (br. s., 1H), 5.16 (br. s., 1H), 4.60 (br. s., 1H), 4.50 (br. s., 1H), 4.28-4.14 (m, 2H), 4.06 (s, 3H), 3.41 (br. s., 2H), 3.27-3.13 (m, 2H), 2.60 (s, 3H). LC-MS: method L, RT=2.37 min, MS (ESI) m/z: 486.9 (M+H)+. Analytical HPLC purity (method B): 100%.

Example 248

(S)-1-((5-fluoro-2-(2-methoxy-7-methylquinoxalin-5-yl)-7,8-dihydrobenzofuro[5,4-d]thiazol-7-yl)methyl)-3-phenylurea

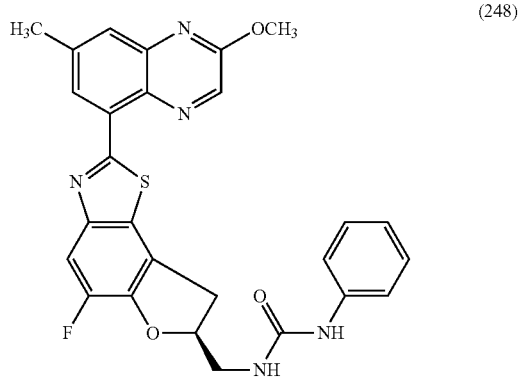

(248)

To a solution of Intermediate 202B (17.0 mg, 0.04 mmol) in THF (1 mL) was added PMe₃ in toluene (0.06 mL, 1N, 0.06 mmol) dropwise. The mixture was stirred at room temperature for 1 hour. TLC and LCMS indicated completion of the reduction. Phenyl isocyanate (7.15 mg, 0.060 mmol) was added to the mixture dropwise, and the mixture was stirred at room temperature for 1 hour. The reaction was quenched with phosphate buffer (pH 7), extracted with EtOAc. The combined organic layer was washed with saturated sodium bicarbonate, brine, dried over sodium sulfate and concentrated. The crude was dissolved in DMSO and purified via preparative LC/MS (Method D: Gradient: 50-100% B over 22 minutes, then a 5-minute hold at 100% B). Fractions containing the desired product were combined and dried via centrifugal evaporation to Example 248 (2.1 mg, 4.07 μmol, 10.18% yield). ¹H NMR (500 MHz, DMSO-d₆) δ 8.62 (s, 1H), 8.58 (s, 1H), 8.47 (s, 1H), 7.79 (d, J=11.0 Hz, 1H), 7.73 (s, 1H), 7.36 (d, J=8.2 Hz, 2H), 7.21 (t, J=7.5 Hz, 2H), 6.89 (t, J=7.2 Hz, 1H), 6.54-6.41 (m, 1H), 5.19 (br. s., 1H), 4.03 (s, 3H), 3.54 (br. s., 1H), 3.21 (dd, J=15.9, 7.3 Hz, 1H), 2.57 (s, 3H). LC-MS: method L, RT=2.45 min, MS (ESI) m/z: 515.9 (M+H)+. Analytical HPLC purity (method B): 97%.

Example 249

(S)-2,2,2-trifluoroethyl ((5-fluoro-2-(2-methoxy-7-methylquinoxalin-5-yl)-7,8-dihydrobenzofuro[5,4-d]thiazol-7-yl)methyl) carbamate

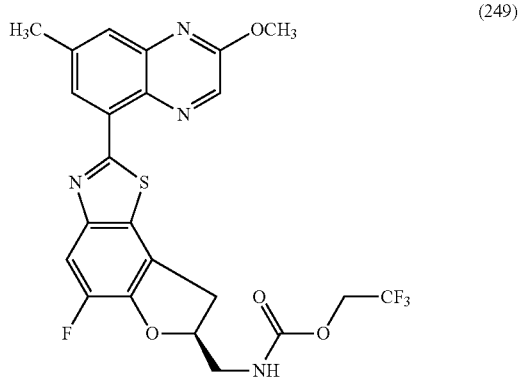 [SMILES: COc1cnc2c(-c3nc4cc(F)c5c(c4s3)C[C@@H](CNC(=O)OCCF)O5)cc(C)cc2n1]

(249)

To a solution of Intermediate 202B (17.0 mg, 0.04 mmol) in THF (1 mL) was added PMe₃ in toluene (0.06 mL, 1N, 0.06 mmol) dropwise. The mixture was stirred at room temperature for 1 hour. TLC and LCMS indicated completion of the reduction. 2,2,2-Trifluoroethyl chloroformate (9.75 mg, 0.060 mmol) was added to the mixture dropwise, followed by DIEA (0.014 mL, 0.080 mmol). The mixture was stirred at room temperature for 1 hour. The reaction was quenched with phosphate buffer (pH 7), extracted with EtOAc. The combined organic layer was washed with saturated sodium bicarbonate, brine, dried over sodium sulfate and concentrated. The crude was dissolved in DMSO and purified via preparative LC/MS (Method D: Gradient: 50-100% B over 22 minutes, then a 5-minute hold at 100% B). Fractions containing the desired product were combined and dried via centrifugal evaporation to Example 249 (4.0 mg, 7.66 µmol, 19.14% yield). ¹H NMR (500 MHz, DMSO-d₆) δ 8.60 (br. s., 1H), 8.45 (br. s., 1H), 8.04 (t, J=5.5 Hz, 1H), 7.76 (d, J=11.0 Hz, 1H), 7.72 (br. s., 1H), 5.15 (br. s., 1H), 4.71-4.58 (m, 2H), 4.03 (s, 3H), 3.57 (br. s., 1H), 3.50-3.39 (m, 2H), 3.17 (dd, J=15.9, 7.0 Hz, 1H), 2.57 (s, 3H). LC-MS: method L, RT=2.56 min, MS (ESI) m/z: 523.1 (M+H)⁺. Analytical HPLC purity (method B): 100%.

Example 250

(S)-2-methoxyethyl ((5-fluoro-2-(2-methoxy-7-methylquinoxalin-5-yl)-7,8-dihydrobenzofuro[5,4-d]thiazol-7-yl)methyl) carbamate

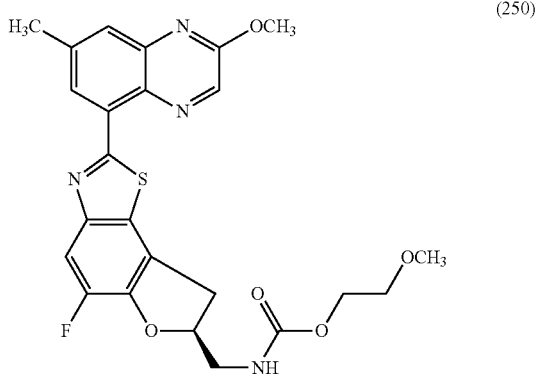 [SMILES: COCCOC(=O)NC[C@@H]1Cc2c(c(F)cc3nc(-c4cc(C)cc5nc(OC)cnc45)sc23)O1]

(250)

To a solution of Intermediate 202B (17.0 mg, 0.04 mmol) in THF (1 mL) was added PMe₃ in toluene (0.06 mL, 1N, 0.06 mmol) dropwise. The mixture was stirred at room temperature for 1 hour. TLC and LCMS indicated completion of the reduction. 2-Methoxyethyl chloroformate (8.31 mg, 0.060 mmol) was added to the mixture dropwise, followed by DIEA (0.014 mL, 0.080 mmol). The mixture was stirred at room temperature for 1 hour. The reaction was quenched with phosphate buffer (pH 7), extracted with EtOAc. The combined organic layer was washed with saturated sodium bicarbonate, brine, dried over sodium sulfate and concentrated. The crude was dissolved in DMSO and purified via preparative LC/MS (Method D: Gradient: 45-90% B over 22 minutes, then a 5-minute hold at 100% B). Fractions containing the desired product were combined and dried via centrifugal evaporation to Example 250 (2.8 mg, 5.62 µmol, 14.04% yield). ¹H NMR (500 MHz, DMSO-d₆) δ 8.71 (s, 1H), 8.55 (s, 1H), 7.85-7.80 (m, 2H), 7.55 (br. s., 1H), 5.15 (br. s., 1H), 4.06 (s, 6H), 3.45 (br. s., 2H), 3.39 (br. s., 2H), 3.27-3.15 (m, 4H), 2.61 (s, 3H). LC-MS: method L, RT=2.34 min, MS (ESI) m/z: 498.9 (M+H)⁺. Analytical HPLC purity (method B): 100%.

Example 251

(R)-(5-fluoro-2-(2-methoxy-7-methylquinoxalin-5-yl)-7-methyl-7,8-dihydrobenzofuro[5,4-d]thiazol-7-yl)methyl (2-(2-hydroxyethoxy)pyrimidin-5-yl)carbamate

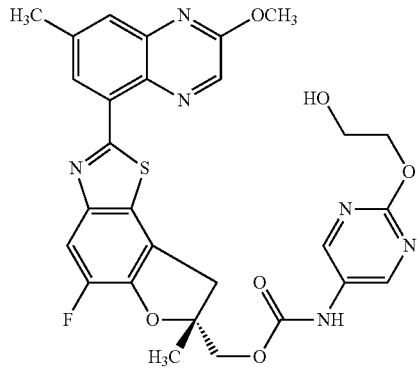

(251)

Intermediate I-57 (34.1 mg, 0.127 mmol) was dissolved in DCM (1.0 mL) along with (0.055 mL, 0.675 mmol) and DIEA (0.044 mL, 0.253 mmol). Intermediate 182A (40 mg, 0.084 mmol) in 2 mL of DCM was added dropwise, and the reaction mixture was stirred at room temperature for 50 minutes. The reaction was quenched with 1.0 N HCl (0.5 mL). All solvent was removed under vacuum. The crude was dried under high vacuum for 1 h, then treated with THF (1.5 mL) and 3 mL of 20:1 MeOH/concentrated HCl at room temperature for 1.5 h. HPLC and LCMS indicated a complete deprotection of the silyl group. Solvent was removed under vacuum. The crude was dissolved in THF/DMSO (1:1, 3 mL) and purified via preparative LC/MS (method C, 45-90% B over 22 min, then a 5-min hold at 100% B). Fractions containing the desired product were combined and dried via centrifugal evaporation to yield Example 251 (8.1 mg, 16% yield). ¹H NMR (500 MHz, DMSO-d₆) δ 9.87 (br. s., 1H), 8.66 (s, 1H), 8.59 (br. s., 2H), 8.51 (s, 1H), 7.82 (d, J=10.1 Hz, 1H), 7.77 (s, 1H), 4.39 (br. s., 2H), 4.24 (br. s., 1H), 4.06 (s, 3H), 3.30 (d, J=16.2 Hz, 1H), 2.60 (s, 3H), 1.60 (s, 3H]; LC-MS: method C, 2 to 98% B. RT=2.24 min, MS (ESI) m/z: 593.2 (M+H)⁺. Analytical HPLC purity (method B): 100%.

Example 252

((7R,8R)-5-fluoro-2-(2-methoxy-7-methylquinoxalin-5-yl)-8-methyl-7,8-dihydrobenzofuro[5,4-d]thiazol-7-yl)methyl (2-(2-hydroxyethoxy)pyrimidin-5-yl)carbamate

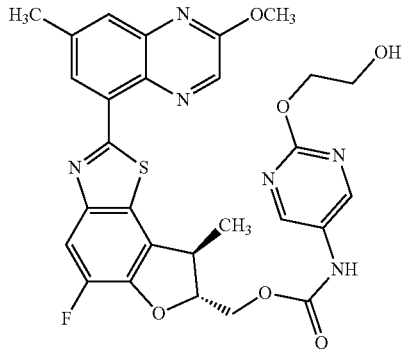

(252)

Intermediate 252A ((7R,8R)-5-fluoro-2-(2-methoxy-7-methylquinoxalin-5-yl)-8-methyl-7,8-dihydrobenzofuro[5,4-d]thiazol-7-yl)methyl chloroformate

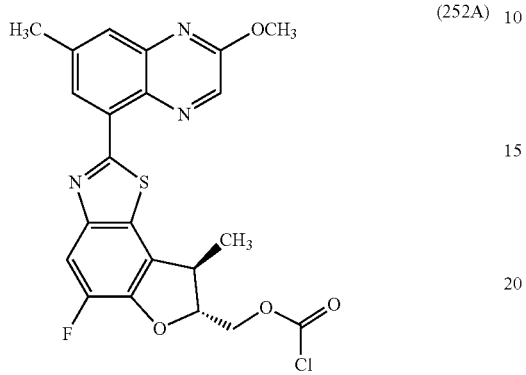

(252A)

To the solution of Example 239 (30 mg, 0.073 mmol) in THF (2 ml) was added 15% phosgene in toluene (0.206 ml, 0.292 mmol), followed by DIEA (0.076 ml, 0.437 mmol). The reaction mixture was stirred at room temperature for 1 hour, at which time LCMS (quenched with MeOH) indicated a completion of reaction. Solvent and excess of phosgene was removed under vacuum to give Intermediate 252A which was used for the next step without purification. LC-MS: method C, RT=2.63 min, MS (ESI) m/z: 469.9 (M+H)$^+$ (methyl carbamate).

Example 252

To Intermediate 252A (17 mg, 0.036 mmol) in dichloromethane (1 mL) was added to a solution of Intermediate I-57 (14.50 mg, 0.054 mmol) and pyridine (0.029 ml, 0.359 mmol) in dichloromethane (0.5 mL) dropwise. The reaction mixture was stirred at room temperature for 1 hour, at which time LCMS and IPLC indicated a completion of reaction. The reaction was quenched with 1.0 N HCl (0.5 mL). Solvent was removed under vacuum. The crude sample was dried under high vacuum overnight, then treated with THF (1 mL) and 2 mL of 20:1 MeOH/concentrated HCl at room temperature for 1.0 hour. TLC and LCMS indicated a complete deprotection. Solvent was removed under vacuum. The crude sample was dissolved in DMSO and purified via preparative LC/MS (Method D: Gradient: 45-90% B over 30 minutes, then a 5-minute hold at 100% B). Fractions containing the desired product were combined and dried via centrifugal evaporation to Example 252 (3 mg, 5.06 µmol, 14.11% yield). $^1$H NMR (500 MHz, DMSO-d$_6$) δ 9.93 (br. s., 1H), 8.71 (s, 1H), 8.60 (br. s., 2H), 8.53 (s, 1H), 7.86 (d, J=10.4 Hz, 1H), 7.79 (s, 1H), 4.89 (br. s., 1H), 4.55 (d, J=11.3 Hz, 1H), 4.42 (dd, J=12.1, 6.0 Hz, 1H), 4.24 (br. s., 1H), 4.05 (s, 3H), 3.77 (br. s., 1H), 3.50 (d, J=4.0 Hz, 3H), 2.60 (s, 3H), 1.52 (d, J=6.1 Hz, 3H). LC-MS: Method L, 0 to 100% B. RT=2.26 min, MS (ESI) m/z: 593.0 (M+H)$^+$. Analytical IPLC purity (method B): 100%.

Example 253

((7S,8S)-2-(7-chloro-2-methoxyquinoxalin-5-yl)-5-fluoro-8-methyl-7,8-dihydrobenzofuro[5,4-d]thiazol-7-yl)methanol (253)

To Intermediate I-28 (9.58 mg, 0.040 mmol), Intermediate 238B (11 mg, 0.040 mmol) and PdCl$_2$(dppf)—CH$_2$Cl$_2$ adduct (1.45 mg, 1.77 µmol) was added dioxane (1 mL). The mixture was sonicated for 1 min, and flushed with argon. To this was added sodium carbonate (80 µl, 1.5M, 0.121 mmol). The reaction mixture was heated in a microwave at 100° C. for 45 min. LCMS indicated the completion of the reaction. The reaction mixture was directly loaded to 40 g ISCO column which was eluted with hexanes for 3 min, then a 20 min gradient from 0% to 100% EtOAc in hexanes. The desired fractions were combined and concentrated. The compound was dissolved in DMSO and purified via preparative LC/MS (Method D: Gradient: 60-100% B over 25 minutes, then a 4-minute hold at 100% B). Fractions containing the desired product were combined and dried via centrifugal evaporation to Example 253 (10.5 mg, 0.023 mmol, 58.1% yield). $^1$H NMR (500 MHz, DMSO-d$_6$) δ 8.80 (s, 1H), 8.55 (s, 1H), 8.01 (s, 1H), 7.86 (d, J=11.0 Hz, 1H), 5.16 (t, J=5.6 Hz, 1H), 4.63 (d, J=3.7 Hz, 1H), 4.07 (s, 3H), 3.82-3.68 (m, 3H), 1.48 (d, J=6.7 Hz, 3H). LC-MS: method L, RT=2.57 min, MS (ESI) m/z: 432.1 (M+H)$^+$. Analytical HPLC purity (method B): 96%.

Example 254

8-((7S,8S)-5-fluoro-7-(hydroxymethyl)-8-methyl-7,8-dihydrobenzofuro[5,4-d]thiazol-2-y 1)-3-methoxyquinoxaline-6-carbonitrile (254)

To Intermediate I-38 (9.20 mg, 0.040 mmol), Intermediate 238B (10 mg, 0.037 mmol) and PdCl$_2$(dppf)—CH$_2$Cl$_2$ adduct (1.313 mg, 1.608 μmol) was added dioxane (1 mL). The mixture was sonicated for 1 min, and flushed with argon. To this was added sodium carbonate (73.1 μl, 1.5M, 0.110 mmol). The reaction mixture was heated in a microwave at 100° C. for 45 min. LCMS indicated the completion of the reaction. The reaction mixture was directly loaded to 40 g ISCO column which was eluted with hexanes for 3 min, then a 20 min gradient from 0% to 100% EtOAc in hexanes. The desired fractions were combined and concentrated. The compound was dissolved in DMSO and purified via preparative LC/MS (Method D: Gradient: 45-90% B over 20 minutes, then a 6-minute hold at 100% B). Fractions containing the desired product were combined and dried via centrifugal evaporation to Example 254 (3.0 mg, 7.10 μmol, 19.44% yield). $^1$H NMR (500 MHz, DMSO-d$_6$) δ 8.91 (s, 1H), 8.74 (s, 1H), 8.45 (s, 1H), 7.84 (d, J=11.0 Hz, 1H), 4.64 (d, J=4.0 Hz, 1H), 4.10 (s, 3H), 3.91-3.63 (m, 3H), 2.54 (s, 3H), 1.48 (d, J=6.7 Hz, 3H). LC-MS: method L, RT=2.13 min, MS (ESI) m/z: 423.1 (M+H)$^+$. Analytical HPLC purity (method B): 100%.

Example 255

Methyl (((7S,8S)-5-fluoro-2-(2-methoxy-7-methylquinoxalin-5-yl)-8-methyl-7,8-dihydrobenzofuro[5,4-d]thiazol-7-yl)methyl)carbamate

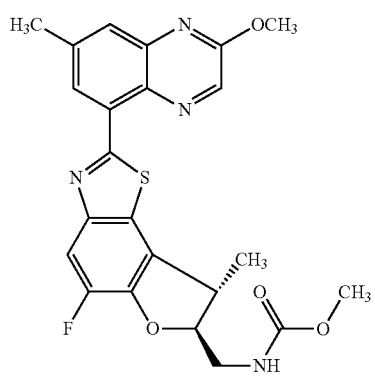

(255)

Intermediate 255A ((7S,8S)-5-fluoro-2-(2-methoxy-7-methylquinoxalin-5-yl)-8-methyl-7,8-dihydrobenzofuro[5,4-d]thiazol-7-yl)methyl methanesulfonate

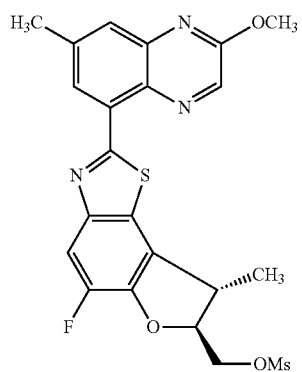

(255A)

To a suspension of Example 238 (30 mg, 0.073 mmol) in DCM (2 mL) was added methanesulfonyl chloride (8.47 μl, 0.109 mmol), followed by triethylamine (0.051 mL, 0.365 mmol). The mixture was stirred at room temperature for 1 hour. The reaction was quenched by 1N HCl and extracted with DCM. The combined organic layer was washed with brine, dried over MgSO$_4$ and concentrated to Intermediate 255A (35.7 mg, 0.073 mmol, 100% yield) as a yellow solid. This material was used directly for the next step without any purification. LC-MS: Method C; RT=2.43 min, MS (ESI) m/z: 489.9 (M+H)$^+$.

Intermediate 255B (7S,8S)-7-(azidomethyl)-5-fluoro-2-(2-methoxy-7-methylquinoxalin-5-yl)-8-methyl-7,8-dihydrobenzofuro[5,4-d]thiazole (255B)

To a suspension of Intermediate 255A (35.7 mg, 0.073 mmol, 100% yield) in DMF (2 mL) was added NaN$_3$ (9.49 mg, 0.146 mmol). The mixture was heated at 75° C. for 4 hours. The mixture was cooled and diluted with EtOAc and water, extracted with EtOAc. The combined organic layer was washed with brine, dried with MgSO$_4$ and concentrated to Intermediate 255B (32 mg, 0.073 mmol, 100% yield) as a yellow solid. This material was used directly for the next step without any purification. LC-MS: Method C; RT=2.70 min, MS (ESI) m/z: 436.9 (M+H)+.

Example 255

To a solution of Intermediate 255B (0.016 g, 0.036 mmol) in THF (1 mL) was added PMe₃ in toluene (0.054 mL, 0.054 mmol) dropwise. The mixture was stirred at room temperature for 30 min. TLC and LCMS indicated completion of the reduction. Methyl chloroformate (5.10 mg, 0.054 mmol) was added to the mixture dropwise, followed by DIEA (0.013 mL, 0.072 mmol). The mixture was stirred at room temperature overnight, quenched with phosphate buffer (pH 7), extracted with EtOAc. The combined organic layer was washed with saturated sodium bicarbonate, brine, dried over sodium sulfate and concentrated. The crude was dissolved in DMSO and purified via preparative LC/MS (Method D: Gradient: 50-100% B over 20 minutes, then a 7-minute hold at 100% B). Fractions containing the desired product were combined and dried via centrifugal evaporation to Example 255 (2.9 mg, 6.19 μmol, 17.19% yield). ¹H NMR (500 MHz, DMSO-d₆) δ 8.74 (s, 1H), 8.55 (s, 1H), 7.86 (d, J=11.3 Hz, 1H), 7.81 (s, 1H), 7.54 (br. s., 1H), 4.65 (d, J=6.1 Hz, 1H), 4.07 (s, 3H), 3.66 (t, J=6.7 Hz, 1H), 3.56 (s, 3H), 3.44 (br. s., 1H), 3.35-3.28 (m, 1H), 2.61 (s, 3H), 1.46 (d, J=6.7 Hz, 3H). LC-MS: method L, RT=2.47 min, MS (ESI) m/z: 469.2 (M+H)+. Analytical HPLC purity (method B): 100%.

Example 256

Isobutyl (((7S,8S)-5-fluoro-2-(2-methoxy-7-methylquinoxalin-5-yl)-8-methyl-7,8-dihydrobenzofuro[5,4-d]thiazol-7-yl)methyl)carbamate

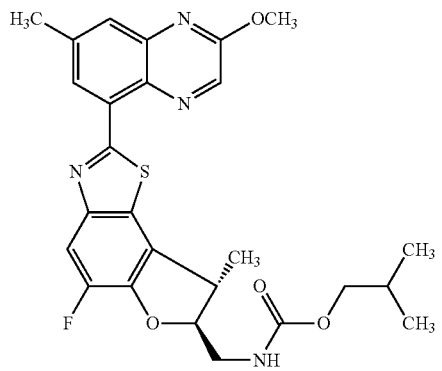

(256)

To a solution of Intermediate 255B (0.016 g, 0.036 mmol) in THF (1 mL) was added PMe₃ in toluene (0.054 mL, 0.054 mmol) dropwise. The mixture was stirred at room temperature for 30 min. TLC and LCMS indicated completion of the reduction. Isobutyl chloroformate (7.38 mg, 0.054 mmol) was added to the mixture dropwise, followed by DIEA (0.013 mL, 0.072 mmol). The mixture was stirred at room temperature overnight, quenched with phosphate buffer (pH 7), extracted with EtOAc. The combined organic layer was washed with saturated sodium bicarbonate, brine, dried over sodium sulfate and concentrated. The crude was dissolved in DMSO and purified via preparative LC/MS (Method D: Gradient: 70-100% B over 25 minutes, then a 4-minute hold at 100% B). Fractions containing the desired product were combined and dried via centrifugal evaporation to Example 256 (1 mg, 1.861 μmol, 5.17% yield). ¹H NMR (500 MHz, DMSO-d₆) δ 8.71 (s, 1H), 8.52 (s, 1H), 7.84 (d, J=11.0 Hz, 1H), 7.79 (s, 1H), 7.50 (br. s., 1H), 4.65 (d, J=6.1 Hz, 1H), 4.06 (s, 3H), 3.75 (d, J=6.4 Hz, 2H), 3.66 (t, J=6.7 Hz, 1H), 3.47-3.29 (m, 2H), 1.90-1.71 (m, 1H), 1.45 (d, J=6.7 Hz, 3H), 0.84 (d, J=6.4 Hz, 6H). LC-MS: method L, RT=2.77 min, MS (ESI) m/z: 511.0 (M+H)+. Analytical HPLC purity (method B): 95%.

Example 257

(S)-1-cyclopropyl-3-((5-fluoro-2-(2-methoxy-7-methylquinoxalin-5-yl)-7,8-dihydrobenzo furo[5,4-d]thiazol-7-yl)methyl)urea

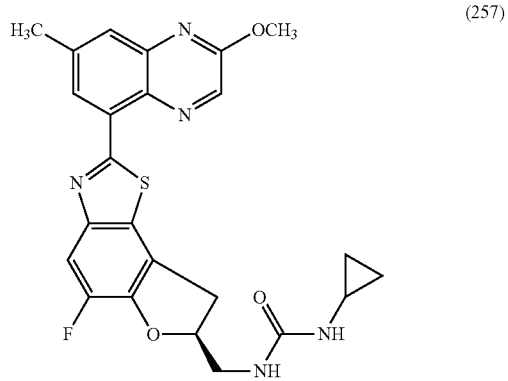 [SMILES: COc1cnc2c(-c3nc4cc(F)c5c(c4s3)C[C@@H](CNC(=O)NC3CC3)O5)cc(C)cc2n1]

(257)

To a solution of Intermediate 202B (15 mg, 0.036 mmol) in THF (1 mL) was added PMe₃ in toluene (0.053 mL, 1M, 0.053 mmol) dropwise. The mixture was stirred at room temperature for 30 min. TLC and LCMS indicated completion of the reduction. Cyclopropyl isocyanate (11.8 mg, 0.142 mmol) was added to the mixture dropwise, and the mixture was stirred at room temperature for 1 hour. The reaction was quenched with phosphate buffer (pH 7), extracted with EtOAc. The combined organic layer was washed with saturated sodium bicarbonate, brine, dried over sodium sulfate and concentrated. The crude was dissolved in DMSO and purified via preparative LC/MS (Method D: Gradient: 45-90% B over 22 minutes, then a 5-minute hold at 100% B). Fractions containing the desired product were combined and dried via centrifugal evaporation to Example 257 (2.1 mg, 4.38 μmol, 12.33% yield). ¹H NMR (500 MHz, DMSO-d₆) δ 8.80 (s, 1H), 8.77 (s, 1H), 8.60 (s, 1H), 7.93-7.81 (m, 2H), 6.20 (br. s., 1H), 5.18 (br. s., 1H), 4.31 (d, J=9.2 Hz, 1H), 4.10 (s, 3H), 3.69-3.41 (m, 3H), 2.91 (d, J=15.9 Hz, 1H), 2.65 (s, 3H), 0.54 (d, J=7.6 Hz, 2H), 0.30 (d, J=13.1 Hz, 2H). LC-MS: method L, RT=2.22 min, MS (ESI) m/z: 480.1 (M+H)+. Analytical HPLC purity (method B): 100%.

Example 258

(S)-N-((5-fluoro-2-(2-methoxy-7-methylquinoxalin-5-yl)-7,8-dihydrobenzofuro[5,4-d]thiazol-7-yl)methyl)morpholine-4-carboxamide (258)

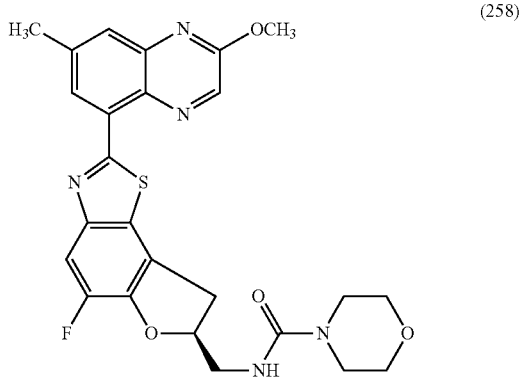 [SMILES: COc1cnc2c(-c3nc4cc(F)c5c(c4s3)C[C@@H](CNC(=O)N3CCOCC3)O5)cc(C)cc2n1]

To a solution of Intermediate 202B (15 mg, 0.036 mmol) and morpholine (6.19 mg, 0.071 mmol) in dioxane (1 mL) was added 0.1 ml of 2M triethylammonium bicarbonate solution (prepared by bubbling $CO_2$ to a mixture of 1.4 ml TEA and 3.6 ml of water for 30 min until pH=8.5) and $PPh_3$ (18.63 mg, 0.071 mmol). The mixture was bubble with $CO_2$, sealed and stirred at room temperature overnight. TLC and LCMS indicated completion of the reaction. The reaction mixture was diluted with water and EtOAc, extracted with EtOAc. The combined organic layer was washed with saturated sodium bicarbonate, brine, dried over sodium sulfate and concentrated. The crude was dissolved in DMSO and purified via preparative LC/MS (Method D: Gradient: 45-90% B over 22 minutes, then a 5-minute hold at 100% B). Fractions containing the desired product were combined and dried via centrifugal evaporation to Example 258 (7.6 mg, 0.015 mmol, 42.0% yield). $^1$H NMR (500 MHz, DMSO-$d_6$) δ 8.69 (s, 1H), 8.53 (s, 1H), 7.89-7.76 (m, 2H), 6.89 (br. s., 1H), 5.16 (br. s., 1H), 4.05 (s, 3H), 3.40-3.01 (m, 12H), 2.60 (s, 3H). LC-MS: method L, RT=2.16 min, MS (ESI) m/z: 510.0 (M+H)$^+$. Analytical HPLC purity (method B): 100%.

Example 259

((7S,8S)-2-(2-ethoxy-7-methylquinoxalin-5-yl)-5-fluoro-8-methyl-7,8-dihydrobenzofuro[5,4-d]thiazol-7-yl)methanol (259)

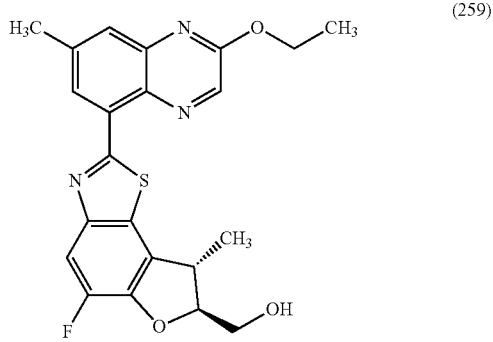 [SMILES: CCOc1cnc2c(-c3nc4cc(F)c5c(c4s3)[C@H](C)[C@@H](CO)O5)cc(C)cc2n1]

Intermediate 259A ((7S,8S)-2-(2-(difluoromethoxy)-7-methylquinoxalin-5-yl)-5-fluoro-8-methyl-7,8-dihydrobenzofuro[5,4-d]thiazol-7-yl)methanol (259A)

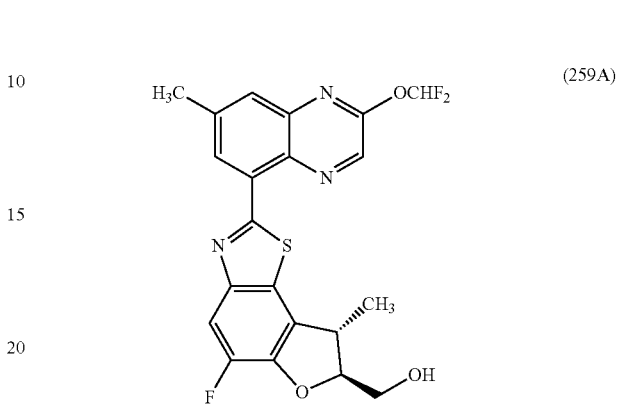

To Intermediate I-53 (46.4 mg, 0.183 mmol), Intermediate 238B (50 mg, 0.183 mmol) and $PdCl_2(dppf)$—$CH_2Cl_2$ adduct (6.56 mg, 8.04 µmol) was added dioxane (1.5 mL). The mixture was sonicated for 1 min, and flushed with argon. To this was added sodium carbonate (0.365 mL, 1.5M, 0.548 mmol). The reaction mixture was heated in a microwave at 100° C. for 1 hour. LCMS indicated the completion of the reaction. The reaction mixture was directly loaded to 40 g ISCO column which was eluted with hexanes for 3 min, then a 20 min gradient from 0% to 100% EtOAc in hexanes. The desired fractions were combined and concentrated to Intermediate 259A (75 mg, 0.168 mmol, 92% yield). $^1$H NMR (400 MHz, CHLOROFORM-d) δ 8.75 (d, J=2.0 Hz, 1H), 8.70 (s, 1H), 7.79 (d, J=0.4 Hz, 1H), 7.73 (d, J=11.0 Hz, 1H), 7.91-7.43 (m, 2H), 4.70 (ddd, J=7.9, 5.1, 3.1 Hz, 1H), 4.05 (d, J=11.9 Hz, 1H), 3.95-3.84 (m, 1H), 3.82-3.72 (m, 1H), 2.68 (s, 3H), 1.61 (d, J=6.8 Hz, 3H). $^{19}$F NMR (376 MHz, CHLOROFORM-d) δ −89.74 (s, 2F), −138.84 (s, 1F). LC-MS: method C, RT=2.40 min, MS (ESI) m/z: 448.0 (M+H)$^+$.

Example 259

To a suspension of Intermediate 259A (15 mg, 0.034 mmol) in THF (1 mL) was added NaOEt (52.6 µl, 20%, 0.134 mmol) dropwise. The mixture was stirred at room temperature overnight. Solvent was removed under vacuum and the crude residual was redissolved in EtOAc and 1N HCl, extracted with EtOAc, the combined organic layer was washed with saturated sodium bicarbonate, brine, dried over sodium sulfate and concentrated. The crude was dissolved in DMSO and purified via preparative LC/MS (Method D: Gradient: 50-100% B over 15 minutes, then a 5-minute hold at 100% B). Fractions containing the desired product were combined and dried via centrifugal evaporation to Example 259 (5.8 mg, 0.014 mmol, 40.7% yield). $^1$H NMR (500 MHz, DMSO-$d_6$) δ 8.62 (s, 1H), 8.46 (s, 1H), 7.79 (d, J=11.3 Hz, 1H), 7.72 (s, 1H), 4.66-4.58 (m, 1H), 4.48 (q, J=7.0 Hz, 2H), 3.85-3.74 (m, 1H), 3.73-3.66 (m, 1H), 3.63 (m, 1H), 2.57 (s, 3H), 1.45 (d, J=7.0 Hz, 3H), 1.41 (t, J=7.0 Hz, 3H). LC-MS: method L, RT=2.53 min, MS (ESI) m/z: 426.2 (M+H)$^+$. Analytical HPLC purity (method B): 100%.

Example 260

(S)-ethyl ((5-fluoro-2-(2-methoxy-7-methylquinoxalin-5-yl)-7,8-dihydrobenzofuro[5,4-d]thiazol-7-yl)methyl)carbamate

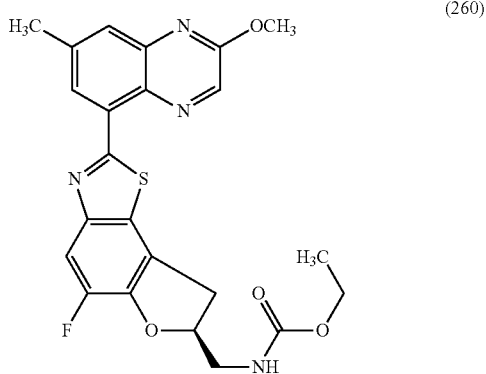 [SMILES: CCOC(=O)NC[C@@H]1Cc2c(c(F)cc3nc(-c4cc(C)cc5nc(OC)cnc45)sc23)O1]

(260)

To a solution of Intermediate 202B (15 mg, 0.036 mmol) in THF (1 mL) was added PMe₃ in toluene (0.053 mL, 1M, 0.053 mmol) dropwise. The mixture was stirred at room temperature for 30 min. TLC and LCMS indicated completion of the reduction. Ethyl chloroformate (7.81 mg, 0.072 mmol) was added to the mixture dropwise and the mixture was stirred at room temperature for 1 hour. The reaction was quenched with phosphate buffer (pH 7), extracted with EtOAc. The combined organic layer was washed with saturated sodium bicarbonate, brine, dried over sodium sulfate and concentrated. The crude was dissolved in DMSO and purified via preparative LC/MS (Method D: Gradient: 50-95% B over 20 minutes, then a 5-minute hold at 100% B). Fractions containing the desired product were combined and dried via centrifugal evaporation to Example 260 (4.9 mg, 10.15 μmol, 28.2% yield). ¹H NMR (500 MHz, DMSO-d₆) δ 8.74 (s, 1H), 8.57 (s, 1H), 7.92-7.80 (m, 2H), 7.46 (br. s., 1H), 5.16 (br. s., 1H), 4.07 (s, 3H), 4.00 (d, J=6.4 Hz, 2H), 3.57 (dd, J=16.2, 9.5 Hz, 1H), 3.41-3.22 (m, 3H), 2.62 (s, 3H), 1.14 (t, J=6.6 Hz, 3H). LC-MS: method L, RT=2.45 min, MS (ESI) m/z: 469.0 (M+H)⁺. Analytical HPLC purity (method B): 100%.

Example 261

(S)-neopentyl ((5-fluoro-2-(2-methoxy-7-methylquinoxalin-5-yl)-7,8-dihydrobenzofuro[5,4-d]thiazol-7-yl)methyl)carbamate

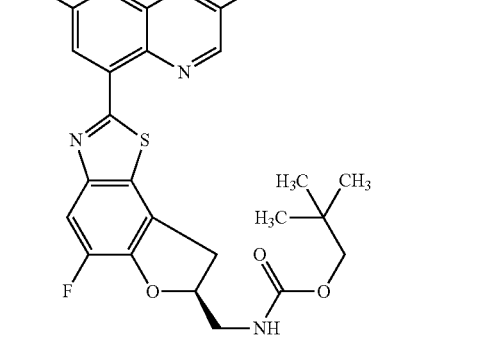

(261)

To a solution of Intermediate 202B (15 mg, 0.036 mmol) in THF (1 mL) was added PMe₃ in toluene (0.053 mL, 1M, 0.053 mmol) dropwise. The mixture was stirred at room temperature for 30 min. TLC and LCMS indicated completion of the reduction. Neopentyl chloroformate (10.84 mg, 0.072 mmol) was added to the mixture dropwise and the mixture was stirred at room temperature for 1 hour. The reaction was quenched with phosphate buffer (pH 7), extracted with EtOAc. The combined organic layer was washed with saturated sodium bicarbonate, brine, dried over sodium sulfate and concentrated. The crude was dissolved in DMSO and purified via preparative LC/MS (Method D: Gradient: 60-100% B over 20 minutes, then a 5-minute hold at 100% B). Fractions containing the desired product were combined and dried via centrifugal evaporation to Example 261 (5.2 mg, 10.18 μmol, 28.3% yield). ¹H NMR (500 MHz, DMSO-d₆) δ 8.69 (s, 1H), 8.53 (s, 1H), 7.82 (d, J=11.0 Hz, 1H), 7.79 (s, 1H), 7.49 (br. s., 1H), 5.25-5.08 (m, 1H), 4.06 (s, 3H), 3.67 (s, 2H), 3.59-3.51 (m, 1H), 3.43-3.30 (m, 2H), 3.24 (dd, J=15.9, 6.7 Hz, 1H), 2.60 (s, 3H), 0.86 (s, 9H). LC-MS: method L, RT=2.76 min, MS (ESI) m/z: 533.2 (M+Na)⁺. Analytical HPLC purity (method B): 100%.

Example 262

1-(2-(2-methoxy-7-methylquinoxalin-5-yl)-7,8-dihydro-[1,4]dioxino[2',3':3,4]benzo[1,2-d]thiazol-4-yl)-2,2-dimethylpropan-1-ol

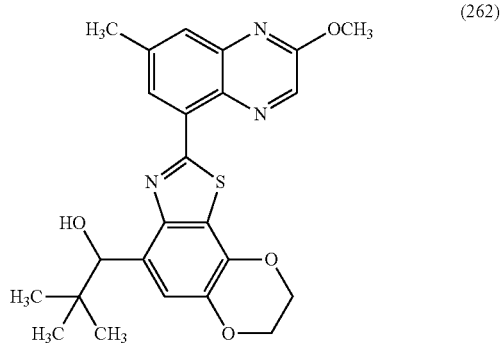 [SMILES: COc1cnc2c(-c3nc4c(C(O)C(C)(C)C)cc5c(c4s3)OCCO5)cc(C)cc2n1]

(262)

Intermediate 262A 1-(2-amino-7,8-dihydro-[1,4]dioxino[2',3':3,4]benzo[1,2-d]thiazol-4-yl)-2,2-dimethylpropan-1-ol

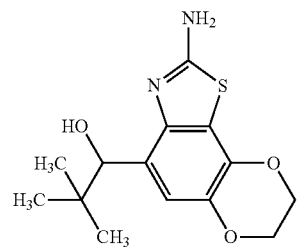

(262A)

Intermediate I-39 (50 mg, 0.174 mmol) was dissolved in THF (1.74 mL). Sodium hydride (7.66 mg, 0.192 mmol) was then added. After 15 minutes, the reaction mixture was cooled to −78° C. and BuLi (2.5 M in hexanes, 151 μL, 0.348 mmol) was added. After 30 minutes, pivalaldehyde (45.0 mg, 0.522 mmol) was added and the reaction mixture was allowed to warm to ambient temperature. After the reaction achieved ambient temperature, it was diluted with

443

EtOAc and washed with water, then brine, dried (Na$_2$SO$_4$), filtered, and concentrated in vacuo to give Intermediate 262A, which was used directly in the subsequent step: LC-MS: Method H, RT=0.74 min, MS (ESI) m/z: 295.2 (M+H)$^+$.

Intermediate 262B 1-(2-chloro-7,8-dihydro-[1,4]dioxino[2',3':3,4]benzo[1,2-d]thiazol-4-yl)-2,2-dimethylpropan-1-ol

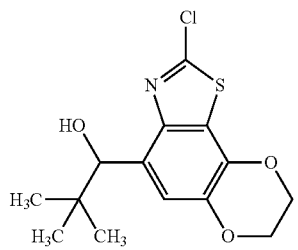

(262B)

Copper(II) chloride (32.6 mg, 0.243 mmol) and t-butyl nitrite (30.9 μL, 0.260 mmol) were dissolved in MeCN (693 μL) and allowed to stir 10 minutes. Intermediate 262A (51 mg, 0.173 mmol) was dissolved in MeCN (1.04 mL) and the copper solution was added to the mixture and heated to 60° C. After 2 hours, the reaction mixture was diluted with EtOAc, washed with 1 N HCl, saturated NaHCO$_3$, then brine, dried (Na$_2$SO$_4$), filtered, and concentrated in vacuo. The crude material was purified by column chromatography (ISCO, 12 g silica gel column, 19 minute gradient from 0 to 100% EtOAc in hexanes) to give Intermediate 262B (6.8 mg, 0.022 mmol, 12% over 2 steps): LC-MS: Method H, RT=1.15 min, MS (ESI) m/z: 314.0 (M+H)$^+$.

Example 262

Intermediate I-9 (7.81 mg, 0.026 mmol) and Intermediate 262B (6.8 mg, 0.022 mmol) were dissolved in DMF (217 μL). PdCl$_2$(dppf)—CH$_2$Cl$_2$ adduct (1.06 mg, 1.3 μmol) was added and the reaction degassed by bubbling with argon for 15 minutes. Sodium carbonate (2 M, 13.00 μL, 0.026 mmol) was added and the reaction degassed for 5 minutes, then sealed and heated to 100° C. in the microwave for 30 minutes. The reaction mixture was heated to 100° C. in the microwave for an additional 30 minutes. The crude material was purified by preparative HPLC (Method D, 50-100% B in 21 minutes) to give Example 262 (3.7 mg, 0.008 mmol, 37%): $^1$H NMR (500 MHz, DMSO-d$_6$) δ 8.81 (s, 1H), 8.59 (s, 1H), 7.88 (s, 1H), 7.14 (s, 1H), 5.41 (d, J=4.6 Hz, 1H), 5.28 (d, J=4.6 Hz, 1H), 4.58-4.38 (m, 4H), 4.14 (s, 3H), 3.43 (s, 3H), 2.70 (s, 3H), 1.00 (s, 9H); LC-MS: Method H, RT=1.34 min, MS (ESI) m/z: 452.2 (M+H)$^+$; Analytical HPLC Method B, 98% purity.

444

Example 263

1-(7-(2-methoxy-7-methylquinoxalin-5-yl)-[1,3]dioxolo[4',5':3,4]benzo[1,2-d]thiazol-5-yl)-2,2-dimethylpropan-1-ol

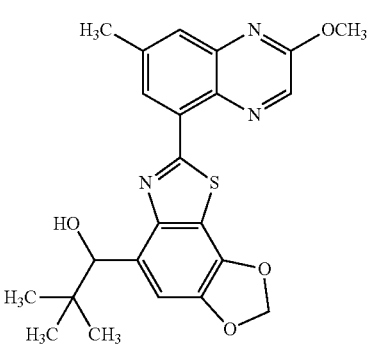

(263)

Intermediate 263A 1-(7-bromo-[1,3]dioxolo[4',5':3,4]benzo[1,2-d]thiazol-5-yl)-2,2-dimethylpropan-1-one

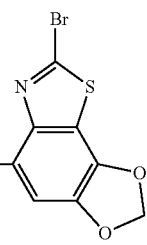

(263A)

Intermediate I-40 (50 mg, 0.151 mmol), Cs$_2$CO$_3$ (74.0 mg, 0.227 mmol), and bromochloromethane (29.4 mg, 0.227 mmol) were dissolved in DMF (1.51 mL) and heated to 110° C. After 2.5 hours, the reaction mixture was cooled to ambient temperature, diluted with EtOAc and washed with water, then brine, dried (Na$_2$SO$_4$), filtered, and concentrated in vacuo. The crude material was purified by column chromatography (ISCO, 4 g silica gel column, 15 minute gradient from 0 to 100% EtOAc in hexanes) to give Intermediate 263A (16.1 mg, 0.047 mmol, 31%) as a white solid: $^1$H NMR (400 MHz, CHLOROFORM-d) δ 6.92 (d, J=6.4 Hz, 1H), 6.17 (d, J=0.4 Hz, 2H), 1.32 (s, 9H); LC-MS: Method H, RT=1.17 min, MS (ESI) m/z: 342/344 (M+H)$^+$.

445

Intermediate 263B 1-(7-bromo-[1,3]dioxolo[4',5':3,4]benzo[1,2-d]thi-azol-5-yl)-2,2-dimethylpropan-1-ol

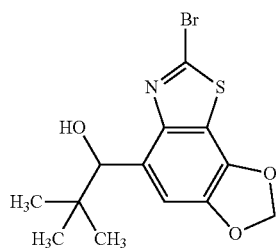

(263B)

Intermediate 263A (26 mg, 0.076 mmol) was dissolved in MeOH (1.52 mL) and cooled to 0° C. Sodium borohydride (8.62 mg, 0.228 mmol) was then added. After 30 minutes, the reaction mixture was diluted with EtOAc, washed with water then brine, dried ($Na_2SO_4$), filtered, and concentrated in vacuo to give Intermediate 263B (25 mg, 0.073 mmol, 96%), which was used directly in the subsequent reaction: LC-MS: Method H, RT=1.15 min, MS (ESI) m/z: 344/346 (M+H)$^+$.

Example 263

Intermediate I-9 (24 mg, 0.080 mmol) and Intermediate 263B (25 mg, 0.073 mmol) were dissolved in DMF (726 μL). $PdCl_2$(dppf)—$CH_2Cl_2$ adduct (3.56 mg, 4.36 μmol) was added and the reaction degassed by bubbling with argon for 15 minutes. $Na_2CO_3$ (2 M, 43.6 μL, 0.087 mmol) was added and the reaction degassed for 5 minutes, then sealed and heated to 100° C. in the microwave for 30 minutes. The reaction mixture was purified by preparative HPLC (Method D, 50-90% B in 20 minutes) to give Example 263 (14.2 mg, 0.031 mmol, 42%): $^1$H NMR (500 MHz, DMSO-d$_6$) δ 8.74 (s, 1H), 8.55 (s, 1H), 7.84 (s, 1H), 7.20 (s, 1H), 6.24 (s, 1H), 6.22 (s, 1H), 5.45 (d, J=4.6 Hz, 1H), 5.32 (d, J=4.6 Hz, 1H), 4.09 (s, 3H), 2.65 (s, 3H), 0.95 (s, 9H); LC-MS: Method H, RT=1.28 min, MS (ESI) m/z: 438.2 (M+H)$^+$; Analytical HPLC Method B, 95% purity.

Example 264

1-(2-(2-methoxy-7-methylquinoxalin-5-yl)-8,9-di-hydro-7H-[1,4]dioxepino[2',3':3,4]benzo[1,2-d]thiazol-4-yl)-2,2-dimethylpropan-1-ol

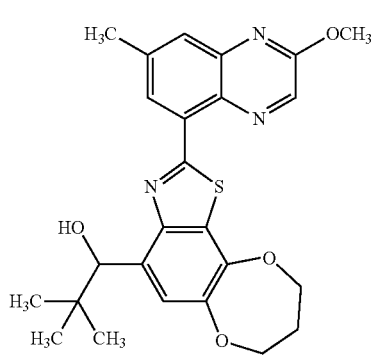

(264)

446

Intermediate 264A 1-(2-bromo-8,9-dihydro-7H-[1,4]dioxepino[2',3':3,4]benzo[1,2-d]thiazol-4-yl)-2,2-dimethylpropan-1-one

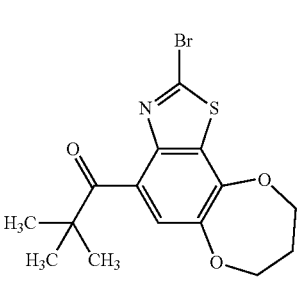

(264A)

Intermediate I-40 (50 mg, 0.151 mmol), $Cs_2CO_3$ (74.0 mg, 0.227 mmol), and 1,3-dibromopropane (45.9 mg, 0.227 mmol) were dissolved in DMF (1.51 mL) and heated to 70° C. After heating overnight, the reaction mixture was cooled to ambient temperature, diluted with EtOAc and washed with water, then brine, dried ($Na_2SO_4$), filtered, and concentrated in vacuo. The crude material was purified by column chromatography (ISCO, 12 g silica gel column, 17 minute gradient from 0 to 100% EtOAc in hexanes) to give Intermediate 264A (17.3 mg, 0.047 mmol, 31%) as a clear oil, which was used directly in the subsequent reaction: LC-MS: Method H, RT=1.20 min, MS (ESI) m/z: 370/372 (M+H)$^+$.

Intermediate 264B 1-(2-bromo-8,9-dihydro-7H-[1,4]dioxepino[2',3':3,4]benzo[1,2-d]thiazol-4-yl)-2,2-dimethylpropan-1-ol

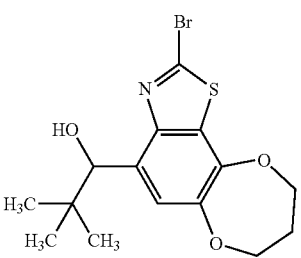

(264B)

Intermediate 264A (17.3 mg, 0.047 mmol) was dissolved in MeOH (934 μL) and cooled to 0° C. Sodium borohydride (5.30 mg, 0.140 mmol) was then added. After 1.5 hours, the reaction mixture was diluted with EtOAc, washed with water then brine, dried ($Na_2SO_4$), filtered, and concentrated in vacuo to give Intermediate 264B (19.5 mg, 0.052 mmol, 100%), which was used directly in the subsequent reaction: LC-MS: Method H, RT=1.19 min, MS (ESI) m/z: 372/374 (M+H)$^+$.

Example 264

Intermediate I-9 (16.45 mg, 0.055 mmol) and Intermediate 264B (17 mg, 0.046 mmol) were dissolved in DMF (457 μL). $PdCl_2$(dppf)—$CH_2Cl_2$ adduct (2.24 mg, 2.74 μmol) was added and the reaction degassed by bubbling with argon for 15 minutes. Na$_2$CO$_3$ (2 M, 27.4 μL, 0.055 mmol) was added and the reaction degassed for 5 minutes, then sealed and heated to 100° C. in the microwave for 30 minutes. The crude material was purified by preparative HPLC (Method D, 50-100% B in 15 minutes) to give Example 264 (10.7 mg, 0.022 mmol, 49%): LC-MS: Method H, RT=1.38 min, MS (ESI) m/z: 466.1 (M+H)$^+$; Analytical HPLC Method B, 97% purity.

Example 265

(2-(2-methoxy-7-methylquinoxalin-5-yl)-7,8-dihydro-[1,4]dioxino[2',3':3,4]benzo[1,2-d]t hiazol-4-yl)(1-(trifluoromethyl)cyclobutyl)methanol

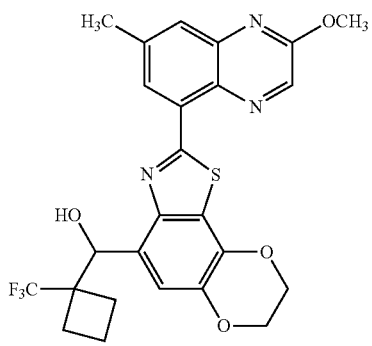

Intermediate 265A (2-amino-7,8-dihydro-[1,4]dioxino[2',3':3,4]benzo[1,2-d]thiazol-4-yl)(1-(trifluoromethyl) cyclobutyl) methanone NH$_2$

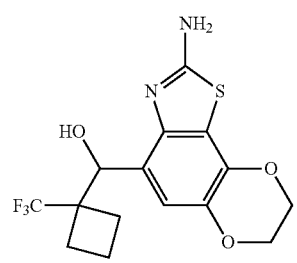

Intermediate I-39 (200 mg, 0.697 mmol) was dissolved in THF (6.97 mL). Sodium hydride (30.6 mg, 0.766 mmol) was added. After 30 minutes, the reaction mixture was cooled to −78° C. and tert-butyllithium (1.5 M in hexanes, 512 μL, 0.871 mmol) was added. After 1 hour, ethyl 1-(trifluoromethyl)cyclobutanecarboxylate (180 μL, 1.045 mmol) was added and the reaction mixture was removed from the cooling bath for 5 minutes and the reaction mixture was diluted with EtOAc and washed with water, then brine, dried (Na$_2$SO$_4$), filtered, and concentrated in vacuo to give Intermediate 265A, which was used directly in the subsequent step: LC-MS: Method H, RT=0.79 min, MS (ESI) m/z: 359.1 (M+H)$^+$.

Intermediate 265B (2-chloro-7,8-dihydro-[1,4]dioxino[2',3':3,4]benzo[1,2-d]thiazol-4-yl)(1-(trifluoromethyl) cyclobutyl) methanone

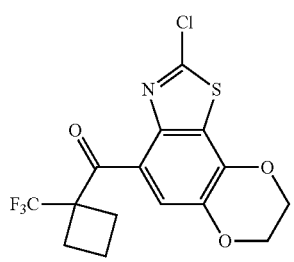

Intermediate 265A (250 mg, 0.698 mmol), copper(II) chloride (131 mg, 0.977 mmol), and t-butyl nitrite (124 μL, 1.05 mmol) were dissolved in MeCN (6.98 mL) and heated to 60° C. After 1.5 hours, the reaction mixture was diluted with EtOAc, washed with 1 N HCl, saturated NaHCO$_3$, then brine, dried (Na$_2$SO$_4$), filtered, and concentrated in vacuo. The crude material was purified by column chromatography (ISCO, 12 g silica gel column, 17 minute gradient from 0 to 100% EtOAc in hexanes) to give Intermediate 265B (32 mg, 0.085 mmol, 12% over 2 steps) as a white solid: $^1$H NMR (400 MHz, CHLOROFORM-d) δ 7.30 (s, 1H), 4.53-4.45 (m, 2H), 4.43-4.37 (m, 2H), 2.99-2.86 (m, 2H), 2.73-2.61 (m, 2H), 2.21-2.10 (m, 1H), 2.00-1.85 (m, 1H); LC-MS: Method H, RT=1.18 min, MS (ESI) m/z: 378.1 (M+H)$^+$.

Intermediate 265C (2-chloro-7,8-dihydro-[1,4]dioxino[2',3':3,4]benzo[1,2-d]thiazol-4-yl)(1-(trifluoromethyl) cyclobutyl) methanol

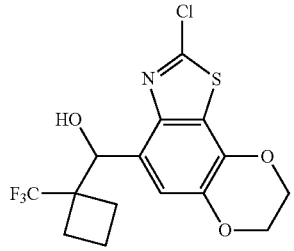

Intermediate 265B (52 mg, 0.138 mmol) was dissolved in MeOH (2.75 mL) and cooled to 0° C. Sodium borohydride (15.6 mg, 0.413 mmol) was then added. After 2 hours, the reaction mixture was diluted with EtOAc, washed with water then brine, dried (Na$_2$SO$_4$), filtered, and concentrated in vacuo. The crude material was purified by chiral SFC (Chiralcel AS-H, 21×250 mm, 5 micron; 15% MeOH/85% CO$_2$, 45 mL/min, 150 Bar, 40° C.) to give Intermediate 265C (peak 1, RT=5.0 min, 19.4 mg, 0.051 mmol, 37%, >99% ee) as a clear oil: $^1$H NMR (400 MHz, CHLOROFORM-d) δ 7.09 (s, 1H), 5.30 (d, J=8.1 Hz, 1H), 4.47-4.41 (m, 2H), 4.40-4.34 (m, 2H), 3.99 (d, J=8.1 Hz, 1H), 2.68-

2.55 (m, 1H), 2.37-2.14 (m, 3H), 1.99-1.85 (m, 1H), 1.69-1.58 (m, 1H); LC-MS: Method H, RT=1.15 min, MS (ESI) m/z: 380.0 (M+H)⁺.

Example 265

Intermediate I-9 (15.3 mg, 0.051 mmol) and Intermediate 265C (19.4 mg, 0.051 mmol) were dissolved in DMF (511 μL). PdCl₂(dppf)—CH₂Cl₂ adduct (2.5 mg, 3.06 μmol) was added and the reaction degassed by bubbling with argon for 15 minutes. Na₂CO₃ (2 M, 30.6 μL, 0.061 mmol) was added and the reaction degassed for 5 minutes, then sealed and heated to 100° C. in the microwave for 30 minutes. The reaction mixture was diluted with EtOAc, washed with water then brine, dried (Na₂SO₄), filtered, and concentrated in vacuo. The crude material was purified by column chromatography (ISCO, 12 g silica gel column, 17 minute gradient from 0 to 100% EtOAc in hexanes) to give Example 265 (12.4 mg, 0.023 mmol, 46%) as a yellow solid: ¹H NMR (500 MHz, CHLOROFORM-d) δ 8.58 (s, 1H), 8.51 (d, J=1.7 Hz, 1H), 7.79 (dd, J=1.8, 1.0 Hz, 1H), 7.03 (s, 1H), 5.60 (d, J=9.1 Hz, 1H), 5.34 (d, J=9.1 Hz, 1H), 4.53-4.48 (m, 2H), 4.42 (q, J=3.9 Hz, 2H), 4.16 (s, 3H), 2.72 (d, J=6.6 Hz, 1H), 2.68 (s, 3H), 2.44-2.31 (m, 2H), 2.29-2.21 (m, 1H), 1.91 (d, J=11.0 Hz, 1H), 1.67-1.61 (m, 1H); LC-MS: Method H, RT=1.35 min, MS (ESI) m/z: 518.0 (M+H)⁺; Analytical HPLC Method A, 97.8% purity.

Example 266

(R)-(2-(6-chloro-3-methoxyquinolin-8-yl)-7,8-dihydro-[1,4]dioxino[2',3':3,4]benzo[1,2-d]thiazol-7-yl)methyl (2-methylpyrimidin-5-yl)carbamate

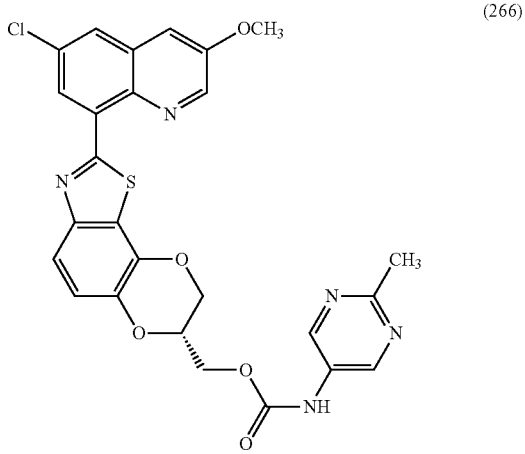 [SMILES: COc1cnc2c(-c3nc4ccc5c(c4s3)OC[C@H](COC(=O)Nc3cnc(C)nc3)O5)cc(Cl)cc2c1]

(266)

Intermediate I-41 (15 mg, 0.047 mmol), Intermediate I-42 (18.4 mg, 0.047 mmol) and PdCl₂(dppf) (2.06 mg, 2.82 μmol) were dissolved in 1,4-dioxane (469 μL) and Na₂CO₃ (2 M, 211 μL, 0.422 mmol) and heated to 100° C. After 1 hour, the reaction mixture was cooled to ambient temperature, diluted with EtOAc, washed with water, then brine, dried (Na₂SO₄), filtered, and concentrated in vacuo. The crude material was purified by preparative HPLC (Method D, 45-85% B in 20 minutes) to give Example 266 (5.5 mg, 0.010 mmol, 21%): ¹H NMR (500 MHz, DMSO-d₆) δ 10.17 (br. s., 1H), 8.90 (br. s., 1H), 8.76 (br. s., 2H), 8.63 (br. s., 1H), 8.19 (br. s., 1H), 7.93 (br. s., 1H), 7.68 (d, J=8.5 Hz, 1H), 7.18 (d, J=8.5 Hz, 1H), 4.65 (d, J=12.5 Hz, 2H), 4.55-4.43 (m, 2H), 4.37-4.29 (m, 1H), 4.00 (s, 3H), 3.58 (s, 3H); LC-MS: Method H, RT=1.22 min, MS (ESI) m/z: 550.1 (M+H)⁺; Analytical HPLC Method B, 100% purity.

Example 267

(R)-(2-(6-chloro-3-methoxyquinolin-8-yl)-5-fluoro-7,8-dihydrobenzofuro[5,4-d]thiazol-7-yl)methyl (2-methylpyrimidin-5-yl)carbamate

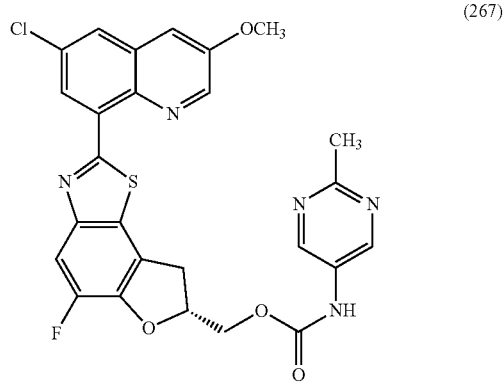 [SMILES: COc1cnc2c(-c3nc4cc(F)c5c(c4s3)C[C@H](COC(=O)Nc3cnc(C)nc3)O5)cc(Cl)cc2c1]

(267)

Intermediate I-41 (15 mg, 0.047 mmol), Intermediate I-45 (18.53 mg, 0.047 mmol) and PdCl₂(dppf) (2.06 mg, 2.82 μmol) were dissolved in 1,4-dioxane (469 μL) and Na₂CO₃ (2 M, 211 μL, 0.422 mmol) and heated to 100° C. After 1 hour, the reaction mixture was cooled to ambient temperature, diluted with EtOAc, washed with water, then brine, dried (Na₂SO₄), filtered, and concentrated in vacuo. The crude material was purified by preparative HPLC (Method D, 0-100% B in 3 minutes) to give Example 267 (3.8 mg, 0.0066 mmol, 14%): ¹H NMR (500 MHz, DMSO-d₆) δ 10.11 (br. s., 1H), 8.92 (br. s., 1H), 8.75 (br. s., 2H), 8.65 (br. s., 1H), 8.22 (br. s., 1H), 7.96 (br. s., 1H), 7.92 (d, J=10.1 Hz, 1H), 5.44 (br. s., 1H), 4.56 (d, J=12.2 Hz, 1H), 4.43 (br. s., 1H), 4.00 (br. s., 3H), 3.73-3.65 (m, 2H); LC-MS: Method H, RT=1.22 min, MS (ESI) m/z: 552.0 (M+H)⁺; Analytical HPLC Method B, 96% purity.

Example 268

(R)-(2-(3-methoxy-6-methylquinolin-8-yl)-7,8-dihydro-[1,4]dioxino[2',3':3,4]benzo[1,2-d]thiazol-7-yl)methyl (2-methylpyrimidin-5-yl)carbamate

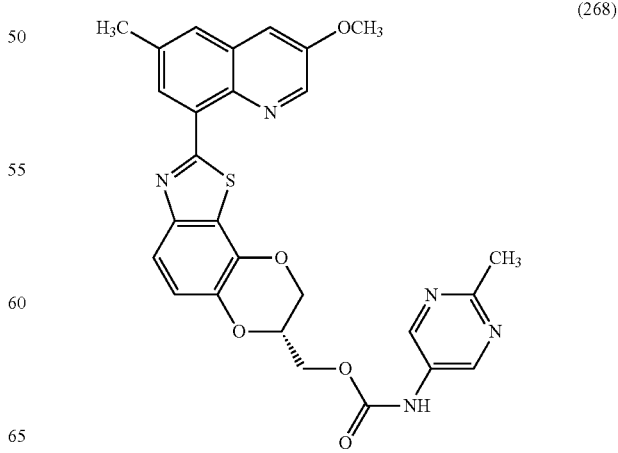

(268)

Intermediate I-46 (15 mg, 0.050 mmol), Intermediate I-42 (19.7 mg, 0.050 mmol) and PdCl$_2$(dppf) (2.2 mg, 3.01 µmol) were dissolved in 1,4-dioxane (501 µL) and Na$_2$CO$_3$ (2 M, 226 µL, 0.451 mmol) and heated to 100° C. After 1 hour, the reaction mixture was cooled to ambient temperature and the solvent removed in vacuo. The crude material was purified by preparative HPLC (Method D, 20-60% B in 15 minutes) to give Example 268 (10.5 mg, 0.019 mmol, 38.4%): $^1$H NMR (500 MHz, DMSO-d$_6$) δ 10.18 (br. s., 1H), 8.82 (br. s., 1H), 8.76 (br. s., 2H), 8.60 (s, 1H), 7.86 (d, J=8.5 Hz, 2H), 7.64 (d, J=8.5 Hz, 1H), 7.15 (d, J=8.5 Hz, 1H), 4.64 (d, J=11.6 Hz, 2H), 4.55-4.41 (m, 2H), 4.31 (dd, J=11.0, 7.3 Hz, 1H), 3.98 (s, 3H), 2.60 (s, 3H), 2.56 (br. s., 3H); LC-MS: Method H, RT=1.24 min, MS (ESI) m/z: 530.1 (M+H)$^+$; Analytical IPLC Method B, 97% purity.

Example 269

(R)-(5-fluoro-2-(3-methoxy-6-methylquinolin-8-yl)-7,8-dihydrobenzofuro[5,4-d]thiazol-7-yl)methyl (2-methylpyrimidin-5-yl)carbamate

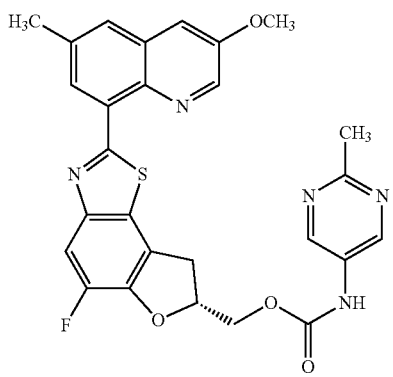

(269)

Intermediate I-46 (15 mg, 0.050 mmol), Intermediate I-45 (19.8 mg, 0.050 mmol) and PdCl$_2$(dppf) (2.2 mg, 3.01 µmol) were dissolved in 1,4-dioxane (501 µL) and Na$_2$CO$_3$ (2 M, 226 µL, 0.451 mmol) and heated to 100° C. After 1 hour, the reaction mixture was cooled to ambient temperature and concentrated in vacuo. The crude material was purified by preparative HPLC (Method D, 45-90% B in 19 minutes) to give Example 269 (7.5 mg, 0.013 mmol, 27%): LC-MS: Method H, RT=1.25 min, MS (ESI) m/z: 532.2 (M+H)$^+$; Analytical HPLC Method B, 98% purity.

Example 270

(R)-(2-(6-chloro-3-ethoxyquinolin-8-yl)-5-fluoro-7,8-dihydrobenzofuro[5,4-d]thiazol-7-y 1)methyl (2-methylpyrimidin-5-yl)carbamate

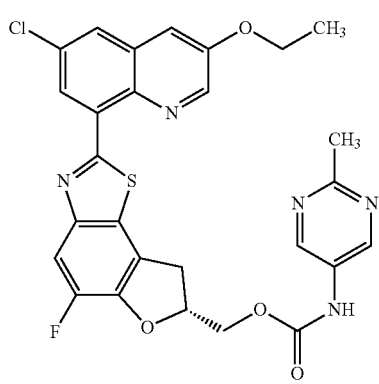

(270)

Intermediate I-48 (15 mg, 0.045 mmol), Intermediate I-45 (17.8 mg, 0.045 mmol) and PdCl$_2$(dppf) (1.97 mg, 2.70 µmol) were dissolved in 1,4-dioxane (450 µL) and Na$_2$CO$_3$ (2 M, 202 µL, 0.405 mmol) and heated to 100° C. After 1 hour, the reaction mixture was cooled to ambient temperature and concentrated in vacuo. The crude material was purified by preparative HPLC (Method D, 50-100% B in 20 minutes) to give Example 270 (5.2 mg, 0.009 mmol, 20%): $^1$H NMR (500 MHz, DMSO-d$_6$) δ 10.04 (br. s., 1H), 8.80 (br. s., 1H), 8.67 (br. s., 2H), 8.55 (s, 1H), 8.10 (s, 1H), 7.90-7.77 (m, 2H), 5.37 (d, J=7.3 Hz, 1H), 4.48 (d, J=12.2 Hz, 1H), 4.35 (dd, J=12.1, 6.6 Hz, 1H), 4.19 (q, J=6.6 Hz, 2H), 3.61 (dd, J=15.7, 9.9 Hz, 1H), 2.48 (s, 3H), 1.39 (t, J=6.7 Hz, 3H) (One peak buried under solvent); LC-MS: Method H, compound did not ionize; Analytical HPLC Method B, 98% purity.

Example 271

(R)-(2-(6-chloro-3-ethoxyquinolin-8-yl)-7,8-dihydro-[1,4]dioxino[2',3':3,4]benzo[1,2-d]th iazol-7-yl)methyl (2-methylpyrimidin-5-yl)carbamate

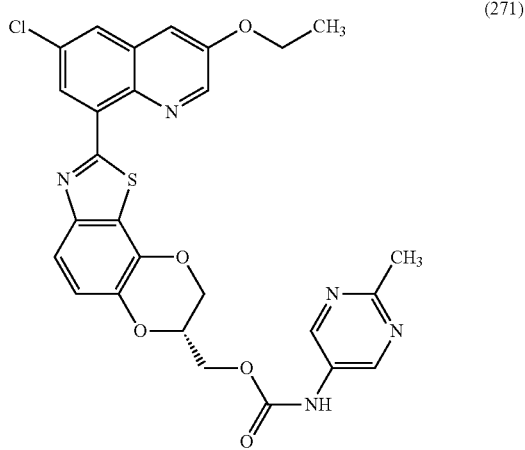 [SMILES: CCOc1cnc2c(-c3nc4ccc5c(c4s3)OC[C@H](COC(=O)Nc3cnc(C)nc3)O5)cc(Cl)cc2c1]

(271)

Intermediate I-48 (15 mg, 0.045 mmol), Intermediate I-42 (17.7 mg, 0.045 mmol) and PdCl$_2$(dppf) (1.97 mg, 2.70 µmol) were dissolved in 1,4-dioxane (450 µL) and Na$_2$CO$_3$ (2 M, 202 µL, 0.405 mmol) and heated to 100° C. After 1 hour, the reaction mixture was cooled to ambient temperature and concentrated in vacuo. The crude material was purified by preparative HPLC (Method D, 50-100% B in 20 minutes) then repurified by preparative HPLC (Method D, 45-90% B in 20 minutes) to give Example 271 (3.2 mg, 0.0056 mmol, 12%): $^1$H NMR (500 MHz, DMSO-d$_6$) δ 10.18 (br. s., 1H), 8.89 (br. s., 1H), 8.77 (br. s., 2H), 8.63 (br. s., 1H), 8.17 (br. s., 1H), 7.92 (br. s., 1H), 7.67 (d, J=8.5 Hz, 1H), 7.18 (d, J=8.5 Hz, 1H), 4.66 (d, J=12.2 Hz, 2H), 4.56-4.42 (m, 2H), 4.36-4.22 (m, 3H), 2.55 (d, J=3.7 Hz, 3H), 1.47 (t, J=6.4 Hz, 3H); LC-MS: Method H, RT=1.09 min, MS (ESI) m/z: 564.4 (M+H)$^+$; Analytical HPLC Method B, 98% purity.

Example 272

(R)-(2-(6-chloro-3-(difluoromethoxy)quinolin-8-yl)-7,8-dihydro-[1,4]dioxino[2',3':3,4]benzo[1,2-d]thiazol-7-yl)methyl (2-methylpyrimidin-5-yl)carbamate

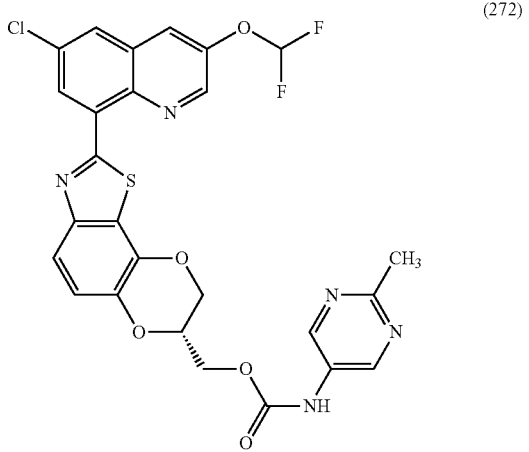 [SMILES: Cc1ncc(NC(=O)OC[C@H]2COc3c(ccc4nc(-c5cc(Cl)cc6cc(OC(F)F)cnc56)sc34)O2)cn1]
(272)

Intermediate I-49 (15 mg, 0.042 mmol), Intermediate I-42 (16.6 mg, 0.042 mmol) and PdCl$_2$(dppf) (1.85 mg, 2.53 µmol) were dissolved in 1,4-dioxane (422 µL) and Na$_2$CO$_3$ (190 µL, 0.380 mmol) and heated to 100° C. After 1 hour, the reaction mixture was cooled to ambient temperature and concentrated in vacuo. The crude material was purified by preparative HPLC (Method D, 45-90% B in 20 minutes) to give Example 272 (3.1 mg, 0.0053 mmol, 12%): $^1$H NMR (500 MHz, DMSO-d$_6$) δ 10.18 (br. s., 1H), 9.10 (br. s., 1H), 8.77 (d, J=9.5 Hz, 3H), 8.35 (br. s., 2H), 7.69 (d, J=8.5 Hz, 1H), 7.66-7.33 (m, 1H), 7.20 (d, J=8.2 Hz, 1H), 4.66 (d, J=12.2 Hz, 2H), 4.56-4.42 (m, 2H), 4.33 (t, J=9.0 Hz, 1H), 2.55 (br. s., 3H); LC-MS: Method H, RT=1.11 min, MS (ESI) m/z: 586.1 (M+H)$^+$; Analytical HPLC Method B, 100% purity.

Example 273

(R)-(2-(6-chloro-3-(difluoromethoxy)quinolin-8-yl)-5-fluoro-7,8-dihydrobenzofuro[5,4-d]thiazol-7-yl)methyl (2-methylpyrimidin-5-yl)carbamate

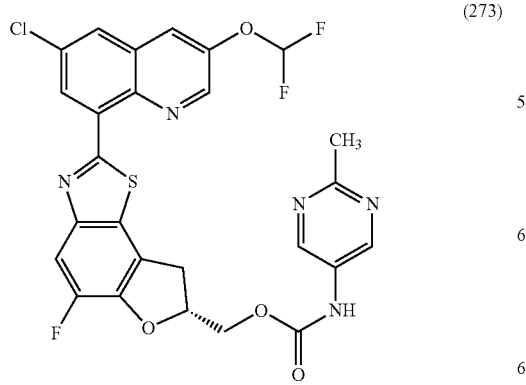
(273)

Intermediate I-49 (15 mg, 0.042 mmol), Intermediate I-45 (16.7 mg, 0.042 mmol) and PdCl$_2$(dppf) (1.85 mg, 2.53 µmol) were dissolved in 1,4-dioxane (422 µL) and Na$_2$CO$_3$ (2 M, 190 µL, 0.380 mmol) and heated to 100° C. After 1 hour, the reaction mixture was cooled to ambient temperature and concentrated in vacuo. The crude material was purified by preparative HPLC (Method D, 30-90% B in 20 minutes) to give Example 273 (4.3 mg, 0.0073 mmol, 17%): LC-MS: Method H, RT=1.10 min, MS (ESI) m/z: 588.0 (M+H)$^+$; Analytical HPLC Method B, 100% purity.

Example 274

1-(2-(6-chloro-3-methoxyquinolin-8-yl)-7,8-dihydro-[1,4]dioxino[2',3':3,4]benzo[1,2-d]thiazol-4-yl)-2,2-dimethylpropan-1-ol

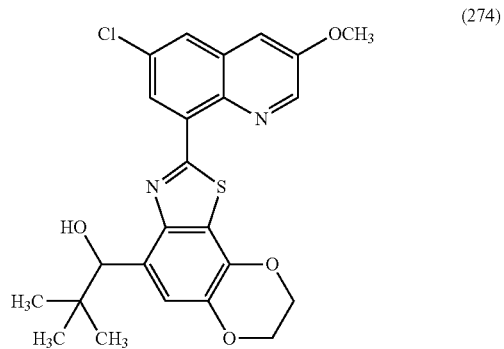 [SMILES: COc1cnc2c(-c3nc4c(C(O)C(C)(C)C)cc5c(c4s3)OCCO5)cc(Cl)cc2c1]
(274)

Intermediate 274A 1-(2-chloro-7,8-dihydro-[1,4]dioxino[2',3':3,4]benzo[1,2-d]thiazol-4-yl)-2,2-dimethylpropan-1-ol

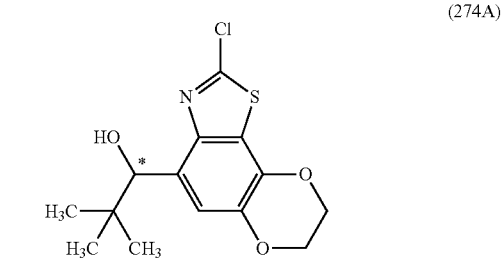 [SMILES: CC(C)(C)C(O)c1cc2c(c3sc(Cl)nc13)OCCO2]
(274A)

Intermediate 262B (145 mg, 0.462 mmol) was purified by preparative chiral IPLC (Chiralpak AD, 16% EtOH/MeOH (50/50) in heptanes) to give Intermediate 274A (peak 2, enantiomer 2, 42.3 mg, 0.135 mmol, 29.2%) as a clear oil ($^1$H NMR and LCMS identical to Intermediate 262B).

Example 274

Intermediate I-41 (15 mg, 0.047 mmol), Intermediate 274A (14.7 mg, 0.047 mmol) and PdCl₂(dppf) (2.06 mg, 2.82 μmol) were dissolved in 1,4-dioxane (469 μL) and Na₂CO₃ (2 M, 211 μL, 0.422 mmol) and heated to 100° C. After 1 hour, the reaction mixture was cooled to ambient temperature and concentrated in vacuo. The crude material was purified by preparative IPLC (Method D, 60-100% B in 22 minutes) to give Example 274 (5.9 mg, 0.013 mmol, 27%): ¹H NMR (500 MHz, DMSO-d₆) δ 8.93 (d, J=2.7 Hz, 1H), 8.61 (d, J=2.1 Hz, 1H), 8.21 (d, J=2.1 Hz, 1H), 7.95 (d, J=2.7 Hz, 1H), 7.10 (s, 1H), 5.35 (d, J=4.6 Hz, 1H), 5.23 (d, J=4.6 Hz, 1H), 4.51-4.34 (m, 4H), 4.01 (s, 3H), 0.99-0.88 (m, 9H); LC-MS: Method H, RT=1.32 min, MS (ESI) m/z: 471.1 (M+H)⁺; Analytical IPLC Method B, 100% purity.

Example 275

(R)-(2-(6-(difluoromethyl)-3-methoxyquinolin-8-yl)-7,8-dihydro-[1,4]dioxino [2',3':3,4]benzo[1,2-d]thiazol-7-yl)methyl (2-methylpyrimidin-5-yl)carbamate

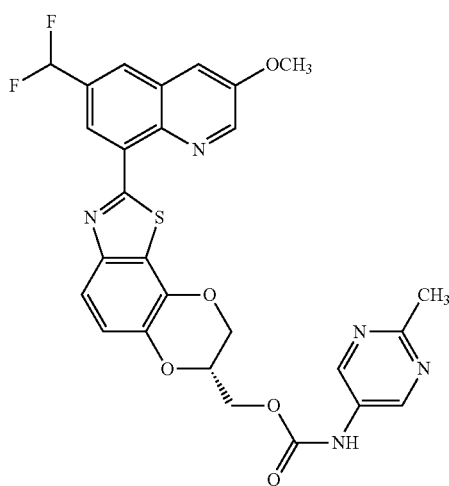

(275)

Intermediate I-50 (17 mg, 0.051 mmol), Intermediate I-42 (19.9 mg, 0.051 mmol) and PdCl₂(dppf) (2.23 mg, 3.04 μmol) were dissolved in 1,4-dioxane (507 μL) and Na₂CO₃ (2 M, 228 μL, 0.457 mmol) and heated to 100° C. After 1 hour, the reaction mixture was cooled to ambient temperature and concentrated in vacuo. The crude material was purified by preparative HPLC (Method D, 40-80% B in 20 minutes) then repurified by preparative HPLC (Method D, 40-80% B in 20 minutes) to give Example 275 (0.5 mg, 0.0008 mmol, 1.6%): ¹H NMR (500 MHz, DMSO-d₆) δ 10.21 (br. s., 1H), 9.01 (br. s., 1H), 8.88 (s, 1H), 8.78 (br. s., 2H), 8.35 (s, 1H), 8.13 (br. s., 1H), 7.70 (d, J=8.9 Hz, 1H), 7.54-7.28 (m, 1H), 7.19 (d, J=8.9 Hz, 1H), 4.67 (d, J=11.3 Hz, 2H), 4.58-4.42 (m, 2H), 4.34 (dd, J=11.3, 7.3 Hz, 1H), 4.03 (s, 3H), 2.57-2.54 (s, 3H); LC-MS: Compound did not ionize; Analytical HPLC Method B, 94% purity.

Example 276

(R)-(2-(6-(fluoromethyl)-3-methoxyquinolin-8-yl)-7,8-dihydro-[1,4]dioxino[2',3':3,4]benzo[1,2-d]thiazol-7-yl)methyl (2-methylpyrimidin-5-yl)carbamate

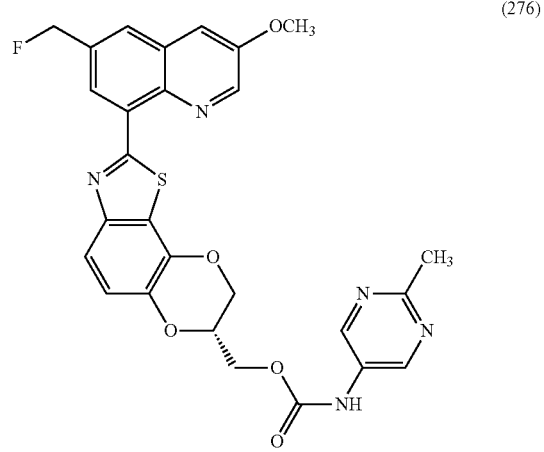 [SMILES: COc1cnc2c(-c3nc4ccc5c(c4s3)OC[C@H](COC(=O)Nc3cnc(C)nc3)O5)cc(CF)cc2c1]

(276)

Intermediate I-51 (12 mg, 0.038 mmol), Intermediate I-42 (14.9 mg, 0.038 mmol) and PdCl₂(dppf) (1.66 mg, 2.27 μmol) were dissolved in 1,4-dioxane (378 μL) and Na₂CO₃ (2 M, 170 μL, 0.341 mmol) and heated to 100° C. After 1 hour, the reaction mixture was cooled to ambient temperature and concentrated in vacuo. The crude material was purified by preparative HPLC (Method D, 30-70% B in 20 minutes) to give Example 276 (0.6 mg, 0.001 mmol, 2.8%): ¹H NMR (500 MHz, DMSO-d₆) δ 10.20 (br. s., 1H), 8.88 (d, J=2.7 Hz, 1H), 8.77 (d, J=7.9 Hz, 3H), 8.02 (s, 1H), 7.97 (d, J=2.7 Hz, 1H), 7.66 (d, J=8.9 Hz, 1H), 7.27-7.01 (m, 3H), 4.66 (d, J=11.0 Hz, 2H), 4.57-4.43 (m, 2H), 4.33 (dd, J=11.3, 7.3 Hz, 1H), 4.01 (s, 3H), 2.56 (s, 3H); LC-MS: Compound did not ionize; Analytical HPLC Method B, 95% purity.

Example 277

1-(2-(2-methoxy-7-methylquinoxalin-5-yl)-7,8-dihydro-[1,4]dioxino[2',3':3,4]benzo[1,2-d]thiazol-4-yl)-2,2-dimethylpropan-1-ol

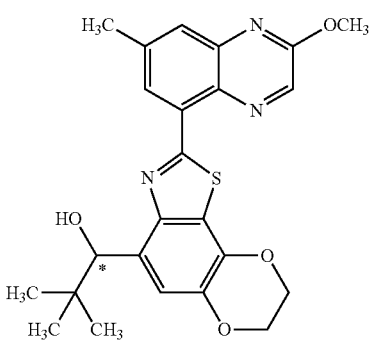

(277)

Example 262 (0.027 g, 0.089 mmol) was further purified 12% MeOH/88% CO₂ in a 30 min run, Chiralpak IB, 30×250 mm, 5 micron column, flow rate 85 mL/min, 150 Bar, 40° C. and UV detection was set to 220 nm to yield Example 277 (0.0036 g, 7.57 μmol, 8.49% yield): $^1$H NMR (400 MHz, CHLOROFORM-d) δ 8.55 (s, 1H), 8.49 (s, 1H), 7.76 (s, 1H), 6.89 (s, 1H), 5.56 (d, J=9.5 Hz, 1H), 4.73 (d, J=8.8 Hz, 1H), 4.46 (d, J=4.2 Hz, 2H), 4.38 (d, J=3.7 Hz, 2H), 4.13 (s, 3H), 2.66 (s, 3H), 1.03 (s, 9H). LC-MS: method H, RT=1.08 min, MS (ESI) m/z: 452.2 (M+H)$^+$. Analytical HPLC Method B: 95% purity.

Example 278

(2-(2-methoxy-7-methylquinoxalin-5-yl)-7,8-dihydro-[1,4]dioxino[2',3':3,4]benzo[1,2-d]t hiazol-4-yl)(1-methylcyclohexyl)methanol

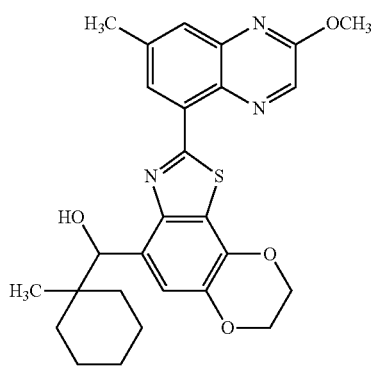

(278)

Intermediate 278A (2-amino-7,8-dihydro-[1,4]dioxino[2',3':3,4]benzo[1,2-d]thiazol-4-yl)(1-methylcyclohexy 1)methanol

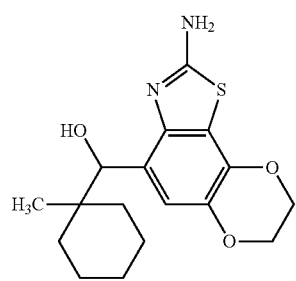

(278A)

Intermediate I-39 (200 mg, 0.697 mmol) was dissolved in THF (6965 μl). NaH (30.6 mg, 0.766 mmol) was added, and the reaction mixture was stirred for 30 min. The reaction mixture was cooled to −78° C. and BuLi (363 μl, 0.836 mmol) was added, and the reaction mixture was allowed to stir for 30 min. 1-methylcyclohexanecarbaldehyde (88 mg, 0.697 mmol) was added, and the reaction mixture was allowed to warm to ambient temperature. Reaction mixture was stirred for 10 min and diluted with water and EtOAc. The layers were separated and the aqueous layer was back extracted with EtOAc. The combined organic layer was washed with water, dried with sodium sulfate, and concentrated under reduced pressure to yield Intermediate 278A (0.230 g, 0.172 mmol, 25%). Will be used without further purification. LC-MS: method H, RT=0.74 min, MS (ESI) m/z: 335.3 (M+H)$^+$.

Intermediate 278B (2-chloro-7,8-dihydro-[1,4]dioxino[2',3':3,4]benzo[1,2-d]thiazol-4-yl)(1-methylcyclohexy l)methanol

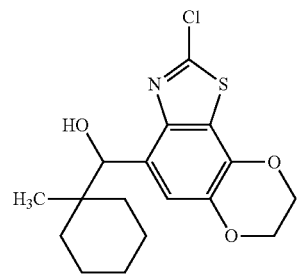

(278B)

Copper(II) chloride (0.157 g, 1.169 mmol) and t-butyl nitrite (0.139 ml, 1.169 mmol) were dissolved in MeCN (2.75 ml) and allowed to stir 10 minutes. Intermediate 278A (0.230 g, 0.688 mmol) was dissolved in MeCN (4.13 ml) and the copper solution was added. The reaction mixture was stirred for 2.5 hours at 60° C. The reaction mixture was diluted with EtOAc, washed with 1 N HCl, washed with saturated NaHCO$_3$, washed with brine, dried with sodium sulfate, filtered, and concentrated in vacuo to yield Intermediate 278B (0.049 g, 0.097 mmol, 14.09% yield). Will be used without further purification in the next step. LC-MS: method H, RT=1.28 min, MS (ESI) m/z: 354.2 (M+H)$^+$.

Example 278

Intermediate I-9 (0.021 g, 0.071 mmol) and Intermediate 278B (0.025 g, 0.071 mmol) were dissolved in DMF (0.706 ml). PdCl$_2$(dppf)—CH$_2$Cl$_2$ adduct (3.46 mg, 4.24 μmol) was added and the reaction degassed by bubbling with argon for 15 minutes. Na$_2$CO$_3$, 3 M aq. soln (0.024 ml, 0.071 mmol) was added and the reaction degassed for 5 minutes, then sealed and heated to 90° C. in the microwave for 30 minutes. The reaction mixture was concentrated, redissolved in DMF, filtered, and purified by preparative HPLC (Method D, 50 to 100% B in 12 minutes, then 25 minute hold time) to yield Example 278 (0.00134 g, 2.73 μmol, 3.86% yield): $^1$H NMR (500 MHz, DMSO-d$_6$) δ 8.76 (s, 1H), 8.54 (d, J=1.9 Hz, 1H), 7.84 (s, 1H), 7.08 (s, 1H), 5.39 (d, J=5.0 Hz, 1H), 5.15 (d, J=4.7 Hz, 1H), 4.49-4.32 (m, 4H), 4.09 (s, 3H), 2.64 (s, 3H), 1.67-1.46 (m, 5H), 1.44-1.01 (m, 6H), 0.89 (s, 3H). LC-MS: method H, RT=1.44 min, MS (ESI) m/z: 492.1 (M+H)$^+$. Analytical HPLC Method B: 100% purity.

Example 279

(2-(2-methoxy-7-methylquinoxalin-5-yl)-7,8-di-hydro-[1,4]dioxino[2',3':3,4]benzo[1,2-d]thiazol-4-yl)(1-(trifluoromethyl)cyclopropyl)methanol

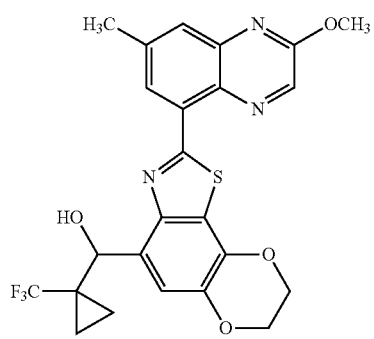

(279)

Intermediate 279A (2-amino-7,8-dihydro-[1,4]dioxino[2',3':3,4]benzo[1,2-d]thiazol-4-yl)(1-(trifluoromethyl) cyclopropyl) methanone

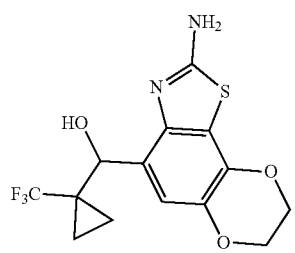

(279A)

Intermediate I-39 (200 mg, 0.697 mmol) was dissolved in THF (6965 μl). NaH (30.6 mg, 0.766 mmol) was added, and the reaction mixture was stirred for 30 min. The reaction mixture was cooled to −78° C. and BuLi (363 μl, 0.836 mmol) was added, and the reaction mixture was allowed to stir for 30 min. methyl 1-(trifluoromethyl)cyclopropanecarboxylate (117 mg, 0.697 mmol) was added and the reaction mixture was allowed to warm to ambient temperature. Reaction mixture was stirred for 10 min and diluted with water and EtOAc. The layers were separated and the aqueous layer was back extracted with EtOAc. The combined organic layer was washed with water, dried with sodium sulfate, and concentrated under reduced pressure to yield Intermediate 279A (0.240 g, 0.314 mmol, 45%). Will be used without further purification. LC-MS: method H, RT=0.75 min, MS (ESI) m/z: 345.1 (M+H)+.

Intermediate 279B (2-chloro-7,8-dihydro-[1,4]dioxino[2',3':3,4]benzo[1,2-d]thiazol-4-yl)(1-(trifluoromethyl) cyclopropyl) methanone

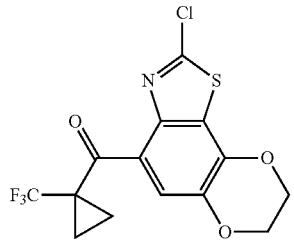

(279B)

Copper(II) chloride (0.159 g, 1.185 mmol) and t-butyl nitrite (0.141 ml, 1.185 mmol) were dissolved in MeCN (2.79 ml) and allowed to stir 10 minutes. Intermediate 279A (0.240 g, 0.697 mmol) was dissolved in MeCN (4.18 ml) and the copper solution was added. The reaction mixture was stirred for 2.5 hours at 60° C. The reaction mixture was diluted with EtOAc, washed with 1 N HCl, saturated NaHCO₃, then brine, dried (Na₂SO₄), filtered, and concentrated in vacuo to yield Intermediate 279B (0.0635 g, 0.087 mmol, 12.52% yield). Will be used without further purification in the next step. LC-MS: method H, RT=1.12 min, MS (ESI) m/z: 364.0 (M+H)+.

Intermediate 279C (2-chloro-7,8-dihydro-[1,4]dioxino[2',3':3,4]benzo[1,2-d]thiazol-4-yl)(1-(trifluoromethyl) cyclopropyl) methanol

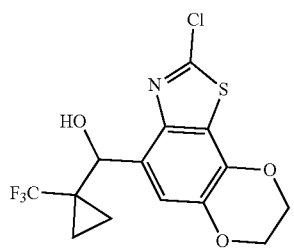

(279C)

Intermediate 279B (0.064 g, 0.176 mmol) was dissolved in MeOH (1.760 ml) followed by addition of NaBH₄ (6.66 mg, 0.176 mmol). The reaction mixture was stirred at room temperature for 2 hours. The reaction mixture was diluted with water and EtOAc. The layers were separated and the organic layer was washed with brine, dried with sodium sulfate, and concentrated under reduced pressure to yield Intermediate 279C (0.057 g, 0.078 mmol, 44.3% yield). LC-MS: method H, RT=1.08 min, MS (ESI) m/z: 366.1 (M+H)+.

Example 279

Intermediate I-9 (0.016 g, 0.055 mmol) and Intermediate 279C (0.020 g, 0.055 mmol) were dissolved in DMF (0.547 ml). PdCl$_2$(dppf)—CH$_2$Cl$_2$ adduct (2.68 mg, 3.28 µmol) was added and the reaction degassed by bubbling with argon for 15 minutes. Na$_2$CO$_3$, 3 M aq. soln (0.018 ml, 0.055 mmol) was added and the reaction degassed for 5 minutes, then sealed and heated to 90° C. in the microwave for 30 minutes. The reaction mixture was concentrated, redissolved in DMF, filtered, and purified by preparative HPLC (Method D, 50 to 100% B in 15 minutes, then 5 minute hold time) to yield Example 279 (0.0017 g, 3.28 µmol, 5.99% yield): $^1$H NMR (500 MHz, DMSO-d$_6$) δ 8.74 (s, 1H), 8.53 (s, 1H), 7.81 (s, 1H), 7.15 (s, 1H), 5.87 (d, J=5.2 Hz, 1H), 5.78 (d, J=5.5 Hz, 1H), 4.48-4.34 (m, 4H), 4.06 (s, 3H), 2.61 (s, 3H), 1.25-1.14 (m, 2H), 0.91 (s, 2H), 0.53 (d, J=8.9 Hz, 1H). LC-MS: method H, RT=1.29 min, MS (ESI) m/z: 504.1 (M+H)$^+$. Analytical HPLC Method B: 97% purity.

Example 280

(R)-(5-fluoro-2-(6-fluoro-3-methoxyquinolin-8-yl)-7,8-dihydrobenzofuro[5,4-d]thiazol-7-yl)methyl (2-methylpyrimidin-5-yl)carbamate

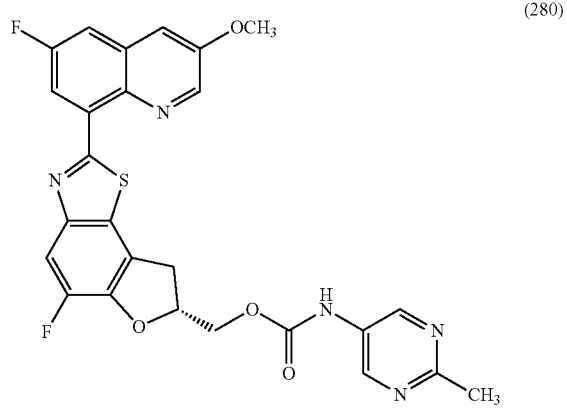 [SMILES: COc1cnc2c(-c3nc4cc(F)c5c(c4s3)C[C@H](COC(=O)Nc3cnc(C)nc3)O5)cc(F)cc2c1]

(280)

Intermediate I-52 (0.010 g, 0.033 mmol) and Intermediate I-45 (0.013 g, 0.033 mmol) were dissolved in DMF (0.330 ml). PdCl$_2$(dppf)—CH$_2$Cl$_2$ adduct (1.5 mg, 1.98 µmol) was added and the reaction degassed by bubbling with argon for 15 minutes. Na$_2$CO$_3$, 3 M aq. soln (0.015 ml, 0.055 mmol) was added and the reaction degassed for 5 minutes, then sealed and heated to 90° C. in the microwave for 30 minutes. The reaction mixture was concentrated, redissolved in DMF, filtered, and purified by preparative HPLC (Method D, 30 to 70% B in 20 minutes, then 5 minute hold time) to yield Example 280 (0.005 g, 8.78 µmol, 26.6% yield): $^1$H NMR (500 MHz, DMSO-d$_6$) δ 10.06 (br. s., 1H), 8.82 (br. s., 1H), 8.70 (br. s., 2H), 8.44 (d, J=9.5 Hz, 1H), 7.90 (br. s., 1H), 7.85 (d, J=11.0 Hz, 2H), 5.40 (d, J=7.3 Hz, 1H), 4.56-4.33 (m, 2H), 3.95 (s, 3H), 3.64 (dd, J=15.3, 10.1 Hz, 1H), 3.40-2.87 (m, 1H), 2.50 (br. s., 3H). LC-MS: method H, RT=1.03 min, MS (ESI) m/z: 536.2 (M+H)$^+$. Analytical HPLC Method B: 98% purity.

Example 281

(R)-(2-(6-fluoro-3-methoxyquinolin-8-yl)-7,8-dihydro-[1,4]dioxino[2',3':3,4]benzo[1,2-d]thiazol-7-yl)methyl (2-methylpyrimidin-5-yl)carbamate

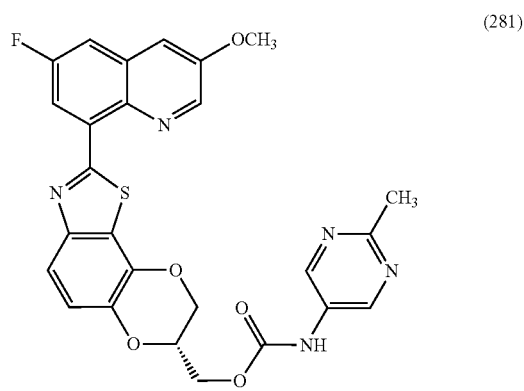 [SMILES: COc1cnc2c(-c3nc4ccc5c(c4s3)OC[C@H](COC(=O)Nc3cnc(C)nc3)O5)cc(F)cc2c1]

(281)

Intermediate I-52 (0.010 g, 0.033 mmol) and Intermediate I-42 (0.013 g, 0.033 mmol) were dissolved in DMF (0.330 ml). PdCl$_2$(dppf)—CH$_2$Cl$_2$ adduct (1.5 mg, 1.98 µmol) was added and the reaction degassed by bubbling with argon for 15 minutes. Na$_2$CO$_3$, 3 M aq. soln (0.015 ml, 0.055 mmol) was added and the reaction degassed for 5 minutes, then sealed and heated to 90° C. in the microwave for 30 minutes. The reaction mixture was concentrated, redissolved in DMF, filtered, and purified by preparative HPLC (Method D, 30 to 70% B in 20 minutes, then 5 minute hold time) to yield Example 281 (0.0017 g, 3.19 µmol, 9.7% yield): $^1$H NMR (500 MHz, DMSO-d$_6$) δ 10.18 (br. s., 1H), 8.89 (br. s., 1H), 8.77 (br. s., 2H), 8.50 (d, J=9.5 Hz, 1H), 7.96 (br. s., 1H), 7.91 (d, J=8.5 Hz, 1H), 7.68 (d, J=8.8 Hz, 1H), 7.19 (d, J=8.5 Hz, 1H), 4.66 (d, J=12.5 Hz, 2H), 4.56-4.44 (m, 2H), 4.32 (t, J=9.0 Hz, 1H), 4.01 (br. s., 3H), 2.58-2.55 (m, 3H). LC-MS: method H, RT=1.02 min, MS (ESI) m/z: 534.1 (M+H)$^+$. Analytical HPLC Method B: 100% purity.

Example 282

(R)-(2-(6-chloro-3-methoxyquinolin-8-yl)-5-fluoro-7,8-dihydrobenzofuro[5,4-d]thiazol-7-yl)methanol

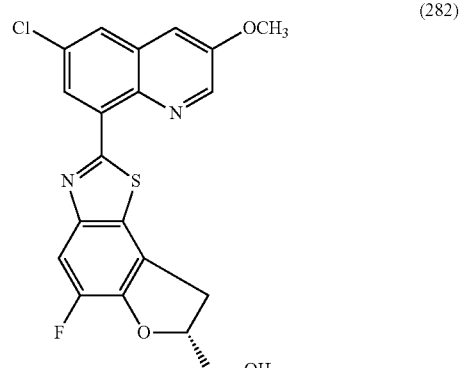

(282)

A solution of Intermediate I-41 (63.0 mg, 0.197 mmol) and Intermediate 145D (60 mg, 0.197 mmol) in toluene/EtOH (3:1) (2.5 mL) was added to PdCl$_2$(dppf)—CH$_2$Cl$_2$ adduct (8.06 mg, 9.86 μmol). The mixture was flushed with argon for 1 min. To this was added 1.5 M Na$_2$CO$_3$ (0.278 mL, 0.434 mmol). The reaction mixture was heated in a microwave at 140° C. for 45 min. HPLC indicated a completion of reaction. The reaction mixture was directly loaded onto a Silica gel column, and was purified by flash chromatography (5% to 75% EtOAc in hexane over 15 min using a 12 g silica gel cartridge). The desired fractions were combined and concentrated to yield crude product (60 mg) which was triturated in MeOH, centrifuged and solid collected to give Example 282 (36 mg, 0.086 mmol, 43.8% yield). $^1$H NMR (500 MHz, DMSO-d$_6$) δ 8.92 (br. s., 1H), 8.65 (br. s., 1H), 8.21 (br. s., 1H), 7.96 (br. s., 1H), 7.88 (d, J=11.3 Hz, 1H), 5.15 (d, J=17.4 Hz, 2H), 4.00 (s, 3H), 3.81-3.64 (m, 2H), 3.60-3.50 (m, 1H), 2.55 (s, 3H); LC-MS: method C, 2 to 98% B. RT=0.800 min, MS (ESI) m/z: 417.00 and 419.00 (M+H)$^+$. Analytical HPLC purity (method B): 100%.

Example 283

(R)-(2-(6-chloro-3-methoxyquinolin-8-yl)-5-fluoro-7,8-dihydrobenzofuro[5,4-d]thiazol-7-yl)methyl pyridin-3-ylcarbamate

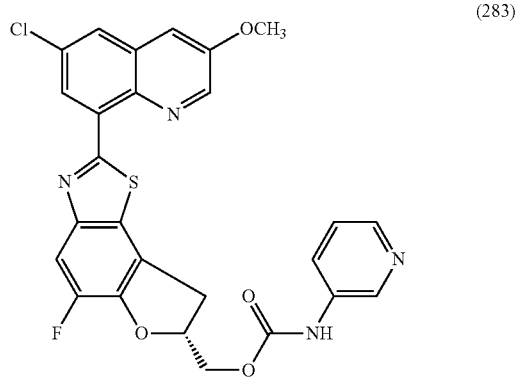 [SMILES: COc1cnc2c(-c3nc4cc(F)c5c(c4s3)C[C@H](COC(=O)Nc3cccnc3)O5)cc(Cl)cc2c1]

(283)

Intermediate 283A (R)-(2-(6-chloro-3-methoxyquinolin-8-yl)-5-fluoro-7,8-dihydrobenzofuro[5,4-d]thiazol-7-yl)methyl chloroformate

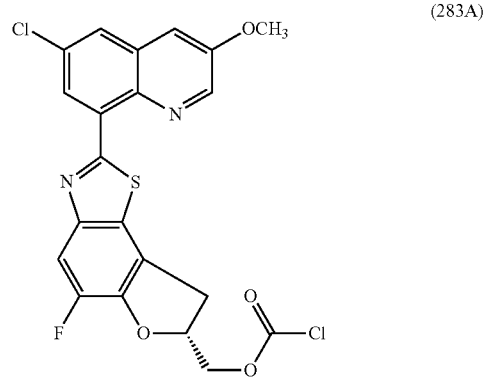 [SMILES: COc1cnc2c(-c3nc4cc(F)c5c(c4s3)C[C@H](COC(=O)Cl)O5)cc(Cl)cc2c1]

(283A)

To a suspension of Example 282 (36 mg, 0.086 mmol) in THF (2 mL) at room temperature was added 15% phosgene in toluene (0.247 mL, 0.345 mmol). The reaction mixture was left stirring at room temperature for 1 min, DIEA (0.045 mL, 0.259 mmol) was added. The reaction was continued at room temperature for 40 min. Solvent was completely removed under high vacuum to give Intermediate 283A (41.4 mg, 0.086 mmol, 100% yield) as a slightly yellow solid. It was used for the next step without any purification. LC-MS: method H, 2 to 98% B. RT=1.13 min, MS (ESI) m/z: 479.00 and 481.00 (M+H)$^+$.

Example 283

Pyridin-3-amine (8.25 mg, 0.088 mmol) was dissolved in DCM (1.0 mL) along with pyridine (0.028 mL, 0.351 mmol). Intermediate 283A (21 mg, 0.044 mmol) in 2 mL of DCM was added dropwise, and the reaction mixture was stirred at room temperature for 30 minutes. The reaction was quenched by addition of 1.0 N HCl (0.6 mL). Dichloromethane was removed. The mixture was dissolved in a mixture of THF/DMSO (1:2, 6 mL), and purified via preparative LC/MS (method C, 45-100% B over 15 min, then a 5-min hold at 100% B). Fractions containing the desired product were combined and dried via centrifugal evaporation to yield Example 283 (20 mg, 82% yield). $^1$H NMR (500 MHz, DMSO-d$_6$) δ 8.91 (br. s., 1H), 8.71 (br. s., 1H), 8.64 (br. s., 1H), 8.29 (br. s., 1H), 8.21 (br. s., 1H), 8.00 (br. s., 1H), 7.97-7.88 (m, 2H), 7.46 (br. s., 1H), 5.45 (d, J=7.3 Hz, 1H), 4.56 (d, J=12.2 Hz, 1H), 4.48-4.39 (m, 1H), 4.00 (br. s., 3H), 3.74-3.64 (m, 1H); LC-MS: method C, 2 to 98% B. RT=1.99 min, MS (ESI) m/z: 537.20 (M+H)$^+$. Analytical IPLC purity (method B): 99%.

Example 284

(R)-(2-(6-chloro-3-methoxyquinolin-8-yl)-5-fluoro-7,8-dihydrobenzofuro[5,4-d]thiazol-7-yl)methyl (3-carbamoylphenyl)carbamate

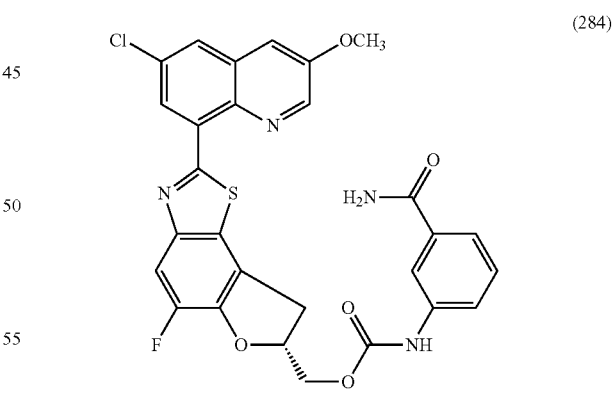

(284)

3-Aminobenzamide (11.93 mg, 0.088 mmol) was dissolved in DCM (1.0 mL) along with pyridine (0.028 mL, 0.351 mmol). Intermediate 283A (21 mg, 0.044 mmol) in 2 mL of DCM was added dropwise and the reaction mixture was stirred at room temperature for 30 minutes. The reaction was quenched by addition of 1.0 N HCl (0.6 mL). Dichloromethane was removed. The mixture was dissolved in a mixture of THF/DMSO (1:2, 7 mL), and was purified via preparative LC/MS (method C, 45-90% B over 22 min, then a 5-min hold at 100% B). Fractions containing the desired product were combined and dried via centrifugal evaporation to yield Example 284 (1.1 mg, 4.3% yield). $^1$H NMR (500 MHz, DMSO-$d_6$) δ 9.94 (br. s., 1H), 8.93 (br. s., 1H), 8.66 (br. s., 1H), 8.22 (br. s., 1H), 7.95-7.84 (m, 2H), 7.59 (br. s., 1H), 7.48 (d, J=7.0 Hz, 1H), 7.31 (br. s., 2H), 5.45 (br. s., 1H), 4.53 (d, J=12.2 Hz, 1H), 4.42 (d, J=7.3 Hz, 1H), 4.00 (s., 3H), 3.75-3.64 (m, 1H), 3.33 (d, J=4.0 Hz, 1H); LC-MS: method C, 2 to 98% B. RT=2.26 min, MS (ESI) m/z: 579.00 (M+H)$^+$. Analytical HPLC purity (method B): 98%.

Example 285

(S)-(2-(6-chloro-3-methoxyquinolin-8-yl)-5-fluoro-7-methyl-7,8-dihydrobenzofuro[5,4-d]thiazol-7-yl)methanol

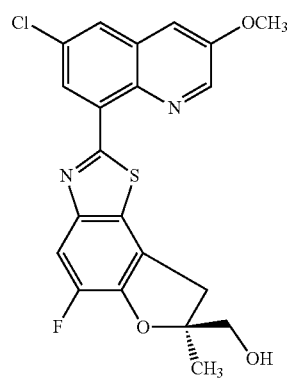

(285)

A solution of Intermediate I-41 (49.0 mg, 0.153 mmol), and Intermediate 172A (35 mg, 0.128 mmol) in toluene/EtOH (3:1) (1.8 mL) was added to PdCl$_2$(dppf)—CH$_2$Cl$_2$ adduct (5.22 mg, 6.39 μmol). The mixture was flushed with argon for 1 min. To this was added Na$_2$CO$_3$ (2.0 M, 0.170 mL, 0.256 mmol). The reaction mixture was heated in a microwave at 140° C. for 45 min. HPLC indicated a completion of reaction. The reaction mixture was diluted with EtOAc/brine. The organic layer was collected, dried over sodium sulfate and concentrated. The crude was dissolved in DMSO and purified via preparative LC/MS (method C, 50-100% B over 22 min, then a 5-min hold at 100% B). Fractions containing the desired product were combined and dried via centrifugal evaporation to yield Example 285 (6.7 mg, 12% yield). $^1$H NMR (500 MHz, DMSO-$d_6$) δ 8.87 (d, J=2.7 Hz, 1H), 8.59 (d, J=2.1 Hz, 1H), 8.16 (d, J=1.8 Hz, 1H), 7.90 (d, J=2.4 Hz, 1H), 7.83 (d, J=11.3 Hz, 1H), 3.98 (s, 3H), 3.66-3.56 (m, 1H), 4.55-3.45 (m, 2H), 3.18 (d, J=15.6 Hz, 1H), 1.49 (s, 3H); LC-MS: method C, 2 to 98% B. RT=2.35 min, MS (ESI) m/z: 431.25 (M+H)$^+$. Analytical HPLC purity (method B): 99%.

Example 286

(R)-(2-(6-chloro-3-methoxyquinolin-8-yl)-5-fluoro-7-methyl-7,8-dihydrobenzofuro[5,4-d]thiazol-7-yl)methyl (2-(2-hydroxyethoxy)pyrimidin-5-yl)carbamate

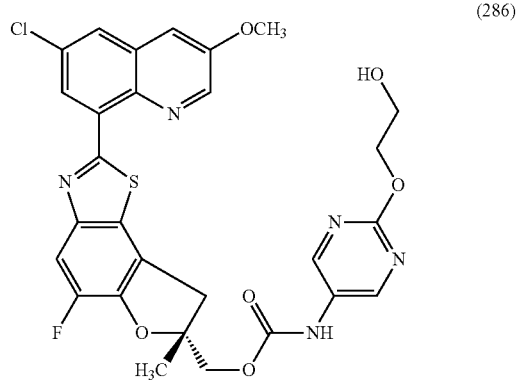 [SMILES: COc1cnc2c(-c3nc4cc(F)c5c(c4s3)C[C@](C)(COC(=O)Nc3cnc(OCCO)nc3)O5)cc(Cl)cc2c1]

(286)

Intermediate 286A (R)-(2-(6-chloro-3-methoxyquinolin-8-yl)-5-fluoro-7-methyl-7,8-dihydrobenzofuro[5,4-d]thiazol-7-yl)methanol

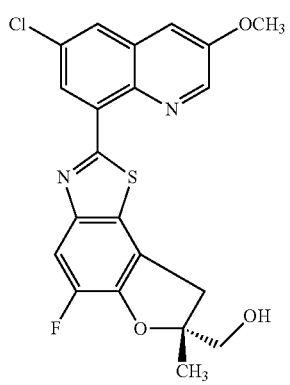

(286A)

A solution of Intermediate I-41 (169 mg, 0.620 mmol), and Intermediate 181A (175 mg, 0.64 mmol) in toluene/EtOH (3:1) (9 mL) was added to PdCl$_2$(dppf)—CH$_2$Cl$_2$ (20.26 mg, 0.025 mmol). The mixture was flushed with argon for 1 min. To this was added Na$_2$CO$_3$ (2.0 M, 0.70 mL, 1.4 mmol). The reaction mixture was heated in a microwave at 140° C. for 45 min. The reaction mixture was diluted with EtOAc/brine. The organic layer was collected, dried over sodium sulfate and concentrated. The crude product was purified by flash chromatography (loading in THF, 0% to 85% THF in dichloromethane over 15 min using a 40 g silica gel cartridge). The desired fractions were combined and concentrated, and triturated in MEOH to yield Intermediate 286A (37 mg, 0.086 mmol, 13.85% yield) as a yellow solid. LC-MS: method H, 2 to 98% B. RT=1.11 min, MS (ESI) m/z: 431.4 and 433.4 (M+H)$^+$.

467

Intermediate 286B (R)-(2-(6-chloro-3-methoxyquinolin-8-yl)-5-fluoro-7-methyl-7,8-dihydrobenzofuro[5,4-d]thiazol-7-yl)methyl chloroformate

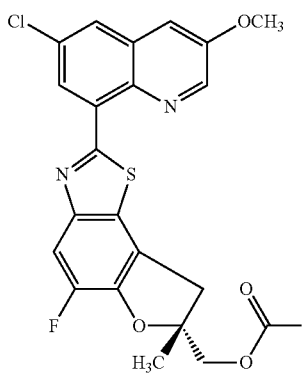
(286B)

To a suspension of Intermediate 286A (37 mg, 0.086 mmol) in THF (2.0 mL) at room temperature was added 15% phosgene in toluene (0.245 mL, 0.343 mmol). The reaction mixture was left stirring for 1 min, DIEA (0.045 mL, 0.258 mmol) was added. The reaction was continued at room temperature for 40 min, at which time HPLC and LCMS indicated the reaction was complete. Solvent was completely removed under high vacuum to give Intermediate 286B (42 mg, 0.085 mmol, 99% yield) as a slightly yellow solid. It was used for the next step without any purification. LC-MS: method H, 2 to 98% B. RT=1.17 min, MS (ESI) m/z: 492.95 and 494.95 (M+H)$^+$.

Example 286

Intermediate I-57 (32.8 mg, 0.122 mmol) was dissolved in DCM (1.0 mL) along with pyridine (0.052 mL, 0.649 mmol) and DIEA (0.042 mL, 0.243 mmol). Intermediate 286B (40 mg, 0.081 mmol) in 2 mL of DCM was added dropwise and the reaction mixture was stirred at room temperature for 50 minutes. The reaction was quenched with 1.0 N HCl (0.5 mL). All solvent was removed under vacuum. The crude was dried under high vacuum for 1 h, then treated with THF (1.5 mL) and 3 mL of 20:1 MeOH/concentrated HCl at room temperature for 1.5 h. HPLC and LCMS indicated a complete deprotection of the silyl group. Solvent was removed under vacuum. The crude was dissolved in THF/DMSO (1:1, 3 mL) and purified via preparative LC/MS (method C, 45-90% B over 22 min, then a 5-min hold at 100% B). Fractions containing the desired product were combined and dried via centrifugal evaporation to yield Example 286 (24 mg, 49% yield). $^1$H NMR (500 MHz, DMSO-$d_6$) δ 8.80 (br. s., 1H), 8.59 (br. s., 2H), 8.53 (br. s., 1H), 8.11 (s, 1H), 7.85 (br. s., 1H), 7.81 (d, J=10.7 Hz, 1H), 4.39 (br. s., 2H), 4.23 (br. s., 1H), 3.96 (s, 3H), 3.31 (d, J=16.2 Hz, 1H), 1.61 (s, 3H); LC-MS: method C, 2 to 98% B. RT=2.26 min, MS (ESI) m/z: 612.1 (M+H)$^+$. Analytical HPLC purity (method B): 100%.

468

Example 287

(R)-(2-(6-chloro-3-methoxyquinolin-8-yl)-7,8-dihydro-[1,4]dioxino[2',3':3,4]benzo[1,2-d]thiazol-7-yl)methyl (2-(2-hydroxyethoxy)pyrimidin-5-yl)carbamate

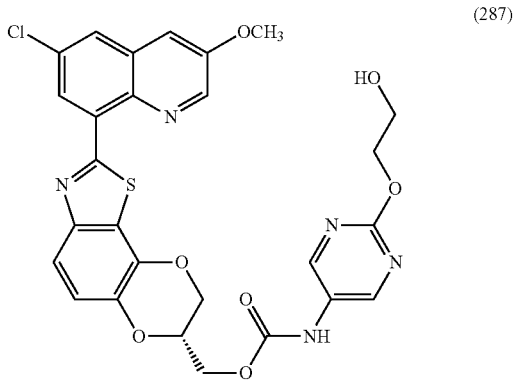 [SMILES: COc1cnc2c(-c3nc4ccc5c(c4s3)OC[C@H](COC(=O)Nc3cnc(OCCO)nc3)O5)cc(Cl)cc2c1]
(287)

Intermediate 287A: [(11R)-4-[bis(tert-butoxycarbonyl)amino]-7-chloro-10,13-dioxa-3-thia-5-azatricyclo[7.4.0.0^{2,6}]trideca-1,4,6,8-tetraen-11-yl] methyl acetate

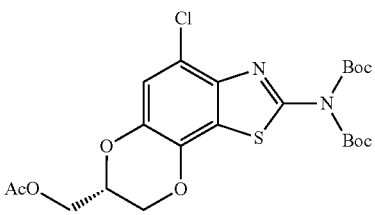
(287A)

To a suspension of Intermediate 25F (1.0 g, 3.18 mmol) in DCM (20 mL) was added (Boc)$_{2}$O (2.213 mL, 9.53 mmol) in 1.0 mL of DMC and DMAP (0.039 g, 0.318 mmol). The reaction mixture was stirred at room temperature for 1 h. The mixture was concentrated and load to a 120 g ISCO column which was eluted with 0-100% EtOAc/hexanes for 40 min. The desired fraction was collected and concentrated to yield Intermediate 287A (1.5 g, 2.91 mmol, 92% yield). $^1$H NMR (400 MHz, CHLOROFORM-d) δ 7.07 (s, 1H), 4.50-4.41 (m, 2H), 4.38-4.31 (m, 2H), 4.19 (dd, J=11.3, 7.2 Hz, 1H), 2.13 (s, 3H), 1.59 (s, 18H); LC-MS: method C, RT=2.39 min, MS (ESI) m/z: 515 (M+H)$^+$.

Intermediate 287B (R)-(2-amino-7,8-dihydro-[1,4]dioxino[2',3':3,4]benzo[1,2-d]thiazol-7-yl)methyl acetate

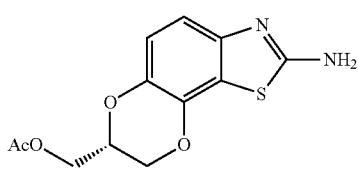
(287B)

Pd(OAc)$_2$ (0.170 g, 0.757 mmol), 2-(di-tert-butylphosphino)biphenyl (0.452 g, 1.515 mmol) were sealed in microwave vial and degassed for 5 times. MeOH (20 mL) was added, and the mixture was stirred at room temperature for 10 min. A suspension of Intermediate 287A (3.9 g, 7.57 mmol) and sodium formate (1.545 g, 22.72 mmol) in THF (12 mL) and MeOH (68 mL) was added. The reaction mixture was degassed with argon for 5 min., sealed and heated up to reflux at 85° C. in an oil bath for 3 h. The reaction mixture was concentrated and directly loaded onto a 330 g ISCO column which was eluted with 0-100% EtOAc in 60 min. Two major products were obtained. The first eluting peak was [(11R)-4-[bis(tert-butoxycarbonyl)amino]-10,13-dioxa-3-thia-5-azatricyclo[7.4.0.0^{2,6}]trideca-1,4,6,8-tetraen-11-yl]methyl acetate (0.9 g, 1.311 mmol, 17.31% yield); LC-MS: method H, RT=2.38 min, MS (ESI) (m z) 481[M+H]+. The second eluting peak was (R)-(2-((tert-butoxycarbonyl)amino)-7,8-dihydro-[1,4]dioxino[2',3':3,4]benzo[1,2-d]thiazol-7-yl)methyl acetate (1.89 g, 4.97 mmol, 65.6% yield). $^1$H NMR (400 MHz, CHLOROFORM-d) δ 7.39 (d, J=8.6 Hz, 1H), 6.98 (d, J=8.8 Hz, 1H), 4.51-4.32 (m, 4H), 4.20 (dd, J=11.8, 7.6 Hz, 1H), 2.14 (s, 3H), 1.59 (s, 9H). LC-MS: method H, RT=2.21 min, MS (ESI) (m z) 381[M+H]+. The above two products were dissolved in 30 ml of DCM. TFA (29.2 mL, 379 mmol) was added. The reaction mixture was stirred at room temperature for 2 h. Solvent was removed and the crude was diluted by EtOAc, washed with 1.5 M K$_2$IPO4, brine. The organic layer was dried over MgSO$_4$ and concentrated to yield Intermediate 287B (1.8 g). $^1$H NMR (400 MHz, CHLOROFORM-d) δ 7.10 (d, J=8.6 Hz, 1H), 6.91 (d, J=8.6 Hz, 1H), 5.05 (br. s., 2H), 4.50-4.32 (m, 4H), 4.18 (dd, J=11.2, 7.0 Hz, 1H), 2.13 (s, 3H)). LC-MS: method H, RT=1.45 min, MS (ESI) (m z) 270[M+H]+.

Intermediate 287C (R)-(2-chloro-7,8-dihydro-[1,4]dioxino[2',3':3,4]benzo[1,2-d]thiazol-7-yl)methyl acetate

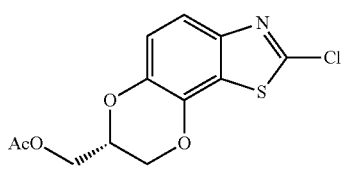
(287C)

To a suspension of Intermediate 287B (1.5 g, 4.55 mmol) in dry acetonitrile (80 mL) was added CuCl$_2$ (1.040 g, 7.73 mmol), followed by tert-butyl nitrite (1.052 mL, 7.96 mmol) dropwise. The reaction mixture was stirred at room temperature for 2 h. Acetonitrile was removed under vacuum, the reaction mixture was diluted with EtOAc, quenched with 1.0 N HCl. The organic layer was collected, washed with 0.5 N HCl (2×), 1.5N K$_2$HIPO$_4$, brine and dried over sodium sulfate. After evaporation of solvent, the crude product was purified ISCO column eluted with 0% to 70% EtOAc in hexane over 45 min. The desired fraction was collected and concentrated to give Intermediate 287C (1.3 g, 4.34 mmol, 95% yield $^1$H NMR (400 MHz, CHLOROFORM-d) δ 7.48 (d, J=8.8 Hz, 1H), 7.08 (d, J=8.8 Hz, 1H), 4.59-4.41 (m, 2H), 4.40-4.33 (m, 2H), 4.21 (dd, J=11.3, 7.2 Hz, 1H), 2.14 (s, 3H). LC-MS: method H, RT=2.03 min, MS (ESI) (m/z) 299.9 [M+H]+.

Intermediate 287D (S)-(2-chloro-7,8-dihydro-[1,4]dioxino[2',3':3,4]benzo[1,2-d]thiazol-7-yl)methanol

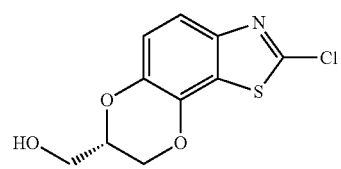
(287D)

To Intermediate 287C (1.5 g, 5.00 mmol) in THF (30 mL) and MeOH (2 mL) cooled with an ice-bath was added 1.0 N NaOH (7.51 mL, 7.51 mmol). The mixture was stirred for 1.5 h, then diluted with EtOAc/THF/water. The organic layer was collected, washed with saturated sodium bicarbonate, brine and dried over sodium sulfate. After evaporation of solvent, Intermediate 287D (430 mg, 1.423 mmol, 100% yield) was obtained as an off-white solid. $^1$H NMR (400 MHz, CHLOROFORM-d) δ 7.48 (d, J=8.6 Hz, 1H), 7.08 (d, J=8.8 Hz, 1H), 4.47 (dd, J=11.0, 2.0 Hz, 1H), 4.39-4.32 (m, 1H), 4.31-4.22 (m, 1H), 4.05-3.86 (m, 2H), 1.90 (t, J=6.4 Hz, 1H). LC-MS: method H, RT=1.89 min, MS (ESI) (m/z) 258.0 [M+H]$^+$.

Intermediate 287E: (S)-(2-(6-chloro-3-methoxyquinolin-8-yl)-7,8-dihydro-[1,4]dioxino[2',3':3,4]benzo[1,2-d]thiazol-7-yl)methanol

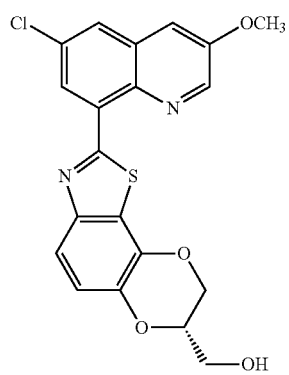
(287E)

A mixture of Intermediate I-41A (200 mg, 0.734 mmol), 4,4,4',4',5,5,5',5'-octamethyl-2,2'-bi(1,3,2-dioxaborolane) (242 mg, 0.954 mmol), potassium acetate (216 mg, 2.202 mmol), PdCl$_2$(dppf)—CH$_2$Cl$_2$ adduct (23.97 mg, 0.029 mmol) in dioxane (8 mL) was degassed by bubbling argon for 5 min. It was then heated at 105° C. in an oil bath for 4.0 h. HPLC indicated a completion of reaction. Intermediate 287D (150 mg, 0.362 mmol, 49.3% yield) was added, followed by 1.5 M sodium carbonate (1.345 mL, 2.018 mmol). The reaction mixture was heated at 105° C. in an oil bath for 2.0 h. HPLC indicated a completion of reaction. The reaction mixture was diluted with EtOAc/brine. The organic layer was collected, washed with brine, dried over sodium sulfate and concentrated. The crude was dissolved in THF and purified by column chromatography (2×). The crude product was purified by flash chromatography (loading in THF, 0% to 85% THF in dichloromethane over 15 min using a 40 g silica gel cartridge). The desired fractions were combined and concentrated to yield Intermediate 287E (150 mg, 0.362 mmol, 49.3% yield) as a yellow solid. LC-MS: method H, 2 to 98% B. RT=1.05 min, MS (ESI) m/z: 415.3 and 417.3 (M+H)$^+$.

Intermediate 287F: (R)-(2-(6-chloro-3-methoxyquinolin-8-yl)-7,8-dihydro-[1,4]dioxino[2',3':3,4]benzo[1,2-d]thiazol-7-yl)methyl chloroformate

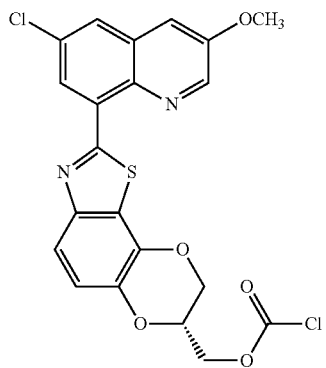

(287F)

To a suspension of Intermediate 287E (35 mg, 0.084 mmol) in THF (2.0 mL) at room temperature was added 15% phosgene in toluene (0.241 mL, 0.337 mmol). The reaction mixture was left stirring for 1 min, DIEA (0.044 mL, 0.253 mmol) was added. The reaction was continued at room temperature for 40 min. Solvent was removed under high vacuum to give Intermediate 287F (40 mg, 0.084 mmol, 99% yield) as a slightly yellow solid. It was used for the next step without any purification. LC-MS: method H, 2 to 98% B. RT=1.14 min, MS (ESI) m/z: 476.95 and 478.95 (M+H)$^+$.

Example 287

Intermediate I-57 (33.9 mg, 0.126 mmol) was dissolved in DCM (1.0 mL) along with pyridine (0.054 mL, 0.670 mmol) and DIEA (0.044 mL, 0.251 mmol). Intermediate 287F (40 mg, 0.084 mmol) in 2 mL of DCM was added dropwise and the reaction mixture was stirred at room temperature for 50 minutes. The reaction was quenched with 1.0 N HCl (0.5 mL). All solvent was removed under vacuum. The crude was dried under high vacuum for 1 h, then treated with THF (2.5 mL) and 3 mL of 20:1 MeOH/concentrated HCl at room temperature for 1.5 h. HPLC and LCMS indicated a complete deprotection of silyl group. Solvent was removed under vacuum. The crude was dissolved in THF/DMSO (1:1, 3 mL) purified via preparative LC/MS (method C, 40-80% B over 22 min, then a 2-min hold at 100% B). Fractions containing the desired product were combined and dried via centrifugal evaporation to yield Example 287 (10 mg, 19% yield). $^1$H NMR (500 MHz, DMSO-d$_6$) δ 10.01 (br. s., 1H), 8.83 (br. s., 1H), 8.63 (br. s., 2H), 8.56 (s, 1H), 8.12 (s, 1H), 7.86 (br. s., 1H), 7.64 (d, J=8.5 Hz, 1H), 7.16 (d, J=8.9 Hz, 1H), 4.68-4.61 (m, 2H), 4.52-4.41 (m, 2H), 4.34-4.25 (m, 3H), 3.97 (s, 3H), 3.71 (br. s., 1H), 3.62-3.56 (m, 2H); LC-MS: method C, 2 to 98% B. RT=2.24 min, MS (ESI) m/z: 596.0 (M+H)$^+$. Analytical HPLC purity (method B): 97.3%.

Example 288

((R)-2-(6-chloro-3-methoxyquinolin-8-yl)-7,8-dihydro-[1,4]dioxino[2',3':3,4]benzo[1,2-d]thiazol-7-yl)methyl (2-((S)-2-hydroxypropoxy)pyrimidin-5-yl) carbamate

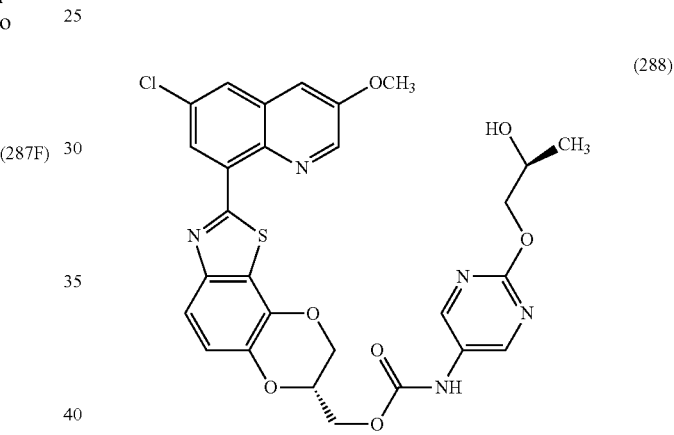

(288)

Intermediate I-58 (30.3 mg, 0.107 mmol) was dissolved in DCM (1.0 mL) along with pyridine (0.046 mL, 0.570 mmol) and DIEA (0.037 mL, 0.214 mmol). Intermediate 287F (34 mg, 0.071 mmol) in 2 mL of DCM was added dropwise and the reaction mixture was stirred at room temperature for 50 minutes. The reaction was quenched with 1.0 N HCl (0.5 mL). All solvent was removed under vacuum. The crude was dried under high vacuum for 1 h, then treated with THF (2.0 mL) and 2.5 mL of 20:1 MeOH/concentrated HCl at room temperature for 1.5 h. HPLC and LCMS indicated a complete deprotection of the silyl group. Solvent was removed under vacuum. The crude was dissolved in THF/DMSO (1:1, 3 mL) and purified via preparative LC/MS (method C, 45-90% B over 22 min, then a 5-min hold at 100% B). Fractions containing the desired product were combined and dried via centrifugal evaporation to yield Example 288 (23 mg, 52% yield). $^1$H NMR (500 MHz, DMSO-d$_6$) δ 10.04 (br. s., 1H), 8.88 (d, J=2.7 Hz, 1H), 8.64 (br. s., 2H), 8.60 (d, J=1.8 Hz, 1H), 8.16 (s, 1H), 7.91 (d, J=2.4 Hz, 1H), 7.66 (d, J=8.5 Hz, 1H), 7.18 (d, J=8.5 Hz, 1H), 4.71-4.63 (m, 2H), 4.54-4.42 (m, 2H), 4.32 (dd, J=11.0, 7.6 Hz, 1H), 4.17-4.11 (m, 1H), 4.10-4.04 (m, 1H), 3.99 (s, 3H), 1.14 (d, J=6.4 Hz, 3H); LC-MS: method C, 2 to 98% B. RT=2.21 min, MS (ESI) m/z: 610.0 (M+H)$^+$. Analytical HPLC purity (method B): 96%.

Example 289

((R)-2-(6-chloro-3-methoxyquinolin-8-yl)-7,8-di-hydro-[1,4]dioxino[2',3':3,4]benzo[1,2-d]thiazol-7-yl)methyl (2-((R)-2-hydroxypropoxy)pyrimidin-5-yl)carbamate

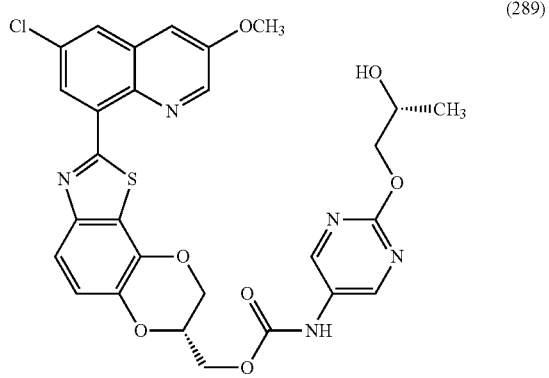 [SMILES: COc1cnc2c(-c3nc4ccc5c(c4s3)OC[C@H](COC(=O)Nc3cnc(OC[C@@H](C)O)nc3)O5)cc(Cl)cc2c1]

(289)

Intermediate I-59 (30.3 mg, 0.107 mmol) was dissolved in DCM (1.0 mL) along with pyridine (0.046 mL, 0.570 mmol) and DIEA (0.037 mL, 0.214 mmol). Intermediate 287F (34 mg, 0.071 mmol) in 2 mL of DCM was added dropwise and the reaction mixture was stirred at room temperature for 50 minutes. The reaction was quenched with 1.0 N HCl (0.5 mL). All solvent was removed under vacuum. The crude was dried under high vacuum for 1 h, then treated with THF (2.0 mL) and 2.5 mL of 20:1 MeOH/concentrated HCl at room temperature for 1.5 h. HPLC and LCMS indicated a complete deprotection of the silyl group. Solvent was removed under vacuum. The crude was dissolved in THF/DMSO (1:1, 3 mL) and purified via preparative LC/MS (method C, 45-85% B over 25 min, then a 4-min hold at 100% B). Fractions containing the desired product were combined and dried via centrifugal evaporation to yield Example 289 (3.8 mg, 6.23 µmol, 8.74% yield). $^1$H NMR (500 MHz, DMSO-$d_6$) δ 10.03 (br. s., 1H), 8.88 (d, J=2.7 Hz, 1H), 8.64 (br. s., 2H), 8.60 (d, J=2.4 Hz, 1H), 8.16 (d, J=2.1 Hz, 1H), 7.91 (d, J=2.7 Hz, 1H), 7.66 (d, J=8.9 Hz, 1H), 7.18 (d, J=8.9 Hz, 1H), 4.91 (d, J=4.9 Hz, 1H), 4.71-4.62 (m, 2H), 4.54-4.42 (m, 2H), 4.32 (dd, J=11.3, 7.3 Hz, 1H), 4.17-4.11 (m, 1H), 4.10-4.05 (m, 1H), 3.99 (s, 3H), 3.97-3.94 (m, 1H), 1.14 (d, J=6.4 Hz, 3H); LC-MS: method C, 2 to 98% B. RT=2.22 min, MS (ESI) m/z: 610.1 (M+H)$^+$. Analytical HPLC purity (method B): 100%.

Example 290

((7S,8S)-2-(6-chloro-3-methoxyquinolin-8-yl)-5-fluoro-8-methyl-7,8-dihydrobenzofuro[5,4-d]thiazol-7-yl)methanol

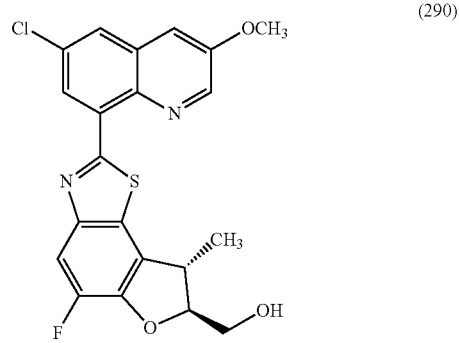 [SMILES: COc1cnc2c(-c3nc4cc(F)c5c(c4s3)[C@H](C)[C@@H](CO)O5)cc(Cl)cc2c1]

(290)

To Intermediate I-41 (12.88 mg, 0.054 mmol), Intermediate 238B (13.5 mg, 0.049 mmol) and PdCl$_2$(dppf)—CH$_2$Cl$_2$ adduct (1.772 mg, 2.170 µmol) was added dioxane (0.4 mL). The mixture was sonicated for 1 min, and flushed with argon. To this was added sodium carbonate (99 µl, 1.5M, 0.148 mmol). The reaction mixture was heated in a microwave at 100° C. for 1 hour. LCMS indicated the completion of the reaction. The reaction mixture was concentrated and dissolved in 2 ml of DMSO which was purified via preparative LC/MS (Method D: Gradient: 55-95% B over 25 minutes, then a 4-minute hold at 100% B). Fractions containing the desired product were combined and dried via centrifugal evaporation to Example 290 (11 mg, 0.026 mmol, 51.8% yield). $^1$H NMR (500 MHz, DMSO-$d_6$) δ 8.90 (d, J=2.4 Hz, 1H), 8.61 (s, 1H), 8.17 (s, 1H), 7.92 (br. s., 1H), 7.87 (d, J=11.3 Hz, 1H), 5.17 (br. s., 1H), 4.65 (br. s., 1H), 3.99 (s, 3H), 3.84-3.69 (m, 3H), 1.51 (d, J=7.0 Hz, 3H). LC-MS: method L, RT=2.35 min, MS (ESI) m/z: 453.1 (M+H)$^+$. Analytical HPLC purity (method B): 100%.

Example 291

(S)-(5-fluoro-2-(2-methoxy-7-methylquinoxalin-5-yl)-7,8-dihydro-[1,4]dioxino[2',3':3,4]benzo[1,2-d]thiazol-7-yl)methanol

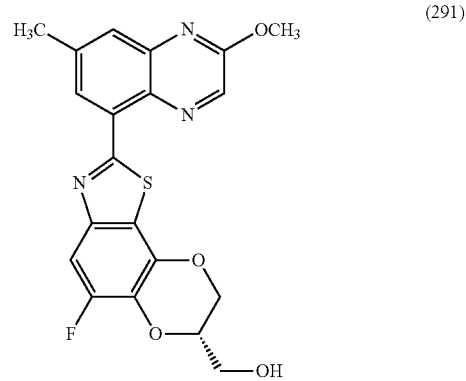 [SMILES: COc1cnc2c(-c3nc4cc(F)c5c(c4s3)OC[C@H](CO)O5)cc(C)cc2n1]

(291)

Intermediate 291A: (R)-2-((2,3-difluoro-5-nitrophenoxy)methyl)oxirane

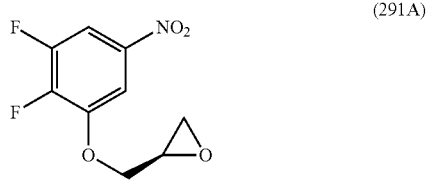 [SMILES: O=[N+]([O-])c1cc(F)c(F)c(OC[C@H]2CO2)c1]

(291A)

To a solution of 2,3-difluoro-5-nitrophenol (1.7 g, 9.71 mmol) in DMF (50 mL) was added (R)-oxiran-2-ylmethyl 3-nitrobenzenesulfonate (2.77 g, 10.68 mmol) and Cs$_2$CO$_3$ (9.49 g, 29.1 mmol). The mixture was stirred at room temperature overnight. LCMS indicated a completion of the reaction. The mixture was diluted with EtOAc and water, extracted with EtOAc. The combined organic layer was washed with brine, dried over MgSO₄ and concentrated. The crude sample was purified with a 120 g ISCO column eluted with 0-100% EtOAc/hexanes for 40 min. The desired fraction was collected and concentrated to give Intermediate 291A (1.75 g, 7.57 mmol, 78% yield) as yellow solid. $^1$H NMR (400 MHz, CHLOROFORM-d) δ 7.96-7.60 (m, 2H), 4.51 (dd, J=11.3, 2.5 Hz, 1H), 4.10 (dd, J=11.4, 5.9 Hz, 1H), 3.51-3.32 (m, 1H), 2.97 (t, J=4.5 Hz, 1H), 2.82 (dd, J=4.7, 2.5 Hz, 1H). $^{19}$F NMR (376 MHz, CHLOROFORM-d) δ −131.89 (d, J=19.5 Hz, 1F), −146.12 (d, J=19.5 Hz, 1F). LC-MS: method C, RT=1.74 min, MS (ESI) m/z: no show (M+H)⁺.

Intermediate 291B: (R)-(2-(2-fluoro-4-nitro-6-(oxiran-2-ylmethoxy)phenoxy)ethyl) trimethylsilane

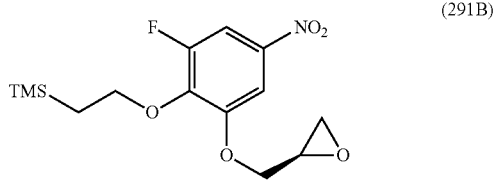 [SMILES: C[Si](C)(C)CCOc1c(F)cc([N+](=O)[O-])cc1OC[C@H]1CO1]

(291B)

To a solution of Intermediate 291A (1.75 g, 7.57 mmol, 78% yield) in THF (30 mL) was added 2-(trimethylsilyl)ethanol (1.579 mL, 11.03 mmol) and KHDMS (8.83 mL, 1M, 8.83 mmol) at 0° C. The mixture was stirred at 0° C. for 1 hour. TLC and LCMS indicated completion of the reaction. The reaction mixture was diluted with EtOAc and water, neutralized with 1.0 N HCl and extracted with EtOAc. The combined organic layer was washed with brine, dried over MgSO₄ and concentrated. The crude sample was purified with a 120 g ISCO column eluted with 0-60% EtOAc/hexanes for 40 min. The desired fraction was collected and concentrated to give Intermediate 291B (2.42 g, 7.35 mmol, 100% yield) was obtained as a light yellow solid. $^1$H NMR (400 MHz, CHLOROFORM-d) δ 7.71 (dd, J=10.3, 2.6 Hz, 1H), 7.67-7.60 (m, 1H), 4.42 (dd, J=11.2, 2.6 Hz, 1H), 4.39-4.30 (m, 2H), 4.03 (dd, J=11.2, 5.9 Hz, 1H), 3.48-3.36 (m, 1H), 2.95 (t, J=4.4 Hz, 1H), 2.80 (dd, J=4.8, 2.6 Hz, 1H), 1.22-1.13 (m, 2H0.08 (s, 9H). $^{19}$F NMR (376 MHz, CHLOROFORM-d) δ −125.72 (s, 1F). LC-MS: method C, RT=2.27 min, MS (ESI) m/z: 352 (M+Na)⁺.

Intermediate 291C: (S)-(8-fluoro-6-nitro-2,3-dihydrobenzo[b][1,4]dioxin-2-yl)methanol

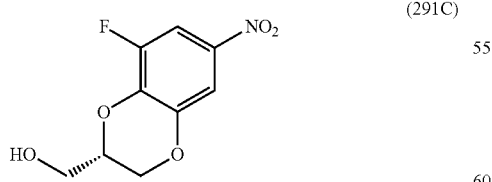

(291C)

To a solution of Intermediate 291B (2.42 g, 7.35 mmol) in THF (20 mL) was added TBAF (22.04 mL, 1M, 22.04 mmol). The mixture was stir at room temperature overnight. TLC and LCMS indicated completion of the reaction. The mixture was diluted with EtOAc and water, extracted with EtOAc. The combined organic layer was washed with brine, dried over MgSO₄ and concentrated. The crude sample was purified with a 80 g ISCO column eluted with 0-100% EtOAc/hexanes for 40 min. The desired fraction was collected and concentrated to give Intermediate 291C (1.35 g, 5.89 mmol, 80% yield) as yellow solid. $^1$H NMR (400 MHz, CHLOROFORM-d) δ 7.74-7.56 (m, 2H), 4.46 (dd, J=11.7, 2.4 Hz, 1H), 4.43-4.36 (m, 1H), 4.28-4.21 (m, 1H), 4.06-4.01 (m, 1H), 3.98-3.90 (m, 1H). $^{19}$F NMR (376 MHz, CHLOROFORM-d) δ −131.73 (s, 1F). LC-MS: method C, RT=1.53 min, MS (ESI) m/z: 230.1 (M+H)⁺.

Intermediate 291D (R)-tert-butyl((8-fluoro-6-nitro-2,3-dihydrobenzo[b][1,4]dioxin-2-yl)methoxy)dimethylsil ane

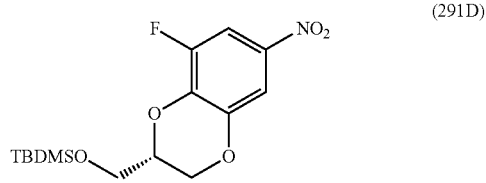 [SMILES: CC(C)(C)[Si](C)(C)OC[C@H]1COc2cc([N+](=O)[O-])cc(F)c2O1]

(291D)

To a stirred solution of Intermediate 291C (1.35 g, 5.89 mmol) in DMF (20 mL) was added TBDMS-Cl (1.332 g, 8.84 mmol) and imidazole (0.722 g, 10.60 mmol). The reaction mixture was stirred at room temperature overnight. LCMS and TLC indicated a completion of the reaction. The mixture was partitioned between EtOAc/water. The organic layer was washed with water, brine, dried over sodium sulfate. After evaporation of solvent, the crude product was dissolved in a small amount of chloroform and charged to a 80 g silica gel cartridge which was eluted with hexanes for 3 min., then a 15 min gradient from 0% to 50% EtOAc in hexanes. The desired fractions were combined and concentrated to give Intermediate 291D (1.85 g, 5.39 mmol, 91% yield) as a white solid. H NMR (400 MHz, CHLOROFORM-d) δ 7.78-7.51 (m, 2H), 4.44 (dd, J=11.7, 2.4 Hz, 1H), 4.39-4.25 (m, 1H), 4.20 (dd, J=11.6, 6.9 Hz, 1H), 4.04-3.93 (m, 1H), 3.92-3.77 (m, 1H), 0.91 (s, 9H), 0.11 (d, J=4.4 Hz, 6H). $^{19}$F NMR (376 MHz, CHLOROFORM-d) 6-132.01 (s, 1F). LC-MS: method H, 2 to 98% B. RT=2.42 min, MS (ESI) m/z: 344.2 (M+H)⁺.

Intermediate 291E (R)-2-(((tert-butyldimethylsilyl)oxy)methyl)-8-fluoro-2,3-dihydrobenzo[b][1,4]dioxin-6-a mine

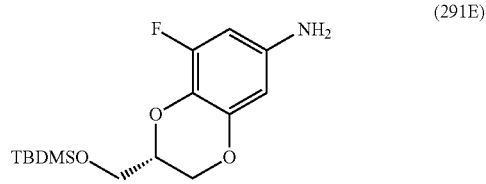 [SMILES: CC(C)(C)[Si](C)(C)OC[C@H]1COc2cc(N)cc(F)c2O1]

(291E)

To a solution of Intermediate 291D (1.6 g, 4.66 mmol) in MeOH (20 mL) and THF (2 mL) cooled with an water bath was added ammonium chloride (3.99 g, 74.5 mmol) and Zn dust (2.437 g, 37.3 mmol). The mixture was stirred at room temperature for 3.0 h. LCMS and TLC indicated a completion of the reaction. Solvent was removed under vacuum. The residue was diluted with EtOAc/1.5 M KH$_2$PO$_4$ and stirred at room temperature for 3 min. The mixture was filtered through a pad of wet celite to remove insoluble material. The filtration was collected, organic layer was washed with brine, dried over sodium sulfate. After evaporation of solvent, the crude product was dissolved in a small amount of chloroform and charged to a 40 g silica gel cartridge which was eluted with hexanes for 3 min, then a 20 min gradient from 0% to 100% EtOAc in hexanes. The desired fraction was collected and concentrated to give Intermediate 291E (1.45 g, 4.63 mmol, 99% yield) as an yellow oil. 11H NMR (400 MHz, CHLOROFORM-d) δ 6.08 (dd, J=11.9, 2.6 Hz, 1H), 6.04-6.02 (m, 1H), 4.32 (dd, J=11.2, 2.2 Hz, 1H), 4.21-4.12 (m, 1H), 4.11-4.01 (m, 1H), 3.93 (dd, J=10.7, 4.5 Hz, 1H), 3.77 (dd, J=10.8, 7.3 Hz, 1H), 0.93-0.85 (m, 9H), 0.13-0.02 (m, 6H). $^{19}$F NMR (376 MHz, CHLOROFORM-d) δ −135.99 (s, 1F). LC-MS: method B, RT=3.41 min, MS (ESI) m/z: 314.1 (M+H)$^m$.

Intermediate 291F (S)-(2-amino-5-fluoro-7,8-dihydro-[1,4]dioxino[2', 3':3,4]benzo[1,2-d]thiazol-7-yl)methan ol and Intermediate 291F'

(S)-(2-amino-9-fluoro-6,7-dihydro-[1,4]dioxino[2', 3':4,5]benzo[1,2-d]thiazol-7-yl)methan ol

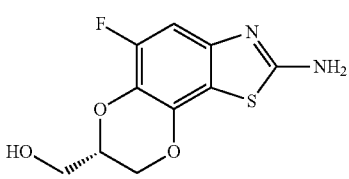

(291F)

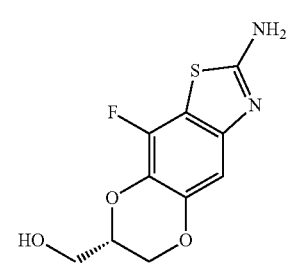

(291F')

To Intermediate 291E (650 mg, 2.074 mmol) in acetonitrile (10 mL) was added ammonium thiocyanate (174 mg, 2.281 mmol). The mixture was stirred at room temperature for 10 min. Benzyltrimethylammonium tribromide (809 mg, 2.074 mmol) in acetonitrile (2 mL) was added dropwise (5 min). The mixture was stirred at room temperature overnight, followed by heating at 55° C. for 3 hours. The mixture was diluted with EtOAc/saturated sodium bicarbonate. The insoluble material was removed by filtration. The organic layer of the filtrate was collected, washed with brine, dried over sodium sulfate. After evaporation of solvent, the crude sample was used for the next step without purification. TLC and NMR indicated a mixture of regio-isomers of Intermediate 291F and 291F' (531 mg, 2.072 mmol, 100% yield). LC-MS: method C, RT=1.08 min, MS (ESI) (m/z): 257.1 [M+1]$^m$.

Intermediate 291G (S)-(2-chloro-5-fluoro-7,8-dihydro-[1,4]dioxino[2', 3':3,4]benzo[1,2-d]thiazol-7-yl)methan ol and

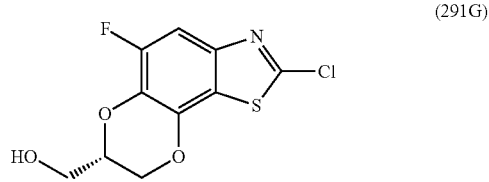 [SMILES: OC[C@H]1COc2c(c(F)cc3nc(Cl)sc23)O1]

(291G)

tert-Butyl nitrite (0.463 mL, 3.50 mmol) was added to copper (II) chloride (457 mg, 3.40 mmol) in dry acetonitrile (4 mL) under argon. The mixture was stirred at room temperature for 10 min. A suspension of Intermediate 291F and 291F' (531 mg, 2.072 mmol) in dry acetonitrile (4 mL) was added dropwise. The reaction mixture was stirred at room temperature for 2 hours. Acetonitrile was removed under vacuum, the reaction mixture was diluted with EtOAc, quenched with 1.0 N HCl. The organic layer was collected, washed with 0.5 N HCl (2×), saturated sodium bicarbonate, brine, dried over sodium sulfate. After evaporation of solvent, the crude product was dissolved in a small amount of chloroform and charged to a 40 g silica gel cartridge which was eluted with hexanes for 3 min., then a 20 min gradient from 0% to 70% EtOAc in hexanes, a mixture of regio-isomers (660 mg) was obtained as an off-white solid. LC-MS: method C, RT=1.93 min, MS (ESI) m/z: 276.0 [M+H]$^+$. The mixture of regio-isomers (400 mg, 1.45 mmol) was separated by preparative SFC (Column: Lux Cellulose-4, 30× 250 mm, 5 micron, Mobile Phase: 10% MeOH/80% CO$_2$, Flow Conditions: 100 mL/min, 150 Bar, 40° C., Detector Wavelength: 220 nm, Injection Details: 0.65 mL of ~20 mg/ml in MeOH). Intermediate 291G (1$^{st}$ peak, RT=9.25 min, 140 mg, 0.508 mmol, 35.0% yield) was obtained. $^1$H NMR (400 MHz, CHLOROFORM-d) δ 7.36 (d, J=10.6 Hz, 1H), 4.59-4.50 (m, 1H), 4.42-4.30 (m, 2H), 4.11-4.03 (m, 1H), 4.00-3.91 (m, 1H), 2.02 (br. s., 1H). $^{19}$F NMR (376 MHz, CHLOROFORM-d) δ −135.16 (s, 1F). LC-MS: method C, RT=1.93 min, MS (ESI) m/z: 276.0 [M+H]$^+$.

Example 291

To Intermediate I-9 (29.3 mg, 0.134 mmol), Intermediate 291G (37 mg, 0.134 mmol) and PdCl$_2$(dppf)—CH$_2$Cl$_2$ adduct (5.48 mg, 6.71 μmol) was added Toluene/EtOH (3:1) (1.5 mL). The mixture was sonicated for 1 min, and flushed with argon. To this was added sodium carbonate (99 μl, 1.5M, 0.148 mmol). The reaction mixture was heated in a microwave at 140° C. for 45 min. After cooling to room temperature, the mixture was loaded on to a 40 g ISCO column eluted with 0-100% EtOAc/DCM for 20 min. The desired fraction was collected and concentrated to give crude Example 291 (30 mg, 0.058 mmol, 43.3% yield). The sample was further purified via preparative LC/MS (Method D: Gradient: 45-90% B over 25 minutes, then a 4-minute hold at 100% B). $^1$H NMR (500 MHz, DMSO-d$_6$) δ 8.70 (s, 1H), 8.52 (s, 1H), 7.80 (s, 1H), 7.60 (d, J=10.8 Hz, 1H), 4.61 (d, J=11.1 Hz, 1H), 4.35 (br. s., 1H), 4.31-4.22 (m, 1H), 4.06 (s, 3H), 3.75 (d, J=4.7 Hz, 2H), 2.60 (s, 3H). LC-MS:

method L, RT=2.35 min, MS (ESI) m/z: 414 (M+H)+. Analytical HPLC purity (method B): 98%.

Example 292

(S)-5-fluoro-2-(2-methoxy-7-methylquinoxalin-5-yl)-7-(((2-methylpyrimidin-5-yl)oxy)methyl)-7,8-dihydro-[1,4]dioxino[2',3':3,4]benzo[1,2-d]thiazole

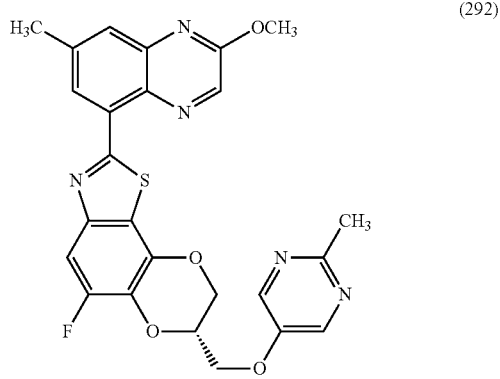

(292)

Intermediate 292A (R)-(5-fluoro-2-(2-methoxy-7-methylquinoxalin-5-yl)-7,8-dihydro-[1,4]dioxino[2',3':3,4]benzo[1,2-d]thiazol-7-yl)methyl chloroformate

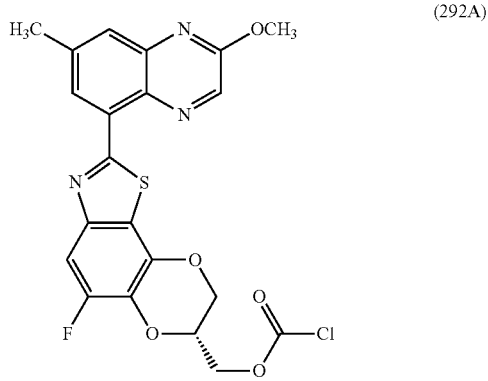 [SMILES: COc1cnc2c(-c3nc4cc(F)c5c(c4s3)OC[C@H](COC(=O)Cl)O5)cc(C)cc2n1]

(292A)

To a solution of Example 291 (60 mg, 0. 0.145 mmol) in THF (2 ml) at room temperature was added 15% phosgene in toluene (0.409 ml, 0.581 mmol). The reaction mixture was stirred for 2 min, DIEA (0.152 ml, 0.871 mmol) was added. The reaction was continued at room temperature for 40 min, at which time HPLC and LCMS indicated completion of reaction. Solvent was removed under high vacuum to give Intermediate 292A (69 mg, 100% yield) as a slightly yellow solid. It was used for the next step without any purification. LC-MS: Method H, 2 to 98% B. RT=2.25 min, MS (ESI) m/z: 472 and 474 (M+H)+.

Example 292

Intermediate 292A (69 mg, 0.145 mmol) in dichloromethane (2 mL) was added to a solution of 2-methylpyrimidin-5-amine (31.7 mg, 0.290 mmol) and pyridine (0.094 ml, 1.161 mmol) in dichloromethane (2 mL) dropwise. The reaction mixture was stirred at room temperature for 0.5 h, at which time LCMS and HPLC indicated a completion of reaction. The reaction mixture was quenched with 0.5 N HCl (2 mL) and extracted with DCM. The combined organic layer was washed with 1N HCl, NaHCO$_3$ and brine, dried with MgSO$_4$ and concentrated. The crude was purified with a 40 g ISCO column eluted with 0-100% EtOAc/DCM for 20 min. The desired fractions were collected and concentrated to give 20 mg of desired product. The product was further purified using a preparative HPLC (method A, 65-100% B over 10 minutes, then a 2-minute hold at 100% B). Fractions containing the desired product were combined and dried via centrifugal evaporation, then lyophilized to yield the Example 292 (35 mg, 34.6% yield) as a yellow lyophilate. $^1$H NMR (400 MHz, CHLOROFORM-d) δ 8.77 (s, 2H), 8.63 (d, J=1.8 Hz, 1H), 8.55 (s, 1H), 7.77 (s, 1H), 7.54 (d, J=10.8 Hz, 1H), 6.86-6.75 (m, 1H), 4.65 (d, J=4.6 Hz, 1H), 4.60-4.54 (m, 3H), 4.36 (dd, J=11.6, 6.7 Hz, 1H), 4.14 (s, 3H), 2.72 (s, 3H), 2.66 (s, 3H). $^{19}$F NMR (376 MHz, CHLOROFORM-d) δ -136.02 (s, 1F). LC-MS: Method H, 0 to 100% B. RT=2.49 min, MS (ESI) m/z: 549.2 (M+H)+. Analytical HPLC purity (method B): 95% purity.

What is claimed is:

1. A compound of Formula (I):

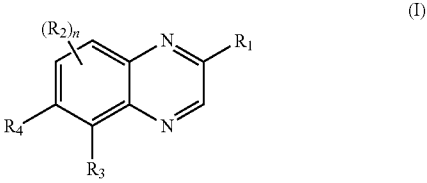

(I)

or a salt thereof, wherein

R$_1$ is F, Cl, —OH, C$_{1-4}$ alkyl, C$_{1-4}$ fluoroalkyl, C$_{2-4}$ alkenyl, C$_{2-4}$ alkynyl, C$_{3-7}$ cycloalkyl, C$_{3-7}$ fluorocycloalkyl, C$_{1-4}$ alkoxy, C$_{1-4}$ fluoroalkoxy, C$_{2-4}$ hydroxyalkoxy, C$_{3-6}$ cycloalkoxy, (C$_{1-3}$ alkoxy)-(C$_{1-3}$ alkylene), (C$_{1-3}$ alkoxy)-(C$_{1-3}$ fluoroalkylene), (C$_{1-3}$ deuteroalkoxy)-(C$_{1-3}$ deuteroalkylene), (C$_{1-3}$ fluoroalkoxy)-(C$_{1-3}$ alkylene), (C$_{1-3}$ fluoroalkoxy)-(C$_{1-3}$ fluoroalkylene), —(CH$_2$)$_{1-3}$O(phenyl), —(CH$_2$)$_{1-3}$NR$_a$R$_a$, —C(O)O(C$_{1-6}$ alkyl), —C(O)NR$_a$R$_a$, —C(O)NR$_b$R$_b$, —NH$_2$, —NH(C$_{1-6}$ alkyl), —N(C$_{1-6}$ alkyl)$_2$, azetidinyl, pyrrolidinyl, furanyl, pyranyl, piperidinyl, morpholinyl, piperazinyl, —S(O)$_2$(C$_{1-3}$ alkyl), —S(O)$_2$NR$_a$R$_a$, C$_{1-3}$ alkylthio, or C$_{1-3}$ fluoroalkylthio;

R$_2$, at each occurrence, is independently H, F, Cl, Br, —OH, —CN, C$_{1-4}$ alkyl, C$_{1-4}$ fluoroalkyl, C$_{1-4}$ hydroxyalkyl, C$_{1-3}$ aminoalkyl, C$_{2-4}$ alkenyl, C$_{2-4}$ alkynyl, C$_{3-7}$ cycloalkyl, C$_{3-7}$ fluorocycloalkyl, C$_{1-6}$ alkoxy, C$_{1-3}$ fluoroalkoxy, C$_{1-3}$ alkylthio, C$_{1-3}$ fluoroalkylthio, (C$_{1-3}$ alkoxy)-(C$_{1-3}$ alkylene), (C$_{1-3}$ fluoroalkoxy)-(C$_{1-3}$ alkylene), —C(O)NH$_2$, —C(O)NH(C$_{1-6}$ alkyl), —C(O)N(C$_{1-6}$ alkyl)$_2$, —C(O)NR$_b$R$_b$, —CH(OH)(C$_{3-6}$ cycloalkyl), —CH(OH)(phenyl), CH(OH)(pyridyl), —S(O)$_2$(C$_{1-3}$ alkyl), —S(O)$_2$NR$_a$R$_a$, or a cyclic group selected from phenyl, 5- to 6-membered heteroaryl, and 5- to 7-membered heterocycle, wherein said cyclic group is substituted with zero to 5 substituents independently selected from F, Cl, hydroxy, C$_{1-3}$ alkyl, C$_{1-3}$ alkoxy, cyclopropyl, and —CN;

$R_3$ is:

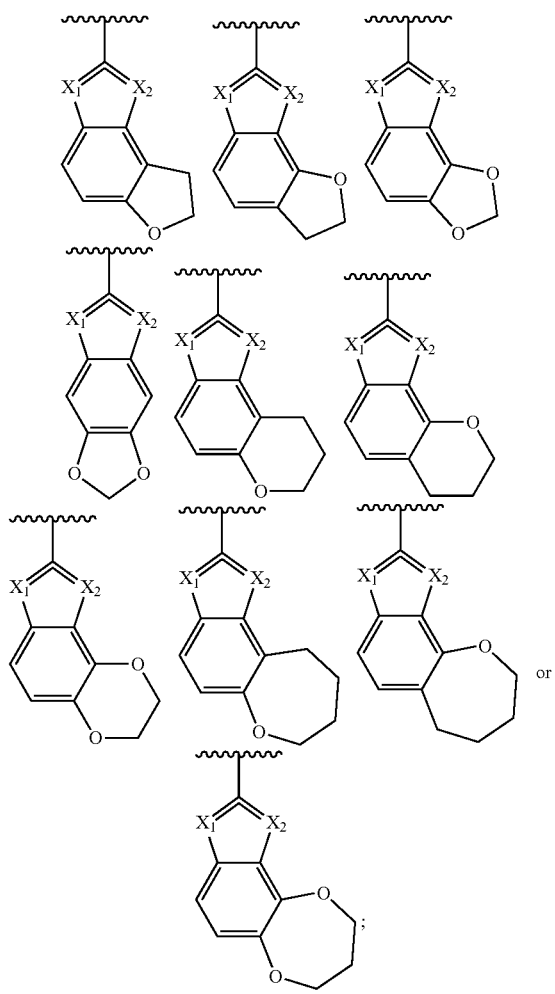

(i) $X_1$ is N and $X_2$ is S, O, or NH;
(ii) $X_1$ is O and $X_2$ is CH or N;
(iii) $X_1$ is NH and $X_2$ is CH; or
(iv) $X_1$ is CH and $X_2$ is S or NH;
and the dashed lines represent the variable position of a double bond to maintain aromaticity, each $R_3$ is substituted with $R_{3a}$ and zero to 3 $R_{3b}$;

$R_{3a}$ is
(i) H, $C_{1-6}$ hydroxyalkyl, $C_{1-6}$ hydroxyfluoroalkyl, —C(O)O($C_{1-6}$ alkyl), —$CR_aR_a$NHC(O)($C_{1-6}$ alkyl), —$CR_aR_a$NHC(O)($C_{1-6}$ fluoroalkyl), —$CR_aR_a$NHC(O)O($C_{1-6}$ alkyl), —$CR_aR_a$NHC(O)O($CH_2$)$_{1-3}$($C_{1-3}$ alkoxy), —$CR_aR_a$NHC(O)O$C_{1-4}$ fluoroalkyl), —$CR_aR_a$NHS(O)$_2$($C_{1-3}$ alkyl), $CR_aR_a$NHS(O)$_2$($C_{1-3}$ fluoroalkyl), —$CR_aR_a$OP(O)(OH)$_2$, —$CR_aR_a$NHC(O)$R_x$, —$CR_aR_a$NHC(O)O$R_x$, —$CR_aR_a$NHC(O)CH$_2R_x$, —$CR_aR_a$NHC(O)OCH$_2R_x$, —$CR_aR_a$OC(O)NHR$_x$, —$CR_aR_a$NHC(O)NHR$_x$, —$CR_aR_a$OR$_x$, or —$CR_aR_a$OC(O)R$_x$;
(ii) —CH(OH)CR$_h$R$_i$R$_j$ wherein R$_h$ and R$_i$ are independently H, F, $C_{1-4}$ alkyl, $C_{1-4}$ fluoroalkyl, $C_{1-3}$ alkoxy, or $C_{1-3}$ fluoroalkoxy, or taken together with the carbon atom to which they are attached, form $C_3$ s cycloalkyl or 4- to 7-membered heterocyclyl ring; and R$_j$ is H, $C_{1-6}$ alkyl, $C_{1-5}$ fluoroalkyl, ($C_{1-3}$ alkoxy)-($C_{1-3}$ alkyl), $C_3$ s cycloalkyl, $C_3$ s heterocyclyl, aryl, or heteroaryl;

$R_x$ is $C_{3-6}$ cycloalkyl, phenyl, pyridinyl, pyridazinyl, pyrimidinyl, pyrazinyl, benzo[d]oxazolyl, benzo[d]thiazolyl, pyrrolopyridinyl, tetrahydroisoquinolinyl, tetrahydrofuranyl, tetrahydropyranyl, morpholinyl, imidazopyridinyl, or oxo-dihydrobenzo[d]oxazolyl, each substituted with zero to two substituents independently selected from F, Cl, Br, —CN, —OH, —CH$_3$, —CF$_3$, $C_{1-3}$ alkoxy, $C_{1-3}$fluoroalkyl, $C_{1-6}$ hydroxyalkyl, $C_{1-6}$ hydroxyalkoxy, $C_{1-6}$ hydroxy-fluoroalkoxy, —NR$_a$R$_a$, —C(O)NR$_a$R$_a$, —C(O)NH($C_{1-6}$ alkyl), —C(O)N($C_{1-6}$ alkyl)$_2$, —C(O)NR$_b$R$_b$, —C(O)NR$_a$($C_{1-6}$hydroxyalkyl), —C(O)O($C_{1-6}$ alkyl), —C(O)(morpholinyl), —S(O)$_2$NR$_a$R$_a$, —CH(OH)CH$_{20}$H, —CH=CH$_2$, —NHC(O)CH$_3$, —OCH$_2$CH$_2$N(CH$_3$)$_2$, —OCH$_2$CH$_{20}$H, —OCH$_2$CH(Me)OH, isoxazolyl, phenoxy, phenyl, pyrrolidinyl, thiophenyl, and methyl triazolyl;

$R_{3b}$, at each occurrence, is independently H, F, Cl, Br, —CN, $C_{1-3}$ alkyl, $C_{1-3}$ fluoroalkyl, $C_{1-3}$ hydroxyalkyl, —OCHF$_2$, $C_{3-6}$ cycloalkyl, $C_{3-6}$ fluorocycloalkyl, $C_{2-4}$ alkenyl, $C_{2-4}$ alkynyl, $C_{1-3}$ alkoxy, $C_{1-3}$ alkylthio, or $C_{1-3}$ fluoroalkoxy;

$R_4$ is H, F, Cl, or —CH$_3$;

$R_a$, at each occurrence, is independently H, $C_{1-4}$alkyl, or $C_{1-4}$fluoroalkyl;

two $R_b$ along with the nitrogen atom to which they are attached form a 4- to 7-membered heterocyclo ring having 1 to 2 nitrogen atoms and 0-1 oxygen or sulfur atoms; and n is zero, 1, or 2.

2. The compound according to claim 1 having the structure of Formula (I):

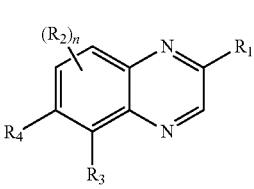

(I)

or a salt thereof, wherein
$R_3$ is:

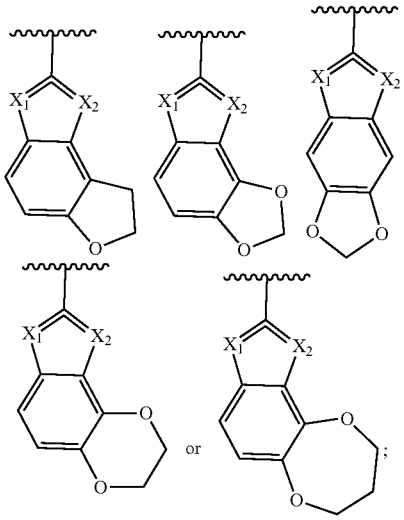

$X_1$ is N and $X_2$ is S or O; or
$X_1$ is O and $X_2$ is CH; and
each $R_3$ is substituted with $R_{3a}$ and zero to 3 $R_{3b}$.

3. The compound according to claim 2 having the structure of Formula (Ia):

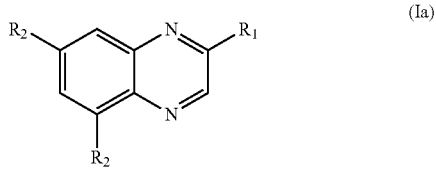

(Ia)

or a salt thereof, wherein
$R_1$ is —$CH_3$, —$OCH_3$, —$OCH_2CH_3$, or —$OCHF_2$;
$R_2$ is F, Cl, —CN, —$CH_3$, —$CH_2F$, —$CHF_2$, —$CH_2OH$, —$CH(CH_3)OH$, or —$CH=CH_2$;
$R_{3a}$ is H, —$CH_2OH$, —$CH(CH_3)OH$, —$CH_2CH(CH_3)$ OH, —$CH(OH)C(CH_3)_3$, —$CH(OH)$(trifluoromethyl cyclopropyl), —$CH(OH)$(trifluoromethyl cyclobutyl), —$CH(OH)$(methyl cyclohexyl), —$CH_2NHC(O)CH_3$, —$CH_2NHC(O)CF_3$, —$CH_2NHC(O)CH_2$(phenyl), —$CH_2NHC(O)$(morpholinyl), —$CH_2NHC(O)OCH_3$, —$CH_2NHC(O)NH$(cyclopropyl), —$CH_2NHC(O)NH$(phenyl), —$CH_2NHC(O)OCH_2CH_3$, —$CH_2NHC(O)OC(CH_3)_3$, —$CH_2NHC(O)OCH_2CH(CH_3)_2$, —$CH_2NHC(O)OCH_2C(CH_3)_3$, —$CH_2NHC(O)OCH_2CH_2F$, —$CH_2NHC(O)OCH_2CF_3$, —$CH_2NHC(O)OCH_2CH_2OCH_3$, —$CH_2NHS(O)_2CH_3$, —$CH_2O$(methyl pyrimidinyl), —$CH_2OC(O)$(dimethylaminopyridinyl), —$CH_2OP(O)(OH)_2$, —$C(O)OCH_3$, —$CH_2NHC(O)OR_x$, —$CH_2NHC(O)OCH_2R_x$, or —$CH_2OC(O)NHR_x$;
$R_x$ is phenyl, pyridinyl, pyridazinyl, pyrimidinyl, benzo[d]oxazolyl, benzo[d]thiazolyl, pyrrolopyridinyl, tetrahydroisoquinolinyl, tetrahydrofuranyl, tetrahydropyranyl, imidazopyridinyl, or oxo-dihydrobenzo[d]oxazolyl, each substituted with zero to two substituents independently selected from F, Cl, Br, —CN, —OH, —$CH_3$, —$CF_3$, —$CH_2CH_2OH$, $C_{1-2}$ alkoxy, phenoxy, —$NR_aR_a$, —$C(O)NR_aR_a$, —$C(O)OCH_3$, —$C(O)OC(CH_3)_3$, —$C(O)$(morpholinyl), —$CH(OH)CH_2OH$, —$OCH_2CH_2OH$, —$OCH_2CF_2OH$, —$OCH_2CH(CH_3)OH$, —$CH=CH_2$, —$NHC(O)CH_3$, —$OCH_2CH_2N(CH_3)_2$, isoxazolyl, phenoxy, phenyl, pyrrolidinyl, thiophenyl, and methyl triazolyl; and
$R_{3b}$ is H, F, Cl, —$CH_3$, or —$CHF_2$.

4. The compound according to claim 3 or a salt thereof, wherein said compound of Formula (Ia) is selected from:

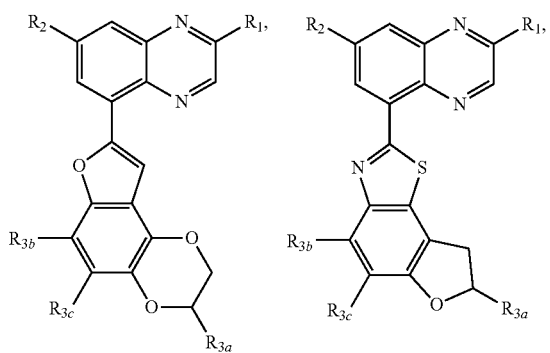

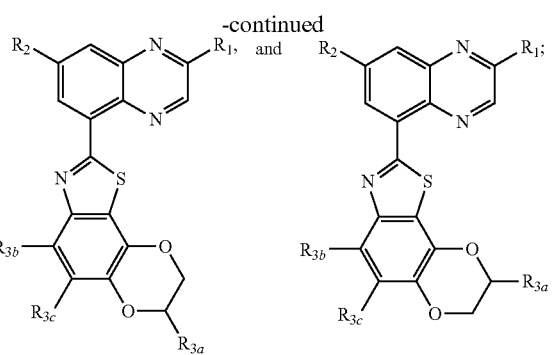

where $R_{3c}$ is H or F.

5. The compound according to claim 4 or a salt thereof, wherein $R_x$ is
(i) pyridazinyl, benzo[d]oxazolyl, benzo[d]thiazolyl, pyrrolopyridinyl, tetrahydroisoquinolinyl, methyl imidazopyridinyl, or oxo-dihydrobenzo[d]oxazolyl;
(ii) phenyl substituted with zero to 1 substituent selected from —CN and —C(O)(morpholinyl);
(iii) pyridinyl substituted with zero to two substituents independently selected from F, Cl, Br, —CN, —OH, —$CH_3$, —$CF_3$, $C_{1-2}$ alkoxy, phenoxy, —$NH_2$, —$N(CH_3)_2$, —$C(O)NH_2$, —$C(O)OC(CH_3)_3$, —$C(O)OCH_3$, —$CH(OH)CH_2OH$, —$CH=CH_2$, —$NHC(O)CH_3$, —$OCH_2CH_2N(CH_3)_2$, phenyl, pyrrolidinyl, thiophenyl, and methyl triazolyl; or
(iv) pyrimidinyl substituted with $C_1$ or —$CH_3$.

6. The compound according to claim 1 or a salt thereof, wherein said compound is selected from
(R)-(4-chloro-2-(2-methoxy-7-methylquinoxalin-5-yl)-7,8-dihydro-[1,4]dioxino[2',3':3,4]benzo[1,2-d]thiazol-7-yl)methyl (6-methoxypyridin-3-yl)carbamate (1);
(S)-(4-chloro-2-(2-methoxy-7-methylquinoxalin-5-yl)-7,8-dihydro-[1,4]dioxino [2',3':3,4]benzo[1,2-d]thiazol-7-yl)methyl (6-methoxypyridin-3-yl)carbamate (2);
(2-(2-methoxy-7-methylquinoxalin-5-yl)-4-methyl-7,8-dihydro-[1,4]dioxino[2',3':3,4]benzo [1,2-d]thiazol-7-yl)methyl (2-hydroxypyridin-4-yl)carbamate (3);
(R)-(2-(2-methoxy-7-methylquinoxalin-5-yl)-4-methyl-7,8-dihydro-[1,4]dioxino[2',3':3,4]benzo[1,2-d]thiazol-7-yl)methyl (6-methoxypyridin-3-yl)carbamate (4);
(R)-(2-(2-methoxy-7-methylquinoxalin-5-yl)-4-methyl-7,8-dihydro-[1,4]dioxino[2',3':3,4]benzo[1,2-d]thiazol-7-yl)methyl pyridin-3-ylcarbamate (5);
(R)-(6-chloro-8-(2-methoxy-7-methylquinoxalin-5-yl)-2,3-dihydro-[1,4]dioxino[2,3-e]benzofuran-3-yl)methyl (6-methylpyridin-3-yl)carbamate (7);
(R)-(6-chloro-8-(2-methoxy-7-methylquinoxalin-5-yl)-2,3-dihydro-[1,4]dioxino[2,3-e]benzofuran-3-yl)methyl (2-methylpyridin-4-yl)carbamate (8);
(R)-(6-chloro-8-(2-methoxy-7-methylquinoxalin-5-yl)-2,3-dihydro-[1,4]dioxino[2,3-e]benzofuran-3-yl) methyl (6-methoxypyridin-3-yl)carbamate (9);
(R)-(6-chloro-8-(2-methoxy-7-methylquinoxalin-5-yl)-2,3-dihydro-[1,4]dioxino[2,3-e]benzofuran-3-yl)methyl pyridin-3-ylcarbamate (10);
(R)-(8-(2-methoxy-7-methylquinoxalin-5-yl)-2,3-dihydro-[1,4]dioxino[2,3-e]benzofuran-3-yl)methyl (6-methoxypyridin-3-yl)carbamate (11);
(R)-(8-(2-methoxy-7-methylquinoxalin-5-yl)-2,3-dihydro-[1,4]dioxino[2,3-e]benzofuran-3-yl) methyl (2-methylpyridin-4-yl)carbamate (12);

(R)-(8-(2-methoxy-7-methylquinoxalin-5-yl)-2,3-dihydro-[1,4]dioxino[2,3-e]benzofuran-3-yl)methy1 (6-methoxypyridin-3-yl) carbamate (13);

(R)-(8-(2-methoxy-7-methylquinoxalin-5-yl)-6-methyl-2,3-dihydro-[1,4]dioxino[2,3-e]benzofuran-3-yl)methyl (6-methylpyridin-3-yl)carbamate (14);

(R)-(8-(2-methoxy-7-methylquinoxalin-5-yl)-6-methyl-2,3-dihydro-[1,4]dioxino[2,3-e]benzofuran-3-yl)methyl (2-methylpyridin-4-yl)carbamate (15);

(R)-(8-(2-methoxy-7-methylquinoxalin-5-yl)-6-methyl-2,3-dihydro-[1,4]dioxino[2,3-e]benzofuran-3-yl)methyl (6-methoxypyridin-3-yl)carbamate (16);

(4-chloro-2-(2-methoxy-7-methylquinoxalin-5-yl)-7,8-dihydrobenzofuro[5,4-d]thiazol-7-yl)methyl (6-methoxypyridin-3-yl)carbamate (17);

(4-chloro-2-(2-methoxy-7-methylquinoxalin-5-yl)-7,8-dihydrobenzofuro[5,4-d] thiazol-7-yl)methyl pyridin-3-ylcarbamate (18);

(4-chloro-2-(2-methoxy-7-methylquinoxalin-5-yl)-7,8-dihydrobenzofuro[5,4-d]thiazol-7-yl)methyl (6-methylpyridin-3-yl)carbamate (19);

(R)-(4-chloro-2-(2-methoxy-7-methylquinoxalin-5-yl)-7,8-dihydrobenzofuro[5,4-d]thiazol-7-yl)methyl (6-methylpyridin-3-yl)carbamate (20);

tert-butyl ((2-(2-(difluoromethoxy)-7-methylquinoxalin-5-yl)-4-fluoro-7,8-dihydro-[1,4]dioxino[2',3':3,4]benzo[1,2-d]thiazol-7-yl)methyl)carbamate (21);

(2-(2-(difluoromethoxy)-7-methylquinoxalin-5-yl)-4-fluoro-7,8-dihydro-[1,4]dioxino[2',3':3,4]benzo[1,2-d]thiazol-8-yl)methanol (22);

tert-butyl ((2-(2-(difluoromethoxy)-7-methylquinoxalin-5-yl)-4-fluoro-7,8-dihydro-[1,4]dioxino[2',3':3,4]benzo[1,2-d]thiazol-8-yl)methyl)carbamate (23);

(4-fluoro-2-(2-methoxy-7-methylquinoxalin-5-yl)-7,8-dihydro-[1,4]dioxino[2',3':3,4]benzo[1,2-d]thi azol-8-yl)methyl phenylcarbamate (24);

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (5-chloropyridin-3-yl)carbamate (25);

(R)-(4-chloro-2-(2-methoxy-7-methylquinoxalin-5-yl)-7,8-dihydro-[1,4]dioxino[2',3':3,4]benzo[1,2-d] thiazol-7-yl)methyl phenylcarbamate (26);

(R)-(4-chloro-2-(2-methoxy-7-methylquinoxalin-5-yl)-7,8-dihydro-[1,4]dioxino[2',3':3,4]benzo[1,2-d]thiazol-7-yl) methyl (3-cyanophenyl)carbamate (27);

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (5-fluoropyridin-3-yl)carbamate (28);

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (6-fluoropyridin-3-yl)carbamate (29);

(R)-(4-chloro-2-(2-methoxy-7-methylquinoxalin-5-yl)-7,8-dihydro-[1,4]dioxino[2',3':3,4]benzo[1,2-d]thiazol-7-yl)methyl pyridin-4-ylcarbamate (30);

(R)-(4-chloro-2-(2-methoxy-7-methylquinoxalin-5-yl)-7,8-dihydro-[1,4]dioxino[2',3':3,4]benzo[1,2-d]thiazol-7-yl)methyl pyridin-3-ylcarbamate (31);

(R)-(4-chloro-2-(2-methoxy-7-methylquinoxalin-5-yl)-7,8-dihydro-[1,4]dioxino[2',3':3,4]benzo[1,2-d] thiazol-7-yl)methyl (6-chloropyridin-3-yl)carbamate (32);

(R)-(4-chloro-2-(2-methoxy-7-methylquinoxalin-5-yl)-7,8-dihydro-[1,4]dioxino[2',3':3,4]benzo[1,2-d]thiazol-7-yl) methyl (2-methylpyridin-4-yl)carbamate (33);

(R)-(4-chloro-2-(2-methoxy-7-methylquinoxalin-5-yl)-7,8-dihydro-[1,4]dioxino[2',3':3,4]benzo[1,2-d]thiazol-7-yl) methyl pyridazin-4-ylcarbamate (34);

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (6-cyanopyridin-3-yl)carbamate (35);

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (2-methoxypyridin-4-yl)carbamate (36);

(R)-(4-chloro-2-(2-methoxy-7-methylquinoxalin-5-yl)-7,8-dihydro-[1,4]dioxino [2',3':3,4]benzo[1,2-d]thiazol-7-yl)methyl (5-cyanopyridin-3-yl)carbamate (37);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (6-cyanopyridin-3-yl)carbamate (38);

(R)-(4-chloro-2-(2-methoxy-7-methylquinoxalin-5-yl)-7,8-dihydro-[1,4]dioxino[2',3':3,4]benzo[1,2-d] thiazol-7-yl)methyl benzo[d]thiazol-5-ylcarbamate (39);

(R)-(4-chloro-2-(2-methoxy-7-methylquinoxalin-5-yl)-7,8-dihydro-[1,4]dioxino[2',3':3,4]benzo[1,2-d]thiazol-7-yl) methyl benzo[d]thiazol-6-ylcarbamate (40);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (6-fluoropyridin-3-yl)carbamate (41);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (5-fluoropyridin-3-yl)carbamate (42);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (5-methoxypyridin-3-yl)carbamate (43);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (2-methylpyridin-4-yl)carbamate (44);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (2-methoxypyridin-4-yl)carbamate (45);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (3-cyanophenyl)carbamate (46);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (6-chloropyridin-3-yl) carbamate (47);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl pyridin-4-ylcarbamate (48);

(R)-(2-(2-methoxy-7-methylquinoxalin-5-yl)-4-methyl-7,8-dihydro-[1,4]dioxino[2',3':3,4]benzo [1,2-d]thiazol-7-yl)methyl benzo[d]thiazol-5-ylcarbamate (49);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl benzo[d]thiazol-6-ylcarbamate (50);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (5-cyanopyridin-3-yl)carbamate (51);

(R)-(2-(2,7-dimethylquinoxalin-5-yl)-4-methyl-7,8-dihydro-[1,4]dioxino[2',3':3,4]benzo[1,2-d]thiazol-7-yl) methyl (6-(dimethylamino) pyridin-3-yl) carbamate (52);

(R)-(2-(2-methoxy-7-methylquinoxalin-5-yl)-4-methyl-7,8-dihydro-[1,4]dioxino [2',3':3,4]benzo[1,2-d]thiazol-7-yl)methyl (6-(thiophen-2-yl) pyridin-3-yl)carbamate (53);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (3-methyl-3H-imidazo [4,5-b]pyridin-6-yl)carbamate (54);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (6-(3-methyl-1H-1,2,4-triazol-1-yl)pyridin-3-yl)carbamate (55);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (6-methylpyridin-3-yl)carbamate (56);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (5-methylpyridin-3-yl)carbamate (57);

(R)-(4-chloro-2-(2-methoxy-7-methylquinoxalin-5-yl)-7,8-dihydro-[1,4]dioxino[2',3':3,4]benzo[1,2-d]thiazol-7-yl) methyl (2-chloropyrimidin-5-yl)carbamate (58);

(R)-(2-(2-methoxy-7-methylquinoxalin-5-yl)-4-methyl-7,8-dihydro-[1,4]dioxino[2',3':3,4]benzo[1,2-d]thiazol-7-yl)methyl (2-chloropyrimidin-5-yl)carbamate (59);

(R)-(4-chloro-2-(2-methoxy-7-methylquinoxalin-5-yl)-7,8-dihydro-[1,4]dioxino[2',3':3,4]benzo[1,2-d]thiazol-7-yl)methyl (5,6-dimethylpyridin-3-yl) carbamate (60);

(R)-(2-(2-methoxy-7-methylquinoxalin-5-yl)-4-methyl-7,8-dihydro-[1,4]dioxino [2',3':3,4]benzo[1,2-d]thiazol-7-yl)methyl (6-fluoro-5-methylpyridin-3-yl)carbamate (61);

(R)-(4-chloro-2-(2,7-dimethylquinoxalin-5-yl)-7,8-dihydro-[1,4]dioxino[2',3':3,4]benzo[1,2-d]thiazol-7-yl) methyl (6-methylpyridin-3-yl) carbamate (62);

(R)-(4-chloro-2-(2,7-dimethylquinoxalin-5-yl)-7,8-dihydro-[1,4]dioxino [2',3':3,4]benzo[1,2-d]thiazol-7-yl) methyl (5-methylpyridin-3-yl)carbamate (63);

(R)-(4-chloro-2-(2-methoxy-7-methylquinoxalin-5-yl)-7,8-dihydro-[1,4]dioxino [2',3':3,4]benzo [1,2-d]thiazol-7-yl)methyl (6-fluoro-5-methylpyridin-3-yl)carbamate (64);

(R)-(4-chloro-2-(2-methoxy-7-methylquinoxalin-5-yl)-7,8-dihydro-[1,4]dioxino [2',3':3,4]benzo[1,2-d] thiazol-7-yl)methyl (6-(dimethylamino)pyridin-3-yl)carbamate (65);

(R)-(4-chloro-2-(2-methoxy-7-methylquinoxalin-5-yl)-7,8-dihydro-[1,4]dioxino[2',3':3,4]benzo[1,2-d] thiazol-7-yl)methyl (2-oxo-2,3-dihydrobenzo[d]oxazol-6-yl) carbamate (66);

(R)-(4-chloro-2-(2-methoxy-7-methylquinoxalin-5-yl)-7,8-dihydro-[1,4]dioxino[2',3':3,4]benzo [1,2-d]thiazol-7-yl)methyl (3-methyl-3H-imidazo[4,5-b]pyridin-6-yl) carbamate (67);

(R)-(4-fluoro-2-(2-methoxy-7-methylquinoxalin-5-yl)-7,8-dihydro-[1,4]dioxino[2',3':3,4]benzo[1,2-d]thiazol-7-yl)methyl (6-methoxypyridin-3-yl)carbamate (68);

(R)-(4-chloro-2-(2-methoxy-7-methylquinoxalin-5-yl)-7,8-dihydro-[1,4]dioxino[2',3':3,4]benzo[1,2-d] thiazol-7-yl)methyl (6-(3-methyl-1H-1,2,4-triazol-1-yl)pyridin-3-yl)carbamate (69);

(R)-(4-fluoro-2-(2-methoxy-7-methylquinoxalin-5-yl)-7,8-dihydro-[1,4]dioxino[2',3':3,4]benzo[1,2-d]thiazol-7-yl)methyl pyridin-3-ylcarbamate (70);

(R)-(4-fluoro-2-(2-methoxy-7-methylquinoxalin-5-yl)-7,8-dihydro-[1,4]dioxino[2',3':3,4]benzo[1,2-d]thiazol-7-yl) methyl (6-fluoropyridin-3-yl)carbamate (71);

(R)-(4-fluoro-2-(2-methoxy-7-methylquinoxalin-5-yl)-7,8-dihydro-[1,4]dioxino[2',3':3,4]benzo[1,2-d]thiazol-7-yl) methyl (3-cyanophenyl)carbamate (72);

(R)-(4-fluoro-2-(2-methoxy-7-methylquinoxalin-5-yl)-7,8-dihydro-[1,4]dioxino[2',3':3,4]benzo[1,2-d]thiazol-7-yl)methyl pyridin-4-ylcarbamate (73);

(4-(difluoromethyl)-2-(2-methoxy-7-methylquinoxalin-5-yl)-7,8-dihydro-[1,4]dioxino[2',3':3,4]benz o[1,2-d] thiazol-7-yl)methyl (2-methylpyridin-4-yl) carbamate (74);

(R)-(4-fluoro-2-(2-methoxy-7-methylquinoxalin-5-yl)-7,8-dihydro-[1,4]dioxino[2',3':3,4]benzo[1,2-d]thiazol-7-yl)methyl (2-methylpyridin-4-yl)carbamate (75);

(R)-(4-fluoro-2-(2-methoxy-7-methylquinoxalin-5-yl)-7,8-dihydro-[1,4]dioxino[2',3':3,4]benzo[1,2-d]thiazol-7-yl)methyl (6-methylpyridin-3-yl)carbamate (76);

(2-(2-methoxy-7-methylquinoxalin-5-yl)-4-methyl-7,8-dihydro-[1,4]dioxino [2',3':3,4]benzo[1,2-d]thiazol-7-yl)methyl (5-carbamoylpyridin-3-yl)carbamate (77);

(2-(2-methoxy-7-methylquinoxalin-5-yl)-4-methyl-7,8-dihydro-[1,4]dioxino[2',3':3,4]benzo[1,2-d]thiazol-7-yl)methyl (1-oxo-1,2,3,4-tetrahydroisoquinolin-7-yl) carbamate (78);

(2-(2-methoxy-7-methylquinoxalin-5-yl)-4-methyl-7,8-dihydro-[1,4]dioxino[2',3':3,4]benzo[1,2-d]thiazol-7-yl)methyl (2-methylpyrimidin-5-yl)carbamate (79);

(R)-(4-(difluoromethyl)-2-(2-methoxy-7-methylquinoxalin-5-yl)-7,8-dihydro-[1,4]dioxino[2',3':3,4]b enzo[1,2-d] thiazol-7-yl)methyl (6-methylpyridin-3-yl)carbamate (80);

(R)-(4-(difluoromethyl)-2-(2-methoxy-7-methylquinoxalin-5-yl)-7,8-dihydro-[1,4]dioxino[2',3':3,4]b enzo[1,2-d] thiazol-7-yl)methyl (6-methoxypyridin-3-yl)carbamate (81);

(2-(2-methoxy-7-methylquinoxalin-5-yl)-4-methyl-7,8-dihydro-[1,4]dioxino[2',3':3,4]benzo[1,2-d]th iazol-7-yl)methyl benzo[d]oxazol-5-ylcarbamate (82);

(R)-(4-fluoro-2-(7-(hydroxymethyl)-2-methoxyquinoxalin-5-yl)-7,8-dihydro-[1,4]dioxino[2',3':3,4]b enzo[1,2-d]thiazol-7-yl) methyl pyridin-3-ylcarbamate (83);

(R)-(2-(7-(difluoromethyl)-2-methoxyquinoxalin-5-yl)-4-methyl-7,8-dihydro-[1,4]dioxino[2',3':3,4]b enzo[1,2-d]thiazol-7-yl)methyl (2-methylpyridin-4-yl)carbamate (84);

(R)-(4-fluoro-2-(7-(hydroxymethyl)-2-methoxyquinoxalin-5-yl)-7,8-dihydro-[1,4]dioxino[2',3':3,4]b enzo[1,2-d]thiazol-7-yl) methyl (2-methylpyridin-4-yl)carbamate (85);

(2-(2-methoxy-7-vinylquinoxalin-5-yl)-4-methyl-7,8-dihydro-[1,4]dioxino[2',3':3,4]benzo[1,2-d]thia zol-7-yl) methyl (6-methoxypyridin-3-yl)carbamate (86);

(2-(7-(hydroxymethyl)-2-methoxyquinoxalin-5-yl)-4-methyl-7,8-dihydro-[1,4]dioxino[2',3':3,4]benz o[1,2-d]thiazol-7-yl)methyl (6-methoxypyridin-3-yl)carbamate (87);

(2-(7-(1-hydroxyethyl)-2-methoxyquinoxalin-5-yl)-4-methyl-7,8-dihydro-[1,4]dioxino[2',3':3,4]benz o[1,2-d]thiazol-7-yl)methyl (6-methoxypyridin-3-yl)carbamate (88);

(2-(2-methoxy-7-vinylquinoxalin-5-yl)-4-methyl-7,8-dihydro-[1,4]dioxino[2',3':3,4]benzo[1,2-d]thia zol-7-yl) methyl pyridin-3-ylcarbamate (89);

(2-(7-(hydroxymethyl)-2-methoxyquinoxalin-5-yl)-4-methyl-7,8-dihydro-[1,4]dioxino[2',3':3,4]benzo[1,2-d]thiazol-7-yl)methyl pyridin-3-ylcarbamate (90);

(R)-(2-(7-cyano-2-methoxyquinoxalin-5-yl)-4-methyl-7,8-dihydro-[1,4]dioxino[2',3':3,4]benzo[1,2-d]thiazol-7-yl)methyl (6-methylpyridin-3-yl)carbamate (91);

(R)-(2-(7-cyano-2-methoxyquinoxalin-5-yl)-4-methyl-7,8-dihydro-[1,4]dioxino[2',3':3,4]benzo[1,2-d] thiazol-7-yl)methyl (2-methylpyridin-4-yl)carbamate (92);

(R)-(2-(7-cyano-2-methoxyquinoxalin-5-yl)-4-methyl-7,8-dihydro-[1,4]dioxino[2',3':3,4]benzo[1,2-d]thiazol-7-yl)methyl pyridin-3-ylcarbamate (93);
(R)-(2-(7-cyano-2-methoxyquinoxalin-5-yl)-4-methyl-7,8-dihydro-[1,4]dioxino[2',3':3,4]benzo[1,2-d]thiazol-7-yl)methyl (6-methoxypyridin-3-yl)carbamate (94);
(2-(7-chloro-2-methoxyquinoxalin-5-yl)-4-methyl-7,8-dihydro-[1,4]dioxino[2',3':3,4]benzo[1,2-d]thiazol-7-yl)methyl pyridin-3-ylcarbamate (95);
(2-(7-chloro-2-methoxyquinoxalin-5-yl)-4-methyl-7,8-dihydro-[1,4]dioxino [2',3':3,4]benzo[1,2-d]thiazol-7-yl)methyl (6-fluoropyridin-3-yl)carbamate (96);
(2-(7-chloro-2-methoxyquinoxalin-5-yl)-4-methyl-7,8-dihydro-[1,4]dioxino[2',3':3,4]benzo [1,2-d]thiazol-7-yl)methyl (6-methylpyridin-3-yl)carbamate (97);
(R)-(2-(7-(hydroxymethyl)-2-methoxyquinoxalin-5-yl)-4-methyl-7,8-dihydro-[1,4]dioxino [2',3':3,4]benzo[1,2-d]thiazol-7-yl)methyl (6-methoxypyridin-3-yl)carbamate (98);
(R)-(2-(7-(hydroxymethyl)-2-methoxyquinoxalin-5-yl)-4-methyl-7,8-dihydro-[1,4]dioxino [2',3':3,4]benzo[1,2-d]thiazol-7-yl)methyl (2-methylpyridin-4-yl)carbamate (99);
(R)-(2-(7-(hydroxymethyl)-2-methoxyquinoxalin-5-yl)-4-methyl-7,8-dihydro-[1,4]dioxino [2',3':3,4]benzo[1,2-d]thiazol-7-yl)methyl (6-methylpyridin-3-yl)carbamate (100);
(R)-(2-(7-(hydroxymethyl)-2-methoxyquinoxalin-5-yl)-4-methyl-7,8-dihydro-[1,4]dioxino [2',3':3,4]benzo[1,2-d]thiazol-7-yl)methyl pyridin-3-ylcarbamate (101);
(R)-(2-(2-methoxy-7-methylquinoxalin-5-yl)-7,8-dihydro-[1,4]dioxino[2',3':3,4]benzo[1,2-d]thiazol-7-yl)methyl (6-methylpyridin-3-yl)carbamate (102);
(R)-(2-(2-methoxy-7-methylquinoxalin-5-yl)-7,8-dihydro-[1,4]dioxino [2',3':3,4]benzo[1,2-d]thiazol-7-yl)methyl (2-methylpyrimidin-5-yl)carbamate (103);
(R)-(2-(2-methoxy-7-methylquinoxalin-5-yl)-7,8-dihydro-[1,4]dioxino[2',3':3,4]benzo[1,2-d]thiazol-7-yl)methyl (6-methoxypyridin-3-yl)carbamate (104);
(R)-(2-(2-methoxy-7-methylquinoxalin-5-yl)-7,8-dihydro-[1,4]dioxino[2',3':3,4]benzo[1,2-d]thiazol-7-yl)methyl (6-cyanopyridin-3-yl)carbamate (105);
(R)-(2-(2-methoxy-7-methylquinoxalin-5-yl)-7,8-dihydro-[1,4]dioxino[2',3':3,4]benzo [1,2-d]thiazol-7-yl)methyl (2-oxo-2,3-dihydrobenzo [d]oxazol-6-yl)carbamate (106);
(R)-(2-(2-methoxy-7-methylquinoxalin-5-yl)-7,8-dihydro-[1,4]dioxino[2',3':3,4]benzo [1,2-d]thiazol-7-yl)methyl 1H-pyrrolo[2,3-b] pyridin-5-ylcarbamate (107);
(R)-(2-(2-methoxy-7-methylquinoxalin-5-yl)-7,8-dihydro-[1,4]dioxino[2',3':3,4]benzo[1,2-d]thiazol-7-yl)methyl pyridin-3-ylcarbamate (108);
(R)-(2-(2-methoxy-7-methylquinoxalin-5-yl)-7,8-dihydro-[1,4]dioxino[2',3':3,4]benzo[1,2-d]thiazol-7-yl)methyl (6-bromopyridin-3-yl)carbamate (109);
(R)-(2-(2-methoxy-7-methylquinoxalin-5-yl)-7,8-dihydro-[1,4]dioxino[2',3':3,4]benzo[1,2-d]thiazol-7-yl)methyl (6-vinylpyridin-3-yl)carbamate (110);
((R)-2-(2-methoxy-7-methylquinoxalin-5-yl)-7,8-dihydro-[1,4]dioxino[2',3':3,4]benzo [1,2-d]thiazol-7-yl)methyl (6-((S)-1,2-dihydroxyethyl)pyridin-3-yl)carbamate (111);
(R)-(2-(2-methoxy-7-methylquinoxalin-5-yl)-7,8-dihydro-[1,4]dioxino[2',3':3,4]benzo[1,2-d]thiazol-7-yl)methyl (6-fluoropyridin-3-yl)carbamate (112);
(R)-(2-(2-methoxy-7-methylquinoxalin-5-yl)-7,8-dihydro-[1,4]dioxino[2',3':3,4]benzo[1,2-d]thiazol-7-yl)methyl (5-cyanopyridin-3-yl)carbamate (113);
(R)-(2-(2-methoxy-7-methylquinoxalin-5-yl)-7,8-dihydro-[1,4]dioxino[2',3':3,4]benzo [1,2-d]thiazol-7-yl)methyl (4-(morpholine-4-carbonyl)phenyl)carbamate (114);
(2-(2-methoxy-7-methylquinoxalin-5-yl)-4-methyl-7,8-dihydro-[1,4]dioxino[2',3':3,4]benzo [1,2-d]thiazol-7-yl)methyl (6-chloropyridin-3-yl)carbamate (115);
(2-(2-methoxy-7-methylquinoxalin-5-yl)-4-methyl-7,8-dihydro-[1,4]dioxino[2',3':3,4]benzo[1,2-d]thiazol-7-yl)methyl (6-(dimethylamino)pyridin-3-yl)carbamate (116);
(2-(2-methoxy-7-methylquinoxalin-5-yl)-4-methyl-7,8-dihydro-[1,4]dioxino[2',3':3,4]benzo[1,2-d]thiazol-7-yl)methyl (2-phenylpyridin-4-yl)carbamate (117);
(2-(2-methoxy-7-methylquinoxalin-5-yl)-4-methyl-7,8-dihydro-[1,4]dioxino[2',3':3,4]benzo[1,2-d]thiazol-7-yl)methyl (2-fluoropyridin-4-yl)carbamate (118);
(2-(2-methoxy-7-methylquinoxalin-5-yl)-4-methyl-7,8-dihydro-[1,4]dioxino[2',3':3,4]benzo[1,2-d]thiazol-7-yl)methyl (5,6-dimethylpyridin-3-yl)carbamate (119);
(2-(2-methoxy-7-methylquinoxalin-5-yl)-4-methyl-7,8-dihydro-[1,4]dioxino[2',3':3,4]benzo[1,2-d]thiazol-7-yl)methyl (6-methylpyridin-3-yl)carbamate (120);
(2-(2-methoxy-7-methylquinoxalin-5-yl)-4-methyl-7,8-dihydro-[1,4]dioxino [2',3':3,4]benzo[1,2-d]thiazol-7-yl)methyl (6-phenoxypyridin-3-yl)carbamate (121);
(2-(2-methoxy-7-methylquinoxalin-5-yl)-4-methyl-7,8-dihydro-[1,4]dioxino[2',3':3,4]benzo[1,2-d]thiazol-7-yl)methyl (6-fluoro-5-methylpyridin-3-yl)carbamate (122);
(2-(2-methoxy-7-methylquinoxalin-5-yl)-4-methyl-7,8-dihydro-[1,4]dioxino[2',3':3,4]benzo [1,2-d]thiazol-7-yl)methyl (6-hydroxypyridin-3-yl)carbamate (123);
(2-(2-methoxy-7-methylquinoxalin-5-yl)-4-methyl-7,8-dihydro-[1,4]dioxino[2',3':3,4]benzo[1,2-d]thiazol-7-yl)methyl (5-methylpyridin-3-yl)carbamate (124);
(2-(2-methoxy-7-methylquinoxalin-5-yl)-4-methyl-7,8-dihydro-[1,4]dioxino[2',3':3,4]benzo[1,2-d]thiazol-7-yl)methyl (6-phenylpyridin-3-yl)carbamate (125);
(2-(2-methoxy-7-methylquinoxalin-5-yl)-4-methyl-7,8-dihydro-[1,4]dioxino[2',3':3,4]benzo[1,2-d]thiazol-7-yl)methyl (5-phenylpyridin-3-yl)carbamate (126);
(2-(2-methoxy-7-methylquinoxalin-5-yl)-4-methyl-7,8-dihydro-[1,4]dioxino[2',3':3,4]benzo[1,2-d]thiazol-7-yl)methyl (6-(thiophen-2-yl)pyridin-3-yl) carbamate (127);
(2-(2-methoxy-7-methylquinoxalin-5-yl)-4-methyl-7,8-dihydro-[1,4]dioxino[2',3:3,4]benzo[1,2-d]thiazol-7-yl)methyl (6-(2-(dimethylamino)ethoxy) pyridin-3-yl) carbamate (128);
(2-(2-methoxy-7-methylquinoxalin-5-yl)-4-methyl-7,8-dihydro-[1,4]dioxino[2',3':3,4]benzo[1,2-d]thiazol-7-yl)methyl (3-methyl-3H-imidazo [4,5-b]pyridin-6-yl) carbamate (129);
(2-(2-methoxy-7-methylquinoxalin-5-yl)-4-methyl-7,8-dihydro-[1,4]dioxino[2',3':3,4]benzo[1,2-d]thiazol-7-yl)methyl (6-(3-methyl-1H-1,2,4-triazol-1-yl)pyridin-3-yl)carbamate (130);
(2-(2-methoxy-7-methylquinoxalin-5-yl)-4-methyl-7,8-dihydro-[1,4]dioxino[2',3':3,4]benzo[1,2-d]thiazol-7-yl)methyl (6-(trifluoromethyl)pyridin-3-yl)carbamate (131);

(2-(2-methoxy-7-methylquinoxalin-5-yl)-4-methyl-7,8-dihydro-[1,4]dioxino[2',3':3,4]benzo[1,2-d]thiazol-7-yl)methyl (5-chloropyridin-3-yl)carbamate (132);

(2-(2-methoxy-7-methylquinoxalin-5-yl)-4-methyl-7,8-dihydro-[1,4]dioxino[2',3':3,4]benzo[1,2-d]thiazol-7-yl)methyl (6-ethoxypyridin-3-yl)carbamate (133);

methyl 4-((((2-(2-methoxy-7-methylquinoxalin-5-yl)-4-methyl-7,8-dihydro-[1,4]dioxino[2',3':3,4]benzo[1,2-d]thiazol-7-yl)methoxy)carbonyl)amino) picolinate (134);

tert-butyl 4-(5-((((2-(2-methoxy-7-methylquinoxalin-5-yl)-4-methyl-7,8-dihydro-[1,4]dioxino[2',3':3,4]benzo[1,2-d]thiazol-7-yl)methoxy)carbonyl)amino)pyridin-2-yl) piperazine-1-carboxylate (136);

(2-(2-methoxy-7-methylquinoxalin-5-yl)-4-methyl-7,8-dihydro-[1,4]dioxino[2',3':3,4]benzo[1,2-d]thiazol-7-yl)methyl (6-(pyrrolidin-1-yl) pyridin-3-yl)carbamate (137);

methyl 5-((((2-(2-methoxy-7-methylquinoxalin-5-yl)-4-methyl-7,8-dihydro-[1,4]dioxino[2',3':3,4]benzo[1,2-d]thiazol-7-yl)methoxy)carbonyl) amino)nicotinate (138);

(2-(2-methoxy-7-methylquinoxalin-5-yl)-4-methyl-7,8-dihydro-[1,4]dioxino[2',3':3,4]benzo[1,2-d]thiazol-7-yl)methyl (6-acetamidopyridin-3-yl)carbamate (140);

(2-(2-methoxy-7-methylquinoxalin-5-yl)-4-methyl-7,8-dihydro-[1,4]dioxino[2',3':3,4]benzo[1,2-d]thiazol-7-yl)methyl (6-aminopyridin-3-yl)carbamate (141);

(2-(2-methoxy-7-methylquinoxalin-5-yl)-4-methyl-7,8-dihydro-[1,4]dioxino[2',3':3,4]benzo[1,2-d]thiazol-7-yl)methyl 1H-pyrrolo[2,3-b]pyridin-5-ylcarbamate (142);

6-(2-(methoxymethyl)-7-methylquinoxalin-5-yl)-[1,3]dioxolo[4',5':4,5]benzo[1,2-d]thiazole (143);

(R)-(2-(2-methoxy-7-methylquinoxalin-5-yl)-7,8-dihydrobenzofuro[5,4-d]thiazol-7-yl)methyl (2-methylpyrimidin-5-yl)carbamate (144);

(R)-(5-fluoro-2-(2-methoxy-7-methylquinoxalin-5-yl)-7,8-dihydrobenzofuro[5,4-d]thiazol-7-yl)methyl (2-methylpyrimidin-5-yl) carbamate (145);

(S)-(5-fluoro-2-(2-methoxy-7-methylquinoxalin-5-yl)-7,8-dihydrobenzofuro[5,4-d]thiazol-7-yl)methanol (146);

(S)-(4-chloro-2-(2-methoxy-7-methylquinoxalin-5-yl)-7,8-dihydrobenzofuro[5,4-d]thiazol-7-yl)methyl(6-methylpyridin-3-yl)carbamate (147);

(4-chloro-2-(7-(hydroxymethyl)-2-methoxyquinoxalin-5-yl)-7,8-dihydrobenzofuro[5,4-d]thiazol-7-yl)methyl (6-methylpyridin-3-yl)carbamate (148);

(S)-(2-(2-methoxy-7-methylquinoxalin-5-yl)-7,8-dihydrobenzofuro[5,4-d]thiazol-7-yl)methanol (149);

(S)-(2-(2-methoxy-7-methylquinoxalin-5-yl)-7,8-dihydrobenzofuro[5,4-d]thiazol-7-yl)methyl(2-methylpyrimidin-5-yl)carbamate (150);

(S)-(5-fluoro-2-(2-methoxy-7-methylquinoxalin-5-yl)-7,8-dihydrobenzofuro[5,4-d]thiazol-7-yl)methyl (2-methylpyrimidin-5-yl) carbamate (151);

(S)-(2-(2-ethoxy-7-methylquinoxalin-5-yl)-5-fluoro-7,8-dihydrobenzofuro[5,4-d]thiazol-7-yl)methanol (152);

(R)-(2-(2-ethoxy-7-methylquinoxalin-5-yl)-5-fluoro-7,8-dihydrobenzofuro[5,4-d]thiazol-7-yl)methyl (2-methylpyrimidin-5-yl)carbamate (153);

(R)-(5-fluoro-2-(2-methoxy-7-methylquinoxalin-5-yl)-7,8-dihydrobenzofuro[5,4-d]thiazol-7-yl)methyl (5-cyanopyridin-3-yl)carbamate (154);

(R)-(5-fluoro-2-(2-methoxy-7-methylquinoxalin-5-yl)-7,8-dihydrobenzofuro[5,4-d]thiazol-7-yl)methyl (2-(2-hydroxyethyl)pyrimidin-5-yl)carbamate (155);

(S)-methyl 2-(2-methoxy-7-methylquinoxalin-5-yl)-7,8-dihydrobenzofuro[5,4-d]thiazole-7-carboxylate (156);

(R)-(5-fluoro-2-(2-methoxy-7-methylquinoxalin-5-yl)-7,8-dihydrobenzofuro[5,4-d]thiazol-7-yl)methyl pyridin-3-ylcarbamate (157);

(R)-(5-fluoro-2-(2-methoxy-7-methylquinoxalin-5-yl)-7,8-dihydrobenzofuro[5,4-d]thiazol-7-yl)methyl pyridazin-4-ylcarbamate (158);

(R)-(5-fluoro-2-(2-methoxy-7-methylquinoxalin-5-yl)-7,8-dihydrobenzofuro[5,4-d]thiazol-7-yl)methyl (6-methylpyridin-3-yl)carbamate (159);

(R)-(5-fluoro-2-(2-methoxy-7-methylquinoxalin-5-yl)-7,8-dihydrobenzofuro[5,4-d]thiazol-7-yl)methyl (2-methylpyridin-4-yl)carbamate (160);

(R)-(5-fluoro-2-(2-methoxy-7-methylquinoxalin-5-yl)-7,8-dihydrobenzofuro[5,4-d]thiazol-7-yl)methyl (5-fluoropyridin-3-yl)carbamate (161);

(R)-(5-fluoro-2-(2-methoxy-7-methylquinoxalin-5-yl)-7,8-dihydrobenzofuro[5,4-d]thiazol-7-yl)methyl (3-cyanophenyl)carbamate (162);

(R)-(5-fluoro-2-(2-methoxy-7-methylquinoxalin-5-yl)-7,8-dihydrobenzofuro[5,4-d]thiazol-7-yl)methyl (2-methoxypyridin-4-yl)carbamate (163);

(R)-(5-fluoro-2-(2-methoxy-7-methylquinoxalin-5-yl)-7,8-dihydrobenzofuro[5,4-d]thiazol-7-yl)methyl (6-methoxypyridin-3-yl)carbamate (164);

(R)-(5-fluoro-2-(2-methoxy-7-methylquinoxalin-5-yl)-7,8-dihydrobenzofuro[5,4-d]thiazol-7-yl)methyl (6-(2-hydroxyethoxy)pyridin-3-yl)carbamate (165);

(R)-(5-fluoro-2-(2-methoxy-7-methylquinoxalin-5-yl)-7,8-dihydrobenzofuro[5,4-d]thiazol-7-yl)methyl (6-(2,2-difluoro-3-hydroxypropoxy)pyridin-3-yl)carbamate (166);

(5-fluoro-2-(2-methoxy-7-methylquinoxalin-5-yl)-7-methyl-7,8-dihydrobenzofuro[5,4-d]thiazol-7-yl) methanol (167);

(R)-(5-fluoro-2-(2-methoxy-7-methylquinoxalin-5-yl)-7,8-dihydrobenzofuro[5,4-d]thiazol-7-yl)methyl(5-methoxypyridin-3-yl)carbamate (168);

(R)-(5-fluoro-2-(2-methoxy-7-methylquinoxalin-5-yl)-7,8-dihydrobenzofuro[5,4-d]thiazol-7-yl)methyl (4-(morpholine-4-carbonyl) phenyl)carbamate (169);

(R)-(5-fluoro-2-(2-methoxy-7-methylquinoxalin-5-yl)-7,8-dihydrobenzofuro[5,4-d]thiazol-7-yl)methyl (6-fluoropyridin-3-yl)carbamate (170);

(2-(2-methoxy-7-methylquinoxalin-5-yl)-7-methyl-7,8-dihydrobenzofuro[5,4-d]thiazol-7-yl)methanol (171);

(S)-(5-fluoro-2-(2-methoxy-7-methylquinoxalin-5-yl)-7-methyl-7,8-dihydrobenzofuro[5,4-d]thiazol-7-yl) methanol (172);

(R)-(5-fluoro-2-(2-methoxy-7-methylquinoxalin-5-yl)-7,8-dihydrobenzofuro[5,4-d]thiazol-7-yl)methyl (2-(2-hydroxyethoxy)pyrimidin-5-yl)carbamate (173);

(S)-(5-fluoro-2-(2-methoxy-7-methylquinoxalin-5-yl)-7-methyl-7,8-dihydrobenzofuro[5,4-d]thiazol-7-yl) methyl (2-methylpyrimidin-5-yl)carbamate (174);

(S)-(5-fluoro-2-(2-methoxy-7-methylquinoxalin-5-yl)-7-methyl-7,8-dihydrobenzofuro[5,4-d]thiazol-7-yl) methyl pyridin-3-ylcarbamate (175);

(S)-(5-fluoro-2-(2-methoxy-7-methylquinoxalin-5-yl)-7-methyl-7,8-dihydrobenzofuro[5,4-d]thiazol-7-yl) methyl (3-cyanophenyl)carbamate (176);

(R)-(5-fluoro-2-(2-methoxy-7-methylquinoxalin-5-yl)-7,8-dihydrobenzofuro[5,4-d]thiazol-7-yl)methyl (2-methoxypyrimidin-5-yl)carbamate (177);

(R)-(5-fluoro-2-(2-methoxy-7-methylquinoxalin-5-yl)-7,8-dihydrobenzofuro[5,4-d]thiazol-7-yl)meth yl (3-cyano-5-fluorophenyl)carbamate (179);

(R)-(5-fluoro-2-(2-methoxy-7-methylquinoxalin-5-yl)-7,8-dihydrobenzofuro[5,4-d]thiazol-7-yl)methyl (3-carbamoylphenyl)carbamate (180);

(R)-(5-fluoro-2-(2-methoxy-7-methylquinoxalin-5-yl)-7-methyl-7,8-dihydrobenzofuro[5,4-d]thiazol-7-yl) methanol (181);

(R)-(5-fluoro-2-(2-methoxy-7-methylquinoxalin-5-yl)-7-methyl-7,8-dihydrobenzofuro[5,4-d]thiazol-7-yl) methyl (2-methylpyrimidin-5-yl)carbamate (182);

(R)-(5-fluoro-2-(2-methoxy-7-methylquinoxalin-5-yl)-7-methyl-7,8-dihydrobenzofuro [5,4-d]thiazol-7-yl) methyl pyridin-3-ylcarbamate (183);

(R)-(5-fluoro-2-(2-methoxy-7-methylquinoxalin-5-yl)-7-methyl-7,8-dihydrobenzofuro[5,4-d]thiazol-7-yl) methyl (3-cyanophenyl)carbamate (184);

(R)-(5-fluoro-2-(2-methoxy-7-methylquinoxalin-5-yl)-7,8-dihydrobenzofuro[5,4-d]thiazol-7-yl)methyl pyrimidin-5-ylcarbamate (185);

2-(2-methoxy-7-methylquinoxalin-5-yl)-7,7-dimethyl-7,8-dihydrobenzofuro[5,4-d]thiazole (186);

(S)-(2-(2-methoxy-7-methylquinoxalin-5-yl)-7-methyl-7,8-dihydrobenzofuro[5,4-d]thiazol-7-yl)met hanol (187);

(R)-(2-(2-methoxy-7-methylquinoxalin-5-yl)-7-methyl-7,8-dihydrobenzofuro[5,4-d]thiazol-7-yl)met hanol (188);

(2-(2-methoxy-7-methylquinoxalin-5-yl)-8-methyl-7,8-dihydrobenzofuro[5,4-d]thiazol-7-yl)methan ol (189);

(S)-2-((2-methoxy-7-methylquinoxalin-5-yl)-7,8-dihydrobenzofuro[5,4-d]thiazol-7-yl)ethanol (190);

Methyl ((2-(2-methoxy-7-methylquinoxalin-5-yl)-7,8-dihydrobenzofuro [5,4-d]thiazol-7-yl)methyl)carbamate (191);

Phenyl ((2-(2-methoxy-7-methylquinoxalin-5-yl)-7,8-dihydrobenzofuro[5,4-d]thiazol-7-yl)methyl)carb amate (192);

benzyl ((2-(2-methoxy-7-methylquinoxalin-5-yl)-7,8-dihydrobenzofuro[5,4-d]thiazol-7-yl)methyl) carbamate (193);

(R)-(2-(2-methoxy-7-methylquinoxalin-5-yl)-7-methyl-7,8-dihydrobenzofuro[5,4-d]thiazol-7-yl)methyl (2-methylpyrimidin-5-yl)carbamate (194);

(R)-(2-(2-methoxy-7-methylquinoxalin-5-yl)-7-methyl-7,8-dihydrobenzofuro[5,4-d]thiazol-7-yl)methyl pyridin-3-ylcarbamate (195);

(R)-(2-(2-methoxy-7-methylquinoxalin-5-yl)-7-methyl-7,8-dihydrobenzofuro[5,4-d]thiazol-7-yl)methyl(3-cyanophenyl) carbamate (196);

ethyl((2-(2-methoxy-7-methylquinoxalin-5-yl)-7,8-dihydrobenzofuro [5,4-d]thiazol-7-yl) methyl)carbamate (197);

Isobutyl ((2-(2-methoxy-7-methylquinoxalin-5-yl)-7,8-dihydrobenzofuro[5,4-d]thiazol-7-yl)methyl)carb amate (198);

(cis-5-fluoro-2-(2-methoxy-7-methylquinoxalin-5-yl)-8-methyl-7,8-dihydrobenzofuro[5,4-d]thiazol-7-yl) methanol (199);

5-fluoro-2-(2-methoxy-7-methylquinoxalin-5-yl)-7,7-dimethyl-7,8-dihydrobenzofuro[5,4-d]thiazole (200);

(trans-5-fluoro-2-(2-methoxy-7-methylquinoxalin-5-yl)-8-methyl-7,8-dihydrobenzofuro[5,4-d]thiazol-7-yl) methanol (201);

(S)-tert-butyl ((5-fluoro-2-(2-methoxy-7-methylquinoxalin-5-yl)-7,8-dihydrobenzofuro[5,4-d]thiazol-7-yl)met hyl)carbamate (202);

(R)-(5-fluoro-2-(2-methoxy-7-methylquinoxalin-5-yl)-7,8-dihydrobenzofuro[5,4-d]thiazol-7-yl)meth yl (3-(dimethylcarbamoyl)phenyl)carbamate (203);

(R)-(5-fluoro-2-(2-methoxy-7-methylquinoxalin-5-yl)-7,8-dihydrobenzofuro[5,4-d]thiazol-7-yl)meth yl (4-(dimethylcarbamoyl)phenyl)carbamate (204);

(R)-(5-fluoro-2-(2-methoxy-7-methylquinoxalin-5-yl)-7,8-dihydrobenzofuro[5,4-d]thiazol-7-yl)meth yl (5-carbamoylpyridin-3-yl)carbamate (205);

(R)-(5-fluoro-2-(2-methoxy-7-methylquinoxalin-5-yl)-8,8-dimethyl-7,8-dihydrobenzofuro[5,4-d]thia zol-7-yl) methanol (206);

(R)-(5-fluoro-2-(2-methoxy-7-methylquinoxalin-5-yl)-7,8-dihydrobenzofuro[5,4-d]thiazol-7-yl)meth yl (4-(methylcarbamoyl)phenyl)carbamate (208);

(S)-N-((5-fluoro-2-(2-methoxy-7-methylquinoxalin-5-yl)-7,8-dihydrobenzofuro[5,4-d]thiazol-7-yl)methyl) acetamide (209);

(S)-methyl ((5-fluoro-2-(2-methoxy-7-methylquinoxalin-5-yl)-7,8-dihydrobenzofuro[5,4-d]thiazol-7-yl)met hyl)carbamate (210);

(S)-benzyl ((5-fluoro-2-(2-methoxy-7-methylquinoxalin-5-yl)-7,8-dihydrobenzofuro[5,4-d]thiazol-7-yl)met hyl) carbamate (211);

(S)-phenyl ((5-fluoro-2-(2-methoxy-7-methylquinoxalin-5-yl)-7,8-dihydrobenzofuro[5,4-d]thiazol-7-yl)met hyl)carbamate (212);

(S)-p-tolyl ((5-fluoro-2-(2-methoxy-7-methylquinoxalin-5-yl)-7,8-dihydrobenzofuro[5,4-d]thiazol-7-yl)met hyl) carbamate (213);

(S)-4-chlorophenyl ((5-fluoro-2-(2-methoxy-7-methylquinoxalin-5-yl)-7,8-dihydrobenzofuro[5,4-d]thiazol-7-yl)met hyl)carbamate (214);

(S)-2,2,2-trifluoro-N-((5-fluoro-2-(2-methoxy-7-methylquinoxalin-5-yl)-7,8-dihydrobenzofuro[5,4-d]thiazol-7-yl)methyl)acetamide (215);

(S)-4-methoxyphenyl ((5-fluoro-2-(2-methoxy-7-methylquinoxalin-5-yl)-7,8-dihydrobenzofuro[5,4-d]thiazol-7-yl)met hyl)carbamate (216);

(R)-N-((5-fluoro-2-(2-methoxy-7-methylquinoxalin-5-yl)-7,8-dihydrobenzofuro [5,4-d]thiazol-7-yl)methyl)-2-phenylacetamide (217);

(R)-methyl ((5-fluoro-2-(2-methoxy-7-methylquinoxalin-5-yl)-7,8-dihydrobenzofuro[5,4-d]thiazol-7-yl)met hyl) carbamate (218);

(R)-N-((5-fluoro-2-(2-methoxy-7-methylquinoxalin-5-yl)-7,8-dihydrobenzofuro[5,4-d]thiazol-7-yl)methyl) acetamide (219);

(R)-phenyl ((5-fluoro-2-(2-methoxy-7-methylquinoxalin-5-yl)-7,8-dihydrobenzofuro[5,4-d]thiazol-7-yl)methyl) carbamate (220);

(R)-benzyl ((5-fluoro-2-(2-methoxy-7-methylquinoxalin-5-yl)-7,8-dihydrobenzofuro[5,4-d]thiazol-7-yl)methyl)carbamate (221);

(R)-2,2,2-trifluoro-N-((5-fluoro-2-(2-methoxy-7-methylquinoxalin-5-yl)-7,8-dihydrobenzofuro[5,4-d]thiazol-7-yl)methyl)acetamide (222);

(R)-tert-butyl ((5-fluoro-2-(2-methoxy-7-methylquinoxalin-5-yl)-7,8-dihydrobenzofuro[5,4-d]thiazol-7-yl)methyl)carbamate (223);

(S)-isobutyl ((2-(2-methoxy-7-methylquinoxalin-5-yl)-7,8-dihydrobenzofuro[5,4-d]thiazol-7-yl)methyl) carbamate (224);

(S)-benzyl ((2-(2-methoxy-7-methylquinoxalin-5-yl)-7,8-dihydrobenzofuro[5,4-d]thiazol-7-yl)methyl)carbamate (225);

(S)-methyl ((2-(2-methoxy-7-methylquinoxalin-5-yl)-7,8-dihydrobenzofuro[5,4-d]thiazol-7-yl)methyl) carbamate (226);

(S)-tetrahydro-2H-pyran-4-yl ((2-(2-methoxy-7-methylquinoxalin-5-yl)-7,8-dihydrobenzofuro[5,4-d]thiazol-7-yl)methyl)carbamate (227);

(S)-N-((2-(2-methoxy-7-methylquinoxalin-5-yl)-7,8-dihydrobenzofuro[5,4-d]thiazol-7-yl)methyl) methanesulfonamide (228);

(Tetrahydrofuran-3-yl)methyl (((S)-2-(2-methoxy-7-methylquinoxalin-5-yl)-7,8-dihydrobenzofuro[5,4-d]thiazol-7-yl)methyl)carbamate (229);

(R)-tetrahydrofuran-3-yl (((S)-2-(2-methoxy-7-methylquinoxalin-5-yl)-7,8-dihydrobenzofuro[5,4-d]thiazol-7-yl)methyl)carbamate (230);

(S)-3-cyanobenzyl ((2-(2-methoxy-7-methylquinoxalin-5-yl)-7,8-dihydrobenzofuro[5,4-d]thiazol-7-yl)methyl) carbamate (231);

(S)-pyridin-3-ylmethyl ((2-(2-methoxy-7-methylquinoxalin-5-yl)-7,8-dihydrobenzofuro[5,4-d]thiazol-7-yl)methyl)carbamate (232);

(S)-pyridin-4-ylmethyl ((2-(2-methoxy-7-methylquinoxalin-5-yl)-7,8-dihydrobenzofuro[5,4-d]thiazol-7-yl)methyl) carbamate (233);

Tetrahydro-2H-pyran-3-yl (((S)-2-(2-methoxy-7-methylquinoxalin-5-yl)-7,8-dihydrobenzofuro[5,4-d]thiazol-7-yl)methyl)carbamate (234);

(Tetrahydro-2H-pyran-2-yl)methyl (((S)-2-(2-methoxy-7-methylquinoxalin-5-yl)-7,8-dihydrobenzofuro [5,4-d]thiazol-7-yl)methyl)carbamate (235);

(S)-tetrahydrofuran-3-yl (((S)-2-(2-methoxy-7-methylquinoxalin-5-yl)-7,8-dihydrobenzofuro[5,4-d]thiazol-7-yl)methyl)carbamate (236);

(S)-(5-fluoro-2-(2-methoxy-7-methylquinoxalin-5-yl)-7-methyl-7,8-dihydrobenzofuro[5,4-d]thiazol-7-yl) methyl dihydrogen phosphate (237);

((7S,8S)-5-fluoro-2-(2-methoxy-7-methylquinoxalin-5-yl)-8-methyl-7,8-dihydrobenzofuro[5,4-d]thiazol-7-yl)methanol (238);

((7R,8R)-5-fluoro-2-(2-methoxy-7-methylquinoxalin-5-yl)-8-methyl-7,8-dihydrobenzofuro[5,4-d]thiazol-7-yl)methanol (239);

(S)-methyl ((5-fluoro-2-(2-methoxy-7-methylquinoxalin-5-yl)-7-methyl-7,8-dihydrobenzofuro[5,4-d]thiazol-7-yl) methyl)carbamate (240);

(S)-isobutyl ((5-fluoro-2-(2-methoxy-7-methylquinoxalin-5-yl)-7-methyl-7,8-dihydrobenzofuro[5,4-d]thiazol-7-yl) methyl) carbamate (241);

(S)-tert-butyl ((5-fluoro-2-(2-methoxy-7-methylquinoxalin-5-yl)-7-methyl-7,8-dihydrobenzofuro[5,4-d]thiazol-7-yl) methyl)carbamate (242);

(R)-1-((S)-2-(2-methoxy-7-methylquinoxalin-5-yl)-7,8-dihydrobenzofuro[5,4-d]thiazol-7-yl)ethanol(243);

(S)-tert-butyl ((2-(2-methoxy-7-methylquinoxalin-5-yl)-7,8-dihydrobenzofuro[5,4-d]thiazol-7-yl)methyl)carbamate (244);

(S)-tetrahydro-2H-pyran-4-yl ((5-fluoro-2-(2-methoxy-7-methylquinoxalin-5-yl)-7,8-dihydrobenzofuro[5,4-d]thiazol-7-yl)methyl)carbamate (245);

(S)-isobutyl ((5-fluoro-2-(2-methoxy-7-methylquinoxalin-5-yl)-7,8-dihydrobenzofuro[5,4-d]thiazol-7-yl)methyl)carbamate (246);

(S)-2-fluoroethyl ((5-fluoro-2-(2-methoxy-7-methylquinoxalin-5-yl)-7,8-dihydrobenzofuro[5,4-d]thiazol-7-yl)methyl)carbamate (247);

(S)-1-((5-fluoro-2-(2-methoxy-7-methylquinoxalin-5-yl)-7,8-dihydrobenzofuro[5,4-d]thiazol-7-yl)methyl)-3-phenylurea (248);

(S)-2,2,2-trifluoroethyl ((5-fluoro-2-(2-methoxy-7-methylquinoxalin-5-yl)-7,8-dihydrobenzofuro[5,4-d]thiazol-7-yl)methyl)carbamate (249);

(S)-2-methoxyethyl ((5-fluoro-2-(2-methoxy-7-methylquinoxalin-5-yl)-7,8-dihydrobenzofuro [5,4-d]thiazol-7-yl)methyl)carbamate (250);

(R)-(5-fluoro-2-(2-methoxy-7-methylquinoxalin-5-yl)-7-methyl-7,8-dihydrobenzofuro[5,4-d]thiazol-7-yl) methyl (2-(2-hydroxyethoxy)pyrimidin-5-yl)carbamate (251);

((7R,8R)-5-fluoro-2-(2-methoxy-7-methylquinoxalin-5-yl)-8-methyl-7,8-dihydrobenzofuro[5,4-d]thiazol-7-yl)methyl (2-(2-hydroxyethoxy)pyrimidin-5-yl)carbamate (252);

((7S,8S)-2-(7-chloro-2-methoxyquinoxalin-5-yl)-5-fluoro-8-methyl-7,8-dihydrobenzofuro[5,4-d]thiazol-7-yl) methanol (253);

8-((7S,8S)-5-fluoro-7-(hydroxymethyl)-8-methyl-7,8-dihydrobenzofuro [5,4-d]thiazol-2-yl)-3-methoxyquinoxaline-6-carbonitrile (254);

Methyl (((7S,8S)-5-fluoro-2-(2-methoxy-7-methylquinoxalin-5-yl)-8-methyl-7,8-dihydrobenzofuro[5,4-d]thiazol-7-yl)methyl)carbamate (255);

Isobutyl (((7S,8S)-5-fluoro-2-(2-methoxy-7-methylquinoxalin-5-yl)-8-methyl-7,8-dihydrobenzofuro[5,4-d]thiazol-7-yl)methyl) carbamate (256);

(S)-1-cyclopropyl-3-((5-fluoro-2-(2-methoxy-7-methylquinoxalin-5-yl)-7,8-dihydrobenzofuro[5,4-d]thiazol-7-yl)methyl)urea (257);

(S)-N-((5-fluoro-2-(2-methoxy-7-methylquinoxalin-5-yl)-7,8-dihydrobenzofuro[5,4-d]thiazol-7-yl)methyl)morpholine-4-carboxamide (258);

((7S,8S)-2-(2-ethoxy-7-methylquinoxalin-5-yl)-5-fluoro-8-methyl-7,8-dihydrobenzofuro[5,4-d]thiazol-7-yl)methanol (259);

(S)-ethyl ((5-fluoro-2-(2-methoxy-7-methylquinoxalin-5-yl)-7,8-dihydrobenzofuro[5,4-d]thiazol-7-yl) methyl)carbamate (260);

(S)-neopentyl ((5-fluoro-2-(2-methoxy-7-methylquinoxalin-5-yl)-7,8-dihydrobenzofuro[5,4-d]thiazol-7-yl)methyl)carbamate (261);

1-(2-(2-methoxy-7-methylquinoxalin-5-yl)-7,8-dihydro-[1,4]dioxino[2',3':3,4]benzo[1,2-d]thiazol-4-yl)-2,2-dimethylpropan-1-ol (262);

1-(7-(2-methoxy-7-methylquinoxalin-5-yl)-[1,3]dioxolo[4',5':3,4]benzo[1,2-d]thiazol-5-yl)-2,2-dimethylpropan-1-ol (263);

1-(2-(2-methoxy-7-methylquinoxalin-5-yl)-8,9-dihydro-7H-[1,4]dioxepino[2',3':3,4]benzo[1,2-d]thiazol-4-yl)-2,2-dimethylpropan-1-ol (264);

(2-(2-methoxy-7-methylquinoxalin-5-yl)-7,8-dihydro-[1,4]dioxino[2',3':3,4]benzo[1,2-d]thiazol-4-yl)(1-(trifluoromethyl)cyclobutyl)methanol (265);

(2-(2-methoxy-7-methylquinoxalin-5-yl)-7,8-dihydro-[1,4]dioxino[2',3':3,4]benzo[1,2-d]thiazol-4-yl)(1-(methylcyclohexyl)methanol (278);

(2-(2-methoxy-7-methylquinoxalin-5-yl)-7,8-dihydro-[1,4]dioxino[2',3':3,4]benzo[1,2-d]thiazol-4-yl)(1-(trifluoromethyl)cyclopropyl)methanol (279);

(S)-(5-fluoro-2-(2-methoxy-7-methylquinoxalin-5-yl)-7,8-dihydro-[1,4]dioxino[2',3':3,4]benzo[1,2-d]thiazol-7-yl)methanol (291); and (S)-5-fluoro-2-(2-methoxy-7-methylquinoxalin-5-yl)-7-(((2-methylpyrimidin-5-yl)oxy)methyl)-7,8-dihydro-[1,4]dioxino[2',3':3,4]benzo[1,2-d]thiazole (292).

7. A pharmaceutical composition, which comprises a pharmaceutically acceptable carrier and a compound according to claim 1 or a pharmaceutically acceptable salt thereof.

8. A compound, wherein the compound is

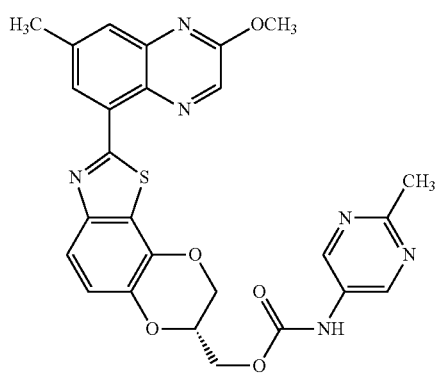

or salt thereof.

9. A pharmaceutical composition, which comprises a pharmaceutically acceptable carrier and a compound according to claim 8 or a pharmaceutically acceptable salt thereof.

10. A compound, wherein the compound is

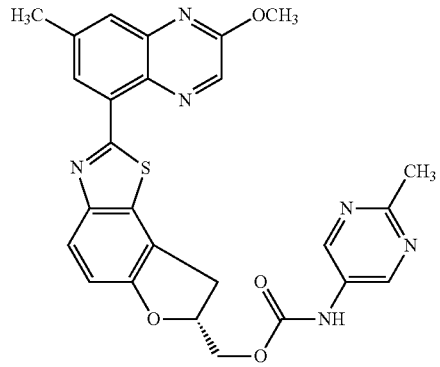

or salt thereof.

11. A pharmaceutical composition, which comprises a pharmaceutically acceptable carrier and a compound according to claim 10 or a pharmaceutically acceptable salt thereof.

12. A compound, wherein the compound is

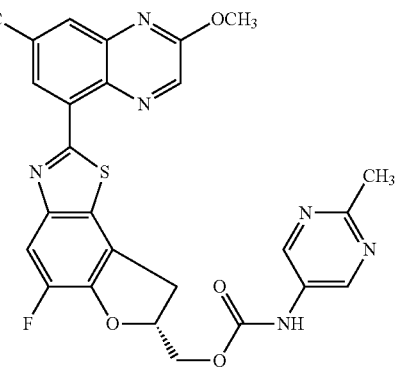

or salt thereof.

13. A pharmaceutical composition, which comprises a pharmaceutically acceptable carrier and a compound according to claim 12 or a pharmaceutically acceptable salt thereof.

14. A compound, wherein the compound is

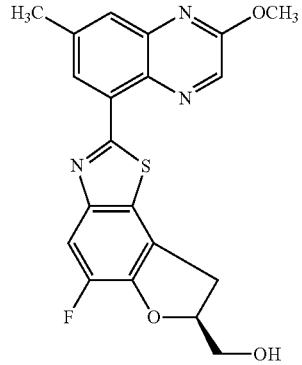 [SMILES: COc1cnc2c(-c3nc4cc(F)c5c(c4s3)C[C@@H](CO)O5)cc(C)cc2n1]

or salt thereof.

15. A pharmaceutical composition, which comprises a pharmaceutically acceptable carrier and a compound according to claim 14 or a pharmaceutically acceptable salt thereof.

16. A compound, wherein the compound is

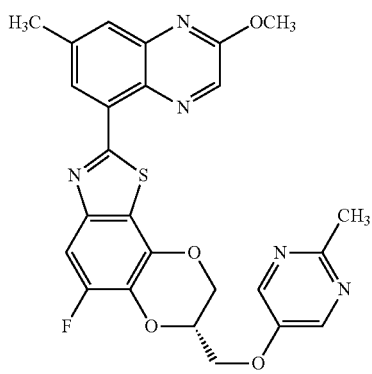

or salt thereof.

17. A pharmaceutical composition, which comprises a pharmaceutically acceptable carrier and a compound according to claim 16 or a pharmaceutically acceptable salt thereof.

18. A compound, wherein the compound is

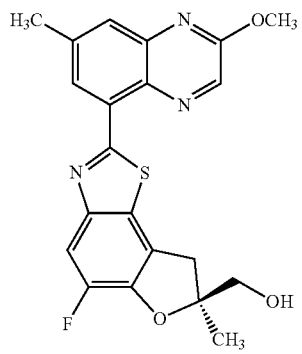 [SMILES: COc1cnc2c(-c3nc4cc(F)c5c(c4s3)C[C@@](C)(CO)O5)cc(C)cc2n1]

or salt thereof.

19. A pharmaceutical composition, which comprises a pharmaceutically acceptable carrier and a compound according to claim 18 or a pharmaceutically acceptable salt thereof.

* * * * *